US012297428B2

(12) United States Patent
Chen et al.

(10) Patent No.: US 12,297,428 B2
(45) Date of Patent: May 13, 2025

(54) COMPOSITIONS FOR IDENTIFICATION OF MEMBRANE TARGETS FOR ENHANCEMENT OF T CELL ACTIVITY AGAINST CANCER

(71) Applicant: YALE UNIVERSITY, New Haven, CT (US)

(72) Inventors: Sidi Chen, Milford, CT (US); Lupeng Ye, New Haven, CT (US); Jonathan Park, Scott AFB, IL (US); Matthew Dong, San Francisco, CA (US); Ryan D. Chow, San Jose, CA (US)

(73) Assignee: Yale University, New Haven, CT (US)

( * ) Notice: Subject to any disclaimer, the term of this patent is extended or adjusted under 35 U.S.C. 154(b) by 1063 days.

(21) Appl. No.: 17/264,691

(22) PCT Filed: Jul. 31, 2019

(86) PCT No.: PCT/US2019/044424
§ 371 (c)(1),
(2) Date: Jan. 29, 2021

(87) PCT Pub. No.: WO2020/028533
PCT Pub. Date: Feb. 6, 2020

(65) Prior Publication Data
US 2022/0340898 A1 Oct. 27, 2022

Related U.S. Application Data

(60) Provisional application No. 62/805,585, filed on Feb. 14, 2019, provisional application No. 62/713,217, filed on Aug. 1, 2018.

(51) Int. Cl.
| | |
|---|---|
| *C12N 15/86* | (2006.01) |
| *A61K 40/11* | (2025.01) |
| *A61K 40/31* | (2025.01) |
| *A61K 40/42* | (2025.01) |
| *C12N 15/11* | (2006.01) |
| *C12N 15/90* | (2006.01) |

(52) U.S. Cl.
CPC ............ *C12N 15/111* (2013.01); *A61K 40/11* (2025.01); *A61K 40/31* (2025.01); *A61K 40/42* (2025.01); *A61K 40/4204* (2025.01); *C12N 15/90* (2013.01); *A61K 2239/31* (2023.05); *A61K 2239/47* (2023.05); *C12N 2310/20* (2017.05); *C12N 2800/90* (2013.01); *C12Y 204/01155* (2013.01); *C12Y 503/04001* (2013.01)

(58) Field of Classification Search
None
See application file for complete search history.

(56) References Cited

U.S. PATENT DOCUMENTS

| 2009/0178153 A1 | 7/2009 | Gaitanaris | |
| 2013/0004983 A1* | 1/2013 | Matsunami | C07K 14/70571 435/369 |
| 2016/0355806 A1 | 12/2016 | Lee | |
| 2018/0156800 A1* | 6/2018 | Lin | G01N 33/5017 |

FOREIGN PATENT DOCUMENTS

| WO | WO-2013173652 A1 * | 11/2013 | ......... A61K 31/7115 |
| WO | 2017046259 | 3/2017 | |
| WO | WO-2017046259 A1 * | 3/2017 | ............. C12N 15/90 |
| WO | 2017064566 | 4/2017 | |
| WO | WO-2018195073 A2 * | 10/2018 | ........... C12N 15/111 |

OTHER PUBLICATIONS

Chow et al Nat Neurosci vol. 20 No 10 pp. 1329-1341 (pp. 1-40) (Year: 2017).*
Chow et al Nature Neuroscience, 1329-1341 (Year: 2017).*
Shifrut et al Cell, 175, 1958-1971 (Year: 2018).*
NCBI accession No. AF287263.1, p. 1 (Year: 2001).*
International Search Report and Written Opinion issued in App. No. PCT/US19/44424, mailing date Jan. 6, 2020, 18 pages.
Agarwalla, Pankaj, et al. "Sequential immunotherapy by vaccination with GM-CSF expressing glioma cells and CTLA-4 blockade effectively treats established murine intracranial tumors." Journal of Immunotherapy (Hagerstown, Md.: 1997) 35.5 (2012): 385.
Anderson, A. C., et al. "Lag-3, Tim-3, and TIGIT: co-inhibitory receptors with specialized functions in immune regulation." Immunity 44.5 (2016): 989-1004.
Brown, Christine E., et al. "Regression of glioblastoma after chimeric antigen receptor T-cell therapy." New England Journal of Medicine 375.26 (2016): 2561-2569.
Chen, Daniel S., et al. "Oncology meets immunology: the cancer-immunity cycle." immunity 39.1 (2013): 1-10.
Chen, Runqiang, et al. "In vivo RNA interference screens identify regulators of antiviral CD4+ and CD8+ T cell differentiation." Immunity 41.2 (2014): 325-338.
Chen, Sidi, et al. "Genome-wide CRISPR screen in a mouse model of tumor growth and metastasis." Cell 160.6 (2015): 1246-1260.
Dai, Hanren, et al. "Chimeric antigen receptors modified T-cells for cancer therapy." Journal of the National Cancer Institute 108.7 (2016): djv439.

(Continued)

*Primary Examiner* — Anoop K Singh
(74) *Attorney, Agent, or Firm* — Saul Ewing, LLP; Kathryn Doyle; Lukas Pfannenstiel

(57) ABSTRACT

The present invention includes compositions and methods for identification of membrane targets for enhancement of T cell activity against a disease, disorder or condition, and/or enhancing T cell anti-tumor activity in a subject in need thereof. In some embodiments, the disease is cancer. In further embodiments, the cancer is glioblastoma (GBM) or breast cancer.

1 Claim, 70 Drawing Sheets

Specification includes a Sequence Listing.

(56) References Cited

OTHER PUBLICATIONS

Fecci, Peter E., et al. "Systemic CTLA-4 blockade ameliorates glioma-induced changes to the CD4+ T cell compartment without affecting regulatory T-cell function." Clinical cancer research 13.7 (2007): 2158-2167.
Gilbert, Mark R., et al. "A randomized trial of bevacizumab for newly diagnosed glioblastoma." New England Journal of Medicine 370.8 (2014): 699-708.
Huang, Ching-Tai, et al. "Role of LAG-3 in regulatory T cells." Immunity 21.4 (2004): 503-513.
Ji, Seung Taek, et al. "Promising therapeutic strategies for mesenchymal stem cell-based cardiovascular regeneration: from cell priming to tissue engineering." Stem cells international 2017 (2017).
Jiang, Peng, et al. "Signatures of T cell dysfunction and exclusion predict cancer immunotherapy response." Nature medicine 24.10 (2018): 1550-1558.
Khalil, Danny N., et al. "The future of cancer treatment: immunomodulation, CARs and combination immunotherapy." Nature reviews Clinical oncology 13.5 (2016): 273-290.
Koboldt, Daniel C., et al. "VarScan: variant detection in massively parallel sequencing of individual and pooled samples." Bioinformatics 25.17 (2009): 2283-2285.
Kvistborg, Pia, et al. "Anti-CTLA-4 therapy broadens the melanoma-reactive CD8+ T cell response." Science translational medicine 6.254 (2014): 254ra128-254ra128.
Langmead, Ben, et al. "Ultrafast and memory-efficient alignment of short DNA sequences to the human genome." Genome biology 10.3 (2009): 1-10.
Li, Heng, et al. "Fast and accurate short read alignment with Burrows-Wheeler transform." bioinformatics 25.14 (2009):1754-1760.
Li, Bo, et al. "Comprehensive analyses of tumor immunity: implications for cancer immunotherapy." Genome biology 17.1 (2016): 1-16.
Louveau, Antoine, et al. "Structural and functional features of central nervous system lymphatics." Nature (2015): 7560, 337-341. Author Manuscript, HHS Public Access, Available in PMC Jan. 16, 2016. doi: 10.1038/nature 14432.
Martin, Marcel. "Cutadapt removes adapter sequences from high-throughput sequencing reads." EMBnet. journal 17.1 (2011): 10-12.
Mates, Lajos, et al. "Molecular evolution of a novel hyperactive Sleeping Beauty transposase enables robust stable gene transfer in vertebrates." Nature genetics 41.6 (2009): 753-761.
Mathios, Dimitrios, et al. "Anti-PD-1 antitumor immunity is enhanced by local and abrogated by systemic chemotherapy in GBM." Science translational medicine 8.370 (2016): 370ra180-370ra180. Author Manuscript, HHS Public Access, available in PMC Dec. 11, 2017. doi: 10.1126/scitranslmed.aag2942.
Mount, Christopher W., et al. "Potent antitumor efficacy of anti-GD2 Car T cells in H3-K27M+ diffuse midline gliomas." Nature medicine 24.5 (2018): 572-579. Author Manuscript, HHS Public Access, available in PMC Nov. 2, 2018. doi: 10.1038/s41591-018-0006-x.
Okada, Masahiro, et al. "Blockage of core fucosylation reduces cell-surface expression of PD-1 and promotes anti-tumor immune responses of T cells." Cell reports 20.5 (2017): 1017-1028.
Omuro, Antonio, et al. "Nivolumab with or without ipilimumab in patients with recurrent glioblastoma: results from exploratory phase I cohorts of CheckMate 143." Neuro-oncology 20.5 (2018): 674-686.
O'Rourke, Donald M., et al. "A single dose of peripherally infused EGFRvIII-directed CAR T cells mediates antigen loss and induces adaptive resistance in patients with recurrent glioblastoma." Science translational medicine 9.399 (2017): eaaa0984. Author Manuscript, HHS Public Access, available in PMC Jan. 19, 2018. doi: 10.1126/scitranslmed.aaa0984.

Pardoll, Drew M. "The blockade of immune checkpoints in cancer immunotherapy." Nature reviews cancer 12.4 (2012): 252-264.
Pellegatta, Serena, et al. "Constitutive and TNFα-inducible expression of chondroitin sulfate proteoglycan 4 in glioblastoma and neurospheres: Implications for CAR-T cell therapy." Science translational medicine 10.430 (2018): eaao2731.
Preusser, Matthias, et al. "Prospects of immune checkpoint modulators in the treatment of glioblastoma." Nature Reviews Neurology 11.9 (2015): 504-514.
Ribas, Antoni. "Tumor immunotherapy directed at PD-1." N Engl J Med 366.26 (2012): 2517-2519.
Ribas, Antoni, et al. "Pembrolizumab versus investigator-choice chemotherapy for ipilimumab-refractory melanoma (KEYNOTE-002): a randomised, controlled, phase 2 trial." The lancet oncology 16.8 (2015): 908-918.
Saha, Dipongkor, et al. "Macrophage polarization contributes to glioblastoma eradication by combination immunovirotherapy and immune checkpoint blockade." Cancer cell 32.2 (2017): 253-267.
Shalem, Ophir, et al. "Genome-scale CRISPR-Cas9 knockout screening in human cells." Science 343.6166 (2014): 84-87.
Shibui, Akiko, et al. "Alteration of immune responses by N-acetylglucosaminyltransferase V during allergic airway inflammation." Allergology International 60.3 (2011): 345-354.
Shifrut, Eric, et al. "Genome-wide CRISPR screens in primary human T cells reveal key regulators of immune function." Cell 175.7 (2018): 1958-1971.
Smith, Logan K., et al. "Interleukin-10 directly inhibits CD8+ T cell function by enhancing N-glycan branching to decrease antigen sensitivity." Immunity 48.2 (2018): 299-312.
Sugiura, Kanematsu, C., et al. "Studies in a tumor spectrum. II. The growth of a variety of mouse and rat tumors." Cancer 5.5 (1952): 979-991.
Tumeh, Paul C., et al. "PD-1 blockade induces responses by inhibiting adaptive immune resistance." Nature 515.7528 (2014): 568-571.
Wang, Guangchuan, et al. "Mapping a functional cancer genome atlas of tumor suppressors in mouse liver using AAV-CRISPR—mediated direct in vivo screening." Science advances 4.2 (2018): eaao5508.
Weller, Michael, et al. "EANO guideline for the diagnosis and treatment of anaplastic gliomas and glioblastoma." The lancet oncology 15.9 (2014): e395-e403.
Workman, Creg J., et al. "Cutting edge: molecular analysis of the negative regulatory function of lymphocyte activation gene-3." The Journal of Immunology 169.10 (2002): 5392-5395.
Workman, Creg J., et al. "Lymphocyte activation gene-3 (CD223) regulates the size of the expanding T cell population following antigen activation in vivo." The Journal of Immunology 172.9 (2004): 5450-5455.
Zhou, Penghui, et al. "In vivo discovery of immunotherapy targets in the tumour microenvironment." Nature 506.7486 (2014): 52-57.
Hogquist, K.A., et al., "T-Cell Receptor Antagonist Peptides Induce Positive Selection". Cell 76, 17-27 (1994).
Schlager, C., et al., "Effector T-cell trafficking between the leptomeninges and the cerebrospinal fluid", Nature 530, 349-+ (2016).
Bernards, R., "Finding effective cancer therapies through loss of function genetic screens", Current Opinion in Genetics & Development 24, 23-29 (2014).
Ting, P.Y., et al., "Guide Swap enables genome-scale pooled CRISPR-Cas9 screening in human primary cells", Nat Methods 15, 941-946 (2018).
Demetriou, M., et al., "Negative regulation of T-cell activation and autoimmunity by Mgat5 N-glycosylation", Nature 409, 733-739 (2001).
Granovsky, M., et al., "Suppression of tumor growth and metastasis in Mgat5-deficient mice.", Nat Med 6, 306-312 (2000).

* cited by examiner

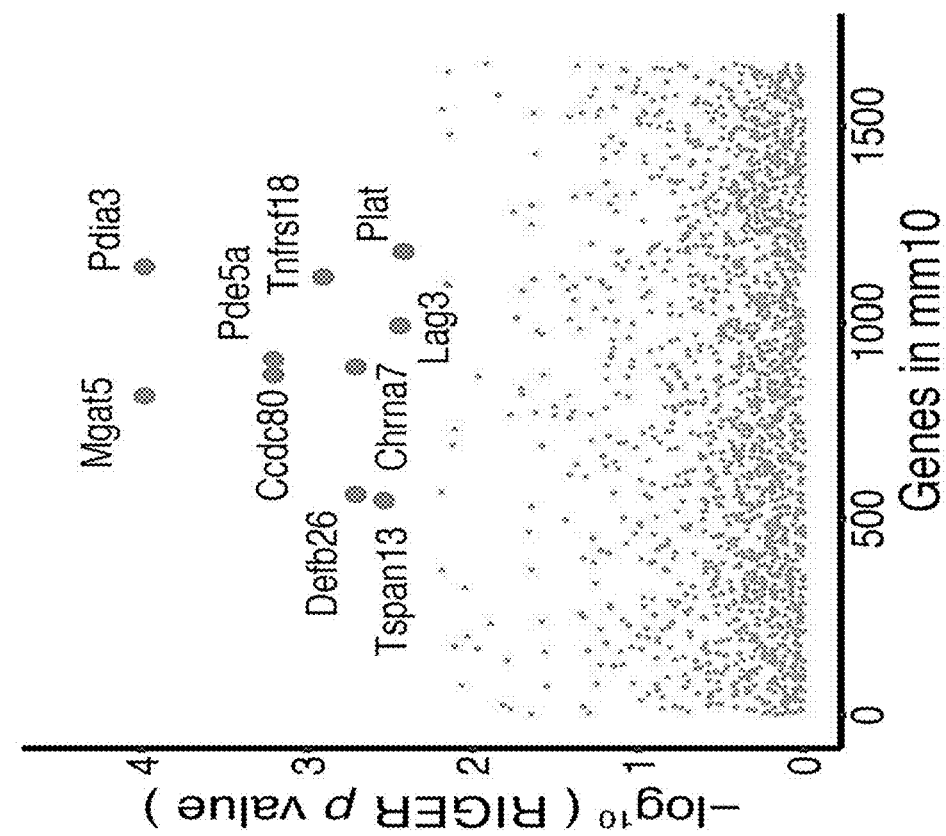
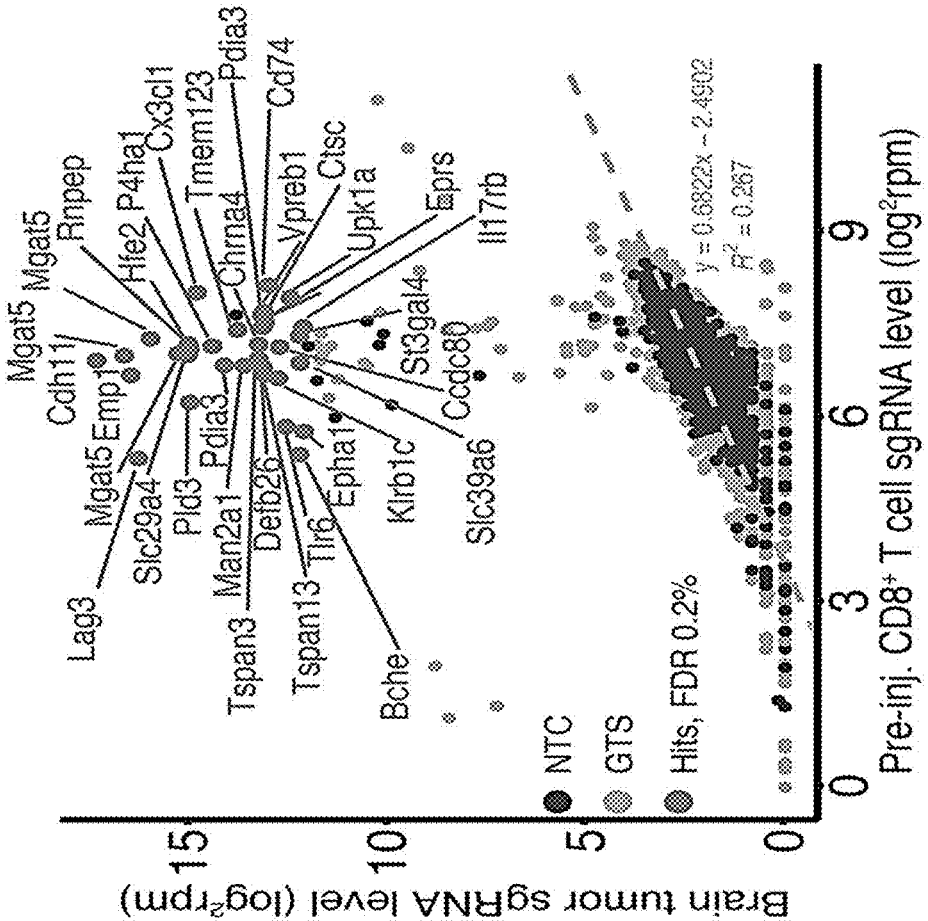
FIG. 1E
FIG. 1D

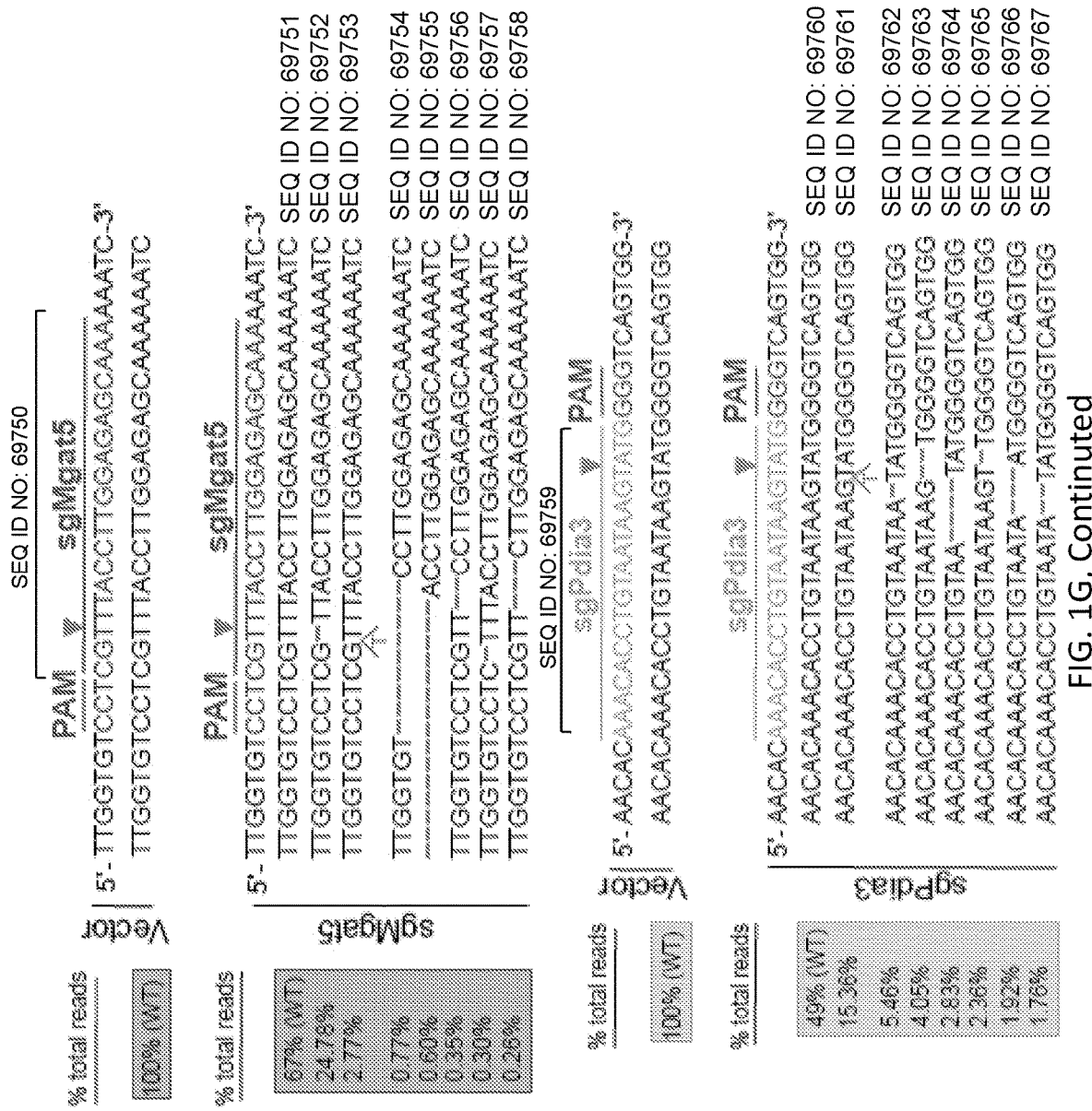
FIG. 1G, Continued

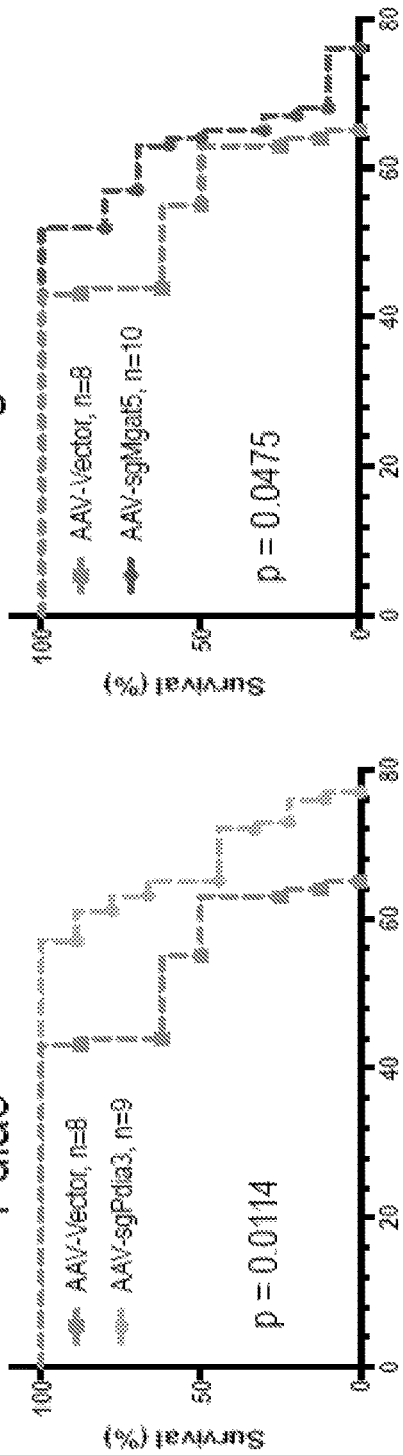
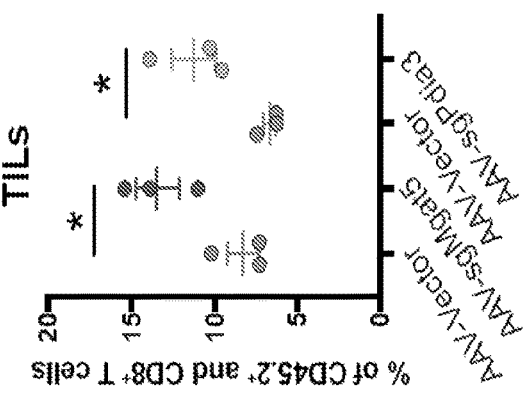
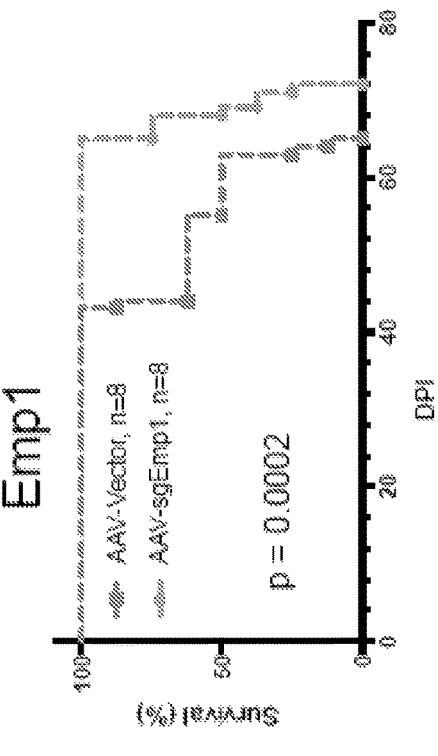
FIG. 1I
FIG. 1J
FIG. 1K
FIG. 1L

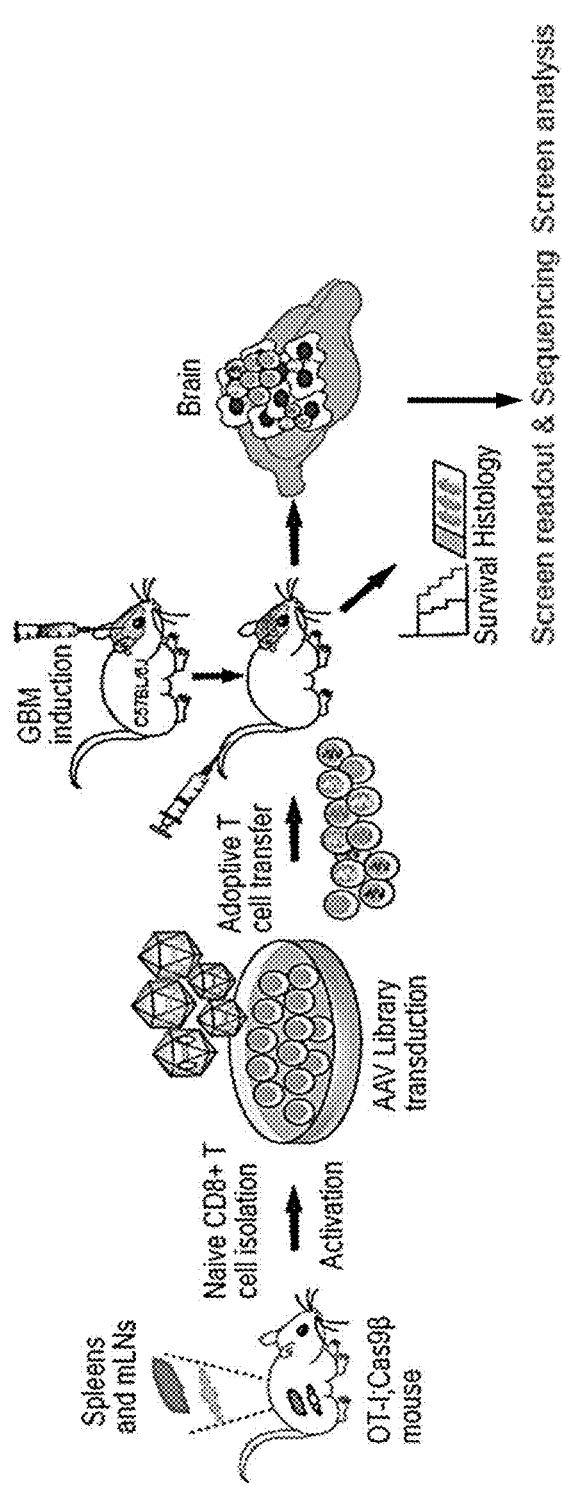
FIG. 2A
FIG. 2B
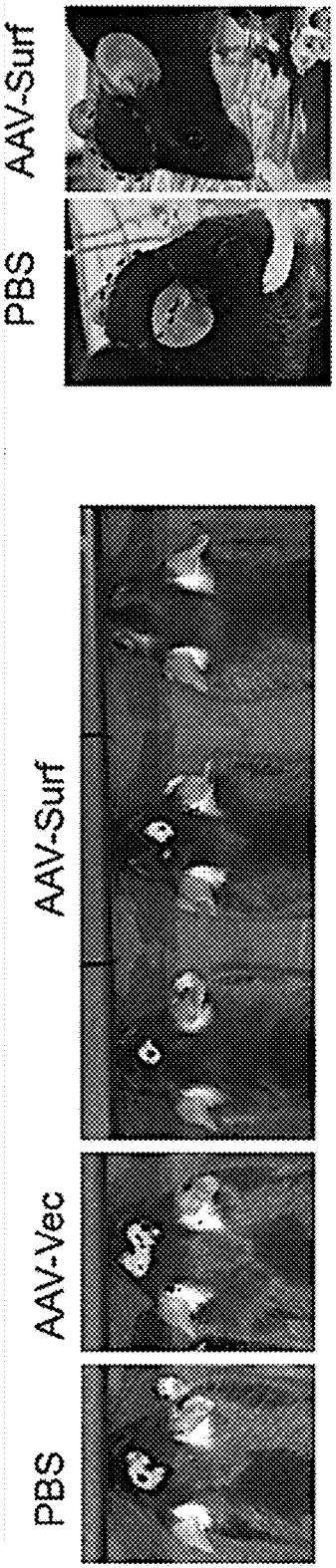
FIG. 2C

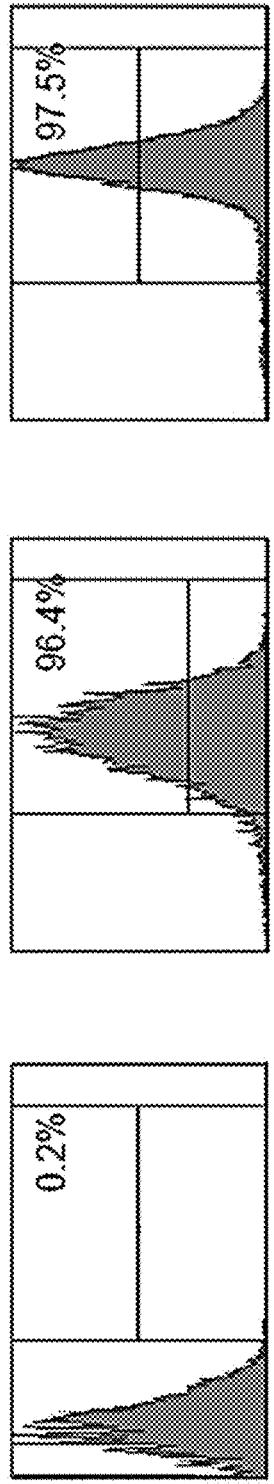
FIG. 3A
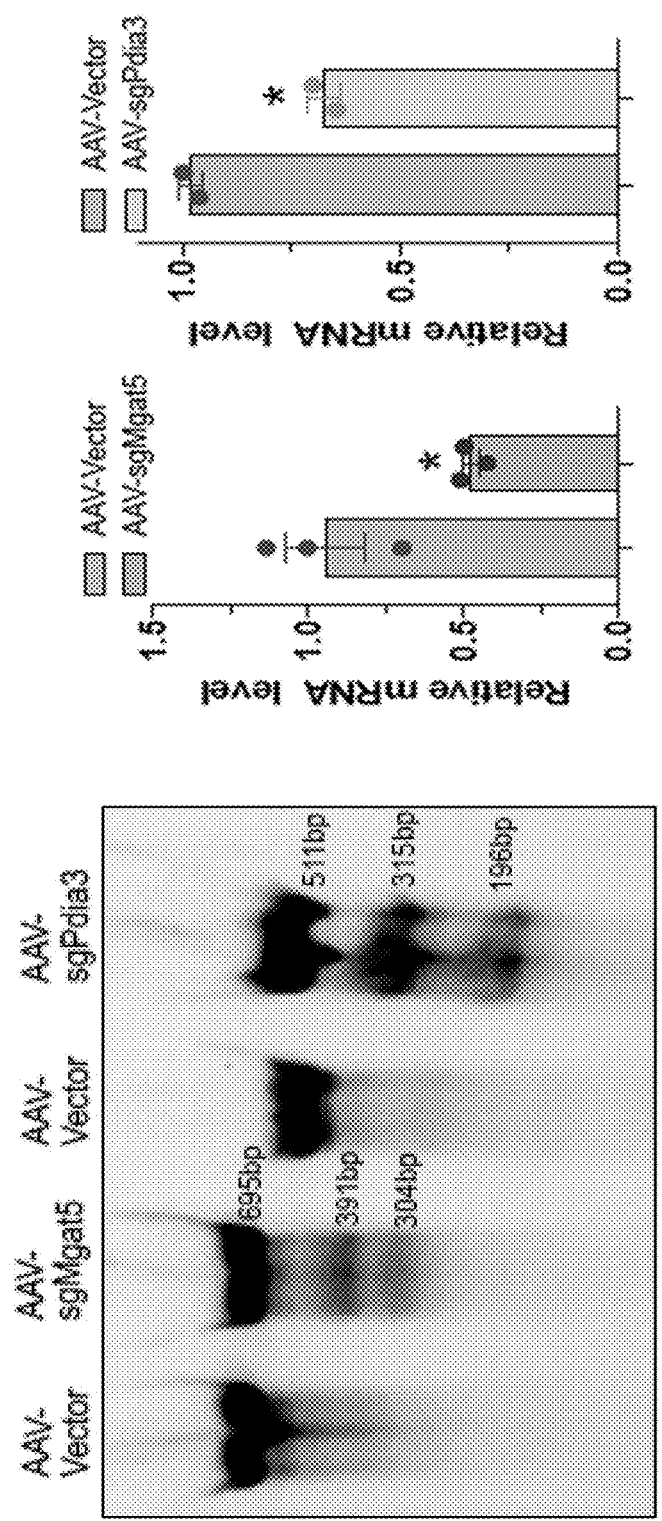
FIG. 3B
FIG. 3C

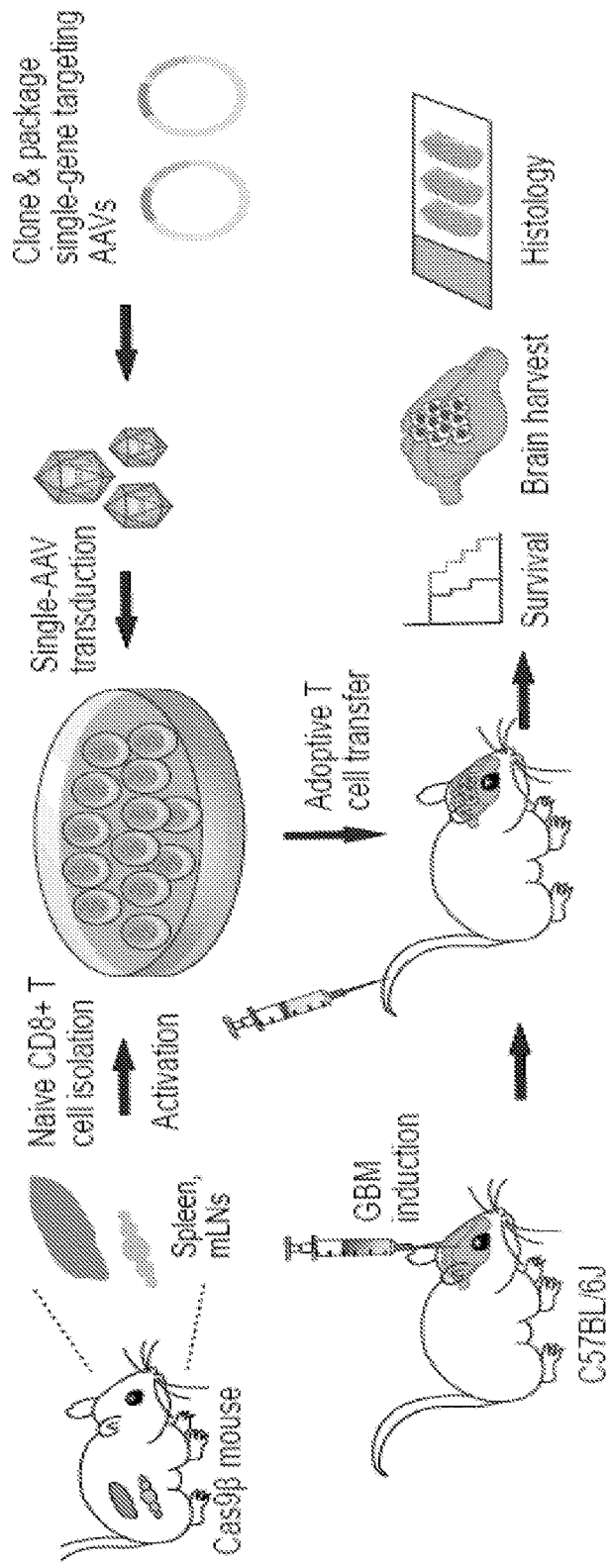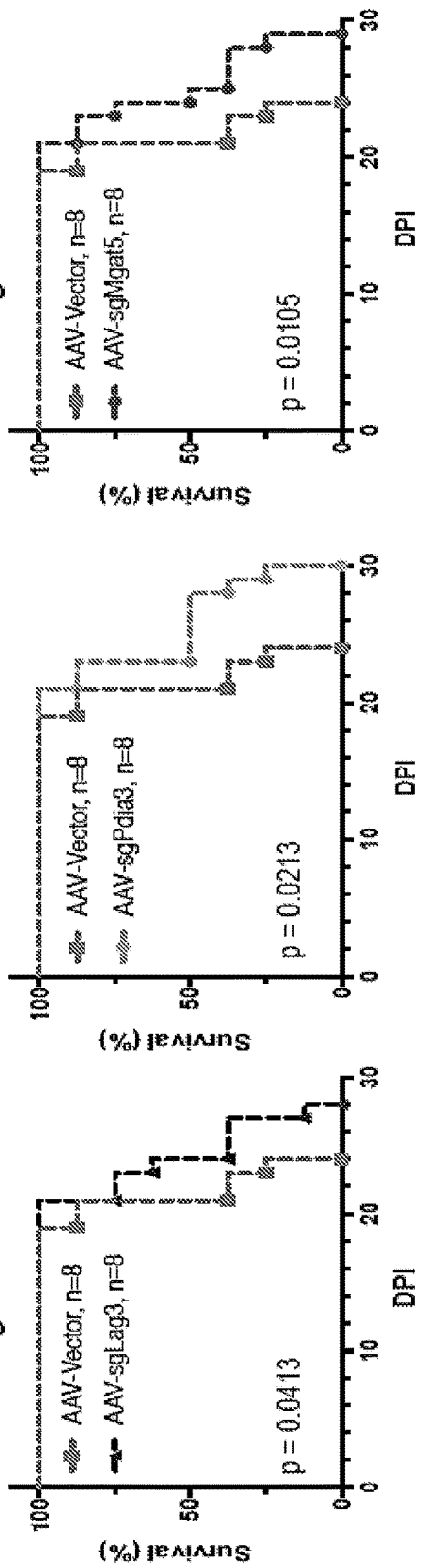
FIG. 3F
FIG. 3G

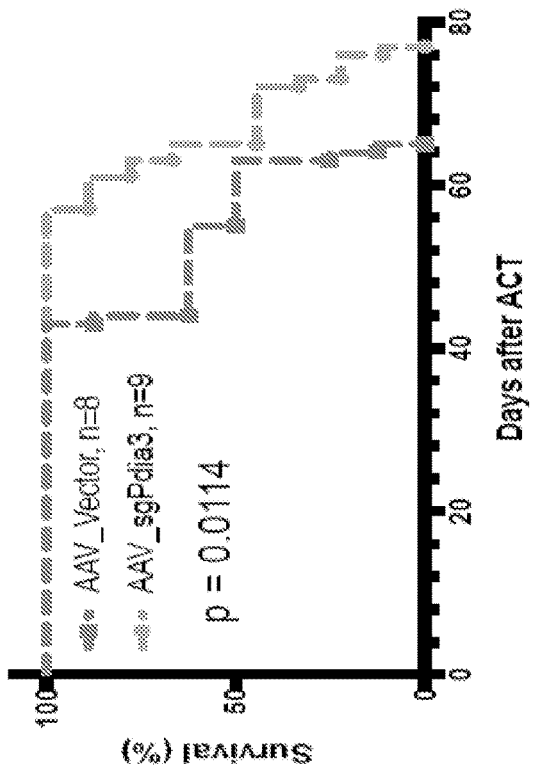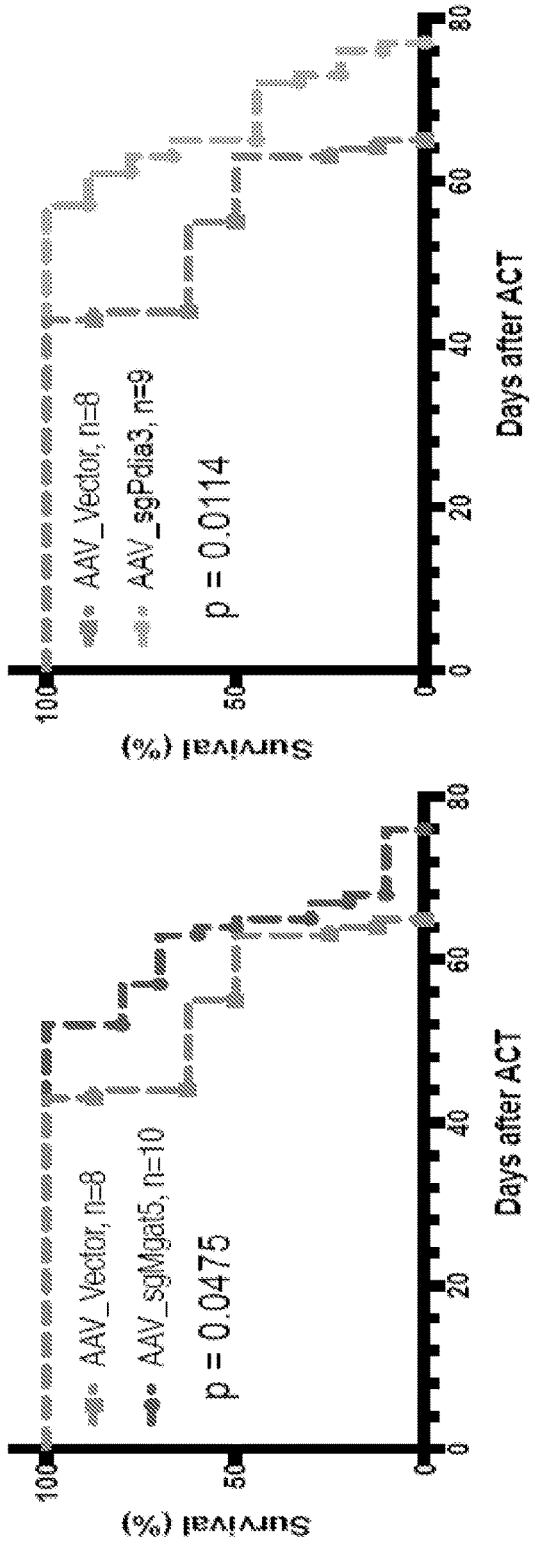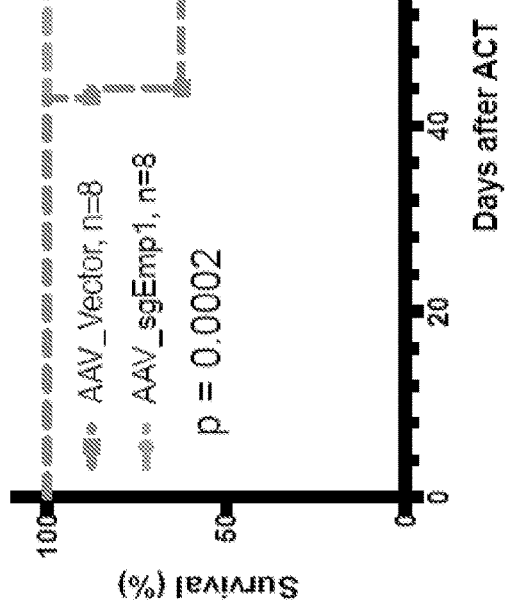
FIG. 5C
FIG. 5D
FIG. 5E

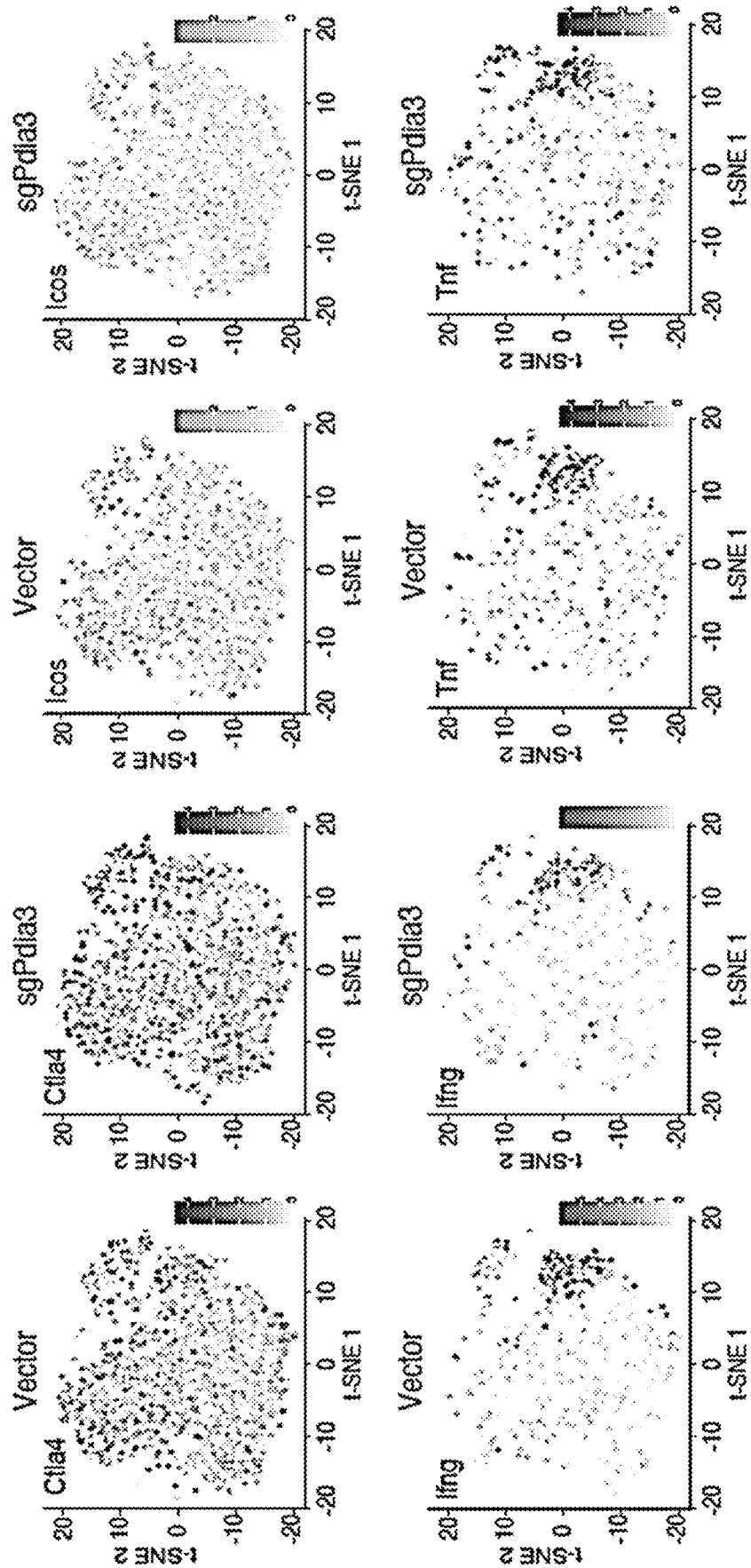
FIG. 9, Continued

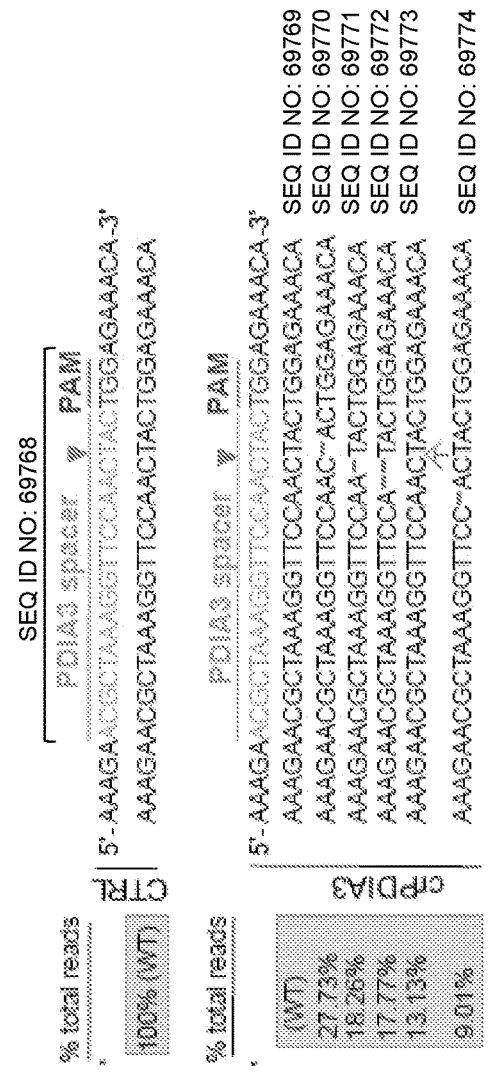
FIG. 11C
FIG. 11B
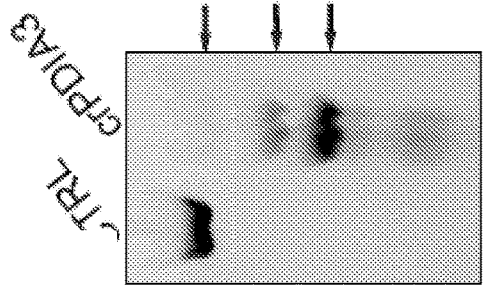
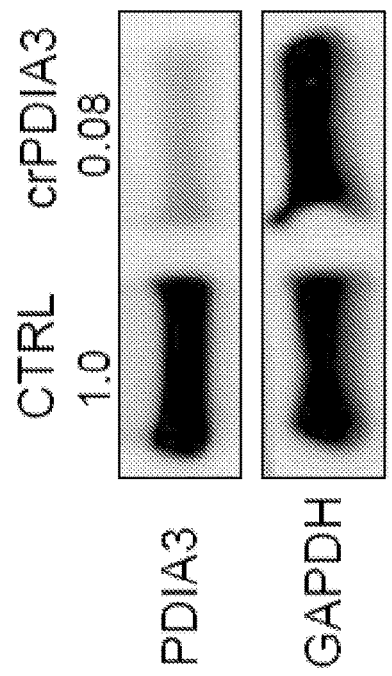
FIG. 11D

Representative SB transposon integration sites

| | Genomic sequence | SB transposon (IR/DR) | |
|---|---|---|---|
| Chr5 | 5'-TAAAAACTATTTTATCAAATACAGTT | GAAGTGGGAAGTTTA-3' | SEQ ID NO: 69799 |
| Chr6 | 5'-TAAAACTATTATCTGATAACTACAGTT | GAAGTGAAGTCGGAAGTTTA-3' | SEQ ID NO: 69800 |
| Chr10 | 5'-GCTTTCAATACATCCTGTTTACAGTT | GAAGTCGGAAGTTTA-3' | SEQ ID NO: 69801 |
| Chr9 | 5'-TTCACGGCGACTACTGCACTTACAGTT | GAAGTGGGAAGTTTA-3' | SEQ ID NO: 69802 |
| Chr14 | 5'-GGATGGGTACAAGATGAGTATACAGTT | GAAGTGAAGTGGGAAGTTTA-3' | SEQ ID NO: 69803 |
| Chr9 | 5'-TCACCCTCTCCAACCAGCCCTACAGTT | GAAGTTCGGAAGTTTA-3' | SEQ ID NO: 69804 |

FIG. 17D

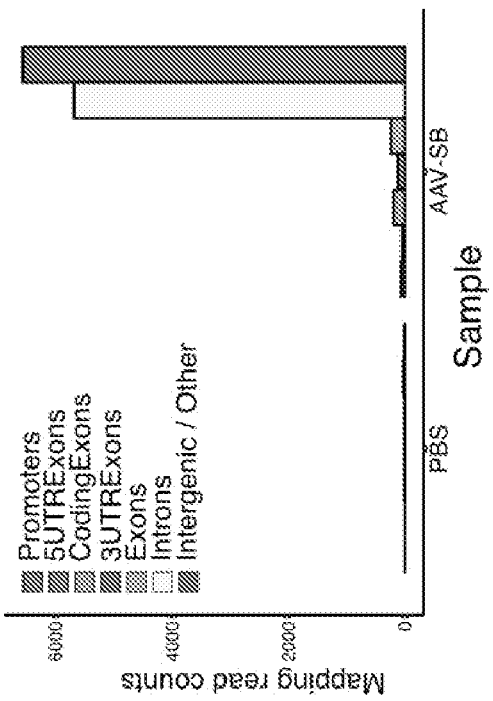

FIG. 17F

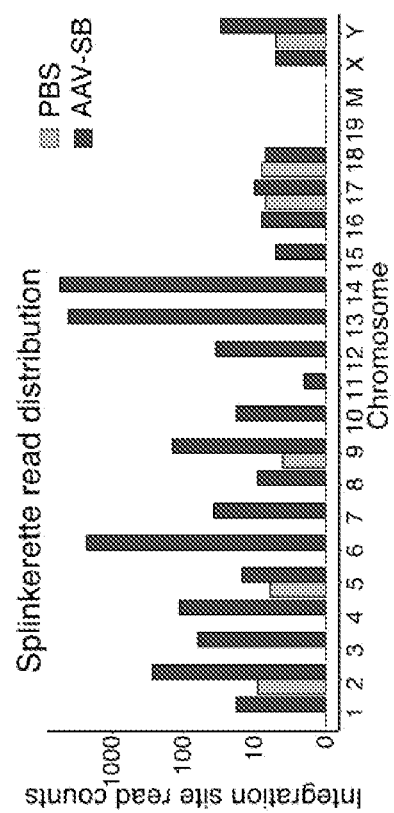

FIG. 17E

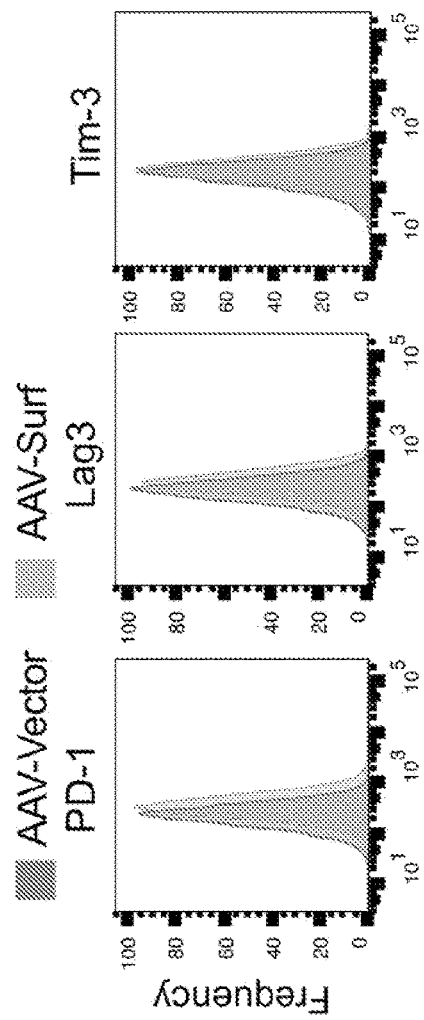
FIG. 20A
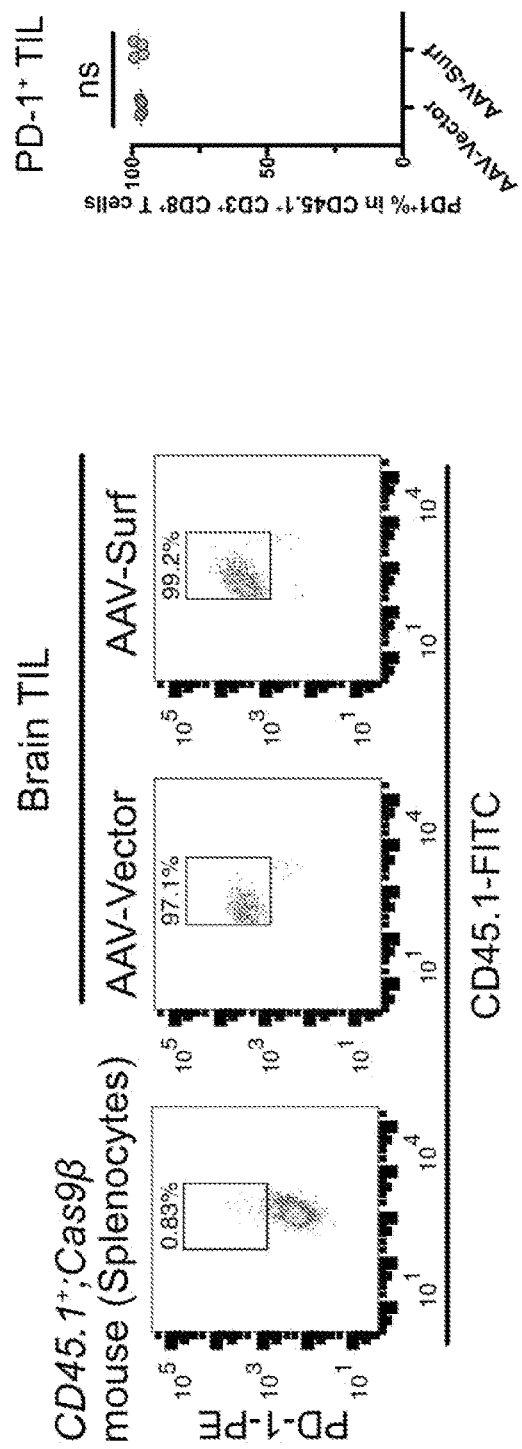
FIG. 20B
FIG. 20C

COMPOSITIONS FOR IDENTIFICATION OF MEMBRANE TARGETS FOR ENHANCEMENT OF T CELL ACTIVITY AGAINST CANCER

CROSS-REFERENCE TO RELATED APPLICATIONS

The present application is a 35 U.S.C. § 371 national phase application from, and claiming priority to, International Application No. PCT/US2019/044424, filed Jul. 31, 2019, which is entitled to priority under 35 U.S.C. § 119(e) to U.S. Provisional Patent Application No. 62/713,217, filed Aug. 1, 2018, and U.S. Provisional Patent Application No. 62/805,585, filed Feb. 14, 2019, each of which are hereby incorporated by reference in their entireties herein.

STATEMENT REGARDING FEDERALLY SPONSORED RESEARCH OR DEVELOPMENT

This invention was made with government support under CA209992, CA231112 and CA238295 awarded by the National Institutes of Health and under W81XH-17-1-0235 awarded by the United States Army Medical Research and Material Command. The government has certain rights in the invention.

BACKGROUND OF THE INVENTION

Glioblastoma (GBM) is the most common and deadliest primary malignant brain tumor in adults. GBM patients only have a median survival period of approximately 15 months under the current standard of care. Once glioblastoma relapses in patients, none of the current treatments can effectively prolong overall survival. Immune checkpoint blockade can enhance the antitumor response of $CD8^+$ T cells by neutralizing cytotoxic T cell lymphocyte antigen 4 (CTLA-4), programmed cell death protein 1 (PD-1) or its ligand PD-L1. However, a recent clinical trial demonstrated that PD-1 blockade does not prolong survival for GBM patients. Combined treatment of anti-PD-1 and anti-CTLA-4 in GBM patients also failed to provide clinical benefits and patients suffered from strong adverse effects. EGFR-vIII CAR-T cell therapy has been through several clinical trials, however, little overall survival benefit was seen for GBM patients. The failure of these immunotherapy modalities revealed an urgent need for identification of novel targets to enhance the anti-tumor activity of $CD8^+$ T cells.

There is an urgent unmet need to develop novel therapeutics for GBM. The present invention satisfies this need.

SUMMARY OF THE INVENTION

As described herein, the present invention relates to compositions and methods for identification of membrane targets for enhancement of T cell activity (e.g. $CD8^+$) against cancer.

In one aspect, the invention includes a non-naturally occurring or engineered sgRNA library (mmSurf) targeting membrane-bound molecules, comprising a plurality of nucleic acids comprising at least one nucleotide sequence selected from the group consisting of SEQ ID NOs: 1-6,628. In another aspect, the invention includes an sgRNA library (mmSurf), comprising a plurality of nucleic acids comprising at least one nucleotide sequence selected from the group consisting of SEQ ID NOs: 1-6,628. In further embodiments, the sgRNA library (mmSurf) further comprises a plurality of nucleic acids comprising at least one nucleotide sequence selected from the group consisting of SEQ ID NOs: 6,629-7,628.

In one aspect, the invention includes a non-naturally occurring or engineered sgRNA library (mSURFEOME2) targeting membrane-bound molecules, comprising a plurality of nucleic acids comprising at least one nucleotide sequence selected from the group consisting of SEQ ID NOs: 7,837-64,747. In another aspect, the sgRNA library (mSURFEOME2), comprises a plurality of nucleic acids comprising at least one nucleotide sequence selected from the group consisting of SEQ ID NOs: 7,837-64,747. In further embodiments, the sgRNA library (mSURFEOME2) further comprises a plurality of nucleic acids comprising at least one nucleotide sequence selected from the group consisting of SEQ ID NOs: 64,748-69,747.

In one aspect, the invention includes an AAV library (AAV-Surf) comprising a plurality of vectors, wherein each vector comprises an expression cassette for an sgRNA comprising a nucleotide sequence selected from the group consisting of SEQ ID NOs: 1-6,628. In further embodiments, the sgRNA library (AAV-Surf) further comprises a plurality of nucleic acids comprising at least one nucleotide sequence selected from the group consisting of SEQ ID NOs: 6,629-7,628.

In one aspect, the invention includes an AAV library (AAV-SURFEOME2) comprising a plurality of vectors, wherein each vector comprises an expression cassette for an sgRNA comprising a nucleotide sequence selected from the group consisting of SEQ ID NOs: 7,837-64,747. In further embodiments, the sgRNA library (AAV-SURFEOME2) further comprises a plurality of nucleic acids comprising at least one nucleotide sequence selected from the group consisting of SEQ ID NOs: 64,748-69,747.

In some embodiments, at least one of the plurality of AAV library vectors comprises SEQ ID NO: 69,821.

In one aspect, the invention includes an AAV-CRISPR T cell vector for efficient gene editing and high-throughput screen in T cells comprising a first ITR, a second ITR, an antibiotic resistance sequence, two sleeping beauty (SB) IR/DR repeats, a first promoter, an sgRNA, a second promoter, a Thy1.1 selection marker, an SB100x transposase, and a poly A sequence.

In some embodiments, the AAV-CRISPR-T cell vector comprises SEQ ID NO: 69,821.

In one aspect, the invention includes a genetically modified cell, wherein at least one gene selected from the group consisting of Mgat5, Pdia3, Lag3, and Emp1 has been mutated in the cell.

In some embodiments, the cell is selected from the group consisting of a primary T cell, a $CD8^+$ cell, a $CD4^+$ cell, a T regulatory (Treg) cell, and a CAR-T cell.

In some embodiments, at least one additional gene has been mutated in the cell.

In some embodiments, the additional gene is selected from the group consisting of Cdh11, Hfe2, Slc29a1, Pld3, Xc3cl1, P4ha1, Rnpep, Man2a1, Tmem123, Vpreb1, Tspan3, Eprs, Chrna4, Ctlc, Ly9, Epha3, Lgals3bp, Plat, Lrrc8b, Crhr1, Vpreb1, Upk1a, Rnpep, Fgb, Vegfa and Kdr.

In one aspect, the invention includes a method of treating a disease, disorder, or condition in a subject in need thereof, the method comprising administering to the subject a genetically modified T cell wherein at least one gene selected from the group consisting of Mgat5, Pdia3, Lag3, and Emp1 has been targeted in the T cell. In some embodiments, the disease is cancer.

In various embodiments of the aspects found elsewhere herein or any other aspect of the invention delineated herein, the T cell is selected from the group consisting of a primary cell, a CD8$^+$ cell, a CD4$^+$ cell, a T regulatory (Treg) cell, and a CAR-T cell.

In some embodiments, the CAR-T cell comprises a CAR encoded by SEQ ID NO: 69,749.

In some embodiments, the subject is a human.

In some embodiments, the T cell is human.

In some embodiments, the cancer is a glioblastoma (GBM). In some embodiments, the cancer is breast cancer. In some embodiments, the breast cancer is triple negative breast cancer. In some embodiments, the cancer is selected from a cancer listed in Table 6.

In some embodiments, the administration comprises intracranial injection. In some embodiments, the administration comprises injection into the lateral ventricle.

In some embodiments, at least one additional gene has been targeted in the T cell.

In some embodiments, the additional gene is selected from the group consisting of Cdh11, Hfe2, Slc29a1, Pld3, Xc3cl1, P4ha1, Rnpep, Man2a1, Tmem123, Vpreb1, Tspan3, Eprs, Chrna4, Ctlc, Ly9, Epha3, Lgals3bp, Plat, Lrrc8b, Crhr1, Vpreb1, Upk1a, Rnpep, Fgb, Vegfa and Kdr.

In some embodiments, the targeted gene is mutated, deleted, transcriptionally repressed, translationally repressed and/or targetedly degraded.

In some embodiments, the method comprises administering an additional treatment to the subject.

In some embodiments, the additional treatment is selected from the group consisting of chemotherapy, radiation, surgery, an immune checkpoint inhibitor, a PD-1 inhibitor, and a CTLA-4 inhibitor.

In some embodiments, the gene is mutated by a CRISPR method.

Another aspect of the invention includes a method of enhancing CD8$^+$ T cell anti-tumor activity in a subject in need thereof, the method comprising administering to the subject a genetically modified T cell wherein at least one gene selected from the group consisting of Mgat5, Pdia3, Lag3, and Emp1 has been mutated in the T cell.

In some embodiments, the subject is a human.

In some embodiments, the subject has GBM.

In some embodiments, the subject has breast cancer.

In some embodiments, the breast cancer is triple negative breast cancer.

In some embodiments, the administration comprises intracranial injection.

In some embodiments, the administration comprises injection into the lateral ventricle.

In some embodiments, at least one additional gene has been mutated in the T cell.

In some embodiments, an additional treatment is administered to the subject.

In some embodiments, the additional treatment is selected from the group consisting of chemotherapy, radiation, surgery, an immune checkpoint inhibitor, a PD-1 inhibitor, and a CTLA-4 inhibitor.

In some embodiments, the gene is mutated by a CRISPR method.

Another aspect of the invention includes a method of performing genome editing and screening of a T cell for a mutation in vitro, the method comprising contacting the T cell with Cas9 and an AAV library, wherein the AAV library comprises a plurality of vectors, wherein each vector comprises an expression cassette for an sgRNA comprising a nucleotide sequence selected from the group consisting of SEQ ID NOs: 1-6,628, whereby the T cell undergoes genome editing; and screening the T cell for a mutation in vitro.

Another aspect of the invention includes a method of performing genome editing and screening of a T cell for a mutation in vitro, the method comprising contacting the T cell with Cas9 and an AAV library, wherein the AAV library comprises a plurality of vectors, wherein each vector comprises an expression cassette for an sgRNA comprising a nucleotide sequence selected from the group consisting of SEQ ID NOs: 7,837-64,747, whereby the T cell undergoes genome editing; and screening the T cell for a mutation in vitro.

Another aspect of the invention includes a method of performing genome editing and screening of a T cell for a mutation in vivo, the method comprising: contacting an isolated T cell with Cas9 and an AAV library, wherein the AAV library comprises a plurality of vectors, wherein each vector comprises an expression cassette for an sgRNA comprising a nucleotide sequence selected from the group consisting of SEQ ID NOs: 1-6,628, whereby the T cell undergoes genome editing to generate a modified T cell, administering to a subject the modified T cell, and screening the T cell for a mutation in vivo.

Another aspect of the invention includes a method of performing genome editing and screening of a T cell for a mutation in vivo, the method comprising: contacting an isolated T cell with Cas9 and an AAV library, wherein the AAV library comprises a plurality of vectors, wherein each vector comprises an expression cassette for an sgRNA comprising a nucleotide sequence selected from the group consisting of SEQ ID NOs: 7,837-64,747, whereby the T cell undergoes genome editing to generate a modified T cell, administering to a subject the modified T cell, and screening the T cell for a mutation in vivo.

In some embodiments, the T cell is selected from the group consisting of: a CD8$^+$ cell, a CD4$^+$ cell, a T regulatory (Treg) cell, a Th1 cell, a Th2 cell, a Th17 cell, a follicular helper T cell (Tfh), a T memory cell, a T effector cell, a T effector memory cell, an engineered T cell, and a CAR T cell In some embodiments, a modified T cell is isolated and enriched.

In some embodiments, the subject is a human.

In some embodiments, the T cell is human.

In some embodiments, the screening provides information about a gene involved in a condition afflicting the subject.

In some embodiments, the condition is cancer.

In some embodiments, the cancer is GBM.

In some embodiments, the cancer is breast cancer.

In some embodiments, the breast cancer is triple negative breast cancer.

In some embodiments, the screening comprises at least one method selected from the group consisting of nucleotide sequencing, sgRNA PCR, and flow cytometry.

Another aspect of the invention includes a method of generating a genetically modified T cell, the method comprising administering to a naïve T cell Cas9 and a vector comprising an expression cassette for an sgRNA comprising a nucleotide sequence selected from the group consisting of SEQ ID NOs: 1-6,628.

Another aspect of the invention includes a method of generating a genetically modified T cell, the method comprising administering to a naïve T cell Cas9 and a vector comprising an expression cassette for an sgRNA comprising a nucleotide sequence selected from the group consisting of SEQ ID NOs: 7,837-64,747.

In one aspect of the invention, the sgRNA targets a gene selected from the group consisting of Mgat5, Pdia3, Lag3, and Emp1.

Another aspect of the invention includes a composition comprising a genetically modified T cell generated by the methods found elsewhere herein.

Another aspect of the invention includes a kit comprising an AAV library and instructional material for use thereof, wherein the AAV library comprises a plurality of vectors, wherein each vector comprises an expression cassette for an sgRNA comprising a nucleotide sequence selected from the group consisting of SEQ ID NOs: 1-6,628. In some embodiments, the AAV library further comprises a plurality of vectors, wherein each vector comprises an expression cassette for an sgRNA comprising a nucleotide sequence selected from the group consisting of SEQ ID NOs: 6,629-7,628.

Another aspect of the invention includes a kit comprising an AAV library and instructional material for use thereof, wherein the AAV library comprises a plurality of vectors, wherein each vector comprises an expression cassette for an sgRNA comprising a nucleotide sequence selected from the group consisting of SEQ ID NOs: 7,837-64,747. In some embodiments, the AAV library further comprises a plurality of vectors, wherein each vector comprises an expression cassette for an sgRNA comprising a nucleotide sequence selected from the group consisting of SEQ ID NOs: 64,748-69,747.

Another aspect of the invention includes a method of treating a disease, disorder, or condition in a subject in need thereof, the method comprising administering to the subject a therapeutically effective amount of an inhibitor of at least one gene selected from the group consisting of Mgat5, Pdia3, Lag3 and Emp1. In some embodiments, the disease is a cancer.

In some embodiments, the inhibitor is selected from the group consisting of an antibody, an siRNA, and a CRISPR system.

In some embodiments, the CRISPR system comprises a Cas9, and at least one sgRNA complementary to Mgat5, Pdia3, Lag3, or Emp1.

Another aspect of the invention includes a method of stimulating a T cell, the method comprising mutating at least one gene selected from the group consisting of Mgat5, Pdia3, Lag3 and Emp1 in the T cell.

In some embodiments, stimulating the T cell results in increased interferon-gamma production by the T cell and/or in increased cytotoxicity of the T cell.

Another aspect of the invention includes a method of stimulating a T cell, the method comprising contacting the T cell with a therapeutically effective amount of an inhibitor of at least one gene selected from the group consisting of Mgat5, Pdia3, Lag3, and Emp1.

In some embodiments, the inhibitor is selected from the group consisting of an antibody, an siRNA, and a CRISPR system.

In some embodiments, the CRISPR system comprises a Cas9, and at least one sgRNA complementary to Mgat5, Pdia3, Lag3, or Emp1.

Another aspect of the invention includes a method of performing genome editing and screening of a T cell for a mutation in vitro, the method comprising contacting the T cell with Cas9 and an AAV library, wherein the AAV library comprises a plurality of vectors, wherein each vector comprises a first ITR, a second ITR, an antibiotic resistance sequence, two sleeping beauty (SB) IR/DR repeats, a first promoter, an sgRNA an expression cassette comprising a nucleotide sequence selected from the group consisting of SEQ ID NOs: 1-6,628, a second promoter, a Thy1.1 selection marker, an SB100x transposase, and a poly A sequence, whereby the T cell undergoes genome editing; and screening the T cell for a mutation in vitro.

Another aspect of the invention includes a method of performing genome editing and screening of a T cell for a mutation in vitro, the method comprising: contacting the T cell with Cas9 and an AAV library, wherein the AAV library comprises a plurality of vectors, wherein each vector comprises a first ITR, a second ITR, an antibiotic resistance sequence, two sleeping beauty (SB) IR/DR repeats, a first promoter, an sgRNA an expression cassette comprising a nucleotide sequence selected from the group consisting of SEQ ID NOs: 7,837-64,747, a second promoter, a Thy1.1 selection marker, an SB100x transposase, and a poly A sequence, whereby the T cell undergoes genome editing; and screening the T cell for a mutation in vitro.

Another aspect of the invention includes a method of performing genome editing and screening of a T cell for a mutation in vivo, the method comprising contacting the T cell with Cas9 and an AAV library, wherein the AAV library comprises a plurality of vectors, wherein each vector comprises a first ITR, a second ITR, an antibiotic resistance sequence, two sleeping beauty (SB) IR/DR repeats, a first promoter, an sgRNA an expression cassette comprising a nucleotide sequence selected from the group consisting of SEQ ID NOs: 1-6,628, a second promoter, a Thy1.1 selection marker, an SB100x transposase, and a poly A sequence, whereby the T cell undergoes genome editing; and screening the T cell for a mutation in vivo.

Another aspect of the invention includes a method of performing genome editing and screening of a T cell for a mutation in vivo, the method comprising: contacting the T cell with Cas9 and an AAV library, wherein the AAV library comprises a plurality of vectors, wherein each vector comprises a first ITR, a second ITR, an antibiotic resistance sequence, two sleeping beauty (SB) IR/DR repeats, a first promoter, an sgRNA an expression cassette comprising a nucleotide sequence selected from the group consisting of SEQ ID NOs: 7,837-64,747, a second promoter, a Thy1.1 selection marker, an SB100x transposase, and a poly A sequence, whereby the T cell undergoes genome editing; and screening the T cell for a mutation in vivo.

In some embodiments, the vector comprises SEQ ID NO: 69,821.

Another aspect of the invention includes an isolated antibody or antigen binding fragment thereof that binds human MGAT5, wherein the isolated antibody or antigen binding fragment thereof comprises at least one of the amino acid sequences of Table 3.

In some embodiments, said antibody or antigen binding fragment thereof comprises a heavy chain comprising at least one amino acid sequence selected from the group consisting of SEQ ID Nos.: 7645-7647, 7649-7651, 7653-7655, 7657-7659, 7661-7663, 7665-7667, 7669-7671, 7673-7675, 7677-7679, 7681-7683, 7685-7687, 7689-7691, 7693-7701, 7703-7705, 7707-7709, 7711-7713, 7715-7717, 7719-7727, 7729, 7730 and 7731; and a light chain comprising at least one amino acid sequence selected from the group consisting of SEQ ID Nos.: 7648, 7652, 7656, 7660, 7664, 7668, 7672, 7676, 7680, 7684, 7688, 7692, 7702, 7706, 7710, 7714, 7718 and 7728.

In some embodiments, the isolated antibody or antigen binding fragment thereof of any one of the preceding embodiments, wherein said antibody or antigen binding fragment thereof comprises H1, H2 and H3 CDRs of a given clone of Table 3.

In some embodiments, the isolated antibody or antigen binding fragment thereof of any one of the preceding embodiments, wherein said antibody or antigen binding fragment thereof comprises L3 CDR of a given clone of Table 3 and further comprises the nucleotide sequence of SEQ ID NO: 69,837.

In some embodiments, said antibody or antigen binding fragment thereof comprises L3 CDR of a given clone of Table 3 and further comprises the amino acid sequence of SEQ ID NO: 7,824.

Another aspect of the invention includes an isolated antibody or antigen binding fragment thereof that binds human MGAT5, wherein the isolated antibody or antigen binding fragment thereof is encoded by a nucleic acid comprising any one of the nucleic acid sequences of Table 5.

In some embodiments, the antibody or antigen binding fragment thereof is humanized, human, or chimeric.

In some embodiments, the antibody or antigen binding fragment thereof is a Fab, Fab', F(ab')$_2$ or IgG.

Another aspect of the invention includes a nucleic acid encoding any of the elsewhere herein antibody or antigen binding fragments.

Another aspect of the invention includes a pharmaceutical composition comprising any of the isolated antibodies or antigen binding fragments found elsewhere herein.

Another aspect of the invention includes a method of treating a disease, disorder, or condition in a subject in need thereof comprising administering to the subject an effective amount of the pharmaceutical composition.

In some embodiments, the disease is cancer.

In some embodiments, the cancer is glioblastoma or breast cancer.

In some embodiments, the disease is autoimmune disease.

In some embodiments, the disease is an immune system disorder.

Another aspect of the invention includes an isolated antibody or antigen binding fragment thereof that binds human PDIA3, wherein the isolated antibody or antigen binding fragment thereof comprises any one of the amino acid sequences of Table 4.

In some embodiments, said antibody or antigen binding fragment thereof comprises a heavy chain comprising at least one amino acid sequence selected from the group consisting of SEQ ID Nos.: 7732-7734, 7736-7738, 7740-7742, 7744-7746, 7748-7750, 7752-7754, 7756-7758, 7760-7762, 7764-7766, 7768-7770, 7772-7774, 7776-7778, 7780-7782, 7784-7786, 7788-7790, 7792-7794, 7796-7798, 7800-7802, 7804-7806, 7808-7810, 7812-7814, 7816-7818, 7820, 7821 and 7822; and a light chain comprising at least one amino acid sequence selected from the group consisting of SEQ ID Nos.: 7735, 7739, 7743, 7747, 7751, 7755, 7759, 7763, 7767, 7771, 7775, 7779, 7783, 7787, 7791, 7795, 7799, 7803, 7807, 7811, 7815, 7819 and 7823.

In some embodiments, said antibody or antigen binding fragment thereof comprises H1, H2 and H3 CDRs of a same clone of Table 4.

In some embodiments, said antibody or antigen binding fragment thereof comprises H1, H2 and H3 CDRs of a same clone of Table 4.

In some embodiments, said antibody or antigen binding fragment thereof comprises H1, H2 and H3 CDRs of a same clone of Table 4.

In some embodiments, said antibody or antigen binding fragment thereof comprises L3 CDR of a clone of Table 4 and further comprises the nucleotide sequence of SEQ ID NO: 69,837.

In some embodiments, said antibody or antigen binding fragment thereof comprises L3 CDR of a clone of Table 4 and further comprises the amino acid sequence of SEQ ID NO: 7,824.

Another aspect of the invention includes an isolated antibody or antigen binding fragment thereof that binds human PDIA3, wherein the isolated antibody or antigen binding fragment thereof is encoded by a nucleic acid comprising any one of the nucleic acid sequences of Table 5.

In some embodiments, the antibody or antigen binding fragment thereof found elsewhere herein is humanized, human, or chimeric.

In some embodiments, the antibody or antigen binding fragment thereof is a Fab, Fab', F(ab')$_2$ or IgG.

Another aspect of the invention includes a nucleic acid encoding any of the antibodies or antigen binding fragments described elsewhere herein.

Another aspect of the invention includes a pharmaceutical composition comprising any of the isolated antibodies or antigen binding fragments described elsewhere herein.

Another aspect of the invention includes a method of treating a disease, disorder, or condition in a subject in need thereof comprising administering to the subject an effective amount of the immunopharmaceutical composition described elsewhere herein In some embodiments, the disease is cancer.

In some embodiments, the cancer is glioblastoma or breast cancer.

In some embodiments, the cancer is selected from a cancer listed in Table 6.

In some embodiments, the disease is autoimmune disease.

In some embodiments, the disease in an immune system disorder.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIGS. 1A-1L illustrate AAV-CRISPR CD8$^+$ T cell screen of surface proteome knockouts in GBM. FIG. 1A top is a schematic of the hybrid AAV-SB-CRISPR vector. FIG. 1A bottom is a diagram of an AAV-CRIPSR screen in a syngeneic mouse model of GBM. A schematic of naïve CD8$^+$ T cell isolation, AAV library transduction, GBM cell transplantation, adoptive cell transfer (ACT), organs isolation, sgRNA readout and deep sequencing are shown. FIG. 1B is a series of plots showing flow cytometry analysis of TILs in the GBM bearing brain. 5×10$^5$ GL261-FLuc cancer cells were injected per mouse, at day 12 after tumor injection, luciferase imaging was performed to reasonably group mice based on luminescence intensity, then 4×10$^6$ CD45.1$^+$; Cas9β CD8$^+$ T cells were i.v. injected. Mice were euthanized at day 6 after T cell injection, brains (without olfactory and hindbrain) were dissected for TIL isolation. The i.v. injected CD45.1$^+$;CD3$^+$;CD8$^+$ T cells were quantified and sorted for TCR-seq. Cas9β mouse and CD45.1$^+$;Cas9β mouse splenocytes were used as gating controls. Data was collected from one experiment. FIG. 1C is a graph showing quantification of TIL number after transduction with AAV-Vector and AAV-Surf virus. Data was collected from two mice per group, two independent stainings were performed for each mouse. Data shown are mean±s.e.m. * p<0.05, Mann Whitney test, two-tailed. FIG. 1D shows bulk analysis for brain tumor vs. pre-injection CD8 T cell sgRNA library representation of an AAV-Surf GBM CD8$^+$ T cell screen experiment. A list of most significantly enriched sgRNAs in brain tumors are labelled (FDR<=0.2%). Among the significant sgRNAs, three independent Mgat5 sgRNAs and two independent Pdia3 sgRNAs were enriched. A well-known immune check-point surface molecule, Lag-3, as well as Man2a1, a member of the Mgat5 pathway, were also enriched at this level. FIG. 1E shows RIGER analysis for brain tumor vs. cell gene level significance of the AAV-Surf screen experiment. The top 10 most highly enriched genes (by RIGER p-value) in brain tumors are highlighted. Weighted Sum method was used for this analysis. Analysis using Second-Best sgRNA method is consistent with the Weighted Sum method. Mgat5 and Pdia3 are the two most significant hits by RIGER p-value. Known immune checkpoint regulators Lag-3 and Tnfrsf18 are also among the top 10 by significance. FIG. 1F displays CD8$^+$ T cell mRNA levels of several top hits from the AAV-Surf GBM screen. FIG. 1G (left) is a Nextera indel analysis for Mgat5 and Pdia3 knockout mouse CD8$^+$ T cells. Shaded text indicates the sgRNA sequence for Mgat5 (SEQ ID NO: 69,750) and Pdia3 (SEQ ID NO: 69,759). Resulting indels and their frequencies are listed (SEQ ID NOs: 69,751-69,758 for Mgat5; SEQ ID NOs. 69,760-69,767 for Pdia3). FIG. 1G (right) shows the quantification of total indel frequency for each gene. FIG. 1H is a schematic of the therapeutic efficacy testing strategy for top candidates from the AAV-Surf screens using an independent model of GBM immunotherapy, where cancer cells express a cognate cOVA model tumor antigen recognized by CD8$^+$ T cells from TCR transgenic OT-I mice. FIG. 1I illustrates a survival plot of mice who received adoptively transferred mutant Pdia3 CD8 T cells. FIG. 1J illustrates a survival plot of mice who received adoptively transferred mutant Mgat5 CD8 T cells. FIG. 1K illustrates a survival plot of mice who received adoptively transferred mutant Emp1 CD8 T cells. FIG. 1L Is a bar plot of quantitative results for CD45.2$^+$ and CD8$^+$ CD8$^+$ T cell infiltration in GBM bearing mice (TILs) with or without Mgat5 or Pdia3 knockout (n=3 for each group). Unpaired t test was used for assess significance. * p<0.05. Data are shown as mean±s.e.m., plus individual data points on the bar graph.

FIGS. 2A-2H describe an AAV-CRISPR CD8$^+$ T cell screen for membrane-bound knockouts in GBM. FIG. 2A is a schematic of the hybrid AAV-SB-CRIPSR CD8$^+$ T cell screen in a syngeneic mouse model of GBM, showing steps of naïve CD8$^+$ T cell isolation, AAV library transduction, GBM cell transplantation, adoptive T cell transfer, brain and tumor isolation, and sgRNA readout by deep sequencing. FIG. 2B are representative in vivo images illustrating the growth of GL261-FLuc tumors in the brains of C57BL/6 mice. FIG. 2C are representative images of mice after GBM transplantation and T cell treatment. Dashed circles indicated macrocephaly suggestive of growing brain tumors. FIG. 2D shows CD8$^+$ T cell qPCR results of several top hits from AAV-Surf GBM screen. The mRNA level of all candidates were measured with RT-qPCR. The results suggested that all of them were expressed in CD8$^+$ T cells. FIG. 2E shows a survival plot of mice after GBM engraftment and adoptive transfer. C57BL/6J mice were transplanted with 1.2×10$^6$ GL261-FLuc into the lateral ventricle (LV). 4×10$^6$ OT-I;Cas9β CD8$^+$ T cells were injected after 10 days of tumor engraftment. Survival significance was assessed by a log-rank Mantel-Cox test. The p-values and number of mice used in each group was indicated in the plots. FIG. 2F are representative H&E stained brain sections from PBS, AAV-Vector and AAV-Surf groups. Areas within gray dashed lines indicate brain tumors. Scale bar, 2 mm for whole brain sections, and 100 μm for zoom-in sections. These are representative images at the endpoint of survival thus not quantitative for comparison in terms of tumor burden. FIG. 2G shows a scatterplot of brain vs. cell sgRNA library representation of the AAV-Surf short-term screen experiment (max survival 20 days post injection). The most enriched sgRNAs in the brain are highlighted. Purple dash line, y=x curve; blue dash line, linear regression of the distribution of the 1,000 NTCs between the brain and cell samples. FIG. 2H shows a scatterplot of brain vs. cell sgRNA library representation of AAV-Surf longer term screen experiment (max survival 92 days post injection). The most enriched sgRNAs in the brain are highlighted. Dark grey dashed line, y=x curve; light grey dashed line, linear regression of the distribution of the 1,000 NTCs between the brain and cell samples.

FIGS. 3A-3G describe the endogenous gene expression of top hits in primary CD8$^+$ T cell, clonal GBM cell line generation, and representative mouse GBM histology with single gene knockout adoptive transfer. FIG. 3A shows representative histograms generated from showing the expression levels of GL261-FLuc-mCh-cOVA clones for cOVA expression level. FIG. 3B shows the gene editing of Mgat5 and Pdia3 with AAV-SB100x vector by T7EI assay indicated. FIG. 3C shows bar graphs of Mgat5 and Pdia3 mRNA expression following infection with AAV6 carrying specific gene-targeting. Unpaired t test was used for the significance assessment, AAV-Vector vs. AAV-sgMgat5, p=0.0242; AAV-Vector vs. AAV-sgPdia3, p=0.0111. * p<0.05. FIG. 3D shows a representative H&E stained brain sections from AAV-Vector and AAV-sgRNA single knockout groups in C57BL/6J mice. Scale bar, 100 μm. These are representative images at the endpoint of survival thus not quantitative for comparison in terms of tumor burden. FIG. 3E shows a representative H&E stained brain sections from AAV-Vector and AAV-sgRNA single knockout groups in Rag1$^{-/-}$ mice. Scale bar, 100 μm. These are representative images at the endpoint of survival thus not quantitative for comparison in terms of tumor burden. FIG. 3F shows the therapeutic efficacy testing strategy for top candidates identified from the AAV-Surf screens using adoptive transfer of single gene-edited CD8$^+$ T cells in a syngeneic mouse model of GBM. FIG. 3G shows survival plots of the top candidate validations in a syngeneic mouse model of GBM. C57BL/6J mice were engrafted with 2×10$^5$ GL261 cancer cells, and adoptive transfer was performed after 10 days of tumor engraftment by intravenous injection of 6×10$^5$ Cas9β CD8$^+$ T cells infected with AAV-Vector (n=8), AAV-sgLag3 (n=8), AAV-sgMgat5 (n=8), and AAV-sgPdia3 (n=8). Survival significance was assessed by a log-rank Mantel-Cox test. The p-values and number of mice used in each group was indicated in the plots. AAV-Vector vs. AAV-sgLag3, p=0.0413; AAV-Vector vs. AAV-sgMgat5, p=0.0213; AAV-Vector vs. AAV-sgPdia3, p=0.0105. DPI, days post tumor implantation.

FIG. 4A shows representative flow plots of CD8+ T cells from mouse brain tumors following adoptive transfer of non-mutated or mutated CD8+ T cells. FIG. 4B is the quantification of FIG. 4A. Unpaired t test was used for assess significance. * p<0.05. Vector vs. sgMgat5, p=0.0328; Vector vs. sgPdia3, p=0.0303. Data are shown as mean±S.E.M., plus individual data points on the bar graph.

FIGS. 5A-5E illustrate the validation of top candidates from AAV-Surf CD8+ T cell screen in GBM. FIG. 5A shows a schematic of the validation strategy for top candidates from the AAV-Surf screens using a cognate TCR-model tumor antigen system. FIG. 5B (top) shows representative in vivo imaging at day 48 after tumor engraftment, illustrating the growth of GL261-FLuc-mCh-cOVA #1 cells in the brains of Rag1$^{-/-}$ mice. FIG. 5B (bottom) shows the quantification of total luciferase flux in each group, demonstrating that T cells with Mgat5, Pdia3 or Emp1 knockout significantly enhance anti-tumor effect. * p<0.05, unpaired t test. (AAV-Vector (n=6) vs. AAV-Mgat5 (n=9), p=0.0374; AAV-Vector (n=6) vs. AAV-Pdia3 (n=9), p=0.0949; AAV-Vector (n=6) vs. AAV-Emp1 (n=8), p=0.0383). FIG. 5C shows a survival plot of mutant Mgat5 CD8 T cells in in Rag1$^{-/-}$ mice (n=10). All mice were engrafted with $1 \times 10^5$ GL261-FLuc-mCh-cOVA #1 cells, and ACT was performed by intravenous injection of $1 \times 10^6$ OT-1;Cas9β CD8+ T cells which were infected with AAV—after 10 days of tumor engraftment. Survival significance was assessed by a log-rank Mantel-Cox test. The p-values and number of mice used in each group are indicated in the plots. FIG. 5D is a survival plot of mutant Pdia3 CD8 T cells in in Rag1$^{-/-}$ mice (n=9). All mice were engrafted with $1 \times 10^5$ GL261-FLuc-mCh-cOVA #1 cells, and ACT was performed by intravenous injection of $1 \times 10^6$ OT-1;Cas9β CD8+ T cells which were infected with AAV—after 10 days of tumor engraftment. Survival significance was assessed by a log-rank Mantel-Cox test. The p-values and number of mice used in each group are indicated in the plots. FIG. 5E is a survival plot of mutant Emp1 CD8 T cells in in Rag1$^{-/-}$ mice (n=8). All mice were engrafted with $1 \times 10^5$ GL261-FLuc-mCh-cOVA #1 cells, and ACT was performed by intravenous injection of $1 \times 10^6$ OT-1;Cas9β CD8+ T cells which were infected with AAV—after 10 days of tumor engraftment. Survival significance was assessed by a log-rank Mantel-Cox test. The p-values and number of mice used in each group are indicated in the plots.

FIG. 6A shows a schematic of the therapeutic efficacy testing of AAV-SB-CRISPR gene editing of the top targets by adoptive transfer of T cells directly into the brain in a syngeneic mouse model of GBM. C57BL/6J mice were implanted intracranially with $5 \times 10^5$ GL261-FLuc cancer cells at day 0. In vivo imaging was performed at day 12 to ensure all mouse brains had growing tumors. $5 \times 10^5$ T cells were intracranially injected at the same coordinate as the tumor injection. The luciferase imaging was performed every 2 days using an IVIS system. A timeline for tumor induction, adoptive transfer and imaging is shown at the bottom. FIG. 6B shows representative IVIS images. In vivo imaging illustrates that all mouse brains had a growing tumor at day 12. The tumor growth rate was significantly slow down after injecting T cells infected with AAV-sgMgat5 or AAV-sgPdia3 virus compared with AAV-Vector group. FIG. 6C is a quantification of tumor burden as total luciferase flux at days 12, 16 and 18, the results demonstrated that T cells with Mgat5 or Pdia3 knockout significantly enhance anti-tumor effect. Day 20 and 22 data points were not used for statistics because most mice in the AAV-Vector group had already reached endpoint. Grouped time series data, Wilcoxon rank sum test with continuity correction, two sided, AAV-sgMgat5 vs. AAV-Vector, p=0.005314; AAV-sgPdia3 vs. AAV-Vector, p=0.04317. Labeled on graph, *p<0.05, **p<0.01. Data are shown as mean±s.e.m. plus individual data points on bar graphs. FIG. 6D are survival plots of mice treated with mutant CD8 T cells. Survival significance was assessed by a log-rank Mantel-Cox test. AAV-sgMgat5 vs. AAV-Vector, p=0.0001; AAV-sgPdia3 vs. AAV-Vector, p=0.0072. DPI, days post tumor implantation. FIG. 6E shows a timeline for tumor induction, adoptive transfer, and imaging of the therapeutic efficacy testing of AAV—SB-CRISPR targeting Pdia3, Mgat5 and combination in CD8+ T cells in a syngeneic mouse model of GBM. C57BL/6J mice were implanted intracranially with $2 \times 10^5$ GL261-FLuc cancer cells on day 0. In vivo imaging was performed at day 14 before T cell injection for randomization with tumor-burden matched subgrouping. $1.5 \times 10^6$ T cells were intracranially injected at the same coordinate as tumor injection. The luciferase imaging was performed every 2-3 days. FIG. 6F shows representative IVIS images of brain tumor growth in GL261-FLuc cancer cell injected mice receiving adoptive transfer of T cells infected with AAV-Vector, AAV-sgMgat5 and AAV-sgPdia3 virus groups. FIG. 6G shows survival plots from GL261-FLuc mice that received adoptively transferred T cells infected with AAV-Vector, AAV-sgMgat5 and AAV-sgPdia3 virus groups. Overall survival significance was assessed by a log-rank Mantel-Cox test between Vector and mutant groups (p=0.0198). Comparison between groups, Wilcox test, AAV-sgMgat5 vs. AAV-Vector, p=0.07; AAV-sgPdia3 vs. AAV-Vector, p=0.005; AAV-sgPdia3+ AAV-sgMgat5 vs. AAV-Vector, p=0.01. DPI, days post tumor implantation. FIG. 6H are a series of micrographs depicting whole brain section H&E staining of four long-term survivor mice. Scale bar, 2 mm for whole brain sections. Data was collected from one independent experiment, survivor mice were from the same experiment as in FIG. 6G.

FIG. 7A is a t-SNE plot of sample distribution based on the transcriptome of 9,193 single cells from AAV-sgPdia3 and AAV-vector infected CD8+ T cells. FIG. 7B shows a volcano plot of scRNA-seq of mouse Pdia3 knockout CD8+ T cells. Pdia3 mRNA was significantly downregulated after infected with AAV-sgPdia3. In addition, Gzma, Gzmb, and Gzmc were significantly upregulated after Pdia3 knockout. FIG. 7C shows t-SNE plots of CD3e, CD8, and Pdia3 clusters. CD3e and CD8 were not significantly changed between groups, while Pdia3 expression level was dramatically reduced at the single-cell level. FIG. 7D shows t-SNE plots of Gzma, Gzmb, and Gzmc clusters.

FIG. 8A shows a t-SNE plot of hierarchical clustering of scRNA-seq results. A total of 9,193 single cells were captured and their transcriptomes were sequenced for the AAV-sgPdia3 (4,549 single cells) and AAV-Vector (4,644 single cells) treated CD8 T cells. FIG. 8B shows a bubble-rank plot of differential gene expression of scRNA-seq. Delta-mean is the difference of mean expression value between AAV-sgPdia3 and AAV-Vector treated single CD8 T cells. Statistical significance is scaled by −log 10 p-value as shown in the size key. FIG. 8C shows a volcano plot of all differentially expressed genes between AAV-Vector and AAV-sgPdia3 transduced mouse primary CD8+ T cells (n=3 biological replicates). Differential gene expression was performed with Sleuth using Wald test, the FDR adjusted q-value was used for the plot. FIG. 8D is a heat map of representative immune-related differentially expressed genes between AAV-Vector and AAV-sgPdia3 transduced mouse primary CD8+ T cells (n=3 biological replicates). FIG. 8E shows a heat map of top 50 variable genes by hierarchical cluster of scRNA-seq data. FIG. 8F is a plot showing RT-qPCR validation of the scRNA-seq and bulk mRNA-seq results that confirmed the upregulation of granzyme genes upon AAV-sgPdia3 perturbation (n=4). Unpaired t test, two-tailed. * p<0.05, **** p<0.0001. FIG. 8G is a series of three plots showing RT-qPCR validation of scRNA-seq and bulk mRNA-seq results of the granzyme gene upregulation using two independent Pdia3 sgRNAs (n=3). Unpaired t test, two-tailed. * p<0.05,  p<0.01, * p<0.001, **** p<0.0001.

FIG. 10A shows RT-qPCR validation of the scRNA-seq upregulation of granzyme transcripts upon AAV-sgPdia3 perturbation. Unpaired t test was used to assess the significance. Gzma, AAV-Vector vs. AAV-sgPdia3, p<0.0001; Gzmb, AAV-Vector vs. AAV-sgPdia3, p=0.0159; Gzmc, AAV-Vector vs. AAV-sgPdia3, p<0.0001. * p<0.05, **** p<0.0001. FIG. 10B shows a dose-dependent TCR signaling for Pdia3 or Mgat5 KO, showing an upregulation in the phosphorylation levels of PLCγ and ERK1/2. Two-sided paired t test, sgPdia3 or sgMgat5 vs vector, * p<0.05,  p<0.01, * p<0.001, **** p<0.0001. FIG. 10C shows dose-dependent TCR signaling experiment for Pdia3 KO showing upregulation of the phosphorylation level of Plcγ and Erk1/2. Original western blot gel of a representative experiment among the three independent replicate experiments. FIG. 10D is two graphs showing quantification of relative phosphorylation level of Plcγ and Erk1/2, (n=3). Data are shown as mean±s.e.m. Two-way ANOVA, sgPdia3 vs vector, * p<0.05, *** p<0.001. FIG. 10E shows representative flow plots showing IFNγ expression in OT-I; Cas913 CD8 T cells infected with AAV-vector alone, AAV-sgMgat5, or AAV-sgPdia3. Prior to IFNγ detection, T cells were rested for 12 hours and reactivated with different concentrations of anti-CD3c for 4 hours. FIG. 10F shows the quantification FIG. 10E. Correct for multiple comparisons using the Holm-Sidak method was used to assess the significance. * p<0.05,  p<0.01, * p<0.001,**** p<0.0001. FIG. 10G shows ifnγ intracellular staining after Pdia3 KO using a different sgRNA. Two-sided multiple t test was used to assess the significance, Holm-Sidak method was used for multiple comparisons correction. *p<0.05,  p<0.01, * p<0.001, ns, not significant. FIG. 10H shows a schematic of the therapeutic efficacy testing strategy for Pdia3 knockout T cell using a subcutaneous model of GBM. Rag1−/− mice were implanted subcutaneously with 4×10$^6$ GL261-FLuc-mCh-rOVA cells on day 1. On day 8, naïve CD8+ T cells were isolated from OT-I;Cas9β mice, activated, transduced with single AAVs and cultured for 3 days. 1×10$^6$ T cells were intravenously injected on day 11 post tumor implantation. Tumor sizes were measured every 3-5 days after T cell adoptive transfer. FIG. 10I shows tumor growth curves of GL261-FLuc-mCh-rOVA tumor-bearing mice injected with CD8 T cells infected with AAV-Vector (n=4) or AAV-sgPdia3 (n=5). Wilcoxon rank sum test with continuity correction, two sided, p=0.005982. DPI, days post tumor implantation. FIGS. 10J-10K describe the efficacy testing of Pdia3 knockout T cells using a syngeneic triple-negative breast cancer (TNBC) model. FIG. 10J shows a schematic describing the experiment. RagF mice implanted with 3×10$^6$ E0771-mCh-cOVA cells into the mammary fat pad on day 1. On day 2, naïve CD8+ T cells were isolated from OT-I;Cas9β mice, activated, transduced with single AAVs on day 4, and cultured for another 3 days. 1.5×10$^6$ and 0.5×10$^6$ T cells were intravenously injected on day 7 and day 17 post tumor implantation. Tumor sizes were measured every 2-3 days after T cell adoptive transfer. FIG. 10K shows tumor growth curves of E0771-mCh-cOVA TNBC bearing mice receiving CD8 T cell therapy. Wilcox test, two sided, using only data points on or after T cell adoptive transfer: AAV-Vector vs. AAV-sgPdia3, p=4.469e-05; AAV-Vector vs. PBS, p=7.007e-11. DPI, days post-tumor implantation.

FIGS. 11A-11J describe CyTOF analysis of PDIA3 knockout human CD8 T cells. FIG. 11A shows a schematic of human CD8+ T cell isolation, culture, RNP electroporation, T7EI assay, Nextera sequencing, and CyTOF analysis. FIG. 11B shows that the T7EI assay yielded high efficiency knockout of PDIA3 in human T cells compared to control. Arrows pointed to pre- and post-cleavage products of predicted sizes. FIG. 11C shows the Nextera data quantification of gene editing efficiency from FIG. 11B. Shaded text indicates the sgRNA targeting PDIA3 (SEQ ID NO: 69,768). The table below indicates resulting indel sequences and their frequencies (SEQ ID NOs: 69,769-69,774). FIG. 11D shows a Western Blot showing PDIA3 protein expression CRISPR knockout versus control cells. FIG. 11E is a series of plots showing IFNγ intracellular staining after PDIA3 KO. FIG. 11F is a plot showing quantification of FIG. 11 E. Two-sided multiple t test was used to assess the significance. Holm-Sidak method was used for multiple comparisons correction. *p<0.05,  p<0.01, ns, not significant. FIG. 11G is a plot showing qPCR validation of GZMA expression. Unpaired t test, two-tailed. *p<0.001. FIGS. 11H-11I show t-SNE plots of CyTOF data with k-means clustering. From a total of 227,848 single cells profiled, 7,000 single cells were randomly sampled for each sample, with a subtotal of 42,000 cells in the plots. FIG. 11H shows a t-SNE plot with k-means clustering yielded 10 major clusters. FIG. 11I shows a t-SNE plot clustered by samples. The 3 PDIA3 KO samples grouped with each other, the 3 WT samples also grouped with each other, and that PDIA3 KO samples and WT samples formed distinct groups. FIG. 11J are t-SNE plots of representative markers detected by the CyTOF. Perforin, two co-stimulatory molecules (CD134/OX40 and CD278/ICOS) and CXCR3 were found to be significantly upregulated at the single cell level upon PDIA3 KO (n=3 replicates each, sampled 7,000 cells per replicate for comparison). Violin plots were used for visualizing marker levels quantitatively in single cells. Violins show kernel probability density on side, and boxplot is standard, i.e. middle band is median, hinges/ends of box are interquartile range (25% and 75% quantiles), lower whisker=smallest observation greater than or equal to lower hinge-1.5*IQR, upper whisker=largest observation less than or equal to upper hinge+1.5*IQR. Wilcoxon test, two-sided, p value adjusted by Benjamini & Hochberg method. KO vs WT, PERFORIN, p=1.35e-294; CD278, p=0 (below algorithm detection limit); CD134, p=0; CXCR3, p=0.

FIG. 13A shows the analyses of PDIA3 expression signatures in cytotoxic T lymphocyte (CTL) are associated with better survival, where high expression of PDIA3 decreases the overall survival of CTL-high patients with GBM. FIG. 13B shows the analyses of PDIA3 expression signatures in cytotoxic T lymphocyte (CTL) are associated with better survival, where high expression of PDIA3 decreases the overall survival of CTL-high patients with TNBC. FIG. 13C shows the analyses of PDIA3 expression signatures in cytotoxic T lymphocyte (CTL) are associated with better survival, where high expression of PDIA3 decreases the overall survival of CTL-high patients with LUAD. FIG. 13D shows PDIA3 expression is linked to better survival in melanoma patients treated with Ipilimumab (anti-CTLA4).

FIG. 16A is a schematic showing human PDIA3$^{-/-}$-EGFRvIII CAR-T cell generation. CD8 T cells were electroporated with crPDIA3:tracRNA:Cas9 first, then PDIA3$^{-/-}$ T cells were knock-in (KI) with an EGFRvIII-CAR construct which consists of TRAC locus homology-directed repair (HDR) 5' and 3' arms, an EFS promoter, an EGFRvIII-CAR expression cassette, and a short polyA. The donor KI constructs were packaged into AAV6, then introduced into T cells by viral transduction after TRAC first-exon targeting RNP electroporation. U87-GFP-Luc-EGFRvIII (U87-GLEvIII) and PDIA3-EGFRvIII CAR-T cell co-culture assay was set up after CAR-T cells were established to test PDIA3$^{-/-}$-EGFRvIII CAR-T cell killing ability. FIGS. 16B-16D are graphs showing killing assays of NTC-EGFRvIII-CAR and PDIA3$^{-/-}$-EGFRvIII-CAR T cells with U87-GLEvIII and U87-GL (parental line control) human GBM cells, with a titration series of Effector:Target (E:T) ratios at 24h post co-culture: FIG. 16B is a kill assay with PDIA3-sg1, on U87-GLEvIII cells; FIG. 16C is a kill assay with PDIA3-sg2, on U87-GLEvIII cells; FIG. 16D is a kill assay with PDIA3-sg1, on U87-GL parental control cells; Data are shown as mean±s e.m., plus individual data points, n=5 biological replicates. Two-way ANOVA test was used to evaluated significance.

FIGS. 17A-17F show Splinkerette PCR identify genome integration of the Sleeping Beauty transposon. FIG. 17A is an illustration showing Nextera indel analysis for Mll3 and B2m knock-out in mouse CD8$^+$ T cells using AAV-sgRNA vectors. Shaded text indicates the Mll3 or B2m sgRNA (SEQ ID NOs: 69,775 and 69,787, respectively). Representative mutations and their frequencies were shown around predicted sgRNA target sites in the indicated tables (Mll3: SEQ ID NOs: 69,776-69,786; B2m: SEQ ID NOs: 69,788-69,798) FIG. 17B is a schematic of splinkerette PCR procedures. The steps include genomic DNA isolation, restriction enzyme digestion, adaptor ligation, PCR, NGS library prep, and sequencing. FIG. 17C displays electrophoresis of the splinkerette PCR products. The gel within red dash line was gel purified for the Nextera library preparation and sequencing. FIG. 17D shows representative SB transposon integration sites in the mouse genome (SEQ ID NOs: 69,799-69,804). FIG. 17E is a bar plot of splinkerette PCR read distribution for the number of integration sites along mouse chromosomes. FIG. 17F is a bar plot showing splinkerette PCR read distribution for the number of integration sites according to functional annotation of genomic regions.

FIG. 19A shows a bar plot of mortality rate of mouse after intracranial GBM induction. Different GBM cell lines, GL261, GL261-Luc-Ova, and GL261-Luc, were used for brain injection, and each cell line injected with different cell number. FIG. 19B is a bar plot of a number of mice that met euthanasia endpoints due to brain tumor growth FIGS. 20A-20F are a series of graphs showing AAV-Surf library transduced mouse CD8$^+$ T cell surface phenotypes and TCR repertoires before and after adoptive transfer. FIG. 20A shows flow cytometry analysis of surface PD-1, Lag3, and Tim-3 expression after transduced with AAV-Vector and AAV-Surf virus. Result from one experiment. FIGS. 20B-20C are flow cytometry analysis of proportion of PD-1$^+$ TILs. ns, non-significant. Data are shown as mean±s.e.m., with individual data points. FIG. 20D is a bar plot of T cell clonal composition from TCR sequencing. Pre injection, mouse CD8$^+$ T cells transduced with AAV-Surf virus and cultured for 5 days; Post injection (TIL), AAV-Surf transduced T cells i.v. injected into GBM-bearing mice and isolated as TILs at day 6 after T cell injection. FIG. 20E is a ring plot of TCR distribution for T cells before i.v. injection. Top TCR sequences were labeled in the plot. Sequence identities from top to bottom: 1. SEQ ID NO: 69,805, SEQ ID NO: 69,806, SEQ ID NO: 69,807; 2. SEQ ID NO: 69,808, SEQ ID NO: 69,809; 3. SEQ ID NO: 69,810, SEQ ID NO: 69,811; 4. SEQ ID NO: 69,812; 5. SEQ ID NO: 69,813, SEQ ID NO: 69,814, SEQ IS NO: 69,815.

FIG. 20F. is a ring plot of TCR distribution for T cells after i.v. injection (TILs). Top TCR sequences were labeled in the plot. Sequence identities from top to bottom: 1. SEQ ID NO: 69,816; 2. SEQ ID NO: 69,817; 3. SEQ ID NO: 69,818; 4. SEQ ID NO: 69,819; 5. SEQ ID NO: 69,820.

FIG. 21A shows quantification of tumor burden as total luciferase flux at days 12, 16, and 18. Day 20 and 22 data points were not used for statistics because most mice in the AAV-Vector group had already reached endpoint. Mice being imaged, n=8 for Vector, n=8 for sgMgat5, n=5 for sgPdia3. Data are shown as mean±s.e.m. plus individual data points on bar graphs. FIG. 21B shows quantification of tumor burden as total luciferase flux at days 14, 15, 17, 19, and 22 after tumor induction. Mice being imaged, n=7 for Vector, n=7 for sgMgat5, n=8 for sgPdia3, n=8 for sgMgat5$^+$sgPdia3. Data are shown as mean±s.e.m. plus individual data points on bar graphs. The numbers of mice that had reached endpoint, euthanized, and therefore removed from the imaging group are indicated on the top table.

DETAILED DESCRIPTION

Definitions

Figure 1A:
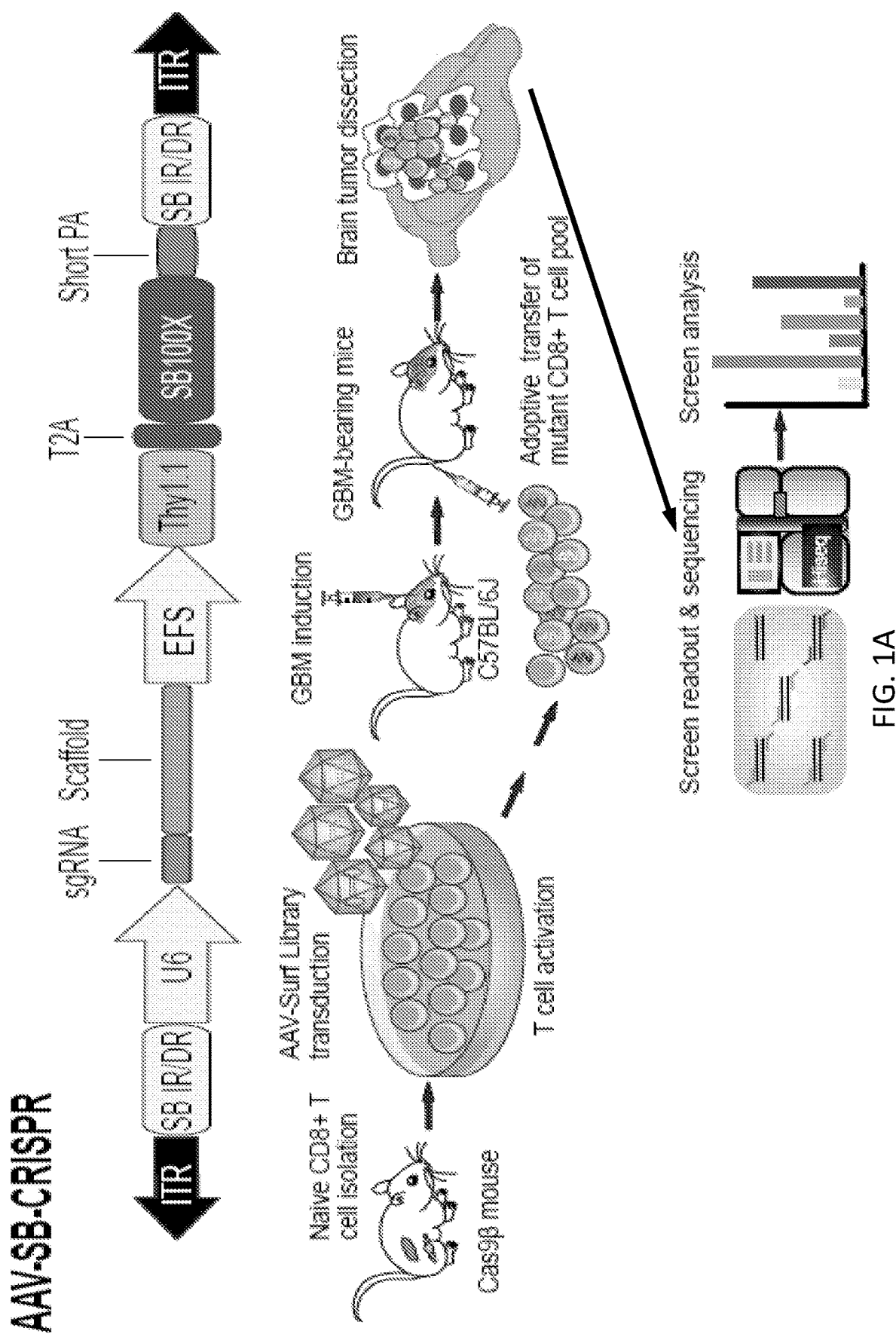

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein the term "amount" refers to the abundance or quantity of a constituent in a mixture.

As used herein, the term "bp" refers to base pair.

The term "complementary" refers to the degree of antiparallel alignment between two nucleic acid strands. Complete complementarity requires that each nucleotide be across from its opposite. No complementarity requires that each nucleotide is not across from its opposite. The degree of complementarity determines the stability of the sequences to be together or anneal/hybridize. Furthermore various DNA repair functions as well as regulatory functions are based on base pair complementarity.

As used herein, a DNA or RNA nucleotide sequence as recited refers to a polynucleotide molecule comprising the indicated bases in a 5' to 3' direction, from left to right.

The term "CRISPR/Cas" or "clustered regularly interspaced short palindromic repeats" or "CRISPR" refers to DNA loci containing short repetitions of base sequences followed by short segments of spacer DNA from previous exposures to a virus or plasmid. Bacteria and archaea have evolved adaptive immune defenses termed CRISPR/CRISPR-associated (Cas) systems that use short RNA to direct degradation of foreign nucleic acids. In bacteria, the CRISPR system provides acquired immunity against invading foreign DNA via. RNA-guided DNA cleavage.

The "CRISPR/Cas" system or "CRISPR/Cas-mediated gene editing" refers to a CRISPR/Cas system that has been modified for genome editing/engineering. For a type II CRISPR/Cas system, it is typically comprised of a "guide" RNA (gRNA) and a non-specific CRISPR-associated endonuclease (Cas9). "Guide RNA (gRNA)" is used interchangeably herein with "short guide RNA (sgRNA)" or "single guide RNA" (sgRNA). The sgRNA is a short synthetic RNA composed of a "scaffold" sequence necessary for Cas9-binding and a user-defined ~20 nucleotide "spacer" or "targeting" sequence which defines the genomic target to be modified. The genomic target of Cas9 can be modified by changing the targeting sequence present in the sgRNA.

The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides can be used for targeting cleaved double-stranded DNA.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

The term "antibody," as used herein, refers to an immunoglobulin molecule that binds with an antigen. Antibodies can be intact immunoglobulins derived from natural sources or from recombinant sources, and can be immunoreactive portions of intact immunoglobulins. Antibodies are typically tetramers of immunoglobulin molecules. The antibody may exist in a variety of forms where the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "high affinity" as used herein refers to high specificity in binding or interacting or attraction of one molecule to a target molecule.

The term "antigen" or "Ag" as used herein is defined as a molecule that provokes an immune response. This immune response may involve either antibody production, or the activation of specific immunologically competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human," in the context of an immunoglobulin, refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

"Chimeric antigen receptor" or "CAR" refers to an engineered receptor that is expressed on a T cell or any other effector cell type capable of cell-mediated cytotoxicity. The CAR comprises an extracellular domain having an antigen binding domain that is specific for a ligand or receptor. The CAR optionally also includes a transmembrane domain, and a costimulatory signaling domain. In some embodiments, the CAR comprises a hinge. In some embodiments, the antigen binding domain is specific for EGFRvIII. In some embodiments, the costimulatory signaling domain is a 4-1BB signaling domain. In some embodiments, the CAR further comprises a CD3 zeta signaling domain. A CAR-T cell is a T cell engineered to express a CAR.

"Costimulatory ligand," as the term is used herein, includes a molecule on an antigen presenting cell (e.g., an aAPC, dendritic cell, B cell, and the like) that specifically binds a cognate costimulatory molecule on a T cell, thereby providing a "second" signal which, in addition to the primary signal provided by, for instance, binding of a TCR/CD3 complex with an WIC molecule loaded with peptide, mediates a T cell response, including, but not limited to, proliferation, activation, differentiation, and the like.

A "costimulatory molecule" refers to the cognate binding partner on a T cell that specifically binds with a costimulatory ligand, thereby mediating a costimulatory response by the T cell, such as, but not limited to, proliferation. Costimulatory molecules include, but are not limited to CD28, CD27, and OX40.

As used herein, an "instructional material" includes a publication, a recording, a diagram, or any other medium of expression that can be used to communicate the usefulness of the compositions and methods of the invention. The instructional material of the kit of the invention may, for example, be affixed to a container that contains the nucleic acid, peptide, and/or composition of the invention or be shipped together with a container which contains the nucleic acid, peptide, and/or composition. Alternatively, the instructional material may be shipped separately from the container with the intention that the instructional material and compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

A "mutation" as used herein is a change in a DNA sequence resulting in an alteration from a given reference sequence (which may be, for example, an earlier collected DNA sample from the same subject). The mutation can comprise deletion and/or insertion and/or duplication and/or substitution of at least one deoxyribonucleic acid base such as a purine (adenine and/or thymine) and/or a pyrimidine (guanine and/or cytosine). Mutations may or may not produce discernible changes in the observable characteristics (phenotype) of an organism (subject).

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T".

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

As used herein, the terms "polypeptide," "peptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

A "sample" or "biological sample" as used herein means a biological material from a subject, including but is not limited to organ, tissue, exosome, blood, plasma, saliva, urine and other body fluid. A sample can be any source of material obtained from a subject.

As used herein, the terms "sequencing" or "nucleotide sequencing" refer to determining the order of nucleotides (base sequences) in a nucleic acid sample, e.g. DNA or RNA. Many techniques are available such as Sanger sequencing and high-throughput sequencing technologies (also known as next-generation sequencing technologies) such as Illumina's HiSeq and MiSeq platforms or the GS FLX platform offered by Roche Applied Science.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in $\alpha/\beta$ and $\gamma/\delta$ forms, which are structurally similar but have distinct anatomical locations and functions. Each chain is composed of two extracellular domains, a variable and constant domain. In some embodiments, the TCR can be modified on any cell comprising a TCR, including, for example, a helper T cell, a cytotoxic T cell, a memory T cell, regulatory T cell, natural killer T cell, and/or gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one that has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for treating cancer, including glioblastoma (GBM), and/or enhancing CD8$^+$ T cell anti-tumor activity in a subject in need thereof.

Membrane-bound proteins are most amenable to monoclonal antibody (mAb)-based therapies, thus representing a class of prime targets for clinical translatability. Thus, the present study focused on the identification of membrane targets for enhancement of CD8$^+$ T cell activity against GBM. A focused CRISPR library, which only targets surface protein encoding genes, was designed, cloned, and packaged. Then regulators of CD8$^+$ T cells that modulate anti-tumor activities in GBM were screened for. Multiple previously undocumented genes (Mgat5, Pdia3, and Emp1) were identified and validated. Knockouts of these genes in CD8$^+$ T cells enhanced the survival of GBM-bearing mice with adoptive transfer across several models, providing promising novel targets for enhancing T cell based immunotherapy efficacy against GBM.

Compositions

In one aspect, the invention includes a genetically modified cell wherein at least one gene selected from the group consisting of Mgat5, Pdia3, Lag3, Emp1 has been mutated in the cell. The cell can be any type of cell including but not limited to CD8$^+$, CD4$^+$, T regulatory (Treg) cells, and CAR-T cells. In some embodiments, the cell is a CD8$^+$ T cell. The genetically modified cell can be for use in treating cancer and/or enhancing CD8$^+$ T cell anti-tumor activity, and can be generated by the methods described herein. Additional genes can be mutated in the cell. In other words, the invention includes a cell wherein a single gene or multiple genes are mutated.

The invention also includes two sgRNA libraries. In some embodiments, one of the sgRNA libraries (mmSurf) comprises a plurality of nucleic acids comprising a nucleotide sequence selected from the group consisting of SEQ ID NOs. 1-6,628. In further embodiments, the library further comprises the a nucleotide sequence selected from the group consisting of SEQ ID NOs. 6,629-7,628. In some embodiments, the sgRNA library comprises a plurality of nucleic acids consisting of the nucleotide sequences of SEQ ID NOs. 1-6,628. In further embodiments, the library further comprises a plurality of nucleic acids consisting of nucleotide sequences of SEQ ID NOs. 6,629-7,628. In some embodiments, the sgRNA library comprises a plurality of nucleic acids comprising at least one nucleotide sequence selected from the group consisting of SEQ ID NOs: 1-6,628. In some embodiments, one of the sgRNA libraries (mSURFEOME2) comprises a plurality of nucleic acids comprising a nucleotide sequence selected from the group consisting of SEQ ID NOs. 7,837-64,747. In further embodiments, the library further comprises the nucleotide sequence selected from the group consistent of SEQ ID NOs. 64,748-69,747. In some embodiments, the sgRNA library comprises a plurality of nucleic acids consisting of the nucleotide sequences of SEQ ID NOs. 7,837-64,747. In further embodiments, the library further comprises a plurality of nucleic acids consisting of nucleotide sequences of SEQ ID NOs. 64,748-69,747. In some embodiments, the sgRNA library comprises a plurality of nucleic acids comprising at least one nucleotide sequence selected from the group consisting of SEQ ID NOs. 7,837-64,747.

In certain embodiments, the library can be packaged into a vector. Any vector known to one of ordinary skill in the art can be used, including but not limited to lentiviral vectors, adenoviral vectors, and adeno-associated viral (AAV) vectors.

Another aspect of the invention includes an AAV library, e.g. an AAV-Surf library. In some embodiments, the AAV library (AAV-mmSurf) comprises a plurality of vectors, wherein each vector comprises an expression cassette for an sgRNA comprising a nucleotide sequence selected from the group consisting of SEQ ID NOs: 1-6,628. In some embodiments, the AAV library (AAV-mmSurf) comprises a plurality of vectors, wherein each vector comprises an expression cassette for an sgRNA comprising a nucleotide sequence selected from the group consisting of SEQ ID NOs: 1-7,628. In some embodiments, the AAV library (AAV-mSURFEOME2) comprises a plurality of vectors, wherein each vector comprises an expression cassette for an sgRNA comprising a nucleotide sequence selected from the group consisting of SEQ ID NOs: 7,837-64,747. In some embodiments, the AAV library (AAV-mSURFEOME2) comprises a plurality of vectors, wherein each vector comprises an expression cassette for an sgRNA comprising a nucleotide sequence selected from the group consisting of SEQ ID NOs: 7,837-69,747. In some embodiments, at least one of the vectors comprises SEQ ID NO: 69,821.

The invention also includes a kit comprising an AAV library, wherein the AAV library comprises a plurality of vectors, wherein each vector comprises an expression cassette for an sgRNA comprising a nucleotide sequence selected from the group consisting of SEQ ID NOs: 1-6,628. In some embodiments, the AAV library in the kit comprises a plurality of vectors, wherein each vector comprises an expression cassette for an sgRNA comprising a nucleotide sequence selected from the group consisting of SEQ ID NOs: 1-7,628. In some embodiments, the AAV library in the kit comprises a plurality of vectors, wherein each vector comprises an expression cassette for an sgRNA comprising a nucleotide sequence selected from the group consisting of SEQ ID NOs: 7,837-64,747. In some embodiments, the AAV library in the kit comprises a plurality of vectors, wherein each vector comprises an expression cassette for an sgRNA comprising a nucleotide sequence selected from the group consisting of SEQ ID NOs: 7,837-69,747. The kit also includes instructional material for use thereof. Instructional material can include directions for using the kit as well as information on interpreting results generated from the kit. In some embodiments, at least one of the vectors comprises SEQ ID NO: 69,821.

Another aspect of the invention includes an AAV-CRISPR T cell vector for efficient gene editing and high-throughput screen in T cells. The vector comprises an antibiotic resistance sequence, two ITRs, two sleeping beauty (SB) IR/DR repeats, a RNA polIII promoter (e.g. U6), an sgRNA (spacer and tracrRNA backbone), a promoter (EFS), a Thy1.1 selection marker, an SB100x transposase, and a short poly A. In some embodiments, the vector comprises SEQ ID NO: 69,821.

With regard to any of the sgRNA libraries or AAV libraries comprising the SEQ ID NOs. 1-6,628 and/or 6,629-7,628, it should be understood by one of ordinary skill in the art that the invention is construed to encompass every individual SEQ ID NO. in the range(s) and all combinations thereof. With regard to any of the sgRNA libraries or AAV libraries comprising the SEQ ID NOs. 7,837-64,747 and/or 64,748-69,747, it should be understood by one of ordinary skill in the art that the invention is construed to encompass every individual SEQ ID NO. in the range(s) and all combinations thereof.

In some embodiments, the sgRNA library comprises about 100 or more sequences. In some embodiments, the library comprises about 1,000 or more sequences. In some embodiments, the library comprises about 10,000 or more sequences. In further embodiments, the library comprises about 20,000 or more sequences. In yet further embodiments, the library comprises about 30,000 or more sequences. In yet further embodiments, the library comprises about 40,000 or more sequences.

Methods

In one aspect, the invention includes a method of treating a disease, disorder, or condition in a subject in need thereof. In some embodiments, the disease is cancer. Another aspect includes a method of enhancing CD8$^+$ T cell anti-tumor activity in a subject in need thereof. In certain embodiments, the method comprises administering to a subject in need thereof a genetically modified cell wherein a gene selected from the group consisting of Mgat5, Pdia3, Lag3, and Emp1 has been targeted in the cell. Types of modified cells that can be used in the invention include, but are not limited to, T cells, primary immune cells, hematopoietic stem cells (HSC), macrophages, natural killer (NK) cells, and dendritic cells (DC).

Additional genes can be targeted by the methods of the invention. Examples of these genes include, but are not limited to, Cdh11, Hfe2, Slc29a1, Pld3, Xc3cl1, P4ha1, Rnpep, Man2a1, Tmem123, Vpreb1, Tspan3, Eprs, Chrna4, Ctlc, Ly9, Epha3, Lgals3bp, Plat, Lrrc8b, Crhr1, Vpreb1, Upk1a, Rnpep, Fgb, Vegfa or Kdr.

The gene or genes that are targeted can be transcriptionally repressed and/or translationally repressed and/or undergo targeted degradation and/or targeted by other targeting methods. Other targeting methods include, but are not limited to, dCas9 coupled with transcriptional repressors, antibodies, small molecule inhibitors, and the like.

In another aspect, the invention includes a method of stimulating a T cell comprising mutating at least one gene selected from the group consisting of Mgat5, Pdia3, and Emp1 in the T cell. In some embodiments, stimulating the T cell results in increased interferon-gamma production by the T cell and/or in increased cytotoxicity of the T cell.

Another aspect of the invention includes a method of stimulating a T cell comprising contacting the T cell with a therapeutically effective amount of an inhibitor of at least one gene selected from the group consisting of Mgat5, Pdia3, and Emp1. In certain embodiments, the inhibitor is selected from the group consisting of an antibody, an siRNA, and a CRISPR system. In certain embodiments the CRISPR system comprises a Cas9, and at least one sgRNA complementary to Mgat5, Pdia3, or Emp1.

In another aspect, the invention includes a method of performing genome editing and screening of a T cell for a mutation in vitro. The method comprises contacting the T cell with Cas9 and an AAV library. In some embodiments, the AAV library (AAV-mmSurf) comprises a plurality of vectors, wherein each vector comprises an expression cassette for an sgRNA comprising a nucleotide sequence selected from the group consisting of SEQ ID NOs: 1-6,628. In some embodiments, the AAV library (AAV-mmSurf) comprises a plurality of vectors, wherein each vector comprises an expression cassette for an sgRNA comprising a nucleotide sequence selected from the group consisting of SEQ ID NOs: 1-7,628.

In some embodiments, the AAV library (AAV-mSURFEOME2) comprises a plurality of vectors, wherein each vector comprises an expression cassette for an sgRNA comprising a nucleotide sequence selected from the group consisting of SEQ ID NOs. 7,837-64,747. In some embodiments, the AAV library (AAV-mSURFEOME2) comprises a plurality of vectors, wherein each vector comprises an expression cassette for an sgRNA comprising a nucleotide sequence selected from the group consisting of SEQ ID NOs. 7,837-69,747.

The T cell undergoes genome editing and is then screened for a mutation in vitro.

Another aspect of the invention includes a method of performing genome editing and screening of a T cell for a mutation in vivo. The method comprises contacting the T cell with Cas9 and an AAV library. In some embodiments, the AAV library (AAV-mmSurf) comprises a plurality of vectors, wherein each vector comprises an expression cassette for an sgRNA comprising a nucleotide sequence selected from the group consisting of SEQ ID NOs: 1-6,628. In some embodiments, the AAV library (AAV-mmSurf) comprises a plurality of vectors, wherein each vector comprises an expression cassette for an sgRNA comprising a nucleotide sequence selected from the group consisting of SEQ ID NOs: 1-7,628.

In some embodiments, the AAV library (AAV-mSURFEOME2) comprises a plurality of vectors, wherein each vector comprises an expression cassette for an sgRNA comprising a nucleotide sequence selected from the group consisting of SEQ ID NOs. 7,837-64,747. In some embodiments, the AAV library (AAV-mSURFEOME2) comprises a plurality of vectors, wherein each vector comprises an expression cassette for an sgRNA comprising a nucleotide sequence selected from the group consisting of SEQ ID NOs. 7,837-69,747.

The modified T cell is administered to a subject and the T cell is screened for a mutation in vivo.

The invention also includes a method of generating a genetically modified T cell. The method comprises administering to a naïve T cell Cas9 and a vector. In some embodiments, the vector comprises an expression cassette for an sgRNA comprising a nucleotide sequence selected from the group consisting of SEQ ID NOs: 1-6,628. In some embodiments, the vector comprises an expression cassette for an sgRNA comprising a nucleotide sequence selected from the group consisting of SEQ ID NOs. 7,837-64,747.

In some embodiments, the sgRNA targets a gene selected from the group consisting of Mgat5, Pdia3, and Emp1.

The T cell of the present invention can be of any subset of T cells, including but not limited to a CD8$^+$ cell, a CD4$^+$ cell, a T regulatory (Treg) cell, a Th1 cell, a Th2 cell, a Th17 cell, a follicular helper T cell (Tfh), a T memory cell, a T effector cell, a T effector memory cell, an engineered T cell, and a chimeric antigen receptor (CAR) T cell. In certain embodiments of the method, the T cell can be further isolated and/or enriched.

In certain embodiments, the subject is a human. In certain embodiments, the subject has glioblastoma (GBM). The cells of the present invention may be administered by any means known to one of ordinary skill in the art. In some embodiments, the cells are administered by intracranial injection. In some embodiments, the cells are injected into the lateral ventricle.

The method can further comprise administering an additional treatment to the subject. Additional treatments include but are not limited to chemotherapy, radiation, surgery, any immune checkpoint inhibitor, any PD-1 inhibitor, and any CTLA-4 inhibitor.

In any of the cells or methods of the present invention, a gene can be mutated by a CRISPR method. CRISPR methods are known to those of ordinary skill in the art and are discussed in detail elsewhere herein. In one non-limiting example, the T cell of the invention is mutated by administration of Cas9 and an AAV library comprised of a plurality of vectors, wherein each vector comprises an expression cassette for an sgRNA comprising a nucleotide sequence selected from the group consisting of SEQ ID NOs: 1-6,628. In one non-limiting example, the T cell of the invention is mutated by administration of Cas9 and an AAV library comprised of a plurality of vectors, wherein each vector comprises an expression cassette for an sgRNA comprising a nucleotide sequence selected from the group consisting of SEQ ID NOs. 7,837-64,747.

In certain embodiments, additional genes are mutated in the T cell.

In certain embodiments, screening T cells after the AAV library has been administered to the subject provides information about the specific genes involved in a condition afflicting the subject. Any condition can be screened for. In some embodiments, the condition is cancer. In some embodiments, the cancer is GBM. Screening T cells can comprise any method commonly known to one of ordinary skill in the art including but not limited to methods of nucleotide sequencing, sgRNA PCR, and/or flow cytometry.

Nucleotide sequencing or "sequencing", as it is commonly known in the art, can be performed by standard methods commonly known to one of ordinary skill in the art. In certain embodiments of the invention sequencing is performed via next-generation sequencing. Next-generation sequencing (NGS), also known as high-throughput sequencing, is used herein to describe a number of different modern sequencing technologies that allow sequencing of DNA and RNA much more quickly and cheaply than the previously used Sanger sequencing (Metzker, 2010, Nature Reviews Genetics 11.1: 31-46). It is based on micro- and nanotechnologies to reduce the size of sample, the reagent costs, and to enable massively parallel sequencing reactions. It can be highly multiplexed which allows simultaneous sequencing and analysis of millions of samples. NGS includes first, second, third as well as subsequent Next Generations Sequencing technologies. Data generated from NGS can be analyzed via a broad range of computational tools. The wide variety of analysis can be appreciated and performed by those skilled in the art.

Genome editing can include introducing mutations throughout the genome of the cell. The mutations introduced can be any combination of insertions or deletions, including but not limited to a single base insertion, a single base deletion, a frameshift, a rearrangement, and an insertion or deletion of 2, 3, 4, 5, 6, 7, 8, 9, 10, 15, 20, 25, 30, 40, 50, 60, 70, 80, 90, 100, 150, 200, 250, 300, any and all numbers in between, bases. The mutation can occur in a gene or in a non-coding region.

Cancer and Other Diseases, Disorders or Conditions

Certain embodiments of the invention include compositions and methods for treating a disease, disorder or condition. Any disease, disorder or condition that can be targeted by a $CD8^+$ T cell and/or wherein binding to the cognate antigen causes degranulation in the $CD8^+$ T cell can be treated with the compositions of the present invention. Diseases, disorders or conditions that can be treated include but are not limited to autoimmune diseases, inflammation, neuroimmune disorders, and other immune system disorders.

Immune system disorders include, but are not limited to: 22q11.2 deletion syndrome, Achondroplasia and severe combined immunodeficiency, Adenosine Deaminase 2 deficiency, Adenosine deaminase deficiency, Adult-onset immunodeficiency with anti-interferon-gamma autoantibodies, Agammaglobulinemia, non-Bruton type, Aicardi-Goutieres syndrome, Aicardi-Goutieres syndrome type 5, Allergic bronchopulmonary aspergillosis, Alopecia areata, Alopecia totalis, Alopecia universalis, Amyloidosis AA, Amyloidosis familial visceral, Ataxia telangiectasia, Autoimmune lymphoproliferative syndrome, Autoimmune lymphoproliferative syndrome due to CTLA4 haploinsufficiency, Autoimmune polyglandular syndrome type 1, Autosomal dominant hyper IgE syndrome, Autosomal recessive early-onset inflammatory bowel disease, Autosomal recessive hyper IgE syndrome, Bare lymphocyte syndrome 2, Barth syndrome, Blau syndrome, Bloom syndrome, Bronchiolitis obliterans, C1q deficiency, Candidiasis familial chronic mucocutaneous, autosomal recessive, Cartilage-hair hypoplasia, CHARGE syndrome, Chediak-Higashi syndrome, Cherubism, Chronic atypical neutrophilic dermatosis with lipodystrophy and elevated temperature, Chronic graft versus host disease, Chronic granulomatous disease, Chronic Infantile Neurological Cutaneous Articular syndrome, Chronic mucocutaneous candidiasis (CMC)-Not a rare disease, Cohen syndrome, Combined immunodeficiency with skin granulomas, Common variable immunodeficiency, Complement component 2 deficiency, Complement component 8 deficiency type 1, Complement component 8 deficiency type 2, Congenital pulmonary alveolar proteinosis, Cryoglobulinemia, Cutaneous mastocytoma, Cyclic neutropenia, Deficiency of interleukin-1 receptor antagonist, Dendritic cell, monocyte, B lymphocyte, and natural killer lymphocyte deficiency, Dyskeratosis congenital, Dyskeratosis congenita autosomal dominant, Dyskeratosis congenita autosomal recessive, Dyskeratosis congenita X-linked, Epidermodysplasia verruciformis, Familial amyloidosis, Finnish type, Familial cold autoinflammatory syndrome, Familial Mediterranean fever, Familial mixed cryoglobulinemia, Felty's syndrome, Glycogen storage disease type 1B, Griscelli syndrome type 2, Hashimoto encephalopathy, Hashimoto's syndrome-Not a rare disease, Hemophagocytic lymphohistiocytosis, Hennekam syndrome, Hepatic venoocclusive disease with immunodeficiency, Hereditary folate malabsorption, Hermansky Pudlak syndrome 2, Herpes simplex encephalitis, Hoyeraal Hreidarsson syndrome, Hyper IgE syndrome, Hyper-IgD syndrome, ICF syndrome, Idiopathic acute eosinophilic pneumonia, Idiopathic CD4 positive T-lymphocytopenia, IL12RB1 deficiency, Immune defect due to absence of thymus, Immune dysfunction with T-cell inactivation due to calcium entry defect 1, Immune dysfunction with T-cell inactivation due to calcium entry defect 2, Immunodeficiency with hyper IgM type 1, Immunodeficiency with hyper IgM type 2, Immunodeficiency with hyper IgM type 3, Immunodeficiency with hyper IgM type 4, Immunodeficiency with hyper IgM type 5, Immunodeficiency with thymoma, Immunodeficiency without anhidrotic ectodermal dysplasia, Immunodysregulation, polyendocrinopathy and enteropathy X-linked, Immunoglobulin A deficiency 2, Intestinal atresia multiple, IRAK-4 deficiency, Isolated growth hormone deficiency type 3, Kawasaki disease, Large granular lymphocyte leukemia, Leukocyte adhesion deficiency type 1, LRBA deficiency, Lupus—Not a rare disease, Lymphocytic hypophysitis, Majeed syndrome, Melkersson-Rosenthal syndrome, MEW class 1 deficiency, Muckle-Wells syndrome, Multifocal fibrosclerosis, Multiple sclerosis, MYD88 deficiency, Neonatal systemic lupus erythematosus, Netherton syndrome, Neutrophil-specific granule deficiency, Nijmegen breakage syndrome, Omenn syndrome, Osteopetrosis autosomal recessive 7, Palindromic rheumatism, Papillon Lefevre syndrome, Partial androgen insensitivity syndrome, PASLI disease, Pearson syndrome, Pediatric multiple sclerosis, Periodic fever, aphthous stomatitis, pharyngitis and adenitis, PGM3-CDG, Poikiloderma with neutropenia, Pruritic urticarial papules plaques of pregnancy, Purine nucleoside phosphorylase deficiency, Pyogenic arthritis, pyoderma gangrenosum and acne, Relapsing polychondritis, Reticular dysgenesis, Sarcoidosis, Say Barber Miller syndrome, Schimke immunoosseous dysplasia, Schnitzler syndrome, Selective IgA deficiency, Selective IgM deficiency, Severe combined immunodeficiency, Severe combined immunodeficiency due to complete RAG1/2 deficiency, Severe combined immunodeficiency with sensitivity to ionizing radiation, Severe combined immunodeficiency, atypical, Severe congenital neutropenia autosomal recessive 3, Severe congenital neutropenia X-linked, Shwachman-Diamond syndrome, Singleton-Merten syndrome, SLC35C1-CDG (CDG-IIc), Specific antibody deficiency, Spondyloenchondrodysplasia, Stevens-Johnson syndrome, T-cell immunodeficiency, congenital alopecia and nail dystrophy, TARP syndrome, Trichohepatoenteric syndrome, Tumor necrosis factor receptor-associated periodic syndrome, Twin to twin transfusion syndrome, Vici syndrome, WHIM syndrome, Wiskott Aldrich syndrome, Woods Black Norbury syndrome, X-linked agammaglobulinemia, X-linked lymphoproliferative syndrome, X-linked lymphoproliferative syndrome 1, X-linked lymphoproliferative syndrome 2, X-linked magnesium deficiency with Epstein-Barr virus infection and neoplasia, X-linked severe combined immunodeficiency, and ZAP-70 deficiency.

Autoimmune diseases (not mutually exclusive with list of immune system disorders) include but are not limited to Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease, and Wegener's granulomatosis (or Granulomatosis with Polyangiitis (GPA)).

The invention includes compositions and methods for treating cancer. Types of cancer that can be treated include, but are not limited to, Acute Lymphoblastic Leukemia (ALL), Acute Myeloid Leukemia (AML), Adrenocortical Carcinoma, AIDS-Related Cancers, Kaposi Sarcoma, AIDS-Related Lymphoma, Primary CNS Lymphoma, Anal Cancer, Appendix Cancer (Gastrointestinal Carcinoid Tumors), Astrocytomas, Atypical Teratoid/Rhabdoid Tumor, Brain Cancer, Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma, Non-Hodgkin Lymphoma, Carcinoid Tumors, Carcinoma of Unknown Primary, Cardiac (Heart) Tumors, Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CIVIL), Chronic Myeloproliferative Neoplasms, Colorectal Cancer, Craniopharyngioma, Cutaneous T-Cell Lymphoma (Mycosis Fungoides and Sézary Syndrome), Ductal Carcinoma In Situ (DCIS), Endometrial Cancer, Ependymoma, Esophageal Cancer, Esthesioneuroblastoma, Ewing Sarcoma, Extracranial Germ Cell Tumor, Eye Cancer, Intraocular Melanoma, Fallopian Tube Cancer, Fibrous Histiocytoma of Bone, Osteosarcoma, Gallbladder Cancer, Gastric Cancer, Stomach Cancer, Gastrointestinal Carcinoid Tumor, Gastrointestinal Stromal Tumors (GIST), Central Nervous System Germ Cell Tumors, Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis (Langerhans Cell), Hodgkin Lymphoma, Hypopharyngeal Cancer, Intraocular Melanoma, Islet Cell Tumors, Pancreatic Neuroendocrine Tumors, Kidney Cancer, Renal Cell Cancer, Langerhans Cell Histiocytosis, Laryngeal Cancer, Leukemia, Lip and Oral Cavity Cancer, Liver Cancer, Lung Cancer (Non-Small Cell and Small Cell), Lymphoma, Male Breast Cancer, Malignant Fibrous Histiocytoma of Bone and Osteosarcoma, Melanoma, Intraocular (Eye) Melanoma, Merkel Cell Carcinoma (Skin Cancer), Malignant Mesothelioma, Metastatic Cancer, Metastatic Squamous Neck Cancer with Occult Primary, Midline Tract Carcinoma With NUT Gene Changes, Mouth Cancer, Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Nasal Cavity and Paranasal Sinus Cancer, Nasopharyngeal Cancer, Neuroblastoma, Non-Small Cell Lung Cancer, Oral Cancer, and Oropharyngeal Cancer, Ovarian Cancer, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Primary Peritoneal Cancer, Prostate Cancer, Rectal Cancer, Recurrent Cancer, Retinoblastoma, Rhabdomyosarcoma, Salivary Gland Cancer, Sarcoma, Vascular Tumors, Uterine Sarcoma, Sézary Syndrome (Lymphoma), Small Cell Lung Cancer, Small Intestine Cancer, Soft Tissue Sarcoma, Squamous Cell Carcinoma, Stomach (Gastric) Cancer, Throat Cancer, Thymoma, Thymic Carcinoma, Thyroid Cancer, Transitional Cell Cancer of the Renal Pelvis and Ureter, Carcinoma of Unknown Primary, Ureter and Renal Pelvis, Transitional Cell Cancer, Urethral Cancer, Uterine Cancer, Vaginal Cancer, Vulvar Cancer, Wilms Tumor, and combinations thereof.

In certain embodiments, the subject can be administered an additional treatment. For example, the subject can be administered a combination of a composition of the present invention and an additional treatment. Examples of additional treatments include but are not limited to, chemotherapy, radiation, surgery, medication, immune checkpoint inhibitors, immune checkpoint blockade (ICB) antibodies, immune checkpoint inhibitors that block CTLA-4 or PD1, anti-CTLA4 monoclonal antibody, anti-PD1 monoclonal antibody, anti-PD-L1 monoclonal antibody, adoptive cell transfer, human recombinant cytokines, cancer vaccines, immunotherapy, targeted therapy, hormone therapy, stem cell transplant, precision medicine, non-specific immunotherapy (e.g. cytokines and chemokines, such as IL-2, IFNa, IFNb, IFNg), oncolytic virus therapy, T-cell therapy (e.g. adoptive transfer of TILs, CAR-T therapy), cancer vaccines (e.g. conventional DC vaccine), Ipilimumab (Yervoy), Nivolumab (Opdivo), Pembrolizumab (Keytruda), Atezolizumab (Tecentriq), Avelumab (Bavencio), Durvalumab (Imfinzi), Anti-LAG-3, anti-TIM1, Anti-TIM3, Anti-CSF-R, IDO inhibitor, OX-40 agonist, GITR agonist, CD80 agonist, CD86 agonist, ICOS agonist, ICOSLG agonist, CD276 agonist, VTCN1 agonist, TNFSF14 agonist, TNFSF9 agonist, TNFSF4 agonist, CD70 agonist, CD40 agonist, LGALS9 agonist, CD80 inhibitor, CD86 inhibitor, ICOS inhibitor, ICOSLG inhibitor, CD276 inhibitor, VTCN1 inhibitor, TNFSF14 inhibitor, TNFSF9 inhibitor, TNFSF4 inhibitor, CD70 inhibitor, CD40 inhibitor, LGALS9 inhibitor, TLR9 agonist, CD20 antibody, CD80 antibody, TIGIT antibody, B7-H1 antibody, B7-H2 antibody, B7-H3 antibody, B7-H4 antibody, CD28 antibody, CD47 antibody, anti-BTLA, anti-Galetin9, anti-IL15R, anti-GD2. In some embodiments the monoclonal antibody is fully human, humanized or chimeric.

CRISPR/Cas9

The CRISPR/Cas9 system is a facile and efficient system for inducing targeted genetic alterations. Target recognition by the Cas9 protein requires a 'seed' sequence within the guide RNA (gRNA) and a conserved dinucleotide containing protospacer adjacent motif (PAM) sequence upstream of the gRNA-binding region. The CRISPR/Cas9 system can thereby be engineered to cleave virtually any DNA sequence by redesigning the gRNA in cell lines (such as 293T cells), primary cells, and CAR T cells. The CRISPR/Cas9 system can simultaneously target multiple genomic loci by co-expressing a single Cas9 protein with two or more gRNAs, making this system uniquely suited for multiple gene editing or synergistic activation of target genes.

The Cas9 protein and guide RNA form a complex that identifies and cleaves target sequences. Cas9 is comprised of six domains: REC I, REC II, Bridge Helix, PAM interacting, HNH, and RuvC, The Red domain binds the guide RNA, while the Bridge helix binds to target DNA. The HNH-14 and RuvC domains are nuclease domains. Guide RNA is engineered to have a 5' end that is complementary to the target DNA sequence. Upon binding of the guide RNA to the Cas9 protein, a conformational change occurs activating the protein. Once activated, Cas9 searches for target DNA by binding to sequences that match its protospacer adjacent motif (PAM) sequence. A PAM is a two or three nucleotide base sequence within one nucleotide downstream of the region complementary to the guide RNA. In one non-limiting example, the PAM sequence is 5'-NGG-3'. When the Cas9 protein finds its target sequence with the appropriate PAM, it melts the bases upstream of the PAM and pairs them with the complementary region on the guide RNA. Then the RuvC and HMI nuclease domains cut the target DNA after the third nucleotide base upstream of the P.I.

One non-limiting example of a CRISPR/Cas system used to inhibit gene expression, CRISPRi, is described in U.S. Patent Appl. Publ. No. US20140068797. CRISPRi induces permanent gene disruption that utilizes the RNA-guided Cas9 endonuclease to introduce DNA double stranded breaks, which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleotide sequence specific for a target gene and a Cas endonuclease are introduced into a cell and form a complex that enables the Cas endonuclease to introduce a double strand break at the target gene. In certain embodiments, the CRISPR/Cas system comprises an expression vector, such as, but not limited to, an pAd5F35-CRISPR vector. In other embodiments, the Cas expression vector induces expression of Cas9 endonuclease. Other endonucleases may also be used, including but not limited to, T7, Cas3, Cas8a, Cas8b, Cas10d, Cse1, Csy1, Csn2, Cas4, Cas10, Csm2, Cmr5, Fok1, other nucleases known in the art, and any combinations thereof.

In certain embodiments, inducing the Cas expression vector comprises exposing the cell to an agent that activates an inducible promoter in the Cas expression vector. In such embodiments, the Cas expression vector includes an inducible promoter, such as one that is inducible by exposure to an antibiotic (e.g., by tetracycline or a derivative of tetracycline, for example doxycycline). However, it should be appreciated that other inducible promoters can be used. The inducing agent can be a selective condition (e.g., exposure to an agent, for example an antibiotic) that results in induction of the inducible promoter. This results in expression of the Cas expression vector.

In certain embodiments, guide RNA(s) and Cas9 can be delivered to a cell as a ribonucleoprotein (RNP) complex. RNPs are comprised of purified Cas9 protein complexed with gRNA and are well known in the art to be efficiently delivered to multiple types of cells, including but not limited to stem cells and immune cells (Addgene, Cambridge, MA, Mirus Bio LLC, Madison, WI).

The guide RNA is specific for a genomic region of interest and targets that region for Cas endonuclease-induced double strand breaks. The target sequence of the guide RNA sequence may be within a loci of a gene or within a non-coding region of the genome. In certain embodiments, the guide nucleotide sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

Guide RNA (gRNA), also referred to as "short guide RNA" or "sgRNA", provides both targeting specificity and scaffolding/binding ability for the Cas9 nuclease. The gRNA can be a synthetic RNA composed of a targeting sequence and scaffold sequence derived from endogenous bacterial crRNA and tracrRNA. gRNA is used to target Cas9 to a specific genomic locus in genome engineering experiments. Guide RNAs can be designed using standard tools well known in the art.

In the context of formation of a CRISPR complex, "target sequence" refers to a sequence to which a guide sequence is designed to have some complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as a DNA or a RNA polynucleotide. In certain embodiments, a target sequence is located in the nucleus or cytoplasm of a cell. In other embodiments, the target sequence may be within an organelle of a eukaryotic cell, for example, mitochondrion or nucleus. Typically, in the context of an endogenous CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) the target sequence. As with the target sequence, it is believed that complete complementarity is not needed, provided this is sufficient to be functional.

In certain embodiments, one or more vectors driving expression of one or more elements of a CRISPR system are introduced into a host cell, such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In certain embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR enzyme are described in U.S. Patent Appl. Publ. No. US20110059502, which is incorporated herein by reference. In certain embodiments, a tagged CRISPR enzyme is used to identify the location of a target sequence.

Conventional viral and non-viral based gene transfer methods can be used to introduce nucleic acids in mammalian and non-mammalian cells or target tissues. Such methods can be used to administer nucleic acids encoding components of a CRISPR system to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell (Anderson, 1992, Science 256:808-813; and Yu, et al., 1994, Gene Therapy 1:13-26).

In certain embodiments, the CRISPR/Cas is derived from a type II CRISPR/Cas system. In some embodiments, the CRISPR/Cas system is derived from a Cas9 protein. The Cas9 protein can be from *Streptococcus pyogenes, Streptococcus thermophilus*, or other species.

In general, Cas proteins comprise at least one RNA recognition and/or RNA binding domain. RNA recognition and/or RNA binding domains interact with the guiding RNA. Cas proteins can also comprise nuclease domains (i.e., DNase or RNase domains), DNA binding domains, helicase domains, RNAse domains, protein-protein interaction domains, dimerization domains, as well as other domains. The Cas proteins can be modified to increase nucleic acid binding affinity and/or specificity, alter an enzymatic activity, and/or change another property of the protein. In certain embodiments, the Cas-like protein of the fusion protein can be derived from a wild type Cas9 protein or fragment thereof. In other embodiments, the Cas can be derived from modified Cas9 protein. For example, the amino acid sequence of the Cas9 protein can be modified to alter one or more properties (e.g., nuclease activity, affinity, stability, and so forth) of the protein. Alternatively, domains of the Cas9 protein not involved in RNA-guided cleavage can be eliminated from the protein such that the modified Cas9 protein is smaller than the wild type Cas9 protein. In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek, et al., 2012, Science, 337:816-821). In certain embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. In any of the elsewhere herein-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In one non-limiting embodiment, a vector drives the expression of the CRISPR system. The art is replete with suitable vectors that are useful in the present invention. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid standard gene delivery protocols. Methods for gene delivery are known in the art (U.S. Pat. Nos. 5,399,346, 5,580,859 & 5,589,466, incorporated by reference herein in their entireties).

Further, the vector may be provided to a cell in the form of a viral vector. Viral vector technology is well known in the art and is described, for example, in Sambrook et al. (4$^{th}$ Edition, Molecular Cloning: A Laboratory Manual, Cold Spring Harbor Laboratory, New York, 2012), and in other virology and molecular biology manuals. Viruses, which are useful as vectors include, but are not limited to, retroviruses, adenoviruses, adeno-associated viruses, herpes viruses, Sindbis virus, gammaretrovirus and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

Sources of T Cells

Prior to genetic modification, T cells (e.g., autologous or allogeneic T cells) are obtained from a subject. Examples of subjects include humans, dogs, cats, mice, rats, and transgenic species thereof. T cells can be obtained from a number of sources, including skin, peripheral blood mononuclear cells, bone marrow, lymph node tissue, cord blood, thymus tissue, tissue from a site of infection, ascites, pleural effusion, spleen tissue, and tumors. In certain embodiments of the present invention, T cells can be obtained from a unit of blood collected from a subject using any number of techniques known to the skilled artisan, such as Ficoll™ separation. In certain embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments of the invention, the cells are washed with phosphate buffered saline (PBS). In an alternative embodiment, the wash solution lacks calcium and may lack magnesium or may lack many if not all divalent cations. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3$^+$, CD28$^+$, CD4$^+$, and CD8$^+$ T cells, can be further isolated by positive or negative selection techniques. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4$^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4$^+$, CD25$^+$, CD62L$^+$, GITR$^+$, and FoxP3$^+$. Alternatively, in certain embodiments, T regulatory cells are depleted by anti-CD25 conjugated beads or other similar method of selection. In other embodiments, subpopulation of T cells, such as, but not limited to, cells positive or expressing high levels of one or more surface markers e.g. CD28$^+$, CD8$^+$, CCR7$^+$, CD27$^+$, CD127$^+$, CD45RA$^+$, and/or CD45RO$^+$ T cells, can be isolated by positive or negative selection techniques.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in some embodiments, a concentration of 2 billion cells/ml is used. In some embodiments, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet some embodiments, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8$^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4$^+$ T cells express higher levels of CD28 and are more efficiently captured than CD8$^+$ T cells in dilute concentrations. In certain embodiments, the concentration of cells used is $5 \times 10^6$/ml. In other embodiments, the concentration used can be from about $1 \times 10^5$/ml to $1 \times 10^6$/ml, and any integer value in between.

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

It should be understood that the method and compositions that would be useful in the present invention are not limited to the particular formulations set forth in the examples. The following examples are put forth so as to provide those of ordinary skill in the art with a complete disclosure and description, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, Molecular Cloning: A Laboratory Manual", fourth edition (Sambrook et al. (2012) Molecular Cloning, Cold Spring Harbor Laboratory); "Oligonucleotide Synthesis" (Gait, M. J. (1984). Oligonucleotide synthesis. IRL press); "Culture of Animal Cells" (Freshney, R. (2010). Culture of animal cells. Cell Proliferation, 15(2.3), 1); "Methods in Enzymology" "Weir's Handbook of Experimental Immunology" (Wiley-Blackwell; 5 edition (Jan. 15, 1996); "Gene Transfer Vectors for Mammalian Cells" (Miller and Carlos, (1987) Cold Spring Harbor Laboratory, New York); "Short Protocols in Molecular Biology" (Ausubel et al., Current Protocols; 5 edition (Nov. 5, 2002)); "Polymerase Chain Reaction: Principles, Applications and Troubleshooting", (Babar, M., VDM Verlag Dr. Muller (Aug. 17, 2011)); "Current Protocols in Immunology" (Coligan, John Wiley & Sons, Inc. Nov. 1, 2002).

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Humanized Antibodies

Humanized forms of non-human murine) antibodies are genetically engineered chimeric antibodies or antigen binding fragments thereof having preferably minimal portions derived from non-human antibodies. Humanized antibodies include antibodies in which CDRs of a human antibody (recipient antibody) are replaced by residues from a CDR region of a non-human species (donor antibody) such as mouse, rat or rabbit having the desired functionality. In some embodiments, Fv framework residues of the human antibody are replaced by corresponding nonhuman residues. Humanized antibodies may also comprise residues that are found neither in the recipient antibody nor in the imported CDR or framework (FR) sequences. In some embodiments, the humanized antibody may comprise substantially all of at least one, typically two, variable domains domains in which all or substantially all of the framework regions correspond to those of a relevant human consensus sequence. Humanized antibodies may also include at least a portion of an antibody constant region, such as an Fc region, typically derived from a human antibody (see, for example, Jones et al., 1986. *Nature* 321:522-525; Riechmann et al., 1988. *Nature* 332:323-329; Presta, 1992, *Curr. Op. Struct. Biol.* 2:593-596).

In order to retain high binding affinity, amino acids in the human acceptor sequence may be replaced by the corresponding amino acids from the donor sequence, for example where: (1) the amino acid is in a CDR; (2) the amino acid is in a human framework region (e.g., the amino acid is immediately adjacent to one of the CDRs). See, U.S. Pat. Nos. 5,530,101 and 5,585,089, incorporated herein by reference, which provide detailed instructions for construction of humanized antibodies.

Although humanized antibodies often incorporate all six CDRs (e.g, as defined by Kabat, but often also including hypervariable loop H1 as defined by Chothia) from a mouse antibody, they can also be made with fewer mouse CDRs and/or less than complete mouse CDR sequence(s) (e.g., a functional fragment of a CDR) (e.g., Pascalis et al. *J. Immunol.* 169:3076, 2002; Vajdos et al., *Journal of Molecular Biology*, 320:415-428, 2002; Iwahashi et al., *Mol. Immunol.* 36:1079-1091, 1999; Tamura et al., *Journal of Immunology*, 164:1432-1441, 2000).

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FR residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A "humanized" antibody retains a similar antigenic specificity as the original antibody. However, using certain methods of humanization, the affinity and/or specificity of binding of the antibody for human CD3 antigen may be increased using methods of "directed evolution," as described by Wu et al., J. Mol. Biol., 294:151 (1999), the contents of which are incorporated herein by reference herein in their entirety.

In some embodiments, the antibody is a synthetic antibody, human antibody, a humanized antibody, single chain variable fragment, single domain antibody, an antigen binding fragment thereof, and any combination thereof.

Pharmaceutical Compositions

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

It will be appreciated by a person skilled in the art that the antibody or antigen binding fragment may be administered in admixture with a suitable pharmaceutical excipient diluent or carrier selected with regard to the intended route of administration and standard pharmaceutical practice. For example, see *Remington: The Science and Practice of Pharmacy*, 19th edition, 1995, Ed. Alfonso Gennaro, Mack Publishing Company, Pennsylvania, USA.

In some embodiments, the antibody or antigen binding fragment may be administered orally, bucally or sublingually in the form of tablets, capsules, ovules, elixirs, solutions or suspensions, which may contain flavoring or coloring agents, for immediate, delayed or controlled-release applications. The antibody or antigen binding fragment may also be administered via intracavernosal injection.

The antibody or antigen binding fragment may also be administered parenterally. In some embodiments, the antibody or antigen binding fragment may be administered intravenously, intra-articularly, intraperitoneally, intrathecally, intraventricularly, intrasternally, intracranially, intramuscularly or subcutaneously. In some embodiments, the antibody or antigen binding fragment is administered by infusion techniques.

In some embodiments, the antibody or antigen binding fragment is used in the form of a sterile aqueous solution that may contain other substances, for example, sufficient salts or glucose (or other sugars) to make the solution isotonic with blood. The aqueous solution should be suitably buffered (preferably to a pH of from 3 to 9), if necessary. The preparation of suitable parenteral formulations under sterile conditions is readily accomplished by standard pharmaceutical techniques well known to a person of skill in the art.

Formulations suitable for parenteral administration include aqueous and non-aqueous sterile injection solutions which may contain anti-oxidants, buffers, bacteriostats and solutes which render the formulation isotonic with blood. Suitable formulations for parenteral administration also include aqueous and non-aqueous suspensions which may include suspending agents and thickening agents. The formulations may be presented in unit-dose or multi-dose containers.

For oral, parenteral or other routes of administration to human patients, the daily dosage level of the antibody or antigen binding fragment that binds MGAT5 or PDIA3 will usually be from 1 to 1000 mg per adult (i.e., from about 0.015 to 15 mg/kg), administered in single or multiple or divided doses.

In some embodiments, the dosage level may be from about 0.5 mg/kg to about 10 mg/kg. In further embodiments, the dosage level may be from about 2 to about 6 mg/kg.

In some embodiments, the antibody or antigen binding fragment is administered intranasally or by inhalation. The antibody or antigen binding fragment may be delivered in the form of a dry powder inhaler or an aerosol spray from a pressurized container, pump, spray or nebulizer with the use of a propellant.

In some embodiments, the antibody or antigen binding fragment is administered by DNA injection and electroporation of the DNA encoded antibody into muscle or skin.

Methods of Treatment Comprising Antibodies or Antigen Binding Fragments

Provided is a method of treating a disease, disorder or condition in a subject in need thereof, comprising administering to the subject an effective amount of any one of the antibody or antigen binding fragments described herein. In some embodiments, the subject is human. In some embodiments, the antibody or antigen binding fragment is provided in a pharmaceutical composition.

In some embodiments, the disease, disorder or condition is as described elsewhere herein.

In some embodiments, the disease is cancer. In further embodiments, the cancer is a cancer from Table 6 or any cancer described elsewhere herein.

In some embodiments, the disease is an autoimmune disease.

In some embodiments, the disorder is an immune system disorder.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Mice: Rosa26-Cas9-2A-EGFP constitutive expressed mice (Cas9(3 mice), OT-1 TCR transgenic mice, $Rag1^{-/-}$, and C57BL/6J mice were used in this study. For OT-1; Cas9β mice, which were generated by breeding OT-1 and Cas9 mice, both female and male, aged 8-12 weeks were used for naïve $CD8^+$ T cell isolation. For the lateral ventricle (LV) injections, 8 week-old C57BL/6J or 7-9 week-old $Rag1^{-/-}$ mice were used. Mice were randomly classified into different groups.

Design and Synthesis of Surface Protein CRISPR Knockout Libraries:

mmSurf library: A total of 1,657 surface protein genes were selected to make a surface protein-specific single-strand RNA (sgRNA) library. Four sgRNAs were designed for each gene, a total of 7,628 sgRNAs were designed including 1,000 non-targeting controls (NTCs) (Table 1: SEQ ID NOs. 1-7,628). The surface protein library was synthesized by massively parallel oligo array synthesis and pooled (CustomArray).

mSURFEOME2 library: A list of proteins in the human surface proteome was obtained (Bausch-Fluck, et al. (2018) *Proceedings of the National Academy of Sciences*, 46: E10988-E10997). The corresponding human genes were mapped to their mouse orthologous counterparts, for a total of 2,867 genes. Exonic sequences for these mouse genes were obtained through Ensembl Biomart based on the mm10 genome assembly. Candidate Cas9 sgRNAs were then identified using FlashFry (McKenna and Shendure, (2018) *BMC Biology* 16: 74), following default settings and using the scoring metrics "deonch2014ontarget", "rank", "minot", "doench2016cfd", and "dangerous". With the resultant scoring matrix, sgRNAs were first filtered for those that did not have high GC content, no polyT tracts, and exactly one match in the mm10 genome. The sgRNAs targeting a given gene were then ranked by using the "doench2014ontarget" and "doench2016cfd" scores, by first converting each score to nonparametric ranks where high "doench2014ontarget" scores correspond to high ranks, while low "doench2016cfd" scores correspond to high ranks. The two nonparametric ranks were then added together, weighting the "doench2014ontarget" rank twice as heavily as the "doench2016cfd" rank. For final library design, all of the sgRNAs that are contained in the Brie library (Doench et al. (2016) *Nature Biotechnology*, 34: 184-191) were first selected, then the composite ranks described elsewhere herein were used to choose the top scoring sgRNAs, up to a total of 20 sgRNAs per gene. The final set of on-target sgRNAs was composed of 56,911 sgRNAs targeting 2863 murine genes. A set of non-targeting control sgRNAs was designed by generating 500,000 random 20 nt sequences, followed by sgRNA scoring in FlashFry. The top 5000 non-targeting control sgRNAs were selected by choosing sgRNAs with a "doench2016cfd" score<0.2 and <100 total potential off-targets (maximum 4 mismatches). These 5000 control sgRNAs were added to the library, for a total of 61,911 sgRNAs.

Generation of AAV-CRISPR vector and AAV-Surf library for primary T cell editing and screening: An AAV vector for targeting primary mouse T cells (AAV-SB100x) was constructed by gBlock fragments (IDT) followed by Gibson assembly (NEB) (SEQ ID NO: 69,821). The synthesized library was PCR amplified, then the sgRNAs cloned into double Bbs I sites of AAV-CRISPR vector by the Gibson assembly (NEB). The Gibson assembly products were transformed into high efficiency competent cells (Endura) by electroporation methods. An estimated library coverage of ≥60× was observed after electroporation. The cloned library was PCR amplified using barcoded primers to ensure proper representation. The cloned library was named AAV-Surf pLY017SB_pAAV-U6sg(BbsI)-EFS-Thy1
(SEQ ID NO: 69,821)

```
   1 cctgcaggca gctgcgcgct cgctcgctca ctgaggccgc
     ccgggcaaag cccgggcgtc
  61 gggcgacctt tggtcgcccg gcctcagtga gcgagcgagc
     gcgcagagag ggagtggcca
 121 actccatcac taggggttcc tgcggccgca cgcgttctag
     aCTATACAGT TGAAGTCGGA
 181 AGTTTACATA CACTTAAGTT GGAGTCATTA AAACTCGTTT
     TTCAACTACT CCACAAATTT
 241 CTTGTTAACA AACAATAGTT TTGGCAAGTC AGTTAGGACA
     TCTACTTTGT GCATGACACA
 301 AGTCATTTTT CCAACAATTG TTTACAGACA GATTATTTCA
     CTTATAATTC ACTGTATCAC
 361 AATTCCAGTG GGTCAGAAGT TTACATACAC TAAGTTGACT
     GTGCCTTTAA ACAGCTTGGA
 421 AAATTCCAGA AAATGATGTC ATGGCTTTAG agaggatccg
     agggcctatt tcccatgatt
 481 ccttcatatt tgcatatacg atacaaggct gttagagaga
     taattagaat taatttgact
 541 gtaaacacaa agatattagt acaaaatacg tgacgtagaa
     agtaataatt tcttgggtag
 601 tttgcagttt taaaattatg ttttaaaatg gactatcata
     tgcttaccgt aacttgaaag
 661 tatttcgatt tcttggcttt atatatcttG TGGAAAGGAC
     GAAACACCGg GTCTTCgaGA
 721 AGACctgttt tagagctaGA AAtagcaagt taaaataagg
     ctagtccgtt atcaacttga
 781 aaaagtggca ccgagtcggt gcTTTTTTgg ctagctGGCC
     GCGTTTAAAC GTCGACtagg
 841 tcttgaaagg agtgggaatt ggctccggtg cccgtcagtg
     ggcagagcgc acatcgccca
 901 cagtccccga gaagttgggg ggaggggtcg gcaattgatc
     cggtgcctag agaaggtggc
 961 gcggggtaaa ctgggaaagt gatgtcgtgt actggctccg
     cctttttccc gagggtgggg
1021 gagaaccgta tataagtgca gtagtcgccg tgaacgttct
     ttttcgcaac gggtttgccg
1081 ccagaacaca ggCTCGAGAT GAACCCAGCC ATCAGCGTCG
     CTCTCCTGCT CTCAGTCTTG
1141 CAGGTGTCCC GAGGGCAGAA GGTGACCAGC CTGACAGCCT
     GCCTGGTGAA CCAAAACCTT
1201 CGCCTGGACT GCCGCCATGA GAATAACACC AAGGATAACT
     CCATCCAGCA TGAGTTCAGC
1261 CTGACCCGAG AGAAGAGGAA GCACGTGCTC TCAGGCACCC
     TTGGGATACC CGAGCACACG
1321 TACCGCTCCC GCGTCACCCT CTCCAACCAG CCCTATATCA
     AGGTCCTTAC CCTAGCCAAC
1381 TTCACCACCA AGGATGAGGG CGACTACTTT TGTGAGCTTC
     GCGTgTCGGG CGCGAATCCC
1441 ATGAGCTCCA ATAAAAGTAT CAGTGTGTAT AGAGACAAGC
     TGGTCAAGTG TGGCGGCATA
1501 AGCCTGCTGG TTCAGAACAC ATCCTGGATG CTGCTGCTGC
     TGCTTTCCCT CTCCCTCCTC
1561 CAAGCCCTGG ACTTCATTTC TCTGGGCAGT GGAGAGGGCA
     GAGGAAGTCT GCTAACATGC
1621 GGTGACGTCG AGGAGAATCC TGGCCCAATG GGAAAATCAA
     AAGAAATCAG CCAAGACCTC
1681 AGAAAAAGAA TTGTAGACCT CCACAAGTCT GGTTCATCCT
     TGGGAGCAAT TTCCAAACGC
1741 CTGGCGGTAC CACGTTCATC TGTACAAACA ATAGTACGCA
     AGTATAAACA CCATGGGACC
1801 ACGCAGCCGT CATACCGCTC AGGAAGGAGA CGCGTTCTGT
     CTCCTAGAGA TGAACGTACT
1861 TTGGTGCGAA AAGTGCAAAT CAATCCCAGA ACAACAGCAA
     AGGACCTTGT GAAGATGCTG
1921 GAGGAAACAG GTACAAAAGT ATCTATATCC ACAGTAAAAC
     GAGTCCTATA TCGACATAAC
1981 CTGAAAGGCC ACTCAGCAAG GAAGAAGCCA CTGCTCCAAA
     ACCGACATAA GAAAGCCAGA
2041 CTACGGTTTG CAACTGCACA TGGGGACAAA GATCGTACTT
     TTTGGAGAAA TGTCCTCTGG
2101 TCTGATGAAA CAAAAATAGA ACTGTTTGGC CATAATGACC
     ATCGTTATGT TTGGAGGAAG
2161 AAGGGGGAGG CTTGCAAGCC GAAGAACACC ATCCCAACCG
     TGAAGCACGG GGGTGGCAGC
2221 ATCATGTTGT GGGGGTGCTT TGCTGCAGGA GGGACTGGTG
     CACTTCACAA AATAGATGGC
2281 ATCATGGACG CGGTGCAGTA TGTGGATATA TTGAAGCAAC
     ATCTCAAGAC ATCAGTCAGG
2341 AAGTTAAAGC TTGGTCGCAA ATGGGTTTTC CAACACGACA
     ATGACCCCAA GCATACTTCC
2401 AAAGTTGTGG CAAAATGGCT TAAGGACAAC AAAGTCAAGG
     TATTGGAGTG GCCATCACAA
2461 AGCCCTGACC TCAATCCTAT AGAAAATTTG TGGGCAGAAC
     TGAAAAAGCG TGTGCGAGCA
2521 AGGAGGCCTA CAAACCTGAC TCAGTTACAC CAGCTCTGTC
     AGGAGGAATG GGCCAAAATT
2581 CACCCAAATT ATTGTGGGAA GCTTGTGAA GGCTACCCGA
     AACGTTTGAC CCAAGTTAAA
2641 CAATTTAAAG GCAATGCTAC CAAATACTAG GGGCCCTAAC
     CGCGGGAATA AAAGATCTTT
2701 ATTTTCATTA GATCTGTGTG TTGGTTTTTT GTGTGAATTC
     TTGAGTGTAT GTAAACTTCT
```

-continued

```
2761 GACCCACTGG GAATGTGATG AAAGAAATAA AAGCTGAAAT
     GAATCATTCT CTCTACTATT

2821 ATTCTGATAT TTCACATTCT TAAAATAAAG TGGTGATCCT
     AACTGACCTA AGACAGGGAA

2881 TTTTTACTAG GATTAAATGT CAGGAATTGT GAAAAAGTGA
     GTTTAAATGT ATTTGGCTAA

2941 GGTGTATGTA AACTTCCGAC TTCAACTGTA TAGgcatgcg
     gtaaccacgt gcggaccgag 3001 cggccgcagg aacccctagt gatggagttg gccactccct
     ctctgcgcgc tcgctcgctc 3061 actgaggccg ggcgaccaaa ggtcgcccga cgcccgggct
     ttgcccgggc ggcctcagtg 3121 agcgagcgag cgcgcagctg cctgcagggg cgcctgatgc
     ggtattttct ccttacgcat 3181 ctgtgcggta tttcacaccg catacgtcaa agcaaccata
     gtacgcgccc tgtagcgggc g 3241 cattaagcgc ggcgggtgtg gtggttacgc gcagcgtgac
     cgctacactt gccagcgccc 3301 tagcgcccgc tcctttcgct ttcttccctt cctttctcgc
     cacgttcgcc ggctttcccc 3361 gtcaagctct aaatcggggg ctcccttag ggttccgatt
     tagtgcttta cggcacctcg 3421 accccaaaaa acttgatttg ggtgatggtt cacgtagtgg
     gccatcgccc tgatagacgg 3481 tttttcgccc tttgacgttg gagtccacgt tctttaatag
     tggactcttg ttccaaactg 3541 gaacaacact caaccctatc tcgggctatt cttttgattt
     ataagggatt ttgccgattt 3601 cggcctattg gttaaaaaat gagctgattt aacaaaaatt
     taacgcgaat tttaacaaaa 3661 tattaacgtt tacaatttta tggtgcactc tcagtacaat
     ctgctctgat gccgcatagt 3721 taagccagcc ccgacacccg ccaacacccg ctgacgcgcc
     ctgacgggct tgtctgctcc 3781 cggcatccgc ttacagacaa gctgtgaccg tctccgggag
     ctgcatgtgt cagaggtttt 3841 caccgtcatc accgaaacgc gcgagacgaa agggcctcgt
     gatacgccta ttttttatagg 3901 ttaatgtcat gataataatg gtttcttaga cgtcaggtgg
     cacttttcgg ggaaatgtgc 3961 gcggaacccc tatttgttta tttttctaaa tacattcaaa
     tatgtatccg ctcatgagac 4021 aataaccctg ataaatgctt caataatatt gaaaaaggaa
     gagtatgagt attcaacatt 4081 tccgtgtcgc ccttattccc ttttttgcgg catttttgcct
     tcctgttttt gctcacccag 4141 aaacgctggt gaaagtaaaa gatgctgaag atcagttggg
     tgcacgagtg ggttacatcg 4201 aactggatct caacagcggt aagatccttg agagttttcg
     ccccgaagaa cgttttccaa 4261 tgatgagcac ttttaaagtt ctgctatgtg gcgcggtatt
     atcccgtatt gacgccggc 4321 aagagcaact cggtcgccgc atacactatt ctcagaatga
     cttggttgag tactcaccag
```

-continued

```
4381 tcacagaaaa gcatcttacg gatggcatga cagtaagaga
     attatgcagt gctgccataa 4441 ccatgagtga taacactgcg gccaacttac ttctgacaac
     gatcggagga ccgaaggagc 4501 taaccgcttt tttgcacaac atggggggatc atgtaactcg
     ccttgatcgt tgggaaccgg 4561 agctgaatga agccatacca aacgacgagc gtgacaccac
     gatgcctgta gcaatggcaa 4621 caacgttgcg caaactatta actggcgaac tacttactct
     agcttcccgg caacaattaa 4681 tagactggat ggaggcggat aaagttgcag gaccacttct
     gcgctcggcc cttccggctg 4741 gctggtttat tgctgataaa tctggagccg gtgagcgtgg
     gtctcgcggt atcattgcag 4801 cactggggcc agatggtaag ccctcccgta tcgtagttat
     ctacacgacg gggagtcagg 4861 caactatgga tgaacgaaat agacagatcg ctgagatagg
     tgcctcactg attaagcatt 4921 ggtaactgtc agaccaagtt tactcatata tactttagat
     tgatttaaaa cttcattttt 4981 aatttaaaag gatctaggtg aagatccttt ttgataatct
     catgaccaaa atcccttaac 5041 gtgagttttc gttccactga gcgtcagacc ccgtagaaaa
     gatcaaagga tcttcttgag 5101 atcctttttt tctgcgcgta atctgctgct tgcaaacaaa
     aaaaccaccg ctaccagcgg 5161 tggtttgttt gccggatcaa gagctaccaa ctctttttcc
     gaaggtaact ggcttcagca 5221 gagcgcagat accaaatact gtccttctag tgtagccgta
     gttaggccac cacttcaaga 5281 actctgtagc accgcctaca tacctcgctc tgctaatcct
     gttaccagtg gctgctgcca 5341 gtggcgataa gtcgtgtctt accgggttgg actcaagacg
     atagttaccg gataaggcgc 5401 agcggtcggg ctgaacgggg ggttcgtgca cacagcccag
     cttggagcga acgacctaca 5461 ccgaactgag atacctacag cgtgagctat gagaaagcgc
     cacgcttccc gaagggagaa 5521 aggcggacag gtatccggta agcggcaggg tcggaacagg
     agagcgcacg agggagcttc 5581 caggggggaaa cgcctggtat ctttatagtc ctgtcgggtt
     tcgccacctc tgacttgagc 5641 gtcgatttttt gtgatgctcg tcagggggggc ggagcctatg
     gaaaaacgcc agcaacgcgg 5701 ccttttttacg gttcctggcc ttttgctggc cttttgctca
     catgt
```

The AAV plasmid library was packaged similarly to a previously described approach (Chow, R. D., et al. (2017) *Nat Neurosci*). Low-passage HEK293FT cells were used for AAV production. Briefly, 2 h before transfection, D10 medium was replaced by pre-warmed DMEM (FBS-free). For each 15 cm-plate, HEK293FT cells were transiently transfected with 5.2 μg transfer (AAV-Surf), 8.9 μg serotype (AAV9) and 10.4 μg packaging (pDF6) plasmids using 130 μL PEI. After 6-12 h of transfection, DMEM was replaced with 20 mL pre-warmed D10 medium. Cells were dislodged and transferred to 50 mL Falcon tubes after 72 h post-transfection. For AAV purification, 1/10 volume of pure chloroform was added and incubated at 37° C. with vigorously shaking for 1 h. NaCl was added to a final concentration of 1 M, shaking the mixture until all NaCl was dissolved, then pelleted at 20,000×g at 4° C. for 15 min. The aqueous layer was gently transferred to another clean tube and the chloroform layer discarded. 10% (w/v) of PEG8000 was added and the tubes shaken until dissolved. The mixture was incubated on ice for 1 h followed by centrifugation at 20,000×g at 4° C. for 15 min. The supernatant was discarded and the pellet was resuspended with 5-15 mL PBS containing $MgCl_2$ and benzonase (Sigma), then incubated at 37° C. for at least 30 min. One volume of chloroform was added, shaken vigorously and spun down at 15,000×g at 4° C. for 15 min. The aqueous fraction was collected carefully and concentrated using AmiconUltra 100 kD ultracentrifugation units (Millipore). Virus was aliquoted and stored in −80° C. To measure the virus titer, RT-qPCR was performed using Taqman assays (ThermoFisher) targeted to human U6 promoter.

Cell culture for cell lines and primary T cells: HEK293FT, U87, GL261, and GL261 cell lines were obtained from the American Type Culture Collection (Manassas, VA) and cultured in DMEM (Gibco) medium supplemented with 10% FBS (Sigma) and 200 U/mL penicillin-streptomycin (Gibco), named D10 medium. Cells were typically passaged every 1-2 d at a split ratio of 1:2 or 1:4. Cells were usually passaged when the confluency reached 80%. Naïve $CD8^+$ T cells were cultured in RPMI-1640 (Gibco) medium supplemented with 10% FBS, 2 mM L-Glutamine, 200 U/mL penicillin-streptomycin (Gibco), and 49 µM β-mercaptoethanol (Sigma). For in vivo experiments, complete RPMI-1640 medium was supplemented with 2 ng/mL IL-2, 1 µg/mL anti-CD28, 2.5 ng/mL IL-7 and 50 ng/mL IL-15 cytokines or antibody. For in vitro experiments, media was supplemented with 2 ng/mL IL-2, 1 µg/mL anti-CD28 and 2 ng/mL IL-12p70. All cytokines and antibody were purchased from BioLegend.

Generation of stable cell lines: For GBM studies, GL261 cancer cells were infected with Firefly Luciferase (FLuc)-expressing lentivirus (with puromycin resistance). After 24 h of virus transduction, cells were selected with 6 µg/mL puromycin, until all cells died in the control group. GL261-FLuc-mCh-cOVA clonal cell lines were generated based on the GL261-FLuc cell line, where GL261-FLuc cells were transduced with mCherry-cOVA (mCh-cOVA) lentivirus, then cultured individually in 96-well plates. 2-3 weeks later, positively expanded clones were identified using fluorescence microscopy. For breast cancer studies, E0771 cancer cells were infected with mCherry-cOVA (mCh-cOVA) lentivirus, then cells were cultured individually in 96-well plates. 2-3 weeks later, positively expanded clones were identified using fluorescence microscopy. Flow cytometry was performed to ensure the purity of each clone. At least two clones from each stable cell lines were established with high purity and used in the study.

Naïve $CD8^+$ T cell isolation and culture: Mesenteric lymph nodes (mLNs) and spleens were dissected from OT-1;Cas9β or Cas9β mice, then placed into ice-cold PBS supplemented with 2% FBS. Organs were mashed through a 100 µm filter and lymphocytes were re-suspended with 2% FBS. Red blood cells (RBCs) were lysed with 2 mL ACK lysis buffer (Lonza) per 5 spleens for 1-2 min at room temperature, then lysis was stopped by adding 48 mL 2% FBS PBS. RBCs lysed lymphocyte solution was filtered with 40 µm filters to remove cell debris. Naïve $CD8a^+$ T cell purification was performed using Naïve $CD8a^+$ T cell Isolation Kits according to Miltenyi Biotec's standard procedures. Naïve $CD8a^+$ T cells were cultured at $1-2\times10^6$ cells/mL density in 2 µg/mL anti-CD3c (BioLegend) treated plates or dishes, and cRPMI medium was supplemented with 2 ng/mL IL-2, 1 µg/mL anti-CD28, 2.5 ng/mL IL-7 and 50 ng/mL IL-15 cytokines or antibody. AAV-Surf $CD8^+$ T cell screen in a syngeneic mouse model of GBM: Naïve $CD8^+$ T cells were isolated from the spleen and lymph nodes of $Cas9^+$ mice. A total of $2\times10^7$ Naïve OT-1;Cas9 $CD8^+$ T cells were transduced with $10^{11}$ AAV-Surf virus. Syngeneic mouse models of GBM were setup with intracranial injection of native or luciferase-expressing GL261 cells (GL261 and GL261-FLuc, respectively) transplanted into the lateral ventricle (LV) of C57BL/6J mice. AAV-Surf infected $CD8^+$ T cells were adoptively transferred into GBM engrafted mice at day 10 via intravenous (tail vein) injection. Two screens were performed. The one with native GL261 GBM reached endpoint sooner (all mice euthanized by 20 dpi, "shorter term screen"), and the one with luciferase-expressing GL261 cells reached endpoint later (all mice euthanized by 92 dpi, "longer term screen").

Splinkerette PCR: Sleeping beauty transposon integration was detected by splinkerette PCR (Uren, A. G. et al., (2009) *Nature Protocols*. 4,789-798). Mouse OT-I;Cas9β $CD8^+$ T cells transduced with AAV-SB-CRISPR were collected for genomic DNA extraction using QIAamp Fast DNA Tissue Kit. A total of 1 µg genomic DNA was digested with Sau3AI (NEB) for 4h, then incubated at 65° C. to inactivate enzymes for 20 min. Splinkerette adaptors were generated by mixing long-strand adaptors and short-strand adaptors, then denatured and annealed by heating to 95° C. for 5 min and then cooled at room temperature. Annealed Splinkerette adaptors were used for ligation immediately or stored at −20° C. ~150 ng digested genomic DNA was ligated with 25 µM adaptor at 4° C. overnight using T4 ligase (NEB). A nested-PCR reaction was used to amplify transposon arm and its junction genomic DNA sequence. Splink 1 and SB-Right1 primers (Table 7) were used for $1^{st}$ round PCR, Splink 2 and SB-Right 2 primers (Table 7) were used for $2^{nd}$ round PCR. PCR products were run on 2% gels, and gel purified PCR products were prepared using a Nextera kit (Illumina) before sequencing.

Splinkerette data processing and analysis: Forward and reverse FASTQ reads and their reverse complements from Splinkerette samples were concatenated to obtain pooled reads for processing. BBDuk was used for quality trimming with the following settings trimq=27 minlen=80 maq=30 qtrim=rl. Cutadapt was used with the following settings -e 0.1--overlap 15 to discard reads outside of the integrating transposon arms (and therefore corresponding to the vector), using the sequences CGCACGCGTTCTAGACTATA (SEQ ID NO: 69,839), TATAGGCATGCGGTAACCAC (SEQ ID NO: 69,840), and their reverse complements. Cutadapt was also used to trim the transposon arms using the sequence CAGTTGAAGTCGGAAGTTTA (SEQ ID NO: 69,841) and the following parameters -e 0.1 -m 15 --overlap 15. The resulting filtered reads were then mapped to the mouse genome (mm10) using BWA MEM to determine transposon integration sites. Mapped reads were converted to the BED format and intersected with reference annotations obtained from UCSC Table Browser to determine associated functional regions of integration sites.

Estimation of functional MOI of AAV-SB-CRISPR screen using single cell RT-qPCR: Mouse $CD8^+$ T cells were transduced with AAV-Surf library, with the same parameters as in the screen. T cells were cultured for 5 days, then diluted as single cells (one cell per well) in a 96-well PCR plate. Untransduced T cells (PBS group) were used as negative control. To detect sgRNA expression as a proxy for functional MOI, a Single Cell-to-CT™ Kit (Ambion) was used for quantification of sgRNA expression at a single-cell level. The fraction of single cells expressing sgRNAs out of total cells was used to estimate functional MOI. The detailed qPCR protocol was provided by the manufacturer.

GBM induction by intracranial surgery and cancer cell transplantation: Same gender mice were used in each batch experiment to ensure consistency. Mice were anesthetized by intraperitoneal injection of ketamine (100 mg/kg) and xylazine (10 mg/kg). Carprofen (5 mg/kg) was also administered intraperitoneally as a pre-emptive analgesic. Once the mice were in deep anesthesia, they were immobilized in a stereotaxic apparatus (Kopf or Stoelting) using intra-aural positioning studs and a tooth bar to immobilize the skull (similar to described in Chow, R. D., et al. (2017) *Nat Neurosci*). According to the mouse brain stereotaxic coordinates, the lateral ventricle (LV) was located at 0.6-1.0 mm caudal/posterior to bregma, 0.8-1.5 mm right-side lateral to bregma and 2.0-3.0 mm deep from the pial surface for injection (coordinates: A/P −0.6 to −1.0, M/L 0.8 to 1.5, D/V −2.0 to −3.0). A ~1 mm hole was drilled on the skull surface and $5 \times 10^4$ to $1.2 \times 10^6$ cancer cells were injected, dependent upon specific experiments. The injection rate was controlled at 2 μL/min by an UltraMicroPump 3 (World Precision Instruments). After injection, the incision was closed with tissue adhesive (3M Vetbond) and 500 μL lactated Ringer's solution was subcutaneously injected. Mice were placed under the heat lamp until they recovered.

Adoptive cell transfer: Naïve CD8$^+$ T cells were infected with virus at day 0, then T cells were cultured for 3 days before intravenous injection. For the shorter term AAV-Surf screen, $1.8 \times 10^6$ OT-1;Cas9β CD8$^+$ T cells were injected. $4 \times 10^6$ OT-1;Cas9β CD8$^+$ T cells were injected for the longer term screen. For the validation experiments, OT-1;Cas9β or Cas9β CD8$^+$ T cells were injected. The number of cancer cells and T cells injected are illustrated in the figures and figure descriptions. After T cell injection, mice were monitored every day and euthanized when signs of discomfort appeared, in accordance with the institutional guidelines (low activity, stop eating and drinking, body start dehydrate). Brains were isolated and stored at −80° C. for genomic DNA extraction and readout, or fixed in 4% PFA for hematoxylin and eosin (H&E) staining.

Organ isolation and genomic DNA extraction: Each mouse was dissected after being euthanized. Whole brains, spleens, draining lymph nodes and non-draining lymph nodes were isolated for genomic DNA extraction. Genomic DNA extraction was performed as previously described (Chen, S., et al. (2015) *Cell* 160, 1246-1260). Briefly, each brain and spleen was put in a 15 mL Falcon tube. 6 mL NK Lysis Buffer (50 mM Tris, 50 mM EDTA, 1% SDS, pH adjusted to 8.0) with 30 μL of 20 mg/mL Proteinase K (Qiagen) was added to each tube and incubated at 55° C. overnight. After the tissue disappeared, 30 μL of 10 mg/mL RNase A (Qiagen) was added to the lysed sample, and the tubes were inverted 20 times and incubated at 37° C. for 30 min. Digested tissues were cooled on ice before adding 2 mL cold 7.5 M ammonium acetate (Sigma) to precipitate the proteins. Samples were mixed thoroughly after adding ammonium acetate and vortexing for 10 s, followed by centrifuging at 4,000×g at 4° C. for 15 min. After the spin, the supernatant was removed to a new 15 mL Falcon tube and the pellet discarded. 6 mL 100% isopropanol was added and the tubes were inverted until flocculent DNA was observed. Samples were centrifuged at 4,000×g at 4° C. for 10 min. Genomic DNA pellets were washed one time with 70% ethanol, and then centrifuged at 4,000×g at 4° C. for 5 min. The supernatant was discarded and remaining ethanol removed using a pipette. Genomic DNA was air dried for 30-60 min, then resuspended in 0.5-1 mL nuclease-free $H_2O$ and incubated overnight at room temperature. The next day, the gDNA solution was transferred to eppendof tubes and concentrations were measured using a Nanodrop (Thermo Scientific). For cell pellets, 100-200 μL QuickExtract solution (Epicentre) was directly added to cells and incubated at 65° C. for 30 min. For mouse lymph nodes, QIAmp Fast DNA Tissue Kit (Qiagen) was used for gDNA extraction following the manufacturer's protocol.

SgRNA readout and deep sequencing: Two rounds of PCR were used for the sgRNA library readout, where the first PCR used enough genomic DNA (~2 μg per reaction) to ensure capture the full representation of the screen and the second PCR used 1 μL PCR #1 product and barcoded primers, each sample amplified used different barcoded primers and pooled same quantity PCR products for Illumina sequencing. For PCR #1, primer forward: 5'-aatggactatcatatgcttaccgtaacttgaaagtatttcg-3' and primer reverse: 5'-ctttagtttgtatgtctgttgctattatgtctactattctttccc-3' were used to amplify sgRNA cassette under cycling condition: 98° C. for 1 min, 25 cycles of (98° C. for 1 s, 62° C. for 5 s, 72° C. for 15 s), and 72° C. 2 min for the final extension. All PCR reactions were performed using Phusion Flash High Fidelity Master Mix or DreamTaq Green DNA Polymerase (ThermoFisher).

PCR #1 products for each biological sample were pooled and used for amplification with barcoded second PCR primers (Table 2; SEQ ID NOs: 7,629-7,644). The cycling condition of PCR #2 were: 98° C. for 30 s, 30-35 cycles of (98° C. for 1 s, 62° C. for 5 s, 72° C. for 15 s), and 72° C. 2 min for the final extension. Second PCR products were pooled and then normalized for each biological sample before combining uniquely barcoded separate biological samples. The pooled product was then gel purified from a 2% E-gel EX (Life Technologies) using the QiaQuick kit (Qiagen). The purified pooled library was then quantified with a gel-based method using the Low-Range Quantitative Ladder (Life Technologies), dsDNA High-Sensitivity Qubit (Life Technologies), BioAnalyzer (Agilent) and/or qPCR. Diluted libraries with 5-20% PhiX were sequenced with MiSeq, HiSeq 2500 or HiSeq 4000 systems (Illumina).

AAV-SB-CRISPR screen data processing: Raw single-end fastq read files were filtered and demultiplexed using Cutadapt (Langmead, B., et al. (2009) *Genome Biol* 10, R25). To remove extra sequences downstream (i.e. 3' end) of the sgRNA spacer sequences, the following settings were used: cutadapt --discard-untrimmed -a GTTTTAGAGCTAGAAATGGC (SEQ ID NO: 69,822). As the forward PCR primers used to readout sgRNA representation were designed to have a variety of barcodes to facilitate multiplexed sequencing, these filtered reads were then demultiplexed with the following settings: cutadapt -g file: fbc.fasta --no-trim, where fbc.fasta contained the 12 possible barcode sequences within the forward primers. Finally, to remove extra sequences upstream (i.e. 5' end) of the sgRNA spacers, the following settings were used: cutadapt --discard-untrimmed -g GTGGAAAGGACGAAACACCG (SEQ ID NO: 69,823). Through this procedure, the raw fastq read files could be pared down to the 20 bp sgRNA spacer sequences. The 20 bp sgRNA spacer sequences from each demulitplexed sample were then mapped and sgRNA spacers designed for the Surface library (SEQ ID NOs. 1-6,628).

A bowtie index of the sgRNA library was generated using the bowtie-build command in Bowtie 1.1.2. The filtered fastq read files were mapped to the index using the following settings: bowtie -v 1 --suppress 4,5,6,7 --chunkmbs 2000 -best. Using the resultant mapping output, the number of reads that had mapped to each sgRNA within the library was quantified.

Analysis of CRISPR screens using RIGER: For RIGER analysis of CRISPR screens, read count tables were used to calculate log fold changes for tumor versus cell samples in order to score and rank sgRNAs, with ties in rank broken by random order. This data was then used as input to a Java-based implementation of RIGER (github.com/broadinstitute/rigerj) in order to generate p-values and gene rankings based on consistent enrichment across multiple sgRNAs for identification of candidate genes (Shalem, O., et al. (2014) Science 343: 84-87). Both the second highest-ranking sgRNA and the weighted sum scoring methods were used for computation of gene rankings, and compared to ensure consistency between methods.

Analysis of CRISPR screens using MAGeCK: Model-based Analysis of Genome-wide CRISPR/Cas9 Knockout (MAGeCK) algorithm (Li, W., et al. (2014) Genome Biol 15, 554) was used as an independent method to quantify enrichment of candidate genes for both the infiltration and survival screens. For MAGeCK analysis, read count tables were used as inputs to a command-line-based tool (sourceforge.net/p/mageck/wiki/Home/). The treatment group was defined as the tumor samples and the control group was defined as the cell pellet samples. A list of non-targeting control sgRNAs were provided for normalization and generation of the null distribution of RRA. Native MAGeCK plotting functions were used for visualization of RRA score and p-value distributions and individual sgRNA read counts of selected genes.

Survival analysis: Mice with glioblastoma (GBM) rapidly deteriorated in their body condition score, which was totally different from other tumor types. Mice with observed macrocephaly and body condition score≤1 were euthanized and the euthanasia date was recorded as the last survival date. Sometimes, mice died unexpectedly because brain tumors progressed fast, so the date of death was recorded as the last survival date. For the subcutaneous and fat pad tumor modeling, once tumor volume was over 2500 mm$^3$, the mouse was euthanized and the euthanasia date was recorded as the last survival date. T cell adoptive transfer with subcutaneous tumor model in Rag1$^{-/-}$ mice: 4×10$^6$ GL261-FLuc-mCh-rOVA #2 cells were subcutaneously injected into male Rag1$^{-/-}$ mice. Seven days post-transplantation, OT-1; Cas9β CD8$^+$ T cells were isolated and transduced with AAV sgRNA. Three days later, 1×10$^6$ of CD8$^+$ T cells were intravenously injected in tumor-bearing Rag1$^{-/-}$ mice. Tumor size was measured in a blinded fashion approximately every 2-3 days after adoptive T cell transfer. Tumor volume was calculated as 7c/6×(length×width×height) of the tumor.

T cell adoptive transfer with a subcutaneous glioma tumor model in Rag1$^{-/-}$ mice: 4×10$^6$ GL261-FLuc-mCh-rOVA cells were subcutaneously injected into male Rag1$^{-/-}$ mice. 7 days post-transplantation, OT-I;Cas9β CD8$^+$ T cells were isolated and transduced with AAV-sgPdia3, 3 days later, 1×10$^6$ of CD8$^+$ T cells were intravenously injected in tumor-bearing Rag1$^{-/-}$ mice. Tumor size was measured in a blinded fashion approximately every 3-5 days after adoptive T cell transfer. Tumor volume was calculated as π/6×(length× width×height) of the tumor.

Mouse brain dissection and histology: Mice were euthanized by cervical dislocation or carbon dioxide asphyxiation. Mouse brains were carefully dissected then fixed in 4% PFA for 2-3 days. Brains were embedded in paraffin, sectioned at 4 μm and stained with hematoxylin and eosin (H&E). Slides were scanned using an Aperio digital slide scanner (Leica) to quantify tumor size.

Brain tumor monitoring and IVIS imaging: Mice were monitored for brain tumor development by observation of macrocephaly, as well as by in vivo luciferase imaging where GL261-FLuc cells were used. Mice were euthanized as poor body condition and/or macrocephaly developed. Mouse IVIS imaging was performed by intraperitoneally injecting 150 mg/kg D-Luciferin (PerkinElmer). Bioluminescence signal intensity was measured by drawing a region of interest over the brain region after 10 min of Luciferin injection. Flow cytometry: T cells were collected and washed one time using MACS buffer (0.2% BSA and 5 mM EDTA in PBS) before staining. T cells were stained on ice for 15-30 min after adding antibodies (1:200 dilution). Samples were run on a BD FACSAria cytometer, and analysis was performed using FlowJo software 9.9.4 (Threestar, Ashland, OR).

Mouse brain TIL analysis: 8-10 week-old Rag 1$^{-/-}$ mice were injected with GL261-mCh-rOVA #1 cells, OT-I;Cas9β CD8$^+$ T cells. T cells were isolated and infected with AAV-sgMgat5 and AAV-sgPdia3 virus after luciferase signal was observed in the mouse brain. 5×10$^6$/mouse OT-I;Cas9β CD8$^+$ T cells were i.v injected. Brain tumors were isolated after 5 days of i.v injection. Mice were sacrificed, and whole brains were quickly isolated and put into cold PBS with 2% FBS. After hindbrain and olfactory bulb removal, the brain tumours were crushed using two glasses with rough surface, then gently mashed into small pieces. Collagenase and dispase (Roche) were used for tissue digest at 37° C. for 1 h in the shaking block. Digested samples were quenched by adding cold RPMI-1640, then centrifuging at 500×g for 5 min. Cell pellets were resuspended with 2 mL ACK lysis buffer for 2 min followed by dilution with 2% FBS PBS, filtered with 40 μm filters to remove tissue aggregates. Ficoll density centrifugation was performed to enrich mononuclear cells. Enriched cells were stained with antibodies for 30 min on the ice, then washed with MACS buffer (0.2% BSA and 5 mM EDTA in PBS) before running on a FACS machine.

Intracellular flow cytometry: Intracellular flow cytometry was performed to detect the expression level of IFNγ. Briefly, naïve CD8 T cells were transduced with AAV after isolation. Five days after infection, T cells were transferred into a new 6-well plate without CD36 incubation, and supplemented with the new media including IL-2. After 12 h rest, T cells were re-stimulated with different concentrations of CD3c. Media was supplied with brefeldin A, 2 ng/mL IL-2, 1 μg/mL anti-CD28, and 2 ng/mL IL-12p70. T cells were incubated for 4 h in the incubator. T cells were collected and stained with anti-CD3 PE and anti-CD8 PE/cy7, after membrane protein staining, cells were fixed and permeabilized, then anti-IFNγ APC was used for intracellular IFNγ staining. RT-qPCR: Total RNA was extracted from CD8$^+$ T cells using RNasy Plus Mini Kit (Qiagen). Gene expression was quantified using Taqman Fast Universal PCR Master Mix (Thermo Fisher) and Taqman probes (Invitrogen). Relative mRNA expression was determined via the ΔΔ$C_t$ method.

T7 endonuclease I assay (T7EI): Mouse CD8$^+$ T cells infected with AAVs, or human CD8$^+$ T cells electroporated with RNPs, were collected for genomic DNA extraction using QIAmp Fast DNA Tissue Kit (Qiagen). PCR was performed using site-specific perimers with Phusion Flash High Fidelity Master Mix (ThermoFisher) under cycling condition as: 98° C. for 1 min, 35 cycles of (98° C. for 1 s, 60° C. for 5 s, 72° C. for 25 s), and 72° C. 2 min for the final extension. PCR products were gel purified using the QIA-quick Gel Extraction Kit (Qiagen). 200 ng of PCR DNA in Buffer 2 (NEB) was annealed on a thermocycler with the following setting: 95° C., 5 min, 90° C., 1 min, 85° C., 1 min, 80° C., 1 min, 75° C., 1 min, 70° C., 1 min, 65° C., 1 min, 60° C., 1 min, 55° C., 1 min, 50° C., 1 min, 45° C., 1 min, 40° C., 1 min, 35° C., 1 min, 30° C., 1 min, 25° C., 1 min, and hold at 4° C. 10 units of T7 endonuclease I (NEB) was added to digest the re-annealed DNA for 30-60 min at 37° C., then being loaded into the 2% E-gel, the gel imaging was performed using image Lab (Bio-Rad).

Detection of AAV-mediated mutagenesis by Nextera: The PCR products were used for Nextera library preparation following manufacturer protocols (Illumina). Reads were mapped to the amplicon sequences using BWA-MEM (Durbin, R. et al. (2009) Bioinformatics 25, 1754) at default settings. Indel variants were first processed with Samtools with the settings samtools mpileup -d 1000000, then piped into VarScan v2.4.1 with the settings pileup2indel --min-coverage 2 --min-reads2 2 --min-var-freq 0.00001.

Human primary $CD8^+$ T cell endogenous gene knockout: Human primary $CD8^+$ T cells were isolated from health donors. $CD8^+$ T cells were stimulated with anti-CD3/CD28 beads (Invitrogen) every 7-10 days. T cells were cultured in X-VIVO™ 15 media (Lonza) supplied with 5% human serum and IL-2. Before the electroporation, crRNA and tracrRNA were 1:1 ratio mixed (final concentration was 44 μM), heat at 95° C. for 5 min, then cool to room temperature. 0.3 μL Cas9 protein (61 μM) was mixed with 0.2 μL Buffer R (Neon Transfection Systerm Kit, Thermo Fisher), then being mixed with 0.5 μL annealed crRNA:tracrRNA duplex, incubated the mixture at room temperature for 20 min. High viability cells were collected and washed with PBS to completely remove the media. $5 \times 10^5$ of T cells were resuspended in 9 μL Buffer R per electroporation, then 1 μL RNP complex was added and mixed well using pipette. 10 μL of cell:RNP mixture was loaded into the Neon pipette without any bubbles. The tip of the loaded Neon pipette was inserted into the pipette station. The setup of the electroporation parameter was set at 1600 V, 10 ms for 3 pluses. After electroporation, cells were transferred to a 24-well plate with pre-warmed media, then cultured in a tissue culture incubator.

Mass cytometry (CyTOF): High targeting efficiency of PDIA3 was confirmed by surveyor assay and Nextera sequencing. Human $CD8^+$ T cells were collected and washed with PBS, resuspended cell to $1 \times 10^7$/mL in PBS and add Cell-ID Cisplatin (Fluidigm) to a final concentration of 5 μM. Cells were incubated at room temperature for 5 min, then washed with Maxpar Cell Staining Buffer (Fluidigm). Each replicate was aliquoted with $2 \times 10^6$ cells in a volume of 50 μL, adding 50 μL of surface marker antibody cocktail (Fluidigm or provided by the Yale CyTOF core) in each tube. The tube was gently mixed with pipette and incubated at room temperature for 30 min. Following the incubation, cells were washed with Maxpar Cell Staining Buffer two times. Cells were fixed by adding 500 μL Maxpar Fix I Buffer (Fluidigm) to each tube, and incubated for 15 min at room temperature. Cells were then washed with Maxpar Perm-S Buffer (Fluidigm) for two times. 50 μL of the cytoplasmic/secreted antibody cocktail was added into fixed cells which was resuspended in 50 μL Maxpar Cell Staining Buffer. Cells were incubated at room temperature for 30 min. After incubation, cells were washed with Maxpar Cell Staining Buffer for two times. Finally, cells were incubated in intercalation solution (Fluidigm) in a final concentration of 125 nM, then incubated overnight at 4° C. Before running on a CyTOF machine, cells were washed with Maxpar Cell Staining Buffer and adjusted cell concentration to $5-7 \times 10^5$/mL with water. All data were collected on a CyTOF Helios instrument (Fluidigm).

CyTOF data processing: CyTOF quality control pre-filtering performed by gating in FlowJo (live-dead, CD3, CD8). Channel signal values were exported as CSV and analyzed using custom scripts in R. Dimensionality reduction was performed by t-SNE (Rtsne package), followed by k-means and hierarchical clustering.

Immunoblot and TCR signaling: Human $CD8^+$ T cells electroporated with RNP were collected and washed with PBS to remove media. $3 \times 10^6$ cells were lysed with RIPA lysis buffer and incubated on the ice for 30 min, followed by centrifuging at 13,000×g for 15 min at 4° C. The supernatant was collected for protein quantification. The total protein concentration was measure by using a Bradford protein assay (Bio-Rad), a total of 10 μg protein per sample was loaded into SDS-PAGE gel (Bio-Rad), proteins in the gel were transferred into Amersham Protran 0.45 μm NC Nitrocellulose Blotting membrane (GE Healthcare) after electrophoresis. Membranes were blocked with 2% BSA in TBST for 1 h at room temperature, followed by the primary antibody incubation at 4° C. overnight.

Anti-PDIA3 antibody was from Atlas Antibodies (HPA003230). Antibody binding was detected using horseradish peroxidase-conjugated secondary antibody and ECL substrate (Bio-Rad). For the TCR signaling experiment, mouse naïve $CD8^+$ T cells were isolated from OT-I;Cas9β mice, then infected with AAV6 packaged with Mgat5, Pdia3 or Vector control sgRNAs. T cells were washed with PBS and cultured with cRPMI media without CD3ε and CD28 antibodies (resting) overnight at day 5 after AAV infection. Following resting, T cells were collected and washed with cold PBS, $3-5 \times 10^6$ cells per sample were resuspended with cold PBS containing biotin anti-mouse CD3ε (BioLegend) and Streptavidin (BioLegend) and incubated on the ice for 30 min. T cells were then re-stimulated at 37° C. after ice incubation. Following stimulation cells were lysed with RIPA lysis buffer which containing protease and phosphatase inhibitor cocktail (ThermoFisher). The standard immunoblot assay was performed as described elsewhere herein.

Single-cell RNA sequencing (scRNA-seq): Naïve $CD8^+$ T cells were isolated from OT-I;Cas9 mice, T cells were stimulated with anti-CD3ε and anti-CD28 as previously described. $CD8^+$ T cells were infected with AAV6-sgPdia3 and AAV6-Vector after being activated. At day 5 after AAV infection, T cells were collected and dead cells were removed using Dead cell removal kit (Miltenyi Biotec). T cells were resuspended in PBS in a concentration of $1 \times 10^6$/mL. 10,000 $CD8^+$ T cells per samples were used for scRNA-seq by following the protocol as 10× Genomics provided.

scRNA-seq data processing: Read count matrices from single cell RNA sequencing samples were obtained by mapping using native 10× Cell Ranger output. Samples were pooled together into a single CSV and analyzed using custom scripts in R. Reads were pre-filtered by ribosomal and mitochondrial genes, normalized by cell per 10000 reads, then log transformed. For cell percentage quantifications, cells were first pre-filtered, in order, by $Ptprc^+$, $Cd3e^+$, $Cd8a^+$, and $Cd4^-$ expression. Marker expression status on high-confidence Cd8 cells was then quantified individually for each marker of interest. Expression status for a given gene was thresholded at 0.1 normalized read value. Differential expression between sgPdia3 and AAV-vector control was performed by two-sided Wilcoxon signed-rank test by gene, with p-values adjusted by Benjamini & Hochberg. Significance was compared to differences in mean expression between populations. Dimensionality reduction was performed by t-SNE (Rtsne package), followed by k-means and hierarchical clustering. Heatmap.2 function used to show normalized gene expression for most variable genes.

Large-scale patient T cell immune signature data analysis using TIDE:The gene signatures of T cell dysfunction and prediction of cancer immunotherapy response on cancer patient data was performed using the TIDE algorithm as previously described in Jiang, P. et al. Signatures of T cell dysfunction and exclusion predict cancer immunotherapy response. *Nat Med* 24, 1550-1558 (2018). Gene expression level of PDIA3 was associated to CTL-mediated patient survival with or without checkpoint blockade treatment.

PDIA3$^{-/-}$-EGFRvIII-CAR-T cell establishment: NTC (non-targeting control crRNA electroporated T cells) and PDIA3$^{-/-}$ primary CD8$^+$ T cells were targeted with TRAC locus RNP complex, a total of ~6×10$^9$ viral genome copy of AAV6 HDR donor (LHA-EFS-EGFRvIII-CAR-RHA, SEQ ID NO: 69,749) was added into each electroporated T cell reaction (3×10$^6$ T cell/reaction) within 1 h after electroporation. See Table 8 for amplification and detection primers.

Human PDIA3$^{-/-}$-EGFRvIII-CAR-T cell co-culture (kill) assay: To sensitively detect PDIA3$^{-/-}$-EGFRvIII-CAR-T cell killing efficacy, U87-GL and U87-GLEvIII cell lines were established (using an EGFRvIII expression construct, SEQ ID NO: 69,748). 2×10$^4$ U87-GL or U87-GLEvIII cells were seeded in a 96-well white polystyrene: plate, then different T cell:cancer cell ratio (E:T ratio) co-cultures were set up. Cancer cell killing was measured after 24 h of co-culture by adding 150 µg/mL D-Luciferin (PerkinElmer) using a multichannel pipette. Luciferase intensity was measured by a Plate Reader (PerkinElmer).

Standard statistical analysis: Data between two groups were analyzed using a two-tailed unpaired t-test or non-parametric Wilcox test. Time-course data used Log-rank (Mantel-Cox) test, one-way ANOVA, two-way ANOVA, Wilcox test or Komogorov-Smirnov test as appropriate. The p values and statistically significance were estimated for all analyses. Prism (GraphPad Software Inc.) and RStudio were used for these analyses.

Phage display antibody generation: Immunoplate wells were coated with 100 µl of purified recombinant protein (5 µg/mL in coating buffer) for 2 h at room temperature or overnight at 4° C. After 5 rounds of selection, the coating protein concentration will be reduced as selection rounds increase (from 5 µg/mL to 1 µg/mL). At the same time, the same immunoplate wells were coated with 100 µl of streptavidin (5 µg/mL in coating buffer), a control plate was coated with 200 µl of cold blocking buffer (0.5% BSA in PBS), followed by incubation at room temperature shaking at 350 rpm for 2 h. After 1 h of blocking, 200 µl of blocking buffer was added to the target plate (with recombinant protein), followed by incubation at room temperature shaking at 350 rpm for 2 h. The solution in control plate was discarded, followed by washing with PT buffer (0.05% Tween 20 in PBS). 100 µl of phage library was then added to each well, followed by incubation at room temperature for 1 h shaking at 350 rpm. The target plate was then washed with PT buffer after 2 h blocking, before the phage library was transferred from control plate to target plate, and incubated at room temperature for 2 h while shaking at 350 rpm. The target plate was then washed with PT buffer, dried by shaking, then 100 µl 0.1 M HCl/well was added to elute bound phage, followed by incubation at room temperature for 5 min shaking at 350 rpm. All eluted phage was collected in 1.5 mL eppendorf tubes and had ⅛ volume of 1 M Tris-HCl added to neutralize pH. 4.5 mL Omni cells in 2YT media (O.D.=0.5-1.0) were then infected with 450 µl library "out", and 1000× KO7 helper phage was added after 30 min culture, followed by incubation at 37° C. for 45-60 min while shaking. All Omni cells infected with phage library and KO7 were pulled into a 250 mL flask containing 30 mL 2YT-Kan/Carb media, and incubated at 37° C. overnight. Omni cells were then spun down and all supernatant was transferred in a new 50 mL tube, added 1/5 volume of PEG/NaCl solution to precipitate the phage, incubated for 20 min on the ice, then centrifuged for 10 min at 13,000 rpm at 4° C. The supernatant was decanted, the remaining bound phage was resuspended with cold PBS for second round selection. Selection rounds 2-5 were performed similarly to further enrich high affinity phages. Phage ELISA was then performed to analyze binding clones. ELISA positive clones were then sequenced to confirm CDR sequence.

The results of the experiments are now described.

Figure 17A:
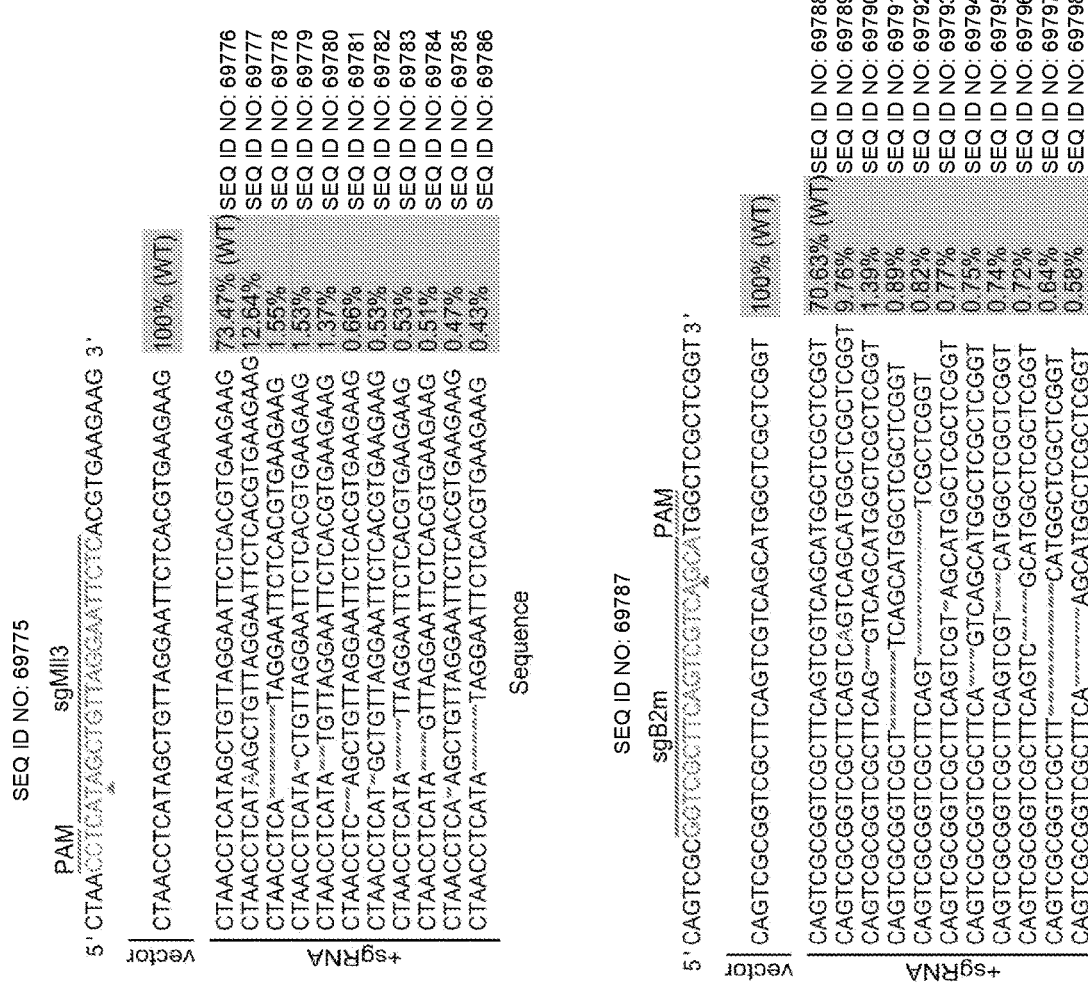
Figure 17C:
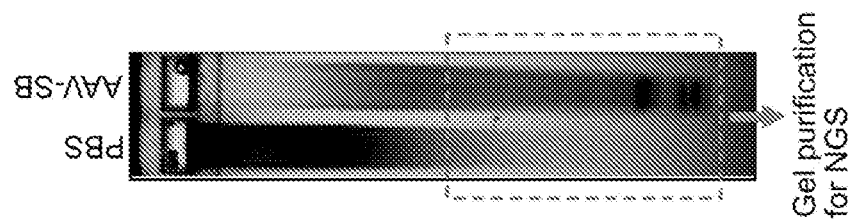
Figure 17B:
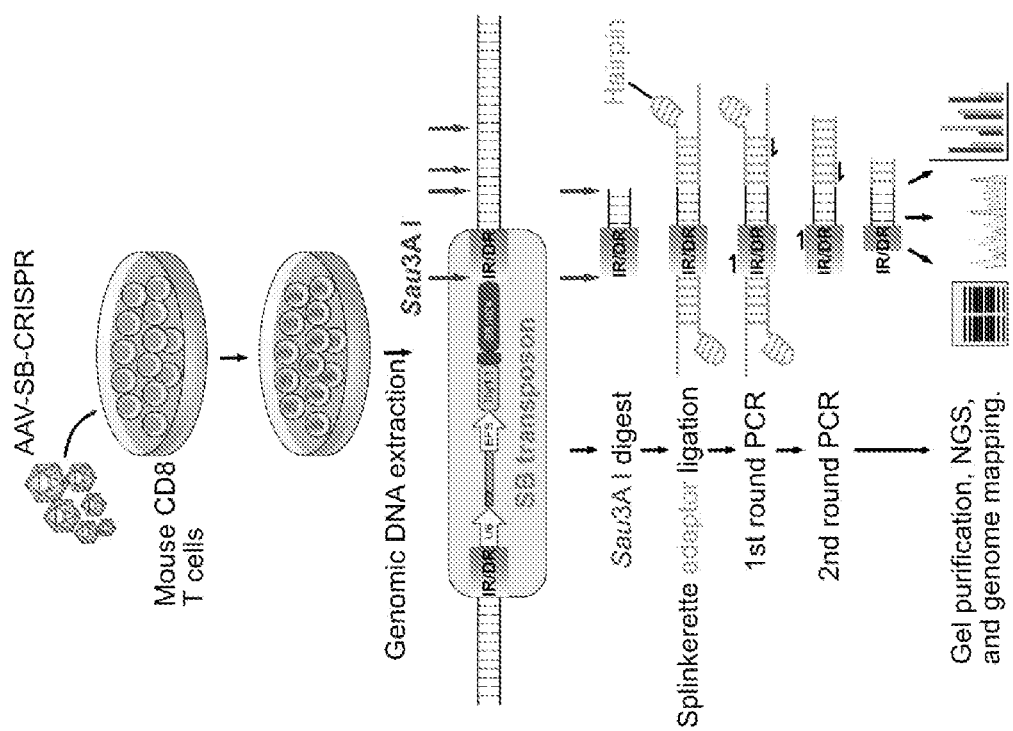

Example 1: Screening Surface Proteome Knockouts for Modulators of CD8$^+$ T Cell Infiltration into GBM A syngeneic mouse model of GBM with fully immunocompetent mice was utilized to perform a primary CD8$^+$ T cell screen in vivo. A hybrid AAV vector for CRISPR perturbation of primary T cells was created that utilizes a hyperactive Sleeping Beauty (SB) transposon system (AAV-SB100x), which enabled high efficiency transduction, efficient gene editing, and high-throughput genetic screens (SEQ ID NO: 69,821) (FIG. 1A). AAV was generated, transduced into mouse primary naïve CD8$^+$ T cells, and the genomic integration of AAV-SB100x was tested using splinkerette PCR (FIG. 17B). Electrophoresis of the splinkerette PCR amplification products from AAV-SB100x infected T cells, but not from uninfected T cells, showed multiple bands of varying intensity, indicating random genomic integration (Methods) (FIG. 17C). Sequencing of splinkerette PCR products revealed that they indeed mapped to the mouse genome with junctions to the SB transposon inverted repeats (IRs) (FIG. 17D). The genomic reads span across 18 out of 19 autosomes and both sex chromosomes (X and Y) in the mouse genome (FIG. 17E). Most of the integration sites mapped to intergenic regions and intronic regions, as compared to promoters, coding regions, or exonic untranslated regions (UTRs) (FIG. 17F), suggesting that these random integrations rarely disrupt essential coding or key functional elements.

Figure 18:
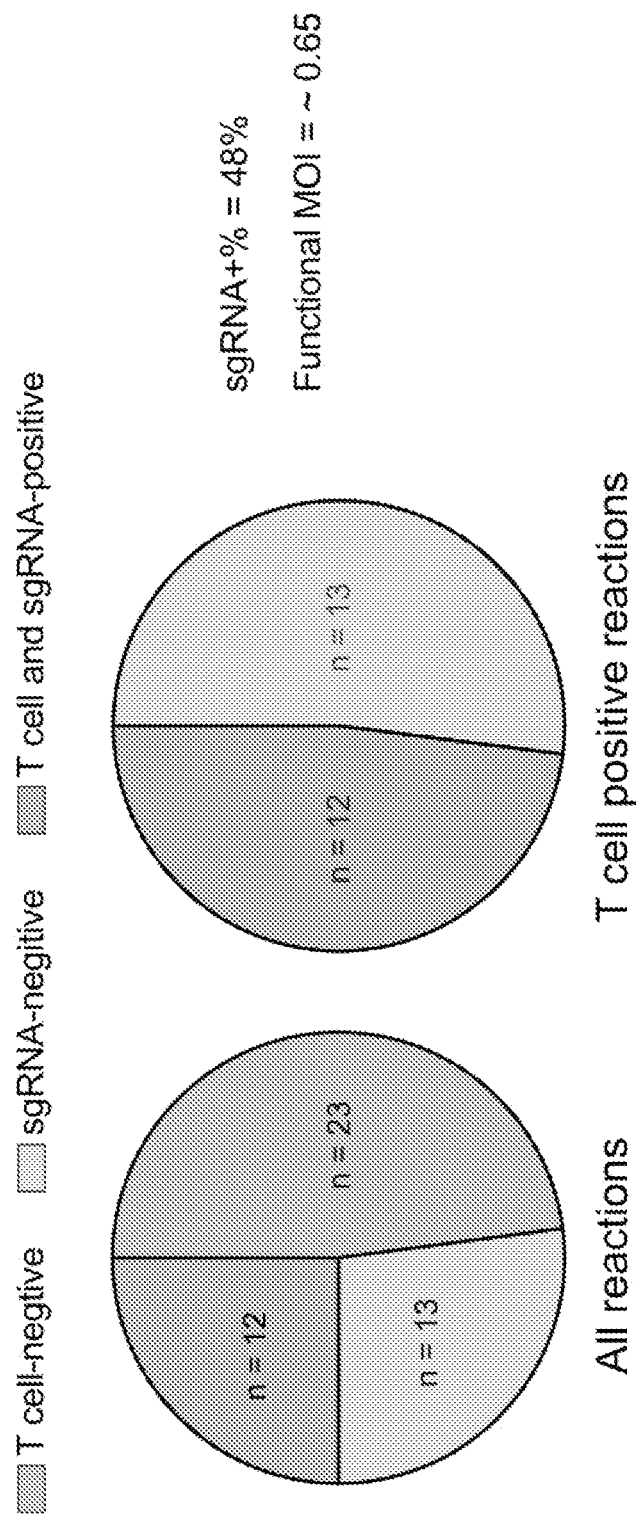
FIG. 18 is a series of graphs showing single cell RT-qPCR estimation of functional MOI of AAV-SB-CRISPR screen. Single cell RT-qPCR detection of single T cell expressing functional sgRNAs, for the estimation of functional MOI with exact transduction parameters in the AAV-Surf screen. PBS treated single T cells were used as a negative control. Numbers of wells without T cells, with sgRNA– T cells and with sgRNA$^+$ T cells were determined to estimate MOI.

To identify surface proteins that influence the CD8$^+$ T cell infiltration into GBM, two focused sgRNA libraries (surface libraries) were designed (first and second library). The libraries contained 6,628 or 61,911 sgRNAs that target 1,657 annotated surface protein encoding genes (4 sgRNAs per gene) (SEQ ID NOs. 1-6,628 and SEQ ID NOs. 7,837-64, 747), together with 1,000 or 5,000 non-targeting controls (NTCs) (SEQ ID NOs. 6,629-7,628 and SEQ ID NOs. 64,748-69,747). The surface library was cloned into the AAV-SB100x vector. Successful cloning of the AAV-surface CRISPR knockout library (AAV-Surf) was verified by sgRNA library readout followed by Illumina sequencing. AAV-Surf plasmid library was pool-packaged into a viral library at a titer of approximately 1.4×10$^{12}$ viral genome copy per milliliter (1.4×10$^{12}$ vg/mL). While AAV titer estimated by gc is often high, functional transduction can be multiple orders of magnitudes lower due to empty viral particles, defective particles, non-infectious particles, non-productive infections, and clearance by host cells. Therefore, functional multiplicity of infection (MOI) analysis was performed via single cell sgRNA qPCR of T cells, which were transduced with AAV-Surf library for 5 days. Single cells with functional sgRNA expression is estimated at 48%, or a functional MOI of 0.65 (FIG. 18).

Figure 1B:
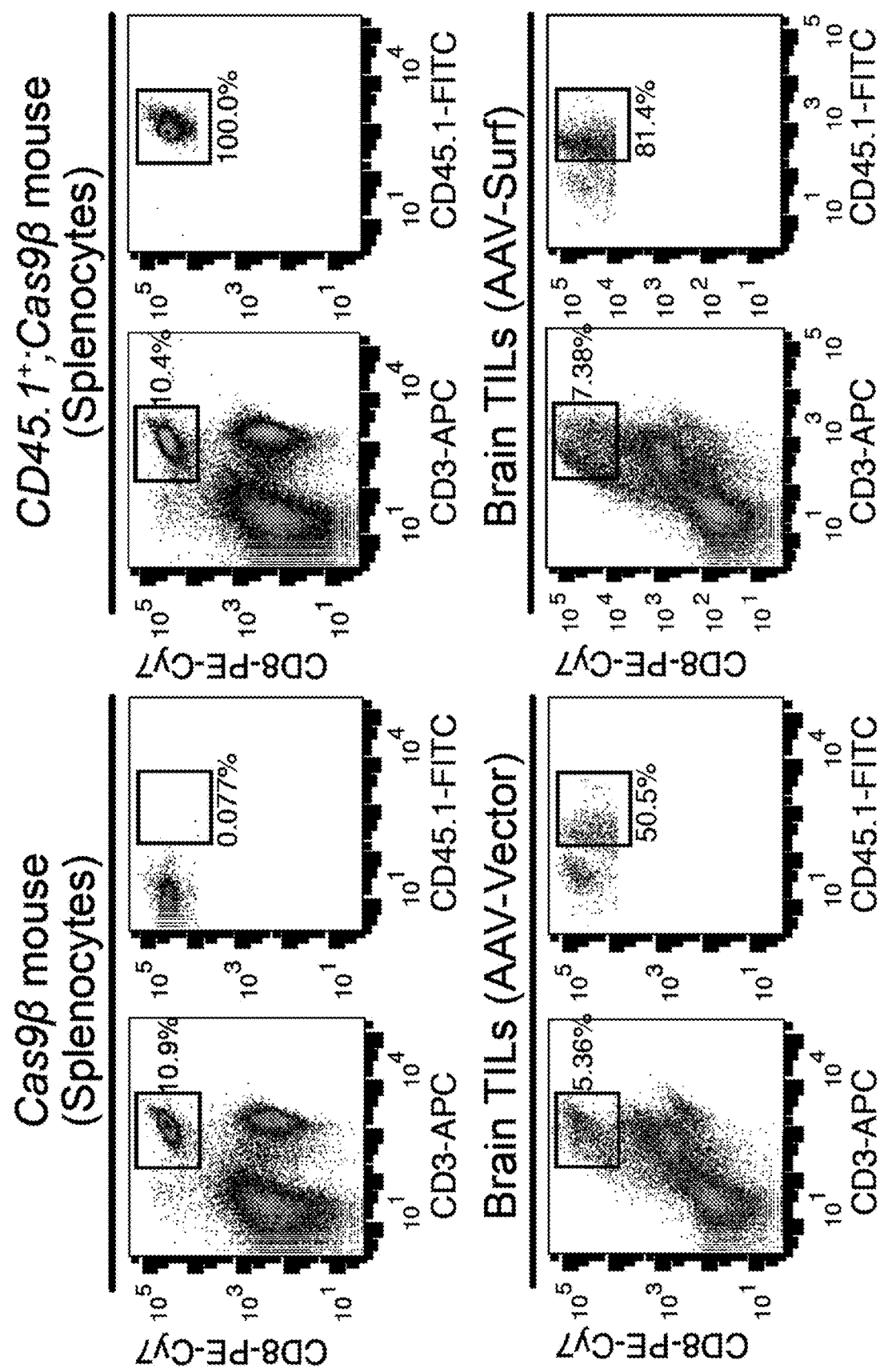
Figure 1C:
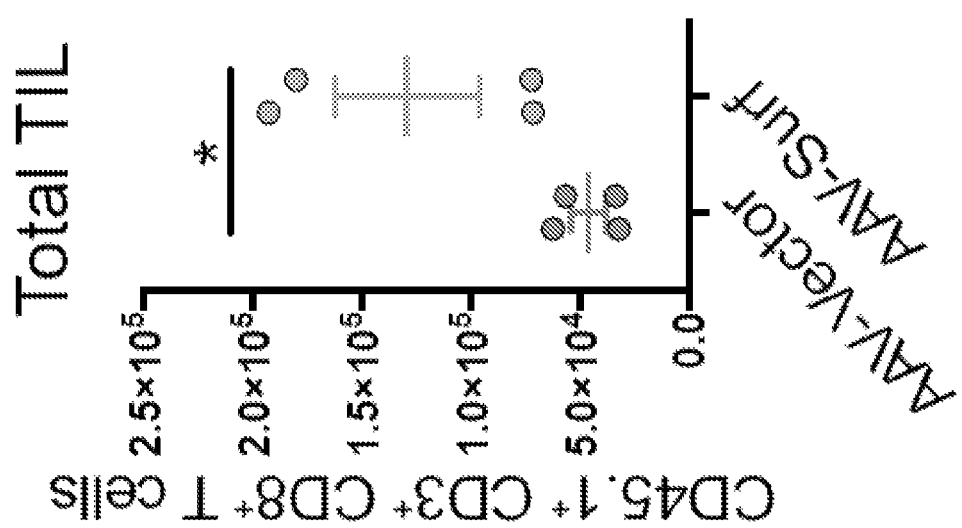
Figure 2D:
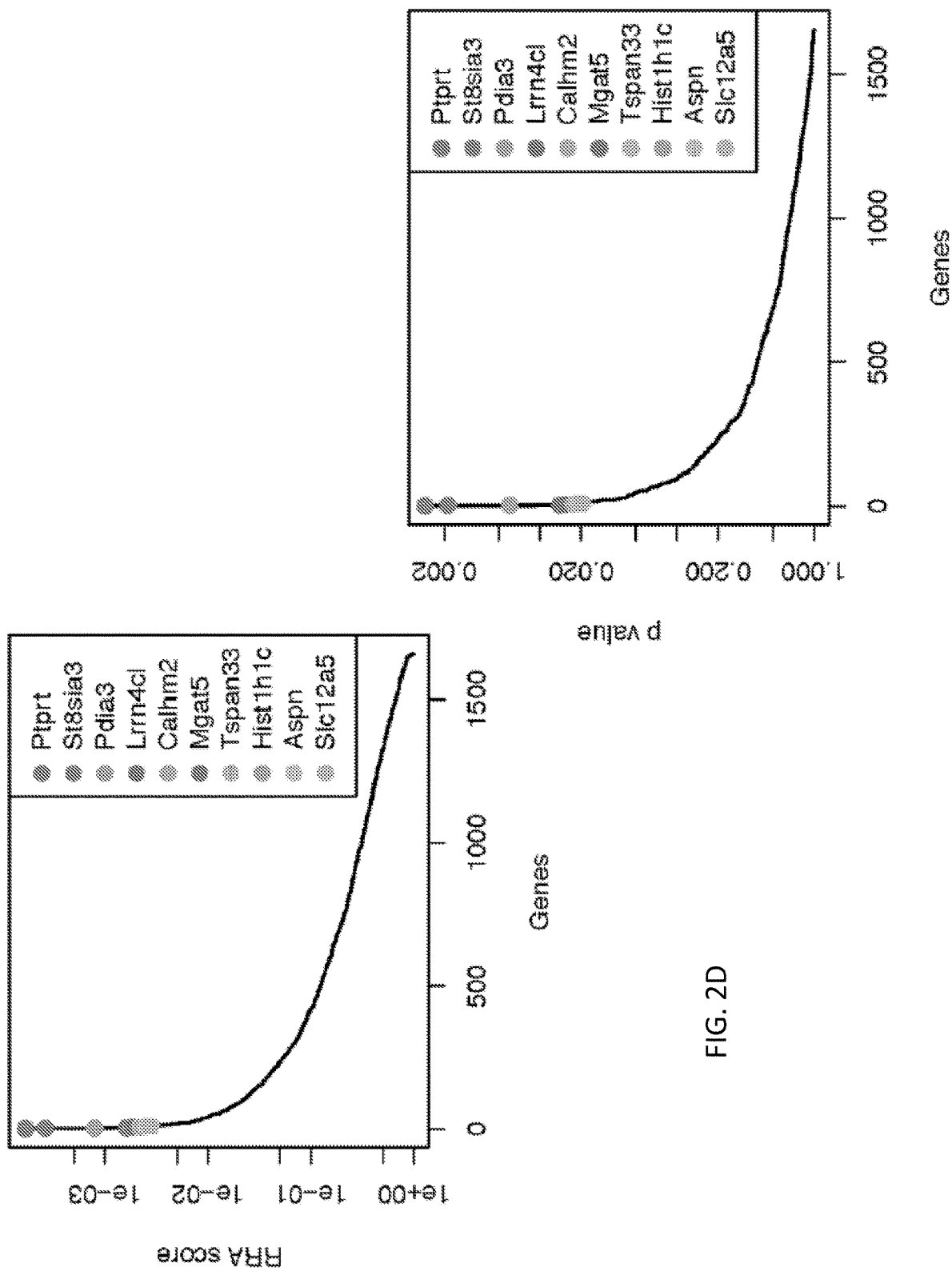
Figure 2F:
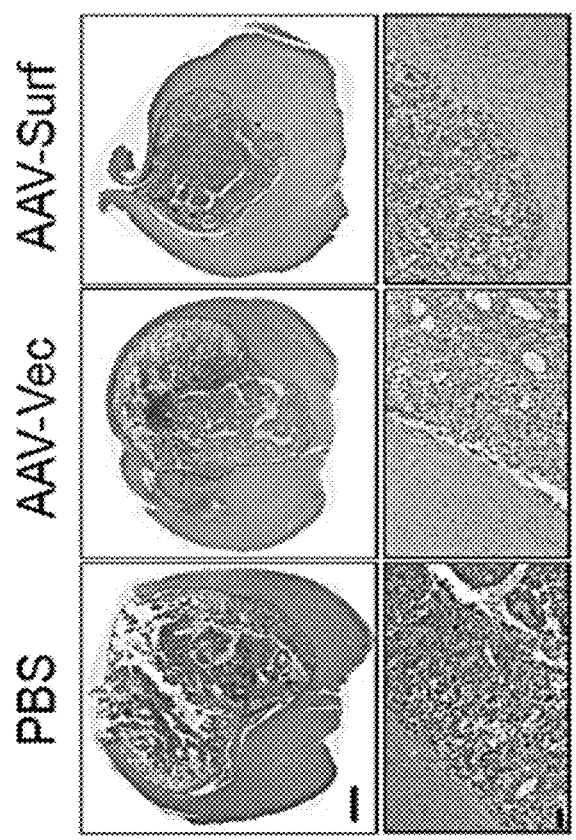
Figure 2E:
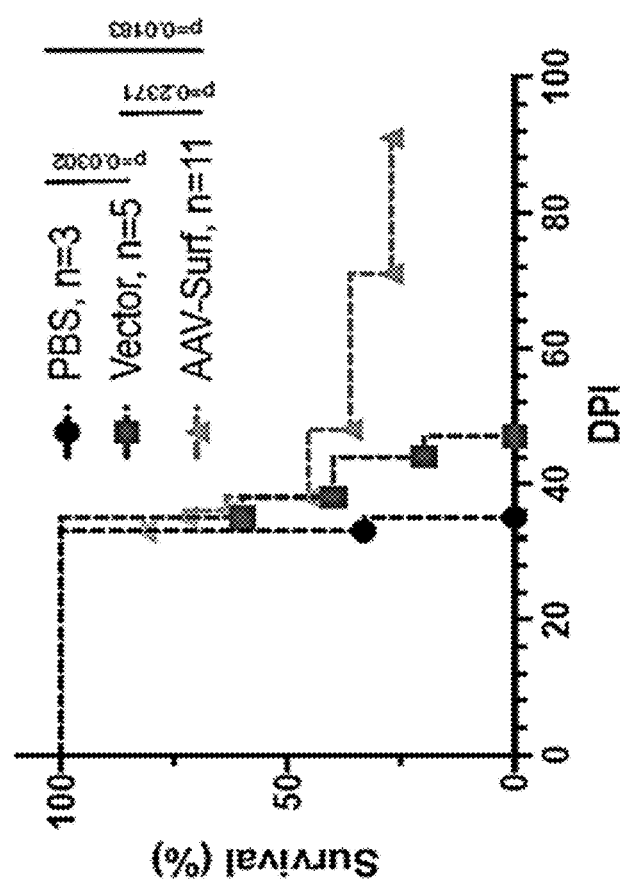
Figures 19A, 19B:
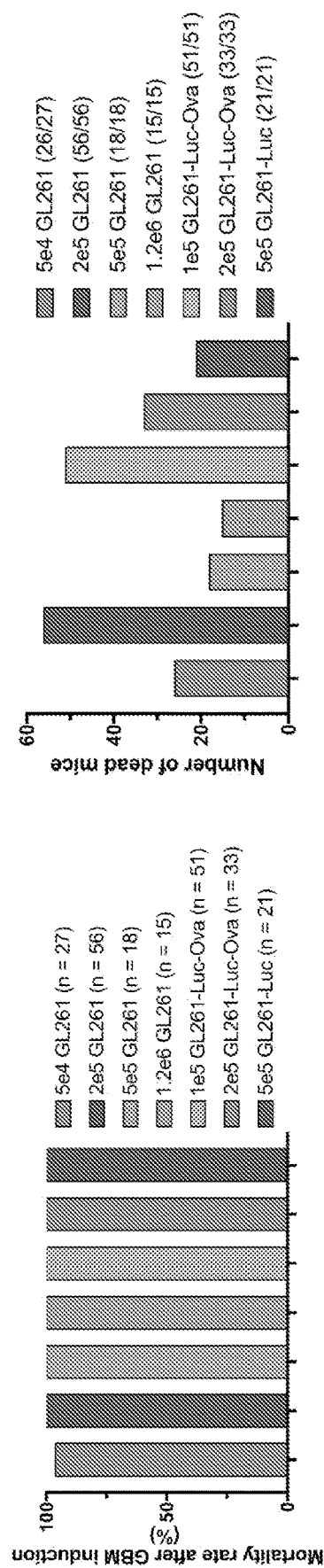
FIGS. 19A-19B are graphs showing penetrance estimation of intracranial brain tumor induction using GL261 and derivatives cell lines.
Figure 20D:
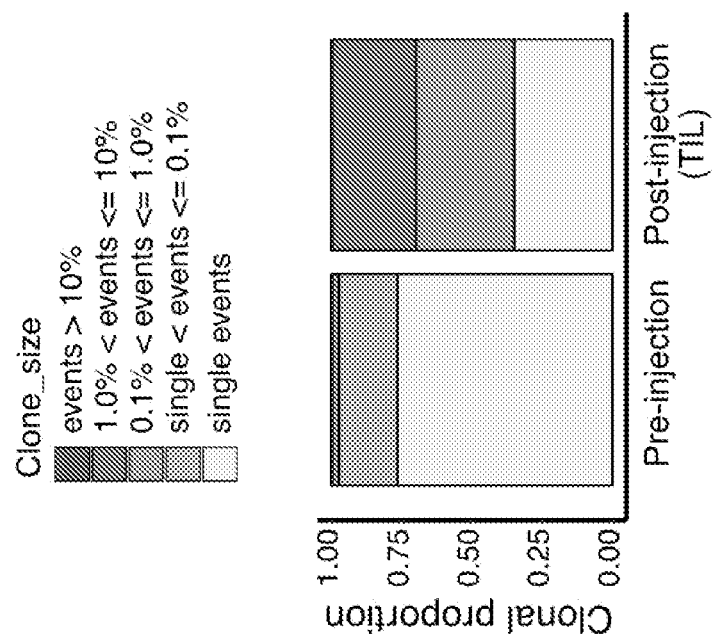
Figure 20E:
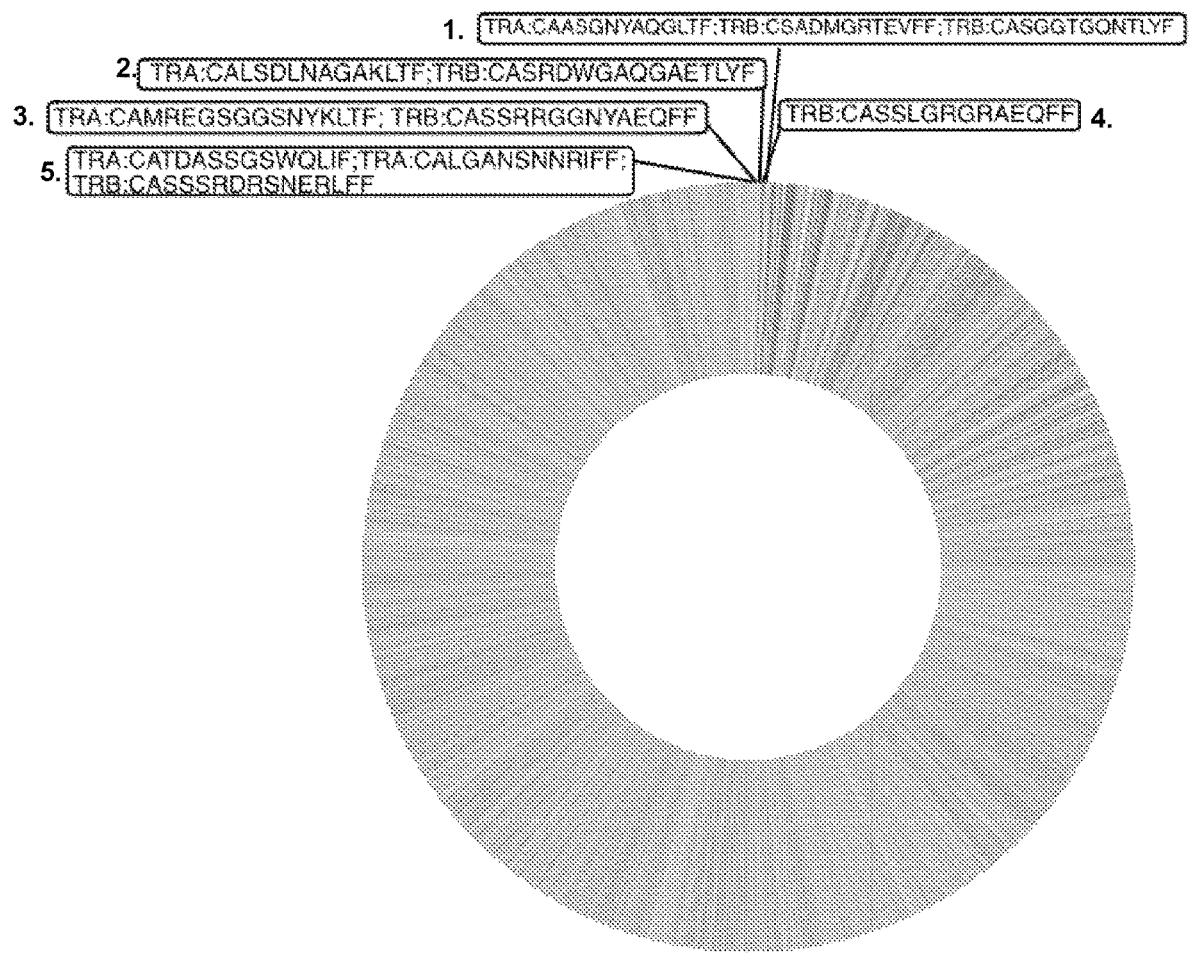
Figure 20F:
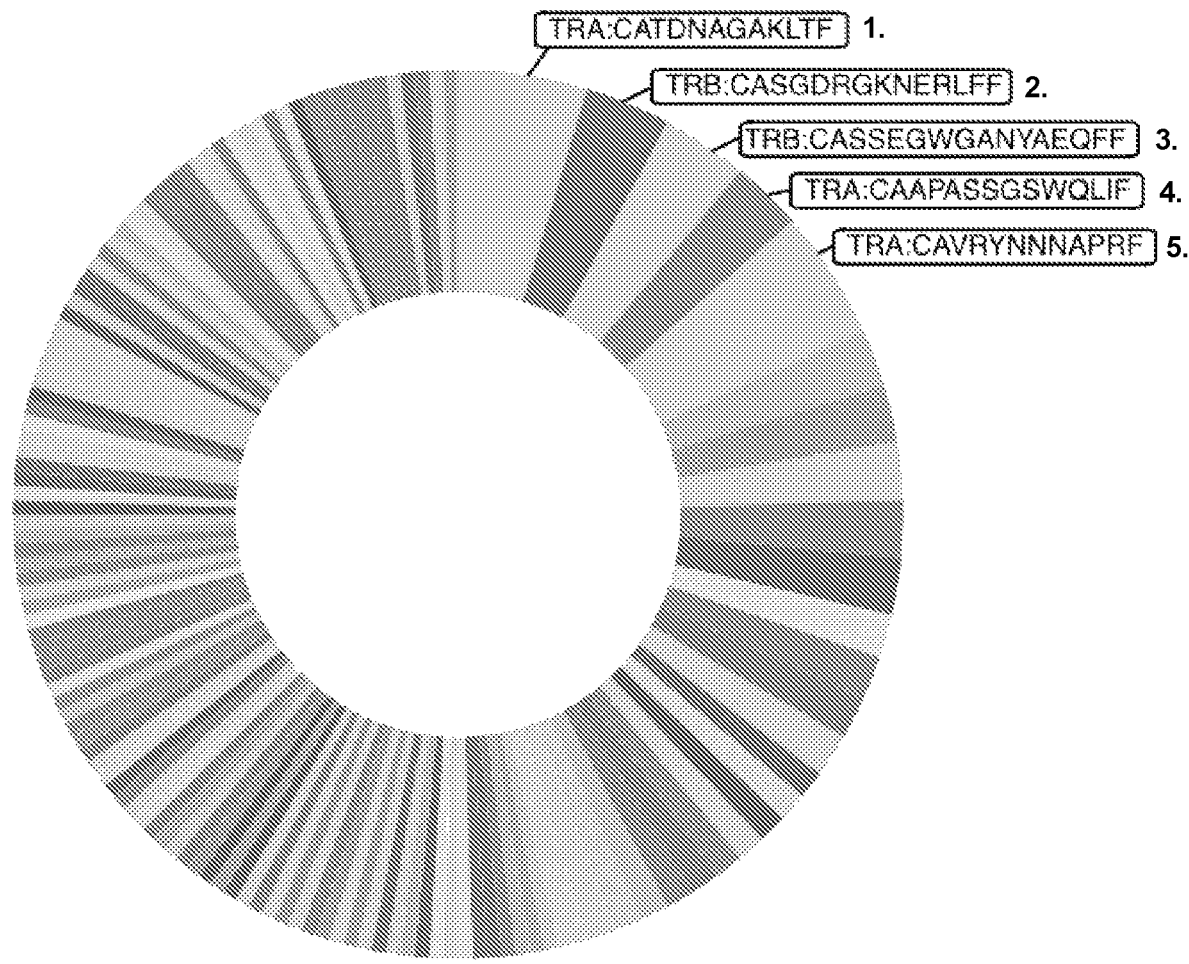

With the high titer AAV-surface library (AAV-Surf), primary T cells were screened in GBM using fully immuno-competent syngeneic models. Syngeneic mouse models were set up with native or luciferase-expressing GL261 cells (GL261 and GL261-FLuc, respectively) and transplanted into the lateral ventricles (LV) of C57BL/6J mice via intracranial injection (FIG. 1A). Intracranial injection of GL261 or its derivatives, the penetrance of brain tumor induction in untreated mice is at or near 100% (FIGS. 19A-19B). Cas9$^+$ CD8$^+$ T cells were then activated with anti-CD3c and anti-CD28, and transduced with AAV-Surf library to mutagenize the membrane proteome. CD8$^+$ T cells 5 days in culture showed no difference between AAV-Surf and AAV-Vector groups in PD-1, Lag3, or Tim-3 (FIG. 20A). Adoptive transfer of the AAV-mutagenized CD8 T cell pool was adoptively transferred into GBM engrafted mice via tail vein injection (FIG. 1A). Using CD45.1 transgenic mice, donor T cells were distinguished from those of the host (FIG. 1B). With CD8$^+$ T cells isolated from Cas9β;CD45.1 mice and transduced with AAV, the number of infiltrated donor-derived CD8$^+$ T cells was determined (FIG. 1C, FIG. 20B). Two parallel screens were also performed using CD8 T cells from T cell receptor (TCR) transgenic (OT-1) mice bred to Cas9β (FIG. 2A). Mice were monitored for brain tumor development by observation of macrocephaly, as well as by in vivo luciferase imaging where GL261-FLuc cells were used (FIG. 2B-2C). The results showed that adoptive transfer of CD8$^+$ T cells increased overall survival (Log-rank (Mantel-Cox) test, Vector vs. PBS, p=0.0302; AAV-Surf vs. PBS, p=0.0183; AAV-Surf vs. Vector, p=0.2371) (FIG. 2E). Brain tumors were found in all mice at the endpoint (FIG. 2F), except 3 mice in the AAV-Surf group that were luciferase-negative after T cell treatment. We observed that mice from the AAV-Surf group had increased numbers of infiltrating T cells, potentially linked to enhanced trafficking and/or survival of certain mutant T cells, or more complicated cell-cell interactions with a complex mutant pool. These TILs also have no difference in surface PD-1 level (FIGS. 20B-20C). TCR-seq was then performed on the pre-injection T cells and post-injection TILs, and observed a large number of different TCR clonotypes in pre-injection T cells as well as reduction of clonality in post-injection T cells, potentially due to limited number of TILs in the brain (FIGS. 20D-20F).

Figure 2H:
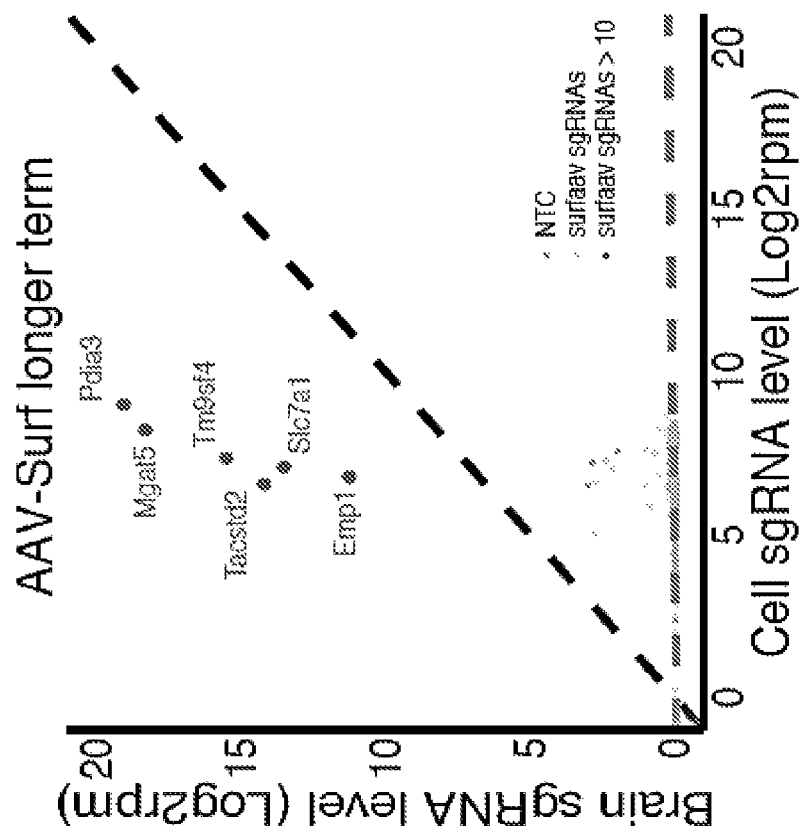
Figure 2G:
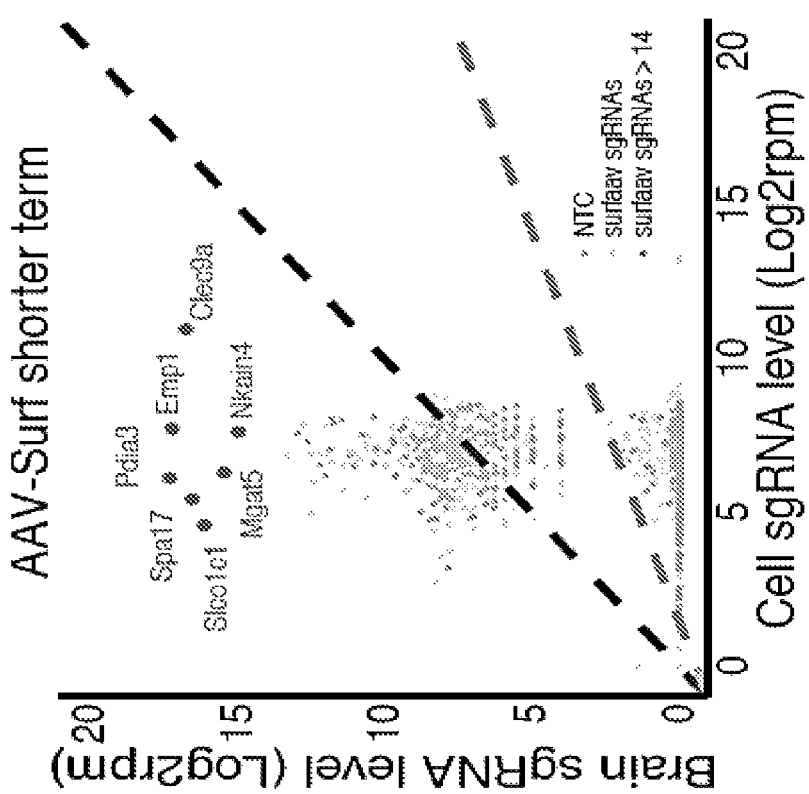

Whole brains were then collected along with spleen and cervical lymph nodes for genomic DNA preparation and sgRNA library readout using barcoded primers (SEQ ID NOs. 7,629-7,644). Deep sequencing data was analyzed within each sample to find enriched sgRNAs compared to the 1,000 NTC sgRNAs. For the shorter term screen, a set of enriched genes, Clec9a, Pdia3, Mgat5, Emp1, Slco1c1, Spa17, and Nkain4, was identified (FIG. 2G). For the longer term screen, most sgRNAs had disappeared after this extended period of selection, with the remaining highly abundant sgRNAs targeting six genes, Pdia3, Mgat5, Emp1, Tm9sf4, Tacstd2, and Slc7a1 (FIG. 2H). Notably, Pdia3, Mgat5 and Emp1 were also top hits in the shorter term screen. The MAGeCK analysis identified a list of significant genes, which include Pdia3 and Mgat5 (FIG. 2D), which implied that these two candidates might be essential genes for T cell anti-tumor activity.

The majority of the 1000 NTC sgRNAs follow a linear regression line between brain and cell pellet (FIG. 1D); whereas a fraction of sgRNAs are highly enriched in the brain suggesting expansion of these specific mutant T cells (FIG. 1D). Thirty-three significantly enriched sgRNAs targeting various membrane proteins were identified, including Mgat5, Cdh11, Emp1, Lag3, Slc29a4, Rnpep, Heft, P4ha1, Man2a1, and Pdia3 (FIG. 1D). RIGER analysis was performed for gene level significance considering multiple independent sgRNAs, which showed Mgat5, Pdia3, Pde5a, Ccdc80, Tnfrsf18, Defb26, Chrna7, Tspan13, Plat, and Lag3 as the top 10 hits (FIG. 1E). In the independent screens using OT-1:Cas9β mice, a similar list of gene hits were identified, with the top gene hits being Pdia3, Mgat5, and Emp1 (FIG. 2G-2H). qRT-PCR confirmed that most of the top hits are highly expressed in mouse CD8 T cells (FIG. 1F) suggesting that these candidate genes may modulate T cell function for anti-tumor activity against GBM.

Figure 1G:
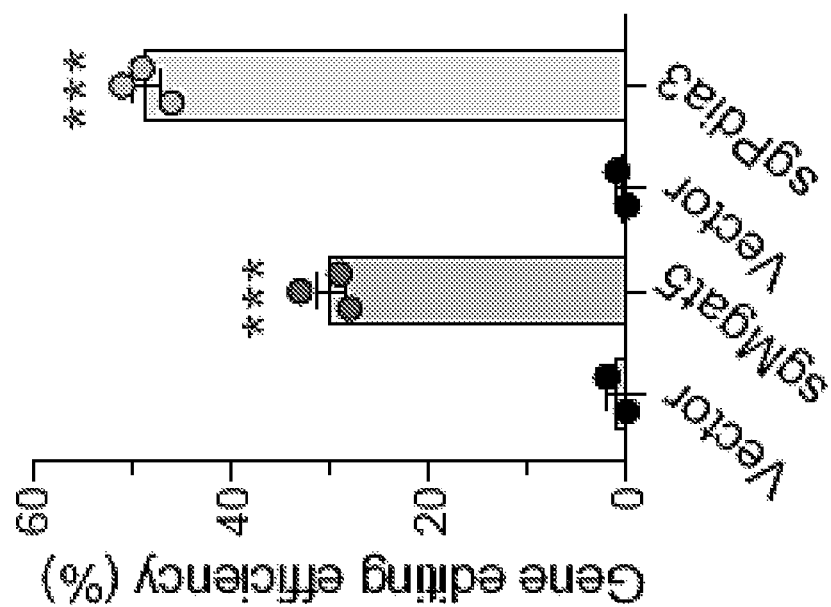
Figure 1F:
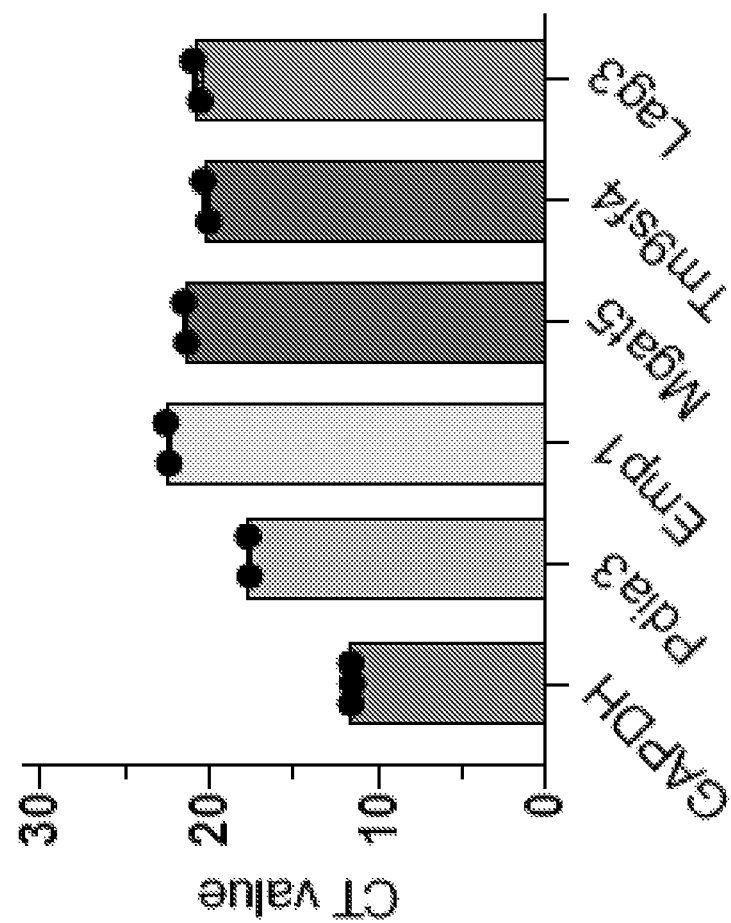
Figure 3D:
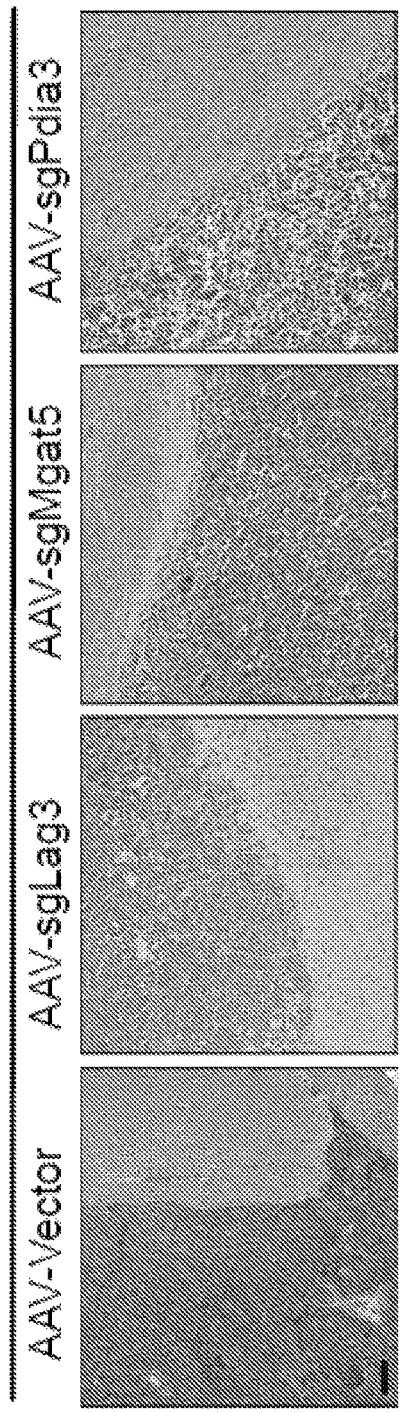
Figure 3E:

Example 2: Pre-Clinical Efficacy Testing of Top Candidates by Direct T Cell Editing and Adoptive Transfer The AAV-SB-CRISPR system can generate high-efficiency on-target gene editing in mouse primary CD8$^+$ T cells (FIG. 1G). To test whether AAV-CRISPR perturbation of these top hits can enhance the anti-tumor efficacy of T cells against GBM, Pdia3 and Mgat5 were specifically targeted, as they were the top hits most significantly enriched in all three screens, alongside with Lag3. Comparison was also performed with Lag3, a well-established immune checkpoint regulator expressed on T cells and a major emerging target of checkpoint blockade, currently with a monoclonal antibody in phase I clinical trial for GBM (NCT02658981). T7EI assays and RT-qPCR were performed on these targets and confirmed that T cells infected with AAV-SB-CRISPR carrying Pdia3 and Mgat5 sgRNAs have on-target gene editing and mRNA downregulation before T cell adoptive transfer (FIGS. 3B-3C). In a syngeneic orthotopic GBM model with GL261 intracranial implantation in C57BL/6J mice, survival analysis of GBM engrafted mice showed that the individual knockouts of each of the three genes (Lag3, Mgat5 and Pdia3) in the adoptively transferred CD8$^+$ T cells prolonged overall survival when compared to AAV-Vector control (FIGS. 3F-3G).

Figure 1H:
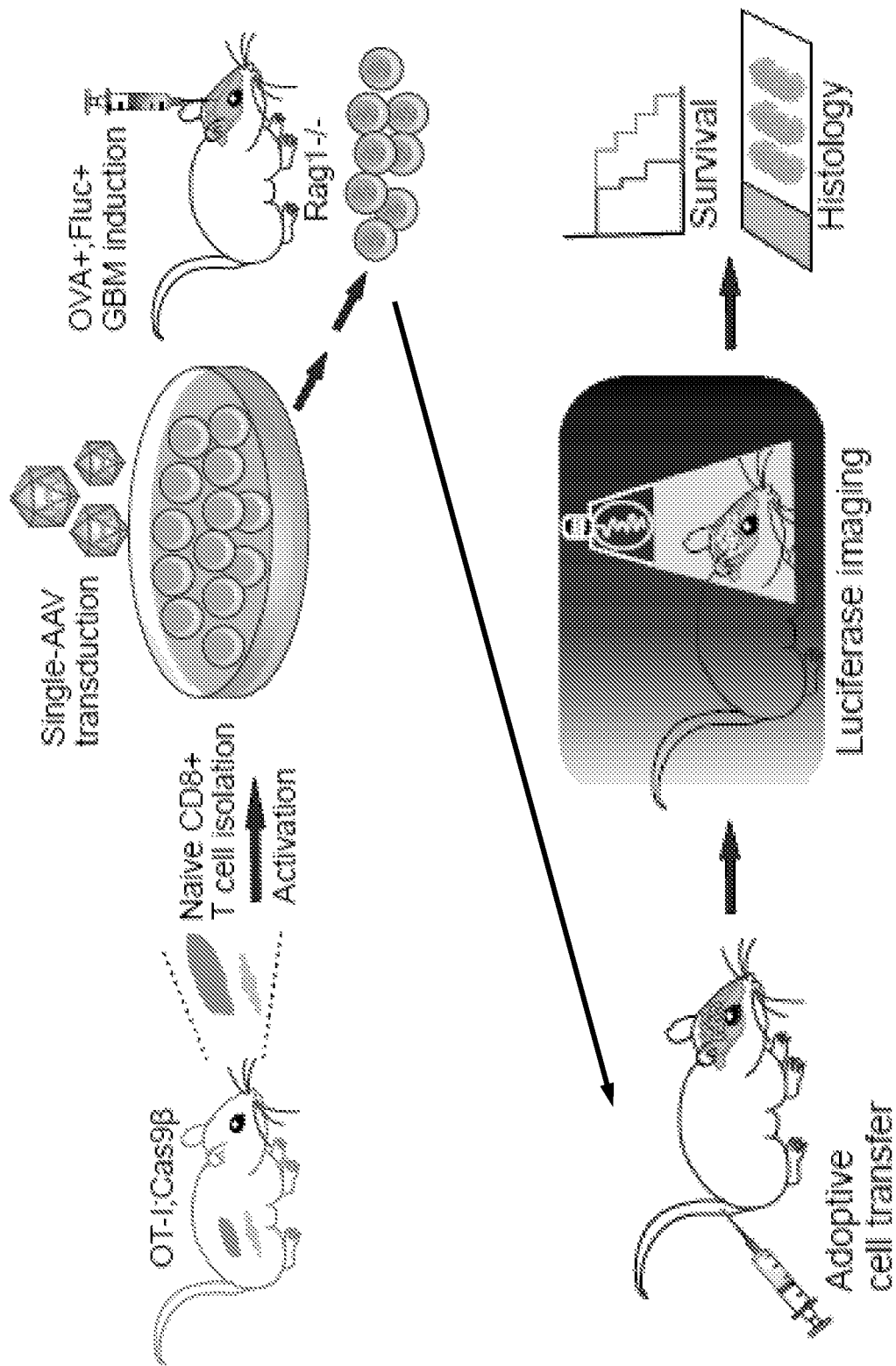
Figure 4A:
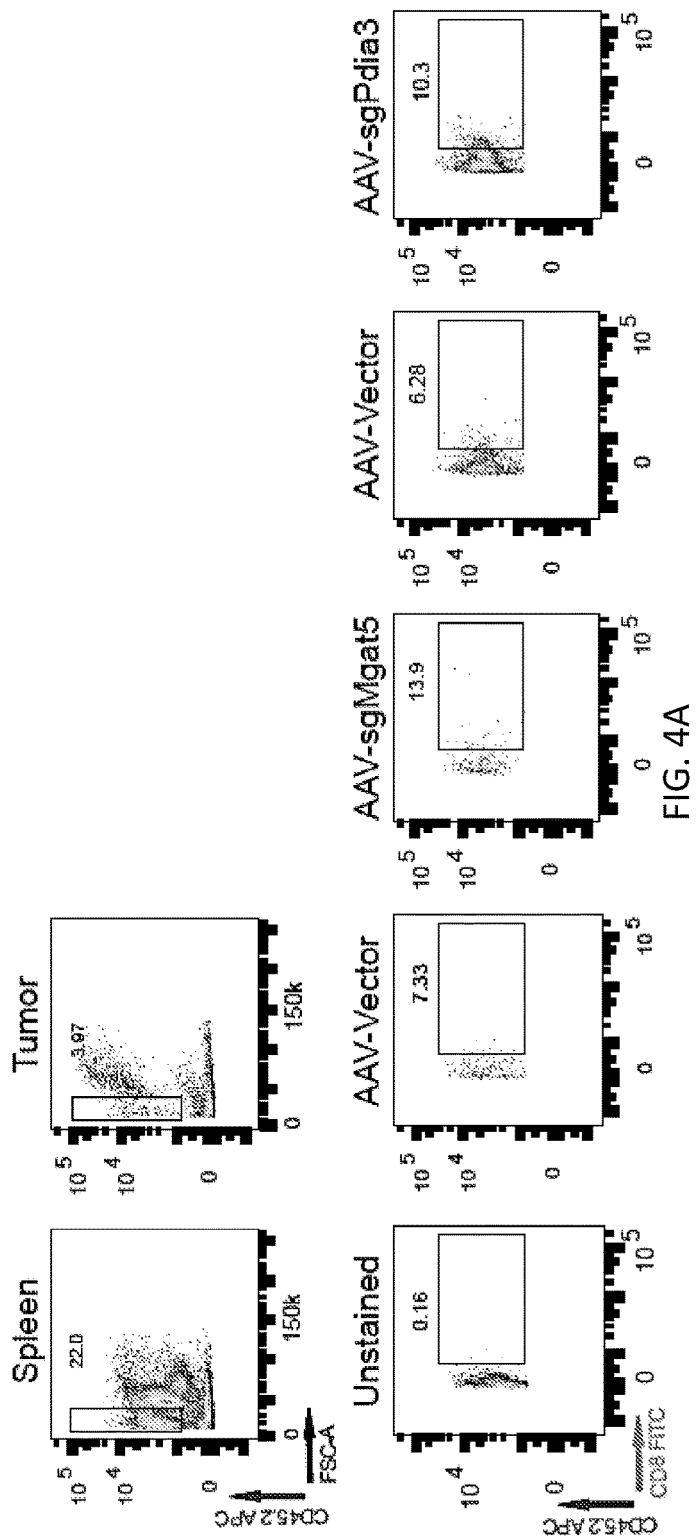
FIGS. 4A-4B show CD8$^+$ T cell infiltration analysis after Pdia3 or Mgat5 knockout using a cognate TCR-model tumor antigen system. Rag1$^{-/-}$ mice were injected with GL261-FLuc-mCh-rOVA #1 cells, OT-I;Cas9β CD8$^+$ T cells were isolated and infected with AAV-sgMgat5 and AAV-sgPdia3 virus after confirmation of brain tumor development by luciferase imaging using IVIS. $5 \times 10^6$/mouse OT-I;Cas9β CD8+ T cells were i.v. injected. Brain tumor were isolated after 5 days of i.v injection.
Figure 4B:
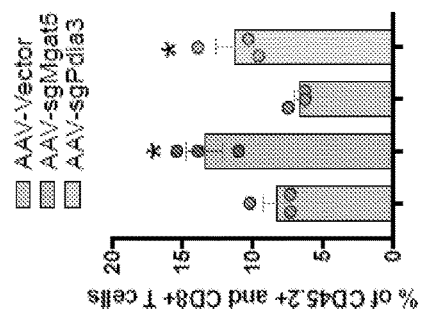

To determine if CRISPR editing of these genes would similarly garner therapeutic enhancement using an antigen-specific OT-I;Cas9β CD8$^+$ T cells against established GL261 brain tumors expressing a model antigen, chicken ovalbumin (cOVA), GL261-FLuc-mCh-cOVA cell lines were expanded from a single cell with clonal expression of cOVA (FIG. 3A). GL261-FLuc-mCh-cOVA #1 cells were transplanted into the lateral ventricle (LV) of each RagF mouse to induce GBM. CD8$^+$ T cells from OT-I;Cas9β donors were isolated, activated, and infected with single AAV construes. Ten days after tumor implantation, adoptively transferred single gene edited or control OT-I;Cas9β CD8$^+$ T cells intravenously into GBM-bearing recipient mice (FIG. 1H). Survival analysis showed that AAV-CRISPR perturbation of Mgat5, Pdia3 or Emp1 each significantly improved overall survival of GL261-cOVA GBM bearing mice when compared to AAV-Vector control (FIGS. 1I-1K). Furthermore, flow cytometry analysis of infiltrating CD45.2+;CD8+ immune cells revealed proportionally higher abundance of Mgat5 and Pdia3 knockout CD8+ T cells following adoptive transfer (FIG. 1L and FIGS. 4A-4B).

Figure 5A:
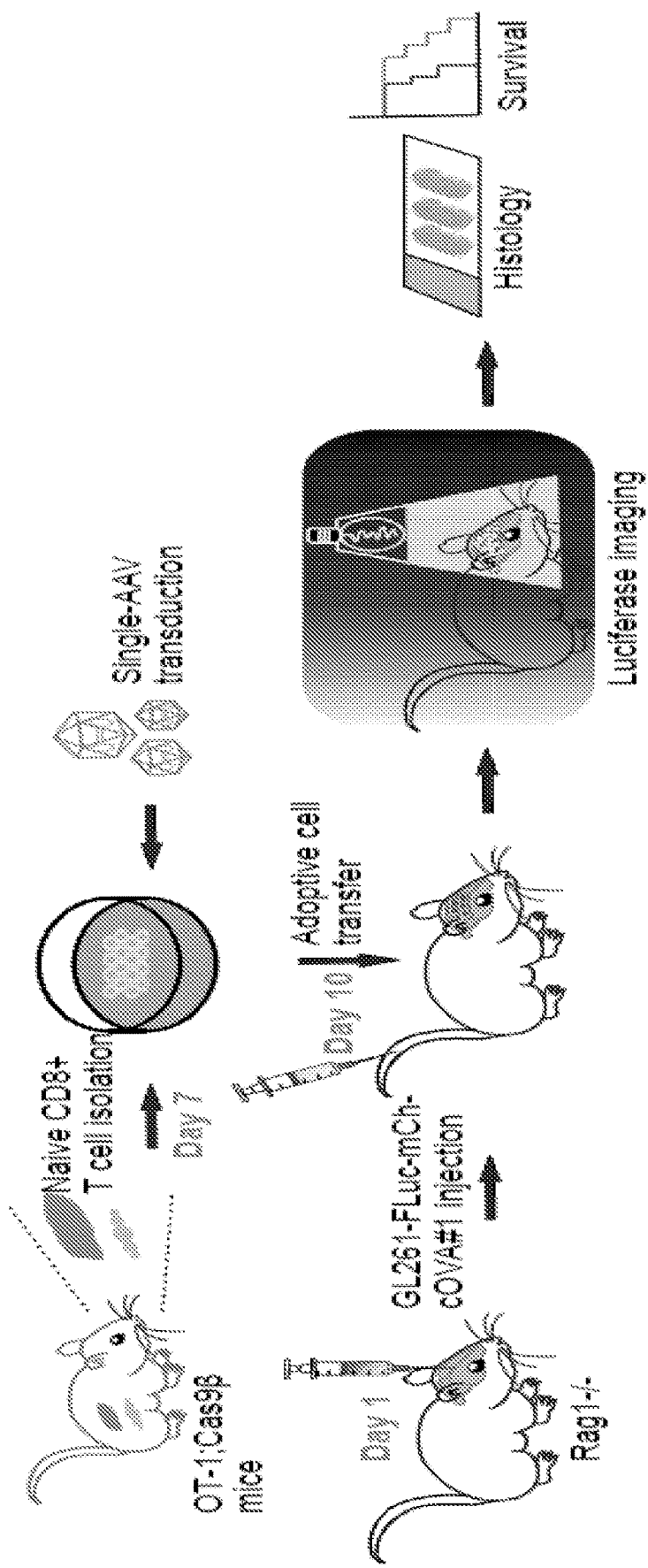
Figure 5B:
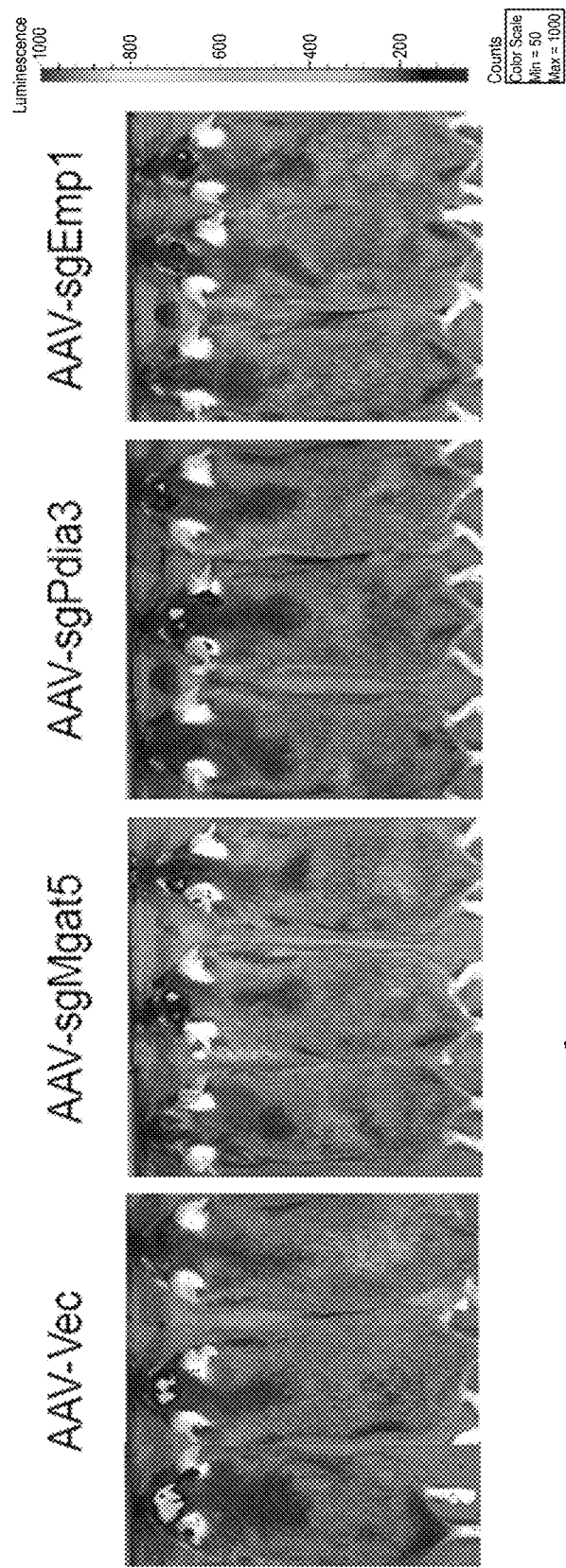
Figure 5B:
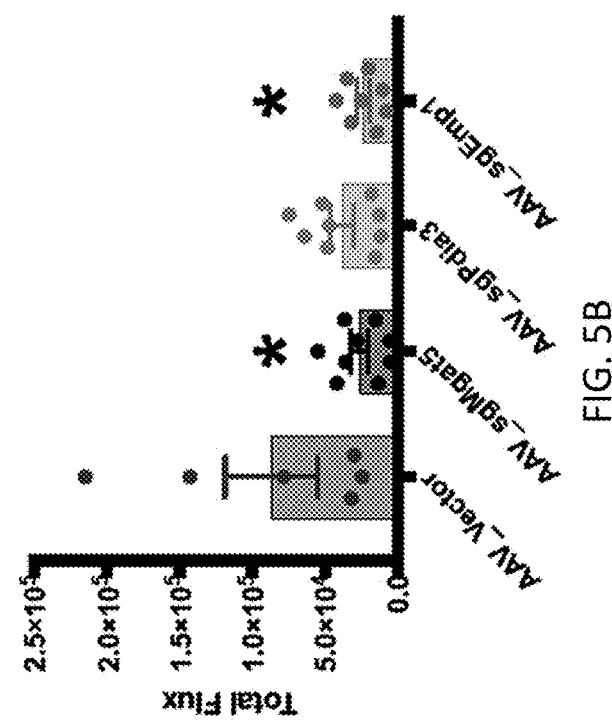

Example 3: Validation of Top Candidates Using a Cognate TCR-Model Tumor Antigen System It was next asked whether perturbation of these candidates would similarly garner therapeutic enhancement using antigen-specific OT-1; Cas9β CD8+ T cells against established GL261 brain tumors expressing a model antigen, chicken ovalbumin (cOVA). To address this, GL261-FLuc-mCh-cOVA cell lines were established, where each cell line was expanded from a single cell with clonal expression of cOVA. $1 \times 10^5$ GL261-FLuc-mCh-cOVA #1 cells were transplanted into lateral vetricles Rag1$^{-/-}$ mice. Ten days after tumor implantation, OT-1;Cas9β CD8+ T cells were adoptively transferred intravenously (FIG. 5A). Once mice in the AAV-Vector group began to show signs of body score deterioration or macrocephaly, in vivo imaging was performed to quantify the relative tumor burden among different groups (FIG. 5B). Although all mice were eventually deemed destined for euthanasia within three months due to the aggressiveness of these brain tumors (FIG. 5B), comparative analysis demonstrated that CRISPR perturbation of Mgat5 or Emp1 in the adoptively transferred T cells significantly repressed tumor growth (FIG. 5B). In addition, overall survival was significantly improved in GL261-cOVA GBM bearing mice with adoptive transfer of OT-1;Cas9β CD8+ T cells transduced with AAV-sgMgatS (Log-rank Mantel-Cox test, p=0.0475), AAV-sgPdia3 (Log-rank Mantel-Cox test, p=0.0114) and AAV-sgEmp1 (Log-rank Mantel-Cox test, p=0.0002) groups as compared to AAV-Vector control (FIGS. 5C-5E).

Figure 6A:
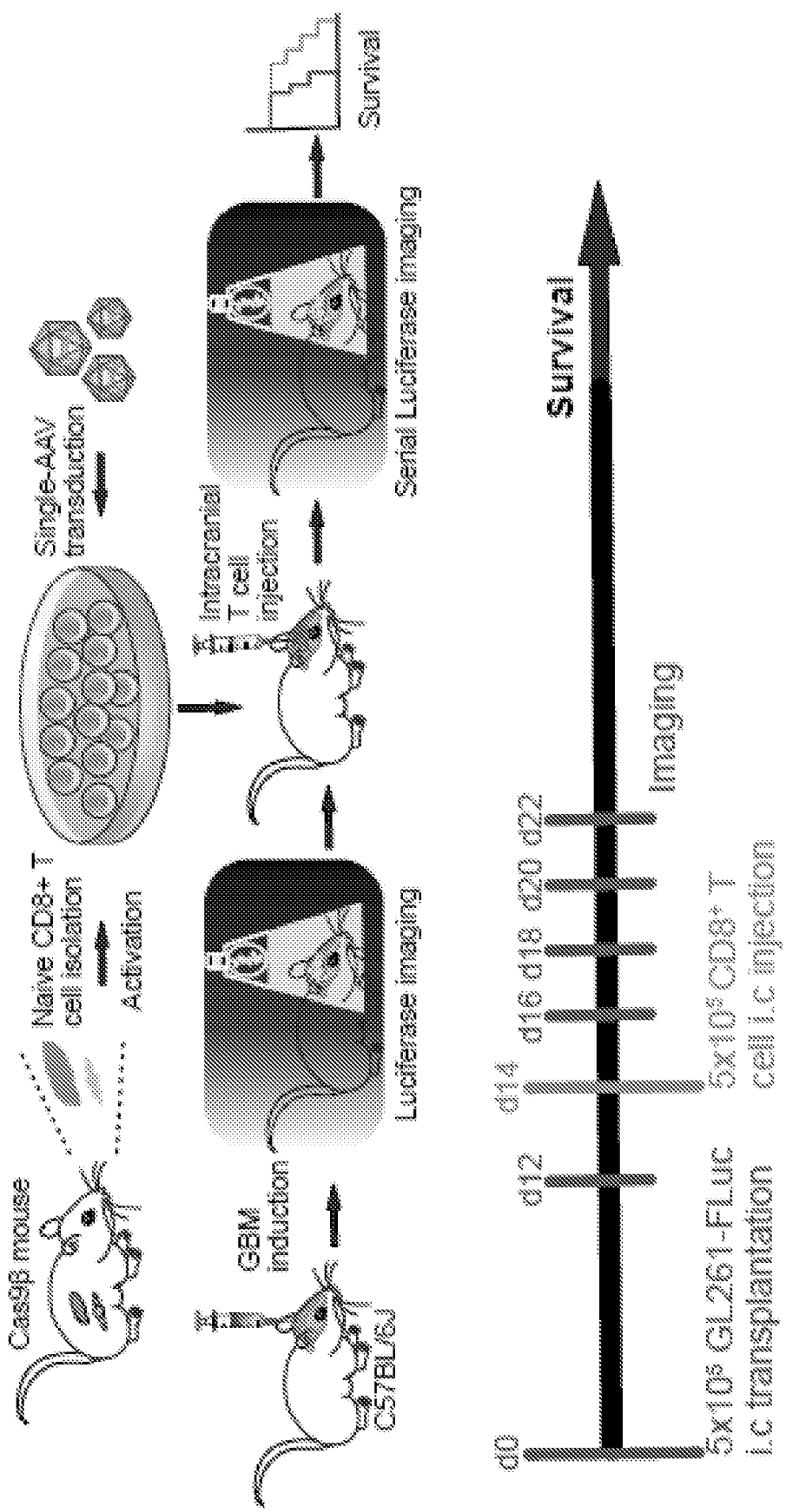
FIGS. 6A-6H describe the efficacy testing of AAV-SB-CRISPR targeting of Pdia3, Mgat5 and in combination in CD8+ T cell in a syngeneic mouse model of GBM.
Figure 6B:
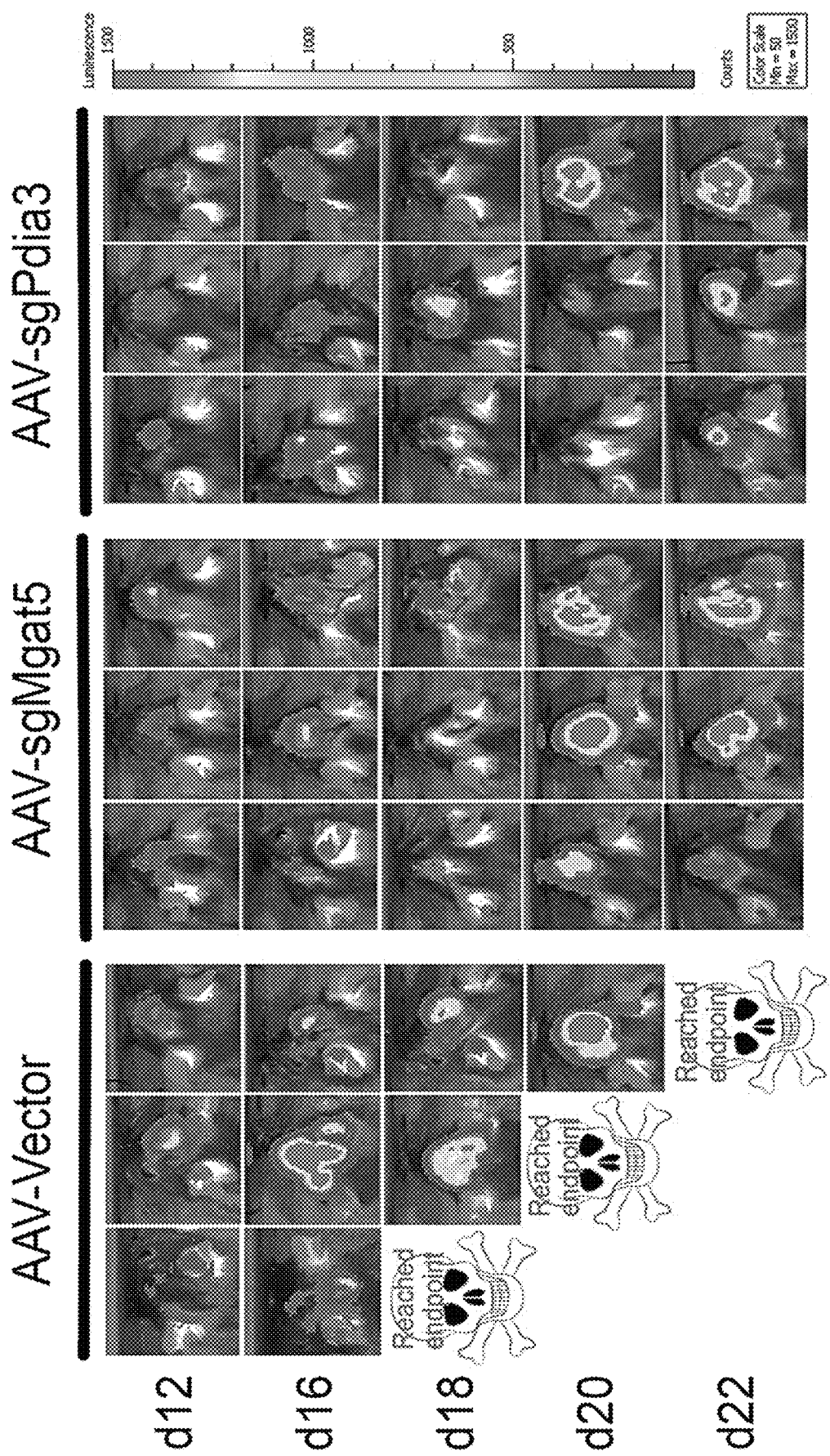
Figure 6C:
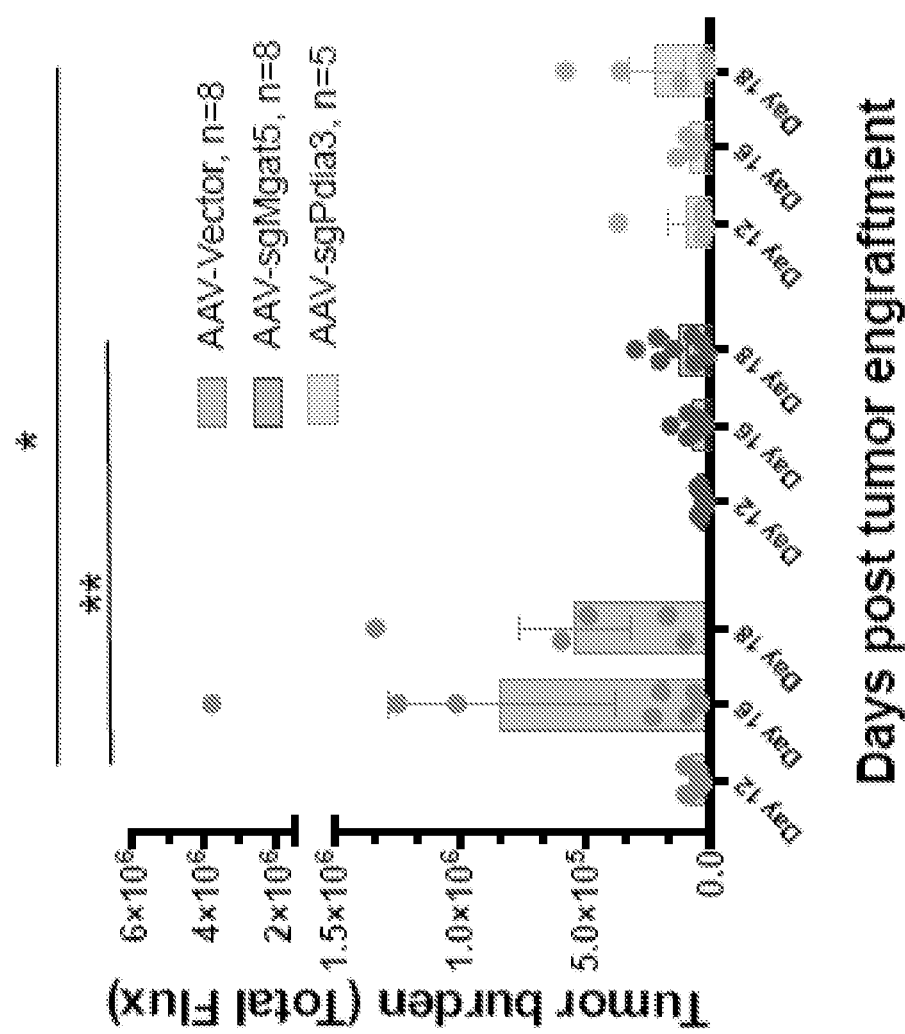
Figure 6D:
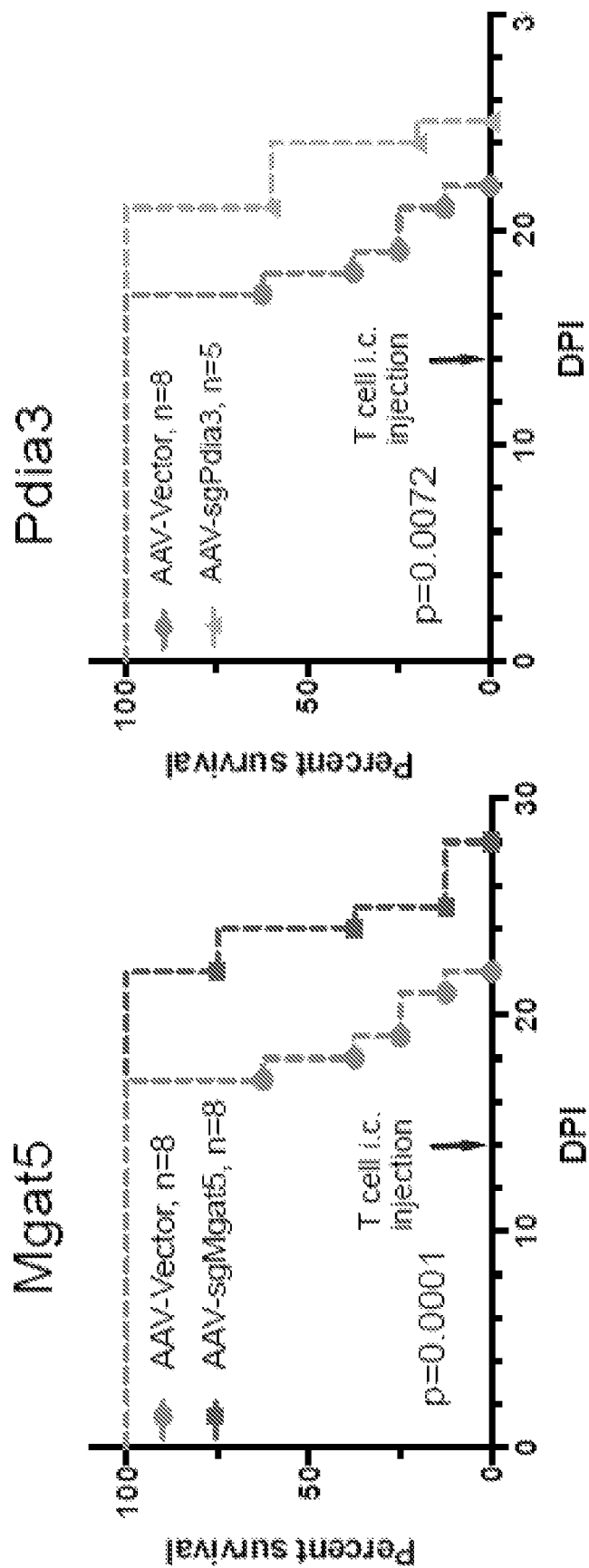
Figure 6E:
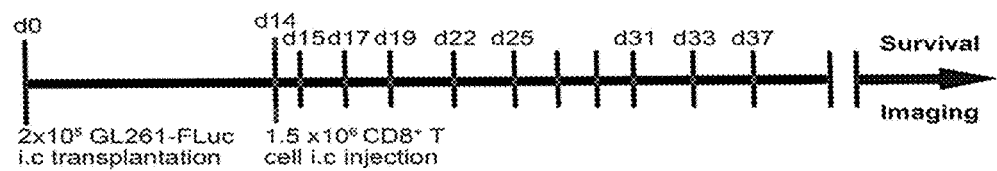
Figure 6F:
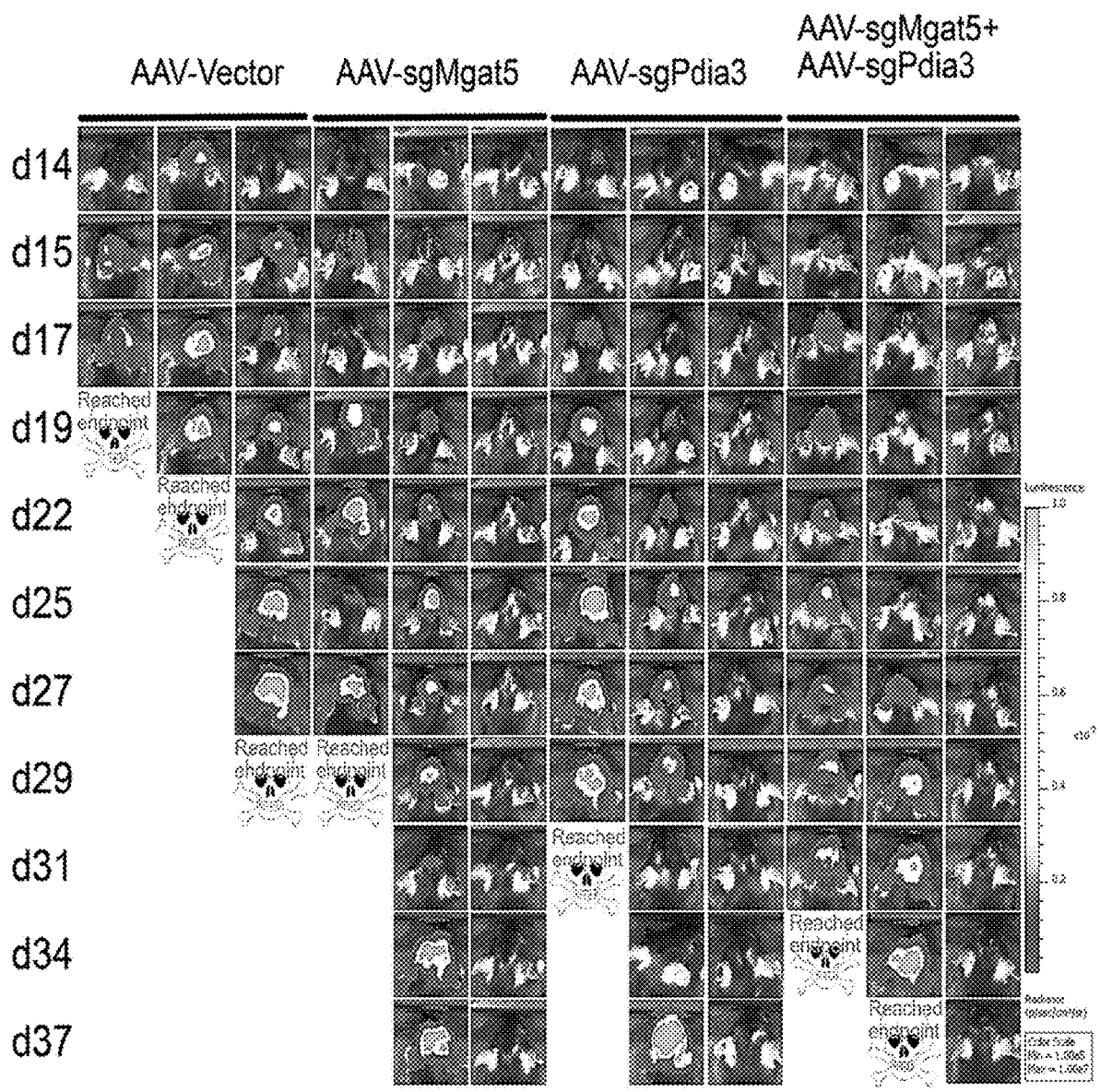
Figure 6G:
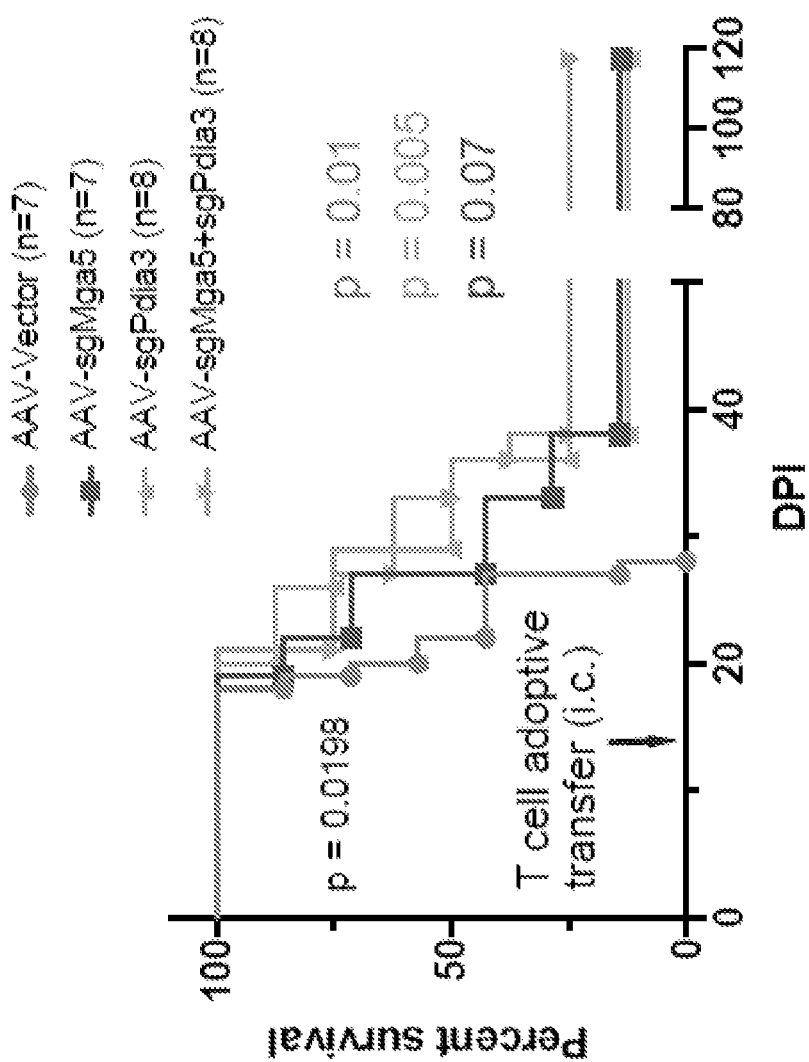
Figure 6H:
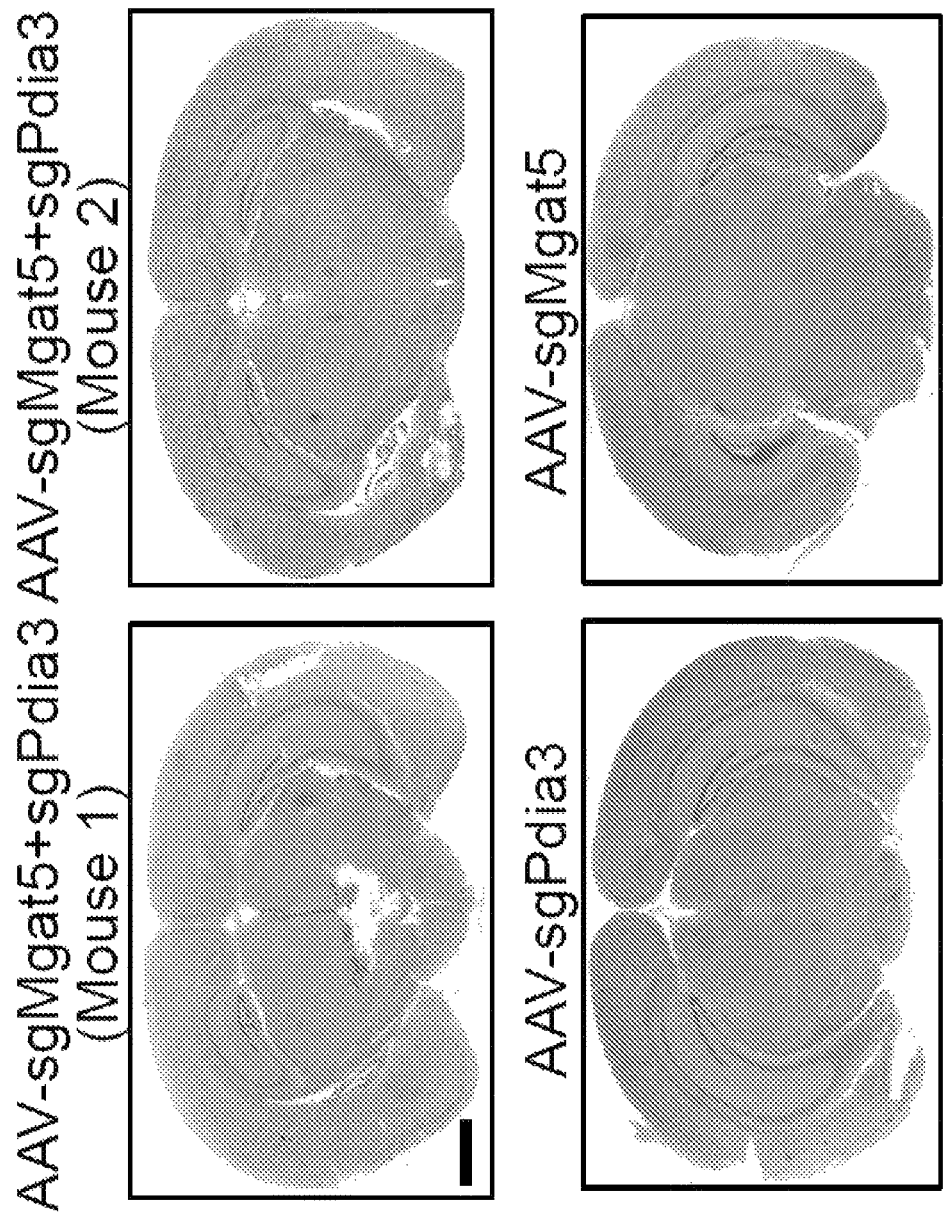
Figure 21A:
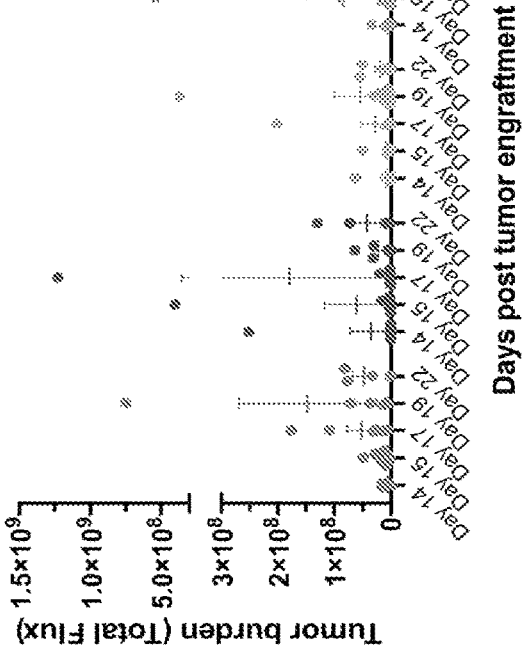
FIGS. 21A-21B show representative luciferase imaging for tumor burden quantification.
Figure 21B:
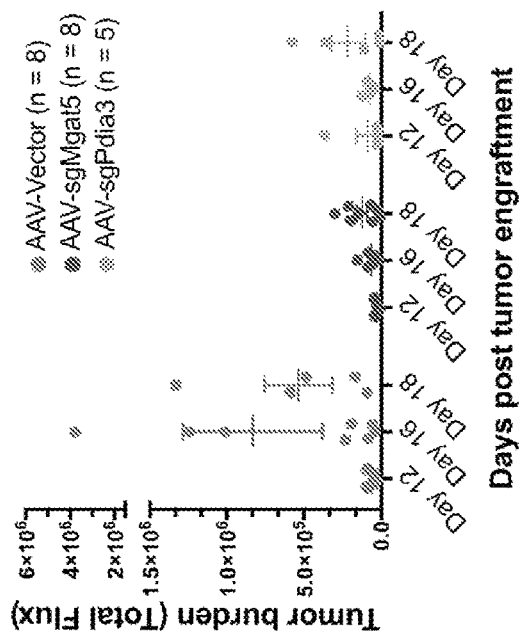

Example 4: Validating Efficacy of Pdia3 and Mgat5 Perturbation in CD8 Tcells Using an Intracranial Injection GBM Cancer Model GL261-FLuc cells were adoptively transferred via intracranial procedure to induce tumor, and IVIS bioluminescent imaging was performed to ensure each mouse had developed brain tumor. 10 days post tumor transplant, intracranial injection of AAV-sgMgatS or AAV-sgPdia3 infected CD8+ T cells at 1:1 initial seeding ratio (cancer cell:T cell) into the LV of the GL261-FLuc tumor bearing mouse brains was performed (FIG. 6A). Tumor growth was monitored closely by in vivo imaging every two days after T cell intracranial injection (FIG. 6B). Luciferase imaging results showed that mice receiving intracranial injection of Mgat5 or Pdia3 knockout CD8+ T cells had significantly lower tumor burden during early disease progression (FIGS. 6B-6C), as well as significantly improved overall survival (FIG. 2D). Intracranial adoptive T cell transfer was repeated but with a lower initial cancer cell:T cell ratio (1:7.5) (FIG. 6E). Additionally, a group of CD8+ T cells infected with both AAV-sgMgat5 and AAV-sgPdia3 was included (FIG. 6E). All mice receiving AAV-Vector infected CD8+ T cells quickly reached survival endpoints due to rapid GBM progression (FIG. 2F-2G), whereas all three AAV-CRISPR CD8+ T cell perturbation groups had prolonged survival (AAV-sgMgat5, AAV-sgPdia3, or AAV-sgMgat5+AAV-sgPdia3), with a fraction of mice become tumor-free and having long-term survival (FIG. 2E-2F; FIG. 6G). Tumor burden was quantified by luciferase flux at various timepoints (FIG. 21A-21B). The brains of long-term survivor mice were then examined by histology at 8 months (approximately 240 days) post injection and found that their brains were indeed tumor-free (FIG. 6H). These data suggested that single gene AAV-CRISPR perturbation of Mgat5, Pdia3, or their combination enhanced the efficacy of intracranial adoptive T cell transfer against GBM.

Figure 7A:
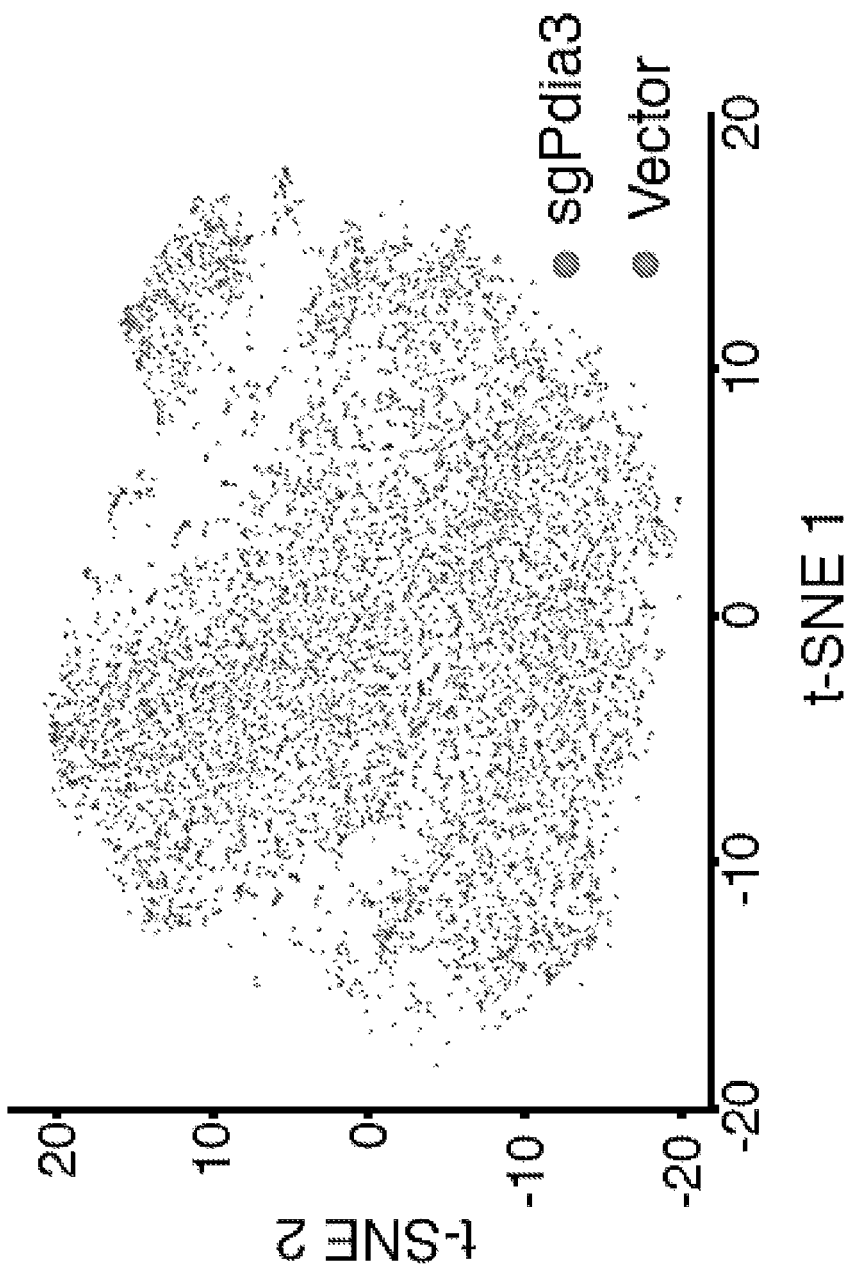
FIGS. 7A-7D illustrate single-cell RNA sequencing (scRNA-seq) analysis in Pdia3 knockout in CD8+ T cells.
Figure 7B:
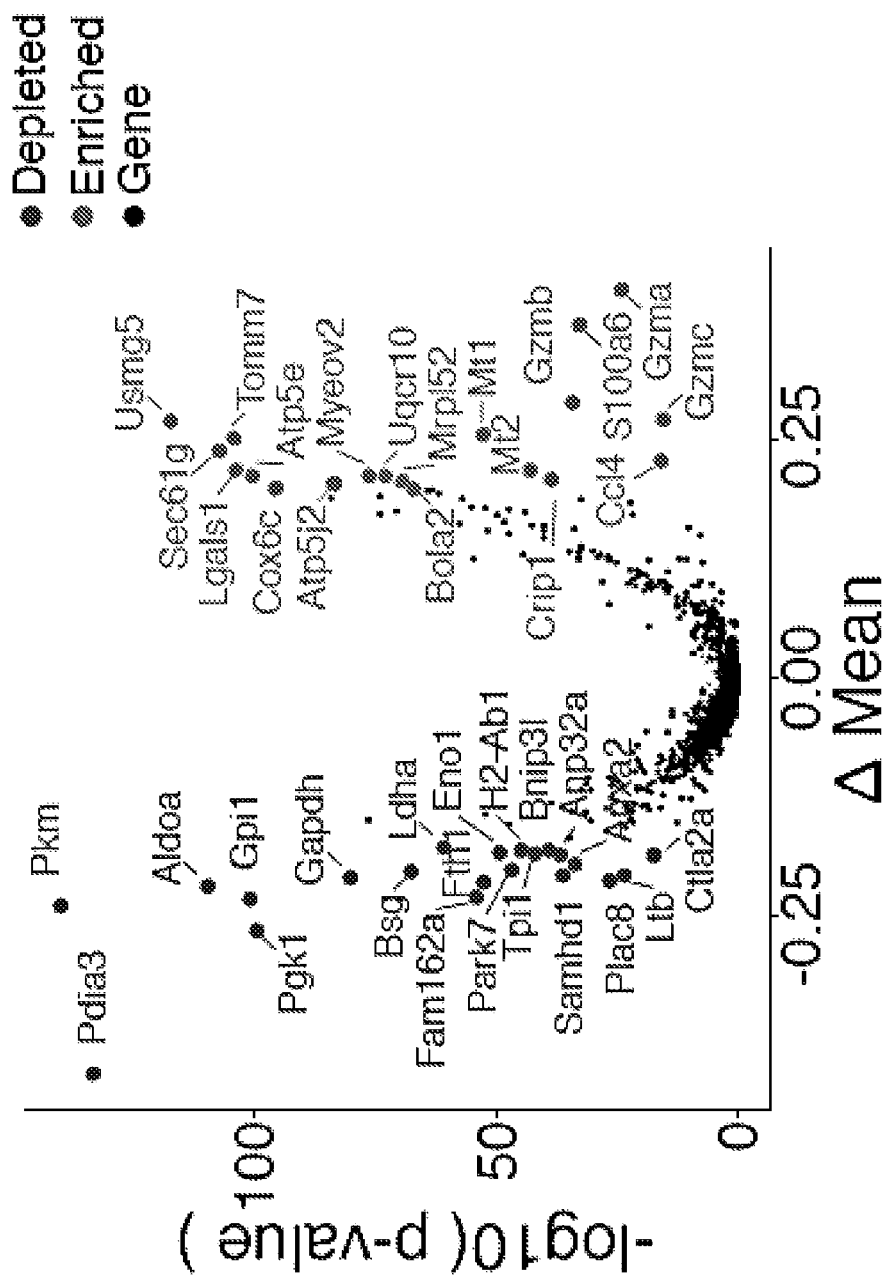
Figure 7C:
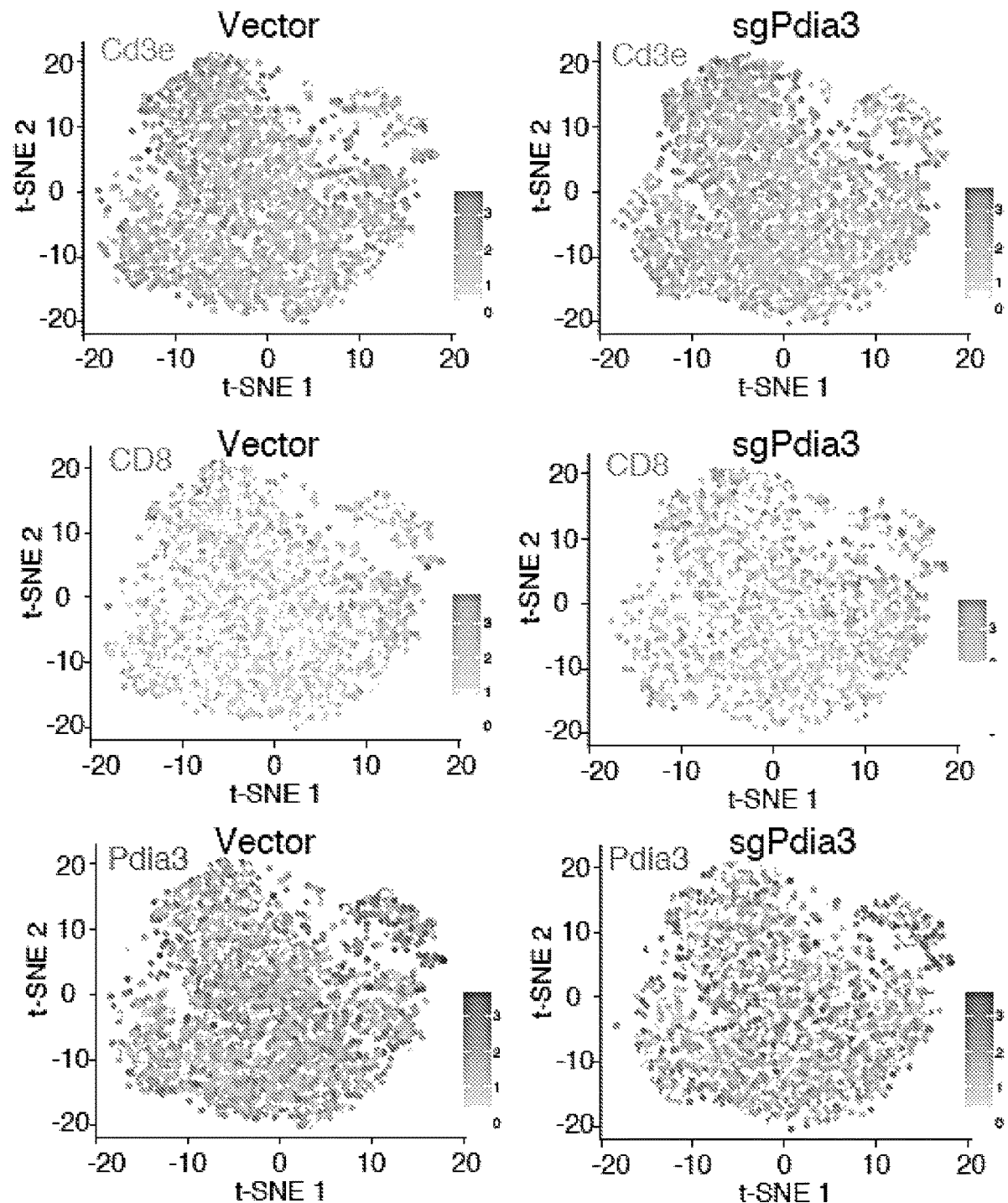
Figure 7D:
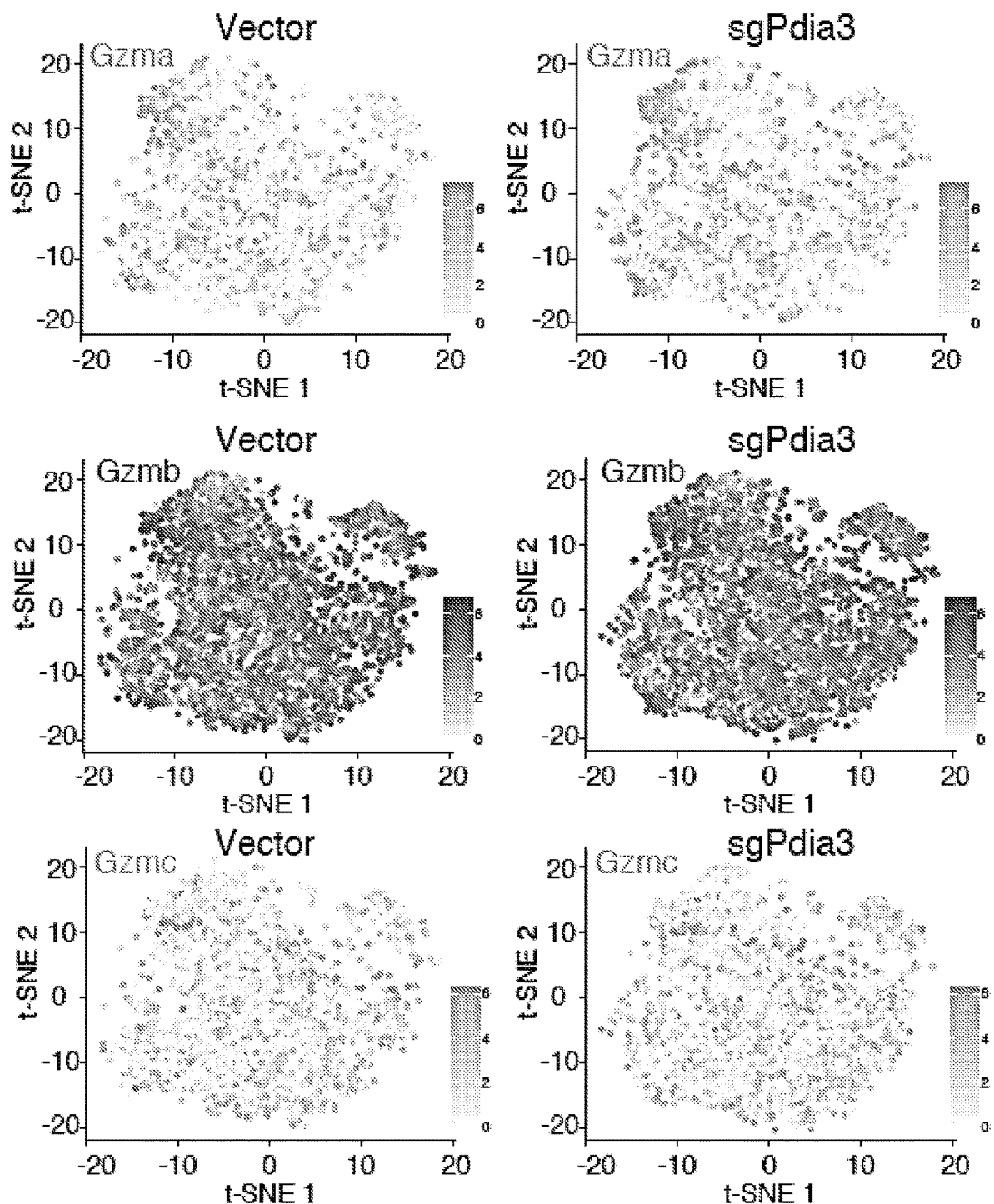
Figure 8A:
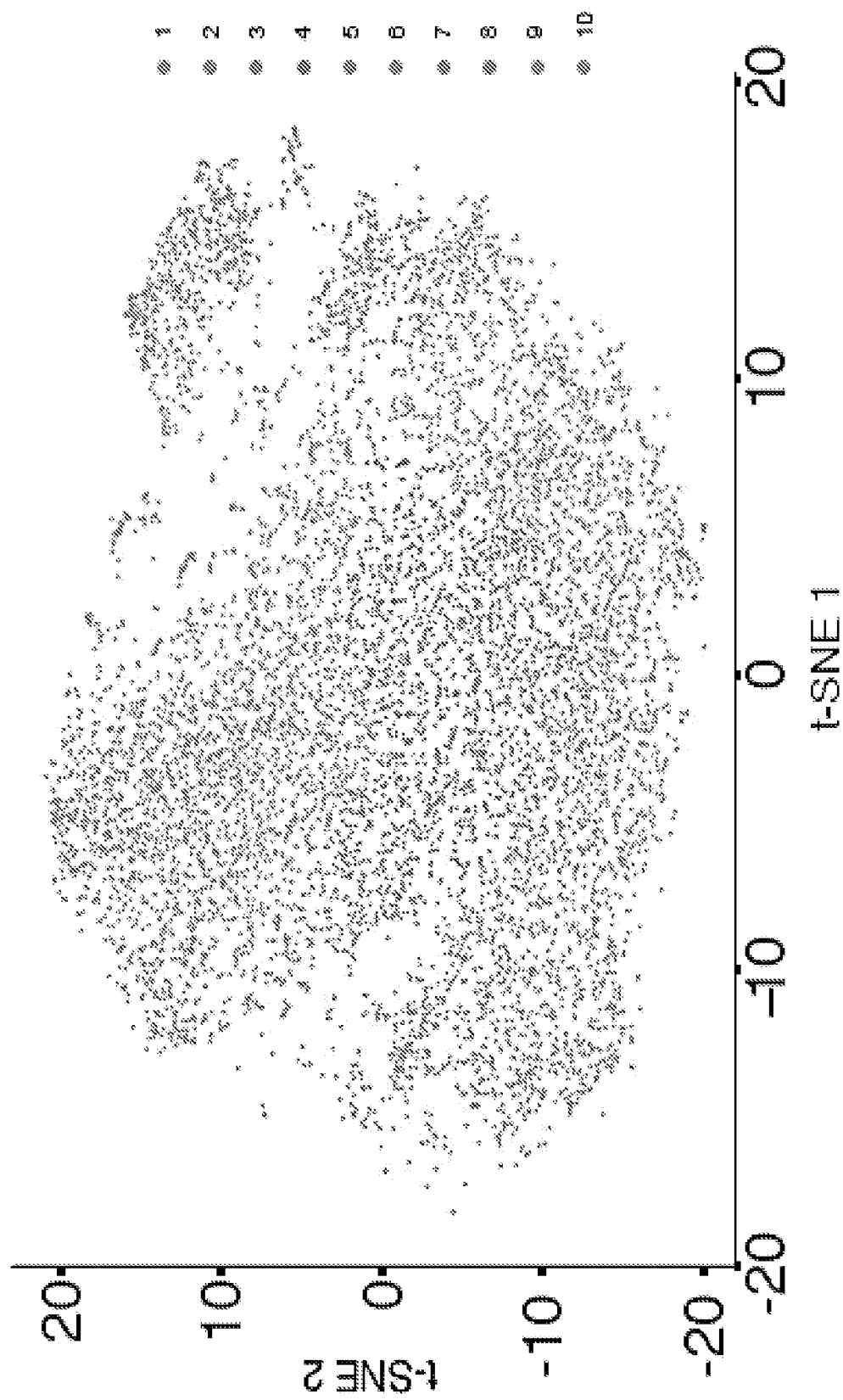
FIGS. 8A-8G describe scRNAseq analysis in Pdia3 knockout in CD8+ T cells.
Figure 8B:
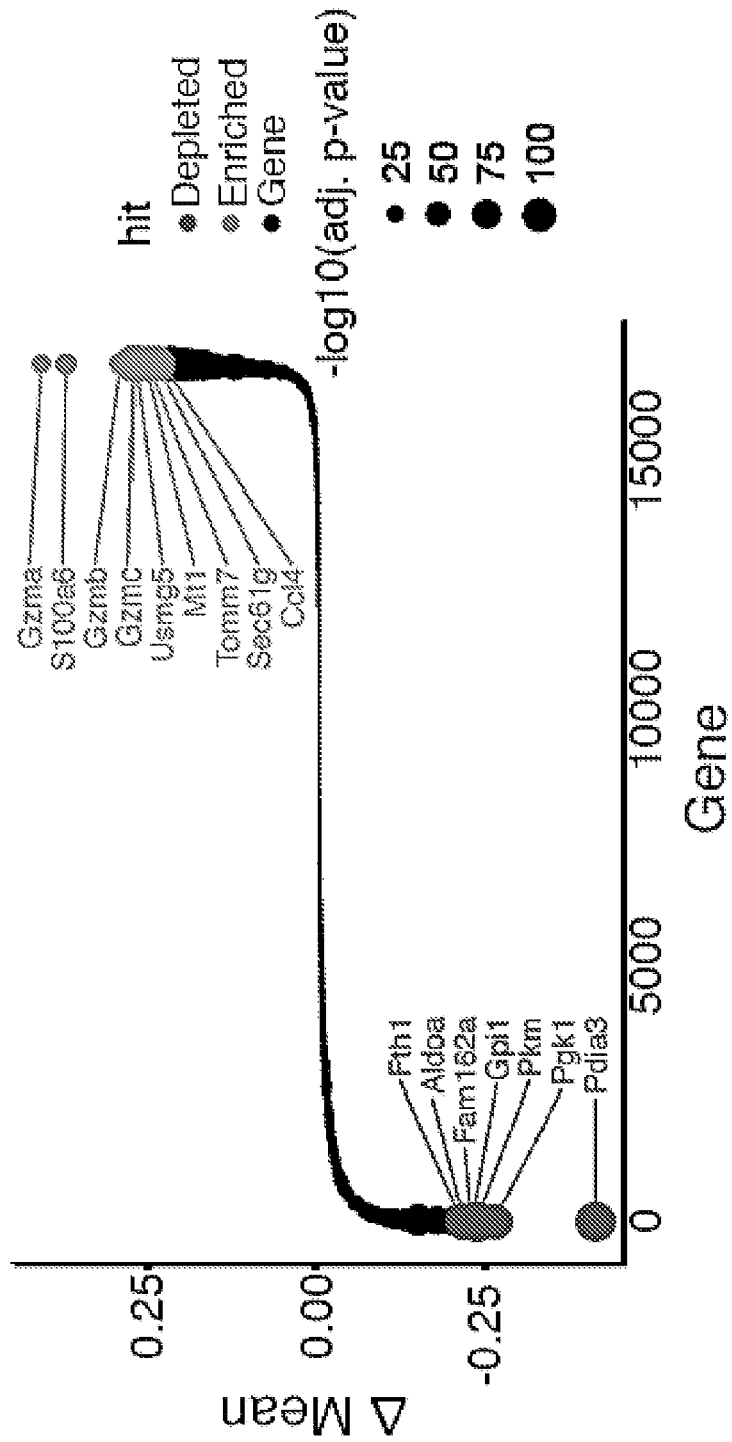
Figure 8C:
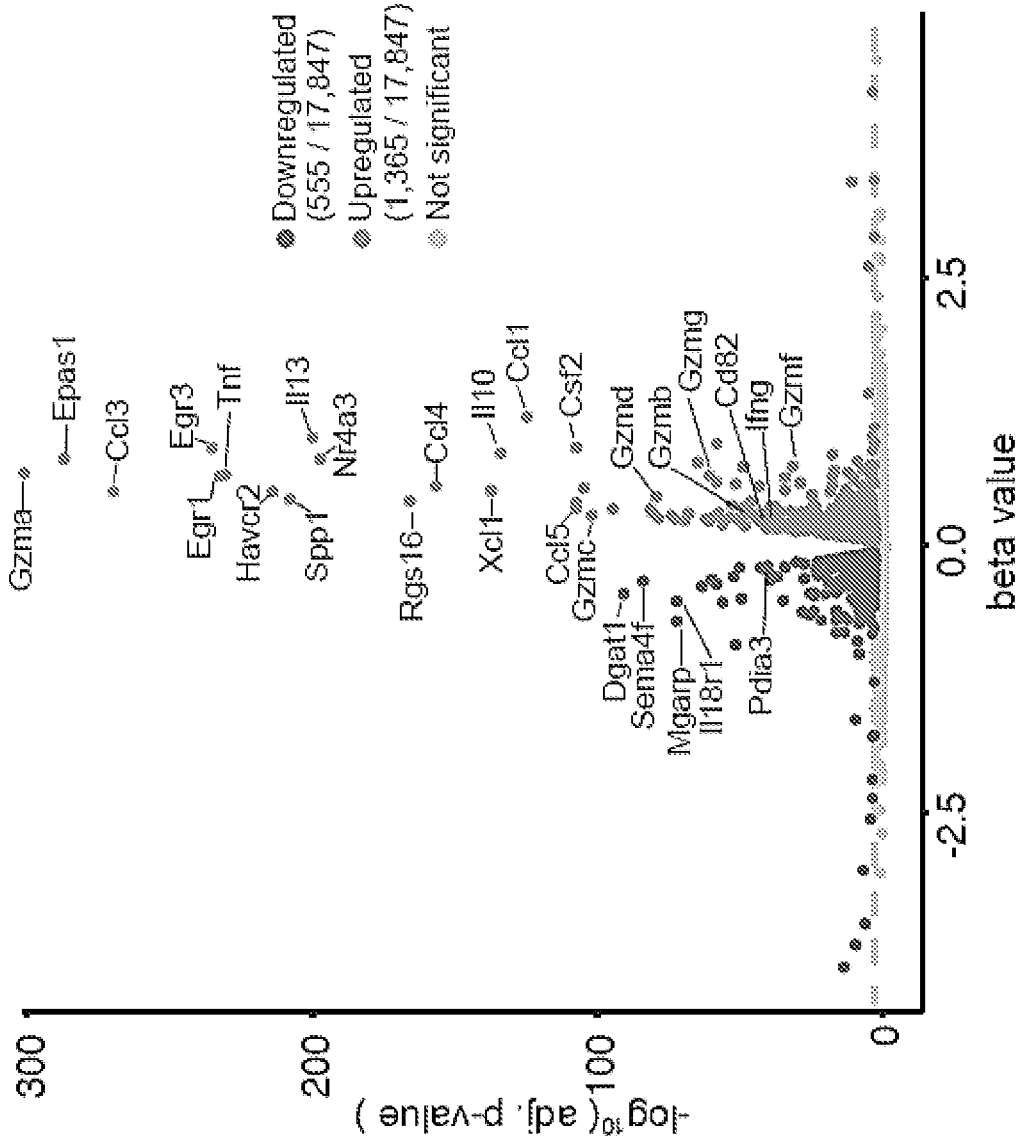
Figure 8D:
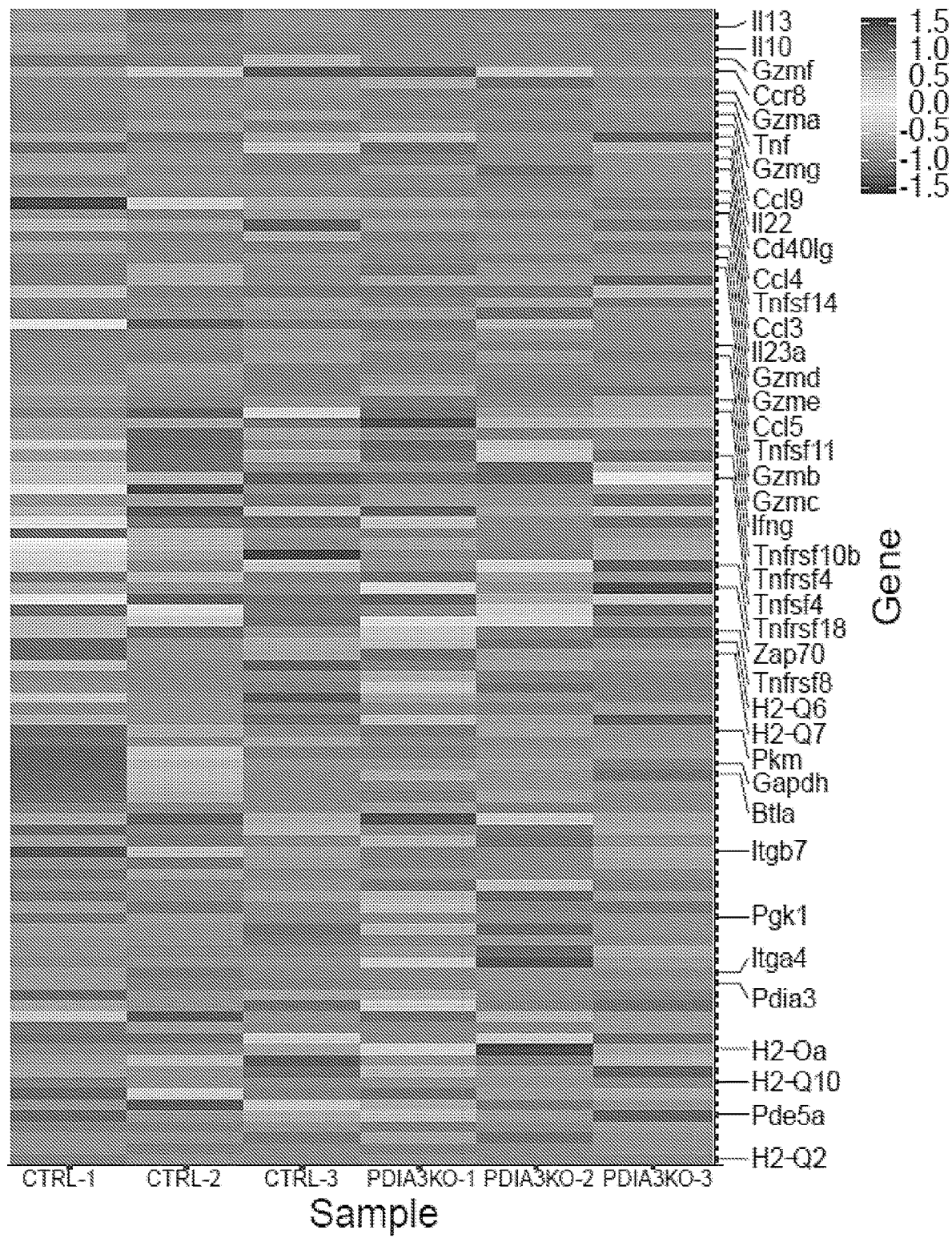
Figure 8E:
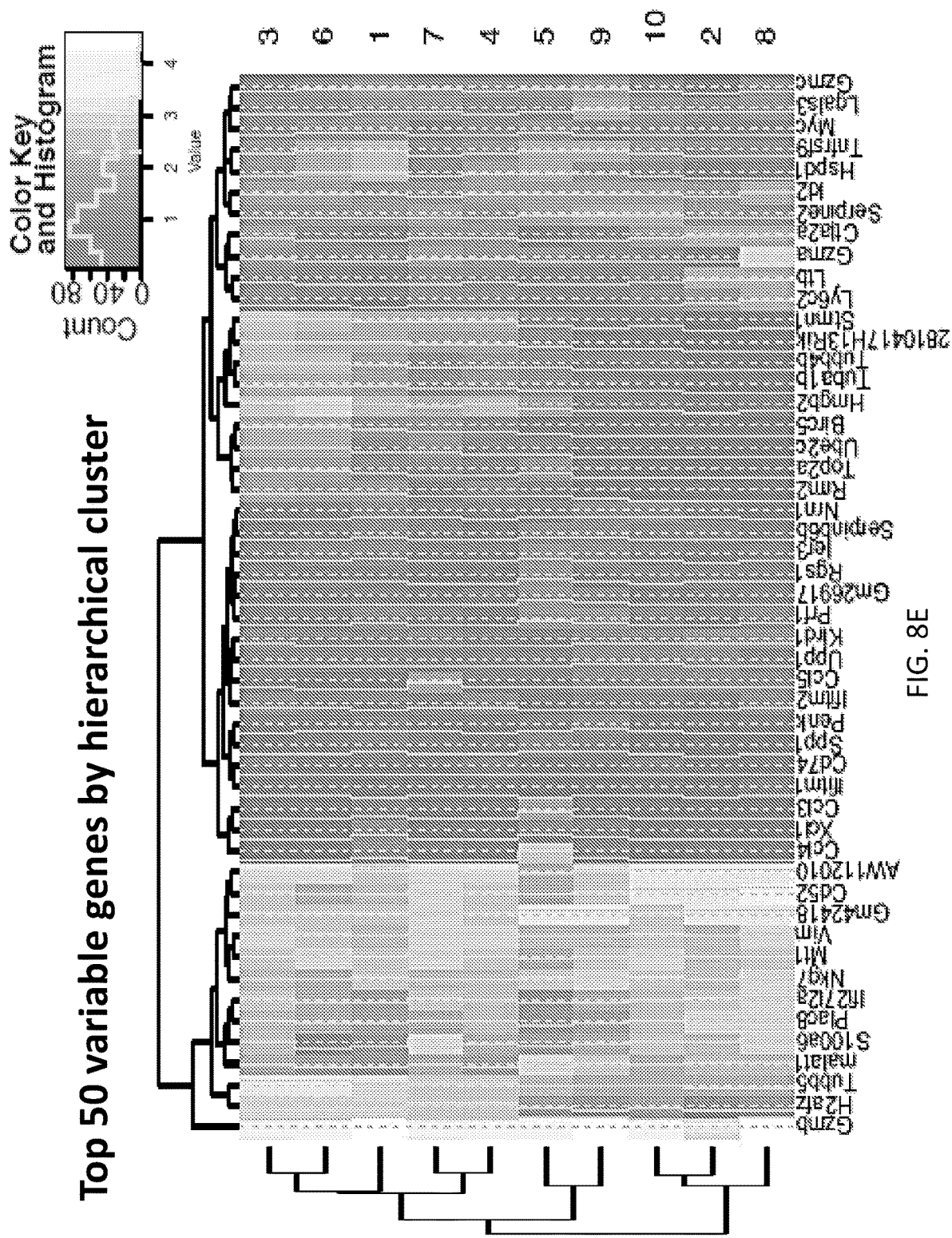
Figure 9:
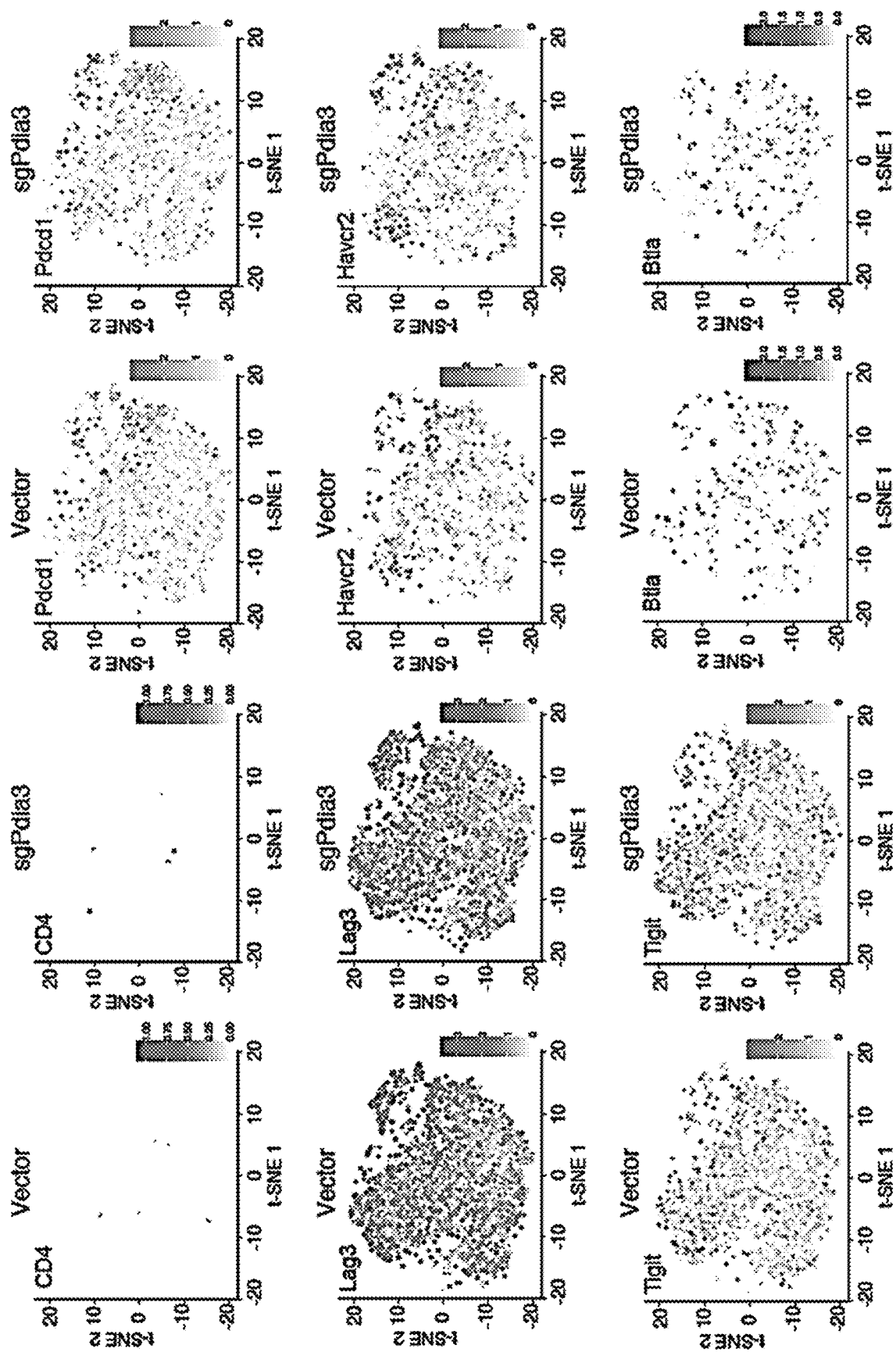
FIG. 9 shows a t-SNE plots of lineage, immune checkpoints, and effector markers of mouse CD8+ T cells from scRNA-seq data. t-SNE plots show multiple T-cell markers at the transcript level, including CD4 (negative control), PD-1, Lag3, Tim3 (Havcr2), Tigit, Btla, Ctla4, Icos, Ifng and Tnf, for both AAV-sgPdia3 and AAV-Vector treated single mouse CD8+ T cells.

Example 5: Effector Molecules Mediate the Enhanced Anti-Tumor Activity of the Pdia3 Mutant T Cells To provide a global map of gene expression level of AAV-sgPdia3 edited T cells, single cell RNA sequencing (scRNA-seq) was performed. The transcriptomes of 9,193 single cells were captured with a 10× Genomics platform, and Illumina-sequenced for AAV-sgPdia3 and AAV-Vector treated CD8 T cells (FIG. 7A). Data analysis of the transcriptomes of these single cells demonstrated that Pdia3 was dramatically and significantly downregulated (FIG. 7B-7C), indicating a clear on-target effect. General T cell lineage markers were not significantly different between Pdia3-edited and control T cells (FIG. 8A, FIG. 9). In addition, the expression of well-known immune checkpoints and co-stimulatory molecules was mapped, including Havcr2 (Tim3), PD-1, Lag3, Tigit, Btla and Icos (FIG. 9). Multiple effector cytokines were significantly upregulated after Pdia3 knockout. The top 5 upregulated genes were Granzyme a (Gzma), S100a6, Gzmb, Gzmc and Usmg5 (FIG. 7B-7D; FIG. 8B-8D), which implied that granzyme family overexpression may be one of the major effector functions that accounts for the Pdia3 mutant T cells' augmented ability to kill tumor cells.

Figure 8F:
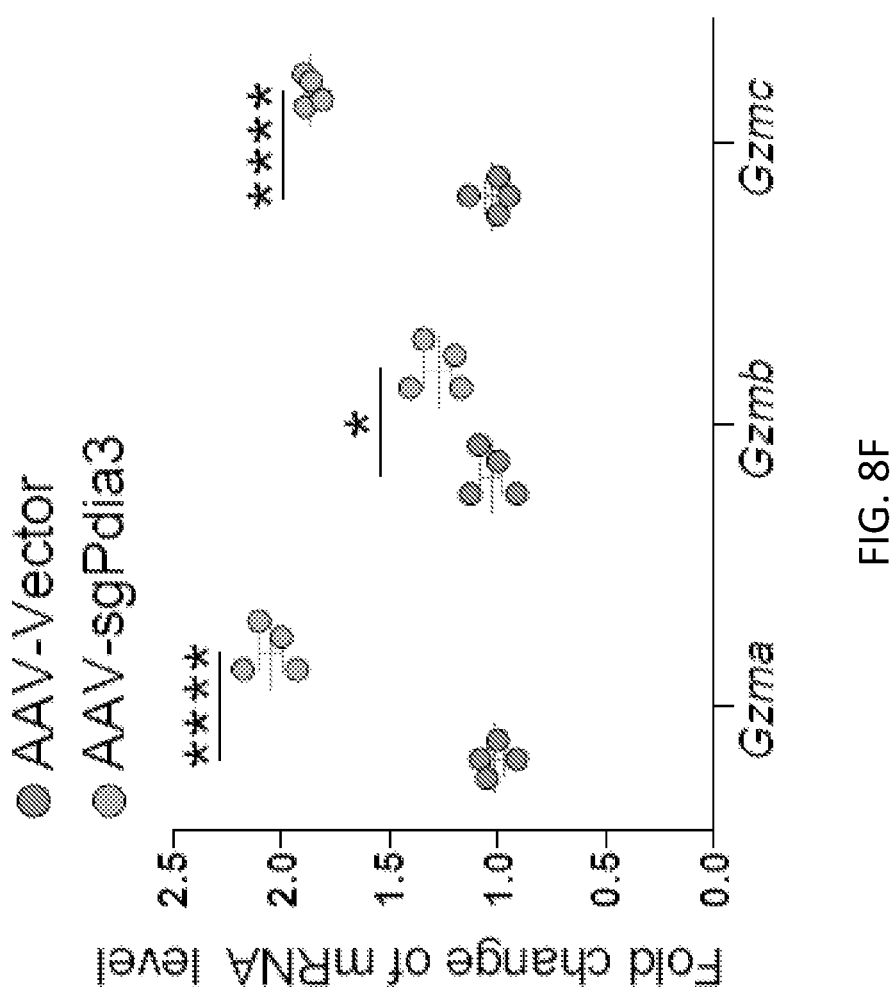
Figure 8G:
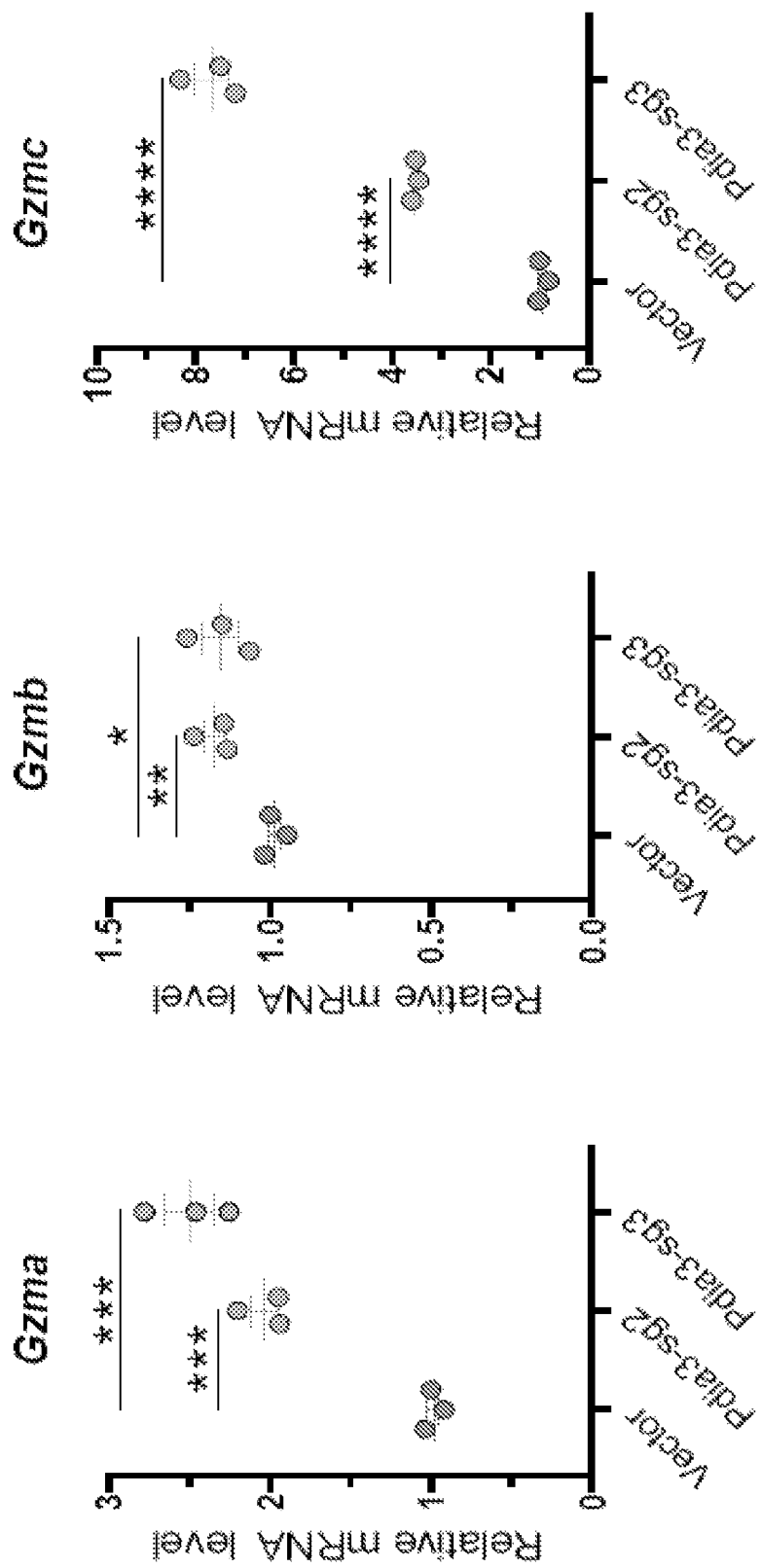
Figure 10A:
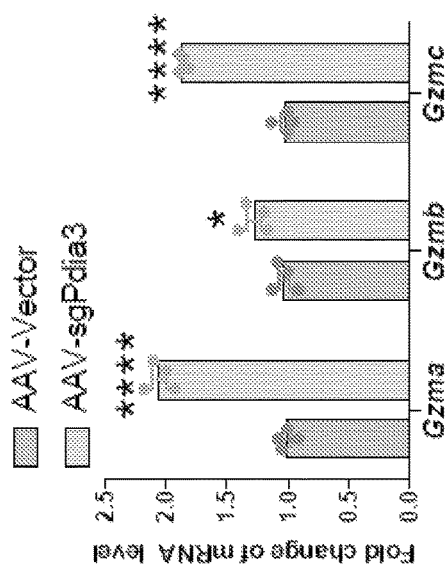
FIGS. 10A-10K show mechanistic analysis and pre-clinical efficacy testing of the anti-tumor activity of Pdia3 knockout CD8 T cells using independent tumor models.
Figure 10B:
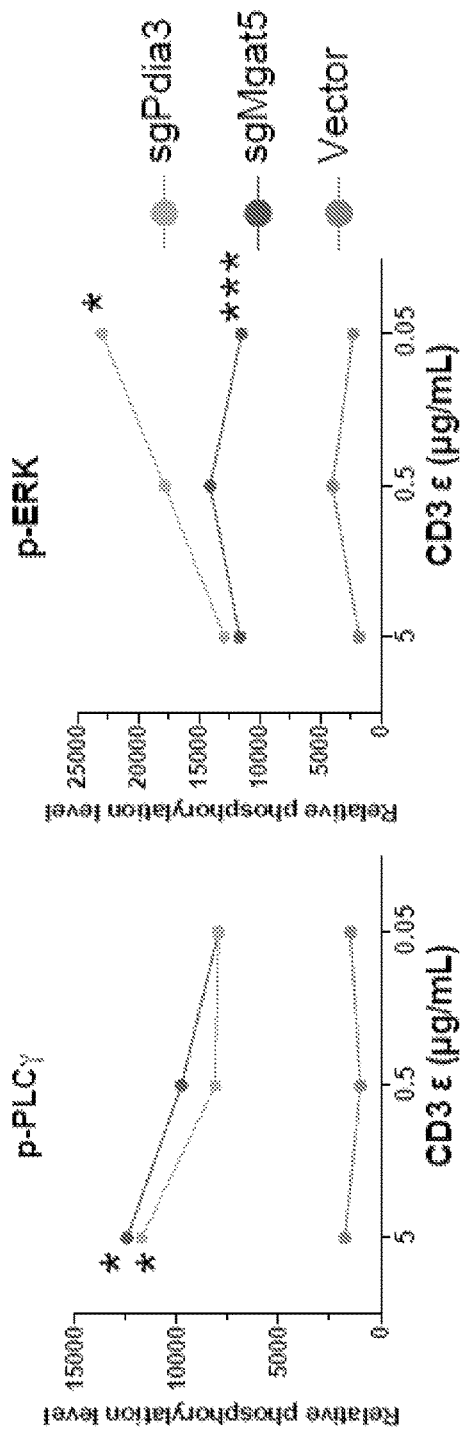
Figure 10C:
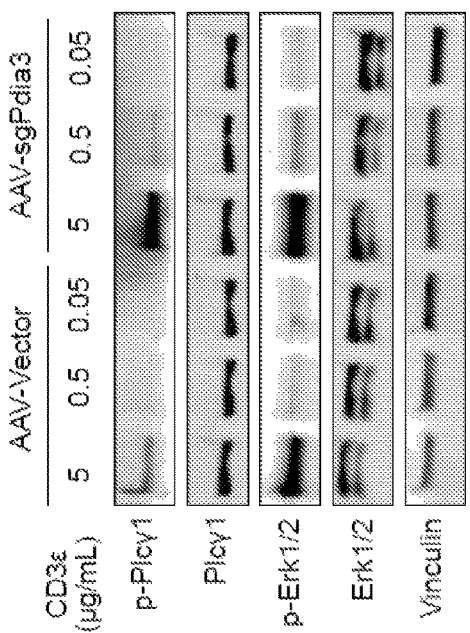
Figure 10D:
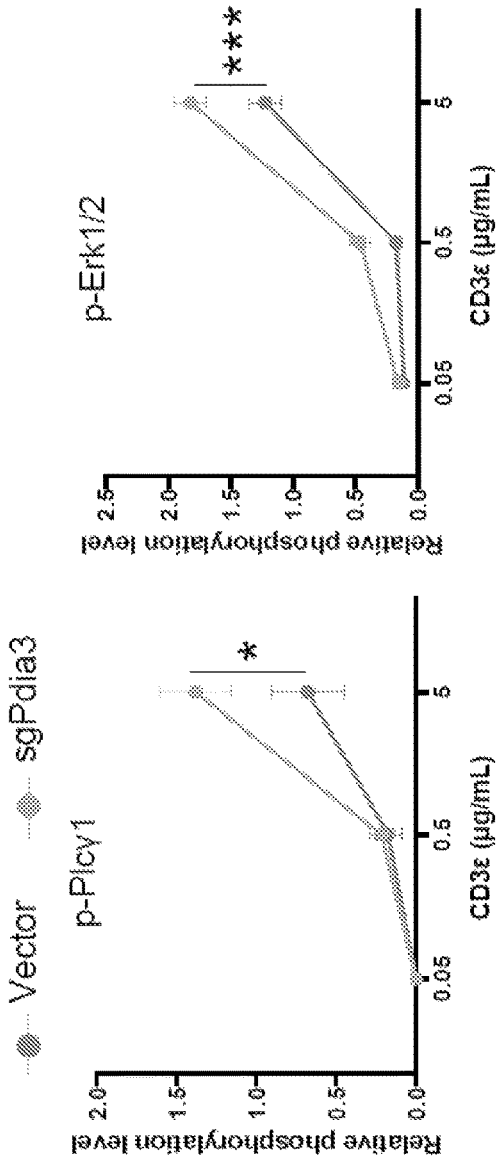
Figure 10E:
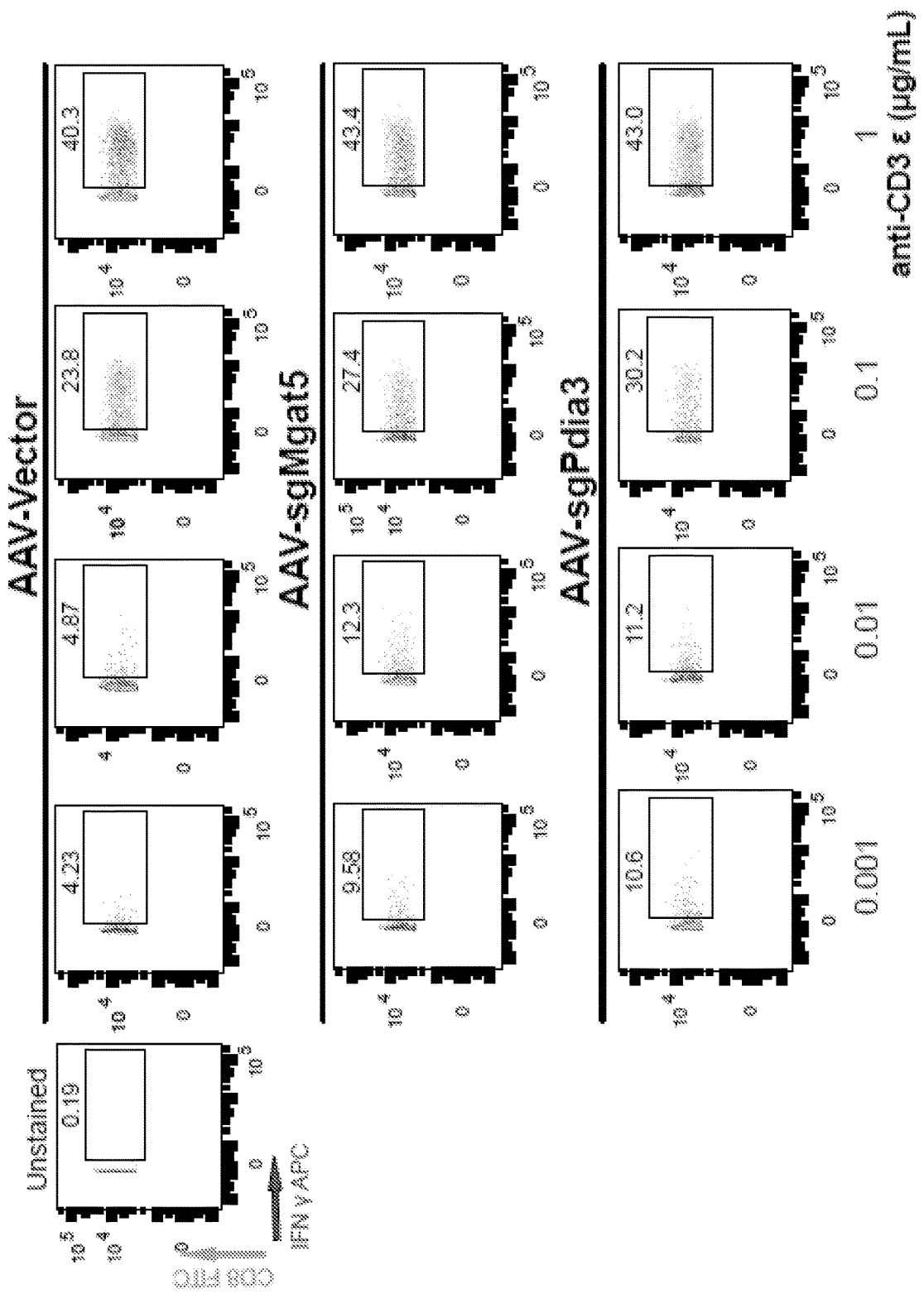
Figure 10G:
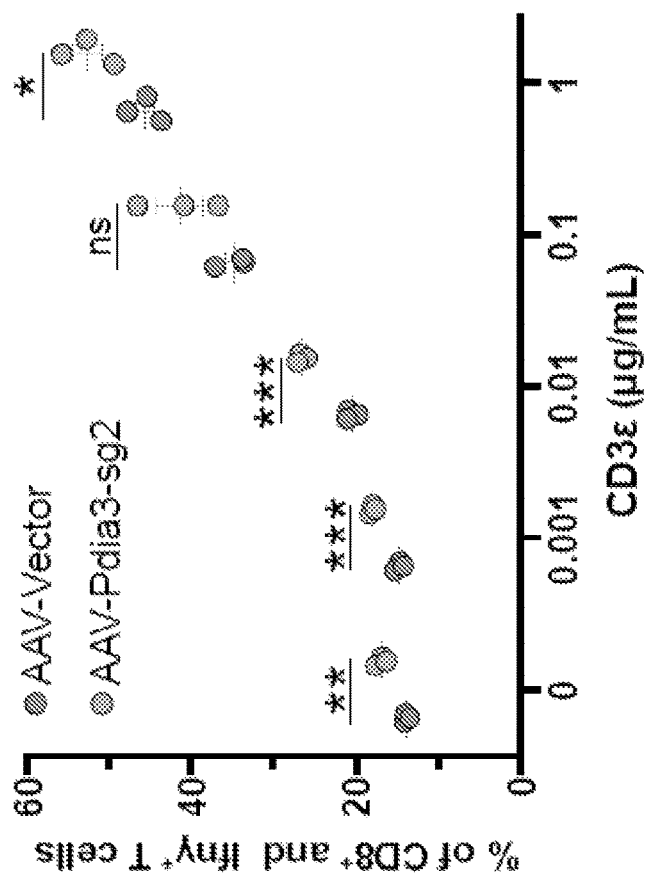
Figure 10F:
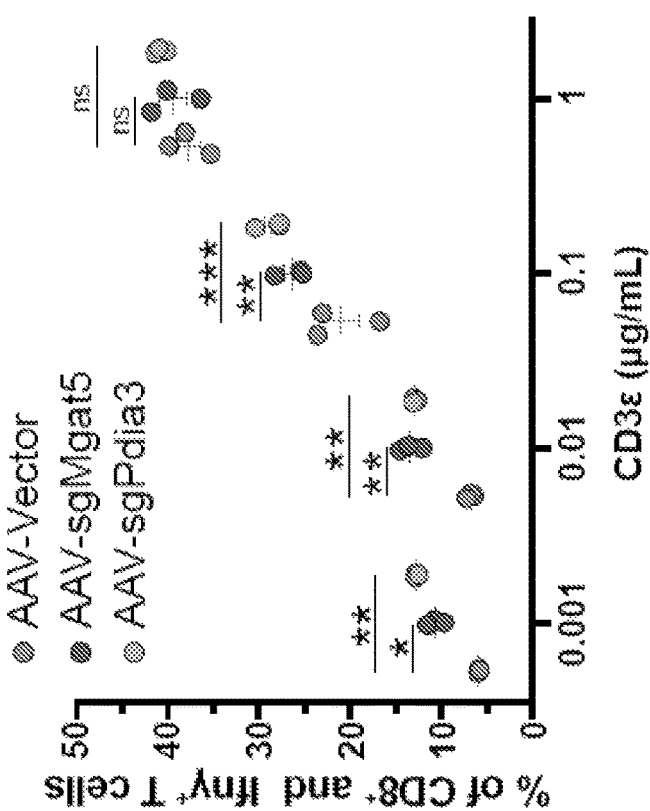

RT-qPCR was performed to validate the scRNA-seq result and confirm the upregulation of granzyme genes upon AAV-sgPdia3 perturbation (FIGS. 8F-8G; FIG. 10A) T cell signaling pathway was next investigated upon Pdia3 perturbation, alongside Mgat5. Quantification of immunoblot results showed that the phosphorylation of PLCγ and ERK1/2 was significantly upregulated across a dose-dependent anti-CD3ε stimulation (FIG. 10B). In concordance with the more sensitive TCR signaling pathway, intracellular flow cytometry experiment revealed that IFNγ production was upregulated in AAV-sgPdia3 infected CD8 T cells, which secreted more IFNγ with low anti-CD3ε stimulation (FIG. 10C-10D). Collectively, these data support a model in which the inhibition of Pdia3 upregulated granzyme gene expression, as well as a more sensitive induction threshold for TCR signaling and IFNγ production.

Example 6: Editing of Pdia3 in CD8 T Cells in Pre-Clinical Tumor Models

Figure 10H:
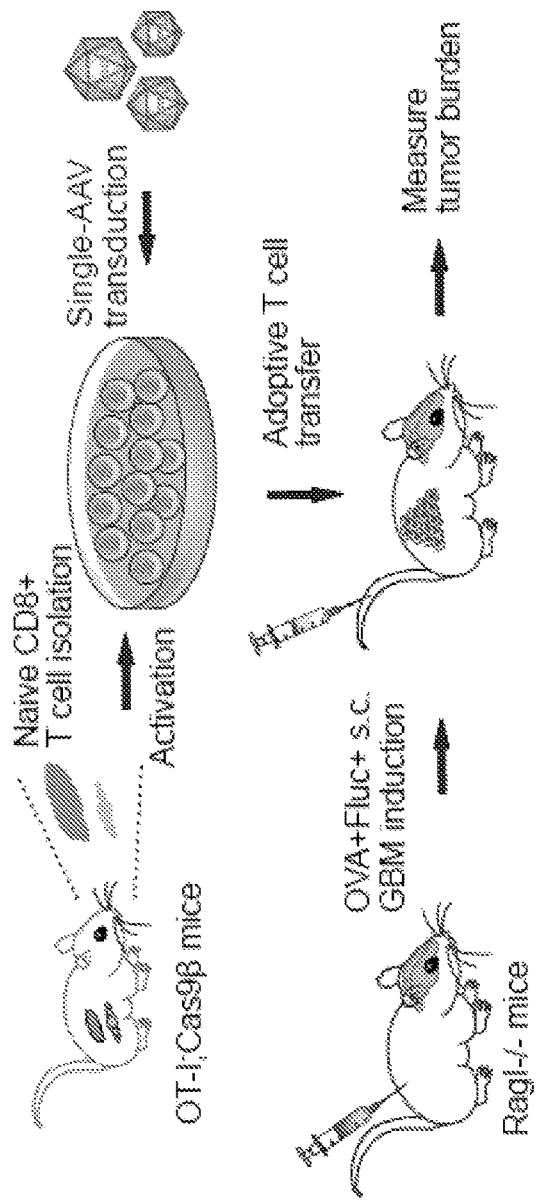
Figure 10I:
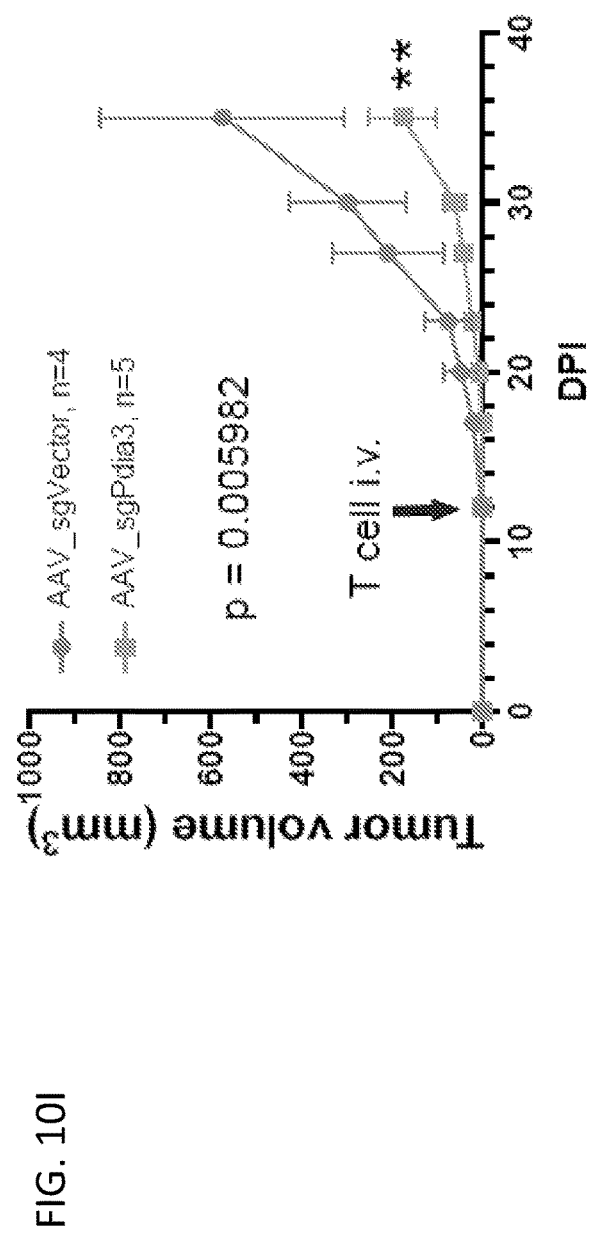
Figure 10J:
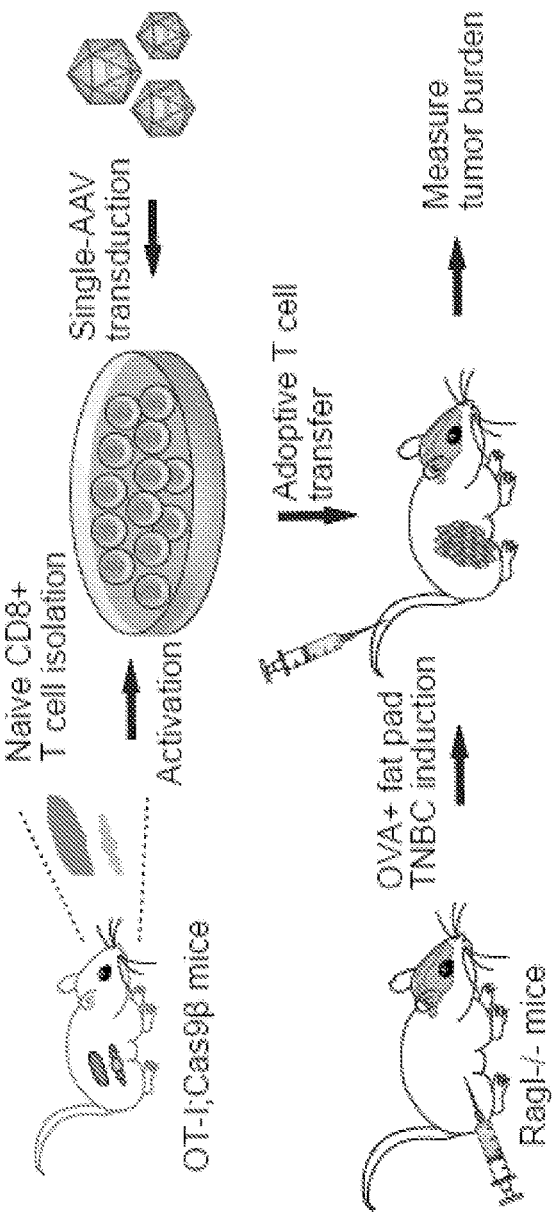
Figure 10K:
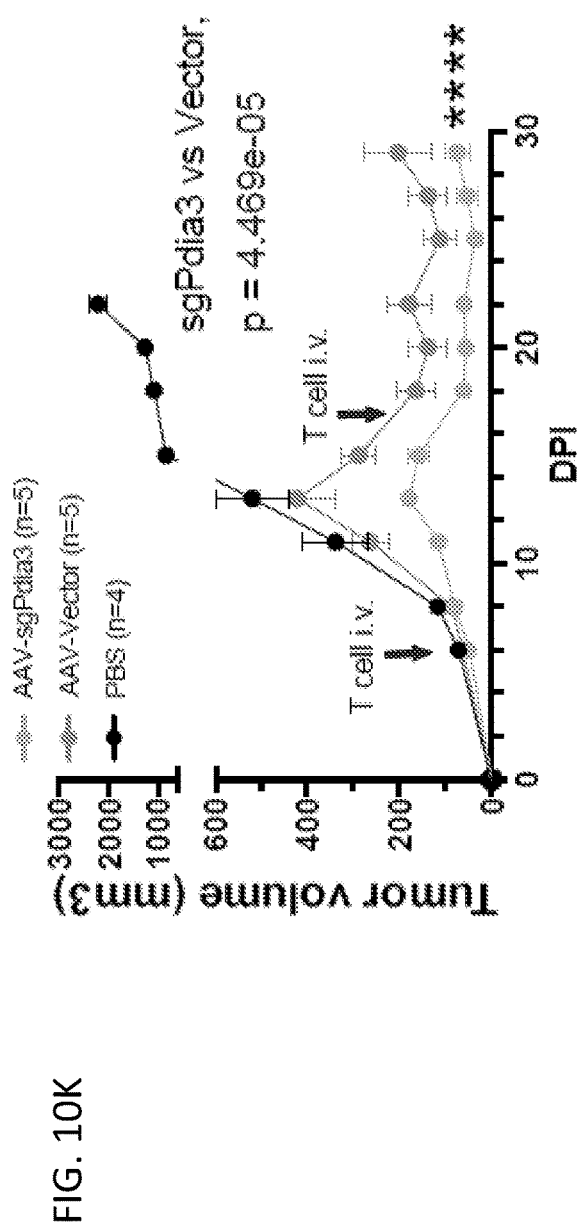

Without wishing to be bound by theory, because granzymes and IFNγ are T cell intrinsic properties, based on the results of Pdia3 edited CD8+ T cells, it is believed that Pdia3 editing could also have anti-tumor effect in other tumor models. To test if genetically editing PDia3 would result in anti-tumor effector function, two models of syngeneic tumor immunotherapy were tested. In the first experiment, GL261 tumors were induced with subcutaneous injection. Pdia3 mutant CD8+ T cells were adoptively transferred via intravenous injection in GL261-tumor bearing mice (FIG. 10H). Knocking out Pdia3 using AAV-sgPdia3 in CD8+ T cells significantly reduced overall tumor volume (FIG. 10I). In the second experiment, we used another cancer cell line, E077, to induce syngeneic orthotopic triple-negative breast cancer (TNBC) via mammary fat pad injection (FIG. 10J). Tumor-bearing mice were again injected with Pdia3 mutant CD8+ T cells by adoptive transfer (FIG. 10J). Compared to vector alone, mice that received Pdia3 mutant CD8+ T cells had significantly lower tumor burden (FIG. 10K). Together, without wishing to be bound by theory, these data suggest that the enhanced anti-tumor activity of Pdia3 perturbation encompasses, at least in part, T cell intrinsic phenotypes.

Example 7: Phenotypic Analysis of Pdia3 Knockout Human CD8 T Cells

Figure 11A:
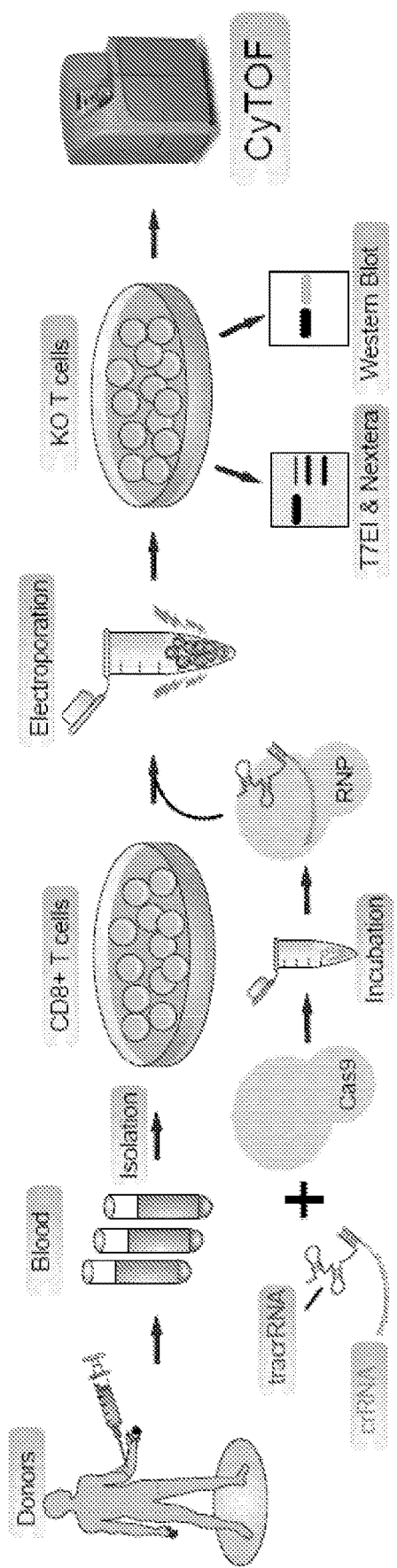
Figure 11E:
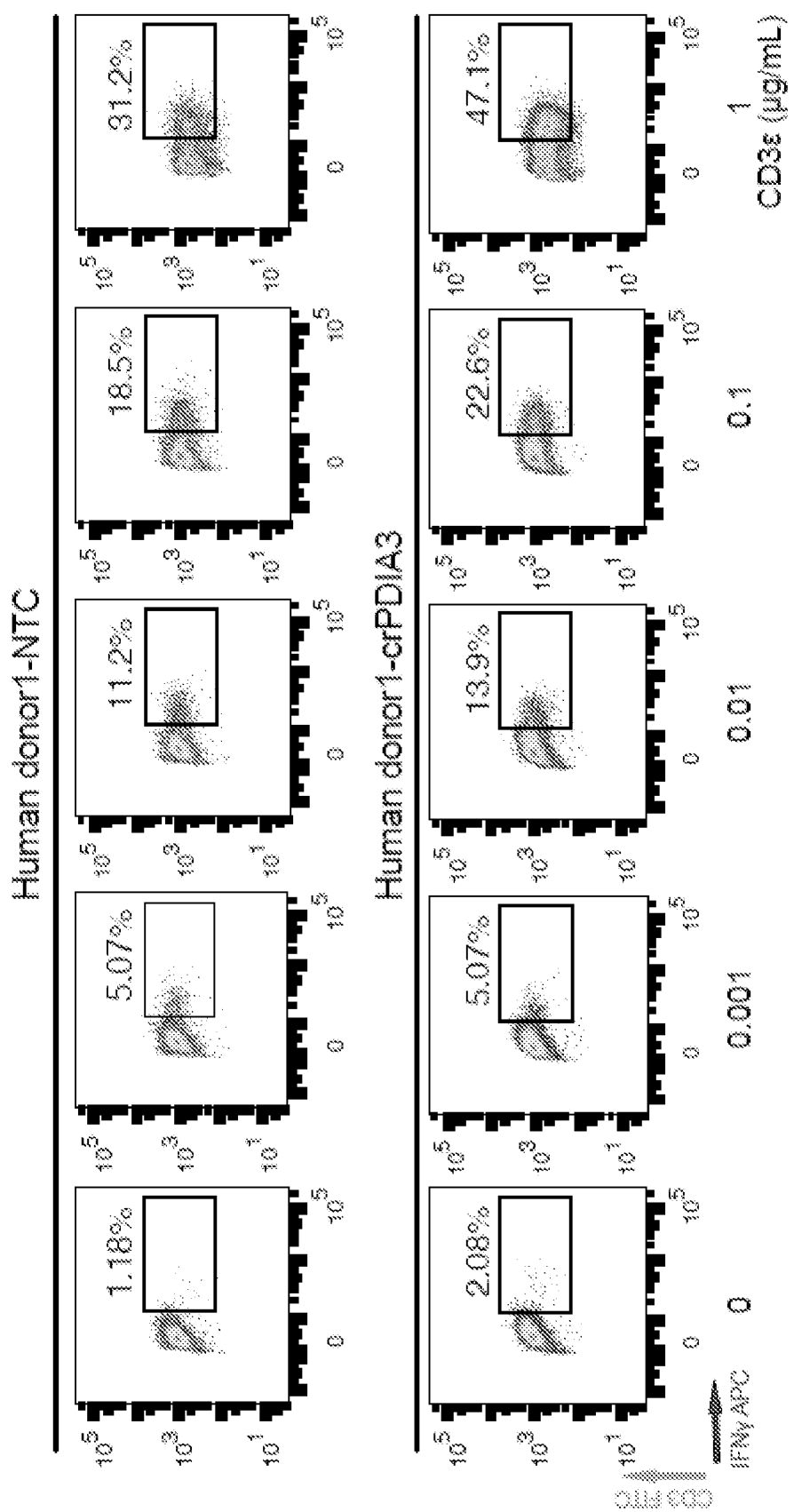
Figure 11G:
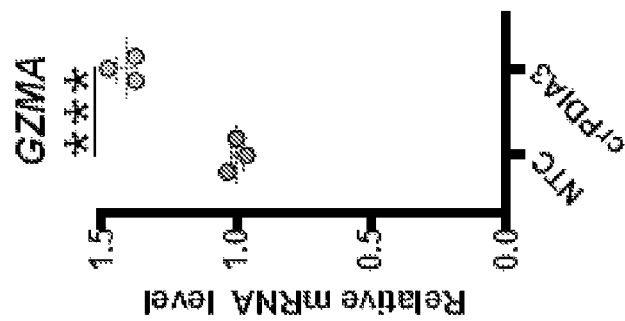
Figure 11F:
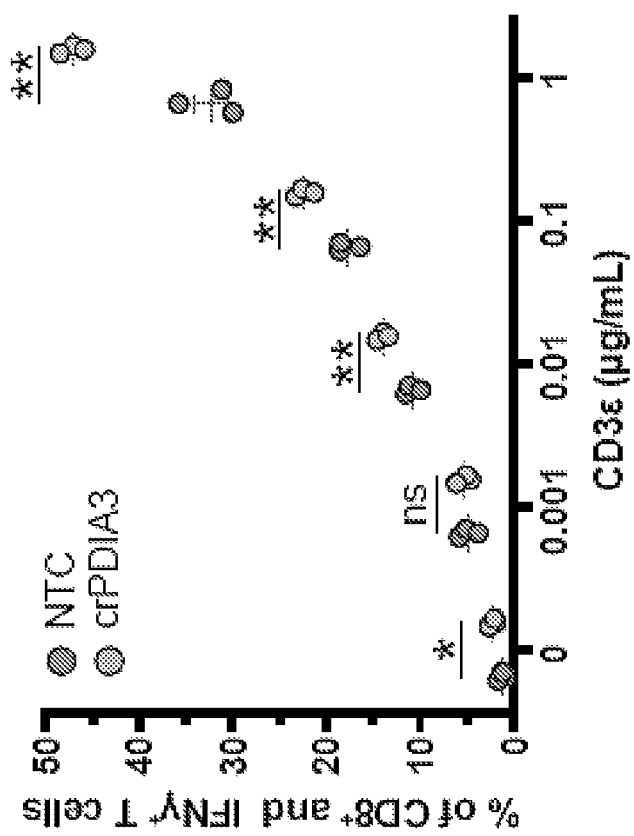
Figures 11H, 11I:
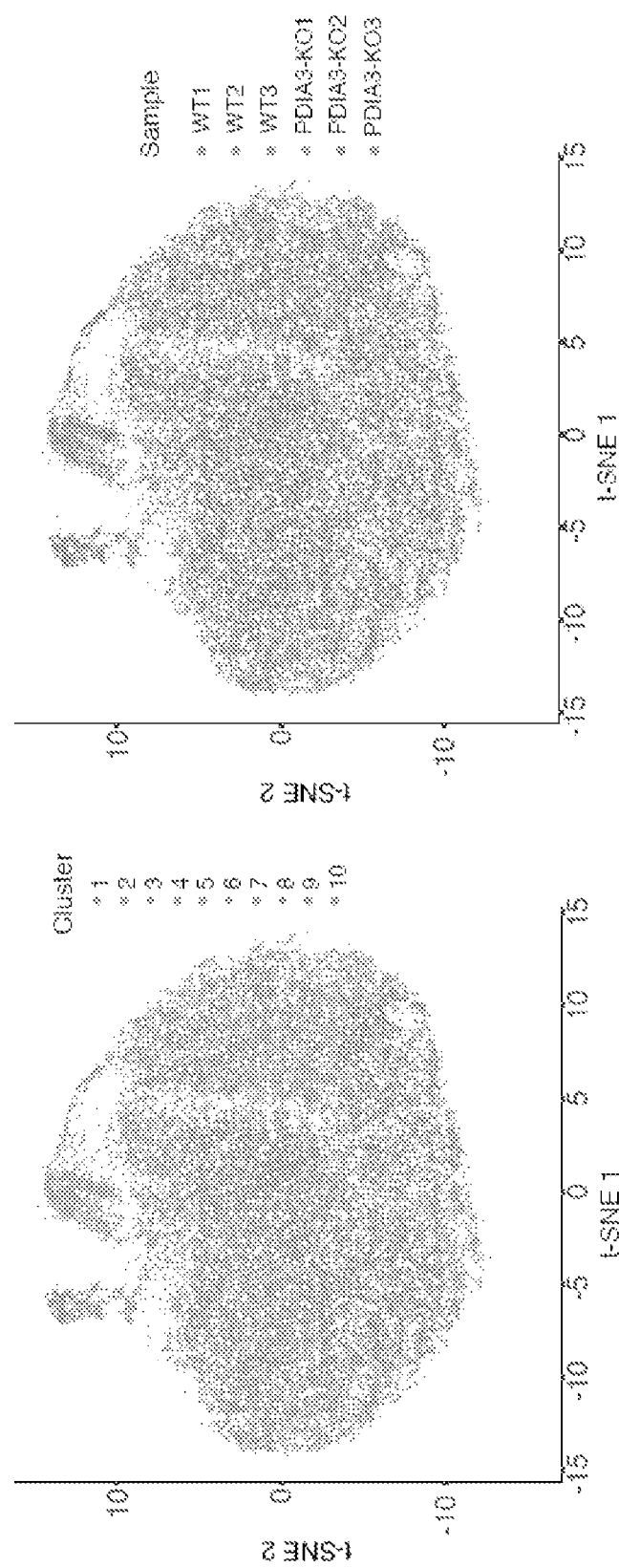
Figure 11J:
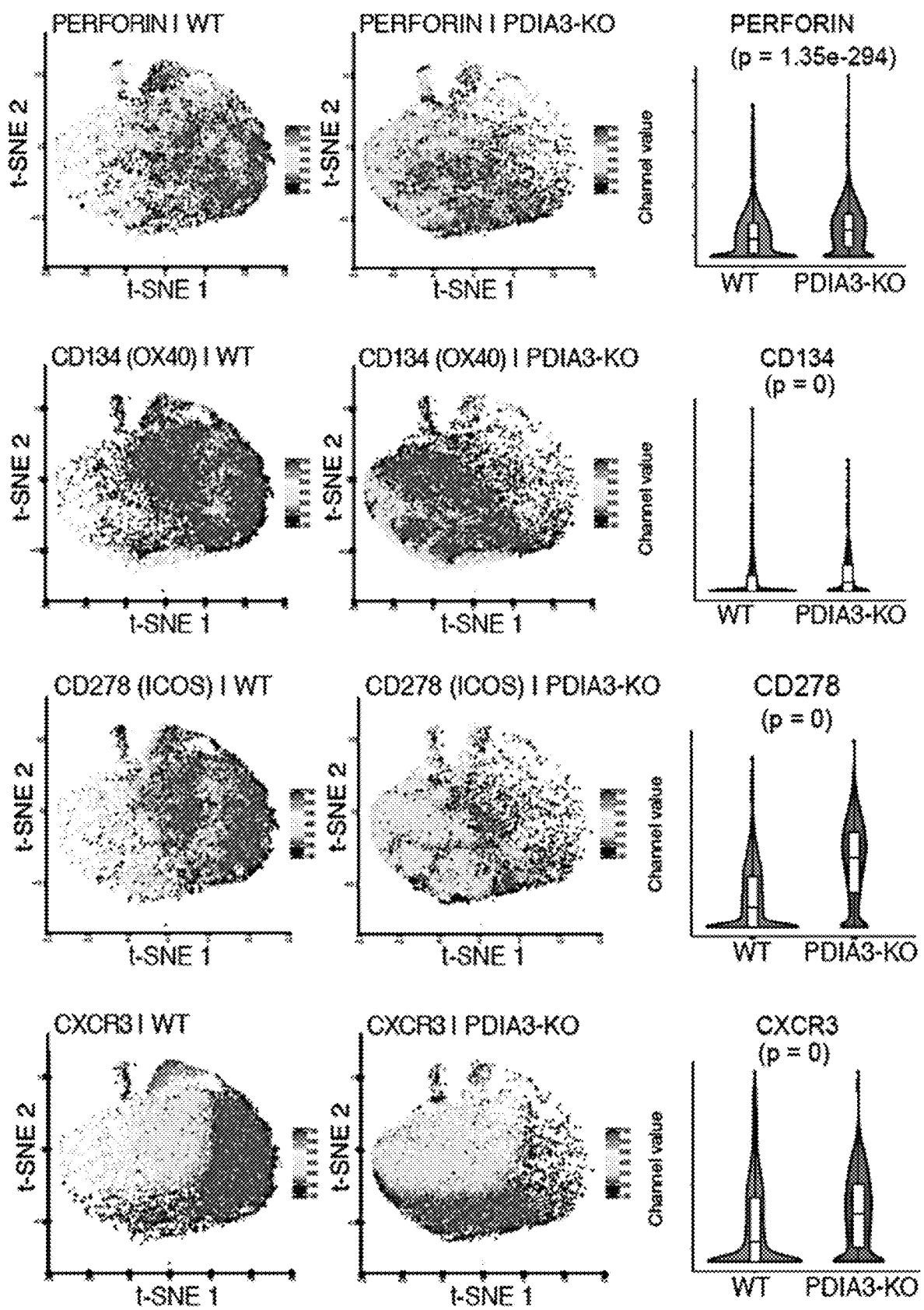
Figure 12:
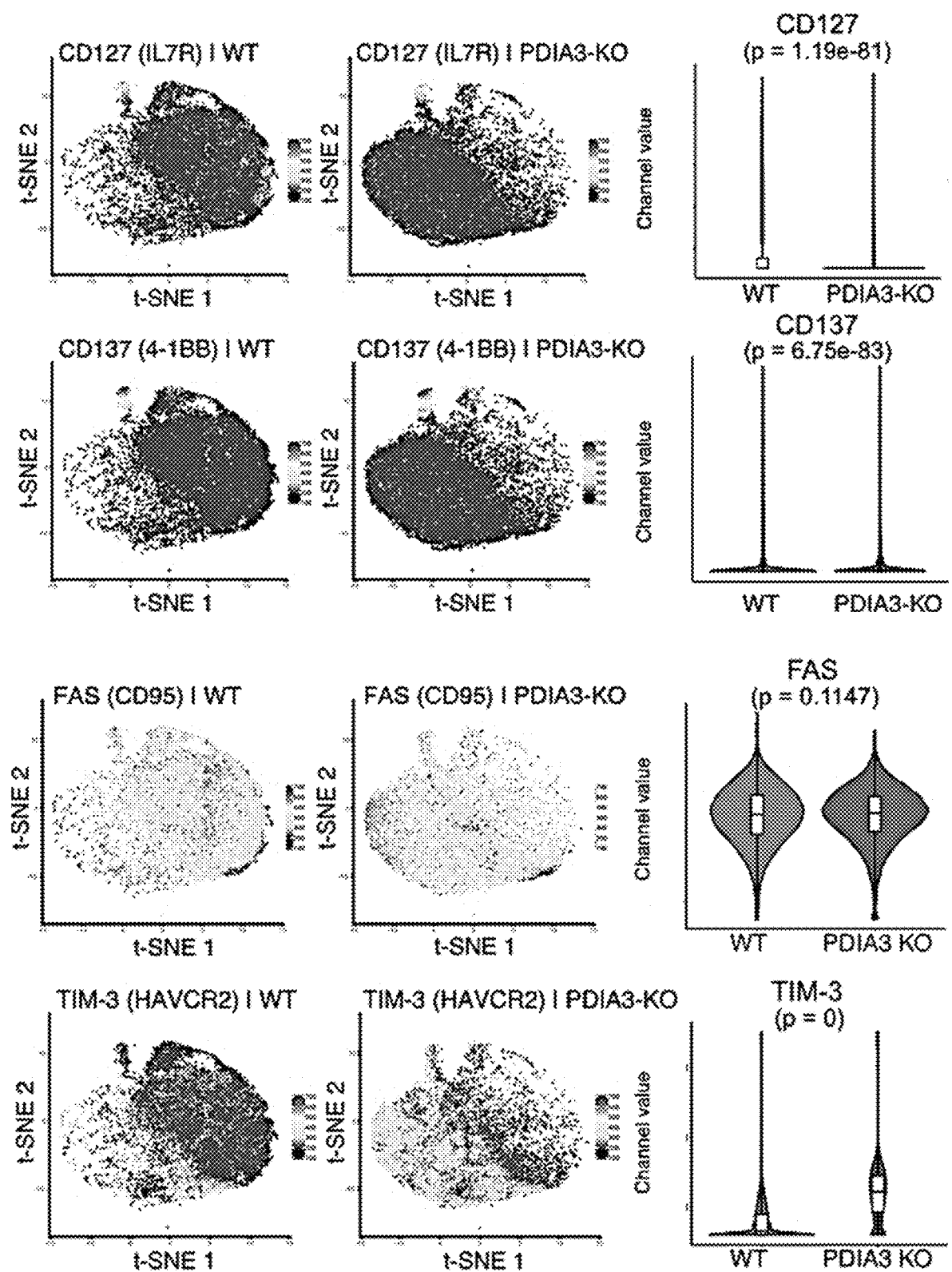
FIG. 12 shows immune checkpoint CyTOF analysis of PDIA3 KO human CD8 T cells. t-SNE and violin plots of CyTOF data of CD127/IL7R, FAS/CD95, 4-1BB/CD137 and TIM-3/HAVCR2 at the surface protein level, for both PDIA3 KO and wildtype single human CD8$^+$ T cells (n=3 replicates each, sampled 7,000 cells per replicate for comparison). Violins show kernel probability density on side, and boxplot is standard, i.e. middle band is median, hinges/ends of box are interquartile range (25% and 75% quantiles), lower whisker=smallest observation greater than or equal to lower hinge-1.5*IQR, upper whisker=largest observation less than or equal to upper hinge+1.5*IQR. Wilcoxon test, two-sided, p value adjusted by Benjamini & Hochberg method. KO vs WT: p=1.91e-81 for CD127/IL7R, p=0.1147 for FAS/CD95, p=6.75e-83 for 4-1BB/CD137, and p=0 for TIM-3/HAVCR2.
Figure 14:
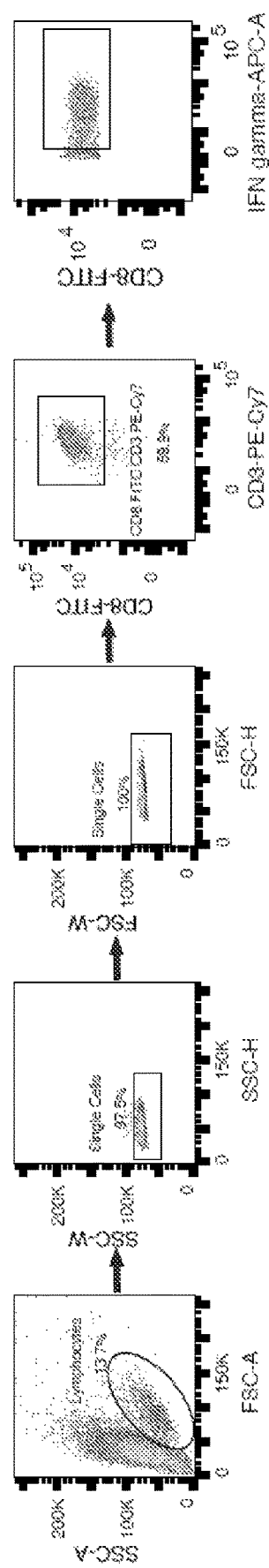
FIG. 14 shows the gating strategy for analyzing CD8 T cells expressing IFNγ.

To investigate the immunological phenotypes of Pdia3 in human CD8+ T cells, the Pdia3 locus in human CD8+ T cells was perturbed using the ribonucleoprotein (RNP) system (FIG. 11A). Analysis of DNA and protein levels demonstrated that the PDIA3 knockout was near-complete (>90% knockout) (FIGS. 11B-11D). Anti-CD3 dose-dependent analysis of IFNγ production was performed and found that PDIA3 edited CD8+ T cells had significantly higher IFNγ (FIGS. 11E-11G, gating strategy illustrated in FIG. 14). RT-qPCR analysis of human GZMA also showed upregulation upon PDIA3 loss (FIG. 11G). CyTOF analysis yielded high-dimensional landscapes of immune checkpoint and other functional molecules in PDIA3 knockout and wildtype human CD8+ T cells from 227,848 single CD8+ T cells (FIGS. 11H-11I). Clustering analysis showed that the PDIA3-KO replicates clustered together and are distinct from the wildtype replicates (FIGS. 11H-11I). The t-SNE plots, either by sample or by clusters, showed that the effector molecule perforin as well as the co-stimulatory markers, OX40 and ICOS, as well as CXCR3, were significantly upregulated in PDIA3 knockouts compared to wildtype CD8 T cells (FIG. 11J). 4-1BB/CD137 and IL7R/CD127 were moderately altered, but not Fas/CD95 (FIG. 12). Uniquely, TIM3 was significantly upregulated in PDIA3 knockout, consistent with mRNA-seq data. Together, these data showed PDIA3 CRISPR editing influenced the surface expression of multiple of immune regulators and effectors in human CD8 T cells.

Figure 13A:
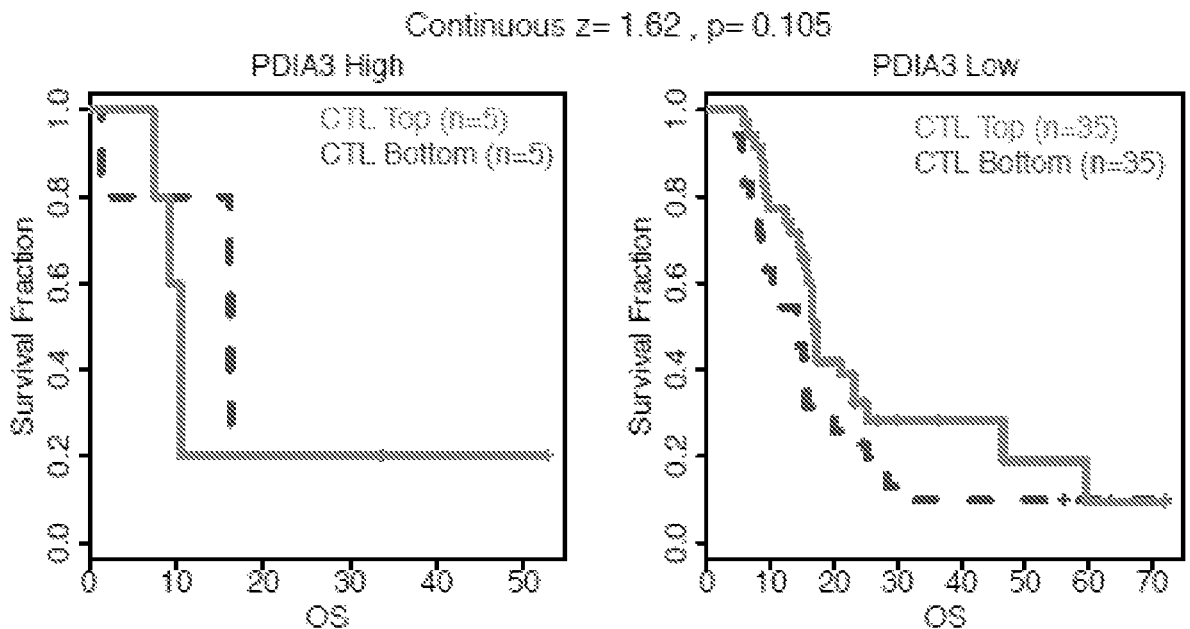
FIGS. 13A-13D describe TIDE analysis of human patient data.
Figure 13B:
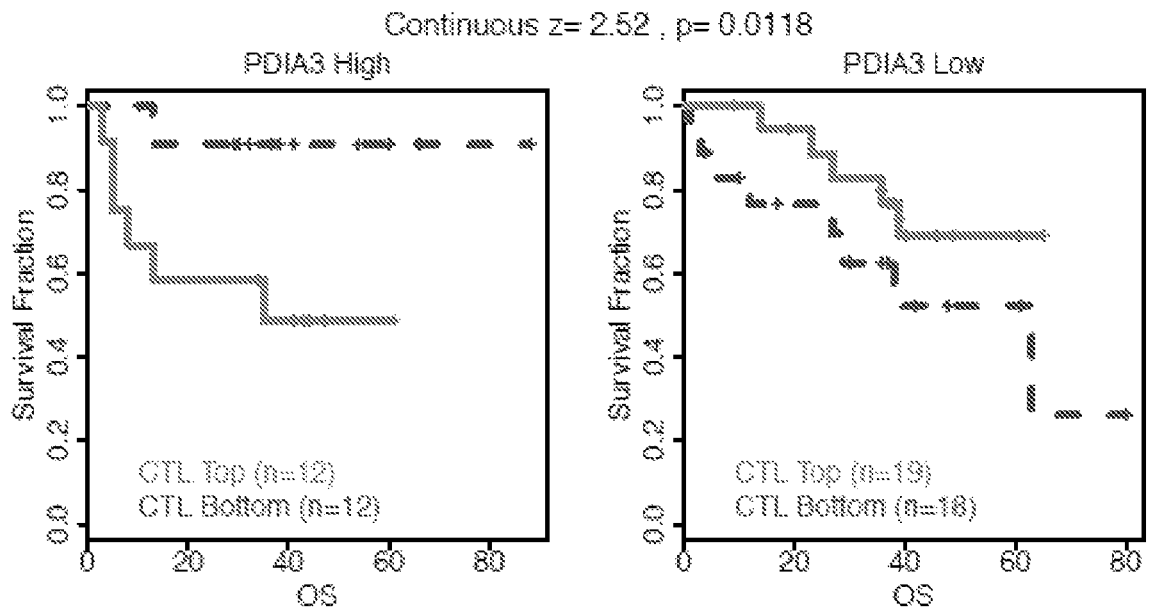
Figures 13C, 13D:
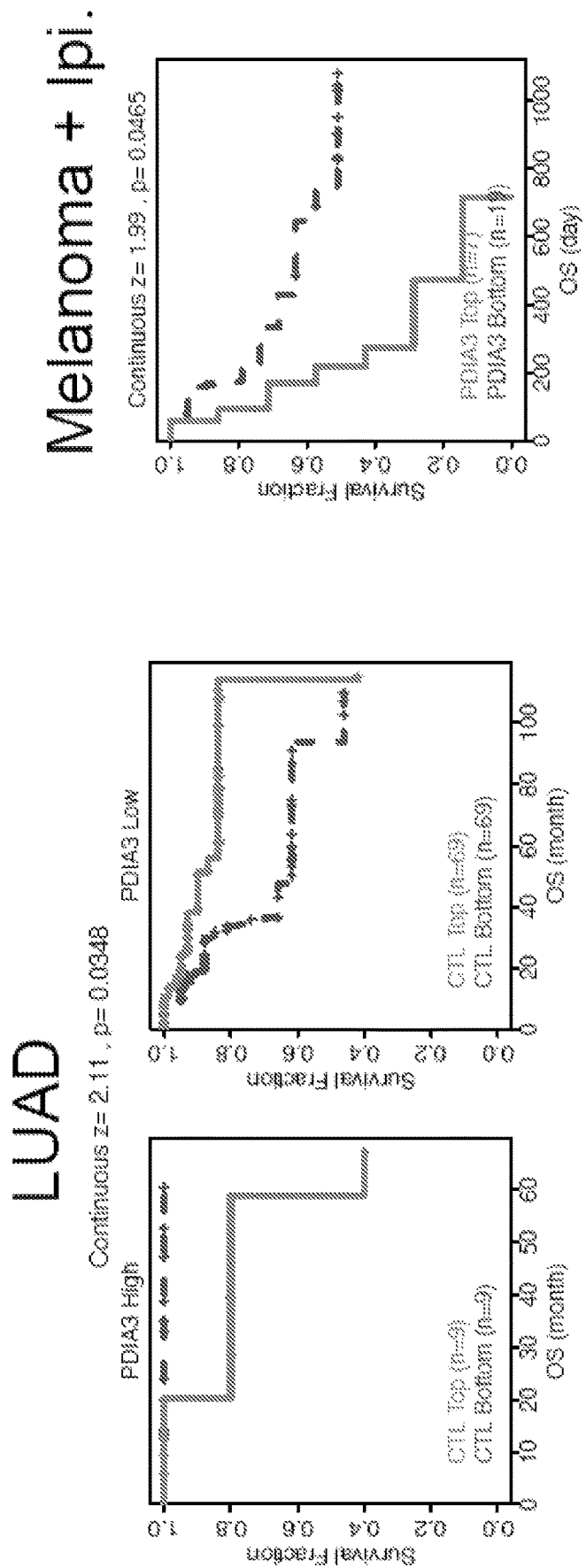

To investigate whether PDIA3 expression was clinically relevant, large-scale patient data analysis using the recently developed Tumor Immune Dysfunction and Exclusion (TIDE) algorithm (Jiang, P. et al. (2018) *Nat Med* 24:1550) was performed. High-levels of PDIA3 abolished or weakened the overall survival of CTL-high patients (FIGS. 13A-13D). Additionally, PDIA3$^{lo}$ patient groups were associated with greater overall survival across multiple cancer types including GBM, TNBC and lung adenocarcinoma (FIGS. 13A-13C). Moreover, in melanoma patients treated with immune checkpoint blockade, PDIA3$^{hi}$ patients had significantly poorer survival than PDIA3$^{lo}$ (FIG. 13D). These data suggest a significant clinical association of PDIA3 with human cancer.

Figure 16A:
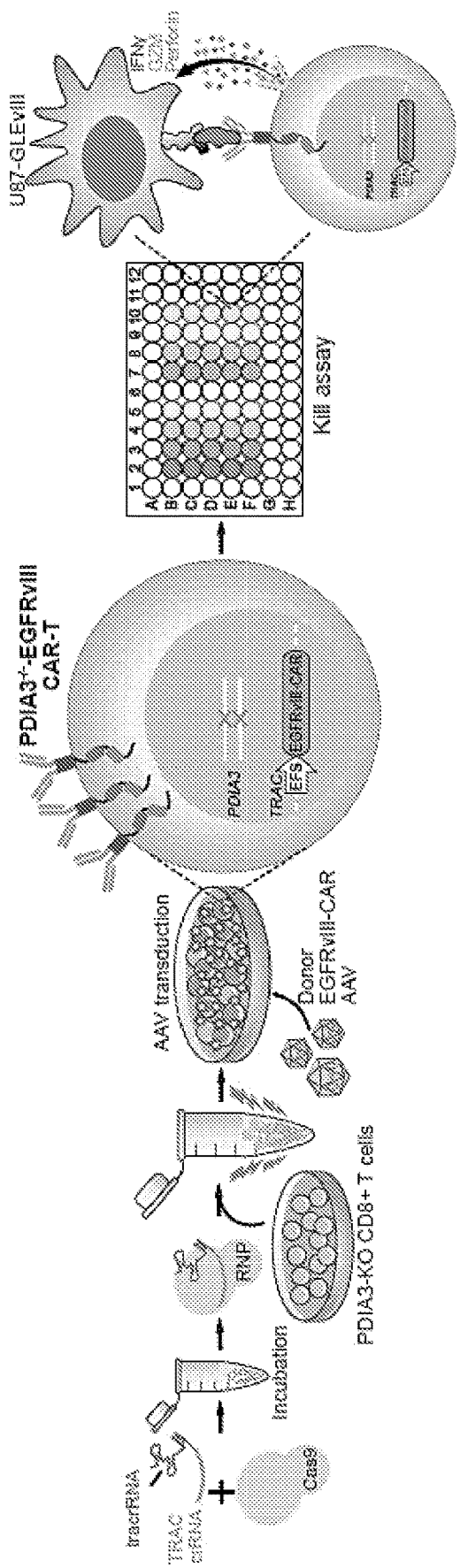
FIGS. 16A-16D show Human PDIA3$^-$-EGFRvIII CAR-T cell establishment and GBM cell killing.
Figures 16B, 16C, 16D:
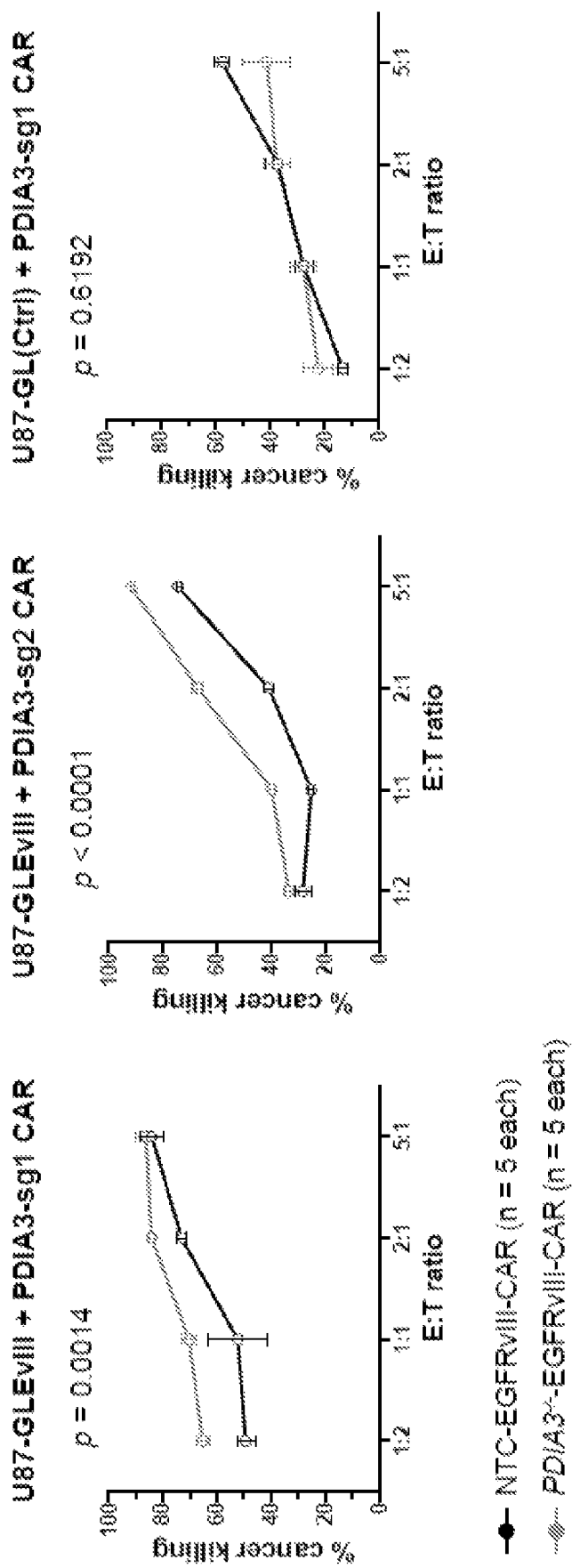

Example 8: PDIA3 Engineering Enhanced CAR-T Killing of Human EGFRvIII+ GBM Cells To further establish PDIA3 as an immunotherapy target of T cell engineering, especially against GBM, a PDIA3 mutant and control human EGFRvIII CAR-T cells were established by Cas9-RNP mediated gene editing of primary CD8+ T cells, along with AAV donor mediated knockin of an EGFRvIII CAR-T cassette into the TCR Alpha Constant chain (TRAC) locus (the EGFRvIII cloning vector is SEQ ID NO: 69,748 the CAR-T construct and vector is SEQ ID NO: 69,749) (FIG. 16A). An EGFRvIII-antigen expressing U87 GBM cell line (U87-Luc-EGFRvIII) was also generated. CAR-T cell:cancer cell co-culture assays were then performed in order to test the cytolytic (killing) activity. PDIA3 knockout compared to wildtype EGFRvIII CAR-T cells had significantly higher killing ability against the cognate U87-Luc-EGFRvIII cells (FIG. 16B). This was confirmed using an independent sgRNA targeting PDIA3 (FIG. 16C), further minimizing the probability of off-target. The killing ability of CAR-T is not different towards the parental U87 cells without EGFRvIII antigen (FIG. 16D), supporting CAR-T's antigen-specificity. These data together demonstrate that the major effect of PDIA3 knockout in EGFRvIII CAR-T cells is dependent on CAR-antigen recognition, and minimally due to TCR off target or gene editing off-target effects.

Example 9: Generation of Novel Monoclonal Antibodies Against Human MGAT5 and PDIA3

Figure 15A:
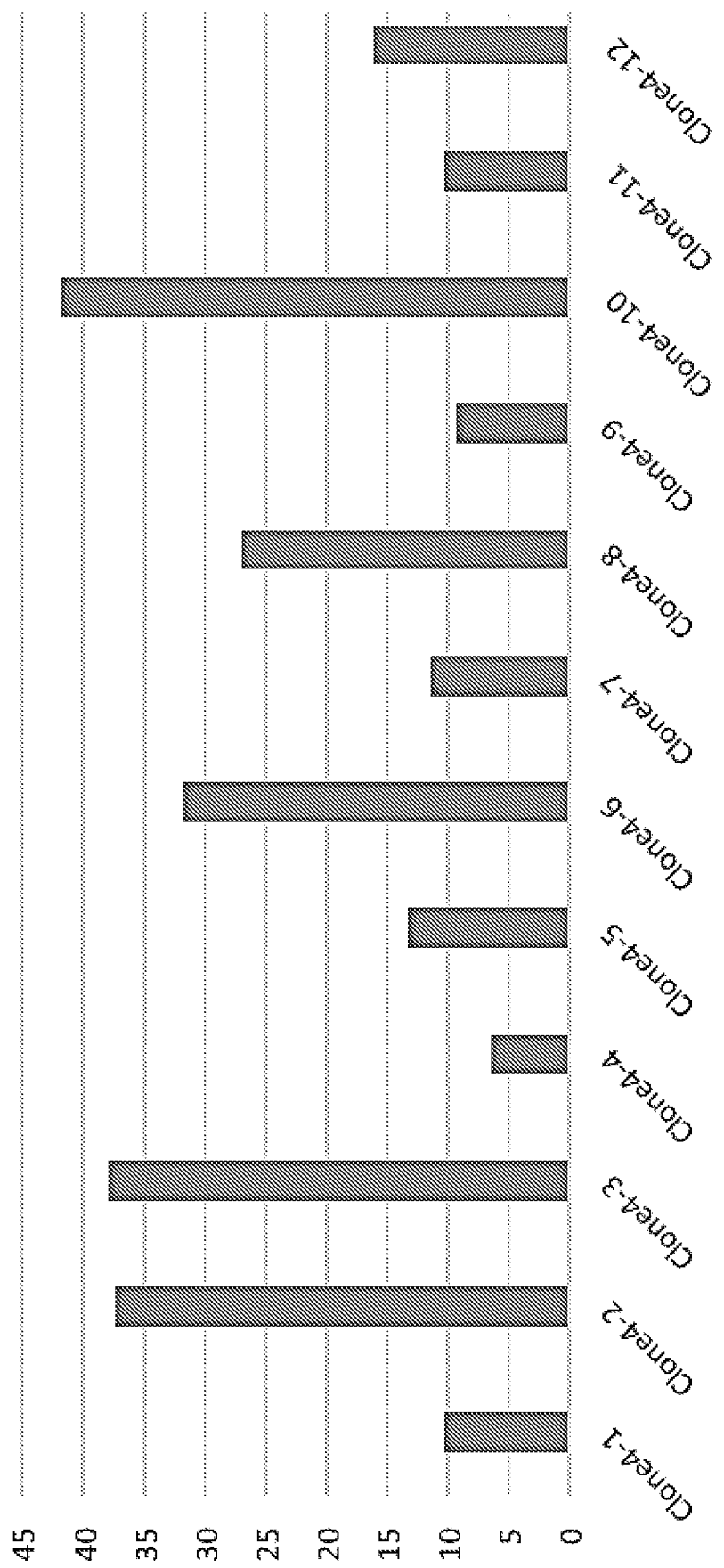
FIGS. 15A-15B show ELISA results of novel antibodies against human MGAT5 (FIG. 15A) or human PDIA3 (FIG. 15B). Phage display was used to generate monoclonal antibodies against MGAT5 or PDIA3, key targets identified by the in vivo AAV-SB-CRISPR screen in T cells. Purified recombinant antibodies were then used to stain HEK293FT cells expressing MGAT5 or PDIA3 antigens using standard flow cytometry protocols (FIG. 15C).
Figure 15B:
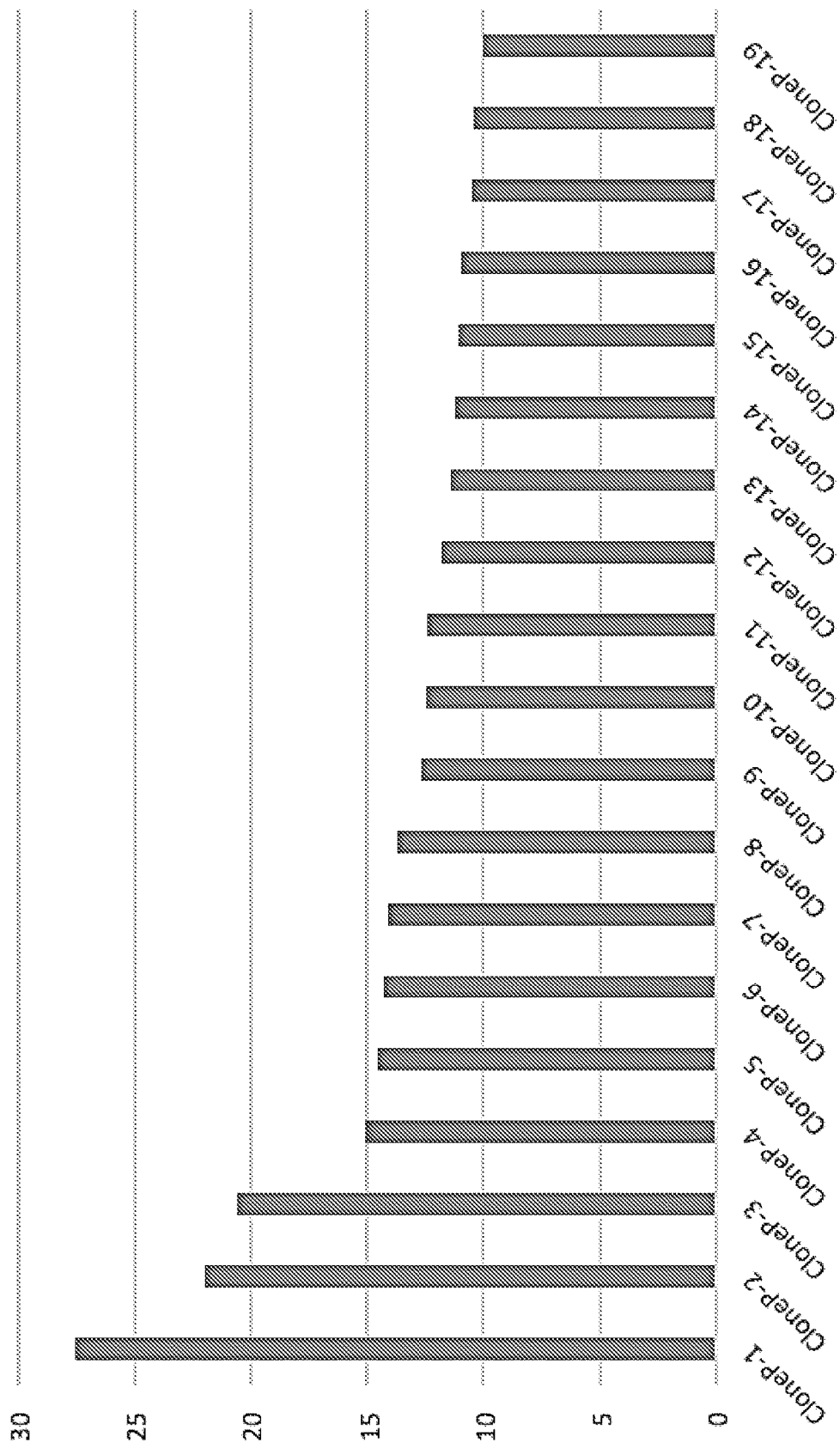
Figure 15C:
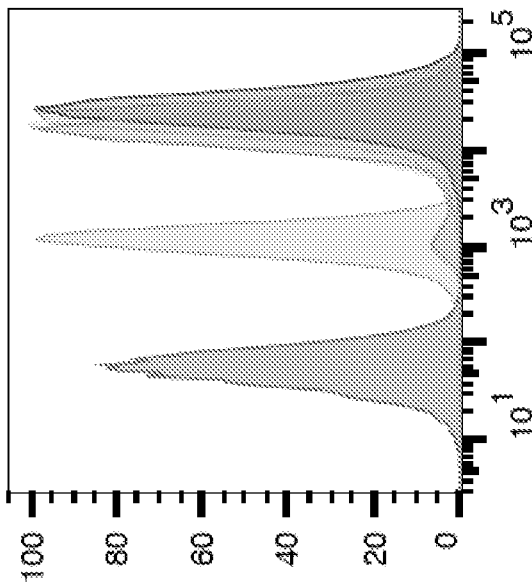
Figure 15C:
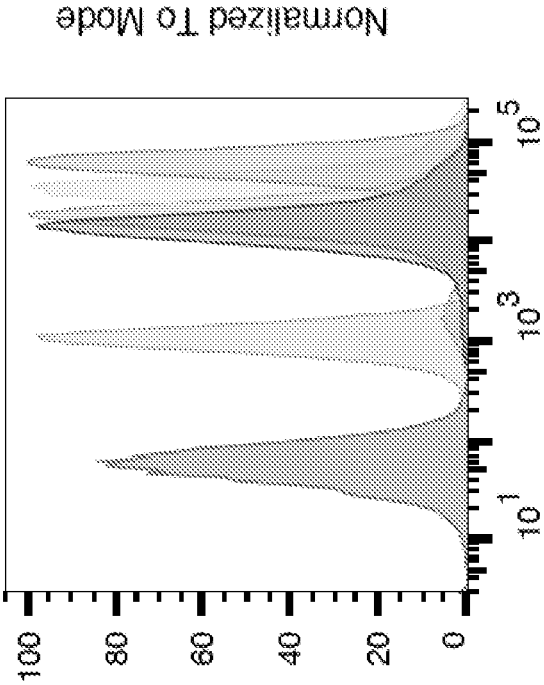

Phage display was used to generate monoclonal antibodies (mAbs) against two key targets revealed by in vivo AAV-SB-CRISPR screen in human and mouse T cells. Monoclonal antibodies against human MGAT5 and PDIA3 were generated successfully. Multiple clones were generated against each protein and target specificity was confirmed by ELISA against recombinant protein (FIG. 15A for MGAT5; FIG. 15B for PDIA3). Complementarity Determining Regions (CDR) were then determined, and are listed in Tables 3 and 4 for MGAT5 and PDIA3, respectively. Purified recombinant antibodies were then used to stain HEK293FT cells expressing MGAT5 or PDIA3 antigens using standard flow cytometry protocols (FIG. 15C). Clone numbers are described in Table 5.

TABLE 1 mmSurf sgRNA library sequences

| SEQ ID NO | id_gRNA Target | Sequence |
|---|---|---|
| SEQ ID NO: 1 | mm00013_Abca1 | ACATGTCATCAACATAACAG |
| SEQ ID NO: 2 | mm00014_Abca1 | GTGGACCCGTACTCTCGCAG |
| SEQ ID NO: 3 | mm00015_Abca1 | CAAGCTGTCAAGCAACACTG |
| SEQ ID NO: 4 | mm00016_Abca1 | GGTATACACAGAGCCATTTG |
| SEQ ID NO: 5 | mm00021_Abca2 | CATGTATGTAGCGATCCGCG |
| SEQ ID NO: 6 | mm00022_Abca2 | CTGGACGCCAATAAGCACGG |
| SEQ ID NO: 7 | mm00023_Abca2 | TAAGGGATAAAGTTGCCACG |

TABLE 1-continued mmSurf sgRNA library sequences

| SEQ ID NO | id_gRNA Target | Sequence |
|---|---|---|
| SEQ ID NO: 8 | mm00024_Abca2 | GAGCCTGAAGCGCTTCGGAG |
| SEQ ID NO: 9 | mm00029_Abcg1 | CAAGGACAATGCGTATACAG |
| SEQ ID NO: 10 | mm00030_Abcg1 | GACTATAAGAGAGACCTCGG |
| SEQ ID NO: 11 | mm00031_Abcg1 | CAGGCCGATCCCAATGTGCG |
| SEQ ID NO: 12 | mm00032_Abcg1 | TTTCCTACTCTGTACCCGAG |
| SEQ ID NO: 13 | mm00073_Asic1 | CCACGTCACCAAGCTCGACG |
| SEQ ID NO: 14 | mm00074_Asic1 | GTGGGCAAGACCGTGCAGCG |
| SEQ ID NO: 15 | mm00075_Asic1 | GGAAAACTGCAACTGCCGTA |
| SEQ ID NO: 16 | mm00076_Asic1 | TCTCTCGTGCCACTTCCGAG |
| SEQ ID NO: 17 | mm00077_Ace | GTTGTTGAACGAGTACGCAG |
| SEQ ID NO: 18 | mm00078_Ace | ACAAATACGTCAATCTCAGG |
| SEQ ID NO: 19 | mm00079_Ace | CTATAACTCGAGTGCCGAGG |
| SEQ ID NO: 20 | mm00080_Ace | GCAATGCACACGGGTCACGA |
| SEQ ID NO: 21 | mm00081_Ache | CAGCAGACCTACATTGCCAG |
| SEQ ID NO: 22 | mm00082_Ache | AAATGTCTGCTACCAGTACG |
| SEQ ID NO: 23 | mm00083_Ache | GACCCCGTAAACCAGAAAGT |
| SEQ ID NO: 24 | mm00084_Ache | CAGTATGTGCATGCCCACGG |
| SEQ ID NO: 25 | mm00109_Acp2 | GGGATTTGGTCAGCTAACCA |
| SEQ ID NO: 26 | mm00110_Acp2 | ACATGGTGGCCAACGAGACA |
| SEQ ID NO: 27 | mm00111_Acp2 | TTCTGCAGCTGCTCATAACG |
| SEQ ID NO: 28 | mm00112_Acp2 | TTCTGAACACCTCTTACCAC |
| SEQ ID NO: 29 | mm00121_Chrna1 | TGACTTGTACAATCTCACGG |
| SEQ ID NO: 30 | mm00122_Chrna1 | AAGGTGCTCCTGGACTACAC |
| SEQ ID NO: 31 | mm00123_Chrna1 | AACATATACTTCCCGATCAG |
| SEQ ID NO: 32 | mm00124_Chrna1 | GAGTAACTTCATGGAGAGCG |
| SEQ ID NO: 33 | mm00125_Chrna4 | TGACATTCTCGTAGTCACCA |
| SEQ ID NO: 34 | mm00126_Chrna4 | GGTGAGCATGCACAGCCGTG |
| SEQ ID NO: 35 | mm00127_Chrna4 | TCTTCTCTGGCTACAACAAG |
| SEQ ID NO: 36 | mm00128_Chrna4 | TGTAGAACAGTGGCAGTCGG |
| SEQ ID NO: 37 | mm00133_Chrna7 | AGATGCATTCACCAAGACGT |
| SEQ ID NO: 38 | mm00134_Chrna7 | ACACAGTAACCATGCGCCGT |
| SEQ ID NO: 39 | mm00135_Chrna7 | TGGAACATGTCTGAGTACCC |
| SEQ ID NO: 40 | mm00136_Chrna7 | AATGGAGAATGGGATCTCAT |
| SEQ ID NO: 41 | mm00141_Chrnb2 | TGTGCGTGGTAGGCGAACGG |
| SEQ ID NO: 42 | mm00142_Chrnb2 | CGTCTGGGTTCTCGTTGCGT |
| SEQ ID NO: 43 | mm00143_Chrnb2 | TCCCTCGACGTACCGCTGGT |
| SEQ ID NO: 44 | mm00144_Chrnb2 | GGAGCCAGATGTGCTTAGAA |
| SEQ ID NO: 45 | mm00157_Adipoq | CGCTGAGCGATACACATAAG |

TABLE 1-continued mmSurf sgRNA library sequences

| SEQ ID NO | id_gRNA Target | Sequence |
|---|---|---|
| SEQ ID NO: 46 | mm00158_Adipoq | ACGTCATCTTCGGCATGACT |
| SEQ ID NO: 47 | mm00159_Adipoq | GGGGTTCCGGGGAAGCCCCG |
| SEQ ID NO: 48 | mm00160_Adipoq | AACCAACAGAATCATTATGA |
| SEQ ID NO: 49 | mm00201_Acvr1 | GGTGGAAATTCTGTGTTCCG |
| SEQ ID NO: 50 | mm00202_Acvr1 | TGTGGGAGACAGCACTCTAG |
| SEQ ID NO: 51 | mm00203_Acvr1 | GCTTTCAGGTTTATGAGCAG |
| SEQ ID NO: 52 | mm00204_Acvr1 | ATTGTACTGTCCATAGCCAG |
| SEQ ID NO: 53 | mm00205_Acvr1b | GTGTCTACCATAACCGCCAG |
| SEQ ID NO: 54 | mm00206_Acvr1b | TCTACGACCTCTCCACGTCA |
| SEQ ID NO: 55 | mm00207_Acvr1b | TGTACGTACCTGCATCCCCA |
| SEQ ID NO: 56 | mm00208_Acvr1b | CAAGAACTCACTCACCGCTG |
| SEQ ID NO: 57 | mm00209_Acvr2a | AGAGACAGAACCAACCAGAC |
| SEQ ID NO: 58 | mm00210_Acvr2a | GGTGTACAGACATCACAAGA |
| SEQ ID NO: 59 | mm00211_Acvr2a | AGGATTGGCATATTTACATG |
| SEQ ID NO: 60 | mm00212_Acvr2a | AGCTGTTAGAAGTGAAAGCA |
| SEQ ID NO: 61 | mm00213_Acvr2b | GTGGAACGAACTGTGCCACG |
| SEQ ID NO: 62 | mm00214_Acvr2b | CCGATGACGATACATCCAGA |
| SEQ ID NO: 63 | mm00215_Acvr2b | GCAGCAGCAGAAGTACACCT |
| SEQ ID NO: 64 | mm00216_Acvr2b | CATCTACTACAACGCCAACT |
| SEQ ID NO: 65 | mm00217_Acvrl1 | TGCCAAAGATCTCCACATGT |
| SEQ ID NO: 66 | mm00218_Acvrl1 | GTTGCGCTGGTAGAGTGTGT |
| SEQ ID NO: 67 | mm00219_Acvrl1 | GTTCCGCGAAGTCATGTCGG |
| SEQ ID NO: 68 | mm00220_Acyrl1 | GCCACAAGCCTAGAGCACCC |
| SEQ ID NO: 69 | mm00225_Ada | GTTGTGGATCTTGTGAACCA |
| SEQ ID NO: 70 | mm00226_Ada | ATTCATCGGACCGTCCACGC |
| SEQ ID NO: 71 | mm00227_Ada | CTTCATCTCCACAAACTCGT |
| SEQ ID NO: 72 | mm00228_Ada | GCTGCGCAACATTATCGGCA |
| SEQ ID NO: 73 | mm00229_Adam10 | GGTTTCATCAAGACTCGTGG |
| SEQ ID NO: 74 | mm00230_Adam10 | CCCATAAATACGGCCCACAG |
| SEQ ID NO: 75 | mm00231_Adam10 | TATCTGTGGAAACGGGATGG |
| SEQ ID NO: 76 | mm00232_Adam10 | CAAACGAGCAGTCTCACATG |
| SEQ ID NO: 77 | mm00237_Adam12 | TCCAGTCTAGAAACTCATGG |
| SEQ ID NO: 78 | mm00238_Adam12 | AGAGCATGACGAACATCCAA |
| SEQ ID NO: 79 | mm00239_Adam12 | GGAGATCCTTATGGTAACTG |
| SEQ ID NO: 80 | mm00240_Adam12 | GGAGCCTGGTACTTACCCCG |
| SEQ ID NO: 81 | mm00241_Adam15 | GGGGGCTGTCCTGAACAACC |
| SEQ ID NO: 82 | mm00242_Adam15 | TGGCACCCGAATGGTCAGCG |
| SEQ ID NO: 83 | mm00243_Adam15 | GATTGTGGCTGATAATTCAG |

TABLE 1-continued mmSurf sgRNA library sequences

| SEQ ID NO | id_gRNA Target | Sequence |
| --- | --- | --- |
| SEQ ID NO: 84 | mm00244_Adam15 | TGTTCCCCTGACTTCTCCGG |
| SEQ ID NO: 85 | mm00245_Adam17 | GGTGTGTGGCAACTCCAGGG |
| SEQ ID NO: 86 | mm00246_Adam17 | ACACGTCGTGGGATAATGCA |
| SEQ ID NO: 87 | mm00247_Adam17 | CATCGACGTACGGCACACAC |
| SEQ ID NO: 88 | mm00248_Adam17 | GCCCCAAATGAGGACCAAGG |
| SEQ ID NO: 89 | mm00249_Adam19 | GGTGTCAATAGATACTGCGT |
| SEQ ID NO: 90 | mm00250_Adam19 | GACACTAGGACGCTGTATGG |
| SEQ ID NO: 91 | mm00251_Adam19 | GCCAATCTCATGGGCCACAG |
| SEQ ID NO: 92 | mm00252_Adam19 | ACCAACTATTATCAGATGGA |
| SEQ ID NO: 93 | mm00253_Adam2 | ATGTTGGCGCTACCTATCAA |
| SEQ ID NO: 94 | mm00254_Adam2 | AAGCAATGGCTACGAAACAC |
| SEQ ID NO: 95 | mm00255_Adam2 | GAATTACTGTAAGATTAAAG |
| SEQ ID NO: 96 | mm00256_Adam2 | TGCATTACTCTACGCCGAGA |
| SEQ ID NO: 97 | mm00257_Adam22 | AACTCACGAAGGGTAATCAG |
| SEQ ID NO: 98 | mm00258_Adam22 | TGAATACCATACCAGACGGA |
| SEQ ID NO: 99 | mm00259_Adam22 | CGCCGCCCAAGCGATAGATG |
| SEQ ID NO: 100 | mm00260_Adam22 | GTTCACTCAGTGCAATGTCG |
| SEQ ID NO: 101 | mm00261_Adam3 | CTGTCTCCGATGTATTCCGA |
| SEQ ID NO: 102 | mm00262_Adam3 | GCATCCAAAGACGTTAGCTG |
| SEQ ID NO: 103 | mm00263_Adam3 | GACTCACCTCTGGTTTGACA |
| SEQ ID NO: 104 | mm00264_Adam3 | AATCTGTACACTGCCTATCT |
| SEQ ID NO: 105 | mm00277_Adam9 | CCACGCAGGTGGGATCAATG |
| SEQ ID NO: 106 | mm00278_Adam9 | GATTCGCTTAGCAAACTACC |
| SEQ ID NO: 107 | mm00279_Adam9 | ACCAGCTTATTACCACAGGA |
| SEQ ID NO: 108 | mm00280_Adam9 | GTTTACACCTACGACAAGGA |
| SEQ ID NO: 109 | mm00285_Adcy6 | CCGGATACATCGCCTCGGAG |
| SEQ ID NO: 110 | mm00286_Adcy6 | CTCACGGGTGCACAGCACCG |
| SEQ ID NO: 111 | mm00287_Adcy6 | GAGTACCACAAAAAGGACAG |
| SEQ ID NO: 112 | mm00288_Adcy6 | CCCGAGGTTACATCCAGGCG |
| SEQ ID NO: 113 | mm00297_Adcy9 | ATGTCATGACATGCACAAAG |
| SEQ ID NO: 114 | mm00298_Adcy9 | TGTACGCCCGGCATTATGCG |
| SEQ ID NO: 115 | mm00299_Adcy9 | GATGGTGAACATGCGTGTTG |
| SEQ ID NO: 116 | mm00300_Adcy9 | TCTGCTGCATCTTAAAGGGG |
| SEQ ID NO: 117 | mm00305_Adcyap1r1 | CCAGGATTATTACTACCTGT |
| SEQ ID NO: 118 | mm00306_Adcyap1r1 | GTCTGGATGACAGAAACCAT |
| SEQ ID NO: 119 | mm00307_Adcyap1r1 | GGCTCTACTTTGATGATGCG |
| SEQ ID NO: 120 | mm00308_Adcyap1r1 | TGTGGGACAATATCACATGT |
| SEQ ID NO: 121 | mm00361_Adora2b | TCACTGGGACACGAGCGAGA |

TABLE 1-continued mmSurf sgRNA library sequences

| SEQ ID NO | id_gRNA Target | Sequence |
|---|---|---|
| SEQ ID NO: 122 | mm00362_Adora2b | TTCTCAAAGAGACATGTCAC |
| SEQ ID NO: 123 | mm00363_Adora2b | CAACGTGCTGGTGTGCGCCG |
| SEQ ID NO: 124 | mm00364_Adora2b | CTTTCTGGTATCCCTGGCGA |
| SEQ ID NO: 125 | mm00381_Adra1b | AGTATCGCACCCCAATGTAG |
| SEQ ID NO: 126 | mm00382_Adra1b | TCTTGGCCACGATGTAGACT |
| SEQ ID NO: 127 | mm00383_Adra1b | CATTCCGACTACAATGCCCA |
| SEQ ID NO: 128 | mm00384_Adra1b | ACCTTGAATACGGCGTCCGG |
| SEQ ID NO: 129 | mm00393_Adra2a | CCAGTAACCCATAACCTCGT |
| SEQ ID NO: 130 | mm00394_Adra2a | GGGGCACCGTTAAGCTGGGT |
| SEQ ID NO: 131 | mm00395_Adra2a | GCAAGATCAACGACCAGAAG |
| SEQ ID NO: 132 | mm00396_Adra2a | GACAGCCGAGATGACCCACA |
| SEQ ID NO: 133 | mm00445_Afp | CTTCTCCGTCACGCACTGGG |
| SEQ ID NO: 134 | mm00446_Afp | CTTGGCTGCTCAGTACGACA |
| SEQ ID NO: 135 | mm00447_Afp | CTTATACTTACGTTGCCTGG |
| SEQ ID NO: 136 | mm00448_Afp | CAAAATGACTAGCGATGTGT |
| SEQ ID NO: 137 | mm00457_Ager | CCTTACGGTAGACTCGGACT |
| SEQ ID NO: 138 | mm00458_Ager | CCACTGGAATTGTCGATGAG |
| SEQ ID NO: 139 | mm00459_Ager | AGACGGGACTCTTTACACTG |
| SEQ ID NO: 140 | mm00460_Ager | ACTTGTGCTAAGCTGTAAGG |
| SEQ ID NO: 141 | mm00461_Angpt1 | ACTGGTTCCTATCTCAAGCA |
| SEQ ID NO: 142 | mm00462_Angpt1 | AGCCTTTGCACTAAAGAAGG |
| SEQ ID NO: 143 | mm00463_Angpt1 | TTGCAATATGGATGTGAATG |
| SEQ ID NO: 144 | mm00464_Angpt1 | AGAATTGGACACCTTGAAGG |
| SEQ ID NO: 145 | mm00473_Agrn | ACACCAGATCAGCCTATACG |
| SEQ ID NO: 146 | mm00474_Agrn | AGAAGGCCAGATGTGAAGCG |
| SEQ ID NO: 147 | mm00475_Agrn | TCTGTATGCCTGTCCCGCCG |
| SEQ ID NO: 148 | mm00476_Agrn | GAAGATTCTAGTGTCCCCGG |
| SEQ ID NO: 149 | mm00489_Agtr1a | GGGCCAGCGGTATTCCATAG |
| SEQ ID NO: 150 | mm00490_Agtr1a | ACACGTGAGCAGGAACACGC |
| SEQ ID NO: 151 | mm00491_Agtr1a | TGGTTAGGCCCAGTCCTATG |
| SEQ ID NO: 152 | mm00492_Agtr1a | TTACATGAAGCTGAAGACTG |
| SEQ ID NO: 153 | mm00497_Agtr2 | GTACCTATCGACACTCATGC |
| SEQ ID NO: 154 | mm00498_Agtr2 | ACAAGCCATACACCAAACAA |
| SEQ ID NO: 155 | mm00499_Agtr2 | ACTGAGCATATTTCTCGGGT |
| SEQ ID NO: 156 | mm00500_Agtr2 | TTTGTGTGAGCAATTAAAGG |
| SEQ ID NO: 157 | mm00521_Ahsg | TCCGTTCAACGATACCAACG |
| SEQ ID NO: 158 | mm00522_Ahsg | ACTCCACCAGAGTAGACACT |
| SEQ ID NO: 159 | mm00523_Ahsg | CTCACAGAACAGTTTGCCAG |

TABLE 1-continued mmSurf sgRNA library sequences

| SEQ ID NO | id_gRNA Target | Sequence |
| --- | --- | --- |
| SEQ ID NO: 160 | mm00524_Ahsg | ACCCAGTGTCATTCCACCCC |
| SEQ ID NO: 161 | mm00573_Alpl | GGATAACGAGATGCCACCAG |
| SEQ ID NO: 162 | mm00574_Alpl | CTAGGAGGCAGGATTGACCA |
| SEQ ID NO: 163 | mm00575_Alpl | ACCTAAGAGGTAGTCCACCC |
| SEQ ID NO: 164 | mm00576_Alpl | GTTGCATCGCGTGCGCTCTG |
| SEQ ID NO: 165 | mm00577_Akp3 | TGTTCGACTTAGCCATCGAG |
| SEQ ID NO: 166 | mm00578_Akp3 | GTGTGAACATATGTGCCCGA |
| SEQ ID NO: 167 | mm00579_Akp3 | CTGTCCCCAGACATACAGTG |
| SEQ ID NO: 168 | mm00580_Akp3 | GTTGCACTGGTCGAATCTCG |
| SEQ ID NO: 169 | mm00605_Alcam | TGCAAGTAGGAACGCGACTG |
| SEQ ID NO: 170 | mm00606_Alcam | CTGAACACCTTGACTAGGGT |
| SEQ ID NO: 171 | mm00607_Alcam | GGTTGTCTTGTACTCCAAGG |
| SEQ ID NO: 172 | mm00608_Alcam | ACTTTCAGGAAAAGCCCGAT |
| SEQ ID NO: 173 | mm00637_Alk | TGGGCAACATATCTCCCCGA |
| SEQ ID NO: 174 | mm00638_Alk | GAATTCCAACTTGAGCGTGG |
| SEQ ID NO: 175 | mm00639_Alk | TACACTTACCATATCGACTG |
| SEQ ID NO: 176 | mm00640_Alk | GGGGTGTACAGGATACCCAA |
| SEQ ID NO: 177 | mm00681_Ambp | GCATGACCAGTACTCGATGG |
| SEQ ID NO: 178 | mm00682_Ambp | TATCTGGCAGTGTTGACGCA |
| SEQ ID NO: 179 | mm00683_Ambp | GGACTGAGCCACTAATAACT |
| SEQ ID NO: 180 | mm00684_Ambp | AAGGATGTGGCCCTGAATGT |
| SEQ ID NO: 181 | mm00689_Amelx | ACCCATGGGTTCGTAACCAT |
| SEQ ID NO: 182 | mm00690_Amelx | GCTCTGGTACCACTTCAAAG |
| SEQ ID NO: 183 | mm00691_Amelx | GGCTGAAGGGTGTGACTCGG |
| SEQ ID NO: 184 | mm00692_Amelx | GGGCTGTTGAGCTGGCACCA |
| SEQ ID NO: 185 | mm00725_Ank3 | CTATACACCACTGCACATCG |
| SEQ ID NO: 186 | mm00726_Ank3 | CAACCACCGAGATGTAACCA |
| SEQ ID NO: 187 | mm00727_Ank3 | ATCTATTCAAGCCGTAACCG |
| SEQ ID NO: 188 | mm00728_Ank3 | GAGGGATTTCCACAATGACG |
| SEQ ID NO: 189 | mm00753_Anxa4 | CCTGGCCTCTCGTACCCCTG |
| SEQ ID NO: 190 | mm00754_Anxa4 | GCTTCATAAGAGCATCATCA |
| SEQ ID NO: 191 | mm00755_Anxa4 | CTGTACGTCATACAGCACTG |
| SEQ ID NO: 192 | mm00756_Anxa4 | GGAACCATCTGCTCCACGGT |
| SEQ ID NO: 193 | mm00757_Anxa5 | TAGGCATCGTAGAGTCGTGA |
| SEQ ID NO: 194 | mm00758_Anxa5 | ATCAATTTCAGGTACCGATG |
| SEQ ID NO: 195 | mm00759_Anxa5 | ATACTTCAGGGTACTACCAG |
| SEQ ID NO: 196 | mm00760_Anxa5 | TGTCCTTGAAGCAATAATCT |
| SEQ ID NO: 197 | mm00773_Aoc3 | ACAATGACTACAGCCCCCCG |

TABLE 1-continued mmSurf sgRNA library sequences

| SEQ ID NO | id_gRNA Target | Sequence |
|---|---|---|
| SEQ ID NO: 198 | mm00774_Aoc3 | ATCAATGTCGACCTGCTACG |
| SEQ ID NO: 199 | mm00775_Aoc3 | TCCCAAACAATGGTACAGGT |
| SEQ ID NO: 200 | mm00776_Aoc3 | TGCATCACGTAGTGTCTTGG |
| SEQ ID NO: 201 | mm00821_Ap2m1 | CCAAAGATACCGTACTACCA |
| SEQ ID NO: 202 | mm00822_Ap2m1 | GAGAAGACACTTACCCTGTG |
| SEQ ID NO: 203 | mm00823_Ap2m1 | CAGCTGATGAAACAAGCAAG |
| SEQ ID NO: 204 | mm00824_Ap2m1 | CCTTTATCCCATATAGACGA |
| SEQ ID NO: 205 | mm00913_Apoa1 | GGAGCTCTACCGCCAGAAGG |
| SEQ ID NO: 206 | mm00914_Apoa1 | CAAGGAGGAGGATTCAAACT |
| SEQ ID NO: 207 | mm00915_Apoa1 | GTCCCAATGGGACAAAGTGA |
| SEQ ID NO: 208 | mm00916_Apoa1 | CTGGAAAACTGGGACACTCT |
| SEQ ID NO: 209 | mm00921_Apoa4 | CAAAGTAACCCAGACGTTCG |
| SEQ ID NO: 210 | mm00922_Apoa4 | GGTGGCAAGGGGCATCATCG |
| SEQ ID NO: 211 | mm00923_Apoa4 | TGCTAGTACGTATGCTGATG |
| SEQ ID NO: 212 | mm00924_Apoa4 | AAAGTAATCCCACACCACAT |
| SEQ ID NO: 213 | mm00949_Apoh | AAAGACATCCTACGACCCTG |
| SEQ ID NO: 214 | mm00950_Apoh | TTTCCGATCATGGCAAAGTG |
| SEQ ID NO: 215 | mm00951_Apoh | CAGCTCATCTAAGTGCACGG |
| SEQ ID NO: 216 | mm00952_Apoh | AGGATTATAGGCCTTCAGCT |
| SEQ ID NO: 217 | mm00957_App | CACGGAAGAGTACTGCATGG |
| SEQ ID NO: 218 | mm00958_App | GCAGCTTGTAGAGACACACA |
| SEQ ID NO: 219 | mm00959_App | AACGGTAAGGAATCACGATG |
| SEQ ID NO: 220 | mm00960_App | CAAAACCTGCATTGGCACCA |
| SEQ ID NO: 221 | mm00965_Aqp1 | AAGTGAATTGTCGACTAGGG |
| SEQ ID NO: 222 | mm00966_Aqp1 | CCTAGGCTTCAATTACCCAC |
| SEQ ID NO: 223 | mm00967_Aqp1 | GGAGCCCCAGTGTGACCGCA |
| SEQ ID NO: 224 | mm00968_Aqp1 | TGATGTACATGACAGCCCGG |
| SEQ ID NO: 225 | mm00977_Aqp4 | GGATCCACCATAAACTGGGG |
| SEQ ID NO: 226 | mm00978_Aqp4 | ACCATGGCTACAGTCACAGC |
| SEQ ID NO: 227 | mm00979_Aqp4 | AAGTGATTATTAACTCCACC |
| SEQ ID NO: 228 | mm00980_Aqp4 | AATCCTCCAACCACACTGGG |
| SEQ ID NO: 229 | mm01017_Areg | AGGGGACTACGACTACTCAG |
| SEQ ID NO: 230 | mm01018_Areg | AGAAGGCATTTCGCTTATGG |
| SEQ ID NO: 231 | mm01019_Areg | CAGATACATCGAGAACCTGG |
| SEQ ID NO: 232 | mm01020_Areg | GAAAGGCGAATCGCTTTCTG |
| SEQ ID NO: 233 | mm01037_Arf6 | CCCCACGGTGGGCTTCAACG |
| SEQ ID NO: 234 | mm01038_Arf6 | TCTGGCGGCATTACTACACC |
| SEQ ID NO: 235 | mm01039_Arf6 | TCTTCGGGAACAAGGAAATG |

TABLE 1-continued mmSurf sgRNA library sequences

| SEQ ID NO | id_gRNA Target | Sequence |
|---|---|---|
| SEQ ID NO: 236 | mm01040_Arf6 | CGACCGCGACCGCATCGACG |
| SEQ ID NO: 237 | mm01049_Rhoa | AAAACACATCAATATAACAT |
| SEQ ID NO: 238 | mm01050_Rhoa | CTATGTGGCGGATATCGAGG |
| SEQ ID NO: 239 | mm01051_Rhoa | GCTACTCACCTAAACTATCA |
| SEQ ID NO: 240 | mm01052_Rhoa | CAGCAAGGACCAGTTCCCAG |
| SEQ ID NO: 241 | mm01053_Rhob | GAAGCACATAAGGATGACGT |
| SEQ ID NO: 242 | mm01054_Rhob | CACATAGTTCTCGAACACGG |
| SEQ ID NO: 243 | mm01055_Rhob | GGGGCAGAAGTGCTTTACCT |
| SEQ ID NO: 244 | mm01056_Rhob | CAGCGACGAGCATGTCCGCA |
| SEQ ID NO: 245 | mm01057_Rhoc | ACGTGCCCATCATCCTAGTG |
| SEQ ID NO: 246 | mm01058_Rhoc | GATGACGTCAGTGTCCGGGT |
| SEQ ID NO: 247 | mm01059_Rhoc | CTATATAGCCGACATCGAAG |
| SEQ ID NO: 248 | mm01060_Rhoc | CAGCAAAGATCAGTTTCCAG |
| SEQ ID NO: 249 | mm01105_Art1 | TGCCGCCCAACAATTTGGCG |
| SEQ ID NO: 250 | mm01106_Art1 | TCAGGCCAACAAAGTATACG |
| SEQ ID NO: 251 | mm01107_Art1 | AAAGCCCCCAGCCTAACGG |
| SEQ ID NO: 252 | mm01108_Art1 | GCTGGCACCCGCGAGATCGG |
| SEQ ID NO: 253 | mm01109_Art2b | GGTTGTAGTTTAGTTTACCG |
| SEQ ID NO: 254 | mm01110_Art2b | AACAGTACGAGTTATCCGGC |
| SEQ ID NO: 255 | mm01111_Art2b | CTCTGTTAAAATCTATAGCG |
| SEQ ID NO: 256 | mm01112_Art2b | CTAGCATGAAAGGCACTGCA |
| SEQ ID NO: 257 | mm01125_Arsb | GGTGGGCAGACTAGGTCTGG |
| SEQ ID NO: 258 | mm01126_Arsb | GAATGTCTGCCGACACGCCG |
| SEQ ID NO: 259 | mm01127_Arsb | AGCACAGACGTATTTATGCA |
| SEQ ID NO: 260 | mm01128_Arsb | GCCAGCACGAAGACCACATG |
| SEQ ID NO: 261 | mm01129_Arsa | AAGCACGTTAGGTTCTGACA |
| SEQ ID NO: 262 | mm01130_Arsa | AGGAGTCCCCAAATGGCCCA |
| SEQ ID NO: 263 | mm01131_Arsa | GTGACCTGGCCAGTAGACCA |
| SEQ ID NO: 264 | mm01132_Arsa | TCGGAGAAAGACACATACC |
| SEQ ID NO: 265 | mm01133_Asah1 | GCAAGGTGTACGTTACCTAG |
| SEQ ID NO: 266 | mm01134_Asah1 | TAACATTTATAACATACCGC |
| SEQ ID NO: 267 | mm01135_Asah1 | AGTGATAAACCCTACCCACT |
| SEQ ID NO: 268 | mm01136_Asah1 | GAATATAAATAATAACACTT |
| SEQ ID NO: 269 | mm01153_Astn1 | CCTTACACGATATTTCAGCG |
| SEQ ID NO: 270 | mm01154_Astn1 | TGCTCAGATGGTTTCAACGG |
| SEQ ID NO: 271 | mm01155_Astn1 | TGACATGAGAAGAGCACACG |
| SEQ ID NO: 272 | mm01156_Astn1 | TGATGATCCTGTACACTCGC |
| SEQ ID NO: 273 | mm01213_Atp1a1 | GTACACGACGATGCCACGTG |

TABLE 1-continued mmSurf sgRNA library sequences

| SEQ ID NO | id_gRNA Target | Sequence |
|---|---|---|
| SEQ ID NO: 274 | mm01214_Atp1a1 | CTTACCACTCTGATTCTCCG |
| SEQ ID NO: 275 | mm01215_Atp1a1 | AATCTGTTCCGTATTTACGA |
| SEQ ID NO: 276 | mm01216_Atp1a1 | GAAAATGAGCATCAATGCGG |
| SEQ ID NO: 277 | mm01217_Atp1b1 | GTACTTACACCAACTACCAC |
| SEQ ID NO: 278 | mm01218_Atp1b1 | TTGAGCTTGATAATGATGCA |
| SEQ ID NO: 279 | mm01219_Atp1b1 | GGCGACATCAATCACGAACG |
| SEQ ID NO: 280 | mm01220_Atp1b1 | AGCTCTTGGGGTCATTAGGA |
| SEQ ID NO: 281 | mm01221_Atp1b2 | GGTTGCTCATAATATCGCCC |
| SEQ ID NO: 282 | mm01222_Atp1b2 | AGGAGTTCGTGTGGAACCCG |
| SEQ ID NO: 283 | mm01223_Atp1b2 | ATTAGTGACACTGAAAGCTG |
| SEQ ID NO: 284 | mm01224_Atp1b2 | CAGTCGATCCTGGTACTTGG |
| SEQ ID NO: 285 | mm01225_Atp1b3 | CTCCATCAGGACAACTTGTG |
| SEQ ID NO: 286 | mm01226_Atp1b3 | TCAACACAATTACCTGGACT |
| SEQ ID NO: 287 | mm01227_Atp1b3 | GCCACAGACTTACAAAAAGT |
| SEQ ID NO: 288 | mm01228_Atp1b3 | CGAGCAGCGGAGAGTTTCTG |
| SEQ ID NO: 289 | mm01257_Atp5b | CTGCTGGCCCCATACGCCAA |
| SEQ ID NO: 290 | mm01258_Atp5b | GCGCTTACCAGGATGAACCC |
| SEQ ID NO: 291 | mm01259_Atp5b | AAATACAGAGTAACCACCAT |
| SEQ ID NO: 292 | mm01260_Atp5b | CCCACCCTAGCCACCGACAT |
| SEQ ID NO: 293 | mm01277_Atp6v1a | TGACTGCTGATATCCGACAG |
| SEQ ID NO: 294 | mm01278_Atp6v1a | AGTCGGCCATCATACTGACG |
| SEQ ID NO: 295 | mm01279_Atp6v1a | ATGTTGCCCCCACGTAACAG |
| SEQ ID NO: 296 | mm01280_Atp6v1a | CTTACGGGAAAAGGGCATCG |
| SEQ ID NO: 297 | mm01325_Slc7a1 | GCCATGGCATAGATAACTCG |
| SEQ ID NO: 298 | mm01326_Slc7a1 | CACAAACGTGAAATACGGTG |
| SEQ ID NO: 299 | mm01327_Slc7a1 | TGACGTGAGAACTCTCCGAT |
| SEQ ID NO: 300 | mm01328_Slc7a1 | CCAGGTCCTTCAGTTCAAAG |
| SEQ ID NO: 301 | mm01329_Slc7a2 | AGGACGTCACTATTCCGATG |
| SEQ ID NO: 302 | mm01330_Slc7a2 | GAACGGAACAAGCATCTACG |
| SEQ ID NO: 303 | mm01331_Slc7a2 | GTATCTATACACTTACGTCA |
| SEQ ID NO: 304 | mm01332_Slc7a2 | CCGAGACAACATATTTGGCG |
| SEQ ID NO: 305 | mm01337_Atrn | CCTCACTGTACAGACAACTG |
| SEQ ID NO: 306 | mm01338_Atrn | ACGATGTGGATACTCAGATG |
| SEQ ID NO: 307 | mm01339_Atrn | GAGGAAAAATTGATTCAACA |
| SEQ ID NO: 308 | mm01340_Atrn | GGCCGCCGTTGACACACGGC |
| SEQ ID NO: 309 | mm01353_Pcdh15 | CTATCATGAAGTACGCATCG |
| SEQ ID NO: 310 | mm01354_Pcdh15 | GAAGCGGGGTAATCCTCAG |
| SEQ ID NO: 311 | mm01355_Pcdh15 | TTAGCAAACGCATCTACAAG |

TABLE 1-continued mmSurf sgRNA library sequences

| SEQ ID NO | id_gRNA Target | Sequence |
|---|---|---|
| SEQ ID NO: 312 | mm01356_Pcdh15 | CTTCCTGAATGACTACACCT |
| SEQ ID NO: 313 | mm01385_B2m | ATTTGGATTTCAATGTGAGG |
| SEQ ID NO: 314 | mm01386_B2m | ACTCACTCTGGATAGCATAC |
| SEQ ID NO: 315 | mm01387_B2m | TGAGTATACTTGAATTTGAG |
| SEQ ID NO: 316 | mm01388_B2m | TCGGCTTCCCATTCTCCGGT |
| SEQ ID NO: 317 | mm01437_Bcan | CGAAGCCTACCGGTTCCGCG |
| SEQ ID NO: 318 | mm01438_Bcan | GATGGAGAGCGAGTCTCGTG |
| SEQ ID NO: 319 | mm01439_Bcan | TGGATGGCTATCCTGGCGTG |
| SEQ ID NO: 320 | mm01440_Bcan | ACACCCAGCCAACGCTGTGG |
| SEQ ID NO: 321 | mm01445_Phb2 | TCTATGACCGCCTTCCACTG |
| SEQ ID NO: 322 | mm01446_Phb2 | TGGGTCGGGACAGCACACGC |
| SEQ ID NO: 323 | mm01447_Phb2 | CATAGTCCAGCCCTAGACGC |
| SEQ ID NO: 324 | mm01448_Phb2 | AGCGCCGTGCCCATGCCCCG |
| SEQ ID NO: 325 | mm01457_Bche | AATTACAACCAAGACCGGAA |
| SEQ ID NO: 326 | mm01458_Bche | GTTTCGATGAACTATAGGGT |
| SEQ ID NO: 327 | mm01459_Bche | CTGGGCAGTAAAGCATCCTG |
| SEQ ID NO: 328 | mm01460_Bche | ACAATGATAGCCTTATCACA |
| SEQ ID NO: 329 | mm01529_Bdkrb2 | GCACAAAAACAGCTGCACTG |
| SEQ ID NO: 330 | mm01530_Bdkrb2 | GGACGGGTAGACGATGACGC |
| SEQ ID NO: 331 | mm01531_Bdkrb2 | TCCCGTTAAGAGCAGACCCG |
| SEQ ID NO: 332 | mm01532_Bdkrb2 | CATCGCCAATAACTTTGACT |
| SEQ ID NO: 333 | mm01565_Bgn | ATGGATTCGTAGTTCTACCA |
| SEQ ID NO: 334 | mm01566_Bgn | GAAGTTCGTTCAGGGTCTCA |
| SEQ ID NO: 335 | mm01567_Bgn | GTTCTGCAGGTCTAGCAGTG |
| SEQ ID NO: 336 | mm01568_Bgn | CTTATTGTTTACCAAGACCA |
| SEQ ID NO: 337 | mm01589_Fabp7 | ACTGTGATTATCAGTCAGGA |
| SEQ ID NO: 338 | mm01590_Fabp7 | TAGATGCTTTCTGCGCAACC |
| SEQ ID NO: 339 | mm01591_Fabp7 | CACGTTTCCCACTTGCCTAG |
| SEQ ID NO: 340 | mm01592_Fabp7 | TCTTGAATGTGCATTGTGTC |
| SEQ ID NO: 341 | mm01605_Cxcr5 | GAAGGTCGGCTACTGCGAGG |
| SEQ ID NO: 342 | mm01606_Cxcr5 | GTGATGGGATGGTGTTACGT |
| SEQ ID NO: 343 | mm01607_Cxcr5 | GGATGGAGAGGAGTCGACGG |
| SEQ ID NO: 344 | mm01608_Cxcr5 | GGATGTTTCCCATCATACCC |
| SEQ ID NO: 345 | mm01613_Bmp1 | CCCACCTCGGCGACCCACGT |
| SEQ ID NO: 346 | mm01614_Bmp1 | AGCCACAGTAGCGCCCAATG |
| SEQ ID NO: 347 | mm01615_Bmp1 | GTAGCCATTGGGATACTCAG |
| SEQ ID NO: 348 | mm01616_Bmp1 | TGTTCAAGGCCCAACCGCGG |
| SEQ ID NO: 349 | mm01617_Bmp10 | TCGCATGATGTATGATGGCG |

TABLE 1-continued mmSurf sgRNA library sequences

| SEQ ID NO | id_gRNA Target | Sequence |
| --- | --- | --- |
| SEQ ID NO: 350 | mm01618_Bmp10 | CTACGGAACCAACAGTGAGT |
| SEQ ID NO: 351 | mm01619_Bmp10 | CTCCGGATGATGTTAGCAGA |
| SEQ ID NO: 352 | mm01620_Bmp10 | ACTGCTCAAGGCCCATAATG |
| SEQ ID NO: 353 | mm01625_Bmp2 | GGGCCGCAAGAAGTTCGCCG |
| SEQ ID NO: 354 | mm01626_Bmp2 | GTGCGCAGCTTCCATCACGA |
| SEQ ID NO: 355 | mm01627_Bmp2 | GCCCATTTAGAGGAGAACCC |
| SEQ ID NO: 356 | mm01628_Bmp2 | TGTGTTCTGATTCACTAACC |
| SEQ ID NO: 357 | mm01657_Bmpr1a | GGGTACCATAAATTTCTGTG |
| SEQ ID NO: 358 | mm01658_Bmpr1a | TGACCTACCTATAACAACAG |
| SEQ ID NO: 359 | mm01659_Bmpr1a | AATCTAGATAGTATGCTCCA |
| SEQ ID NO: 360 | mm01660_Bmpr1a | CATACACCCAGAAGTTAATG |
| SEQ ID NO: 361 | mm01665_Bmpr2 | GTAGGATGTTGGTCTCACAT |
| SEQ ID NO: 362 | mm01666_Bmpr2 | CACACAGAATTACCACGAGG |
| SEQ ID NO: 363 | mm01667_Bmpr2 | GCTGGACATCGAATGCTCAG |
| SEQ ID NO: 364 | mm01668_Bmpr2 | AGATAATGCGGCTATAAGTG |
| SEQ ID NO: 365 | mm01697_Bst1 | AGACTGTGAAAACAACGCCG |
| SEQ ID NO: 366 | mm01698_Bst1 | TTCTGGGGCAAGAGCGCGG |
| SEQ ID NO: 367 | mm01699_Bst1 | CCTGCTCGTTATGAGCTATG |
| SEQ ID NO: 368 | mm01700_Bst1 | AAAGGAGCCTATCCCACGAG |
| SEQ ID NO: 369 | mm01733_Bsg | GGACGCAGATGACCGCTCTG |
| SEQ ID NO: 370 | mm01734_Bsg | CCACCTTACTCGGCCACCCA |
| SEQ ID NO: 371 | mm01735_Bsg | GAAATCAGAGCATTCCAGTG |
| SEQ ID NO: 372 | mm01736_Bsg | CAAACCACCACTGGATCTCG |
| SEQ ID NO: 373 | mm01737_Bsn | CCACAGCCAGTCCGACACGA |
| SEQ ID NO: 374 | mm01738_Bsn | AGACATGTCACTGCAAACCG |
| SEQ ID NO: 375 | mm01739_Bsn | ACCGAGCTATAGCGCCGCAG |
| SEQ ID NO: 376 | mm01740_Bsn | GAGGACGACTCCTTGGCATG |
| SEQ ID NO: 377 | mm01797_C1qa | CACAGATGAAGCGACCCGTG |
| SEQ ID NO: 378 | mm01798_C1qa | CCCAATGACGCTTGGCAACG |
| SEQ ID NO: 379 | mm01799_C1qa | TTCAGCCACTGTCCATACTA |
| SEQ ID NO: 380 | mm01800_C1qa | AGGCAATCCAGGCAATATCA |
| SEQ ID NO: 381 | mm01805_C1qbp | ATCAGTCAAGAATTCAACGA |
| SEQ ID NO: 382 | mm01806_C1qbp | CGTACGCTGAGCAAACCGAA |
| SEQ ID NO: 383 | mm01807_C1qbp | GTTGAAGTTACCAAGACTGA |
| SEQ ID NO: 384 | mm01808_C1qbp | TCCTCCTCACCATCAAATGT |
| SEQ ID NO: 385 | mm01817_Ciita | AGCTCGACTAAGGCTCCGGG |
| SEQ ID NO: 386 | mm01818_Ciita | AGGTCCTTGATTATATCGTG |
| SEQ ID NO: 387 | mm01819_Ciita | TCCAGTGTCCTAATCTACCA |

TABLE 1-continued mmSurf sgRNA library sequences

| SEQ ID NO | id_gRNA Target | Sequence |
|---|---|---|
| SEQ ID NO: 388 | mm01820_Ciita | AGCAGGCCAAGACTTACATG |
| SEQ ID NO: 389 | mm01821_C3ar1 | GCTTATGTACTATCAGACAT |
| SEQ ID NO: 390 | mm01822_C3ar1 | GGAGGCTTTCCACCATAATG |
| SEQ ID NO: 391 | mm01823_C3ar1 | TGGATGGGATAAGTTTGCAC |
| SEQ ID NO: 392 | mm01824_C3ar1 | GAGACCAAGAATGACCATGG |
| SEQ ID NO: 393 | mm01833_C5ar1 | CGAGGGCAGGACTATACAGG |
| SEQ ID NO: 394 | mm01834_C5ar1 | TCCATCCTTCGTGTACCGGG |
| SEQ ID NO: 395 | mm01835_C5ar1 | GAACACCAGCAGGAAACGGT |
| SEQ ID NO: 396 | mm01836_C5ar1 | GCAGTGCCAAGCACGAGAGG |
| SEQ ID NO: 397 | mm01841_Hyou1 | ACAGGCGGATAACCCTCATG |
| SEQ ID NO: 398 | mm01842_Hyou1 | ACATCGTACTCACTTGCCCA |
| SEQ ID NO: 399 | mm01843_Hyou1 | TGGAATTGATATCTTTCCGG |
| SEQ ID NO: 400 | mm01844_Hyou1 | TGGCGTGCTCAGTTTAGACA |
| SEQ ID NO: 401 | mm01853_Cacna1b | GAGCGACGAGCAAGACACCG |
| SEQ ID NO: 402 | mm01854_Cacna1b | TCTGTGCTTTCACCATACGC |
| SEQ ID NO: 403 | mm01855_Cacna1b | CATGGGATTGAGTCGCAAGG |
| SEQ ID NO: 404 | mm01856_Cacna1b | AAGGGCTCCTACCTTCGGAA |
| SEQ ID NO: 405 | mm01857_Cacna1c | CCAGTAAATTCCAACCATTG |
| SEQ ID NO: 406 | mm01858_Cacna1c | AATCAGGGTGGATAAGACGT |
| SEQ ID NO: 407 | mm01859_Cacna1c | GACATCGAGGGAGAAAACTG |
| SEQ ID NO: 408 | mm01860_Cacna1c | CCAGTACAAAGTGTGGTACG |
| SEQ ID NO: 409 | mm01873_Cacna1s | CTGATGGAATAGGAAGCCGT |
| SEQ ID NO: 410 | mm01874_Cacna1s | TCTCCAGCATTACAACCAGT |
| SEQ ID NO: 411 | mm01875_Cacna1s | TCCAGCTCATGTAACCACGG |
| SEQ ID NO: 412 | mm01876_Cacna1s | AAATGCACACCAGCACACCA |
| SEQ ID NO: 413 | mm01877_Cacna2d1 | TTGCAGCTTACTGTAAAACG |
| SEQ ID NO: 414 | mm01878_Cacna2d1 | ATTCCCACGGACATCTATGA |
| SEQ ID NO: 415 | mm01879_Cacna2d1 | GGTCAACATAATTATGACAG |
| SEQ ID NO: 416 | mm01880_Cacna2d1 | ATGATGTACGCAGAAGACCA |
| SEQ ID NO: 417 | mm01909_Pdia4 | CTGACTGTTAACATACCACG |
| SEQ ID NO: 418 | mm01910_Pdia4 | GTACAGCAAACGCCCCCTGG |
| SEQ ID NO: 419 | mm01911_Pdia4 | TACTGGAGTTCTATGCACCA |
| SEQ ID NO: 420 | mm01912_Pdia4 | AGCATCCTGATACTGCAAGT |
| SEQ ID NO: 421 | mm01917_Anxa2 | CAGATCAGTCTTGTACACTG |
| SEQ ID NO: 422 | mm01918_Anxa2 | GTTTGTCAGGATGTTGACAA |
| SEQ ID NO: 423 | mm01919_Anxa2 | AAGGAACCGACGTCCCCAAG |
| SEQ ID NO: 424 | mm01920_Anxa2 | TTGCCTTCGCCTATCAGAGA |
| SEQ ID NO: 425 | mm01937_Calcr | GTGATGGCGTGGATAATGGT |

TABLE 1-continued mmSurf sgRNA library sequences

| SEQ ID NO | id_gRNA Target | Sequence |
|---|---|---|
| SEQ ID NO: 426 | mm01938_Calcr | CAAAGTCCGGGAAGTAGTCA |
| SEQ ID NO: 427 | mm01939_Calcr | CCTACCAATCTCACTGACTC |
| SEQ ID NO: 428 | mm01940_Calcr | ACATATGTGGACAATGCAGT |
| SEQ ID NO: 429 | mm01957_Calr | TGAGCAGAATATCGACTGTG |
| SEQ ID NO: 430 | mm01958_Calr | CAAGAATGTGCTGATCAACA |
| SEQ ID NO: 431 | mm01959_Calr | TATGTTTGGATTCGACCCAG |
| SEQ ID NO: 432 | mm01960_Calr | GCGGCCAGACAACACCTATG |
| SEQ ID NO: 433 | mm01965_Calu | GAAGGGCACGACCTCAATG |
| SEQ ID NO: 434 | mm01966_Calu | CCTACCTAAAACGTAGCCGT |
| SEQ ID NO: 435 | mm01967_Calu | TGAACTTTATCGCTGAGCTG |
| SEQ ID NO: 436 | mm01968_Calu | AAGTAAAATAGATGACGACA |
| SEQ ID NO: 437 | mm02017_Capn5 | AGCTTGATATGATCCGTCTG |
| SEQ ID NO: 438 | mm02018_Capn5 | CCTGAGCATCCATAAGACAT |
| SEQ ID NO: 439 | mm02019_Capn5 | TTTACTATAAGGGCACCCCA |
| SEQ ID NO: 440 | mm02020_Capn5 | ATGAGCTGGTTGTTGACTGT |
| SEQ ID NO: 441 | mm02061_Car4 | CTGTACAGCCTCGTACCGGG |
| SEQ ID NO: 442 | mm02062_Car4 | GAAGTTGACATCTAGCAAGG |
| SEQ ID NO: 443 | mm02063_Car4 | TCACGGGGTTTGGAGATACT |
| SEQ ID NO: 444 | mm02064_Car4 | GAGGATACCTTCAGTAGAGG |
| SEQ ID NO: 445 | mm02125_Casr | GATAATGTCAGCCATCGCGG |
| SEQ ID NO: 446 | mm02126_Casr | CCCAACTTCCTTGAACACAA |
| SEQ ID NO: 447 | mm02127_Casr | AGCCTTCAGACCGAACCCAA |
| SEQ ID NO: 448 | mm02128_Casr | TTCCTCGTGACTTCTCACGA |
| SEQ ID NO: 449 | mm02145_Cav1 | CAAGCATCTCAACGACGACG |
| SEQ ID NO: 450 | mm02146_Cav1 | ATGTGATTGCAGAACCAGAA |
| SEQ ID NO: 451 | mm02147_Cav1 | CGAAGATCGTAGACAACAAG |
| SEQ ID NO: 452 | mm02148_Cav1 | AGTGTATGACGCGCACACCA |
| SEQ ID NO: 453 | mm02149_Cav2 | GCAGATCCACACTTTGTCAA |
| SEQ ID NO: 454 | mm02150_Cav2 | AGATGAGAGTTGAGCTGGTG |
| SEQ ID NO: 455 | mm02151_Cav2 | CTGCGTAGTCAACGCCACTG |
| SEQ ID NO: 456 | mm02152_Cav2 | ATACCCGCAATGAAGGCCAA |
| SEQ ID NO: 457 | mm02153_Cav3 | CCAGCAGTGTAGACAACAGG |
| SEQ ID NO: 458 | mm02154_Cav3 | CCATACACCGTCGAAGCTGT |
| SEQ ID NO: 459 | mm02155_Cav3 | CGACCCCAAGAACATCAATG |
| SEQ ID NO: 460 | mm02156_Cav3 | TCACTGCAAGGAGATAGACT |
| SEQ ID NO: 461 | mm02201_Serpinh1 | TGGGTGTTACGATGATGCAC |
| SEQ ID NO: 462 | mm02202_Serpinh1 | CATCGCCTGATATAGGCTGA |
| SEQ ID NO: 463 | mm02203_Serpinh1 | AGACTCACGCTTAAAGAACA |

TABLE 1-continued mmSurf sgRNA library sequences

| SEQ ID NO | id_gRNA Target | Sequence |
|---|---|---|
| SEQ ID NO: 464 | mm02204_Serpinh1 | CGGAGCTGGGCCCGTACAGG |
| SEQ ID NO: 465 | mm02249_Cckbr | GATGGCCGCGAGATTTAGAG |
| SEQ ID NO: 466 | mm02250_Cckbr | AGCCGGGTCCGAAACCAAGG |
| SEQ ID NO: 467 | mm02251_Cckbr | CGAAGATGAATGTGCCCATG |
| SEQ ID NO: 468 | mm02252_Cckbr | CCCGGTTCCGCGGATACGAG |
| SEQ ID NO: 469 | mm02313_Ccr6 | ACTGATGAAAGGCACATATG |
| SEQ ID NO: 470 | mm02314_Ccr6 | TCTGAGACAGACCTGTACCG |
| SEQ ID NO: 471 | mm02315_Ccr6 | AGAGGTCAGAAACTTCACCA |
| SEQ ID NO: 472 | mm02316_Ccr6 | AGATTTGGTTGCCTGGACGA |
| SEQ ID NO: 473 | mm02349_Cd14 | AATCCGACTAGGAATCCGCG |
| SEQ ID NO: 474 | mm02350_Cd14 | GCAGATGTGGAATTGTACGG |
| SEQ ID NO: 475 | mm02351_Cd14 | TTGCCCACGACACGTTGCGG |
| SEQ ID NO: 476 | mm02352_Cd14 | TGGAGGGTCGGGAACTTGAG |
| SEQ ID NO: 477 | mm02353_Cd151 | TACCTGCTGATAATAGACAT |
| SEQ ID NO: 478 | mm02354_Cd151 | TACCACCAGTCAGGCCACGA |
| SEQ ID NO: 479 | mm02355_Cd151 | AGCCACGGCCTACATCTTAG |
| SEQ ID NO: 480 | mm02356_Cd151 | GACTAATGTAGTCACTCTTG |
| SEQ ID NO: 481 | mm02357_Ctla4 | TGTGATGGTGAATATTCACA |
| SEQ ID NO: 482 | mm02358_Ctla4 | GGACTGAGAGCTGTTGACAC |
| SEQ ID NO: 483 | mm02359_Ctla4 | ACAGGTGACCCAACCTTCAG |
| SEQ ID NO: 484 | mm02360_Ctla4 | TGCCCACAAAGTATGGCGGT |
| SEQ ID NO: 485 | mm02361_Cd19 | GAATGACTGACCCCGCCAGG |
| SEQ ID NO: 486 | mm02362_Cd19 | AATGTCTCAGACCATATGGG |
| SEQ ID NO: 487 | mm02363_Cd19 | GGCACCTATTATTGTCTCCG |
| SEQ ID NO: 488 | mm02364_Cd19 | TTTAGCCCACACATACAGCT |
| SEQ ID NO: 489 | mm02365_Cd1d1 | GGAGACCACGGACAAATAGG |
| SEQ ID NO: 490 | mm02366_Cd1d1 | CTGGTCCCGCACAGACAGCG |
| SEQ ID NO: 491 | mm02367_Cd1d1 | AAATATGTCGTGAGATTCTG |
| SEQ ID NO: 492 | mm02368_Cd1d1 | TGGCTTCGTGAAGCTGATGG |
| SEQ ID NO: 493 | mm02369_Cd2 | CCGATGATGAGAAACGACAG |
| SEQ ID NO: 494 | mm02370_Cd2 | GAACGCACCATTCAAGTGTG |
| SEQ ID NO: 495 | mm02371_Cd2 | TGATATTGATGAGGTGCGAT |
| SEQ ID NO: 496 | mm02372_Cd2 | AGAGACAATGAGACCATCTG |
| SEQ ID NO: 497 | mm02373_Ms4a1 | GTTACAGTACTGTGTAGATG |
| SEQ ID NO: 498 | mm02374_Ms4a1 | TACCATACACTCAAACAGAT |
| SEQ ID NO: 499 | mm02375_Ms4a1 | CAGTCGTAGATATCAACATA |
| SEQ ID NO: 500 | mm02376_Ms4a1 | CCACACAAAGCTTCTTCATG |
| SEQ ID NO: 501 | mm02377_Cd22 | GTAATTCCCAGCATGCCACG |

TABLE 1-continued mmSurf sgRNA library sequences

| SEQ ID NO | id_gRNA Target | Sequence |
|---|---|---|
| SEQ ID NO: 502 | mm02378_Cd22 | CGATACGTGCCAATGACAGT |
| SEQ ID NO: 503 | mm02379_Cd22 | CAGCGCGGATCTCTGATGCG |
| SEQ ID NO: 504 | mm02380_Cd22 | GTACAAAACTCCACTACCCA |
| SEQ ID NO: 505 | mm02381_Cd24a | GAACAGGGTCTCACCTGCGT |
| SEQ ID NO: 506 | mm02382_Cd24a | GCAGAAATATTCTGGTTACC |
| SEQ ID NO: 507 | mm02383_Cd24a | GAAACGGTGCAACAGATGTT |
| SEQ ID NO: 508 | mm02384_Cd24a | GGTAGCGTTACTTGGATTTG |
| SEQ ID NO: 509 | mm02385_Cd28 | TCGGCATTCGAGCGAAACTG |
| SEQ ID NO: 510 | mm02386_Cd28 | GCTTGTGGTAGATAGCAACG |
| SEQ ID NO: 511 | mm02387_Cd28 | CAAGGGCGTGAACAGCGACG |
| SEQ ID NO: 512 | mm02388_Cd28 | TTCCTACAACCTTCTCGCAA |
| SEQ ID NO: 513 | mm02393_Cd33 | CTCCTGACATTATAATCCCG |
| SEQ ID NO: 514 | mm02394_Cd33 | AGGTGTGAACGTCAGCACGG |
| SEQ ID NO: 515 | mm02395_Cd33 | GCCCGAGTCAGTGACAGTCG |
| SEQ ID NO: 516 | mm02396_Cd33 | CTAGTGCAGAAGGCAACACA |
| SEQ ID NO: 517 | mm02397_Cd34 | TGATGTGTAAGCATATGGCT |
| SEQ ID NO: 518 | mm02398_Cd34 | GCTCTGGAATCCGAGAAGTG |
| SEQ ID NO: 519 | mm02399_Cd34 | TGTCCTGATAGATCAAGTAG |
| SEQ ID NO: 520 | mm02400_Cd34 | CTCATTGGTAGGAACTGATG |
| SEQ ID NO: 521 | mm02401_Cd36 | AAATATAACTCAGGACCCCG |
| SEQ ID NO: 522 | mm02402_Cd36 | CCAAAACTGTCTGTACACAG |
| SEQ ID NO: 523 | mm02403_Cd36 | TAGGATATGGAACCAAACTG |
| SEQ ID NO: 524 | mm02404_Cd36 | TTAATCATGTCGCAATAGCT |
| SEQ ID NO: 525 | mm02405_Scarb2 | ATAGAACAGGCCGAAATTCG |
| SEQ ID NO: 526 | mm02406_Scarb2 | AAATAAAACTGGATGTACAC |
| SEQ ID NO: 527 | mm02407_Scarb2 | AATATGATTAACGGGACAGA |
| SEQ ID NO: 528 | mm02408_Scarb2 | ATAATGACACGTACCAACAG |
| SEQ ID NO: 529 | mm02409_Cd37 | CCAAGTCTGCAGTGGCACGA |
| SEQ ID NO: 530 | mm02410_Cd37 | ATCTCCGCGGGACTGGAACA |
| SEQ ID NO: 531 | mm02411_Cd37 | CTGTCTCATCCGGATTCGTG |
| SEQ ID NO: 532 | mm02412_Cd37 | TTTGCCACACAGATTACCCT |
| SEQ ID NO: 533 | mm02413_Cd38 | AGCCCAGATCGGTCTCGGAG |
| SEQ ID NO: 534 | mm02414_Cd38 | TCAAACCATACCATGTAACA |
| SEQ ID NO: 535 | mm02415_Cd38 | GGAGGATCTGAGTGTAGATG |
| SEQ ID NO: 536 | mm02416_Cd38 | CATCAATATACTTGGATCCA |
| SEQ ID NO: 537 | mm02417_Entpd2 | GCCAGCACTCCACTCTACCT |
| SEQ ID NO: 538 | mm02418_Entpd2 | TGGCCACTTGTAGACAAACA |
| SEQ ID NO: 539 | mm02419_Entpd2 | GGACGCTGACCCATAGTGCA |

TABLE 1-continued mmSurf sgRNA library sequences

| SEQ ID NO | id_gRNA Target | Sequence |
|---|---|---|
| SEQ ID NO: 540 | mm02420_Entpd2 | GGGCACCACGGAAGTCAAAG |
| SEQ ID NO: 541 | mm02421_Entpd6 | GGCTGGTTACCTCGACACGT |
| SEQ ID NO: 542 | mm02422_Entpd6 | TCTATGTTGCCTATATCAAG |
| SEQ ID NO: 543 | mm02423_Entpd6 | TTAGACAGGTTACCTCCAGG |
| SEQ ID NO: 544 | mm02424_Entpd6 | ACAAGCTGTACTCCTACAGG |
| SEQ ID NO: 545 | mm02429_Cd3d | TTACACAGATATATCCCTCG |
| SEQ ID NO: 546 | mm02430_Cd3d | TCCATCTAGATGCATGACGC |
| SEQ ID NO: 547 | mm02431_Cd3d | AAGAATAAAACACTCAACTT |
| SEQ ID NO: 548 | mm02432_Cd3d | GATACAAGTGACCGAATATG |
| SEQ ID NO: 549 | mm02433_Cd3e | AGGGCACGTCAACTCTACAC |
| SEQ ID NO: 550 | mm02434_Cd3e | TTCTCGGAAGTCGAGGACAG |
| SEQ ID NO: 551 | mm02435_Cd3e | TACTTGTACCTGAAAGCTCG |
| SEQ ID NO: 552 | mm02436_Cd3e | TCAGAAGCATGATAAGCACC |
| SEQ ID NO: 553 | mm02437_Cd3g | TGACACTGATACGTGCCTCG |
| SEQ ID NO: 554 | mm02438_Cd3g | TTCTGTAATACACTTGCAGG |
| SEQ ID NO: 555 | mm02439_Cd3g | AACTGCATTGAGCTAAACAT |
| SEQ ID NO: 556 | mm02440_Cd3g | GTACAAGTGGATGGCAGCCG |
| SEQ ID NO: 557 | mm02445_Cd4 | TCAAAACGATCAAACTGCGA |
| SEQ ID NO: 558 | mm02446_Cd4 | TATCACGGCCTATAAGAGTG |
| SEQ ID NO: 559 | mm02447_Cd4 | ACTCACCCTCAAGATACCCC |
| SEQ ID NO: 560 | mm02448_Cd4 | TTCTTCTGGGAACTCTCGCA |
| SEQ ID NO: 561 | mm02449_Cd44 | GCAATATGTGTCATAGTGGG |
| SEQ ID NO: 562 | mm02450_Cd44 | TCATGGAGAAAATTGGACCC |
| SEQ ID NO: 563 | mm02451_Cd44 | TCTGTGCGGGCAGAAACCCG |
| SEQ ID NO: 564 | mm02452_Cd44 | CAGTCCGGGAGATACTGTAG |
| SEQ ID NO: 565 | mm02453_Cd48 | ATACGTTTATATGGTCCAAG |
| SEQ ID NO: 566 | mm02454_Cd48 | TCACCTGAGGCTATCGTGTG |
| SEQ ID NO: 567 | mm02455_Cd48 | GAACGAGTTGAAGATAACCC |
| SEQ ID NO: 568 | mm02456_Cd48 | CCTTGAAATCCAGTTCCCAA |
| SEQ ID NO: 569 | mm02457_Cd5 | ACTGCAGAGACTTACAGATG |
| SEQ ID NO: 570 | mm02458_Cd5 | CACTGCTGCCCCCGACCAGG |
| SEQ ID NO: 571 | mm02459_Cd5 | GTGTGCAAACAGCTGAGATG |
| SEQ ID NO: 572 | mm02460_Cd5 | TGAGACACAGCTCCCGTTCG |
| SEQ ID NO: 573 | mm02461_Cd53 | GTTACGGAAGAGTACTCCAT |
| SEQ ID NO: 574 | mm02462_Cd53 | CATTGTGGGATCCATTATCA |
| SEQ ID NO: 575 | mm02463_Cd53 | GCTGATTATTCTCCTTGCTG |
| SEQ ID NO: 576 | mm02464_Cd53 | AATGACTCACCGACATAAGC |
| SEQ ID NO: 577 | mm02465_Cd59a | TGGAAACAATCAGATTGTCA |

TABLE 1-continued mmSurf sgRNA library sequences

| SEQ ID NO | id_gRNA Target | Sequence |
|---|---|---|
| SEQ ID NO: 578 | mm02466_Cd59a | AAACCACCGGTTGGAAACAG |
| SEQ ID NO: 579 | mm02467_Cd59a | CAGGAATGCAAGTGTATCAA |
| SEQ ID NO: 580 | mm02468_Cd59a | TAGAGACAGGAATCCTGGTC |
| SEQ ID NO: 581 | mm02469_Cd6 | GCAGCGCCGGGAATACGACG |
| SEQ ID NO: 582 | mm02470_Cd6 | GAGCCAAAGGACAATACGGT |
| SEQ ID NO: 583 | mm02471_Cd6 | AGCAGTTCACCTGATCGCGG |
| SEQ ID NO: 584 | mm02472_Cd6 | AATACCTGAGCAGACAACCC |
| SEQ ID NO: 585 | mm02473_Cd63 | CCCCGCACTACTCACGCAGA |
| SEQ ID NO: 586 | mm02474_Cd63 | CCTTCCTAGAATAACTGCTG |
| SEQ ID NO: 587 | mm02475_Cd63 | GACAGGAAGATGGCAAACTG |
| SEQ ID NO: 588 | mm02476_Cd63 | ATTACCCATGAGACTACTGC |
| SEQ ID NO: 589 | mm02481_Cd69 | GTGGGCAAGTACAATTGCCC |
| SEQ ID NO: 590 | mm02482_Cd69 | CAAAATGTATACTGGTGCCA |
| SEQ ID NO: 591 | mm02483_Cd69 | CATTCTTGCAGGTAGCAACA |
| SEQ ID NO: 592 | mm02484_Cd69 | ATGAGTGGATTTCATACAAG |
| SEQ ID NO: 593 | mm02489_Cd72 | GGGTAAGACTACGCACAGCG |
| SEQ ID NO: 594 | mm02490_Cd72 | GCATCTAACCATCTAGGACA |
| SEQ ID NO: 595 | mm02491_Cd72 | GTCCTGTCTGATGTTAGGGG |
| SEQ ID NO: 596 | mm02492_Cd72 | AGGGAGAAGATAAGTCAGCT |
| SEQ ID NO: 597 | mm02493_Cd79a | GGAACCCTAATATCACATGG |
| SEQ ID NO: 598 | mm02494_Cd79a | CCTACTCACTGCGCACGCGG |
| SEQ ID NO: 599 | mm02495_Cd79a | CGAAGTAAACAAGAACCACA |
| SEQ ID NO: 600 | mm02496_Cd79a | AGGCGTATGACAAGAAGAGG |
| SEQ ID NO: 601 | mm02497_Cd80 | TGAGGAGAGTTGTAACGGCA |
| SEQ ID NO: 602 | mm02498_Cd80 | GAAATTGTCGTATTGATGCC |
| SEQ ID NO: 603 | mm02499_Cd80 | CTGGCAAAAACATGACAAAG |
| SEQ ID NO: 604 | mm02500_Cd80 | TGCCCCGGTCTGAAAGGACC |
| SEQ ID NO: 605 | mm02505_Cd82 | TGCCACCAGTAGCCGCGAGG |
| SEQ ID NO: 606 | mm02506_Cd82 | CTGTATCGGTGCTGTCAATG |
| SEQ ID NO: 607 | mm02507_Cd82 | GAAGTAGAAGAGGACCCCTA |
| SEQ ID NO: 608 | mm02508_Cd82 | AGGGGGTGCCTTACGTAGGA |
| SEQ ID NO: 609 | mm02509_Cd83 | GGGCGCTGTGCAAGGCAAGT |
| SEQ ID NO: 610 | mm02510_Cd83 | ACCCGCGATGGCGATGCGGG |
| SEQ ID NO: 611 | mm02511_Cd83 | CAAGCAAAACAGCTCCTTCG |
| SEQ ID NO: 612 | mm02512_Cd83 | CACACTCTCAGTGCCACTCT |
| SEQ ID NO: 613 | mm02513_Cd84 | GAATCCCATTCATTACCACC |
| SEQ ID NO: 614 | mm02514_Cd84 | CATAGATCAGAAGTATGACC |
| SEQ ID NO: 615 | mm02515_Cd84 | AGGAGCTGGTTACCTGTACA |

TABLE 1-continued mmSurf sgRNA library sequences

| SEQ ID NO | id_gRNA Target | Sequence |
|---|---|---|
| SEQ ID NO: 616 | mm02516_Cd84 | ATAACTTACGGTAGATATGA |
| SEQ ID NO: 617 | mm02517_Cd86 | AGTGTGAATGCCAAGTACCT |
| SEQ ID NO: 618 | mm02518_Cd86 | TTGACCTGCACGTCTAAGCA |
| SEQ ID NO: 619 | mm02519_Cd86 | TCTGCCGTGCCCATTTACAA |
| SEQ ID NO: 620 | mm02520_Cd86 | TGGAGGATAATTGATCCTGT |
| SEQ ID NO: 621 | mm02521_Cd8a | TGGGTGAGTCGATTATCCTG |
| SEQ ID NO: 622 | mm02522_Cd8a | ATCCCACAACAAGATAACGT |
| SEQ ID NO: 623 | mm02523_Cd8a | GTGTTGGGGTCCGTTTCGCA |
| SEQ ID NO: 624 | mm02524_Cd8a | GGACGCCGAACTTGGTCAGA |
| SEQ ID NO: 625 | mm02525_Cd8b1 | ACAGGGACGAAGCTGACTGT |
| SEQ ID NO: 626 | mm02526_Cd8b1 | TGACTTCTACTTCTGCGCGA |
| SEQ ID NO: 627 | mm02527_Cd8b1 | GCTGGTTCAAACCAACCATA |
| SEQ ID NO: 628 | mm02528_Cd8b1 | GGACGAAGGGGTCTGAATGA |
| SEQ ID NO: 629 | mm02529_Cd9 | CAATGGCGAATATCACCAAG |
| SEQ ID NO: 630 | mm02530_Cd9 | AAAGCCATCCATATGGCGGT |
| SEQ ID NO: 631 | mm02531_Cd9 | CTTGTGGGTATAGCCCCAGA |
| SEQ ID NO: 632 | mm02532_Cd9 | TCTTGGTCTGAGAGTCGAAT |
| SEQ ID NO: 633 | mm02573_Cdh1 | ATGATGAAAACGCCAACGGG |
| SEQ ID NO: 634 | mm02574_Cdh1 | CCCTCCAAATCCGATACCTG |
| SEQ ID NO: 635 | mm02575_Cdh1 | GGTGGCTGAGACCTTCATCA |
| SEQ ID NO: 636 | mm02576_Cdh1 | AAATGCCATCATTGGTCGTG |
| SEQ ID NO: 637 | mm02577_Cdh11 | CACCAAGACATTGGACCGAG |
| SEQ ID NO: 638 | mm02578_Cdh11 | AGGACAACCCTATTTCTCGG |
| SEQ ID NO: 639 | mm02579_Cdh11 | TTTGTGATAGAAGAGTACAC |
| SEQ ID NO: 640 | mm02580_Cdh11 | CTGTGAGAGCGATCACCCCA |
| SEQ ID NO: 641 | mm02581_Cdh13 | CCAGCCTGCCGAATTCATCG |
| SEQ ID NO: 642 | mm02582_Cdh13 | GCAGAGATCTCATAGTCCAG |
| SEQ ID NO: 643 | mm02583_Cdh13 | CGCTGTCATCCGCATCACCG |
| SEQ ID NO: 644 | mm02584_Cdh13 | GCAGAACTCGTGATTGTCGG |
| SEQ ID NO: 645 | mm02585_Cdh15 | CCATCGACAAGTTCACCGGG |
| SEQ ID NO: 646 | mm02586_Cdh15 | GTATAATCTGACCTTGCAAG |
| SEQ ID NO: 647 | mm02587_Cdh15 | CTGAGGACGAGCATAGCTGA |
| SEQ ID NO: 648 | mm02588_Cdh15 | CCTTCAAAAGGGTGAAGCA |
| SEQ ID NO: 649 | mm02593_Cdh17 | TCAGTACAACTTAAGTATCG |
| SEQ ID NO: 650 | mm02594_Cdh17 | CTGGAGACAGACATGTCGGT |
| SEQ ID NO: 651 | mm02595_Cdh17 | TGTAGCTTGGATGATTAGGA |
| SEQ ID NO: 652 | mm02596_Cdh17 | TACATAACATCGTTGATTTG |
| SEQ ID NO: 653 | mm02597_Cdh2 | TTACCGAAGGATGTGCACGA |

TABLE 1-continued mmSurf sgRNA library sequences

| SEQ ID NO | id_gRNA Target | Sequence |
| --- | --- | --- |
| SEQ ID NO: 654 | mm02598_Cdh2 | AATGCGGCATACAGAATCAG |
| SEQ ID NO: 655 | mm02599_Cdh2 | TCTGTTGCATATATCGATCG |
| SEQ ID NO: 656 | mm02600_Cdh2 | GTGTTTGAAAGGCCATAAGT |
| SEQ ID NO: 657 | mm02601_Cdh3 | ATGGTGAAGACTCCTTCGGG |
| SEQ ID NO: 658 | mm02602_Cdh3 | ATGGTGAACATGAGGTCGTG |
| SEQ ID NO: 659 | mm02603_Cdh3 | ATCACCTCCCACGATGTGGT |
| SEQ ID NO: 660 | mm02604_Cdh3 | AAACTCCGGAGCGTTATCGT |
| SEQ ID NO: 661 | mm02605_Cdh4 | GGATATGAACGGTAACAAGG |
| SEQ ID NO: 662 | mm02606_Cdh4 | CGTCTACCGAATCATAAGTG |
| SEQ ID NO: 663 | mm02607_Cdh4 | CACCATCAACAGTGAAACAG |
| SEQ ID NO: 664 | mm02608_Cdh4 | CTTGGACTTCAAAGTCGGGG |
| SEQ ID NO: 665 | mm02609_Cdh5 | ACAGACCCCAAACGTAACGA |
| SEQ ID NO: 666 | mm02610_Cdh5 | GCCAACGAACTGGATTCTCG |
| SEQ ID NO: 667 | mm02611_Cdh5 | GCTTACATTGAGTAAAGACG |
| SEQ ID NO: 668 | mm02612_Cdh5 | TCGGGTCGATGCTAACACA |
| SEQ ID NO: 669 | mm02613_Cdh6 | GGATCCGATTATCAGTACGT |
| SEQ ID NO: 670 | mm02614_Cdh6 | CAATGAGCCAATATTCACCA |
| SEQ ID NO: 671 | mm02615_Cdh6 | CTACATCCTACAGATACGGG |
| SEQ ID NO: 672 | mm02616_Cdh6 | CAACATCACAGTGATCGCAA |
| SEQ ID NO: 673 | mm02733_Celsr1 | GTACGGATCACACCAGACGT |
| SEQ ID NO: 674 | mm02734_Celsr1 | GCTGGTGCAGTACTACAACA |
| SEQ ID NO: 675 | mm02735_Celsr1 | AGTCCCGGATAACTGACGGG |
| SEQ ID NO: 676 | mm02736_Celsr1 | CTTTGCTACTCCAATCCGTG |
| SEQ ID NO: 677 | mm02781_Cftr | GCCGTGTGACTGACATACGT |
| SEQ ID NO: 678 | mm02782_Cftr | TTCTAACTGAGACCTTACGC |
| SEQ ID NO: 679 | mm02783_Cftr | GTGGCGATCATGTTGCTGCG |
| SEQ ID NO: 680 | mm02784_Cftr | TATGGAGAGTAAAATATCGT |
| SEQ ID NO: 681 | mm02837_Chl1 | TTGTTAGCCGCAATTATCCG |
| SEQ ID NO: 682 | mm02838_Chl1 | TGAAGAAAACTACGCGACAG |
| SEQ ID NO: 683 | mm02839_Chl1 | GTACAGCCAACAATTTGTTG |
| SEQ ID NO: 684 | mm02840_Chl1 | TGTTGGGTAGACAATGCCAT |
| SEQ ID NO: 685 | mm02861_Chrm4 | CCAGTTCTTGTCCAACCCGG |
| SEQ ID NO: 686 | mm02862_Chrm4 | CATTAAGAAACCTCCACCAG |
| SEQ ID NO: 687 | mm02863_Chrm4 | TGTTCACAAGCATCGACCCG |
| SEQ ID NO: 688 | mm02864_Chrm4 | GGCCTGCCATCTTAGTAGTG |
| SEQ ID NO: 689 | mm02929_Clcn2 | TCTGTTTGACAACCGGACGT |
| SEQ ID NO: 690 | mm02930_Clcn2 | GAAATGAAAACCATCCTTCG |
| SEQ ID NO: 691 | mm02931_Clcn2 | GCCTCCAGGTACAATTCGGT |

TABLE 1-continued mmSurf sgRNA library sequences

| SEQ ID NO | id_gRNA Target | Sequence |
|---|---|---|
| SEQ ID NO: 692 | mm02932_Clcn2 | TGATGTCCTCGACTCGCACC |
| SEQ ID NO: 693 | mm02933_Clcn3 | GGTTGTACCACAATGCACTG |
| SEQ ID NO: 694 | mm02934_Clcn3 | GAGAATTGTGGGGATCGCTG |
| SEQ ID NO: 695 | mm02935_Clcn3 | AGATGACAATTTGTTAGACG |
| SEQ ID NO: 696 | mm02936_Clcn3 | CTAAAAAGAACTCCTCCGAT |
| SEQ ID NO: 697 | mm02941_Clcn5 | GGGCAAGTATCCTGTCGTCG |
| SEQ ID NO: 698 | mm02942_Clcn5 | TAAAAGCAAAGAGTCAACAT |
| SEQ ID NO: 699 | mm02943_Clcn5 | AAAAGAAGGGATATGTACAG |
| SEQ ID NO: 700 | mm02944_Clcn5 | TGGGCATCTACAGTGCCATG |
| SEQ ID NO: 701 | mm02949_Clcnka | AGAACAGGTAAACGCAACTG |
| SEQ ID NO: 702 | mm02950_Clcnka | GTCCCAAAGATGGTGAACCG |
| SEQ ID NO: 703 | mm02951_Clcnka | CAAAGCCGTCGGGGATACTG |
| SEQ ID NO: 704 | mm02952_Clcnka | ATGAAACGGCCCACACCAGG |
| SEQ ID NO: 705 | mm02985_Tpp1 | TGAGTTTCATCGCTATGTAG |
| SEQ ID NO: 706 | mm02986_Tpp1 | TTATGGTAGAAGGTTACCTG |
| SEQ ID NO: 707 | mm02987_Tpp1 | AACCTGACAGCCAAAGATGT |
| SEQ ID NO: 708 | mm02988_Tpp1 | GATCGAGGCCAGTCTAGATG |
| SEQ ID NO: 709 | mm03001_Clu | AGAAATGAGGCCTCTTGTGT |
| SEQ ID NO: 710 | mm03002_Clu | AACATGTTGTGGAAGCTCGG |
| SEQ ID NO: 711 | mm03003_Clu | TTCCTCTAAACTGTTGAGCA |
| SEQ ID NO: 712 | mm03004_Clu | AGATGACCGCACTGTGTGCA |
| SEQ ID NO: 713 | mm03013_Cxcr2 | TGTGGTTGTAATATACGTCC |
| SEQ ID NO: 714 | mm03014_Cxcr2 | GATATTCTCATACGTGAAGG |
| SEQ ID NO: 715 | mm03015_Cxcr2 | TCGTAGAATTAAGATGGGCA |
| SEQ ID NO: 716 | mm03016_Cxcr2 | CAGGTTCAGCAGGTAGACAT |
| SEQ ID NO: 717 | mm03017_Cxcr3 | TGAGGGCTACACGTACCCGG |
| SEQ ID NO: 718 | mm03018_Cxcr3 | AGTTAACACCAGCAGAACAT |
| SEQ ID NO: 719 | mm03019_Cxcr3 | TCTGCGTGTACTGCAGCTAG |
| SEQ ID NO: 720 | mm03020_Cxcr3 | ACTGGCAATGGGTGGCATTG |
| SEQ ID NO: 721 | mm03021_Cxcr4 | ACAGGCTATCGGGGTAAAGG |
| SEQ ID NO: 722 | mm03022_Cxcr4 | TGGTGGCGTGGACAATAGCG |
| SEQ ID NO: 723 | mm03023_Cxcr4 | TCTTCTGGTAACCCATGACC |
| SEQ ID NO: 724 | mm03024_Cxcr4 | TGGAGACTATGACTCCAACA |
| SEQ ID NO: 725 | mm03025_Ccr1 | GAACACTAGAGAATACAGGG |
| SEQ ID NO: 726 | mm03026_Ccr1 | ACGGTGAGTGAACTCCCACT |
| SEQ ID NO: 727 | mm03027_Ccr1 | CAGATTATCATGACTAACAG |
| SEQ ID NO: 728 | mm03028_Ccr1 | AGTAACAGTTCGGGCCCTCA |
| SEQ ID NO: 729 | mm03029_Ccr9 | TGGTATTGCCACATGTACCA |

TABLE 1-continued mmSurf sgRNA library sequences

| SEQ ID NO | id_gRNA Target | Sequence |
|---|---|---|
| SEQ ID NO: 730 | mm03030_Ccr9 | TCTCATCATGTGCATCAGTG |
| SEQ ID NO: 731 | mm03031_Ccr9 | TTGTGCAATACCAGTAGACA |
| SEQ ID NO: 732 | mm03032_Ccr9 | AGGCCATGACCATAAAGGGG |
| SEQ ID NO: 733 | mm03041_Ccr2 | ATCATCGTAGTCATACGGTG |
| SEQ ID NO: 734 | mm03042_Ccr2 | TACACTTGTTATCACCCCAA |
| SEQ ID NO: 735 | mm03043_Ccr2 | GATGATCACCATTACACCTG |
| SEQ ID NO: 736 | mm03044_Ccr2 | CCAGGGAGTAGAGTGGAGGC |
| SEQ ID NO: 737 | mm03045_Ccr4 | GGAGAATACCGCGTGCACGA |
| SEQ ID NO: 738 | mm03046_Ccr4 | ACTCGGTCAACTCGACGACG |
| SEQ ID NO: 739 | mm03047_Ccr4 | CAAGAGGCTCAAGTCCATGA |
| SEQ ID NO: 740 | mm03048_Ccr4 | GGAAGGTATCAAGGCATTTG |
| SEQ ID NO: 741 | mm03049_Ccr5 | AGTCAGAACGGTCAACTTTG |
| SEQ ID NO: 742 | mm03050_Ccr5 | GAATACCAGGGAGTAGAGTG |
| SEQ ID NO: 743 | mm03051_Ccr5 | CAGAAATGATACTGAGTGTG |
| SEQ ID NO: 744 | mm03052_Ccr5 | AGTACCTATCAATTGTCAGG |
| SEQ ID NO: 745 | mm03053_Ccr7 | TTTGGCGTCTACCTGTGTAA |
| SEQ ID NO: 746 | mm03054_Ccr7 | TGACGTACATCTATTTCAAG |
| SEQ ID NO: 747 | mm03055_Ccr7 | TAGGAACCCAAAAACCATCT |
| SEQ ID NO: 748 | mm03056_Ccr7 | AGCGGTCAATGCTGATGCAT |
| SEQ ID NO: 749 | mm03061_Ccr10 | GTGAAGGCCAACGACGCTGT |
| SEQ ID NO: 750 | mm03062_Ccr10 | AGACTGAAACCAAGTGCGCT |
| SEQ ID NO: 751 | mm03063_Ccr10 | CAGGCTGCCATGACGCCCAG |
| SEQ ID NO: 752 | mm03064_Ccr10 | CCATCAGGGAGACACTGGGT |
| SEQ ID NO: 753 | mm03065_Ackr3 | ACACCAAGATGCATACAACA |
| SEQ ID NO: 754 | mm03066_Ackr3 | GCATAACCAGTGGCCCATGG |
| SEQ ID NO: 755 | mm03067_Ackr3 | GGTCCACGCTCATGCAGGCG |
| SEQ ID NO: 756 | mm03068_Ackr3 | CCAACAATGAGACCTACTGC |
| SEQ ID NO: 757 | mm03069_Abcc2 | AAGACCCTGACTCATATCCG |
| SEQ ID NO: 758 | mm03070_Abcc2 | GCATTCGGAAGAAAGAACTC |
| SEQ ID NO: 759 | mm03071_Abcc2 | ACTCGGATCTTGGTTACACA |
| SEQ ID NO: 760 | mm03072_Abcc2 | GTTTAAGACGATCATGACAA |
| SEQ ID NO: 761 | mm03117_Cnr1 | GCTGGATCATGCGAACTGCG |
| SEQ ID NO: 762 | mm03118_Cnr1 | GGCAGGAGACAACTCCCCGT |
| SEQ ID NO: 763 | mm03119_Cnr1 | TGTACCTGTCGATGGCCGTG |
| SEQ ID NO: 764 | mm03120_Cnr1 | AACGAGGACAACATCCAGTG |
| SEQ ID NO: 765 | mm03125_Cntfr | AGACGCTCATACTGCACGTG |
| SEQ ID NO: 766 | mm03126_Cntfr | ATACTGCGAAGCTTAGAACT |
| SEQ ID NO: 767 | mm03127_Cntfr | AACCCACATGTAGAAGGACT |

TABLE 1-continued mmSurf sgRNA library sequences

| SEQ ID NO | id_gRNA Target | Sequence |
|---|---|---|
| SEQ ID NO: 768 | mm03128_Cntfr | GGCCGTAGTGTTGTGACCCA |
| SEQ ID NO: 769 | mm03129_Cntn1 | GATCGGTACAGTATGGTCGG |
| SEQ ID NO: 770 | mm03130_Cntn1 | GTGCACGGCGCAGACAATCG |
| SEQ ID NO: 771 | mm03131_Cntn1 | TACCCTTCAGTATCACAAAG |
| SEQ ID NO: 772 | mm03132_Cntn1 | TGAAGGACCACACAAACGTG |
| SEQ ID NO: 773 | mm03161_Col12a1 | GTTGTGTATCGCCCTCAAGG |
| SEQ ID NO: 774 | mm03162_Col12a1 | CAGAACCTCTGAATACCGTG |
| SEQ ID NO: 775 | mm03163_Col12a1 | GTGGCGAACTTACCATACAA |
| SEQ ID NO: 776 | mm03164_Col12a1 | CAATGTTCGTGACCTTACAG |
| SEQ ID NO: 777 | mm03181_Col2a1 | TGGGACAGCACTCTCCGAAG |
| SEQ ID NO: 778 | mm03182_Col2a1 | ACATGAGATTTACTCACCGG |
| SEQ ID NO: 779 | mm03183_Col2a1 | CTTCTTGTCAGGGTAACCCA |
| SEQ ID NO: 780 | mm03184_Col2a1 | CAGGCTAATAGACTTACAGA |
| SEQ ID NO: 781 | mm03185_Col3a1 | GTTAGCCCTGCAATTCCAAG |
| SEQ ID NO: 782 | mm03186_Col3a1 | GGCAAGAATGGAGAACGGGG |
| SEQ ID NO: 783 | mm03187_Col3a1 | ACATCATATGAGTCGAATTG |
| SEQ ID NO: 784 | mm03188_Col3a1 | GGACTGCCGTTATTCCCGGG |
| SEQ ID NO: 785 | mm03209_Col5a1 | TTGGCGTGCCCGGATTACCG |
| SEQ ID NO: 786 | mm03210_Col5a1 | GGAGTGTAATAGTCATCTGG |
| SEQ ID NO: 787 | mm03211_Col5a1 | TTCAAACCGCCACTCCCAGG |
| SEQ ID NO: 788 | mm03212_Col5a1 | TGGAATTCCGATGGGCCCAG |
| SEQ ID NO: 789 | mm03217_Col6a1 | AGGCAAGCGCGGAATCGACG |
| SEQ ID NO: 790 | mm03218_Col6a1 | GTGGCAATGATACTTAGACG |
| SEQ ID NO: 791 | mm03219_Col6a1 | CAACGACATTTCACCCCGTG |
| SEQ ID NO: 792 | mm03220_Col6a1 | TCATACCCAGGGTCGCCTCG |
| SEQ ID NO: 793 | mm03221_Col6a2 | TGCAGCTGGCTGATAAACTG |
| SEQ ID NO: 794 | mm03222_Col6a2 | TGCAACCAGGAGGCCCAATG |
| SEQ ID NO: 795 | mm03223_Col6a2 | ACCTAAACGAACAAGGCCTG |
| SEQ ID NO: 796 | mm03224_Col6a2 | GGCTGTCCTGAATCCCCTCG |
| SEQ ID NO: 797 | mm03249_Col1a1 | ACTGTCTTACAGGGTAACGT |
| SEQ ID NO: 798 | mm03250_Col1a1 | GGGGCACCATTGTTTCCTCG |
| SEQ ID NO: 799 | mm03251_Col1a1 | ACACTTACACGCTCGCCAGG |
| SEQ ID NO: 800 | mm03252_Col1a1 | GATACTTACAACAGCGCCAG |
| SEQ ID NO: 801 | mm03325_Cp | CATATAAGCATCAATTAGGG |
| SEQ ID NO: 802 | mm03326_Cp | GCTGTGAGGAGCGACCTGGT |
| SEQ ID NO: 803 | mm03327_Cp | ATGAAAAGTGTAGATCCTAG |
| SEQ ID NO: 804 | mm03328_Cp | GCTGAACAAATACCACACGA |
| SEQ ID NO: 805 | mm03329_Cpa3 | GAGATTCCTTCTCACTAACT |

TABLE 1-continued mmSurf sgRNA library sequences

| SEQ ID NO | id_gRNA Target | Sequence |
|---|---|---|
| SEQ ID NO: 806 | mm03330_Cpa3 | ACCATGCCTCAATGTCTACA |
| SEQ ID NO: 807 | mm03331_Cpa3 | GAACTTGACCCAAAGCATTG |
| SEQ ID NO: 808 | mm03332_Cpa3 | GAGGTCAGTGCCAATGCAGG |
| SEQ ID NO: 809 | mm03333_Cpd | GCTGGGCAGCAAATACACGT |
| SEQ ID NO: 810 | mm03334_Cpd | TGGCGCGCACTGGTATGACG |
| SEQ ID NO: 811 | mm03335_Cpd | ATGGAGATATCTGATAACCC |
| SEQ ID NO: 812 | mm03336_Cpd | TTTGAAGTAACTATCGAACT |
| SEQ ID NO: 813 | mm03337_Cpe | TCATCGTCATTCTTGCGACA |
| SEQ ID NO: 814 | mm03338_Cpe | CGGCTTTCTCAAAGCCGTCG |
| SEQ ID NO: 815 | mm03339_Cpe | TTTGGAAAATTGCGTCATCA |
| SEQ ID NO: 816 | mm03340_Cpe | CTTTCTGGTACTCGTTACAC |
| SEQ ID NO: 817 | mm03377_Cr2 | ATGTTGACCAGTTTGTTGCG |
| SEQ ID NO: 818 | mm03378_Cr2 | CTATACATTGCACCCCTGAG |
| SEQ ID NO: 819 | mm03379_Cr2 | AGACGGATTTCTATAAACCA |
| SEQ ID NO: 820 | mm03380_Cr2 | ATGCAATGCTCATGGCACAT |
| SEQ ID NO: 821 | mm03429_Crhr1 | GAGCTGGACCACAAACCACG |
| SEQ ID NO: 822 | mm03430_Crhr1 | GGTGGAGTACGTGAGTACGA |
| SEQ ID NO: 823 | mm03431_Crhr1 | GGCACTCAGAATAATTCACA |
| SEQ ID NO: 824 | mm03432_Crhr1 | CCTGCAGTGCAATGCCTCCG |
| SEQ ID NO: 825 | mm03449_Crlf1 | CGGTCAGGATAACACATGTG |
| SEQ ID NO: 826 | mm03450_Crlf1 | GTGCACGTGAGCCGCGTTGG |
| SEQ ID NO: 827 | mm03451_Crlf1 | GTGGAAGCCACCAATCGCCT |
| SEQ ID NO: 828 | mm03452_Crlf1 | ATCCGCCCCGAGGCACCCCG |
| SEQ ID NO: 829 | mm03489_Crll | TTGTTGAGTTCAATGCACTG |
| SEQ ID NO: 830 | mm03490_Crll | ATGCCTGGGGGTATCTCACA |
| SEQ ID NO: 831 | mm03491_Crll | TTAATTATACTTGTAATCAA |
| SEQ ID NO: 832 | mm03492_Crll | AAGGCGCTCTTTAACCTGGT |
| SEQ ID NO: 833 | mm03513_Cryab | AGTCCGGTGTCAATCCAGCT |
| SEQ ID NO: 834 | mm03514_Cryab | CTCTTGGATTAGGACGAACA |
| SEQ ID NO: 835 | mm03515_Cryab | CTCCGAAGAACTGGTCGAAG |
| SEQ ID NO: 836 | mm03516_Cryab | GGGGACGTGATTGAGGTCCA |
| SEQ ID NO: 837 | mm03577_Csf1 | TTTGCTAAGTGCTCTAGCCG |
| SEQ ID NO: 838 | mm03578_Csf1 | TCCATTCCCTAAATCAACAG |
| SEQ ID NO: 839 | mm03579_Csf1 | GTGCCAAGCAGCGACCACCC |
| SEQ ID NO: 840 | mm03580_Csf1 | GGTGTCCATTCCCAATCATG |
| SEQ ID NO: 841 | mm03581_Csf1r | GATAACGTTGAATCCCACTT |
| SEQ ID NO: 842 | mm03582_Csf1r | AAGATCATCGAGAGATACGA |
| SEQ ID NO: 843 | mm03583_Csf1r | TTCAAGCTCGGTACAACGGT |

TABLE 1-continued mmSurf sgRNA library sequences

| SEQ ID NO | id_gRNA Target | Sequence |
|---|---|---|
| SEQ ID NO: 844 | mm03584_Csf1r | CGGATAATGAACCCTCGCCA |
| SEQ ID NO: 845 | mm03589_Csf2ra | AGGACGCGGTGACGTCACGT |
| SEQ ID NO: 846 | mm03590_Csf2ra | CCTACTTGGTCGTGACCGGT |
| SEQ ID NO: 847 | mm03591_Csf2ra | CTAGCGTCACTAACCCAGAA |
| SEQ ID NO: 848 | mm03592_Csf2ra | TGACATCCAGCGTGACACCG |
| SEQ ID NO: 849 | mm03641_Vcan | GGCTTGTTTGGATATCGGGG |
| SEQ ID NO: 850 | mm03642_Vcan | TGTTAATTATAGTAGCACGC |
| SEQ ID NO: 851 | mm03643_Vcan | TTTCCATGGATGTTACTAAG |
| SEQ ID NO: 852 | mm03644_Vcan | TATGTCTAGTACAGTACTCG |
| SEQ ID NO: 853 | mm03645_Ncan | CACCCCCTCACCGAACCGTG |
| SEQ ID NO: 854 | mm03646_Ncan | GGGAGATTGTGTCAGCAGAG |
| SEQ ID NO: 855 | mm03647_Ncan | TGGGCTGTATCGCTGCCAAG |
| SEQ ID NO: 856 | mm03648_Ncan | TTGGGGACAAGTGTAGAGCG |
| SEQ ID NO: 857 | mm03653_Csrp1 | CTGGGCGGTACTCACTACAC |
| SEQ ID NO: 858 | mm03654_Csrp1 | GCACGCTGAGCACAGACAAG |
| SEQ ID NO: 859 | mm03655_Csrp1 | TTCTCCATGCACTGCCACGG |
| SEQ ID NO: 860 | mm03656_Csrp1 | TAGACCGCCTGGCTACAGCG |
| SEQ ID NO: 861 | mm03673_Cst8 | TTGACAGATCACAGACCGAA |
| SEQ ID NO: 862 | mm03674_Cst8 | CCAAACACACTGCTTCACAT |
| SEQ ID NO: 863 | mm03675_Cst8 | CATGGAGTATCTTGTCCACA |
| SEQ ID NO: 864 | mm03676_Cst8 | TCAGTCCAAGAATGAAGTGA |
| SEQ ID NO: 865 | mm03713_Ctsb | CAATGGCCGAGTCAACGTGG |
| SEQ ID NO: 866 | mm03714_Ctsb | TTGACATGGTGCTCGCAGGG |
| SEQ ID NO: 867 | mm03715_Ctsb | TCCTCACCGAACGCAACCCT |
| SEQ ID NO: 868 | mm03716_Ctsb | TGTAGACTCCACCTGAAACC |
| SEQ ID NO: 869 | mm03717_Ctsc | CTGCAAGATACAACCTCCTG |
| SEQ ID NO: 870 | mm03718_Ctsc | GGCAGTAACTGATAGCTGTG |
| SEQ ID NO: 871 | mm03719_Ctsc | TCACAACCACAACTTTGTGA |
| SEQ ID NO: 872 | mm03720_Ctsc | CTGTATTTCATCAGTCATCG |
| SEQ ID NO: 873 | mm03721_Ctsd | TATCCGTCGGACTATGACGG |
| SEQ ID NO: 874 | mm03722_Ctsd | TGACTCCAAGTACTACCACG |
| SEQ ID NO: 875 | mm03723_Ctsd | GACTGTGAAACACTGCGGCG |
| SEQ ID NO: 876 | mm03724_Ctsd | ACGTCCTTTGACATCCACTA |
| SEQ ID NO: 877 | mm03741_Ctsl | TTGGGGATCTTAAGCATCAG |
| SEQ ID NO: 878 | mm03742_Ctsl | AATGATCCAGCTACACAACG |
| SEQ ID NO: 879 | mm03743_Ctsl | CAATTACCTTCGCTTCATAG |
| SEQ ID NO: 880 | mm03744_Ctsl | TTAGTGCAGAGTGGCACCAG |
| SEQ ID NO: 881 | mm03745_Ctss | GAAGAAATCTTGTGTCGGAT |

TABLE 1-continued mmSurf sgRNA library sequences

| SEQ ID NO | id_gRNA Target | Sequence |
|---|---|---|
| SEQ ID NO: 882 | mm03746_Ctss | CACCGTGGCTTTGTAGGGAT |
| SEQ ID NO: 883 | mm03747_Ctss | GAGATCCCAATGGTAGTCCA |
| SEQ ID NO: 884 | mm03748_Ctss | ATCGTTCATGCCCACTTGGT |
| SEQ ID NO: 885 | mm03773_Cxadr | GCATCACTACACCCGAACAG |
| SEQ ID NO: 886 | mm03774_Cxadr | ACTCTCAGTCCCGAAGACCA |
| SEQ ID NO: 887 | mm03775_Cxadr | AACTACTATCCGGATCTGAA |
| SEQ ID NO: 888 | mm03776_Cxadr | ACGCTAGCCTCCAACCGAGC |
| SEQ ID NO: 889 | mm03817_Cyp1a2 | CAATGGCGGTCTCATCCCCG |
| SEQ ID NO: 890 | mm03818_Cyp1a2 | GCACTACCAAGACTTCAACA |
| SEQ ID NO: 891 | mm03819_Cyp1a2 | GAACATCGTGAATAACAGCA |
| SEQ ID NO: 892 | mm03820_Cyp1a2 | CTTCGAACCAGTCAGCCAGG |
| SEQ ID NO: 893 | mm03977_Cd55 | CTCTTATACGTATAGCCAGG |
| SEQ ID NO: 894 | mm03978_Cd55 | CTGCTGTCCCCAACTGTACG |
| SEQ ID NO: 895 | mm03979_Cd55 | TGTGACAGAACAGAAAGTAG |
| SEQ ID NO: 896 | mm03980_Cd55 | CGAAAACAACCTCCACTCCC |
| SEQ ID NO: 897 | mm03985_Dag1 | TGGTTAGGTTCTCCCCCACG |
| SEQ ID NO: 898 | mm03986_Dag1 | GTCTGGAATGCCAACCACGG |
| SEQ ID NO: 899 | mm03987_Dag1 | GACCTCGATAGAGAACACAC |
| SEQ ID NO: 900 | mm03988_Dag1 | GGCGTAGGCACTATCCGCGA |
| SEQ ID NO: 901 | mm04005_Slc6a3 | TAGATGATGAAGATCAACCC |
| SEQ ID NO: 902 | mm04006_Slc6a3 | GCTCGTCAGGGAGTTAATGG |
| SEQ ID NO: 903 | mm04007_Slc6a3 | CAGGGAGGGTGACTCCACGC |
| SEQ ID NO: 904 | mm04008_Slc6a3 | TTACTCAAAATACTCAGCAG |
| SEQ ID NO: 905 | mm04049_Dcc | GCAAAGGATAATAATCAACG |
| SEQ ID NO: 906 | mm04050_Dcc | CACCTGGTTACGAGGCGAGG |
| SEQ ID NO: 907 | mm04051_Dcc | CACAGAAAGACTACCCGCAG |
| SEQ ID NO: 908 | mm04052_Dcc | AACCCATGCCAACAATACAC |
| SEQ ID NO: 909 | mm04061_Dcn | TAGATATCAGGGGATTGTCA |
| SEQ ID NO: 910 | mm04062_Dcn | TTGAGGGATCGCAGTTATGT |
| SEQ ID NO: 911 | mm04063_Dcn | TAGGTTTGGACAAAGTGCCC |
| SEQ ID NO: 912 | mm04064_Dcn | CCTGTCTAAGAACCAACTAA |
| SEQ ID NO: 913 | mm04193_Dgcr2 | GGGCAGTTTGCATGTCACGG |
| SEQ ID NO: 914 | mm04194_Dgcr2 | AGAGGCCCGTCCTTATGGGA |
| SEQ ID NO: 915 | mm04195_Dgcr2 | TTCCTAGGGAAATGCCCAAG |
| SEQ ID NO: 916 | mm04196_Dgcr2 | CGGTACTGCTGACACCCCTG |
| SEQ ID NO: 917 | mm04249_Dlk1 | CCTAACCCATGCGAGAACGA |
| SEQ ID NO: 918 | mm04250_Dlk1 | TATTTACCCATTGATCACGC |
| SEQ ID NO: 919 | mm04251_Dlk1 | CCTCGCAGAATCCATACTGG |

TABLE 1-continued mmSurf sgRNA library sequences

| SEQ ID NO | id_gRNA Target | Sequence |
|---|---|---|
| SEQ ID NO: 920 | mm04252_Dlk1 | CACGTGGGACCCATGAACGG |
| SEQ ID NO: 921 | mm04297_Dmd | AAGGCATAACTCTTGAATCG |
| SEQ ID NO: 922 | mm04298_Dmd | CATGGATGAACTGATCAATG |
| SEQ ID NO: 923 | mm04299_Dmd | AGGACCGTTTGACATAAAGG |
| SEQ ID NO: 924 | mm04300_Dmd | AGAATGTACAAGGAACGACA |
| SEQ ID NO: 925 | mm04305_Tmc1 | TGCCGTACGGTAAACCCCAG |
| SEQ ID NO: 926 | mm04306_Tmc1 | TGAAGGCCAATATTACCCTG |
| SEQ ID NO: 927 | mm04307_Tmc1 | TTCAGCAAATAAGTCAAACA |
| SEQ ID NO: 928 | mm04308_Tmc1 | TGAAGTTCTCAAAATCTCGG |
| SEQ ID NO: 929 | mm04401_Dpep1 | TCACCCGTCGATGACCGGTG |
| SEQ ID NO: 930 | mm04402_Dpep1 | GACAACTGGCTTGTGGACAG |
| SEQ ID NO: 931 | mm04403_Dpep1 | AGTGGCCAGTCTGATCGGCG |
| SEQ ID NO: 932 | mm04404_Dpep1 | ATGTATGCGGACCAGAACTG |
| SEQ ID NO: 933 | mm04413_Dpp4 | CTACGATGTAGAGTGTAGAG |
| SEQ ID NO: 934 | mm04414_Dpp4 | CTTGGAATACAACTACGTGA |
| SEQ ID NO: 935 | mm04415_Dpp4 | GTCGATGTGATCCTATGACT |
| SEQ ID NO: 936 | mm04416_Dpp4 | TAGAAGGAGTATTCAATGAG |
| SEQ ID NO: 937 | mm04417_Dpp6 | GTGACCACCAATGAGCGATG |
| SEQ ID NO: 938 | mm04418_Dpp6 | GCGGAGCGACTGTGACGAGG |
| SEQ ID NO: 939 | mm04419_Dpp6 | TTTGCCTTCTATTAACACCG |
| SEQ ID NO: 940 | mm04420_Dpp6 | GGTGTTATGCACAGTAACAG |
| SEQ ID NO: 941 | mm04473_Dsc2 | TGGTGTGATCACTACCACGT |
| SEQ ID NO: 942 | mm04474_Dsc2 | GCATTGGAGGGATACACTCG |
| SEQ ID NO: 943 | mm04475_Dsc2 | TCTTACCTGCATCTAACGCA |
| SEQ ID NO: 944 | mm04476_Dsc2 | TCATCTCACTTACCTCTACT |
| SEQ ID NO: 945 | mm04489_Dsg2 | GTCTTCAACAGTGATAACGA |
| SEQ ID NO: 946 | mm04490_Dsg2 | TCTGTGTGTCAGTCTCAATG |
| SEQ ID NO: 947 | mm04491_Dsg2 | GAAGTGGAAAATAACGCACC |
| SEQ ID NO: 948 | mm04492_Dsg2 | TCAAAGACGAATATGCCGAA |
| SEQ ID NO: 949 | mm04505_Slc26a2 | GAGCCGACACCATGACTCCG |
| SEQ ID NO: 950 | mm04506_Slc26a2 | ATGGCCGGAGAGCTTTCCGT |
| SEQ ID NO: 951 | mm04507_Slc26a2 | ACTGTGCCTTATGATTGGTG |
| SEQ ID NO: 952 | mm04508_Slc26a2 | TCCAAAATGAGAAGCCAATG |
| SEQ ID NO: 953 | mm04613_Ecel1 | CCTGTCCTCACCATTCCGAG |
| SEQ ID NO: 954 | mm04614_Ecel1 | CCTGTACCTAGCTCAAGACG |
| SEQ ID NO: 955 | mm04615_Ecel1 | ACCTCGCGTCGATTCCAGCG |
| SEQ ID NO: 956 | mm04616_Ecel1 | GCTTGTCGTCGGGGATAGCG |
| SEQ ID NO: 957 | mm04617_Ecm1 | CAAGCTTCAAACAGTCTAGG |

TABLE 1-continued mmSurf sgRNA library sequences

| SEQ ID NO | id_gRNA Target | Sequence |
|---|---|---|
| SEQ ID NO: 958 | mm04618_Ecm1 | GCCAGTCTTCCTCGTACACA |
| SEQ ID NO: 959 | mm04619_Ecm1 | GTCCGGTGTGGGCAACCCCG |
| SEQ ID NO: 960 | mm04620_Ecm1 | GCTCTGGCGTCATCTCTCGC |
| SEQ ID NO: 961 | mm04629_Ect2 | AGCATACTCGTACAATACAG |
| SEQ ID NO: 962 | mm04630_Ect2 | TAGGAGTGTATATTACCTTG |
| SEQ ID NO: 963 | mm04631_Ect2 | AGAATGGATTTATAAAGCGT |
| SEQ ID NO: 964 | mm04632_Ect2 | ACTTCTAGAAGACTTAGCAC |
| SEQ ID NO: 965 | mm04641_S1pr1 | GTCCGGCATTACAACTACAC |
| SEQ ID NO: 966 | mm04642_S1pr1 | GCCTGCTAATAGGTCCGAGA |
| SEQ ID NO: 967 | mm04643_S1pr1 | CTGAAGATGAAACTACACAA |
| SEQ ID NO: 968 | mm04644_S1pr1 | GGCAGGTGTGAGCTTGTAAG |
| SEQ ID NO: 969 | mm04645_S1pr3 | GGGAACATTACGATTACGTG |
| SEQ ID NO: 970 | mm04646_S1pr3 | AATCACTACGGTCCGCAGAA |
| SEQ ID NO: 971 | mm04647_S1pr3 | GCCAGCACATCCCAATCAGA |
| SEQ ID NO: 972 | mm04648_S1pr3 | GCGCGCATACAAGATGACGA |
| SEQ ID NO: 973 | mm04649_S1pr4 | CAGCAGCACGTTGACCACGT |
| SEQ ID NO: 974 | mm04650_S1pr4 | ACATAGCCCTTGGAGTAGAG |
| SEQ ID NO: 975 | mm04651_S1pr4 | GATTGTAGTGCAGGACAATG |
| SEQ ID NO: 976 | mm04652_S1pr4 | CTCTAAAGATGGCCCCGTAG |
| SEQ ID NO: 977 | mm04669_Ednra | CCTTGGAGACCTTATCTACG |
| SEQ ID NO: 978 | mm04670_Ednra | GAGAGCACAGAGGTTCAAGA |
| SEQ ID NO: 979 | mm04671_Ednra | AAGGGGTGAAGTCTTCCATG |
| SEQ ID NO: 980 | mm04672_Ednra | CCTAGCAATGGCTCAATGCA |
| SEQ ID NO: 981 | mm04673_Ednrb | TCAATATTTCGTTGGCACGG |
| SEQ ID NO: 982 | mm04674_Ednrb | GTAGATGATTCTTAGCAGCG |
| SEQ ID NO: 983 | mm04675_Ednrb | ATGATTACGTCGGACTACAA |
| SEQ ID NO: 984 | mm04676_Ednrb | GTCACTTCTCGGGACTAAAG |
| SEQ ID NO: 985 | mm04693_Eef2 | GTTGTGAGCTGCTATACGAG |
| SEQ ID NO: 986 | mm04694_Eef2 | CCTACGGCGAGGGCGAGAGT |
| SEQ ID NO: 987 | mm04695_Eef2 | CCGATTGAGGACGTGCCATG |
| SEQ ID NO: 988 | mm04696_Eef2 | AGTCAGCCAATAGCCCAGAT |
| SEQ ID NO: 989 | mm04705_Efna2 | GGTTCCAGTAGACTGCGTAT |
| SEQ ID NO: 990 | mm04706_Efna2 | TATCTACTGCCCACACTACG |
| SEQ ID NO: 991 | mm04707_Efna2 | GCCGCTGCGTGCGCGCAACG |
| SEQ ID NO: 992 | mm04708_Efna2 | TGGCGGCGGCTATACCGTGG |
| SEQ ID NO: 993 | mm04709_Efna3 | TGTTCCAGTATACCGCATGC |
| SEQ ID NO: 994 | mm04710_Efna3 | AGTAGTATTCTTGGCCGGCA |
| SEQ ID NO: 995 | mm04711_Efna3 | GGCCCTGAGCTGTTGTAGTG |

TABLE 1-continued mmSurf sgRNA library sequences

| SEQ ID NO | id_gRNA Target | Sequence |
|---|---|---|
| SEQ ID NO: 996 | mm04712_Efna3 | CTGTACATGGTGAACCTGAG |
| SEQ ID NO: 997 | mm04717_Efna5 | TGTTCCAGTAGACGGCGTAG |
| SEQ ID NO: 998 | mm04718_Efna5 | GGACAGAGTCCTCATAGTGA |
| SEQ ID NO: 999 | mm04719_Efna5 | TCCGTTGTCTGGGATTGCAG |
| SEQ ID NO: 1000 | mm04720_Efna5 | TGAGCGCTACGTCCTGTACA |
| SEQ ID NO: 1001 | mm04721_Efnb1 | CACATGTAATGTAGTAATCG |
| SEQ ID NO: 1002 | mm04722_Efnb1 | ATCGTTATGAAGGTTGGGCA |
| SEQ ID NO: 1003 | mm04723_Efnb1 | TACAGCTTGTAGTACTCGTA |
| SEQ ID NO: 1004 | mm04724_Efnb1 | CAGGTTCTTGGCCAACGGCG |
| SEQ ID NO: 1005 | mm04729_Efnb3 | GGAGGGACACCATACCAGGT |
| SEQ ID NO: 1006 | mm04730_Efnb3 | GGAGGCGTGTGCCTAACCAG |
| SEQ ID NO: 1007 | mm04731_Efnb3 | GGGGACAAAGTAGATCTAGC |
| SEQ ID NO: 1008 | mm04732_Efnb3 | AATTATGTAGTAATCGTGGT |
| SEQ ID NO: 1009 | mm04749_Egfr | ACCAGACAGTCACTCTCTCG |
| SEQ ID NO: 1010 | mm04750_Egfr | TGGGCCTGACTACTACGAAG |
| SEQ ID NO: 1011 | mm04751_Egfr | CATGAATAGGCCAATCCCAA |
| SEQ ID NO: 1012 | mm04752_Egfr | GAGAACCTAGAAATAATACG |
| SEQ ID NO: 1013 | mm04753_Rhbdf1 | ATTCACGTTTGCGACGCCGA |
| SEQ ID NO: 1014 | mm04754_Rhbdf1 | GATGTCCACGTACCCAGATG |
| SEQ ID NO: 1015 | mm04755_Rhbdf1 | CACCACCTCCCCTCTACGTG |
| SEQ ID NO: 1016 | mm04756_Rhbdf1 | CTTCACCCACACCGCCAACG |
| SEQ ID NO: 1017 | mm04869_Aimp1 | CTGGCAGAAATTCATAACGG |
| SEQ ID NO: 1018 | mm04870_Aimp1 | TCCAGACGCGATGCGTCGAT |
| SEQ ID NO: 1019 | mm04871_Aimp1 | TGATGCAGATTCACTGTATG |
| SEQ ID NO: 1020 | mm04872_Aimp1 | TACAAAAGAGCAGATCAAAG |
| SEQ ID NO: 1021 | mm04873_Emb | AGTCGTTGATCGCTTACGTG |
| SEQ ID NO: 1022 | mm04874_Emb | AAGTCACCCGTAGTCTCAAG |
| SEQ ID NO: 1023 | mm04875_Emb | ACACCTTAACCAGTCAGTAC |
| SEQ ID NO: 1024 | mm04876_Emb | TTAAATTGGACTTGGTACAT |
| SEQ ID NO: 1025 | mm04885_Emp1 | ATGCATACCTTCATTGCCGT |
| SEQ ID NO: 1026 | mm04886_Emp1 | ATTACGCAAATGCATCTGTA |
| SEQ ID NO: 1027 | mm04887_Emp1 | ATACTCACAGCACACCAGCA |
| SEQ ID NO: 1028 | mm04888_Emp1 | GCATAATGGCAGTGGCAATG |
| SEQ ID NO: 1029 | mm04889_Emp2 | GGAGTGCCGTGGACACGATG |
| SEQ ID NO: 1030 | mm04890_Emp2 | AGGTTATTCTGTGATGCAGG |
| SEQ ID NO: 1031 | mm04891_Emp2 | ACAGGAACTTACATTGTCAA |
| SEQ ID NO: 1032 | mm04892_Emp2 | TGAGCTGGATGATGGACGTC |
| SEQ ID NO: 1033 | mm04897_Adgre1 | ACCCAAGATCCATTACAATG |

TABLE 1-continued mmSurf sgRNA library sequences

| SEQ ID NO | id_gRNA Target | Sequence |
|---|---|---|
| SEQ ID NO: 1034 | mm04898_Adgre1 | TTGGCAAAGAGAATCCAGCT |
| SEQ ID NO: 1035 | mm04899_Adgre1 | TATTACTGCACCTGTAAACG |
| SEQ ID NO: 1036 | mm04900_Adgre1 | AAGGAGGAGACATCCACTCT |
| SEQ ID NO: 1037 | mm04933_Eng | TCAGGGACATGAGTAGCACG |
| SEQ ID NO: 1038 | mm04934_Eng | CAAGTGCAATGGGATTTCCG |
| SEQ ID NO: 1039 | mm04935_Eng | CACACCCCAAGGCCTGATAG |
| SEQ ID NO: 1040 | mm04936_Eng | GTGGTTGATGTCGATGAACC |
| SEQ ID NO: 1041 | mm04937_Eno2 | GCCATCGCGGTAAAACTCAG |
| SEQ ID NO: 1042 | mm04938_Eno2 | GGTGTACCACACCCTCAAGG |
| SEQ ID NO: 1043 | mm04939_Eno2 | TCCTTCCCGATACATCACTG |
| SEQ ID NO: 1044 | mm04940_Eno2 | AAACAGCGTTACTTAGGCAA |
| SEQ ID NO: 1045 | mm04945_Enpep | TAGATGAGGCCGATAGTAGG |
| SEQ ID NO: 1046 | mm04946_Enpep | GGGAGTCGTCCTCTTGCACG |
| SEQ ID NO: 1047 | mm04947_Enpep | TGTTGGGTTCGTCGAAACAA |
| SEQ ID NO: 1048 | mm04948_Enpep | GGGAGCAGGTACCAATTCGA |
| SEQ ID NO: 1049 | mm04989_Epha1 | CCATGATATCAGATACAGCG |
| SEQ ID NO: 1050 | mm04990_Epha1 | GCTGTGGCTAAAACCCTATG |
| SEQ ID NO: 1051 | mm04991_Epha1 | AAGCTAAGTAGAGGCCACGG |
| SEQ ID NO: 1052 | mm04992_Epha1 | AGAATGGCACCAGATGGTGT |
| SEQ ID NO: 1053 | mm04993_Epha2 | CTTCTTGTAGTAGACGCGAA |
| SEQ ID NO: 1054 | mm04994_Epha2 | CGAGATCCACCCATCCTGTG |
| SEQ ID NO: 1055 | mm04995_Epha2 | CGTGTGCAAGACATGGACAG |
| SEQ ID NO: 1056 | mm04996_Epha2 | TGTTTGGTTAATACTGACGC |
| SEQ ID NO: 1057 | mm04997_Epha3 | ACTCCAGTCCAGGATAACCG |
| SEQ ID NO: 1058 | mm04998_Epha3 | AGCAGTTCATGAGTTCGCGA |
| SEQ ID NO: 1059 | mm04999_Epha3 | ACAGCCAAAATAATTGGCTG |
| SEQ ID NO: 1060 | mm05000_Epha3 | CTGACTGCGGCATACTGTCT |
| SEQ ID NO: 1061 | mm05001_Epha4 | TGACTGGATCACCCGCGAAG |
| SEQ ID NO: 1062 | mm05002_Epha4 | AAACTGGGCTAGATTTCGAA |
| SEQ ID NO: 1063 | mm05003_Epha4 | TCAGGACATTTCTTACAACG |
| SEQ ID NO: 1064 | mm05004_Epha4 | TGACAACCAACCAAGCAGGT |
| SEQ ID NO: 1065 | mm05017_Ephb2 | AGCAGGTGATCGGAGCAGGT |
| SEQ ID NO: 1066 | mm05018_Ephb2 | CATCAAACTCTACTGTAACG |
| SEQ ID NO: 1067 | mm05019_Ephb2 | TTGTGCAAGGCATGTCTAAG |
| SEQ ID NO: 1068 | mm05020_Ephb2 | AGGTCACTGATGTAGATGCG |
| SEQ ID NO: 1069 | mm05021_Ephb3 | ACAACGTAGAGTTTGTACCT |
| SEQ ID NO: 1070 | mm05022_Ephb3 | CTACCGTGCAGACTCAGACT |
| SEQ ID NO: 1071 | mm05023_Ephb3 | TGTGTCCTGTGTCAAGATCG |

TABLE 1-continued mmSurf sgRNA library sequences

| SEQ ID NO | id_gRNA Target | Sequence |
|---|---|---|
| SEQ ID NO: 1072 | mm05024_Ephb3 | CCCGGACCTGAACTACGTAG |
| SEQ ID NO: 1073 | mm05025_Ephb4 | GGCAGCGTACAGCATAAGTG |
| SEQ ID NO: 1074 | mm05026_Ephb4 | GGTAATACCCAATTCGACAC |
| SEQ ID NO: 1075 | mm05027_Ephb4 | ACATTGACAGGCTCAAAAGG |
| SEQ ID NO: 1076 | mm05028_Ephb4 | AGCGTATCGTGGCATACACG |
| SEQ ID NO: 1077 | mm05029_Ephb6 | AGAGTCGAGTGTTAGTTGGG |
| SEQ ID NO: 1078 | mm05030_Ephb6 | ACACACTTTGTGGAACGGCG |
| SEQ ID NO: 1079 | mm05031_Ephb6 | AGGGCTCAACCGTGTCACAG |
| SEQ ID NO: 1080 | mm05032_Ephb6 | ACCTCAAACCATAGCTCCCG |
| SEQ ID NO: 1081 | mm05041_Stx2 | CAGTGGATCTGCGGATACGA |
| SEQ ID NO: 1082 | mm05042_Stx2 | AAAACTGCTAACAGGATCCG |
| SEQ ID NO: 1083 | mm05043_Stx2 | TATCAGATTCACAAATCACT |
| SEQ ID NO: 1084 | mm05044_Stx2 | GTCATTAAATACCCACCTGA |
| SEQ ID NO: 1085 | mm05057_Epo | GAGGCTACGTAGACCACTGA |
| SEQ ID NO: 1086 | mm05058_Epo | TGAGGCGTGGGGGAGCACAG |
| SEQ ID NO: 1087 | mm05059_Epo | GCGACAGTCGAGTTCTGGAG |
| SEQ ID NO: 1088 | mm05060_Epo | CTATGCTTGGAAAAGAATGG |
| SEQ ID NO: 1089 | mm05061_Epor | GCGTCACTACTGACCGCTAG |
| SEQ ID NO: 1090 | mm05062_Epor | GTCCACTTCATATCGGATGT |
| SEQ ID NO: 1091 | mm05063_Epor | AGCGTGATGGTTGTCTGTGG |
| SEQ ID NO: 1092 | mm05064_Epor | TGGATGATGCGGTGATAGCG |
| SEQ ID NO: 1093 | mm05093_Erbb2 | TTGGAATCCTAATCAAACGA |
| SEQ ID NO: 1094 | mm05094_Erbb2 | CTGTCCCCGAACAACCAAG |
| SEQ ID NO: 1095 | mm05095_Erbb2 | CTGACTGCAGTTGACACACT |
| SEQ ID NO: 1096 | mm05096_Erbb2 | TCAATGAGTAAGCACCACTG |
| SEQ ID NO: 1097 | mm05097_Erbb3 | GCCCTTACCTAACCTCCGAG |
| SEQ ID NO: 1098 | mm05098_Erbb3 | TCCAACCTGACGACCATCGG |
| SEQ ID NO: 1099 | mm05099_Erbb3 | CTAGGGTATGTATTACCTCG |
| SEQ ID NO: 1100 | mm05100_Erbb3 | TGGACTCTAGCAATATCGAT |
| SEQ ID NO: 1101 | mm05101_Erbb4 | ATGGCAGCAGTCACTAACGT |
| SEQ ID NO: 1102 | mm05102_Erbb4 | GTAGAGCCCTTAACTCCCAG |
| SEQ ID NO: 1103 | mm05103_Erbb4 | TTGCTGATCCTCAAACAACA |
| SEQ ID NO: 1104 | mm05104_Erbb4 | AAAGAAATGTACCCGCAGGA |
| SEQ ID NO: 1105 | mm05205_Mpzl2 | TGTGGAAATTTACACCTCCG |
| SEQ ID NO: 1106 | mm05206_Mpzl2 | AGTTAGCGCATCTCCCACAG |
| SEQ ID NO: 1107 | mm05207_Mpzl2 | AATTTCCGACCTCGAGATGG |
| SEQ ID NO: 1108 | mm05208_Mpzl2 | CGGACGGTTCAAAGACCGGG |
| SEQ ID NO: 1109 | mm05285_F2r | GTTCCCGTAAAACGCTGCGG |

TABLE 1-continued mmSurf sgRNA library sequences

| SEQ ID NO | id_gRNA Target | Sequence |
|---|---|---|
| SEQ ID NO: 1110 | mm05286_F2r | GATTCCTTAGAAAGAATGAG |
| SEQ ID NO: 1111 | mm05287_F2r | GGTTCTCACTGAGGACGTCG |
| SEQ ID NO: 1112 | mm05288_F2r | AGTAGTAGCTGATCTTGAAG |
| SEQ ID NO: 1113 | mm05301_F3 | GAGGTCGCACTCGGTGTCTG |
| SEQ ID NO: 1114 | mm05302_F3 | AGATGGTAGAAAACTGAACG |
| SEQ ID NO: 1115 | mm05303_F3 | CATGAACTGAGTTCCTCCGT |
| SEQ ID NO: 1116 | mm05304_F3 | TCGGTAAGGTAAAAACTTTG |
| SEQ ID NO: 1117 | mm05365_Fap | ACCACCTACCCTCACCACGT |
| SEQ ID NO: 1118 | mm05366_Fap | ATGCACTCGTCTGCTATGGT |
| SEQ ID NO: 1119 | mm05367_Fap | AATGCTATTCAAATTACAAG |
| SEQ ID NO: 1120 | mm05368_Fap | CATAGATACTGAATTGGACG |
| SEQ ID NO: 1121 | mm05369_Fas | CAGTTAAGAGTTCATACTCA |
| SEQ ID NO: 1122 | mm05370_Fas | TATTTATATATCGAAAGTAC |
| SEQ ID NO: 1123 | mm05371_Fas | CATTTGCATACTCACACGAC |
| SEQ ID NO: 1124 | mm05372_Fas | GAGGACTGCAAAATGAATGG |
| SEQ ID NO: 1125 | mm05373_Fasl | AGGACCACAACACAAATCTG |
| SEQ ID NO: 1126 | mm05374_Fasl | CTTCACTCCAGAGATCAGAG |
| SEQ ID NO: 1127 | mm05375_Fasl | CCTCTGAAAAAAAAGAGCCG |
| SEQ ID NO: 1128 | mm05376_Fasl | GGAACTGGCAGAACTCCGTG |
| SEQ ID NO: 1129 | mm05405_Fbln2 | GTGGCAGTGTAGATAGAGTG |
| SEQ ID NO: 1130 | mm05406_Fbln2 | TACTACGACTGCGTACAAGG |
| SEQ ID NO: 1131 | mm05407_Fbln2 | AACGCACATAGGAAGTGTGT |
| SEQ ID NO: 1132 | mm05408_Fbln2 | CTGCACGAGAGTCTGCACCG |
| SEQ ID NO: 1133 | mm05409_Fbn1 | GAATGCAGCATAATGAACGG |
| SEQ ID NO: 1134 | mm05410_Fbn1 | GCTTACCGATGCATTCGCCA |
| SEQ ID NO: 1135 | mm05411_Fbn1 | AGCCCATGTCGCATTCACAG |
| SEQ ID NO: 1136 | mm05412_Fbn1 | GAGCTGTGTAGCAGTAACCA |
| SEQ ID NO: 1137 | mm05413_Fbn2 | GTTGAGGTTACGAAGCCACG |
| SEQ ID NO: 1138 | mm05414_Fbn2 | CAGACTTGGTCACCGCACCC |
| SEQ ID NO: 1139 | mm05415_Fbn2 | GAGTGTATGATAATGAATGG |
| SEQ ID NO: 1140 | mm05416_Fbn2 | AAGGTGTGACTTGCGAAGGT |
| SEQ ID NO: 1141 | mm05429_Fcer1a | GTGTACTTGAATGTAACGCA |
| SEQ ID NO: 1142 | mm05430_Fcer1a | GAAGAACTGGAATGTCCGCA |
| SEQ ID NO: 1143 | mm05431_Fcer1a | GTAAATATTCTAATCCATGG |
| SEQ ID NO: 1144 | mm05432_Fcer1a | AGTGCCACCGTTCAAGACAG |
| SEQ ID NO: 1145 | mm05433_Ms4a2 | TTGTCAGTAGCATCGCTGCA |
| SEQ ID NO: 1146 | mm05434_Ms4a2 | AAAGTCTGAAACATAGAGTA |
| SEQ ID NO: 1147 | mm05435_Ms4a2 | AAACTAGGCTATCCATTCTG |

TABLE 1-continued mmSurf sgRNA library sequences

| SEQ ID NO | id_gRNA Target | Sequence |
|---|---|---|
| SEQ ID NO: 1148 | mm05436_Ms4a2 | CAGGCAACACAAATTCTGGT |
| SEQ ID NO: 1149 | mm05437_Fcer1g | CCTACTCTACTGTCGACTCA |
| SEQ ID NO: 1150 | mm05438_Fcer1g | ACTCCAGATCCAGGTCCGAA |
| SEQ ID NO: 1151 | mm05439_Fcer1g | TCCAGGATATAGCAGAGCTG |
| SEQ ID NO: 1152 | mm05440_Fcer1g | TTTGGTGGAACAAGCAGGTA |
| SEQ ID NO: 1153 | mm05441_Fcer2a | GAACCTGACCGGACTCCAGG |
| SEQ ID NO: 1154 | mm05442_Fcer2a | CTTCCCCCTAGACTGGGAAA |
| SEQ ID NO: 1155 | mm05443_Fcer2a | ACGTGGGACACAGCTCATGT |
| SEQ ID NO: 1156 | mm05444_Fcer2a | CGATTCTCTAGAGAAACTCC |
| SEQ ID NO: 1157 | mm05445_Fcgr1 | AGAGTACCATATAGCAAGGG |
| SEQ ID NO: 1158 | mm05446_Fcgr1 | TGGGATGCTATAACTAGGCG |
| SEQ ID NO: 1159 | mm05447_Fcgr1 | TGGAAAATACTGACCCATGG |
| SEQ ID NO: 1160 | mm05448_Fcgr1 | GAATAAACTGGTGTACAATG |
| SEQ ID NO: 1161 | mm05449_Fcgr2b | AGGTCCCGACTTACTTAGCA |
| SEQ ID NO: 1162 | mm05450_Fcgr2b | CGGTGACACTGACATGCGAA |
| SEQ ID NO: 1163 | mm05451_Fcgr2b | TTCCAGAAACACCAGCTGAG |
| SEQ ID NO: 1164 | mm05452_Fcgr2b | ACTGCAAAGGAAGTCTAGGA |
| SEQ ID NO: 1165 | mm05453_Fcgr3 | TGGTGACACTGATGTGCGAA |
| SEQ ID NO: 1166 | mm05454_Fcgr3 | ATGCACACTCTGGAAGCCAA |
| SEQ ID NO: 1167 | mm05455_Fcgr3 | TGGTGAAACTGGACCCCCCA |
| SEQ ID NO: 1168 | mm05456_Fcgr3 | TGCTGCTCCAGACCCCTCAG |
| SEQ ID NO: 1169 | mm05457_Fcgrt | AAGAATCGGCAATTGGACTG |
| SEQ ID NO: 1170 | mm05458_Fcgrt | GGGCACTGAGGAATTATCCG |
| SEQ ID NO: 1171 | mm05459_Fcgrt | CGTGAGATGATACATCAGTG |
| SEQ ID NO: 1172 | mm05460_Fcgrt | AGGTGGCCTAGCAGTCGCTC |
| SEQ ID NO: 1173 | mm05465_Fcnb | CCGGCATTACCTACCCTGGG |
| SEQ ID NO: 1174 | mm05466_Fcnb | GGGACTGGACCTCATACAAG |
| SEQ ID NO: 1175 | mm05467_Fcnb | CTGAAGGTCCTAGATCTGGA |
| SEQ ID NO: 1176 | mm05468_Fcnb | ATGTCACACAGCACAGTCAG |
| SEQ ID NO: 1177 | mm05513_Fgf10 | TTTCTCACGATTGAGAAGAA |
| SEQ ID NO: 1178 | mm05514_Fgf10 | TGTCCTGGAGATAACATCAG |
| SEQ ID NO: 1179 | mm05515_Fgf10 | CCAGTGCGGGAAGGCATGTG |
| SEQ ID NO: 1180 | mm05516_Fgf10 | AGGAGAACAGCCTTCTCCAG |
| SEQ ID NO: 1181 | mm05537_Fgf17 | CTCTGCTGTCAAACACAGGT |
| SEQ ID NO: 1182 | mm05538_Fgf17 | GTGAATACCAGCTCTACAGC |
| SEQ ID NO: 1183 | mm05539_Fgf17 | TCGCATCTCTGCCACCGCAG |
| SEQ ID NO: 1184 | mm05540_Fgf17 | AACCAGTACGTGAGGGACCA |
| SEQ ID NO: 1185 | mm05565_Fgf8 | GGGAATGCACCTTACCGAAG |

TABLE 1-continued mmSurf sgRNA library sequences

| SEQ ID NO | id_gRNA Target | Sequence |
|---|---|---|
| SEQ ID NO: 1186 | mm05566_Fgf8 | ATGCTGTGTAAAATTAGGTG |
| SEQ ID NO: 1187 | mm05567_Fgf8 | CGAGTTCGCGGCGCAGAGAC |
| SEQ ID NO: 1188 | mm05568_Fgf8 | AGAGCTGGTAGGTCCGGATG |
| SEQ ID NO: 1189 | mm05573_Fgfbp1 | CTGGTGAACCCCAACGCACG |
| SEQ ID NO: 1190 | mm05574_Fgfbp1 | TTCTGGGCCTTCCCTAACGA |
| SEQ ID NO: 1191 | mm05575_Fgfbp1 | ACATCTAAATCTCTGACGCA |
| SEQ ID NO: 1192 | mm05576_Fgfbp1 | AACACAAGAAAACTCCTGAT |
| SEQ ID NO: 1193 | mm05577_Fgfr1 | TGGAGTTAATACCACCGACA |
| SEQ ID NO: 1194 | mm05578_Fgfr1 | GCATCGTGGAGAATGAGTAT |
| SEQ ID NO: 1195 | mm05579_Fgfr1 | TCTCCGAGATCAGATCCGAC |
| SEQ ID NO: 1196 | mm05580_Fgfr1 | TCTCGTGGCAGCTCCCAGCG |
| SEQ ID NO: 1197 | mm05581_Fgfr2 | CAACTCTAGCGATTCCCCGG |
| SEQ ID NO: 1198 | mm05582_Fgfr2 | GGAGACCCCTGCTAGCATCG |
| SEQ ID NO: 1199 | mm05583_Fgfr2 | GGTGCCACACCTAGAGACTC |
| SEQ ID NO: 1200 | mm05584_Fgfr2 | GGCCGCCGGTGTTAACACCA |
| SEQ ID NO: 1201 | mm05585_Fgfr3 | GTATAGTTGCCACGATCGGA |
| SEQ ID NO: 1202 | mm05586_Fgfr3 | GAGGCTGGCAGCGTGTACGC |
| SEQ ID NO: 1203 | mm05587_Fgfr3 | TGACAAGGACCTGTCGGACC |
| SEQ ID NO: 1204 | mm05588_Fgfr3 | TCTGTTACCTGTCGCTTAAG |
| SEQ ID NO: 1205 | mm05637_Smc2 | CCTCATGGAACATTGAGTGG |
| SEQ ID NO: 1206 | mm05638_Smc2 | ATGAAGAAGCTAAATTACGA |
| SEQ ID NO: 1207 | mm05639_Smc2 | CACCAAGGAACGCTCAGCTG |
| SEQ ID NO: 1208 | mm05640_Smc2 | TCATGAGCTTCAAATCCCAA |
| SEQ ID NO: 1209 | mm05673_Fkbp10 | GCTGGATGTCCACAACCCGA |
| SEQ ID NO: 1210 | mm05674_Fkbp10 | GCGGCCTACGCCCACAACGA |
| SEQ ID NO: 1211 | mm05675_Fkbp10 | TACAATACCTATGTCGGGCA |
| SEQ ID NO: 1212 | mm05676_Fkbp10 | GACCACGTCAAAATAGAGGG |
| SEQ ID NO: 1213 | mm05737_Flt1 | AGTGATGGAGTAATCTTGAG |
| SEQ ID NO: 1214 | mm05738_Flt1 | CCTCGTATTGAGCTCCGTGG |
| SEQ ID NO: 1215 | mm05739_Flt1 | CTTACCATACACATGCACGG |
| SEQ ID NO: 1216 | mm05740_Flt1 | TCTATTGTAGGCAAATCGCT |
| SEQ ID NO: 1217 | mm05741_Flt3 | CAGTACTCTAAATATGAGTG |
| SEQ ID NO: 1218 | mm05742_Flt3 | CCCACTTTCAGGAATAACTG |
| SEQ ID NO: 1219 | mm05743_Flt3 | TCCACGTGCATCGGATTCGT |
| SEQ ID NO: 1220 | mm05744_Flt3 | CTATGAATATGACCTTAAGT |
| SEQ ID NO: 1221 | mm05745_Flt3l | TAAAGATTACCCAGTCACTG |
| SEQ ID NO: 1222 | mm05746_Flt3l | GCTAACCTGGAAGGTACATG |
| SEQ ID NO: 1223 | mm05747_Flt3l | GCACCGAGAGAAATTCTGGC |

TABLE 1-continued mmSurf sgRNA library sequences

| SEQ ID NO | id_gRNA Target | Sequence |
|---|---|---|
| SEQ ID NO: 1224 | mm05748_Flt3l | CAGTTGCTCTATCCAGCGCT |
| SEQ ID NO: 1225 | mm05749_Flt4 | AGCTGTCCAGACTCTCGATG |
| SEQ ID NO: 1226 | mm05750_Flt4 | CAGTTTGAATATCCCCCGAG |
| SEQ ID NO: 1227 | mm05751_Flt4 | CTCACCTCTTACAAACACAT |
| SEQ ID NO: 1228 | mm05752_Flt4 | GGGTCTACACTCTCGCCCTG |
| SEQ ID NO: 1229 | mm05765_Fmod | GAGTTATAACCACCTTCGGA |
| SEQ ID NO: 1230 | mm05766_Fmod | ACAATGAGATCCAGGAAGTG |
| SEQ ID NO: 1231 | mm05767_Fmod | GGACCCGTGAGATCTGGTTG |
| SEQ ID NO: 1232 | mm05768_Fmod | TGCCATGTAGAGCGACCCAG |
| SEQ ID NO: 1233 | mm05773_Fn1 | CATTCCACCTTACAACACCG |
| SEQ ID NO: 1234 | mm05774_Fn1 | TGGGACGTCCTACGTCGTGG |
| SEQ ID NO: 1235 | mm05775_Fn1 | TTATGGTGGCAATTCAAACG |
| SEQ ID NO: 1236 | mm05776_Fn1 | GTGAATCGCAGATCCGTGGG |
| SEQ ID NO: 1237 | mm05789_Folr1 | GACAATTTACACGACCAGGT |
| SEQ ID NO: 1238 | mm05790_Folr1 | AGTTCGGGAACACTCATAG |
| SEQ ID NO: 1239 | mm05791_Folr1 | CCAGTTGAACCGGTACAGGT |
| SEQ ID NO: 1240 | mm05792_Folr1 | CTCCACCTACTCCTTACCCG |
| SEQ ID NO: 1241 | mm05793_Folr2 | CATCCATGCAAACGTTGAGT |
| SEQ ID NO: 1242 | mm05794_Folr2 | CTCCCGTCTGTACTTCAACT |
| SEQ ID NO: 1243 | mm05795_Folr2 | AACGCTCTTTACGCCAACTC |
| SEQ ID NO: 1244 | mm05796_Folr2 | GAGAGACTGGCATAAAGGCT |
| SEQ ID NO: 1245 | mm05857_Fshr | TCTTACAGATATCGGAGACT |
| SEQ ID NO: 1246 | mm05858_Fshr | ATCCATGTGAAGACATCATG |
| SEQ ID NO: 1247 | mm05859_Fshr | AGGTTACACATAAGGAACCG |
| SEQ ID NO: 1248 | mm05860_Fshr | ACAGTTCAATGGCGTTCCGG |
| SEQ ID NO: 1249 | mm05873_Fstl1 | CCTGGATCTTGGATCCAGTG |
| SEQ ID NO: 1250 | mm05874_Fstl1 | ACCGGTCACCTACCTCGCCG |
| SEQ ID NO: 1251 | mm05875_Fstl1 | ACCTCAATGCAGAGGCACGT |
| SEQ ID NO: 1252 | mm05876_Fstl1 | GGCGCCGTCGGAGCTCATCG |
| SEQ ID NO: 1253 | mm05901_Fut4 | GCGTCCACGAGTGGCCACCG |
| SEQ ID NO: 1254 | mm05902_Fut4 | CGCGTGTTCGACGACCAGGA |
| SEQ ID NO: 1255 | mm05903_Fut4 | AATCGCCCTCCCATACTCCA |
| SEQ ID NO: 1256 | mm05904_Fut4 | GCTGTTCCACCACCGCGACC |
| SEQ ID NO: 1257 | mm05933_Fzd1 | AGCCCGCTAGCCCAACGCCG |
| SEQ ID NO: 1258 | mm05934_Fzd1 | ACCAGTAATCCGCAGCACGG |
| SEQ ID NO: 1259 | mm05935_Fzd1 | TCACGTACCTAGTGGACATG |
| SEQ ID NO: 1260 | mm05936_Fzd1 | GCTGGGCCACACGAATCAGG |
| SEQ ID NO: 1261 | mm05941_Fzd4 | TTGGCACATAAACCGAACAA |

TABLE 1-continued mmSurf sgRNA library sequences

| SEQ ID NO | id_gRNA Target | Sequence |
|---|---|---|
| SEQ ID NO: 1262 | mm05942_Fzd4 | GGTTCTGGCACATGGCGATG |
| SEQ ID NO: 1263 | mm05943_Fzd4 | ACATACTGAGAAATATGATG |
| SEQ ID NO: 1264 | mm05944_Fzd4 | CTGGTCCTTCCATGCACATG |
| SEQ ID NO: 1265 | mm05945_Fzd5 | CCAGTTCAACCATGACACGC |
| SEQ ID NO: 1266 | mm05946_Fzd5 | GGAATCGTTCCATGTCAATG |
| SEQ ID NO: 1267 | mm05947_Fzd5 | GTCACACCCACTCTACAACA |
| SEQ ID NO: 1268 | mm05948_Fzd5 | GTACTGTGCATAACCTGCGA |
| SEQ ID NO: 1269 | mm05961_Fzd9 | CCCGCACGCACTCTGTATGG |
| SEQ ID NO: 1270 | mm05962_Fzd9 | GACCTGGTCGGTGCACATTG |
| SEQ ID NO: 1271 | mm05963_Fzd9 | GAGTGTGGCATGCGACCAGG |
| SEQ ID NO: 1272 | mm05964_Fzd9 | TACTTCCACATGGCAGCGTG |
| SEQ ID NO: 1273 | mm05997_Gaa | ACCATCCCCACTTTACAGCG |
| SEQ ID NO: 1274 | mm05998_Gaa | GAGTTACAGGCCCTACGACG |
| SEQ ID NO: 1275 | mm05999_Gaa | CTAACCTGGAGGTCAACGGG |
| SEQ ID NO: 1276 | mm06000_Gaa | ACCTGAGCTCTACAGAGTCG |
| SEQ ID NO: 1277 | mm06025_Gabra3 | TTTGTGAAACAAGATATTGG |
| SEQ ID NO: 1278 | mm06026_Gabra3 | CCATATCAGTGTCTGACACA |
| SEQ ID NO: 1279 | mm06027_Gabra3 | CCACAATGGTAAAAAATCAG |
| SEQ ID NO: 1280 | mm06028_Gabra3 | AGTCATGATACATGGCAAGT |
| SEQ ID NO: 1281 | mm06033_Gabra6 | GGAAGTTAACCAATCTCATG |
| SEQ ID NO: 1282 | mm06034_Gabra6 | GGGACTTCTACTGAGTAAAG |
| SEQ ID NO: 1283 | mm06035_Gabra6 | TCTACTCTGAAAATGTCAGT |
| SEQ ID NO: 1284 | mm06036_Gabra6 | TTAAGCTCAGAATCTCAGCA |
| SEQ ID NO: 1285 | mm06045_Gabrb3 | CCTCACGCTTGACAATCGAG |
| SEQ ID NO: 1286 | mm06046_Gabrb3 | CCTGGTAGATGGCTACACTA |
| SEQ ID NO: 1287 | mm06047_Gabrb3 | CGCCTGAGACCCGACTTCGG |
| SEQ ID NO: 1288 | mm06048_Gabrb3 | CGAAAACTCAATGAAAGTCG |
| SEQ ID NO: 1289 | mm06057_Gabrg1 | ACTTATGCTCAACAGCAACA |
| SEQ ID NO: 1290 | mm06058_Gabrg1 | CATTCCGTGTATTCTAACAG |
| SEQ ID NO: 1291 | mm06059_Gabrg1 | TTTAACTATGAACAAAACAT |
| SEQ ID NO: 1292 | mm06060_Gabrg1 | ACATCTGTTTCAATCACTGT |
| SEQ ID NO: 1293 | mm06061_Gabrg2 | AACAAACTTCGACCTGACAT |
| SEQ ID NO: 1294 | mm06062_Gabrg2 | GGTTGAATAGCAATATGGTG |
| SEQ ID NO: 1295 | mm06063_Gabrg2 | TCCTGCTATCGCTCTACCCA |
| SEQ ID NO: 1296 | mm06064_Gabrg2 | TACAACTGGAGAACTCCAGG |
| SEQ ID NO: 1297 | mm06077_Slc6a12 | CTGAATCACTCATCGGCCAG |
| SEQ ID NO: 1298 | mm06078_Slc6a12 | TCTTGGGCCTCATGTAGGTG |
| SEQ ID NO: 1299 | mm06079_Slc6a12 | GATGGAGTTTGTGCTGTCAG |

TABLE 1-continued mmSurf sgRNA library sequences

| SEQ ID NO | id_gRNA Target | Sequence |
|---|---|---|
| SEQ ID NO: 1300 | mm06080_Slc6a12 | GGGAATACCCATTTCTGAAG |
| SEQ ID NO: 1301 | mm06101_B4galnt1 | TCTAGCAGATCGAGTCTCGG |
| SEQ ID NO: 1302 | mm06102_B4galnt1 | TGACCGTAGGGTAAAAGCGT |
| SEQ ID NO: 1303 | mm06103_B4galnt1 | GTTCGCAGGTCGGAACCTGG |
| SEQ ID NO: 1304 | mm06104_B4galnt1 | TGCAGTTGTGAATCCAAGGG |
| SEQ ID NO: 1305 | mm06109_Galnt1 | CTAGTGCAGAAACCTCATGA |
| SEQ ID NO: 1306 | mm06110_Galnt1 | ATAGTGACATGCTCCCATGT |
| SEQ ID NO: 1307 | mm06111_Galnt1 | TGACACTTTCGAGTACATGG |
| SEQ ID NO: 1308 | mm06112_Galnt1 | TAACCTTCCTACAACAAGTG |
| SEQ ID NO: 1309 | mm06141_Gapdh | GCTGTGGCGTGATGGCCGTG |
| SEQ ID NO: 1310 | mm06142_Gapdh | AAACAGGCCCACTTGAAGGG |
| SEQ ID NO: 1311 | mm06143_Gapdh | TGCCATTTGCAGTGGCAAAG |
| SEQ ID NO: 1312 | mm06144_Gapdh | GGCCGGTGCTGAGTATGTCG |
| SEQ ID NO: 1313 | mm06145_Gapdhs | GCCAGCTAGAGAGCTGACAG |
| SEQ ID NO: 1314 | mm06146_Gapdhs | GGTTGAGGATCCACCACCCA |
| SEQ ID NO: 1315 | mm06147_Gapdhs | AACTTGTCTGGCTCTATCTG |
| SEQ ID NO: 1316 | mm06148_Gapdhs | CTCTATAGGGAATCCCTACG |
| SEQ ID NO: 1317 | mm06149_Gart | ACTCGTAGTTGTCGGACCAG |
| SEQ ID NO: 1318 | mm06150_Gart | TGACGGCTTCAGTTGTACTG |
| SEQ ID NO: 1319 | mm06151_Gart | GCTAGAAAGGATCACCGAAG |
| SEQ ID NO: 1320 | mm06152_Gart | GGCAAAGTAGTGACCAGCGG |
| SEQ ID NO: 1321 | mm06197_Gba | CGTTACGAGAGCACTCGACG |
| SEQ ID NO: 1322 | mm06198_Gba | GGATAACTGGAAGTCGTTAG |
| SEQ ID NO: 1323 | mm06199_Gba | GACTGGCAAAGAGTGAAATG |
| SEQ ID NO: 1324 | mm06200_Gba | CGGAGAATGAACCTACAGCA |
| SEQ ID NO: 1325 | mm06301_Gdf3 | CACGTAGCATAAGTCCTGCG |
| SEQ ID NO: 1326 | mm06302_Gdf3 | CGCAGGTTATAGTAGGACCT |
| SEQ ID NO: 1327 | mm06303_Gdf3 | TCAAAGAGGACAGATACTCC |
| SEQ ID NO: 1328 | mm06304_Gdf3 | CAATCTGCCCACCTTAGGGT |
| SEQ ID NO: 1329 | mm06337_Gfap | AGAGATTCGCACTCAATACG |
| SEQ ID NO: 1330 | mm06338_Gfap | TCCAAGATGAAACCAACCTG |
| SEQ ID NO: 1331 | mm06339_Gfap | TGCGGGACGCAGCGTCTGTG |
| SEQ ID NO: 1332 | mm06340_Gfap | TCTCGATGTAGCTAGCAAAG |
| SEQ ID NO: 1333 | mm06357_Gfra1 | GCACCAAGTACCGCACACTG |
| SEQ ID NO: 1334 | mm06358_Gfra1 | CTTACCAATCAGTCCCGAGT |
| SEQ ID NO: 1335 | mm06359_Gfra1 | CATATGGGGAATCTTCCAGT |
| SEQ ID NO: 1336 | mm06360_Gfra1 | TCAAGGCCTCCATAGCGCTG |
| SEQ ID NO: 1337 | mm06361_Gfra2 | ATGCCTGGTAGTTGTCCGCA |

TABLE 1-continued mmSurf sgRNA library sequences

| SEQ ID NO | id_gRNA Target | Sequence |
|---|---|---|
| SEQ ID NO: 1338 | mm06362_Gfra2 | TCTATTGGAGCATCCATCTG |
| SEQ ID NO: 1339 | mm06363_Gfra2 | GGCCAATAAGGAGTGCCAGG |
| SEQ ID NO: 1340 | mm06364_Gfra2 | CCGGGCCAATGAGCTGTGTG |
| SEQ ID NO: 1341 | mm06365_Gfra3 | CCGCAGATCCAGGCAATTGG |
| SEQ ID NO: 1342 | mm06366_Gfra3 | GGTCCAATAAATGTCCAGAC |
| SEQ ID NO: 1343 | mm06367_Gfra3 | GACATGGCAGACTCCTCTAA |
| SEQ ID NO: 1344 | mm06368_Gfra3 | CCTGCGCAAGGCCTACGGGG |
| SEQ ID NO: 1345 | mm06373_Ggh | AGATTCAGGTTATTCCCGAG |
| SEQ ID NO: 1346 | mm06374_Ggh | AGACTCTATATACTTCACAT |
| SEQ ID NO: 1347 | mm06375_Ggh | CCTACAACCATGGCTCCGAG |
| SEQ ID NO: 1348 | mm06376_Ggh | CATGTGATACCTTCACAGAG |
| SEQ ID NO: 1349 | mm06385_B4galt1 | GGCCAGAGAGGTAATAGACG |
| SEQ ID NO: 1350 | mm06386_B4galt1 | CAGGGCTGGAGTCGAGACCC |
| SEQ ID NO: 1351 | mm06387_B4galt1 | GCTCAATATTGGCTTTCAAG |
| SEQ ID NO: 1352 | mm06388_B4galt1 | TGATGTGGACCTCATTCCGA |
| SEQ ID NO: 1353 | mm06389_Ggt1 | ACTGACGTATCACCGTATCG |
| SEQ ID NO: 1354 | mm06390_Ggt1 | CGTACAGGGTCGCATCACCG |
| SEQ ID NO: 1355 | mm06391_Ggt1 | GAATTCAGGCTCATAGTAGG |
| SEQ ID NO: 1356 | mm06392_Ggt1 | CGACCACGTGTACTCCAGGG |
| SEQ ID NO: 1357 | mm06397_Ghr | ATTGATTCTTTGCAGAACTG |
| SEQ ID NO: 1358 | mm06398_Ghr | GCTTCCAATATGTTCGTCTG |
| SEQ ID NO: 1359 | mm06399_Ghr | AATTGCTCATGAATGGACCC |
| SEQ ID NO: 1360 | mm06400_Ghr | GTCCAGTTGAGGCCAATGGG |
| SEQ ID NO: 1361 | mm06405_Ghrhr | ACGTACCAGTGCATAGCACG |
| SEQ ID NO: 1362 | mm06406_Ghrhr | AGGTGGCAAACAGCTGCGTG |
| SEQ ID NO: 1363 | mm06407_Ghrhr | GATGGCAATAGCCACGCAGA |
| SEQ ID NO: 1364 | mm06408_Ghrhr | CATGGTGGCCAAATGTGAGA |
| SEQ ID NO: 1365 | mm06489_Ostm1 | CATCAGCCGAAACATCGGGG |
| SEQ ID NO: 1366 | mm06490_Ostm1 | TTGCCTAACAAACAATGGTG |
| SEQ ID NO: 1367 | mm06491_Ostm1 | AGCGCTGCGCACCATACAGG |
| SEQ ID NO: 1368 | mm06492_Ostm1 | CAGAATGCAGATAGTTCTCA |
| SEQ ID NO: 1369 | mm06521_Glp1r | AGAAATGGAGAGAATACCGG |
| SEQ ID NO: 1370 | mm06522_Glp1r | CCTGTACATTATCTACACAG |
| SEQ ID NO: 1371 | mm06523_Glp1r | ACATTCACGAAGGAACCTGG |
| SEQ ID NO: 1372 | mm06524_Glp1r | CACTCCGACAGGTCCCTCCA |
| SEQ ID NO: 1373 | mm06525_Glra1 | CCACTTCCACGAAATCACCA |
| SEQ ID NO: 1374 | mm06526_Glra1 | TTCCATCGCTGAGACAACCA |
| SEQ ID NO: 1375 | mm06527_Glra1 | ATGCTGCACCAGCTCGTGTG |

TABLE 1-continued mmSurf sgRNA library sequences

| SEQ ID NO | id_gRNA Target | Sequence |
|---|---|---|
| SEQ ID NO: 1376 | mm06528_Glra1 | TCCTGGATAAGCTCATGGGG |
| SEQ ID NO: 1377 | mm06533_Glrb | AGGTTACTACACTTGTGTGG |
| SEQ ID NO: 1378 | mm06534_Glrb | GGAAACAGAGTTAAGTCTAG |
| SEQ ID NO: 1379 | mm06535_Glrb | CACAGCGTACTCCACGAGGG |
| SEQ ID NO: 1380 | mm06536_Glrb | CCACCATGTATAAGTGCTTG |
| SEQ ID NO: 1381 | mm06553_Slc6a9 | ATACCTCTGCTATCGCAACG |
| SEQ ID NO: 1382 | mm06554_Slc6a9 | GTAGTACATGATACCCGTGA |
| SEQ ID NO: 1383 | mm06555_Slc6a9 | ATGGTGGTGTCCACATACAT |
| SEQ ID NO: 1384 | mm06556_Slc6a9 | TGTGCTACCAGCGTCTACGC |
| SEQ ID NO: 1385 | mm06633_Gnb2l1 | GATAGGGTTGCTGCTGTTCG |
| SEQ ID NO: 1386 | mm06634_Gnb2l1 | AAGCTAAAGACCAACCACAT |
| SEQ ID NO: 1387 | mm06635_Gnb2l1 | TGTCTGCAAGTACACGGTCC |
| SEQ ID NO: 1388 | mm06636_Gnb2l1 | CTTGCCTCCAGAAGCACAGA |
| SEQ ID NO: 1389 | mm06669_Bscl2 | GTTTCATGTTATACCAGAGG |
| SEQ ID NO: 1390 | mm06670_Bscl2 | CCTGGGCCCACAGTAAGGCG |
| SEQ ID NO: 1391 | mm06671_Bscl2 | CAAAGGATCAGACAAAGACG |
| SEQ ID NO: 1392 | mm06672_Bscl2 | AATGTCTCACTGGCTAAGAG |
| SEQ ID NO: 1393 | mm06713_Got2 | TGGAGGTCCCATTTCAACAT |
| SEQ ID NO: 1394 | mm06714_Got2 | TTTCTGCCCAAACCATCCTG |
| SEQ ID NO: 1395 | mm06715_Got2 | CATCCTCCTCACCTTCACCA |
| SEQ ID NO: 1396 | mm06716_Got2 | AGCTCACCTTCCGGACACTG |
| SEQ ID NO: 1397 | mm06717_Gp1ba | CAAGGACACAACTCCTAACG |
| SEQ ID NO: 1398 | mm06718_Gp1ba | TGGCTTCGCACAATACCAAA |
| SEQ ID NO: 1399 | mm06719_Gp1ba | CACCTGGGCGAGAACCAACT |
| SEQ ID NO: 1400 | mm06720_Gp1ba | TGCAGGCAATGCCCATCCTA |
| SEQ ID NO: 1401 | mm06725_Lrp2 | GATATGACCGTTGTTCGACG |
| SEQ ID NO: 1402 | mm06726_Lrp2 | TGGATGGCAATTATTCCGAG |
| SEQ ID NO: 1403 | mm06727_Lrp2 | GTATCCTATTGGACACACGC |
| SEQ ID NO: 1404 | mm06728_Lrp2 | TGATAGGCGCAACGACTGTG |
| SEQ ID NO: 1405 | mm06729_Pdpn | TACCAACGCAGAGAGAGCGT |
| SEQ ID NO: 1406 | mm06730_Pdpn | GAAGATGATATTGTGACCCC |
| SEQ ID NO: 1407 | mm06731_Pdpn | AGTGGTGACTAGCCACTCTG |
| SEQ ID NO: 1408 | mm06732_Pdpn | TTCTCTGTGATCATGGTCTG |
| SEQ ID NO: 1409 | mm06733_Gp49a | AATGAATCTGCCAAATAGTG |
| SEQ ID NO: 1410 | mm06734_Gp49a | AGAACAAAAGTAGCATGGGT |
| SEQ ID NO: 1411 | mm06735_Gp49a | GTGAGTCCAGGGTCCACGAG |
| SEQ ID NO: 1412 | mm06736_Gp49a | AAAGGATATGGAAACTCCAG |
| SEQ ID NO: 1413 | mm06737_Lilrb4 | TTTATACAGATGATAATACT |

TABLE 1-continued mmSurf sgRNA library sequences

| SEQ ID NO | id_gRNA Target | Sequence |
|---|---|---|
| SEQ ID NO: 1414 | mm06738_Lilrb4 | AGAACAAAAGTAGCATAGGA |
| SEQ ID NO: 1415 | mm06739_Lilrb4 | CTGATCCAGGAAGGAAAGCA |
| SEQ ID NO: 1416 | mm06740_Lilrb4 | AGCATGACAACCTCATATGC |
| SEQ ID NO: 1417 | mm06741_Gp5 | TCTGTTCGAGAACCCCTGG |
| SEQ ID NO: 1418 | mm06742_Gp5 | ATCTTATCCAGGATCGCACG |
| SEQ ID NO: 1419 | mm06743_Gp5 | GAATGGACCAGGGCATATTG |
| SEQ ID NO: 1420 | mm06744_Gp5 | GAGGTTTCCGGATAGAGTCA |
| SEQ ID NO: 1421 | mm06749_Gpc1 | GCTGCGCCTCTACTACCGTG |
| SEQ ID NO: 1422 | mm06750_Gpc1 | CCCGAGGAGAAGCGTCGCCG |
| SEQ ID NO: 1423 | mm06751_Gpc1 | GCACATTTCGGCAATAGTCG |
| SEQ ID NO: 1424 | mm06752_Gpc1 | CCGCAGGCGCAGTTCTCGAG |
| SEQ ID NO: 1425 | mm06753_Gpc3 | TTGCGGTGGTTATTGCAATG |
| SEQ ID NO: 1426 | mm06754_Gpc3 | CTTGGGTTCTGATATCAACG |
| SEQ ID NO: 1427 | mm06755_Gpc3 | GGTCACGTCTTGCTCCTCGG |
| SEQ ID NO: 1428 | mm06756_Gpc3 | CTTACTAAACTTGAGGTGGT |
| SEQ ID NO: 1429 | mm06757_Gpc4 | CCCTCTATGAGATCAACGGT |
| SEQ ID NO: 1430 | mm06758_Gpc4 | TATTGCTCAAACATCATGCG |
| SEQ ID NO: 1431 | mm06759_Gpc4 | TGTAGTAAGCAAAGTGTCCG |
| SEQ ID NO: 1432 | mm06760_Gpc4 | TAAAGATGATTTCAAAACCG |
| SEQ ID NO: 1433 | mm06765_S1pr2 | AATCAGCGATATCAGCCAAG |
| SEQ ID NO: 1434 | mm06766_S1pr2 | CATCGCCATCGAGAGACAAG |
| SEQ ID NO: 1435 | mm06767_S1pr2 | GGAACACTACAATTACACCA |
| SEQ ID NO: 1436 | mm06768_S1pr2 | CAGAAGATTCTCCACCACGA |
| SEQ ID NO: 1437 | mm06773_Lpar1 | TCTTTGGCTATGTTCGCCAG |
| SEQ ID NO: 1438 | mm06774_Lpar1 | GGAGACTGACTGTTAGCACG |
| SEQ ID NO: 1439 | mm06775_Lpar1 | AAGTAGGAGTCACTGTAGAG |
| SEQ ID NO: 1440 | mm06776_Lpar1 | ACGAATGAGCAACCGGCGCG |
| SEQ ID NO: 1441 | mm06777_Cmklr1 | ACTCGCAAGTAGTTTCCACA |
| SEQ ID NO: 1442 | mm06778_Cmklr1 | GGCCGTTGCCTAGGAGACCG |
| SEQ ID NO: 1443 | mm06779_Cmklr1 | GGAGGAGGCGAGTCCGTGGG |
| SEQ ID NO: 1444 | mm06780_Cmklr1 | AGACGCTGGTGTACATGTTG |
| SEQ ID NO: 1445 | mm06797_Gpm6b | GTGTTGCTCAAGAATTGCCA |
| SEQ ID NO: 1446 | mm06798_Gpm6b | CCACTCCCAGCACATAGGTG |
| SEQ ID NO: 1447 | mm06799_Gpm6b | TACTCACACTTCACTCAGCA |
| SEQ ID NO: 1448 | mm06800_Gpm6b | ACAGATCTGCTCCACACCCG |
| SEQ ID NO: 1449 | mm06861_Gsr | GGCTATGCAACATTCGCAGA |
| SEQ ID NO: 1450 | mm06862_Gsr | CGGCCCCACGATGACGCTG |
| SEQ ID NO: 1451 | mm06863_Gsr | GCTGTGAGGGTAAATTCAGT |

TABLE 1-continued mmSurf sgRNA library sequences

| SEQ ID NO | id_gRNA Target | Sequence |
|---|---|---|
| SEQ ID NO: 1452 | mm06864_Gsr | AACATCTGGAATCATGGTCG |
| SEQ ID NO: 1453 | mm06913_Gria1 | ATGTTCACAATATCGATCTG |
| SEQ ID NO: 1454 | mm06914_Gria1 | CGTCGCTGACAATCTCAAGT |
| SEQ ID NO: 1455 | mm06915_Gria1 | TGTCAACATTCTAACAACCA |
| SEQ ID NO: 1456 | mm06916_Gria1 | AGTTTAACGAGAAAGGGCGC |
| SEQ ID NO: 1457 | mm06917_Gria2 | TGTCAGTCTGAACTCCGAAG |
| SEQ ID NO: 1458 | mm06918_Gria2 | TTGGACAGCATCATAAGTCA |
| SEQ ID NO: 1459 | mm06919_Gria2 | AGCTCAAAACAAATGGACCC |
| SEQ ID NO: 1460 | mm06920_Gria2 | CAGGTGACTGCTATCAATGT |
| SEQ ID NO: 1461 | mm06921_Gria4 | TGCATACATTGGTGTCAGCG |
| SEQ ID NO: 1462 | mm06922_Gria4 | GCATGTCAGTGCGATATGTG |
| SEQ ID NO: 1463 | mm06923_Gria4 | ACGTAGAGTTAATTACACAA |
| SEQ ID NO: 1464 | mm06924_Gria4 | TGCACCTCTGACAATCACGT |
| SEQ ID NO: 1465 | mm06925_Grid1 | GGCCAATAATCCGTTCCAGG |
| SEQ ID NO: 1466 | mm06926_Grid1 | GAAACTCCATAACCCCTGTG |
| SEQ ID NO: 1467 | mm06927_Grid1 | ATTCAAATATGAGATATACC |
| SEQ ID NO: 1468 | mm06928_Grid1 | GGACCAGATCCAGGATCTCG |
| SEQ ID NO: 1469 | mm06929_Grid2 | GATCCCATTTGCAATCGTGG |
| SEQ ID NO: 1470 | mm06930_Grid2 | AAACTGGAGAACAACATGCG |
| SEQ ID NO: 1471 | mm06931_Grid2 | GTAATAATCCTAGATATCCG |
| SEQ ID NO: 1472 | mm06932_Grid2 | CAAATATGGAAGCCCACAAG |
| SEQ ID NO: 1473 | mm06933_Grik2 | AAGCGAGTCCCAAAGCGCCA |
| SEQ ID NO: 1474 | mm06934_Grik2 | ACAGTGGCGTAAATATGACA |
| SEQ ID NO: 1475 | mm06935_Grik2 | CGAACATAGGTAATAGCCAG |
| SEQ ID NO: 1476 | mm06936_Grik2 | CTGTGTATCATATGTTAACG |
| SEQ ID NO: 1477 | mm06945_Grin1 | AACATCACTGATCCACCGCG |
| SEQ ID NO: 1478 | mm06946_Grin1 | GTGGACATCTGGTATCCTCG |
| SEQ ID NO: 1479 | mm06947_Grin1 | CTGTCCTATGACAACAAGCG |
| SEQ ID NO: 1480 | mm06948_Grin1 | AACCAGGCCAATAAGCGACA |
| SEQ ID NO: 1481 | mm06949_Grin2a | ATGGTAAAAGAAGGCCCATG |
| SEQ ID NO: 1482 | mm06950_Grin2a | AGAAGAAATCGTAGCCGGTG |
| SEQ ID NO: 1483 | mm06951_Grin2a | ATCTTGACAAACTTCCGACA |
| SEQ ID NO: 1484 | mm06952_Grin2a | TGTGTGCGACCTCATGTCCG |
| SEQ ID NO: 1485 | mm06953_Grin2b | TATCCTACGCTTGCTCCGAA |
| SEQ ID NO: 1486 | mm06954_Grin2b | GGCACCGGTTGTAACCCACA |
| SEQ ID NO: 1487 | mm06955_Grin2b | ACATCATGGAAGAATACGAC |
| SEQ ID NO: 1488 | mm06956_Grin2b | TGACTGGCTACGGCTACACA |
| SEQ ID NO: 1489 | mm06977_Grn | CCTATCCAAGAACTACACCA |

TABLE 1-continued mmSurf sgRNA library sequences

| SEQ ID NO | id_gRNA Target | Sequence |
|---|---|---|
| SEQ ID NO: 1490 | mm06978_Grn | CCCTGCACAAAAGACCAACA |
| SEQ ID NO: 1491 | mm06979_Grn | GACACTGGACAGCACCCAAG |
| SEQ ID NO: 1492 | mm06980_Grn | CACCTAGTGAAGTCATCACA |
| SEQ ID NO: 1493 | mm06985_Pdia3 | CTTCACCAGAGACTCAATGT |
| SEQ ID NO: 1494 | mm06986_Pdia3 | ATAGTCCACATCATAGTAAG |
| SEQ ID NO: 1495 | mm06987_Pdia3 | CTGCTACTTACCCACCACTG |
| SEQ ID NO: 1496 | mm06988_Pdia3 | AAACACCTGTAATAAGTATG |
| SEQ ID NO: 1497 | mm06989_Hspa5 | TGTGTTCAAGAACGGCCGCG |
| SEQ ID NO: 1498 | mm06990_Hspa5 | CCGTGGCATAAACCCCGATG |
| SEQ ID NO: 1499 | mm06991_Hspa5 | TGTGCAGAAACTCCGGCGTG |
| SEQ ID NO: 1500 | mm06992_Hspa5 | CATTCCAAGTGCGTCCGATG |
| SEQ ID NO: 1501 | mm07157_Gypa | TCTTCAAATAACCACTCCTG |
| SEQ ID NO: 1502 | mm07158_Gypa | TCAGCAACAATGTCAACACC |
| SEQ ID NO: 1503 | mm07159_Gypa | CATATCAACATACCTAGTGC |
| SEQ ID NO: 1504 | mm07160_Gypa | ACGCAGCAGACACTTCAGTA |
| SEQ ID NO: 1505 | mm07165_Gzma | CAAGAACTTACACGTTACAG |
| SEQ ID NO: 1506 | mm07166_Gzma | ATGATGAATATACACGTGAG |
| SEQ ID NO: 1507 | mm07167_Gzma | GCCATATACGGTCTTGAGTG |
| SEQ ID NO: 1508 | mm07168_Gzma | GATGCCGAGTAGCAGGATGG |
| SEQ ID NO: 1509 | mm07197_H13 | GGTATTCGGCACCAACGTGA |
| SEQ ID NO: 1510 | mm07198_H13 | CCCCAGCCAACGGCACGACG |
| SEQ ID NO: 1511 | mm07199_H13 | GAAAAAACTTATTCATGAAG |
| SEQ ID NO: 1512 | mm07200_H13 | TGAGTTTGACACTAAGGACC |
| SEQ ID NO: 1513 | mm07201_Hist1h1d | TCTTCAGCCCGAGCTTGATG |
| SEQ ID NO: 1514 | mm07202_Hist1h1d | TTCCGGTGAGGCTAAGCCCA |
| SEQ ID NO: 1515 | mm07203_Hist1h1d | AGAAGACCGGCGCCGCTGCT |
| SEQ ID NO: 1516 | mm07204_Hist1h1d | TGTCTTCTCCACAGGTGCAG |
| SEQ ID NO: 1517 | mm07209_H2-Aa | AATCCATCAGCCGACCACGT |
| SEQ ID NO: 1518 | mm07210_H2-Aa | GCTGTAGTAAAACACAACTT |
| SEQ ID NO: 1519 | mm07211_H2-Aa | AATTCCACCCCAGCTACCAA |
| SEQ ID NO: 1520 | mm07212_H2-Aa | AATAGCAAGTCAGTCGCAGA |
| SEQ ID NO: 1521 | mm07213_H2-Ab1 | GGTGTGCAGACACAACTACG |
| SEQ ID NO: 1522 | mm07214_H2-Ab1 | CAGATACATCTACAACCGGG |
| SEQ ID NO: 1523 | mm07215_H2-Ab1 | TCGTATGCGCTGCGTCCCGT |
| SEQ ID NO: 1524 | mm07216_H2-Ab1 | AGCAGACCGAGAGTGTTGTGG |
| SEQ ID NO: 1525 | mm07217_H2-D1 | GGCCCCGACTCAGACCCGCG |
| SEQ ID NO: 1526 | mm07218_H2-D1 | CGACGCAAGTGGGAGCAGAG |
| SEQ ID NO: 1527 | mm07219_H2-D1 | TAGCCGACAGAGATGTACCG |

TABLE 1-continued mmSurf sgRNA library sequences

| SEQ ID NO | id_gRNA Target | Sequence |
|---|---|---|
| SEQ ID NO: 1528 | mm07220_H2-D1 | GTGAGCCTGAGGAACCTGCT |
| SEQ ID NO: 1529 | mm07241_H2-M2 | ATAGCCAACAGTCATGTAGT |
| SEQ ID NO: 1530 | mm07242_H2-M2 | AGAGTGGGAGGCAACTAATG |
| SEQ ID NO: 1531 | mm07243_H2-M2 | CAGGTTCTCACACCATCCAA |
| SEQ ID NO: 1532 | mm07244_H2-M2 | TGCGATGTCGAAGTACCGCA |
| SEQ ID NO: 1533 | mm07245_H2-M3 | ACTGCGCTATTTCCACACTG |
| SEQ ID NO: 1534 | mm07246_H2-M3 | ATAGCATTGAGGAAATTCCG |
| SEQ ID NO: 1535 | mm07247_H2-M3 | AAAGTGCCAGAGCAAACCTT |
| SEQ ID NO: 1536 | mm07248_H2-M3 | GGAAAGACCAGAGTACTGGA |
| SEQ ID NO: 1537 | mm07253_H2-DMa | GTTTGGCAAGCCCAACACGT |
| SEQ ID NO: 1538 | mm07254_H2-DMa | ATAGAGTGTGCCGGAATGTG |
| SEQ ID NO: 1539 | mm07255_H2-DMa | AGGACGGGATTCCCAACATA |
| SEQ ID NO: 1540 | mm07256_H2-DMa | TCTGCAAAGTCAGGCAGTCG |
| SEQ ID NO: 1541 | mm07273_H2-Q1 | GCTGCGGTATTTCGAGACCT |
| SEQ ID NO: 1542 | mm07274_H2-Q1 | TCAGATGGGCGCCTTCAAAG |
| SEQ ID NO: 1543 | mm07275_H2-Q1 | AGTATTGGGAACGGAACACA |
| SEQ ID NO: 1544 | mm07276_H2-Q1 | GAAACACAGGACCTACCTGG |
| SEQ ID NO: 1545 | mm07277_H2-Q10 | TACCTGCAATACGCATACGA |
| SEQ ID NO: 1546 | mm07278_H2-Q10 | CCCCAGGCTCACACTCCATG |
| SEQ ID NO: 1547 | mm07279_H2-Q10 | TGGTGCTGCAGAGTATTACA |
| SEQ ID NO: 1548 | mm07280_H2-Q10 | TAACCGACAATAATGAACCG |
| SEQ ID NO: 1549 | mm07281_H2-Q2 | TGACATCACCTTGAGAACTG |
| SEQ ID NO: 1550 | mm07282_H2-Q2 | GTATTGGGAGCGGAACACAC |
| SEQ ID NO: 1551 | mm07283_H2-Q2 | TGGAGGTCGATTGCTTGACG |
| SEQ ID NO: 1552 | mm07284_H2-Q2 | GAAACTGACTGAGACACGCG |
| SEQ ID NO: 1553 | mm07285_H2-Q4 | TGGTGCTACAGAGAAAAGCA |
| SEQ ID NO: 1554 | mm07286_H2-Q4 | GATATGAGCCGCGGGCACCG |
| SEQ ID NO: 1555 | mm07287_H2-Q4 | GACCCTGATCGAGATCCGCG |
| SEQ ID NO: 1556 | mm07288_H2-Q4 | TGTCGGTTACGTGGACAACA |
| SEQ ID NO: 1557 | mm07289_H2-Q7 | CTGGTTGTAGTAGCTCTGTG |
| SEQ ID NO: 1558 | mm07290_H2-Q7 | TGGTATTGCAGAGAAAGACC |
| SEQ ID NO: 1559 | mm07291_H2-Q7 | GTGGACGGCGGTGGACATGG |
| SEQ ID NO: 1560 | mm07292_H2-Q7 | CGTGCGCTTCGACAGCGATG |
| SEQ ID NO: 1561 | mm07297_H2-T23 | TACTACAATCAGAGTAACGA |
| SEQ ID NO: 1562 | mm07298_H2-T23 | CTGAAGATGAAGTCACCCTG |
| SEQ ID NO: 1563 | mm07299_H2-T23 | GTGTCTCATTTCCCAGCCGT |
| SEQ ID NO: 1564 | mm07300_H2-T23 | CTTGTGCTTAGAGATCTGTG |
| SEQ ID NO: 1565 | mm07409_Hcn1 | GAGTACCTATCCGATCGAGT |

TABLE 1-continued mmSurf sgRNA library sequences

| SEQ ID NO | id_gRNA Target | Sequence |
|---|---|---|
| SEQ ID NO: 1566 | mm07410_Hcn1 | TAATCAGATACATACACCAG |
| SEQ ID NO: 1567 | mm07411_Hon1 | GTGTGCTTCAAGGTGGACGG |
| SEQ ID NO: 1568 | mm07412_Hon1 | CAGAGCAGACGACAACACCG |
| SEQ ID NO: 1569 | mm07465_Hbegf | ACTCTCACCGGTCACCAACG |
| SEQ ID NO: 1570 | mm07466_Hbegf | CAAGGACTACTGCATCCACG |
| SEQ ID NO: 1571 | mm07467_Hbegf | ACAAACCAGCTGCTACCCAC |
| SEQ ID NO: 1572 | mm07468_Hbegf | GTGGAGCACTTACTTGCAAG |
| SEQ ID NO: 1573 | mm07477_Heph | CATGTGCAAGGGTGATACTG |
| SEQ ID NO: 1574 | mm07478_Heph | TTGGAGCATCTACATGCGAG |
| SEQ ID NO: 1575 | mm07479_Heph | GTTTATAAGGAATACAGTGA |
| SEQ ID NO: 1576 | mm07480_Heph | AAAAGTCACATACTACTGGA |
| SEQ ID NO: 1577 | mm07505_Hexa | ACGCCCCGGTGAGGGAATCG |
| SEQ ID NO: 1578 | mm07506_Hexa | AGGAGGTCATTGAATACGCA |
| SEQ ID NO: 1579 | mm07507_Hexa | AGTGAAGCTCTCATATGGGA |
| SEQ ID NO: 1580 | mm07508_Hexa | AGCAAGGTGTTAATAACCCA |
| SEQ ID NO: 1581 | mm07509_Hexb | GCTCAGCTCGAAATCTAGCA |
| SEQ ID NO: 1582 | mm07510_Hexb | TACACCAAACGATGTCCGGA |
| SEQ ID NO: 1583 | mm07511_Hexb | GCGGAGATGTACAACAGCCG |
| SEQ ID NO: 1584 | mm07512_Hexb | TAACGCTCCCCAAACGCTGT |
| SEQ ID NO: 1585 | mm07521_Hfe | TGCTCCACGTACCCTTACTG |
| SEQ ID NO: 1586 | mm07522_Hfe | TTCCTCCCGCACTCACGCGG |
| SEQ ID NO: 1587 | mm07523_Hfe | GATCCGTGCCAAACAGAACA |
| SEQ ID NO: 1588 | mm07524_Hfe | CATGAAGACAACAGTACCAG |
| SEQ ID NO: 1589 | mm07573_Hhip | TTGAAGTGAGGGTTACTCCG |
| SEQ ID NO: 1590 | mm07574_Hhip | AAGACTACGAGAAAGTGGGG |
| SEQ ID NO: 1591 | mm07575_Hhip | TGCGACTTCCAGAAACACCC |
| SEQ ID NO: 1592 | mm07576_Hhip | GTGGGTAGAAGCCACCACAC |
| SEQ ID NO: 1593 | mm07669_Hmgcr | TCATCATCCTGACGATAACG |
| SEQ ID NO: 1594 | mm07670_Hmgcr | CATTAGGTCGTGGCTCGATG |
| SEQ ID NO: 1595 | mm07671_Hmgcr | GCCAAATTGGACGACCCTCA |
| SEQ ID NO: 1596 | mm07672_Hmgcr | AACTGCCAGAGAGAAACACT |
| SEQ ID NO: 1597 | mm07749_Hnrnpk | GATGATATGAGCCCTCGTCG |
| SEQ ID NO: 1598 | mm07750_Hnrnpk | CTGTTGGGACATACCGCTCG |
| SEQ ID NO: 1599 | mm07751_Hnrnpk | ATCCCTACCTTGGAAGAGGT |
| SEQ ID NO: 1600 | mm07752_Hnrnpk | ATACCTCAGATATAAGGTCA |
| SEQ ID NO: 1601 | mm07925_Lipc | TTATCATGATCATCCACGGG |
| SEQ ID NO: 1602 | mm07926_Lipc | AGGAGAAAGGCGCTCGTTGG |
| SEQ ID NO: 1603 | mm07927_Lipc | CATAACCCAGAGTGTTGCAA |

TABLE 1-continued mmSurf sgRNA library sequences

| SEQ ID NO | id_gRNA Target | Sequence |
|---|---|---|
| SEQ ID NO: 1604 | mm07928_Lipc | GGTGTAGTGCTGGTATGCCA |
| SEQ ID NO: 1605 | mm07929_Hpn | GGTGGGTCCATCATAACGC |
| SEQ ID NO: 1606 | mm07930_Hpn | GGAGCTAGAGAGGTGGACCA |
| SEQ ID NO: 1607 | mm07931_Hpn | CTCACGCTCCAATGCCAGGG |
| SEQ ID NO: 1608 | mm07932_Hpn | ACCCCCAGTTGCACAGCATG |
| SEQ ID NO: 1609 | mm07985_Hspa8 | TTAGACCGTTACCAACGCTG |
| SEQ ID NO: 1610 | mm07986_Hspa8 | GAAAGCAACATAGCTTGGCG |
| SEQ ID NO: 1611 | mm07987_Hspa8 | TGGTGGTATTGCGCTTGATG |
| SEQ ID NO: 1612 | mm07988_Hspa8 | CTACAGGGTCCAGTGTGCCA |
| SEQ ID NO: 1613 | mm08061_Hspd1 | CGGAGAAGCTCTAAGCACGC |
| SEQ ID NO: 1614 | mm08062_Hspd1 | TCTTGAACTAGGTGTGATGT |
| SEQ ID NO: 1615 | mm08063_Hspd1 | AGGGACAATGGACTGAACAC |
| SEQ ID NO: 1616 | mm08064_Hspd1 | TGACTTAGGAAAAGTTGGGG |
| SEQ ID NO: 1617 | mm08069_Hspa2 | CAAGAGCATTAATCCCGACG |
| SEQ ID NO: 1618 | mm08070_Hspa2 | GAAGCACTGGCCGTTCCGAG |
| SEQ ID NO: 1619 | mm08071_Hspa2 | GAGATCGACTCGCTCTACGA |
| SEQ ID NO: 1620 | mm08072_Hspa2 | GGTCAGGATGGACACATCGA |
| SEQ ID NO: 1621 | mm08073_Hsp90ab1 | CATTAGAGATCAACTCGCGG |
| SEQ ID NO: 1622 | mm08074_Hsp90ab1 | CCTCGGAGTCAACCACACCG |
| SEQ ID NO: 1623 | mm08075_Hsp90ab1 | AGGTCGAAGGGAGCCCGCCG |
| SEQ ID NO: 1624 | mm08076_Hsp90ab1 | TGAAGATGTGGGATCCGATG |
| SEQ ID NO: 1625 | mm08077_Hsp90aa1 | GCTTCAGCTTGGAATTCACG |
| SEQ ID NO: 1626 | mm08078_Hsp90aa1 | CAGTAAACTGGACTCGGGGA |
| SEQ ID NO: 1627 | mm08079_Hsp90aa1 | CCTACTTACTCAGATACTCA |
| SEQ ID NO: 1628 | mm08080_Hsp90aa1 | AGACCAAACAGAGTATTTGG |
| SEQ ID NO: 1629 | mm08093_Sdc2 | GGGGAAGCAGCACTAGTGAG |
| SEQ ID NO: 1630 | mm08094_Sdc2 | GTCACCTGAAGAAACTGACA |
| SEQ ID NO: 1631 | mm08095_Sdc2 | CCTTGACAATAGCTCCATTG |
| SEQ ID NO: 1632 | mm08096_Sdc2 | GATGACTATTCTTCTGCCTC |
| SEQ ID NO: 1633 | mm08097_Hspg2 | TCTACGGCTACACCACATGT |
| SEQ ID NO: 1634 | mm08098_Hspg2 | GGGAGGACGAGGATTCAATG |
| SEQ ID NO: 1635 | mm08099_Hspg2 | TACTATGGGGATGCCCAACG |
| SEQ ID NO: 1636 | mm08100_Hspg2 | GTGCGCTATGAACTGGCACG |
| SEQ ID NO: 1637 | mm08129_Htr2c | TATTGATATTGCCCAAACGA |
| SEQ ID NO: 1638 | mm08130_Htr2c | ACATCAGGGTTTGACGGCGT |
| SEQ ID NO: 1639 | mm08131_Htr2c | AAACAAGCGTCCACCATCGG |
| SEQ ID NO: 1640 | mm08132_Htr2c | AAGAAAGAAAAGCGGCCTAG |
| SEQ ID NO: 1641 | mm08133_Htr3a | CCTGGCTAACTACAAGAAGG |

TABLE 1-continued mmSurf sgRNA library sequences

| SEQ ID NO | id_gRNA Target | Sequence |
|---|---|---|
| SEQ ID NO: 1642 | mm08134_Htr3a | CTGCCGGTACCATATGTAGG |
| SEQ ID NO: 1643 | mm08135_Htr3a | GGACTCACAACTCATTGATG |
| SEQ ID NO: 1644 | mm08136_Htr3a | AGGACATCAACATTACCCTG |
| SEQ ID NO: 1645 | mm08185_Hyal2 | AAAGTTGCGGCTGTGTACGG |
| SEQ ID NO: 1646 | mm08186_Hyal2 | GAACACTCTCCGTTACGTCA |
| SEQ ID NO: 1647 | mm08187_Hyal2 | GGGACGCGTGAAGACGTACA |
| SEQ ID NO: 1648 | mm08188_Hyal2 | ACCTTCTACTACGACCGTCT |
| SEQ ID NO: 1649 | mm08201_Icam1 | GTGAAGTGTGAAGCCCACAG |
| SEQ ID NO: 1650 | mm08202_Icam1 | GCCCTGCCACTCACAATACA |
| SEQ ID NO: 1651 | mm08203_Icam1 | GAGAACAATGCCAGCCCTTG |
| SEQ ID NO: 1652 | mm08204_Icam1 | GCGGTGCTCCACCATCCACG |
| SEQ ID NO: 1653 | mm08205_Icam2 | TCTTCACCCACAAACACCCG |
| SEQ ID NO: 1654 | mm08206_Icam2 | GGACCATATGTAGACCTCAA |
| SEQ ID NO: 1655 | mm08207_Icam2 | AACTGCGCAGCCCCAGACAT |
| SEQ ID NO: 1656 | mm08208_Icam2 | ATGTTGGAAGAGCATCCTCA |
| SEQ ID NO: 1657 | mm08269_Cxcl10 | ACTCACATGATCTCAACACG |
| SEQ ID NO: 1658 | mm08270_Cxcl10 | CAGCGGACCGTCCTTGCGAG |
| SEQ ID NO: 1659 | mm08271_Cxcl10 | ACTGCATCCATATCGATGAC |
| SEQ ID NO: 1660 | mm08272_Cxcl10 | TGACGGGCCAGTGAGAATGA |
| SEQ ID NO: 1661 | mm08333_Ifnar1 | ACAGTTGACATAAACAAGCA |
| SEQ ID NO: 1662 | mm08334_Ifnar1 | CTTCTAAACGTACTTCTGGG |
| SEQ ID NO: 1663 | mm08335_Ifnar1 | TCTCCATGTACAAGCCTCAG |
| SEQ ID NO: 1664 | mm08336_Ifnar1 | GTGCAGTGTATAAGCACCAC |
| SEQ ID NO: 1665 | mm08337_Ifnar2 | CAAAGACGAAAATCTGACGA |
| SEQ ID NO: 1666 | mm08338_Ifnar2 | GCCATCGTCATAGTGCACAG |
| SEQ ID NO: 1667 | mm08339_Ifnar2 | TAACCTGGATAATCCCTGAA |
| SEQ ID NO: 1668 | mm08340_Ifnar2 | ACTGTGGAATTACGATTATG |
| SEQ ID NO: 1669 | mm08345_Ifng | TCTATGCCACTTGAGTTCTG |
| SEQ ID NO: 1670 | mm08346_Ifng | GTTTCTGGCTGTTACTGCCA |
| SEQ ID NO: 1671 | mm08347_Ifng | TGCTGAAGAAGGTAGTAATC |
| SEQ ID NO: 1672 | mm08348_Ifng | TCAAGACTTCAAAGAGTCTG |
| SEQ ID NO: 1673 | mm08365_Cd79b | TGACCTGGTTCCGAAAGCGA |
| SEQ ID NO: 1674 | mm08366_Cd79b | TCCCCCAGGATTCAGCACGT |
| SEQ ID NO: 1675 | mm08367_Cd79b | CATAATGTCACCGACAGCTG |
| SEQ ID NO: 1676 | mm08368_Cd79b | CGAGGTTTGCAGCCAAAAAG |
| SEQ ID NO: 1677 | mm08373_Igf1r | AGAACCGAATCATCATAACG |
| SEQ ID NO: 1678 | mm08374_Igf1r | GGAAAACGACCATATCCGTG |
| SEQ ID NO: 1679 | mm08375_Igf1r | CTATGGTGGAGAGGTAACAG |

TABLE 1-continued mmSurf sgRNA library sequences

| SEQ ID NO | id_gRNA Target | Sequence |
|---|---|---|
| SEQ ID NO: 1680 | mm08376_Igf1r | CTGCTTATTAACATCCGGAG |
| SEQ ID NO: 1681 | mm08381_Igf2r | AGGACATTGACTCCACACGA |
| SEQ ID NO: 1682 | mm08382_Igf2r | TGAAAATGAACTATACTGGG |
| SEQ ID NO: 1683 | mm08383_Igf2r | GTCACACCGTCTGTCCACTG |
| SEQ ID NO: 1684 | mm08384_Igf2r | GGACAGACGAGGATCAGTGT |
| SEQ ID NO: 1685 | mm08401_Igfbp3 | GGCGTCTACACGGAGCGCTG |
| SEQ ID NO: 1686 | mm08402_Igfbp3 | ACGGTTCGCAGCGCACCACG |
| SEQ ID NO: 1687 | mm08403_Igfbp3 | GGAACTTGGAATCGGTCACT |
| SEQ ID NO: 1688 | mm08404_Igfbp3 | CCGAGGAGGAGCACAATGCT |
| SEQ ID NO: 1689 | mm08425_Igll1 | CTGTTCCAGATCATCCCACG |
| SEQ ID NO: 1690 | mm08426_Igll1 | GCTCACCAAACACACTAGTG |
| SEQ ID NO: 1691 | mm08427_Igll1 | CCAAAGACATACCAAAACTG |
| SEQ ID NO: 1692 | mm08428_Igll1 | GGAGAACTTCACACTGCCTG |
| SEQ ID NO: 1693 | mm08437_Cd74 | GCTGATGCGTCCAATGTCCA |
| SEQ ID NO: 1694 | mm08438_Cd74 | CCATGTGATGCATCTGCTCA |
| SEQ ID NO: 1695 | mm08439_Cd74 | CATGGATGGCGTGAACTGGA |
| SEQ ID NO: 1696 | mm08440_Cd74 | AGCCGTGGAGCTCTGTACAC |
| SEQ ID NO: 1697 | mm08457_Il10rb | TGGCGGATGAACATTCGGAG |
| SEQ ID NO: 1698 | mm08458_Il10rb | ATTTCAAGAACATTCTACAG |
| SEQ ID NO: 1699 | mm08459_Il10rb | CGGAGGACCTCAGAGTCGTA |
| SEQ ID NO: 1700 | mm08460_Il10rb | AGAGAAGTCGCACTGAGTCG |
| SEQ ID NO: 1701 | mm08473_Il12rb1 | GTCGGTGAGGAACCAAACCG |
| SEQ ID NO: 1702 | mm08474_Il12rb1 | CCTCCGAACCATACCCACAC |
| SEQ ID NO: 1703 | mm08475_Il12rb1 | TGAGAAGACATCGTTCCCAG |
| SEQ ID NO: 1704 | mm08476_Il12rb1 | TCAAGGTGTCACAATCACAC |
| SEQ ID NO: 1705 | mm08477_Il12rb2 | ACTGAGAACACGAACACCAG |
| SEQ ID NO: 1706 | mm08478_Il12rb2 | ATTAACATAGTGGACCTATG |
| SEQ ID NO: 1707 | mm08479_Il12rb2 | AGAGCAGACATGTTGTCCGG |
| SEQ ID NO: 1708 | mm08480_Il12rb2 | CTATCAGGTGACGTTACAAG |
| SEQ ID NO: 1709 | mm08481_Il13 | ACCATGCTGCCGTTGCACAG |
| SEQ ID NO: 1710 | mm08482_Il13 | AGAGACACAGATCTTGGCAC |
| SEQ ID NO: 1711 | mm08483_Il13 | AGATGTTGGTCAGGGAATCC |
| SEQ ID NO: 1712 | mm08484_Il13 | CAGGTTCCTTACCCCGCCAG |
| SEQ ID NO: 1713 | mm08493_Il15 | ATATCTTACATCTATCCAGT |
| SEQ ID NO: 1714 | mm08494_Il15 | GAAACACAAGTAGCACGAGA |
| SEQ ID NO: 1715 | mm08495_Il15 | AATGTGTACTCACTTGAATA |
| SEQ ID NO: 1716 | mm08496_Il15 | GTCACTGTCAGTGTATAAAG |
| SEQ ID NO: 1717 | mm08505_Il17a | CTCAGCGTGTCCAAACACTG |

TABLE 1-continued mmSurf sgRNA library sequences

| SEQ ID NO | id_gRNA Target | Sequence |
|---|---|---|
| SEQ ID NO: 1718 | mm08506_Il17a | GAACGGTTGAGGTAGTCTGA |
| SEQ ID NO: 1719 | mm08507_Il17a | CTTACGTACTGGAGAGTCCA |
| SEQ ID NO: 1720 | mm08508_Il17a | CTGAGCTTCCCAGATCACAG |
| SEQ ID NO: 1721 | mm08509_Il17ra | ACTGAAGTAGCAAACAACGT |
| SEQ ID NO: 1722 | mm08510_Il17ra | ATGAGGCCATACACCCACAG |
| SEQ ID NO: 1723 | mm08511_Il17ra | GAAGGTCTGGATCGTCTACT |
| SEQ ID NO: 1724 | mm08512_Il17ra | GACCTGGAGATGTTTGAACC |
| SEQ ID NO: 1725 | mm08521_Il1a | ATGTATGCCTACTCGTCGGG |
| SEQ ID NO: 1726 | mm08522_Il1a | TTACCTGATTCAGAGAGAGA |
| SEQ ID NO: 1727 | mm08523_Il1a | TCCATAACCCATGATCTGGA |
| SEQ ID NO: 1728 | mm08524_Il1a | GGACATCTTTGACGTTTCAG |
| SEQ ID NO: 1729 | mm08529_Il1r1 | AGCATACAATTGTAGCCGTG |
| SEQ ID NO: 1730 | mm08530_Il1r1 | CAGCAAGACCCCCATATCAG |
| SEQ ID NO: 1731 | mm08531_Il1r1 | CGTATGTCCTATACGTTCCG |
| SEQ ID NO: 1732 | mm08532_Il1r1 | ACTGTGTTAGAGAATGACCC |
| SEQ ID NO: 1733 | mm08533_Il1r2 | TGTCGGAGTGAGGTGCCAAG |
| SEQ ID NO: 1734 | mm08534_Il1r2 | AGGGCACACTAGTAACCCGG |
| SEQ ID NO: 1735 | mm08535_Il1r2 | GACTATCAGTCTTGACCCTG |
| SEQ ID NO: 1736 | mm08536_Il1r2 | GGGCTTCTCCGATGTAATGG |
| SEQ ID NO: 1737 | mm08541_Il1rap | TACACAGTAGAACTCGCCTG |
| SEQ ID NO: 1738 | mm08542_Il1rap | TTTCATAATGTACTACCCGA |
| SEQ ID NO: 1739 | mm08543_Il1rap | TGGTCCACCAGACCTCATTG |
| SEQ ID NO: 1740 | mm08544_Il1rap | CATCAAGAAAGTCACCCCGG |
| SEQ ID NO: 1741 | mm08549_Il18r1 | TCACCGATCACAAATTCATG |
| SEQ ID NO: 1742 | mm08550_Il18r1 | CTGTCCACCATAATGGGACA |
| SEQ ID NO: 1743 | mm08551_Il18r1 | ATTCTGGCCAGTTGAGATGG |
| SEQ ID NO: 1744 | mm08552_Il18r1 | TGTCAACTTCTATCTAGGAA |
| SEQ ID NO: 1745 | mm08557_Il2ra | GTGTCTGTATGACCCACCCG |
| SEQ ID NO: 1746 | mm08558_Il2ra | ATCTTGCAGATGCTAATAGC |
| SEQ ID NO: 1747 | mm08559_Il2ra | GAGAGGTTTCCGAAGACTAA |
| SEQ ID NO: 1748 | mm08560_Il2ra | GAATCTTCATGTTTCCAAGG |
| SEQ ID NO: 1749 | mm08561_Il2rb | GGACCTCCTTGACATAAATG |
| SEQ ID NO: 1750 | mm08562_Il2rb | TCTCCGTCGAGCACTTCCAG |
| SEQ ID NO: 1751 | mm08563_Il2rb | AAGCTCAACGAAACAATACC |
| SEQ ID NO: 1752 | mm08564_Il2rb | AGGTATCTGAGCCATGACAT |
| SEQ ID NO: 1753 | mm08565_Il2rg | TTCCACAGATTGGGTTATAG |
| SEQ ID NO: 1754 | mm08566_Il2rg | GGAGCAACAGAGATCGAAGC |
| SEQ ID NO: 1755 | mm08567_Il2rg | CCCGATTACCAAGATTCTGT |

TABLE 1-continued mmSurf sgRNA library sequences

| SEQ ID NO | id_gRNA Target | Sequence |
|---|---|---|
| SEQ ID NO: 1756 | mm08568_Il2rg | CATACCTATAGTGCAGCGTG |
| SEQ ID NO: 1757 | mm08573_Il3ra | TTGCACTCCACTGTCAACGT |
| SEQ ID NO: 1758 | mm08574_Il3ra | GGATGTTCTGGCGTGATGTG |
| SEQ ID NO: 1759 | mm08575_Il3ra | GACAACAGCTGCGGTCCGTG |
| SEQ ID NO: 1760 | mm08576_Il3ra | CGGCGCTGACATCACGACAG |
| SEQ ID NO: 1761 | mm08577_Il4 | CAGAGAGTGAGCTCGTCTGT |
| SEQ ID NO: 1762 | mm08578_Il4 | TGTACCAGGAGCCATATCCA |
| SEQ ID NO: 1763 | mm08579_Il4 | CTAGAGTTCTTCTTCAAGCA |
| SEQ ID NO: 1764 | mm08580_Il4 | AATCACTTGAGAGAGATCAT |
| SEQ ID NO: 1765 | mm08593_Il6 | TATACCACTTCACAAGTCGG |
| SEQ ID NO: 1766 | mm08594_Il6 | CCTACTTCACAAGTCCGGAG |
| SEQ ID NO: 1767 | mm08595_Il6 | ATGGTACTCCAGAAGACCAG |
| SEQ ID NO: 1768 | mm08596_Il6 | ACATGTTCTCTGGGAAATCG |
| SEQ ID NO: 1769 | mm08597_Il6ra | CTGTGCGTTGCAAACAGTGT |
| SEQ ID NO: 1770 | mm08598_Il6ra | GGGGCAAATCAGGGTAACGG |
| SEQ ID NO: 1771 | mm08599_Il6ra | CAGGTATGGCTGATACCACA |
| SEQ ID NO: 1772 | mm08600_Il6ra | CACCCCCTCTCCAACCACGA |
| SEQ ID NO: 1773 | mm08601_Il6st | TAACTCCGTATTCGCCACG |
| SEQ ID NO: 1774 | mm08602_Il6st | TCTAAGTACCTTTATCCACG |
| SEQ ID NO: 1775 | mm08603_Il6st | ATCCGGTCCATTAAGGACAG |
| SEQ ID NO: 1776 | mm08604_Il6st | GAGTAGTGATACGTTGTACA |
| SEQ ID NO: 1777 | mm08609_Il7r | GGGAGACTAGGCCATACGAC |
| SEQ ID NO: 1778 | mm08610_Il7r | AGACCTAGAAGATGCAGACG |
| SEQ ID NO: 1779 | mm08611_Il7r | CAGAACCCAAGAATCAAGGT |
| SEQ ID NO: 1780 | mm08612_Il7r | CCTTTGAAGTAATCGTTATG |
| SEQ ID NO: 1781 | mm08637_Lrig1 | GTAGCGAACCTAAGACTGTG |
| SEQ ID NO: 1782 | mm08638_Lrig1 | TGTCCTTCAACAACCTCACG |
| SEQ ID NO: 1783 | mm08639_Lrig1 | GGTACAATCGAGGATACCAG |
| SEQ ID NO: 1784 | mm08640_Lrig1 | GAGCATTTGATGGTCTGTCG |
| SEQ ID NO: 1785 | mm08705_Insr | CGAGGATTACCTGCACAACG |
| SEQ ID NO: 1786 | mm08706_Insr | GTGATACCAGAGCATAGGAG |
| SEQ ID NO: 1787 | mm08707_Insr | CACACTGCACCTCTCATCTG |
| SEQ ID NO: 1788 | mm08708_Insr | TATAGCCAGACGGGCACTCG |
| SEQ ID NO: 1789 | mm08773_Itga2 | TGGCCAGTATAATTTGCTCG |
| SEQ ID NO: 1790 | mm08774_Itga2 | TACAACTACAACATCCACGA |
| SEQ ID NO: 1791 | mm08775_Itga2 | TCAGAGCTATCGAATTCGCA |
| SEQ ID NO: 1792 | mm08776_Itga2 | TTTCAATGTGGCCGACGAAG |
| SEQ ID NO: 1793 | mm08777_Itga2b | GCCTATCTGCCACACCACGG |

TABLE 1-continued mmSurf sgRNA library sequences

| SEQ ID NO | id_gRNA Target | Sequence |
|---|---|---|
| SEQ ID NO: 1794 | mm08778_Itga2b | GCCACAAAAGGGTACCCGGG |
| SEQ ID NO: 1795 | mm08779_Itga2b | CCTACACAGCGTGTCCATCG |
| SEQ ID NO: 1796 | mm08780_Itga2b | CGATGTCTACAGCACCACGA |
| SEQ ID NO: 1797 | mm08781_Itga3 | GGCTATGGAGAATCACACTG |
| SEQ ID NO: 1798 | mm08782_Itga3 | GTGGGCAAGTGCTATGTGCG |
| SEQ ID NO: 1799 | mm08783_Itga3 | GTACACAGCACCAGTCCGGT |
| SEQ ID NO: 1800 | mm08784_Itga3 | AGGTAGCTGTACAAAGCGCA |
| SEQ ID NO: 1801 | mm08785_Itga5 | TTTGCTGTCAAATTGAATGG |
| SEQ ID NO: 1802 | mm08786_Itga5 | GTCTTACATAGCCATAGGTG |
| SEQ ID NO: 1803 | mm08787_Itga5 | GACCCACAGAATGACCCAGT |
| SEQ ID NO: 1804 | mm08788_Itga5 | GTCGTATTTATATTCCCGGG |
| SEQ ID NO: 1805 | mm08789_Itga6 | GAGGGGACATCGCCTTACTT |
| SEQ ID NO: 1806 | mm08790_Itga6 | GCAGAGGGCGAACAGAACAG |
| SEQ ID NO: 1807 | mm08791_Itga6 | GAGTATATATTTGACGGAGA |
| SEQ ID NO: 1808 | mm08792_Itga6 | GGAGACTGGAGTTTCTGCGA |
| SEQ ID NO: 1809 | mm08793_Itga7 | GGTTCGGAGACCATATGACA |
| SEQ ID NO: 1810 | mm08794_Itga7 | GTGTATGTGTACATGAACCA |
| SEQ ID NO: 1811 | mm08795_Itga7 | CCCACTCAATGCGAACAGGG |
| SEQ ID NO: 1812 | mm08796_Itga7 | CTTAGATTATATGTTAGATG |
| SEQ ID NO: 1813 | mm08797_Itgae | TACTCACCAAAACACCATTG |
| SEQ ID NO: 1814 | mm08798_Itgae | TCCTTCTATCCGTCGCACAA |
| SEQ ID NO: 1815 | mm08799_Itgae | ATACGGTCAGGTCAACCACA |
| SEQ ID NO: 1816 | mm08800_Itgae | CTGTGCGAGTTGATATTGAA |
| SEQ ID NO: 1817 | mm08801_Itgal | CATAACCCGCTACATCATCG |
| SEQ ID NO: 1818 | mm08802_Itgal | CGCTGCCTAGCAGAACATCG |
| SEQ ID NO: 1819 | mm08803_Itgal | GAAACACGGAGTCAAGCTCA |
| SEQ ID NO: 1820 | mm08804_Itgal | AACACCAAGGGACCAAAAGG |
| SEQ ID NO: 1821 | mm08805_Itgam | AGGGATGACCCTGATCACCG |
| SEQ ID NO: 1822 | mm08806_Itgam | TGGGCGCCTATGATCCGCTG |
| SEQ ID NO: 1823 | mm08807_Itgam | CCTGCGCCTCAATTATACAC |
| SEQ ID NO: 1824 | mm08808_Itgam | GGTCATTCGCTACGTAATTG |
| SEQ ID NO: 1825 | mm08809_Itgav | GGTGCCATCTCAAATCCTCG |
| SEQ ID NO: 1826 | mm08810_Itgav | TCATGGACCGAGGTTCCGAT |
| SEQ ID NO: 1827 | mm08811_Itgav | CCTGCATGGAGCATACTCAA |
| SEQ ID NO: 1828 | mm08812_Itgav | ATAATAACCAATTAGCAACA |
| SEQ ID NO: 1829 | mm08813_Itgax | CCATGAATACGTATTCAGCG |
| SEQ ID NO: 1830 | mm08814_Itgax | TCTTCAAGGAGACAAAGACC |
| SEQ ID NO: 1831 | mm08815_Itgax | CATGACATGCTTGATAGCCG |

TABLE 1-continued mmSurf sgRNA library sequences

| SEQ ID NO | id_gRNA Target | Sequence |
|---|---|---|
| SEQ ID NO: 1832 | mm08816_Itgax | TACAAATGTGGCTATCACAC |
| SEQ ID NO: 1833 | mm08817_Itgb1 | GAGGAATGTAACACGACTGC |
| SEQ ID NO: 1834 | mm08818_Itgb1 | TCCCAACATTCCTACCAATG |
| SEQ ID NO: 1835 | mm08819_Itgb1 | GGAAATGGGACATTTGAGTG |
| SEQ ID NO: 1836 | mm08820_Itgb1 | GCAATTGAAGGATAATCCTA |
| SEQ ID NO: 1837 | mm08825_Itgb2 | GAGTATAGGCAAATCCCGTG |
| SEQ ID NO: 1838 | mm08826_Itgb2 | TTGGCTGGCGCAATGTCACG |
| SEQ ID NO: 1839 | mm08827_Itgb2 | ATCCTGAGTTCGACCAACGG |
| SEQ ID NO: 1840 | mm08828_Itgb2 | TGGAGTAGGAGAGATCCATG |
| SEQ ID NO: 1841 | mm08833_Itgb3 | GCAGGTGGAGGATTACCCCG |
| SEQ ID NO: 1842 | mm08834_Itgb3 | AATATGGGTCTTGGCATCCG |
| SEQ ID NO: 1843 | mm08835_Itgb3 | TTCTCCTTCAGGTTACATCG |
| SEQ ID NO: 1844 | mm08836_Itgb3 | CGATACAGGCTTGTCCACGA |
| SEQ ID NO: 1845 | mm08841_Itgb5 | CAAAAGACCCGAAACCTAAG |
| SEQ ID NO: 1846 | mm08842_Itgb5 | CCGCATCAAACCCCCCCTCG |
| SEQ ID NO: 1847 | mm08843_Itgb5 | GAACCACTATATGCTCTACA |
| SEQ ID NO: 1848 | mm08844_Itgb5 | TGCTGAGAGGTAGGTTCCGG |
| SEQ ID NO: 1849 | mm08845_Itgb6 | TGTCTACACTAAAGGAACTG |
| SEQ ID NO: 1850 | mm08846_Itgb6 | TGAGGTAATACAGATCTACT |
| SEQ ID NO: 1851 | mm08847_Itgb6 | ATGGGTCCTCACTGCGAGTG |
| SEQ ID NO: 1852 | mm08848_Itgb6 | TTTGGCTAAAAGATTCGCTG |
| SEQ ID NO: 1853 | mm08849_Itgb7 | ACAGTGTGCGACTGTAACTG |
| SEQ ID NO: 1854 | mm08850_Itgb7 | CGTGACGCGGATCCGCTGCG |
| SEQ ID NO: 1855 | mm08851_Itgb7 | GTGGCTGACAACGCTCCAGT |
| SEQ ID NO: 1856 | mm08852_Itgb7 | TGATGTCCGAGTCAACCAGA |
| SEQ ID NO: 1857 | mm08853_Cd47 | ATCAGCCTGTTCTTACGAGG |
| SEQ ID NO: 1858 | mm08854_Cd47 | GGATAAGCGCGATGCCATGG |
| SEQ ID NO: 1859 | mm08855_Cd47 | CACTTCATGCAATGAAACTG |
| SEQ ID NO: 1860 | mm08856_Cd47 | GAATGATTCTCTTATTCGTA |
| SEQ ID NO: 1861 | mm08881_Stt3a | AAGGTGGTACGTAACGATGG |
| SEQ ID NO: 1862 | mm08882_Stt3a | TACCATGTAGAAATAAGCGA |
| SEQ ID NO: 1863 | mm08883_Stt3a | GTTTACCTGGAAACCAACAA |
| SEQ ID NO: 1864 | mm08884_Stt3a | ACTTTAATTATCGGACTACC |
| SEQ ID NO: 1865 | mm08901_Itpr1 | CTGTGAAATATGCCCGACTG |
| SEQ ID NO: 1866 | mm08902_Itpr1 | ACACGAACGATGTCATCGAG |
| SEQ ID NO: 1867 | mm08903_Itpr1 | AAACGTGTCAATCTCTGCCG |
| SEQ ID NO: 1868 | mm08904_Itpr1 | GGAAGCTGAGAACTCCACAG |
| SEQ ID NO: 1869 | mm08921_Jag1 | TCTGACCCCTGCCATAACCG |

TABLE 1-continued mmSurf sgRNA library sequences

| SEQ ID NO | id_gRNA Target | Sequence |
|---|---|---|
| SEQ ID NO: 1870 | mm08922_Jag1 | GAAGCCACGTGTAATAATGG |
| SEQ ID NO: 1871 | mm08923_Jag1 | TGACTTACGTACCCGACAGG |
| SEQ ID NO: 1872 | mm08924_Jag1 | ACTGGCACGATTGTAGCACT |
| SEQ ID NO: 1873 | mm08941_F11r | AGGTGGCCAGAACTACGGGG |
| SEQ ID NO: 1874 | mm08942_F11r | GTGGAGTGGAAGTTCGTCCA |
| SEQ ID NO: 1875 | mm08943_F11r | TTGAACCAGGAATATTCAGA |
| SEQ ID NO: 1876 | mm08944_F11r | CACTATTGATCCAAAGTCGG |
| SEQ ID NO: 1877 | mm08981_Kcna1 | CGACACAATGGCAATAACCC |
| SEQ ID NO: 1878 | mm08982_Kcna1 | TTCTGAACACCCTTACCAAG |
| SEQ ID NO: 1879 | mm08983_Kcna1 | GGACTGGTAGTAATAAGGA |
| SEQ ID NO: 1880 | mm08984_Kcna1 | CGCAGCATTCGTGGTCGTCG |
| SEQ ID NO: 1881 | mm08993_Kcna4 | CCACCATCATCAGACACGTG |
| SEQ ID NO: 1882 | mm08994_Kcna4 | TGTACGAACACCCATCCCCA |
| SEQ ID NO: 1883 | mm08995_Kcna4 | TGGAGACAGTGTGTATTGTG |
| SEQ ID NO: 1884 | mm08996_Kcna4 | CAATGGCTATACCCCTGGCA |
| SEQ ID NO: 1885 | mm09021_Kcnb1 | GTGCGACGACTACAGCCTCG |
| SEQ ID NO: 1886 | mm09022_Kcnb1 | GGAGAAGCCCAACTCATCGG |
| SEQ ID NO: 1887 | mm09023_Kcnb1 | AGCCAGGAGCTGGACTACTG |
| SEQ ID NO: 1888 | mm09024_Kcnb1 | CATCGAGATGATGGACATCG |
| SEQ ID NO: 1889 | mm09025_Kcnc1 | CCATGATCTACTACGCCGAG |
| SEQ ID NO: 1890 | mm09026_Kcnc1 | AGACGCCCTCGATGTAGGTG |
| SEQ ID NO: 1891 | mm09027_Kcnc1 | TGTGAGCGAAGACGCCCGGG |
| SEQ ID NO: 1892 | mm09028_Kcnc1 | CCTACTCATCCCGCTACGCG |
| SEQ ID NO: 1893 | mm09045_Kcnh1 | TTACATCGAGTATGGAGCCG |
| SEQ ID NO: 1894 | mm09046_Kcnh1 | CTGTGTCTTTAAGACCACGT |
| SEQ ID NO: 1895 | mm09047_Kcnh1 | TCTCTCCAGCATGATAGATG |
| SEQ ID NO: 1896 | mm09048_Kcnh1 | ATCTTCACAAAAAACCACAC |
| SEQ ID NO: 1897 | mm09049_Kcnh2 | GGCCTGCGCGATCTGCGCGG |
| SEQ ID NO: 1898 | mm09050_Kcnh2 | CTGCCCCGTACTCCGAGTAG |
| SEQ ID NO: 1899 | mm09051_Kcnh2 | CACCTATGTTAATGCCAACG |
| SEQ ID NO: 1900 | mm09052_Kcnh2 | CGGATGACATTGAGGCAATG |
| SEQ ID NO: 1901 | mm09081_Kcnj5 | CCACGTGATCCAGATCACCT |
| SEQ ID NO: 1902 | mm09082_Kcnj5 | ACAATGCCGTCATCTCCATG |
| SEQ ID NO: 1903 | mm09083_Kcnj5 | GGCAAGTGCAATGTACACCA |
| SEQ ID NO: 1904 | mm09084_Kcnj5 | ATTAACAATCGAGCCCAGAA |
| SEQ ID NO: 1905 | mm09085_Kcnj6 | ACCAGACTGATATCAACGTG |
| SEQ ID NO: 1906 | mm09086_Kcnj6 | GGTGACACAAGGAGTCCACG |
| SEQ ID NO: 1907 | mm09087_Kcnj6 | GGAAAATCCAGAGGTACGTG |

TABLE 1-continued mmSurf sgRNA library sequences

| SEQ ID NO | id_gRNA Target | Sequence |
|---|---|---|
| SEQ ID NO: 1908 | mm09088_Kcnj6 | GACCCGGTAGCCATAACCGA |
| SEQ ID NO: 1909 | mm09101_Kcnk2 | ATAGTGGCAGCAATAAACGC |
| SEQ ID NO: 1910 | mm09102_Kcnk2 | CTGCTCAGAACTCCAAACCG |
| SEQ ID NO: 1911 | mm09103_Kcnk2 | CATTGGATTTGGAGACTACG |
| SEQ ID NO: 1912 | mm09104_Kcnk2 | AACATCTCCCCACGAACTGA |
| SEQ ID NO: 1913 | mm09121_Kcnma1 | ATACGGGGCTCCTATAGCG |
| SEQ ID NO: 1914 | mm09122_Kcnma1 | AGTCTATGAAGTATATTACG |
| SEQ ID NO: 1915 | mm09123_Kcnma1 | CATTGCCAGGAATTAACAAG |
| SEQ ID NO: 1916 | mm09124_Kcnma1 | TGTCCACGTTACCACGCACA |
| SEQ ID NO: 1917 | mm09141_Kcnq2 | CCACGTGGCAGTACTACGAG |
| SEQ ID NO: 1918 | mm09142_Kcnq2 | ATCGCGGGCCACTTACACGT |
| SEQ ID NO: 1919 | mm09143_Kcnq2 | ATGATCCGTATGGACCGGAG |
| SEQ ID NO: 1920 | mm09144_Kcnq2 | CAAGACTCTGATCCGCACTG |
| SEQ ID NO: 1921 | mm09157_Kdr | TTACCCGCTTAACGGTCCGT |
| SEQ ID NO: 1922 | mm09158_Kdr | ATACGTTTGAGAACCTCACG |
| SEQ ID NO: 1923 | mm09159_Kdr | TTGTAAAGAATGGAGACACG |
| SEQ ID NO: 1924 | mm09160_Kdr | CATAGCTGATCATGTAACTG |
| SEQ ID NO: 1925 | mm09221_Kif21b | TCGCCTGATCAACTCCCAGG |
| SEQ ID NO: 1926 | mm09222_Kif21b | GGAGTTGATGGAGTACAAAG |
| SEQ ID NO: 1927 | mm09223_Kif21b | CCTCATGAAGCAAATGCGTG |
| SEQ ID NO: 1928 | mm09224_Kif21b | ACCCCATTCGCAGAAAAGGG |
| SEQ ID NO: 1929 | mm09281_Kit | AAGCACAATAGCTGGCACCG |
| SEQ ID NO: 1930 | mm09282_Kit | ACACGTAAATAGAACTCGTG |
| SEQ ID NO: 1931 | mm09283_Kit | AGATTTGGTTGTTGAATACG |
| SEQ ID NO: 1932 | mm09284_Kit | TGGTTGCAGCTGGCGCGATG |
| SEQ ID NO: 1933 | mm09373_Klra1 | GCAGAAACAAGTGAGACCTG |
| SEQ ID NO: 1934 | mm09374_Klra1 | TCGTCATGGACAGAAAAACA |
| SEQ ID NO: 1935 | mm09375_Klra1 | TGATCAACAAAAAAAACTGC |
| SEQ ID NO: 1936 | mm09376_Klra1 | CTGAAACAGCTACCAGAAGA |
| SEQ ID NO: 1937 | mm09381_Klra2 | TGACCTGGTACTCTTGACGG |
| SEQ ID NO: 1938 | mm09382_Klra2 | AGGATGTAAACAGATCTGCC |
| SEQ ID NO: 1939 | mm09383_Klra2 | GTTGTAGGCAAGCAAGTGGA |
| SEQ ID NO: 1940 | mm09384_Klra2 | CAGGGTTGCAGAACCCAGTG |
| SEQ ID NO: 1941 | mm09389_Klra4 | ACATACTGTGTGATAAAACC |
| SEQ ID NO: 1942 | mm09390_Klra4 | CCTGAAAAGCTCGCCTCAG |
| SEQ ID NO: 1943 | mm09391_Klra4 | CAGGGTTGCAGAACGAGATG |
| SEQ ID NO: 1944 | mm09392_Klra4 | CTGCAACAGTTACCAGTCGA |
| SEQ ID NO: 1945 | mm09401_Klra7 | AGTTGACGTCACTTTGCGTG |

TABLE 1-continued mmSurf sgRNA library sequences

| SEQ ID NO | id_gRNA Target | Sequence |
|---|---|---|
| SEQ ID NO: 1946 | mm09402_Klra7 | TCTTCTGGAATCCCTCAGCA |
| SEQ ID NO: 1947 | mm09403_Klra7 | AAAATGTTATTATTTCAACA |
| SEQ ID NO: 1948 | mm09404_Klra7 | GCAGAAACTAGTGAGGACTG |
| SEQ ID NO: 1949 | mm09413_Klrc1 | GACAAAACAGATGAGGCCCA |
| SEQ ID NO: 1950 | mm09414_Klrc1 | ATGACTGAAATGGAGCTGCG |
| SEQ ID NO: 1951 | mm09415_Klrc1 | CCAGTGGCTCACCTTTGCAG |
| SEQ ID NO: 1952 | mm09416_Klrc1 | AAAAGCATGCTTACATGGTG |
| SEQ ID NO: 1953 | mm09417_Klrc2 | TCACACGCCTTGCTCTCCAA |
| SEQ ID NO: 1954 | mm09418_Klrc2 | AATCTTGGAATGACAGTTTG |
| SEQ ID NO: 1955 | mm09419_Klrc2 | TCTGGGTTCTAACCAAGAAG |
| SEQ ID NO: 1956 | mm09420_Klrc2 | ACTGAAACGGAACTGCGCCT |
| SEQ ID NO: 1957 | mm09421_Klrd1 | ACCTTCCTGGAATTCTACAG |
| SEQ ID NO: 1958 | mm09422_Klrd1 | TTTGCCTGGACAAGTGGGTT |
| SEQ ID NO: 1959 | mm09423_Klrd1 | TTGCCAATTCATTTCTGGAT |
| SEQ ID NO: 1960 | mm09424_Klrd1 | TTTCCAAAGAAGAAAAGTCT |
| SEQ ID NO: 1961 | mm09537_Krt4 | GAGTCCTCTATGAAGCGGTG |
| SEQ ID NO: 1962 | mm09538_Krt4 | AGAAGTCTTTACAACCTCGG |
| SEQ ID NO: 1963 | mm09539_Krt4 | TCTGCTCACGCTCCGCCGTG |
| SEQ ID NO: 1964 | mm09540_Krt4 | GGCTCCTTCAACGGTCGAGG |
| SEQ ID NO: 1965 | mm09597_L1cam | CATCCAGTAGATCCTAAGTG |
| SEQ ID NO: 1966 | mm09598_L1cam | GTCCAGGCAGTGAACAACCA |
| SEQ ID NO: 1967 | mm09599_L1cam | TCAGCGTTCCATTGGCATAG |
| SEQ ID NO: 1968 | mm09600_L1cam | ACCCTGCAACTACTCAATGT |
| SEQ ID NO: 1969 | mm09613_Lag3 | GATCCTAACTTTCTACGAAG |
| SEQ ID NO: 1970 | mm09614_Lag3 | GAGAGAAGTCCCCGCGCTGG |
| SEQ ID NO: 1971 | mm09615_Lag3 | TCAGCAGCGTACACTGTCAG |
| SEQ ID NO: 1972 | mm09616_Lag3 | GTTTCAGCTAAAAAATGACG |
| SEQ ID NO: 1973 | mm09625_Lama1 | ATGTAGCTGCTCAATGAACG |
| SEQ ID NO: 1974 | mm09626_Lama1 | GGAAACCCAACCGTGCCAGG |
| SEQ ID NO: 1975 | mm09627_Lama1 | GCTACAAAATAACTCCACGG |
| SEQ ID NO: 1976 | mm09628_Lama1 | CTTGAAGGAACGAAACCCCG |
| SEQ ID NO: 1977 | mm09629_Lama2 | GATGAGAAATATGCCCAGCG |
| SEQ ID NO: 1978 | mm09630_Lama2 | ATGACGTGGAGTACAAACCC |
| SEQ ID NO: 1979 | mm09631_Lama2 | TTGTTGCTGGGCGAAATCAG |
| SEQ ID NO: 1980 | mm09632_Lama2 | GAGTGTCCTATTGGGTACAC |
| SEQ ID NO: 1981 | mm09637_Lama4 | AAAGATACAGATAAACAACT |
| SEQ ID NO: 1982 | mm09638_Lama4 | GTCTGCAGACATACTCAGAG |
| SEQ ID NO: 1983 | mm09639_Lama4 | GGAAGCTAACAAGACGACAG |

TABLE 1-continued mmSurf sgRNA library sequences

| SEQ ID NO | id_gRNA Target | Sequence |
|---|---|---|
| SEQ ID NO: 1984 | mm09640_Lama4 | ATCCGAACACCAGCTGACAA |
| SEQ ID NO: 1985 | mm09641_Lama5 | CCTACAGCATCGAGTAACGG |
| SEQ ID NO: 1986 | mm09642_Lama5 | GGCCGTTAATACCACCCGGG |
| SEQ ID NO: 1987 | mm09643_Lama5 | GATGTGACCAGTGTCGCGTG |
| SEQ ID NO: 1988 | mm09644_Lama5 | CTGCCAGCCCTACCAAACAG |
| SEQ ID NO: 1989 | mm09645_Lamb2 | ACAACTTGCTTGACCCACGG |
| SEQ ID NO: 1990 | mm09646_Lamb2 | GCAGCGGTAGCGTTCAAAGG |
| SEQ ID NO: 1991 | mm09647_Lamb2 | TAAGTGGAGGCGTATGCGAT |
| SEQ ID NO: 1992 | mm09648_Lamb2 | CAGAGGCCCTACCTGCAATG |
| SEQ ID NO: 1993 | mm09657_Lamp1 | ACCATTCGCAGTCTCGTAGG |
| SEQ ID NO: 1994 | mm09658_Lamp1 | GCCCAAATGACACATCTAGT |
| SEQ ID NO: 1995 | mm09659_Lamp1 | CATTGTACTTGGATACAGTG |
| SEQ ID NO: 1996 | mm09660_Lamp1 | CTCTTCCAAAAGTAATTGTG |
| SEQ ID NO: 1997 | mm09661_Lamp2 | GAGTGTAGTTGTAGTCGACG |
| SEQ ID NO: 1998 | mm09662_Lamp2 | CCTGACAAGGCGACACACGA |
| SEQ ID NO: 1999 | mm09663_Lamp2 | CACTTAAAGATGACATCCAA |
| SEQ ID NO: 2000 | mm09664_Lamp2 | GCTGCAGCTGAACATCACTG |
| SEQ ID NO: 2001 | mm09669_Anpep | AGAGCGTACTGAGTACCTGG |
| SEQ ID NO: 2002 | mm09670_Anpep | GTCCATGATAGTGCGCACCG |
| SEQ ID NO: 2003 | mm09671_Anpep | AGCACCCAGATATTCCACGT |
| SEQ ID NO: 2004 | mm09672_Anpep | GACCAGGGAGCTCTCACGGT |
| SEQ ID NO: 2005 | mm09673_Large | GATGTGTCTGATTTAAAGGT |
| SEQ ID NO: 2006 | mm09674_Large | CAGCAATAGAATCAGCAATG |
| SEQ ID NO: 2007 | mm09675_Large | GCAGGTAACAGCTCTGAGTG |
| SEQ ID NO: 2008 | mm09676_Large | ACAGCAGAGAGGGAACTCAT |
| SEQ ID NO: 2009 | mm09693_Lbp | ACCCAGCCTGGTGATAAACC |
| SEQ ID NO: 2010 | mm09694_Lbp | GTGGCCAGGATCACCGACAA |
| SEQ ID NO: 2011 | mm09695_Lbp | GTGCACATATCAGGAAATGT |
| SEQ ID NO: 2012 | mm09696_Lbp | TCCGATTAAAAATTTCACCC |
| SEQ ID NO: 2013 | mm09753_Ldlr | AAAATGCATCGCTAGCAAGT |
| SEQ ID NO: 2014 | mm09754_Ldlr | GGTGTCGTAGGACAAGTTAG |
| SEQ ID NO: 2015 | mm09755_Ldlr | GCAGACTGGTGTACTCGCTG |
| SEQ ID NO: 2016 | mm09756_Ldlr | TGACCGTGAACATGACTGCA |
| SEQ ID NO: 2017 | mm09777_Lfng | GGCGATGAAGACGTCGCGAG |
| SEQ ID NO: 2018 | mm09778_Lfng | AGACGCGGATCCACCGCCCG |
| SEQ ID NO: 2019 | mm09779_Lfng | CACACCCAAGACGTGTACAT |
| SEQ ID NO: 2020 | mm09780_Lfng | GGAGAGGCTATGCACCTCGC |
| SEQ ID NO: 2021 | mm09781_Lgals1 | TCTCCATGGGCATTGAAGCG |

TABLE 1-continued mmSurf sgRNA library sequences

| SEQ ID NO | id_gRNA Target | Sequence |
| --- | --- | --- |
| SEQ ID NO: 2022 | mm09782_Lgals1 | CCAGCCCGGGAGCATCACAG |
| SEQ ID NO: 2023 | mm09783_Lgals1 | GGTGTTACACACAATGGTGT |
| SEQ ID NO: 2024 | mm09784_Lgals1 | TCTCAAAGTTCGGGGAGAGG |
| SEQ ID NO: 2025 | mm09785_Lgals3 | TCTGGAAACCCAAACCCTCA |
| SEQ ID NO: 2026 | mm09786_Lgals3 | ATTGTTCTAGATTTCAGGAG |
| SEQ ID NO: 2027 | mm09787_Lgals3 | CCATGATTGTGATCAGCATG |
| SEQ ID NO: 2028 | mm09788_Lgals3 | TTCTTACCAGTGGTCCAGCG |
| SEQ ID NO: 2029 | mm09809_Lhcgr | TATACATAACCACCATACCA |
| SEQ ID NO: 2030 | mm09810_Lhcgr | AACCTGCTATACATTGAACC |
| SEQ ID NO: 2031 | mm09811_Lhcgr | GTGGCTAGGGTAGGTCAGCG |
| SEQ ID NO: 2032 | mm09812_Lhcgr | GACCAGTCGTTATAAACTGA |
| SEQ ID NO: 2033 | mm09849_Lifr | CGACGATGTGTACGGAACGG |
| SEQ ID NO: 2034 | mm09850_Lifr | CATTTGCACGCCTAACCGGT |
| SEQ ID NO: 2035 | mm09851_Lifr | TCACAGTAGAGCAAGCGGTG |
| SEQ ID NO: 2036 | mm09852_Lifr | TGTTTCGTGTTCATTGAACG |
| SEQ ID NO: 2037 | mm09873_Lipg | CGGATGTTAAAAGCCACAGA |
| SEQ ID NO: 2038 | mm09874_Lipg | GAAAGATGCTAACGTCGTGG |
| SEQ ID NO: 2039 | mm09875_Lipg | AAGGGGTGGACATCAACAGA |
| SEQ ID NO: 2040 | mm09876_Lipg | AAGAACCGTTGTAATAACAT |
| SEQ ID NO: 2041 | mm09953_Anxa1 | GTGCAAGGCAGCAACATCCG |
| SEQ ID NO: 2042 | mm09954_Anxa1 | CAAGCTGTAAAATCATACAA |
| SEQ ID NO: 2043 | mm09955_Anxa1 | GTACTTACAGGAGAATGGAA |
| SEQ ID NO: 2044 | mm09956_Anxa1 | GCTCCTGCTGGTCAGAATTG |
| SEQ ID NO: 2045 | mm09957_Lpl | GAAAAACGTACCGTCTGCTG |
| SEQ ID NO: 2046 | mm09958_Lpl | CCATCCATGGATCACCACGA |
| SEQ ID NO: 2047 | mm09959_Lpl | TGGATTCCAATACTTCGACC |
| SEQ ID NO: 2048 | mm09960_Lpl | TGACACTGGATAATGTTGCT |
| SEQ ID NO: 2049 | mm09973_Lrp1 | GCTGCGGAACAGTACCACGT |
| SEQ ID NO: 2050 | mm09974_Lrp1 | AAATGCCGGGTAAATAACGG |
| SEQ ID NO: 2051 | mm09975_Lrp1 | ACTGCGTCTTACCCAGACTG |
| SEQ ID NO: 2052 | mm09976_Lrp1 | TGACGGTAGCGATGATTGCG |
| SEQ ID NO: 2053 | mm09977_Lrp5 | CGTGTACTGGACCGACGATG |
| SEQ ID NO: 2054 | mm09978_Lrp5 | TGGGACCAATTGTATGACAC |
| SEQ ID NO: 2055 | mm09979_Lrp5 | GGAGACTAACAACAACGATG |
| SEQ ID NO: 2056 | mm09980_Lrp5 | TGGGTGAGTACAGAGCACTA |
| SEQ ID NO: 2057 | mm09981_Lrp6 | GGATCTAACACGATAGCCCG |
| SEQ ID NO: 2058 | mm09982_Lrp6 | TTGCCTTAGATCCATCAAGT |
| SEQ ID NO: 2059 | mm09983_Lrp6 | TGTGTCCTCAAATAACGTCA |

TABLE 1-continued mmSurf sgRNA library sequences

| SEQ ID NO | id_gRNA Target | Sequence |
|---|---|---|
| SEQ ID NO: 2060 | mm09984_Lrp6 | GTTGTTCATCAATCACCATG |
| SEQ ID NO: 2061 | mm09985_Lrpap1 | AGACTGCGCAGTATCAACCA |
| SEQ ID NO: 2062 | mm09986_Lrpap1 | CTGACCTGAAGATACAAGAG |
| SEQ ID NO: 2063 | mm09987_Lrpap1 | AGAATAGGAAGGTACCGTTG |
| SEQ ID NO: 2064 | mm09988_Lrpap1 | CGCCAAGCGCGAGTCCGGGG |
| SEQ ID NO: 2065 | mm09997_Lrrn1 | CACTACGGAAAGCCAAACGG |
| SEQ ID NO: 2066 | mm09998_Lrrn1 | CCATGCCACCGGAATACAGG |
| SEQ ID NO: 2067 | mm09999_Lrrn1 | GAGGTCATTACAATCCACGG |
| SEQ ID NO: 2068 | mm10000_Lrrn1 | TGGGAGTGGAATCAAACCAG |
| SEQ ID NO: 2069 | mm10025_Ltb | AGGTAATAGACGCCGTCCTG |
| SEQ ID NO: 2070 | mm10026_Ltb | GATAGGCACTGCCAACAACA |
| SEQ ID NO: 2071 | mm10027_Ltb | TGTTGCGCAGTCCTCTCGGG |
| SEQ ID NO: 2072 | mm10028_Ltb | ACCCGACGTCCCTGATCCTG |
| SEQ ID NO: 2073 | mm10033_Ltbr | GGAAGTGTCCCGGCTTACAG |
| SEQ ID NO: 2074 | mm10034_Ltbr | CTCATTGTCCAGATACACAC |
| SEQ ID NO: 2075 | mm10035_Ltbr | TGTTCATTATAGGAATTATG |
| SEQ ID NO: 2076 | mm10036_Ltbr | AGCTCCAGGTACCTCCTACT |
| SEQ ID NO: 2077 | mm10041_Ltf | AACCTGAGTATGGCTCCTCG |
| SEQ ID NO: 2078 | mm10042_Ltf | AGAAGCGCAAGTGTGATCAG |
| SEQ ID NO: 2079 | mm10043_Ltf | GATGCCATGACTCTTGATGG |
| SEQ ID NO: 2080 | mm10044_Ltf | AGTTACCAAATAAAGCCGAA |
| SEQ ID NO: 2081 | mm10049_Lum | AACAACCTGACCGAGTCCGT |
| SEQ ID NO: 2082 | mm10050_Lum | ATTTGCCCATACATGAAGAG |
| SEQ ID NO: 2083 | mm10051_Lum | TAAAGGTACTTGATGCCAGG |
| SEQ ID NO: 2084 | mm10052_Lum | TCTGATTGAAGCTCAAATCC |
| SEQ ID NO: 2085 | mm10065_Klrb1c | GAGATGCAACACTTAACTGG |
| SEQ ID NO: 2086 | mm10066_Klrb1c | TCCTGGGTGGCTTTAAACCG |
| SEQ ID NO: 2087 | mm10067_Klrb1c | TAAGACACTCATCCCAATCA |
| SEQ ID NO: 2088 | mm10068_Klrb1c | GAGGAAGGTCAAGCTGACTG |
| SEQ ID NO: 2089 | mm10077_Cd93 | ACTCCAGGAATATTTCACTG |
| SEQ ID NO: 2090 | mm10078_Cd93 | GCCTGCTATACAGCCCATTG |
| SEQ ID NO: 2091 | mm10079_Cd93 | TGGGTTGGTTACCAACCCAG |
| SEQ ID NO: 2092 | mm10080_Cd93 | AGTGGCATGAGAGTCCCTGT |
| SEQ ID NO: 2093 | mm10081_Ly6c1 | CACAAGAAGAATGAGCACAC |
| SEQ ID NO: 2094 | mm10082_Ly6c1 | CCCTGATTGGCACACCAGCA |
| SEQ ID NO: 2095 | mm10083_Ly6c1 | GCAGAAAGAAAGGCACTGAC |
| SEQ ID NO: 2096 | mm10084_Ly6c1 | ACTGTGTGCAGAAAGAGGTG |
| SEQ ID NO: 2097 | mm10085_Ly6d | CTGGCAGCATTGTGTGACCT |

TABLE 1-continued mmSurf sgRNA library sequences

| SEQ ID NO | id_gRNA Target | Sequence |
|---|---|---|
| SEQ ID NO: 2098 | mm10086_Ly6d | TGCCAACTGTAAGAACCCTC |
| SEQ ID NO: 2099 | mm10087_Ly6d | CACGTGACATCGAAGTGCCC |
| SEQ ID NO: 2100 | mm10088_Ly6d | ACCTCCGACTACAGCCAGCA |
| SEQ ID NO: 2101 | mm10097_Epcam | CGGAGTCCGAAGAACCGACA |
| SEQ ID NO: 2102 | mm10098_Epcam | GGGCGATCCAGAACAACGAT |
| SEQ ID NO: 2103 | mm10099_Epcam | GATAACATTATTCTCATACT |
| SEQ ID NO: 2104 | mm10100_Epcam | GCAAGCTCTGATGGTCGTAG |
| SEQ ID NO: 2105 | mm10101_Ly75 | GTCACGAAACTCCATAATGG |
| SEQ ID NO: 2106 | mm10102_Ly75 | TAAGCTGTGTCCGCCAGACG |
| SEQ ID NO: 2107 | mm10103_Ly75 | GCTTGCTTGAGAAAACGTAA |
| SEQ ID NO: 2108 | mm10104_Ly75 | TCCTGTGAACGATGTTATCG |
| SEQ ID NO: 2109 | mm10105_Cd180 | AACACGAAGAGACTTGAGCT |
| SEQ ID NO: 2110 | mm10106_Cd180 | GTCTCTGCCATAAATATCAG |
| SEQ ID NO: 2111 | mm10107_Cd180 | TTCACAGAGACCCTCAAACA |
| SEQ ID NO: 2112 | mm10108_Cd180 | ACATTGCAGGAATAGAGCTG |
| SEQ ID NO: 2113 | mm10109_Il1rl1 | CACTTGTCAATTCACACACG |
| SEQ ID NO: 2114 | mm10110_Il1rl1 | ACCAGTTATCCTTAACACTG |
| SEQ ID NO: 2115 | mm10111_Il1rl1 | TTGATGTACTCGACAGTACG |
| SEQ ID NO: 2116 | mm10112_Il1rl1 | AGGACGCTCGACTTATCCTG |
| SEQ ID NO: 2117 | mm10121_Ly9 | TGCAGGTATAGGGTAGGTCG |
| SEQ ID NO: 2118 | mm10122_Ly9 | GAAACAATGTGACATACACA |
| SEQ ID NO: 2119 | mm10123_Ly9 | CGAGTGGCCCGAAATTCCAA |
| SEQ ID NO: 2120 | mm10124_Ly9 | ACAGATTCCACGATGATCTG |
| SEQ ID NO: 2121 | mm10157_Tm4sf1 | TGCTGCGGCTACGAAAACTA |
| SEQ ID NO: 2122 | mm10158_Tm4sf1 | ATCCCAATGAACACAAACGC |
| SEQ ID NO: 2123 | mm10159_Tm4sf1 | GGAGACAAAGTATGCTACGG |
| SEQ ID NO: 2124 | mm10160_Tm4sf1 | GGTGTAGTTCCATACTCCAT |
| SEQ ID NO: 2125 | mm10161_M6pr | ATCATGCTGATATATAAAGG |
| SEQ ID NO: 2126 | mm10162_M6pr | GGATAAGGAGTCAAAGAACG |
| SEQ ID NO: 2127 | mm10163_M6pr | AGGAGATCATCACCACTGCA |
| SEQ ID NO: 2128 | mm10164_M6pr | GGCTGCTATCCATCTCAAAG |
| SEQ ID NO: 2129 | mm10301_Man1a2 | AGTGGAGTAGGTCGAAACTG |
| SEQ ID NO: 2130 | mm10302_Man1a2 | AATTACAGAACATACGGATG |
| SEQ ID NO: 2131 | mm10303_Man1a2 | CTGACAGGTAATATGCAGCG |
| SEQ ID NO: 2132 | mm10304_Man1a2 | GGCAAAGGAGCTAAAAACCC |
| SEQ ID NO: 2133 | mm10305_Man2a1 | TGCGTCGAAATAATCTGACA |
| SEQ ID NO: 2134 | mm10306_Man2a1 | AGGAACCGCGAAAGACTGGG |
| SEQ ID NO: 2135 | mm10307_Man2a1 | CAGCTGGAAATTGTGACCGG |

TABLE 1-continued mmSurf sgRNA library sequences

| SEQ ID NO | id_gRNA Target | Sequence |
|---|---|---|
| SEQ ID NO: 2136 | mm10308_Man2a1 | ACAATCCCTTTGAACAAGAA |
| SEQ ID NO: 2137 | mm10309_Man2b1 | ATGTTGTAAATGACTACGCG |
| SEQ ID NO: 2138 | mm10310_Man2b1 | TGAGTTCAATGCAAAAACGT |
| SEQ ID NO: 2139 | mm10311_Man2b1 | CTTGATAGTCAATGCGCCCA |
| SEQ ID NO: 2140 | mm10312_Man2b1 | AGCTCCCAGAGGTAACACGT |
| SEQ ID NO: 2141 | mm10325_Marco | TTCCAGATTAAAGGTGAACG |
| SEQ ID NO: 2142 | mm10326_Marco | TAGGTCTCACTGGCCCCAAG |
| SEQ ID NO: 2143 | mm10327_Marco | CAATGGATCACTAGCTATCG |
| SEQ ID NO: 2144 | mm10328_Marco | GTGCACCCGTAAGTCCCTGG |
| SEQ ID NO: 2145 | mm10337_Mas1 | GTGCTGGACACTAACATGAG |
| SEQ ID NO: 2146 | mm10338_Mas1 | ATATGGGTAGAGGACCGAT |
| SEQ ID NO: 2147 | mm10339_Mas1 | AATACACATGACATACTCCA |
| SEQ ID NO: 2148 | mm10340_Mas1 | TTCTCGGAGTGACTGCCGGG |
| SEQ ID NO: 2149 | mm10349_Masp1 | TTAATGTAGTCATAGGGACA |
| SEQ ID NO: 2150 | mm10350_Masp1 | GCGGCAATCTCTTTACCCAG |
| SEQ ID NO: 2151 | mm10351_Masp1 | GGAATATTACTGTCCCGGAG |
| SEQ ID NO: 2152 | mm10352_Masp1 | GACAACTCAGGAGAGAACCG |
| SEQ ID NO: 2153 | mm10429_Mc2r | ATGGGTTATCTTAAGCCTCG |
| SEQ ID NO: 2154 | mm10430_Mc2r | ACAATCGGAGTTATTTCTTG |
| SEQ ID NO: 2155 | mm10431_Mc2r | GGCGCATGGTCACAATGCTA |
| SEQ ID NO: 2156 | mm10432_Mc2r | AGATAGAGCCCAGCAAAGAG |
| SEQ ID NO: 2157 | mm10477_Cd46 | CTGTGAGCCAAATCATACAT |
| SEQ ID NO: 2158 | mm10478_Cd46 | TCCATAGCTTCAAATGGCCG |
| SEQ ID NO: 2159 | mm10479_Cd46 | GGCCTCAGCATAGACGCCCA |
| SEQ ID NO: 2160 | mm10480_Cd46 | ACAGTTGTGATCCTACCCCA |
| SEQ ID NO: 2161 | mm10497_Cma1 | AAACATCTAAAGAAGACACG |
| SEQ ID NO: 2162 | mm10498_Cma1 | GCCAAGCTAACCCTAGGTGT |
| SEQ ID NO: 2163 | mm10499_Cma1 | TTTCCAGATAGGCCATGTAG |
| SEQ ID NO: 2164 | mm10500_Cma1 | CTGCAGCTCACTGTGCGGGA |
| SEQ ID NO: 2165 | mm10537_Abcc1 | GGTGAAGTACAGATAGAACG |
| SEQ ID NO: 2166 | mm10538_Abcc1 | GGCTAGGATGACTTGCAGAG |
| SEQ ID NO: 2167 | mm10539_Abcc1 | AGCTGTAGGCACATTCACGT |
| SEQ ID NO: 2168 | mm10540_Abcc1 | GAGCGGAGGTCGATCAAGAG |
| SEQ ID NO: 2169 | mm10545_Slc3a2 | GTTCACCGGCTTATCCAAGG |
| SEQ ID NO: 2170 | mm10546_Slc3a2 | CGCCCGAACGATGATAACCA |
| SEQ ID NO: 2171 | mm10547_Slc3a2 | TATCACCAAGAACTTAAGTG |
| SEQ ID NO: 2172 | mm10548_Slc3a2 | GTACTGAATCCCTAGTCACT |
| SEQ ID NO: 2173 | mm10585_Men1 | TCCTCACTCTTGGATAACAG |

TABLE 1-continued mmSurf sgRNA library sequences

| SEQ ID NO | id_gRNA Target | Sequence |
| --- | --- | --- |
| SEQ ID NO: 2174 | mm10586_Men1 | GCGCTGCGACCGTAAGATGG |
| SEQ ID NO: 2175 | mm10587_Men1 | GGTGGTGTTTGGGCCCAACG |
| SEQ ID NO: 2176 | mm10588_Men1 | CACAGCGCCGCGGATCTGAG |
| SEQ ID NO: 2177 | mm10601_Mertk | AGGTACGGTTAGGACAGACG |
| SEQ ID NO: 2178 | mm10602_Mertk | TGTATCTGATCCCATATACG |
| SEQ ID NO: 2179 | mm10603_Mertk | GCTACCGGATATCTCACGTG |
| SEQ ID NO: 2180 | mm10604_Mertk | AGCGATGCTGTAATTAGCCA |
| SEQ ID NO: 2181 | mm10617_Met | GTATCGGACAGAGTTTACCA |
| SEQ ID NO: 2182 | mm10618_Met | TAATAACAAGCATTTCTCCG |
| SEQ ID NO: 2183 | mm10619_Met | CCCTGGTTTACTGACATACG |
| SEQ ID NO: 2184 | mm10620_Met | GGTGGATTTCATAGACAACG |
| SEQ ID NO: 2185 | mm10633_Mfge8 | CAGCAGAGTTAACTCACGGG |
| SEQ ID NO: 2186 | mm10634_Mfge8 | ACTCAAACTTGCGTCCGTCG |
| SEQ ID NO: 2187 | mm10635_Mfge8 | AGTGCTTACCGGTTTCACAG |
| SEQ ID NO: 2188 | mm10636_Mfge8 | GTGTGCAATGAGACTGAGAG |
| SEQ ID NO: 2189 | mm10673_Mif | CCCTCTGGCACGGAGGCGCG |
| SEQ ID NO: 2190 | mm10674_Mif | ACAGCAGCTTACTGTAGTTG |
| SEQ ID NO: 2191 | mm10675_Mif | GGCCACCGGCAAGCCCGCAC |
| SEQ ID NO: 2192 | mm10676_Mif | CACAGCATCGGCAAGATCGG |
| SEQ ID NO: 2193 | mm10677_Cxcl9 | ATCGTGCATTCCTTATCACT |
| SEQ ID NO: 2194 | mm10678_Cxcl9 | TTTGTTGCAATTGGGGCTTG |
| SEQ ID NO: 2195 | mm10679_Cxcl9 | CACAGTGCTACACTGAAGAA |
| SEQ ID NO: 2196 | mm10680_Cxcl9 | AGATCAAACCTGCCTAGATC |
| SEQ ID NO: 2197 | mm10741_Mme | CTTGCTCCTGACTATCATAG |
| SEQ ID NO: 2198 | mm10742_Mme | TGTTACCAGATATATATGGG |
| SEQ ID NO: 2199 | mm10743_Mme | TTTGACCAGCTGAATGACTG |
| SEQ ID NO: 2200 | mm10744_Mme | CTGGAAGGGAGGCCAAGTCG |
| SEQ ID NO: 2201 | mm10765_Mmp15 | AGACGCCGAAGTGTACGCCG |
| SEQ ID NO: 2202 | mm10766_Mmp15 | TGGGGTAGTTGTCTAGAACG |
| SEQ ID NO: 2203 | mm10767_Mmp15 | AAGCCAACCTGCGTCGACGG |
| SEQ ID NO: 2204 | mm10768_Mmp15 | AGGGTGCCATAATAGCGCTG |
| SEQ ID NO: 2205 | mm10785_Mmp7 | TGTTCCCTGGCCCATCAAAG |
| SEQ ID NO: 2206 | mm10786_Mmp7 | ATTTGATCCACTACGATCCG |
| SEQ ID NO: 2207 | mm10787_Mmp7 | GATCCCACTGAACTTCAAGA |
| SEQ ID NO: 2208 | mm10788_Mmp7 | ATAATGCAGAAACCTAGGTG |
| SEQ ID NO: 2209 | mm10829_Mog | CGATGAGAGTCAGCACACCG |
| SEQ ID NO: 2210 | mm10830_Mog | AATTCAGAGTGATAGGACCA |
| SEQ ID NO: 2211 | mm10831_Mog | TCACCTCTACCGAAATGGCA |

TABLE 1-continued mmSurf sgRNA library sequences

| SEQ ID NO | id_gRNA Target | Sequence |
|---|---|---|
| SEQ ID NO: 2212 | mm10832_Mog | TCTCACGTTCTGAATCCTAA |
| SEQ ID NO: 2213 | mm10857_Cd200 | AGGAACCCTTGATTGTGACA |
| SEQ ID NO: 2214 | mm10858_Cd200 | CACCTACAGCAAAACCCATG |
| SEQ ID NO: 2215 | mm10859_Cd200 | TTGTAGTGAAGGTGTACTAT |
| SEQ ID NO: 2216 | mm10860_Cd200 | GCCCCAAATCAGGCTGTAGG |
| SEQ ID NO: 2217 | mm10873_Mpl | GCTGTCGGATGAACACACGG |
| SEQ ID NO: 2218 | mm10874_Mpl | GGAACTTCAGATCCACTGGG |
| SEQ ID NO: 2219 | mm10875_Mpl | GTGAACGGCACCTTGCGCTG |
| SEQ ID NO: 2220 | mm10876_Mpl | GCTACGCAGCCAACCCGACG |
| SEQ ID NO: 2221 | mm10889_Mpz | GGGACAACCTTACATCGATG |
| SEQ ID NO: 2222 | mm10890_Mpz | AAAAACCCACCGGACATAGT |
| SEQ ID NO: 2223 | mm10891_Mpz | CATTGTGGTTTACACGGACA |
| SEQ ID NO: 2224 | mm10892_Mpz | CAACACCACCCCATACCTAG |
| SEQ ID NO: 2225 | mm10897_Mrc1 | TTCTGGAATGACATCAACTG |
| SEQ ID NO: 2226 | mm10898_Mrc1 | TCTCGAGCACAGGTCATCCG |
| SEQ ID NO: 2227 | mm10899_Mrc1 | AGCCATGCTGTAGTACCGGA |
| SEQ ID NO: 2228 | mm10900_Mrc1 | TTTCTCACCATATCCGAGCT |
| SEQ ID NO: 2229 | mm10901_Mrc2 | ATGGCAGTGTCGTACACTAG |
| SEQ ID NO: 2230 | mm10902_Mrc2 | GAACCAGACATTGGTCGACA |
| SEQ ID NO: 2231 | mm10903_Mrc2 | ACAGATCAGCCGGACAACCC |
| SEQ ID NO: 2232 | mm10904_Mrc2 | GTATACATGACAGCCAGACA |
| SEQ ID NO: 2233 | mm10953_Msn | CGCTTGTTAATCCGAAGCCG |
| SEQ ID NO: 2234 | mm10954_Msn | CCGGGCCAAGTTCTACCCAG |
| SEQ ID NO: 2235 | mm10955_Msn | GAAGCAACTTATCTCCAGCC |
| SEQ ID NO: 2236 | mm10956_Msn | CAGACTAAGAAGGCTCAGCA |
| SEQ ID NO: 2237 | mm11085_Muc1 | AGCTCTCCAGTAGTCCACGG |
| SEQ ID NO: 2238 | mm11086_Muc1 | TTGTAGTTGAGGTACCACTG |
| SEQ ID NO: 2239 | mm11087_Muc1 | TGGCCATGGTAGGAGAAACA |
| SEQ ID NO: 2240 | mm11088_Muc1 | AGAACTGGTAGGTAGCACCG |
| SEQ ID NO: 2241 | mm11097_Mug1 | GGGGAGATAGTTCATCACAG |
| SEQ ID NO: 2242 | mm11098_Mug1 | ACATCCTTCTCAGTTCCATG |
| SEQ ID NO: 2243 | mm11099_Mug1 | GGAAGAGCCCGAGATGCATG |
| SEQ ID NO: 2244 | mm11100_Mug1 | GCTACGTCCCCTGAATGAGT |
| SEQ ID NO: 2245 | mm11214_Myh9 | GCTGGTACTCACGAATCGAG |
| SEQ ID NO: 2246 | mm11215_Myh9 | TGGACTATAAAGCTGACGAG |
| SEQ ID NO: 2247 | mm11216_Myh9 | TCAAGGAGCGATACTACTCA |
| SEQ ID NO: 2248 | mm11217_Myh9 | ACTGCAGGTCAAGTTCAGCG |
| SEQ ID NO: 2249 | mm11330_Naga | GCTAGGAAGGCAATCCCGTG |

TABLE 1-continued mmSurf sgRNA library sequences

| SEQ ID NO | id_gRNA Target | Sequence |
|---|---|---|
| SEQ ID NO: 2250 | mm11331_Naga | TGTTGAGGTATACATAGCCC |
| SEQ ID NO: 2251 | mm11332_Naga | TCTCACAAACCAGTCCAGGA |
| SEQ ID NO: 2252 | mm11333_Naga | TGTTCAGGTGAACTACACCG |
| SEQ ID NO: 2253 | mm11382_Ncam1 | GAAGATCTTCACGTTGACAG |
| SEQ ID NO: 2254 | mm11383_Ncam1 | CTCCTGGTTCTCCCCCAATG |
| SEQ ID NO: 2255 | mm11384_Ncam1 | GCCATCGGCATCACACACCA |
| SEQ ID NO: 2256 | mm11385_Ncam1 | ACCTACCAAAGACCTTGAGG |
| SEQ ID NO: 2257 | mm11386_Ncam2 | GTGCCCACCAATCCGACTAG |
| SEQ ID NO: 2258 | mm11387_Ncam2 | TACCAAAATACTAACTGTCG |
| SEQ ID NO: 2259 | mm11388_Ncam2 | GTGAGCCTGAGAGTATCGAC |
| SEQ ID NO: 2260 | mm11389_Ncam2 | AGGAAGAAAGATGATACTCG |
| SEQ ID NO: 2261 | mm11410_Ncl | AGCCAAAGTCATTCCAACAC |
| SEQ ID NO: 2262 | mm11411_Ncl | CCTCTCTTTCAACATCACTG |
| SEQ ID NO: 2263 | mm11412_Ncl | TAAAAATGATCTTGCTGTTG |
| SEQ ID NO: 2264 | mm11413_Ncl | TCCTATGAAAGCCAAGAGTG |
| SEQ ID NO: 2265 | mm11430_Ndp | ACAGTGCTGAAGGACACCAA |
| SEQ ID NO: 2266 | mm11431_Ndp | ACTGTACAAATGTAGCTCAA |
| SEQ ID NO: 2267 | mm11432_Ndp | TGCTCCTGGCCAGATGTGAG |
| SEQ ID NO: 2268 | mm11433_Ndp | AACAGACAGTTCATTTCTGA |
| SEQ ID NO: 2269 | mm11438_Ndufa2 | GCAGGGATTTCATCGTGCAA |
| SEQ ID NO: 2270 | mm11439_Ndufa2 | TCTGATCCGCGAATGCTCGG |
| SEQ ID NO: 2271 | mm11440_Ndufa2 | ATTCGCGGATCAGAATGGGC |
| SEQ ID NO: 2272 | mm11441_Ndufa2 | GGCTGCCGCTGCTAGCCGAG |
| SEQ ID NO: 2273 | mm11462_Sept2 | AGTGGACACTCCCGGCTACG |
| SEQ ID NO: 2274 | mm11463_Sept2 | CGCTACCTACATGATGAGAG |
| SEQ ID NO: 2275 | mm11464_Sept2 | CACCGAAAATCAGTGAAGAA |
| SEQ ID NO: 2276 | mm11465_Sept2 | GCGTGAGCGGCTTAAGAAAA |
| SEQ ID NO: 2277 | mm11482_Neo1 | CGTAACCGATGGCATAACCT |
| SEQ ID NO: 2278 | mm11483_Neo1 | GGTTCCAAGATTATCCACAG |
| SEQ ID NO: 2279 | mm11484_Neo1 | AACACCGTTATCTGGCAATG |
| SEQ ID NO: 2280 | mm11485_Neo1 | ACTCCCGCTACTACACAGTC |
| SEQ ID NO: 2281 | mm11490_Neu1 | ACAGCCTTCATCGTAGACGA |
| SEQ ID NO: 2282 | mm11491_Neu1 | TTGGTTTGGAGTAAGGACGA |
| SEQ ID NO: 2283 | mm11492_Neu1 | TGTGTGTGGACACGGGACGC |
| SEQ ID NO: 2284 | mm11493_Neu1 | GAAAAAATCTGCATCCGATG |
| SEQ ID NO: 2285 | mm11514_Nf2 | GACCCCTCTGTGCACAAGCG |
| SEQ ID NO: 2286 | mm11515_Nf2 | TGTGAACTACTTTACAATCC |
| SEQ ID NO: 2287 | mm11516_Nf2 | GTCGCCTCATAAATAGGTCA |

TABLE 1-continued mmSurf sgRNA library sequences

| SEQ ID NO | id_gRNA Target | Sequence |
| --- | --- | --- |
| SEQ ID NO: 2288 | mm11517_Nf2 | CAAGAGATGAGTTAGAGAGG |
| SEQ ID NO: 2289 | mm11626_Ngfr | TGGAGCAATAGACAGGAATG |
| SEQ ID NO: 2290 | mm11627_Ngfr | ACAAGGTCTACGCCCCCGGA |
| SEQ ID NO: 2291 | mm11628_Ngfr | AGGGTAGGCACGGGTCCACG |
| SEQ ID NO: 2292 | mm11629_Ngfr | TATGTCCGCTCCCTGTGTGG |
| SEQ ID NO: 2293 | mm11642_Nid1 | TGGCTGTGTAAGAGCGCCCG |
| SEQ ID NO: 2294 | mm11643_Nid1 | AGCCCTCTACACACTCGCAG |
| SEQ ID NO: 2295 | mm11644_Nid1 | TGTGCACCGAGGCTCCATAG |
| SEQ ID NO: 2296 | mm11645_Nid1 | CTGACCCACACAATGTACCT |
| SEQ ID NO: 2297 | mm11646_Nid2 | TGAGATACATACCTTCAACA |
| SEQ ID NO: 2298 | mm11647_Nid2 | GTATCACTCAAACTGCCGAG |
| SEQ ID NO: 2299 | mm11648_Nid2 | CTTGATCATTAGATCCCACG |
| SEQ ID NO: 2300 | mm11649_Nid2 | GGATCTACACGCTTACATCG |
| SEQ ID NO: 2301 | mm11722_Cd244 | AAAGATACATTTGACCAACT |
| SEQ ID NO: 2302 | mm11723_Cd244 | CTGCTGGAGATCACCAACAC |
| SEQ ID NO: 2303 | mm11724_Cd244 | AGTGCCCCCACTTACTCGAA |
| SEQ ID NO: 2304 | mm11725_Cd244 | GTGAGCTACGCTTTGTACAG |
| SEQ ID NO: 2305 | mm11782_Notch1 | ATATACATACCCGTCCACTC |
| SEQ ID NO: 2306 | mm11783_Notch1 | CTGCCCACCAGGCTTCGTCG |
| SEQ ID NO: 2307 | mm11784_Notch1 | CAGTGTAATAATCACGCATG |
| SEQ ID NO: 2308 | mm11785_Notch1 | ACCTGCAAGGACATGACCAG |
| SEQ ID NO: 2309 | mm11786_Notch2 | GGGCTGTGTAGAGTTCGCAG |
| SEQ ID NO: 2310 | mm11787_Notch2 | CAGCAACCCTTGTCACAAGG |
| SEQ ID NO: 2311 | mm11788_Notch2 | AGGGACCAGTGAAACCCACG |
| SEQ ID NO: 2312 | mm11789_Notch2 | TGGCCACCGTTAAGGCAGTG |
| SEQ ID NO: 2313 | mm11798_Notch4 | GCTGTGACAGGCACTCATTG |
| SEQ ID NO: 2314 | mm11799_Notch4 | ACCTGCAAGACACACCTCG |
| SEQ ID NO: 2315 | mm11800_Notch4 | CTCACTACAGGTCAACCCTG |
| SEQ ID NO: 2316 | mm11801_Notch4 | CACAGGGCAGAGACACTGGT |
| SEQ ID NO: 2317 | mm11826_Npc1 | GGGGAAGGTGATCACAAGCG |
| SEQ ID NO: 2318 | mm11827_Npc1 | CATCATGTGGGTCACCTACG |
| SEQ ID NO: 2319 | mm11828_Npc1 | CGGTTCGTAGATATGAACAC |
| SEQ ID NO: 2320 | mm11829_Npc1 | CCATCCCTACCTGAAAACAC |
| SEQ ID NO: 2321 | mm11854_Npr3 | ACAGCGACGACAAACTCGAG |
| SEQ ID NO: 2322 | mm11855_Npr3 | GCTGGCGGCTCAAAAGATCG |
| SEQ ID NO: 2323 | mm11856_Npr3 | TCCAAACAGTCACCCTACTG |
| SEQ ID NO: 2324 | mm11857_Npr3 | GTGGTGATCATGTGTGCCAG |
| SEQ ID NO: 2325 | mm11886_Slc11a1 | GGGTGTGCTACCACATACTG |

TABLE 1-continued mmSurf sgRNA library sequences

| SEQ ID NO | id_gRNA Target | Sequence |
|---|---|---|
| SEQ ID NO: 2326 | mm11887_Slc11a1 | GAGAAGTAGACAGAACCCGC |
| SEQ ID NO: 2327 | mm11888_Slc11a1 | CCTAGCATGATACCGTCCAG |
| SEQ ID NO: 2328 | mm11889_Slc11a1 | GAATGGGGATCTTCTCACTC |
| SEQ ID NO: 2329 | mm11890_Slc11a2 | ATGTCACCGTCAGTATCCCA |
| SEQ ID NO: 2330 | mm11891_Slc11a2 | AAACACAAAAGTGTCTGCGA |
| SEQ ID NO: 2331 | mm11892_Slc11a2 | TGAGAAAATCCCCATTCCTG |
| SEQ ID NO: 2332 | mm11893_Slc11a2 | CCTTGACTAAGGCAGAATGC |
| SEQ ID NO: 2333 | mm11914_Nrp1 | CTCTGACTATGAGACACATG |
| SEQ ID NO: 2334 | mm11915_Nrp1 | CAAGACTCGAATCCTCCCGG |
| SEQ ID NO: 2335 | mm11916_Nrp1 | TGAACTACCCTGAAAATGGG |
| SEQ ID NO: 2336 | mm11917_Nrp1 | TGTCCTCCAAATCGAAATGT |
| SEQ ID NO: 2337 | mm11918_Nrp2 | AGCGAACAATGATGCGACCG |
| SEQ ID NO: 2338 | mm11919_Nrp2 | GGTGAACTTGATGTATAACA |
| SEQ ID NO: 2339 | mm11920_Nrp2 | CCAAACTCCGCTCGTCCACG |
| SEQ ID NO: 2340 | mm11921_Nrp2 | CAGAGCGGCTACTAACCAGG |
| SEQ ID NO: 2341 | mm11926_Nrxn1 | GCTCTACATCGACCGCGCCG |
| SEQ ID NO: 2342 | mm11927_Nrxn1 | GTATTCAGATCCCTTGAACG |
| SEQ ID NO: 2343 | mm11928_Nrxn1 | TGAATGGCACACAGTGCGTG |
| SEQ ID NO: 2344 | mm11929_Nrxn1 | GACGACGAGCCTCCCAACAG |
| SEQ ID NO: 2345 | mm11958_Musk | CACCCGCAGAGAGTCGACCG |
| SEQ ID NO: 2346 | mm11959_Musk | AGAAAAGTTCAGTACCGCAA |
| SEQ ID NO: 2347 | mm11960_Musk | TGCAGGACAGTACCGCTGTG |
| SEQ ID NO: 2348 | mm11961_Musk | ATGGAAGGAAAGGCCCACCG |
| SEQ ID NO: 2349 | mm11978_Ntn1 | TCTGTTTGGTGATAGGCGCG |
| SEQ ID NO: 2350 | mm11979_Ntn1 | TGGGATCCGAAGAGTTGCAG |
| SEQ ID NO: 2351 | mm11980_Ntn1 | TGTCCATTCTCATCCGAGCA |
| SEQ ID NO: 2352 | mm11981_Ntn1 | GTGTGACTGTAGGCACAACA |
| SEQ ID NO: 2353 | mm11986_Ntrk1 | GCGGAGGCCACTCTTCACGA |
| SEQ ID NO: 2354 | mm11987_Ntrk1 | GACACAACACCAGTTGTGGT |
| SEQ ID NO: 2355 | mm11988_Ntrk1 | ACTAATGAGACCATGCGGCA |
| SEQ ID NO: 2356 | mm11989_Ntrk1 | ACCCAGTGTCATGAAGTGTA |
| SEQ ID NO: 2357 | mm11990_Ntrk2 | ATGACGTTGAAGCTTACGTG |
| SEQ ID NO: 2358 | mm11991_Ntrk2 | AACCTGCAGATACCCAATTG |
| SEQ ID NO: 2359 | mm11992_Ntrk2 | AATGCACCAGTGGTGATCTG |
| SEQ ID NO: 2360 | mm11993_Ntrk2 | CTCAGTACACCAAATCCTAG |
| SEQ ID NO: 2361 | mm11994_Ntrk3 | ACTCACATATAACGCAAGTG |
| SEQ ID NO: 2362 | mm11995_Ntrk3 | CCACTGCATCACATCAACCA |
| SEQ ID NO: 2363 | mm11996_Ntrk3 | CCAGGCTCACCACACGTGGA |

TABLE 1-continued mmSurf sgRNA library sequences

| SEQ ID NO | id_gRNA Target | Sequence |
|---|---|---|
| SEQ ID NO: 2364 | mm11997_Ntrk3 | GTCAACCTGACTGTCCGAGA |
| SEQ ID NO: 2365 | mm12002_Ntsr1 | CCTGGTGTGCACACCCACGG |
| SEQ ID NO: 2366 | mm12003_Ntsr1 | AGCACTGTGCATTACCACCT |
| SEQ ID NO: 2367 | mm12004_Ntsr1 | AGGATGGAGATGATCAGCAT |
| SEQ ID NO: 2368 | mm12005_Ntsr1 | CCCACATCCACAGTTCGGAC |
| SEQ ID NO: 2369 | mm12006_Ntsr2 | CGAGATCGCCGAAGACCCAG |
| SEQ ID NO: 2370 | mm12007_Ntsr2 | GAAGATGAGCGAATAGAGCG |
| SEQ ID NO: 2371 | mm12008_Ntsr2 | TGTCCCATGATAACCGCCAT |
| SEQ ID NO: 2372 | mm12009_Ntsr2 | TAGCACCGTGCACACACGCG |
| SEQ ID NO: 2373 | mm12066_Ocln | CTTTCCGCATAGTCAGATGG |
| SEQ ID NO: 2374 | mm12067_Ocln | TCCCATTATGTACACGATCG |
| SEQ ID NO: 2375 | mm12068_Ocln | TCCGGATAAAAGAGTACGC |
| SEQ ID NO: 2376 | mm12069_Ocln | ATATTTGTATCACTACTGTG |
| SEQ ID NO: 2377 | mm12122_Olfr13 | GTAAGGGTAAAAGTAACACG |
| SEQ ID NO: 2378 | mm12123_Olfr13 | CAGGCAGATGAGCCCCACGA |
| SEQ ID NO: 2379 | mm12124_Olfr13 | AGGACATCACCACTAGGAGA |
| SEQ ID NO: 2380 | mm12125_Olfr13 | TGATGGCAGAGTAACGGAGT |
| SEQ ID NO: 2381 | mm12294_Omg | AAATACCCTAAGAAGTCTCG |
| SEQ ID NO: 2382 | mm12295_Omg | ATATACCAATCTGAGAACCC |
| SEQ ID NO: 2383 | mm12296_Omg | AACTTGACTACATTACCACC |
| SEQ ID NO: 2384 | mm12297_Omg | ACAAGGAGTCCCTATCACAT |
| SEQ ID NO: 2385 | mm12370_Osmr | TATACCTGGCAAATCACTGA |
| SEQ ID NO: 2386 | mm12371_Osmr | CCCGTATCTGGAGACACGAT |
| SEQ ID NO: 2387 | mm12372_Osmr | AGAGGTAGTTTGCGCTCATG |
| SEQ ID NO: 2388 | mm12373_Osmr | ATCAATTGTCAAGCCACGAA |
| SEQ ID NO: 2389 | mm12422_Mybbp1a | ACAGGCACTAGACCTGATCG |
| SEQ ID NO: 2390 | mm12423_Mybbp1a | CCAGAGATAAGTACATACGT |
| SEQ ID NO: 2391 | mm12424_Mybbp1a | TTTGGACGACCGCAACCGTG |
| SEQ ID NO: 2392 | mm12425_Mybbp1a | AGATATGACCAAATACACTC |
| SEQ ID NO: 2393 | mm12426_P2rx1 | ACTGCTGATAAGGCCACTTG |
| SEQ ID NO: 2394 | mm12427_P2rx1 | ACTCTCGCACCACATAGCCA |
| SEQ ID NO: 2395 | mm12428_P2rx1 | GCTGGTACGAAACAAGAAGG |
| SEQ ID NO: 2396 | mm12429_P2rx1 | GGCATATGCCAAGATGACAG |
| SEQ ID NO: 2397 | mm12430_P2rx4 | AGTGGGGCTCATGAACCGCG |
| SEQ ID NO: 2398 | mm12431_P2rx4 | GTCACCGTGAACCAGACGCA |
| SEQ ID NO: 2399 | mm12432_P2rx4 | CTGAGCTGGGACCACATAGT |
| SEQ ID NO: 2400 | mm12433_P2rx4 | CTACCAGGAAACGGACTCTG |
| SEQ ID NO: 2401 | mm12434_P2rx7 | CTGACCGGCGTTGTAAAAAG |

TABLE 1-continued mmSurf sgRNA library sequences

| SEQ ID NO | id_gRNA Target | Sequence |
|---|---|---|
| SEQ ID NO: 2402 | mm12435_P2rx7 | GTTACCTGAAGTTGTAGCCG |
| SEQ ID NO: 2403 | mm12436_P2rx7 | GTGTTCCATCTTCCGACTAG |
| SEQ ID NO: 2404 | mm12437_P2rx7 | ACCTCTTACCAAGCCAAAGT |
| SEQ ID NO: 2405 | mm12442_P2ry1 | TGCTACCGTAGAGATTTACG |
| SEQ ID NO: 2406 | mm12443_P2ry1 | AGCCTGCCCAGAGACTTGAG |
| SEQ ID NO: 2407 | mm12444_P2ry1 | CGGTCTTGGTCAGGGCACAT |
| SEQ ID NO: 2408 | mm12445_P2ry1 | AGCCAAATTGAACATGTACA |
| SEQ ID NO: 2409 | mm12450_P4ha1 | TCATGGAAACGGATAATCCG |
| SEQ ID NO: 2410 | mm12451_P4ha1 | GATCCATAATGAGAAAGACC |
| SEQ ID NO: 2411 | mm12452_P4ha1 | TGAAACGTCTGAACACTGAG |
| SEQ ID NO: 2412 | mm12453_P4ha1 | GGACACAAATACCATCTCAA |
| SEQ ID NO: 2413 | mm12454_P4ha2 | CTGTCAAATCAGACAGACGC |
| SEQ ID NO: 2414 | mm12455_P4ha2 | CACCAGGGACTTGGTAACAG |
| SEQ ID NO: 2415 | mm12456_P4ha2 | ATCCGGACACGATTTCCAGA |
| SEQ ID NO: 2416 | mm12457_P4ha2 | CTTCTCTGCGTAAATCAGAT |
| SEQ ID NO: 2417 | mm12458_P4hb | TAGGGTAATAAGCCGCACAG |
| SEQ ID NO: 2418 | mm12459_P4hb | TTTGGAATCACGTCCAACAG |
| SEQ ID NO: 2419 | mm12460_P4hb | GGTGGACTCAAGCGAAGTGA |
| SEQ ID NO: 2420 | mm12461_P4hb | AAGAGTGTATCTGACTATGA |
| SEQ ID NO: 2421 | mm12506_Pam | ATGGTGAGTATGGACTCGGT |
| SEQ ID NO: 2422 | mm12507_Pam | AGAATCTTACCCGATGTGGG |
| SEQ ID NO: 2423 | mm12508_Pam | ACTGGATATTCGCATGCCTG |
| SEQ ID NO: 2424 | mm12509_Pam | AATTCCTGTAAAATCCGACA |
| SEQ ID NO: 2425 | mm12510_Cntn3 | CATCGTTACAAACTGAATGG |
| SEQ ID NO: 2426 | mm12511_Cntn3 | TGTCGTGGAGTTAAACCCAT |
| SEQ ID NO: 2427 | mm12512_Cntn3 | AACATTCAATTGAAACACAG |
| SEQ ID NO: 2428 | mm12513_Cntn3 | CGCACCTGTCACAACCAAGT |
| SEQ ID NO: 2429 | mm12602_Pcna | ATACGTGCAAATTCACCCGA |
| SEQ ID NO: 2430 | mm12603_Pcna | GCGCAGAGTAAGCTGTACCA |
| SEQ ID NO: 2431 | mm12604_Pcna | GATATCCTGTGCAAAGAATG |
| SEQ ID NO: 2432 | mm12605_Pcna | TGCTTCGAATACTAGTGCTA |
| SEQ ID NO: 2433 | mm12626_Pcsk2 | TCCTGGGCTAGACTTGAACG |
| SEQ ID NO: 2434 | mm12627_Pcsk2 | AGAGCAACTCTCATCATACA |
| SEQ ID NO: 2435 | mm12628_Pcsk2 | GGATTTGACCGTAAAAGAG |
| SEQ ID NO: 2436 | mm12629_Pcsk2 | TTATCACAATGGGCTTGCAA |
| SEQ ID NO: 2437 | mm12630_Furin | ACCCTGTCTTACAATCGCCG |
| SEQ ID NO: 2438 | mm12631_Furin | ACAGCCCGTAGCCATACGAA |
| SEQ ID NO: 2439 | mm12632_Furin | GGGCACATTGCCGAACTGTG |

TABLE 1-continued mmSurf sgRNA library sequences

| SEQ ID NO | id_gRNA Target | Sequence |
|---|---|---|
| SEQ ID NO: 2440 | mm12633_Furin | ACAATGCCCGAATTGGAGGT |
| SEQ ID NO: 2441 | mm12642_Pcsk6 | GTTGCTGGCGTCATATCTCG |
| SEQ ID NO: 2442 | mm12643_Pcsk6 | CTGATAAGAACAGTCGCTGT |
| SEQ ID NO: 2443 | mm12644_Pcsk6 | GGCCACGCATACGTGCTGGG |
| SEQ ID NO: 2444 | mm12645_Pcsk6 | GGAAAGACAGTAGATGGACC |
| SEQ ID NO: 2445 | mm12666_Pdcd1 | CAATACAGGGATACCCACTA |
| SEQ ID NO: 2446 | mm12667_Pdcd1 | GACACACGGCGCAATGACAG |
| SEQ ID NO: 2447 | mm12668_Pdcd1 | CAGCTTGTCCAACTGGTCGG |
| SEQ ID NO: 2448 | mm12669_Pdcd1 | GCTCAAACCATTACAGAAGG |
| SEQ ID NO: 2449 | mm12738_Pdgfa | AGCCGCTCGATCAACTCCCG |
| SEQ ID NO: 2450 | mm12739_Pdgfa | CGGTCATTTACGAGATACCT |
| SEQ ID NO: 2451 | mm12740_Pdgfa | CTCTTGGAGATAGACTCCGT |
| SEQ ID NO: 2452 | mm12741_Pdgfa | ATTCGCAGGAAGAGAAGTAT |
| SEQ ID NO: 2453 | mm12742_Pdgfb | CCTCGGCGCTGACCAGACGC |
| SEQ ID NO: 2454 | mm12743_Pdgfb | CGAGTGCAAGACGCGCACAG |
| SEQ ID NO: 2455 | mm12744_Pdgfb | TGGAAAGCTCATCTCGAGGG |
| SEQ ID NO: 2456 | mm12745_Pdgfb | AGGCCCGGCATTGCACATTG |
| SEQ ID NO: 2457 | mm12746_Pdgfra | TAAGGCAGGAGAAACGATCG |
| SEQ ID NO: 2458 | mm12747_Pdgfra | TAACCTTGCACAATAACGGG |
| SEQ ID NO: 2459 | mm12748_Pdgfra | AGATATACTCATGTCCATCG |
| SEQ ID NO: 2460 | mm12749_Pdgfra | CACAGAATACTGCTTCTATG |
| SEQ ID NO: 2461 | mm12750_Pdgfrb | CGGACAGTGGCTGATCCACG |
| SEQ ID NO: 2462 | mm12751_Pdgfrb | CCGCAGAGAATGGCTACGTG |
| SEQ ID NO: 2463 | mm12752_Pdgfrb | ATGGACGTACCCCGCATGA |
| SEQ ID NO: 2464 | mm12753_Pdgfrb | CGGTCATGAGTACATCTACG |
| SEQ ID NO: 2465 | mm12782_Enpp1 | TACAACGCAAGTTGCCACTG |
| SEQ ID NO: 2466 | mm12783_Enpp1 | GGTGACCGCTAATCATCAGG |
| SEQ ID NO: 2467 | mm12784_Enpp1 | ATGTGAAAGCATCGATACCC |
| SEQ ID NO: 2468 | mm12785_Enpp1 | AACGTCTTGGTAGGGTACAT |
| SEQ ID NO: 2469 | mm12922_Abcb1a | ACTGAATGCTCCAATTAACA |
| SEQ ID NO: 2470 | mm12923_Abcb1a | CAGGAAGCTTAGTACCAAAG |
| SEQ ID NO: 2471 | mm12924_Abcb1a | CAAAGATCAGCATCATAAGT |
| SEQ ID NO: 2472 | mm12925_Abcb1a | AATGACGTCAGCATTACGAA |
| SEQ ID NO: 2473 | mm12926_Phb | GTGATGACTGGTACGTTCCG |
| SEQ ID NO: 2474 | mm12927_Phb | TTACCAGGGACACGTCATCC |
| SEQ ID NO: 2475 | mm12928_Phb | CCAATGCTGGTGTAGATACG |
| SEQ ID NO: 2476 | mm12929_Phb | CACTCACCACCACCGACTTG |
| SEQ ID NO: 2477 | mm13110_Pkd1 | ATTCCCGTACCGATATACCT |

TABLE 1-continued mmSurf sgRNA library sequences

| SEQ ID NO | id_gRNA Target | Sequence |
| --- | --- | --- |
| SEQ ID NO: 2478 | mm13111_Pkd1 | ACAGTTGCGTAGATCAACAT |
| SEQ ID NO: 2479 | mm13112_Pkd1 | AGCTCGCAGACATAACTATG |
| SEQ ID NO: 2480 | mm13113_Pkd1 | TGATGGTGTCCTATATACGT |
| SEQ ID NO: 2481 | mm13158_Pla2g1b | CCTTCAGGGGATCACTCCCG |
| SEQ ID NO: 2482 | mm13159_Pla2g1b | CCTGTCTAAGTCGTCCACTG |
| SEQ ID NO: 2483 | mm13160_Pla2g1b | GCATGAGTAGGAGTAAGTGT |
| SEQ ID NO: 2484 | mm13161_Pla2g1b | TGGTGCACTTGATCATATTG |
| SEQ ID NO: 2485 | mm13162_Pla2r1 | TGGATCGCCTACACGTCCAG |
| SEQ ID NO: 2486 | mm13163_Pla2r1 | ATTCCCAATCCATATAGCAG |
| SEQ ID NO: 2487 | mm13164_Pla2r1 | TCTGTGATGCTACGTGGCAA |
| SEQ ID NO: 2488 | mm13165_Pla2r1 | TTTGCATATATAAGGCAAGG |
| SEQ ID NO: 2489 | mm13174_Pla2g5 | CCGTTGTTATGGGCAACTGG |
| SEQ ID NO: 2490 | mm13175_Pla2g5 | GGTCGCGGGACACCCAAGGA |
| SEQ ID NO: 2491 | mm13176_Pla2g5 | GTCATAGGACTGGGTCCGAA |
| SEQ ID NO: 2492 | mm13177_Pla2g5 | TGAGTTCTAGCAAGCCCCCT |
| SEQ ID NO: 2493 | mm13194_Plat | TGAAGCCCTACAATGCAAGG |
| SEQ ID NO: 2494 | mm13195_Plat | CGAACCAAGATGCTTCAATG |
| SEQ ID NO: 2495 | mm13196_Plat | CCTCCTTTAATTCTAAACTG |
| SEQ ID NO: 2496 | mm13197_Plat | GACCACTTTAAGATGATTGG |
| SEQ ID NO: 2497 | mm13198_Plau | CCCCCAACAATCTTAAAGCG |
| SEQ ID NO: 2498 | mm13199_Plau | ACTCCCACCACATTTAAAGG |
| SEQ ID NO: 2499 | mm13200_Plau | CCAACACTGATACCAAAGGT |
| SEQ ID NO: 2500 | mm13201_Plau | GCTGGTACGTATCTTCAGCA |
| SEQ ID NO: 2501 | mm13202_Plaur | AGGACCATGAGTTACCGCAT |
| SEQ ID NO: 2502 | mm13203_Plaur | AAGGATGAGGACTACACCCG |
| SEQ ID NO: 2503 | mm13204_Plaur | AGGTGCAGGACGCACACTCG |
| SEQ ID NO: 2504 | mm13205_Plaur | TGCAACTACACCCACTGCAA |
| SEQ ID NO: 2505 | mm13238_Pld3 | TATCGGGTGTCAAAGGACCG |
| SEQ ID NO: 2506 | mm13239_Pld3 | ATGCGAACCTTTACACCTCG |
| SEQ ID NO: 2507 | mm13240_Pld3 | ACTGCCCTTGAATGAAATCG |
| SEQ ID NO: 2508 | mm13241_Pld3 | GCTGTTTCTATGGGAATACG |
| SEQ ID NO: 2509 | mm13254_Pa2g4 | CAGGACTATATACTCAAGGA |
| SEQ ID NO: 2510 | mm13255_Pa2g4 | TCAGGCCATATTGTTTAGAG |
| SEQ ID NO: 2511 | mm13256_Pa2g4 | TGCTGAAGCTGCCTTACGAC |
| SEQ ID NO: 2512 | mm13257_Pa2g4 | GTGACCAAGTATAAGATGGG |
| SEQ ID NO: 2513 | mm13258_Prl7d1 | TGAGGATGTCCGAAAGACAT |
| SEQ ID NO: 2514 | mm13259_Prl7d1 | GAACGTTGATGGGAACAGTG |
| SEQ ID NO: 2515 | mm13260_Prl7d1 | GATGTCAAATCTCTTCCTGT |

TABLE 1-continued mmSurf sgRNA library sequences

| SEQ ID NO | id_gRNA Target | Sequence |
|---|---|---|
| SEQ ID NO: 2516 | mm13261_Prl7d1 | CCTTTGATAGGATCCTATAA |
| SEQ ID NO: 2517 | mm13262_Plg | GCAGCAATGCGTGATCATGG |
| SEQ ID NO: 2518 | mm13263_Plg | GAAGAGGTGAAAATTACCGA |
| SEQ ID NO: 2519 | mm13264_Plg | AGAGCTTACTTGGGTACGTG |
| SEQ ID NO: 2520 | mm13265_Plg | AGGAATGCTACCAGAGCGAT |
| SEQ ID NO: 2521 | mm13266_Serpinf2 | ACGTTCCACTCAAAATAAGT |
| SEQ ID NO: 2522 | mm13267_Serpinf2 | TCCAGCAGGAACCATCGAAG |
| SEQ ID NO: 2523 | mm13268_Serpinf2 | AGCCATTTCTACCAGAACCT |
| SEQ ID NO: 2524 | mm13269_Serpinf2 | GTGACCATGCTACCCTCAAG |
| SEQ ID NO: 2525 | mm13278_Plod1 | AGCATATCTACCCGGACCGG |
| SEQ ID NO: 2526 | mm13279_Plod1 | CACTGGATACTCACACACGA |
| SEQ ID NO: 2527 | mm13280_Plod1 | TGTCAACGAAGAGAATAACC |
| SEQ ID NO: 2528 | mm13281_Plod1 | CCGTAGGCCCTCGTCACACA |
| SEQ ID NO: 2529 | mm13298_Pltp | ACATCTCCAACGCATCCTTG |
| SEQ ID NO: 2530 | mm13299_Pltp | AAAATGAATATGGCCTTCGG |
| SEQ ID NO: 2531 | mm13300_Pltp | AGTGGGGAGTTAATCACTGT |
| SEQ ID NO: 2532 | mm13301_Pltp | CGACGAGAGGATGGTGTACG |
| SEQ ID NO: 2533 | mm13306_Plxna1 | TGACTACCAAGGCCGCACCG |
| SEQ ID NO: 2534 | mm13307_Plxna1 | TCCAACAGTACTCCTATGAG |
| SEQ ID NO: 2535 | mm13308_Plxna1 | AGTATACGAACTGCTCGCTG |
| SEQ ID NO: 2536 | mm13309_Plxna1 | CGGCGCCCGGCACACCATGG |
| SEQ ID NO: 2537 | mm13310_Plxna2 | ACTGTTCACATGATTCAACA |
| SEQ ID NO: 2538 | mm13311_Plxna2 | CTGCAGACTGCTATCCACCC |
| SEQ ID NO: 2539 | mm13312_Plxna2 | TACAATGCACAGGTTCACGT |
| SEQ ID NO: 2540 | mm13313_Plxna2 | ATGTGGTACCTATAACGGCA |
| SEQ ID NO: 2541 | mm13366_Sept5 | GACATCGACAAGCAGTACGT |
| SEQ ID NO: 2542 | mm13367_Sept5 | TTTCCGGTCCTTATACAGGT |
| SEQ ID NO: 2543 | mm13368_Sept5 | CACACACCCGTGTCCGAACG |
| SEQ ID NO: 2544 | mm13369_Sept5 | AAAGCCGGGCGTGTCCACAA |
| SEQ ID NO: 2545 | mm13410_Pon1 | CTGGATGGTTTACCACCAGT |
| SEQ ID NO: 2546 | mm13411_Pon1 | CTTACTGATAGGAAGACCGA |
| SEQ ID NO: 2547 | mm13412_Pon1 | AAATGTACTTGGGTCTGTCG |
| SEQ ID NO: 2548 | mm13413_Pon1 | GAAGGGTTTGATTTCGCGAA |
| SEQ ID NO: 2549 | mm13478_Ppap2a | AAAGTATATCCATTTCAGAG |
| SEQ ID NO: 2550 | mm13479_Ppap2a | GTATGGCGAGTATACGGGAC |
| SEQ ID NO: 2551 | mm13480_Ppap2a | CCCGAGTAGAAAGACAACCT |
| SEQ ID NO: 2552 | mm13481_Ppap2a | ATACTTAGCGATGTCAGTCA |
| SEQ ID NO: 2553 | mm13514_Ctsa | GTGGTGCTTTGGCTTAACGG |

TABLE 1-continued mmSurf sgRNA library sequences

| SEQ ID NO | id_gRNA Target | Sequence |
| --- | --- | --- |
| SEQ ID NO: 2554 | mm13515_Ctsa | GGACTCGATATACAGCACGT |
| SEQ ID NO: 2555 | mm13516_Ctsa | CTCCGGCTACCTCAGAGCAT |
| SEQ ID NO: 2556 | mm13517_Ctsa | CATGACCAGTACAGCCAAGG |
| SEQ ID NO: 2557 | mm13522_Ppib | GTGGCCAACGATAAGAAGAA |
| SEQ ID NO: 2558 | mm13523_Ppib | GGGCAGCAAAAGGAAGACGA |
| SEQ ID NO: 2559 | mm13524_Ppib | TGAAGTCCTTGATGACACGA |
| SEQ ID NO: 2560 | mm13525_Ppib | CCAGGGTGGAGACTTCACCA |
| SEQ ID NO: 2561 | mm13530_Lgals3bp | AGAAACCATTGCCTCACACG |
| SEQ ID NO: 2562 | mm13531_Lgals3bp | TGTCCATCCCAGATACCACG |
| SEQ ID NO: 2563 | mm13532_Lgals3bp | GCGTACGCATAAAGGTCCAA |
| SEQ ID NO: 2564 | mm13533_Lgals3bp | AACGGGCCTCAGCCAATGA |
| SEQ ID NO: 2565 | mm13666_Prkcsh | AAGACCAGGTAGAAACACTG |
| SEQ ID NO: 2566 | mm13667_Prkcsh | CAGGGACAAGTACCGCTCTG |
| SEQ ID NO: 2567 | mm13668_Prkcsh | GGCACAGACGAGTACAACAG |
| SEQ ID NO: 2568 | mm13669_Prkcsh | AACTTGACGACAACATGGAT |
| SEQ ID NO: 2569 | mm13670_Prkdc | AGAGCCAATTCAGTGACCCG |
| SEQ ID NO: 2570 | mm13671_Prkdc | TGGCCCTTGTAAGTAGACGA |
| SEQ ID NO: 2571 | mm13672_Prkdc | CATGCAGGGTAAGTAATCGT |
| SEQ ID NO: 2572 | mm13673_Prkdc | ACAGAGGATGCTCAAAAATG |
| SEQ ID NO: 2573 | mm13722_Prlr | ATCCACATAAAGTGGATCCG |
| SEQ ID NO: 2574 | mm13723_Prlr | ATGTCAATGAATAATTGGTG |
| SEQ ID NO: 2575 | mm13724_Prlr | ATTTGATACTCATCTGCTAG |
| SEQ ID NO: 2576 | mm13725_Prlr | TCCCATTCCAAAGAGTATCC |
| SEQ ID NO: 2577 | mm13734_Prnp | TGGCCCCATCCACCGCCATG |
| SEQ ID NO: 2578 | mm13735_Prnp | GTGACTATGTGGACTGATGT |
| SEQ ID NO: 2579 | mm13736_Prnp | AAAAACCAACCTCAAGCATG |
| SEQ ID NO: 2580 | mm13737_Prnp | ACCCTAACCAAGTGTACTAC |
| SEQ ID NO: 2581 | mm13742_Procr | TCCAAGACAACCATCATGTG |
| SEQ ID NO: 2582 | mm13743_Procr | TGCGCCCTTTGTAACTCCGA |
| SEQ ID NO: 2583 | mm13744_Procr | GCTGGTATATCGCGAGCGCA |
| SEQ ID NO: 2584 | mm13745_Procr | GCCACATCGAAGAAGACATG |
| SEQ ID NO: 2585 | mm13750_Prom1 | GAGTGAAGACTCACGCCATG |
| SEQ ID NO: 2586 | mm13751_Prom1 | AAGGACTCCGATCTCATAGA |
| SEQ ID NO: 2587 | mm13752_Prom1 | CAGCAACAGATACTTAAACC |
| SEQ ID NO: 2588 | mm13753_Prom1 | CAAAGCCATATATAATGCCA |
| SEQ ID NO: 2589 | mm13794_St14 | AGGAGCCCACTGGTACGTTG |
| SEQ ID NO: 2590 | mm13795_St14 | GGGTCCCTACCACAAGAAGT |
| SEQ ID NO: 2591 | mm13796_St14 | GGGGCTCAGGCTATCATACA |

TABLE 1-continued mmSurf sgRNA library sequences

| SEQ ID NO | id_gRNA Target | Sequence |
|---|---|---|
| SEQ ID NO: 2592 | mm13797_St14 | GTGACAGTGTCAACGACTGT |
| SEQ ID NO: 2593 | mm13818_Psap | CTACGTGGACCAGTATTCCG |
| SEQ ID NO: 2594 | mm13819_Psap | GTCAACCACCTCCTTGCACG |
| SEQ ID NO: 2595 | mm13820_Psap | CCTCAGCTAACCTTAGGTTG |
| SEQ ID NO: 2596 | mm13821_Psap | TCTGGCATAAAATCACATTG |
| SEQ ID NO: 2597 | mm13834_Psen1 | TTTCAACCAGCATACGAAGT |
| SEQ ID NO: 2598 | mm13835_Psen1 | TGCTACTGTAACGTAGTCCA |
| SEQ ID NO: 2599 | mm13836_Psen1 | CTGAGCCAATATCTAATGGG |
| SEQ ID NO: 2600 | mm13837_Psen1 | AGTCAGCTTCTATACCCGGA |
| SEQ ID NO: 2601 | mm13838_Psen2 | TGTCACGCTGTGTATGATCG |
| SEQ ID NO: 2602 | mm13839_Psen2 | GAGCCCCACTGCATGCGTAG |
| SEQ ID NO: 2603 | mm13840_Psen2 | GATACTTGTAGAGTACCACG |
| SEQ ID NO: 2604 | mm13841_Psen2 | AGTGCTCAAGACCTACAATG |
| SEQ ID NO: 2605 | mm13922_Pstpip1 | CTGGTTACAGTGCACCCACA |
| SEQ ID NO: 2606 | mm13923_Pstpip1 | TGTTTGTAGAAAGAGTGTAC |
| SEQ ID NO: 2607 | mm13924_Pstpip1 | ATTGGCACTCACACGCTCGA |
| SEQ ID NO: 2608 | mm13925_Pstpip1 | GTCGCTCTACAAGAAGACCA |
| SEQ ID NO: 2609 | mm13934_Ptafr | ATTGTCTACTACTACAACGA |
| SEQ ID NO: 2610 | mm13935_Ptafr | CATCAATACCTACTGCAGTG |
| SEQ ID NO: 2611 | mm13936_Ptafr | AGAGATGCCACGCTTGCGGG |
| SEQ ID NO: 2612 | mm13937_Ptafr | AAGACATGAACAACAAGGAT |
| SEQ ID NO: 2613 | mm13942_Ptch1 | AGCTAATCTCGAGACCAACG |
| SEQ ID NO: 2614 | mm13943_Ptch1 | TGTGAGGGTCATACTCTGTG |
| SEQ ID NO: 2615 | mm13944_Ptch1 | CTGGCAGAGGACTTACGTGG |
| SEQ ID NO: 2616 | mm13945_Ptch1 | TAAAAATGGATCAGATGACG |
| SEQ ID NO: 2617 | mm13978_Ptger3 | TCAAGTACTACCGACGACTG |
| SEQ ID NO: 2618 | mm13979_Ptger3 | ATGTGGCTGGCATACCAGTG |
| SEQ ID NO: 2619 | mm13980_Ptger3 | GGGAGCAGCTCGACCCATCG |
| SEQ ID NO: 2620 | mm13981_Ptger3 | TGGCGCTCACCGACTTAGTG |
| SEQ ID NO: 2621 | mm13990_Ptgfrn | GGTCACGCTTACACCAGACG |
| SEQ ID NO: 2622 | mm13991_Ptgfrn | CATTCTATAGTACCACGACA |
| SEQ ID NO: 2623 | mm13992_Ptgfrn | ATCCTAGCCCTAAGCCACGA |
| SEQ ID NO: 2624 | mm13993_Ptgfrn | AGCGGGTGATATCCTGTTG |
| SEQ ID NO: 2625 | mm14006_Ptgs2 | AACATCATATTTGAGCCTTG |
| SEQ ID NO: 2626 | mm14007_Ptgs2 | TAGTGCACATTGTAAGTAGG |
| SEQ ID NO: 2627 | mm14008_Ptgs2 | GACTACGTGCAACACCTGAG |
| SEQ ID NO: 2628 | mm14009_Ptgs2 | CGTGGGAATGTATGAGCAC |
| SEQ ID NO: 2629 | mm14018_Pth1r | TCCAGGGCACAACCGGACGT |

TABLE 1-continued mmSurf sgRNA library sequences

| SEQ ID NO | id_gRNA Target | Sequence |
|---|---|---|
| SEQ ID NO: 2630 | mm14019_Pth1r | TCATAAATGTAATCGGGACA |
| SEQ ID NO: 2631 | mm14020_Pth1r | CCGCCCACCTAAAATAGGCT |
| SEQ ID NO: 2632 | mm14021_Pth1r | GAGCAACCTTGGCCAACACT |
| SEQ ID NO: 2633 | mm14042_Ptn | TGTGTGCGTGCCTACCAGCG |
| SEQ ID NO: 2634 | mm14043_Ptn | AAGGTGAAAAGTCTGACTG |
| SEQ ID NO: 2635 | mm14044_Ptn | AAGTACCAGTTCCAGGCTTG |
| SEQ ID NO: 2636 | mm14045_Ptn | CCAAGATGAAAATCAATGCC |
| SEQ ID NO: 2637 | mm14106_Sirpa | TAATTCTAAGGTCATCTGCG |
| SEQ ID NO: 2638 | mm14107_Sirpa | TGGAGAATGGAAACGTATCA |
| SEQ ID NO: 2639 | mm14108_Sirpa | GGAACAGAGGTCTATGTACT |
| SEQ ID NO: 2640 | mm14109_Sirpa | CACCTGGTTCATTGACGTCG |
| SEQ ID NO: 2641 | mm14118_Ptprc | GTAGCAGAAATCTTATATCG |
| SEQ ID NO: 2642 | mm14119_Ptprc | TTTCACAATGGAGTGTACGA |
| SEQ ID NO: 2643 | mm14120_Ptprc | TTGTCAAGCTAAGGCGACAG |
| SEQ ID NO: 2644 | mm14121_Ptprc | ACCACAACGAAGCAAACATG |
| SEQ ID NO: 2645 | mm14130_Ptprf | GGGTTCCCGACTATCGACAT |
| SEQ ID NO: 2646 | mm14131_Ptprf | GGCAGCGAGCCGGAAGACGT |
| SEQ ID NO: 2647 | mm14132_Ptprf | CTGTACACCTGACTAGCGAG |
| SEQ ID NO: 2648 | mm14133_Ptprf | CGAAGACCGTAAGCGACATG |
| SEQ ID NO: 2649 | mm14134_Ptprg | TAAAAGCCTATGTCCCGAG |
| SEQ ID NO: 2650 | mm14135_Ptprg | TCCACTATTTCACTACAGGG |
| SEQ ID NO: 2651 | mm14136_Ptprg | AGCATAGTGTCAATGGCCGG |
| SEQ ID NO: 2652 | mm14137_Ptprg | GGCACTTCACGGGAACGTCG |
| SEQ ID NO: 2653 | mm14138_Ptprj | ACTGACCGATGTAATATTAG |
| SEQ ID NO: 2654 | mm14139_Ptprj | CCTGGAAAAGCAATTACGAT |
| SEQ ID NO: 2655 | mm14140_Ptprj | AGACACCAGGGATTAACTCA |
| SEQ ID NO: 2656 | mm14141_Ptprj | GAGTGACAAATGTCAGCACA |
| SEQ ID NO: 2657 | mm14142_Ptprk | TACCAGAACGCCCTAAGTGG |
| SEQ ID NO: 2658 | mm14143_Ptprk | TGCGTAACTCAGTCAGAACG |
| SEQ ID NO: 2659 | mm14144_Ptprk | ACCTACCGCAAGGATAACTC |
| SEQ ID NO: 2660 | mm14145_Ptprk | AGAAGCGCAAAGATGCAATG |
| SEQ ID NO: 2661 | mm14150_Ptprm | AGAGCCGACACAAACATATG |
| SEQ ID NO: 2662 | mm14151_Ptprm | GTAGTGAAAGTCGATGCAGT |
| SEQ ID NO: 2663 | mm14152_Ptprm | TAAAAATAGATCCCATGCG |
| SEQ ID NO: 2664 | mm14153_Ptprm | CAAAATTGACTGTGTCCGAG |
| SEQ ID NO: 2665 | mm14154_Ptprn2 | CTCACCATCATCCATACTCG |
| SEQ ID NO: 2666 | mm14155_Ptprn2 | AGATCACAGACTATCAGAGG |
| SEQ ID NO: 2667 | mm14156_Ptprn2 | TGCTGATGTGTGGGCCACGT |

TABLE 1-continued mmSurf sgRNA library sequences

| SEQ ID NO | id_gRNA Target | Sequence |
|---|---|---|
| SEQ ID NO: 2668 | mm14157_Ptprn2 | CAAGGCCTACCTATGGCATG |
| SEQ ID NO: 2669 | mm14166_Ptprs | ATGATGTCCTTGATGCGCGG |
| SEQ ID NO: 2670 | mm14167_Ptprs | CAATTACGTAGTAGGACACG |
| SEQ ID NO: 2671 | mm14168_Ptprs | AGAAGCGTGGGGCCACACGG |
| SEQ ID NO: 2672 | mm14169_Ptprs | ATGGAGCCGGAACACCCAGT |
| SEQ ID NO: 2673 | mm14170_Ptprt | ACCTCCCAATGAGACCAATG |
| SEQ ID NO: 2674 | mm14171_Ptprt | CAAAGTAGTGTAGCGAATCG |
| SEQ ID NO: 2675 | mm14172_Ptprt | CCTGCGACTCCAAAACGTTG |
| SEQ ID NO: 2676 | mm14173_Ptprt | ACAGGGTCACAAGTCCGGTA |
| SEQ ID NO: 2677 | mm14190_Igdcc3 | ACAGCTCGGACATTGCGTGG |
| SEQ ID NO: 2678 | mm14191_Igdcc3 | CCTGACAGTGCACCAGACTG |
| SEQ ID NO: 2679 | mm14192_Igdcc3 | CAAAGCCTACACACCACGAG |
| SEQ ID NO: 2680 | mm14193_Igdcc3 | AGGTACACACTACTGCCCAA |
| SEQ ID NO: 2681 | mm14206_Pvrl2 | TCCCAACGGTACCCGCAGGG |
| SEQ ID NO: 2682 | mm14207_Pvrl2 | GCGGGTACGAGTGCTTCCCG |
| SEQ ID NO: 2683 | mm14208_Pyrl2 | TTTCCACCCATCCTTCGGAG |
| SEQ ID NO: 2684 | mm14209_Pyrl2 | TGACCATTCGATCCACAGAG |
| SEQ ID NO: 2685 | mm14494_Robo3 | TCTGCGTAGACCAATAAACC |
| SEQ ID NO: 2686 | mm14495_Robo3 | GGCCTCGACCCAACATCGAG |
| SEQ ID NO: 2687 | mm14496_Robo3 | CATCACTGAAGTAAAGATCG |
| SEQ ID NO: 2688 | mm14497_Robo3 | TGTGGCCAAGAGTTCCATAG |
| SEQ ID NO: 2689 | mm14578_Rdx | AAAAACAGTTGGCTTACGTG |
| SEQ ID NO: 2690 | mm14579_Rdx | GAGAATACAGAACTGGCATG |
| SEQ ID NO: 2691 | mm14580_Rdx | ACCATGAACTGTACATGCGA |
| SEQ ID NO: 2692 | mm14581_Rdx | AATAAAGAGATTCACAAACC |
| SEQ ID NO: 2693 | mm14670_Rfng | CGGGACGCGCACCTGCCGTG |
| SEQ ID NO: 2694 | mm14671_Rfng | AGCAATTGGTGTTGATCATG |
| SEQ ID NO: 2695 | mm14672_Rfng | TCCGGGTCGGGACCCGATCG |
| SEQ ID NO: 2696 | mm14673_Rfng | AGCACTGTGCTGCAAAATGT |
| SEQ ID NO: 2697 | mm14734_Rhag | CCTGCATAATCGTACCCCAT |
| SEQ ID NO: 2698 | mm14735_Rhag | GCAATGGCTGAATTAAAGCT |
| SEQ ID NO: 2699 | mm14736_Rhag | GGCATAGGCTGTGATCACAC |
| SEQ ID NO: 2700 | mm14737_Rhag | TCATGATCAACATTTGAATG |
| SEQ ID NO: 2701 | mm14810_Robo1 | TTCGATGTAAGCGCTCCACG |
| SEQ ID NO: 2702 | mm14811_Robo1 | GCTGGACGTTCGTAATGGTG |
| SEQ ID NO: 2703 | mm14812_Robo1 | GATACAGTTACACTTCGGGG |
| SEQ ID NO: 2704 | mm14813_Robo1 | CTGGGTCTCTTCACAAACGA |
| SEQ ID NO: 2705 | mm14830_Mst1r | AAGTATCAGACTTTAGACGA |

TABLE 1-continued mmSurf sgRNA library sequences

| SEQ ID NO | id_gRNA Target | Sequence |
|---|---|---|
| SEQ ID NO: 2706 | mm14831_Mst1r | GGGAACACACCAGATCACCG |
| SEQ ID NO: 2707 | mm14832_Mst1r | ATGTGGTCCGAAACCCTCAG |
| SEQ ID NO: 2708 | mm14833_Mst1r | AAGACGTGTCACATGCAGTG |
| SEQ ID NO: 2709 | mm14842_Ros1 | GGGTTGTAGAACATGTTGCG |
| SEQ ID NO: 2710 | mm14843_Ros1 | AGAGATATGAGATACGGACA |
| SEQ ID NO: 2711 | mm14844_Ros1 | GTCATGGTGTGACATTACGC |
| SEQ ID NO: 2712 | mm14845_Ros1 | GTCACTCCTTATACCTACTG |
| SEQ ID NO: 2713 | mm14878_Rpl18 | TGTGACCGTCCCCACAACCA |
| SEQ ID NO: 2714 | mm14879_Rpl18 | TGGCTGACTACTAACCATGC |
| SEQ ID NO: 2715 | mm14880_Rpl18 | TTACCTTGACAAGCAGCCGC |
| SEQ ID NO: 2716 | mm14881_Rpl18 | TCGCCACAACAAGGACCGAA |
| SEQ ID NO: 2717 | mm14886_Rpl21 | ATTCGCATGTATGTGGCCAA |
| SEQ ID NO: 2718 | mm14887_Rpl21 | AAGGCCTAGAGAACATGTAC |
| SEQ ID NO: 2719 | mm14888_Rpl21 | GGGCATCATTGTCAACAAGC |
| SEQ ID NO: 2720 | mm14889_Rpl21 | ATGCCCCATAAGTGCTACCA |
| SEQ ID NO: 2721 | mm14918_Rpl32 | TGTGTCTTCAGCGAAACTGG |
| SEQ ID NO: 2722 | mm14919_Rpl32 | ACCAAGCACATGCTGCCCAG |
| SEQ ID NO: 2723 | mm14920_Rpl32 | GAGGCATTGACAACAGGGTG |
| SEQ ID NO: 2724 | mm14921_Rpl32 | CCACAATGTCAAGGAGCTGG |
| SEQ ID NO: 2725 | mm14938_Rpl9 | AGGGCTTCCGATACAAGATG |
| SEQ ID NO: 2726 | mm14939_Rpl9 | CTGTCCTCATCCGAACCCTG |
| SEQ ID NO: 2727 | mm14940_Rpl9 | ACTGCAGATGGTCCTGACGG |
| SEQ ID NO: 2728 | mm14941_Rpl9 | GGACTTCAATCACATCAACG |
| SEQ ID NO: 2729 | mm14942_Rpn2 | GCACAACCACCACTGGTACG |
| SEQ ID NO: 2730 | mm14943_Rpn2 | TGGACGGTTCGGTCCCCACG |
| SEQ ID NO: 2731 | mm14944_Rpn2 | TGTGAAGGGCGGTCCAGTG |
| SEQ ID NO: 2732 | mm14945_Rpn2 | TGCAACTGCATGGTAGATCT |
| SEQ ID NO: 2733 | mm14958_Polr1a | TGTCAAACACAATATTGACG |
| SEQ ID NO: 2734 | mm14959_Polr1a | GATTGATATGAAGTTCAAGG |
| SEQ ID NO: 2735 | mm14960_Polr1a | GAGGAGGGTCGACACAACCT |
| SEQ ID NO: 2736 | mm14961_Polr1a | GAATTGACAAGGCTCAGATG |
| SEQ ID NO: 2737 | mm15046_Rps8 | ACGGCCCGCTGCCAACACGA |
| SEQ ID NO: 2738 | mm15047_Rps8 | CACGATGCAGTTCTTCACCA |
| SEQ ID NO: 2739 | mm15048_Rps8 | TTTCATTCAGACTCCTGAGG |
| SEQ ID NO: 2740 | mm15049_Rps8 | ACAGCACGCCGTACCGACAG |
| SEQ ID NO: 2741 | mm15130_Ryk | ACTGATGTAAAACACACGCG |
| SEQ ID NO: 2742 | mm15131_Ryk | TGAGCAGAAATATTGACCTG |
| SEQ ID NO: 2743 | mm15132_Ryk | TGCACACATGAGTAATAGGA |

TABLE 1-continued mmSurf sgRNA library sequences

| SEQ ID NO | id_gRNA Target | Sequence |
|---|---|---|
| SEQ ID NO: 2744 | mm15133_Ryk | CCTCAGGTTATCCTACCTTG |
| SEQ ID NO: 2745 | mm15318_Scn5a | AGTCGAAGCTGGTGTAACCG |
| SEQ ID NO: 2746 | mm15319_Scn5a | GCAAATCCCAGACCTCGGGG |
| SEQ ID NO: 2747 | mm15320_Scn5a | CTGGTCAAGATTCTAGCTCG |
| SEQ ID NO: 2748 | mm15321_Scn5a | GCATGGTGGACACTTACGGT |
| SEQ ID NO: 2749 | mm15330_Scn9a | GCCAGTTCCAAGGGTCACGG |
| SEQ ID NO: 2750 | mm15331_Scn9a | GTGTCCGTAGAGATTTAATG |
| SEQ ID NO: 2751 | mm15332_Scn9a | TATCTCAAACCGTACCCTTG |
| SEQ ID NO: 2752 | mm15333_Scn9a | CTGAGTACACGAGTTTAGGG |
| SEQ ID NO: 2753 | mm15334_Scnn1a | CCAGACATACTCATCCGGGG |
| SEQ ID NO: 2754 | mm15335_Scnn1a | TGTAGCAGTTCCCATACATG |
| SEQ ID NO: 2755 | mm15336_Scnn1a | CTGCCAGTACATCATGCCGA |
| SEQ ID NO: 2756 | mm15337_Scnn1a | AAAGCGTCTGTTCCGTGATG |
| SEQ ID NO: 2757 | mm15338_Scnn1b | CAAGACGATGAACTTCCCGG |
| SEQ ID NO: 2758 | mm15339_Scnn1b | GACGTACCCCTTCATTAGAG |
| SEQ ID NO: 2759 | mm15340_Scnn1b | AGCTAGGATTATGCGATCAG |
| SEQ ID NO: 2760 | mm15341_Scnn1b | AGAGAAATACTGCAACAACA |
| SEQ ID NO: 2761 | mm15342_Scnn1g | TACCCTTTCATCGAAGACGT |
| SEQ ID NO: 2762 | mm15343_Scnn1g | GGCGCACTGCCAGATAATGA |
| SEQ ID NO: 2763 | mm15344_Scnn1g | GGGTGGTGTGCCTTCCCACG |
| SEQ ID NO: 2764 | mm15345_Scnn1g | ACGAAGATGGTGGAAAAATG |
| SEQ ID NO: 2765 | mm15362_Msr1 | GTATTAGTACTGCAAACACA |
| SEQ ID NO: 2766 | mm15363_Msr1 | TTTCGTCAGTCCAGGAACAT |
| SEQ ID NO: 2767 | mm15364_Msr1 | AAAAGCCGACCTTATAGACA |
| SEQ ID NO: 2768 | mm15365_Msr1 | GAAAGAAGAACAAGCGCACG |
| SEQ ID NO: 2769 | mm15442_Cx3cl1 | GGGTGGACAATGTGACACCT |
| SEQ ID NO: 2770 | mm15443_Cx3cl1 | GATGACCTCACGAATCCCAG |
| SEQ ID NO: 2771 | mm15444_Cx3cl1 | ACTGACTACTATTTCCCAGG |
| SEQ ID NO: 2772 | mm15445_Cx3cl1 | GGCCAACCCCCATGGGTCCA |
| SEQ ID NO: 2773 | mm15446_Cxcl12 | CTAGGACTTACACAATCTGA |
| SEQ ID NO: 2774 | mm15447_Cxcl12 | ACCGTCACTGATGCAGAGCG |
| SEQ ID NO: 2775 | mm15448_Cxcl12 | TGGCTCTCGAAGAACCGGCA |
| SEQ ID NO: 2776 | mm15449_Cxcl12 | GGGCACAGTTTGGAGTGTTG |
| SEQ ID NO: 2777 | mm15466_Nptn | TGACAAAATGATATACACAG |
| SEQ ID NO: 2778 | mm15467_Nptn | GTTGCTGGCATTCTTACGGG |
| SEQ ID NO: 2779 | mm15468_Nptn | GAGCTATTAGAAATCTCCTG |
| SEQ ID NO: 2780 | mm15469_Nptn | ATGATGTACTGCAAGTCAGT |
| SEQ ID NO: 2781 | mm15470_Frrs1 | GCTTTAGGTGTCGTAAGGG |

TABLE 1-continued mmSurf sgRNA library sequences

| SEQ ID NO | id_gRNA Target | Sequence |
|---|---|---|
| SEQ ID NO: 2782 | mm15471_Frrs1 | TCAGTGATGGTTGAAATGAG |
| SEQ ID NO: 2783 | mm15472_Frrs1 | CAGGACTCCAATGCTGACCG |
| SEQ ID NO: 2784 | mm15473_Frrs1 | CAGAAATCGTATGTGATCTG |
| SEQ ID NO: 2785 | mm15498_Sel1l | CAAGCCCGCTCTGTCCCACG |
| SEQ ID NO: 2786 | mm15499_Sel1l | AAAACCCGGGGATGAACAGT |
| SEQ ID NO: 2787 | mm15500_Sel1l | GCCAGCAACTACTTTGCCCG |
| SEQ ID NO: 2788 | mm15501_Sel1l | TCGGCTCTATGTACTACAGT |
| SEQ ID NO: 2789 | mm15506_Glg1 | CATTCAAAGCTCGATCAATG |
| SEQ ID NO: 2790 | mm15507_Glg1 | TCCTGCTTGGTGGATCATCG |
| SEQ ID NO: 2791 | mm15508_Glg1 | GTCTAAATGAAAGTCATCCG |
| SEQ ID NO: 2792 | mm15509_Glg1 | GTGGAATGCAGAGACATCGT |
| SEQ ID NO: 2793 | mm15518_Sell | TGACGCCTGTCACAAACGAA |
| SEQ ID NO: 2794 | mm15519_Sell | GTCCATGGTACCCAACTCAG |
| SEQ ID NO: 2795 | mm15520_Sell | ACACGTGCATCTGTGATGCA |
| SEQ ID NO: 2796 | mm15521_Sell | TTCTGAAAAGCCCATGAACT |
| SEQ ID NO: 2797 | mm15522_Selp | ATGTACCGTCACACTTCGGG |
| SEQ ID NO: 2798 | mm15523_Selp | GGGAACAAATAAGACACTCA |
| SEQ ID NO: 2799 | mm15524_Selp | TGGTACGTCAAGGTACCGAA |
| SEQ ID NO: 2800 | mm15525_Selp | TTGTAGGTGGAATTCCCAAG |
| SEQ ID NO: 2801 | mm15530_Sema3a | TAGAATAGGTCAGATATGCA |
| SEQ ID NO: 2802 | mm15531_Sema3a | GTGAACACTCCATAGACGAT |
| SEQ ID NO: 2803 | mm15532_Sema3a | GAACGGAGTAGACTATATGT |
| SEQ ID NO: 2804 | mm15533_Sema3a | ACAAATTGTTGTAGACCGAG |
| SEQ ID NO: 2805 | mm15538_Sema3c | GTGTGCACCTACCTGAACCG |
| SEQ ID NO: 2806 | mm15539_Sema3c | TATCTCTCCCATCTAGATCG |
| SEQ ID NO: 2807 | mm15540_Sema3c | ATCAAGACCGGATATATGTG |
| SEQ ID NO: 2808 | mm15541_Sema3c | ACATGTGCGTCCACAAACAT |
| SEQ ID NO: 2809 | mm15554_Sema4b | TCGGGCAACTCGGGACACGA |
| SEQ ID NO: 2810 | mm15555_Sema4b | CTACTGATACCTACCGCTCC |
| SEQ ID NO: 2811 | mm15556_Sema4b | GGGTCTTGCGCCAATCCTGA |
| SEQ ID NO: 2812 | mm15557_Sema4b | TCCCTCAACTGGCTACAAGG |
| SEQ ID NO: 2813 | mm15558_Sema4d | GATGGCATACTCCGTCCTCA |
| SEQ ID NO: 2814 | mm15559_Sema4d | GGCTGGATTCAGGACATGAG |
| SEQ ID NO: 2815 | mm15560_Sema4d | CTTGGGTCTGTTGTCTATCG |
| SEQ ID NO: 2816 | mm15561_Sema4d | ATTGGTCCCACACACATAGA |
| SEQ ID NO: 2817 | mm15570_Sema5b | GTTCGGCCTATCATAGCCAG |
| SEQ ID NO: 2818 | mm15571_Sema5b | TTATACTGGGCAGTGCGAAG |
| SEQ ID NO: 2819 | mm15572_Sema5b | CCAGAGCAAAGGGAAAACGG |

TABLE 1-continued mmSurf sgRNA library sequences

| SEQ ID NO | id_gRNA Target | Sequence |
|---|---|---|
| SEQ ID NO: 2820 | mm15573_Sema5b | CTCTATCACGTACTCTACAT |
| SEQ ID NO: 2821 | mm15586_Sema7a | CCTCGGTTTCGACGCATTCG |
| SEQ ID NO: 2822 | mm15587_Sema7a | TGGTACTTAGAATGGAACAA |
| SEQ ID NO: 2823 | mm15588_Sema7a | GGTGAACATCGGCTCCACAA |
| SEQ ID NO: 2824 | mm15589_Sema7a | ACAACGAACTCTCACCACCC |
| SEQ ID NO: 2825 | mm15606_Sez6 | GAGTCGGACTGGTAAAGACG |
| SEQ ID NO: 2826 | mm15607_Sez6 | CCGCAATGGAAATAACGTGG |
| SEQ ID NO: 2827 | mm15608_Sez6 | AGGAACGACTGGTTAGCCAA |
| SEQ ID NO: 2828 | mm15609_Sez6 | CTACCCTGTGGGTACAACTG |
| SEQ ID NO: 2829 | mm15618_Sfrp1 | GACATCGGCTCGTATCAGAG |
| SEQ ID NO: 2830 | mm15619_Sfrp1 | CAAATGTGACAAGTTCCCCG |
| SEQ ID NO: 2831 | mm15620_Sfrp1 | TTCAACTCGTTGTCGCATGG |
| SEQ ID NO: 2832 | mm15621_Sfrp1 | CTGAGGCTGTGCCACAACGT |
| SEQ ID NO: 2833 | mm15626_Sfrp4 | TTGCAATGAGGTCACAACTG |
| SEQ ID NO: 2834 | mm15627_Sfrp4 | AGGGCTTGATGGGATCGTGC |
| SEQ ID NO: 2835 | mm15628_Sfrp4 | TGTGGTTATACATCTTCATG |
| SEQ ID NO: 2836 | mm15629_Sfrp4 | GAGCTGCCGGTCTATGACCG |
| SEQ ID NO: 2837 | mm15658_Sgce | GATGGCTTCGATATATCCAA |
| SEQ ID NO: 2838 | mm15659_Sgce | AGAATGTGCCAGTGGTCGCG |
| SEQ ID NO: 2839 | mm15660_Sgce | CGACTGGTGCAAGATTTCAC |
| SEQ ID NO: 2840 | mm15661_Sgce | GCTTCCTATTAATGACATGA |
| SEQ ID NO: 2841 | mm15730_Shh | TGGCGCCGCACAACGACTCG |
| SEQ ID NO: 2842 | mm15731_Shh | AGGAAAACACGGGAGCAGAC |
| SEQ ID NO: 2843 | mm15732_Shh | GTGCTGGCGGCTGACGACCA |
| SEQ ID NO: 2844 | mm15733_Shh | AAACTGCTTGTAGGCTAAAG |
| SEQ ID NO: 2845 | mm15770_St3gal1 | ACCAGCCTCTTGTTCAACAT |
| SEQ ID NO: 2846 | mm15771_St3gal1 | GTCGATCTCAGGCCCATACG |
| SEQ ID NO: 2847 | mm15772_St3gal1 | AGGATACACGAGATGGTGGG |
| SEQ ID NO: 2848 | mm15773_St3gal1 | GCTGTGACTTGATGAACCTG |
| SEQ ID NO: 2849 | mm15774_St3gal4 | CAACACAGCGACGACACTCG |
| SEQ ID NO: 2850 | mm15775_St3gal4 | TCAAGATGGTCTCAATCCAG |
| SEQ ID NO: 2851 | mm15776_St3gal4 | TGTCATCAACAAGTACGACG |
| SEQ ID NO: 2852 | mm15777_St3gal4 | AAGGGCAGCTCATAGGTGGA |
| SEQ ID NO: 2853 | mm15798_St8sia1 | GTGTACTCACTTGACAAGGG |
| SEQ ID NO: 2854 | mm15799_St8sia1 | CCGCGTACCCGGCTACCCGT |
| SEQ ID NO: 2855 | mm15800_St8sia1 | GGAGTACGTGGAATTATCGA |
| SEQ ID NO: 2856 | mm15801_St8sia1 | ACCCCAGCATAATTCGCCAG |
| SEQ ID NO: 2857 | mm15802_St8sia2 | AGGACCTTGTGAACGCCACG |

TABLE 1-continued mmSurf sgRNA library sequences

| SEQ ID NO | id_gRNA Target | Sequence |
|---|---|---|
| SEQ ID NO: 2858 | mm15803_St8sia2 | TTTCCAGACTTGTGCCATCG |
| SEQ ID NO: 2859 | mm15804_St8sia2 | ACAACCAGACGCTCTCTCTG |
| SEQ ID NO: 2860 | mm15805_St8sia2 | AGGATATTTCTGTCCTTAAG |
| SEQ ID NO: 2861 | mm15806_St8sia3 | GCGTGGAACATGTACATTCG |
| SEQ ID NO: 2862 | mm15807_St8sia3 | TGCTCGGATTGAAGGTTGTG |
| SEQ ID NO: 2863 | mm15808_St8sia3 | TCATAATGGGCGACACATCT |
| SEQ ID NO: 2864 | mm15809_St8sia3 | GAAACAGTGGAATCTTGACA |
| SEQ ID NO: 2865 | mm15814_St3gal5 | GTTCGGGCAGCATATCCAAG |
| SEQ ID NO: 2866 | mm15815_St3gal5 | TAGTATTCAACGTCCGACAG |
| SEQ ID NO: 2867 | mm15816_St3gal5 | CGCCCTCAACCAGTTCGATG |
| SEQ ID NO: 2868 | mm15817_St3gal5 | AGCTGAGAAGTGATTGCTCA |
| SEQ ID NO: 2869 | mm15910_Slc12a1 | CATCATCGGTTCCATCACCG |
| SEQ ID NO: 2870 | mm15911_Slc12a1 | ACAAACGGAGTGGTGCGAGG |
| SEQ ID NO: 2871 | mm15912_Slc12a1 | GTGGGTTATATCCAAGAGAG |
| SEQ ID NO: 2872 | mm15913_Slc12a1 | CCATGGCTATCACAAAAGTG |
| SEQ ID NO: 2873 | mm15914_Slc12a2 | CGGTTTCCGAGAACGCGGG |
| SEQ ID NO: 2874 | mm15915_Slc12a2 | AAACGTCCCTATGACGAAGT |
| SEQ ID NO: 2875 | mm15916_Slc12a2 | GTTAAGATGTAACCACGAAG |
| SEQ ID NO: 2876 | mm15917_Slc12a2 | TCCGACAACATACATAGCAA |
| SEQ ID NO: 2877 | mm15922_Slc12a4 | AGCAAACGGTGAACCGACGT |
| SEQ ID NO: 2878 | mm15923_Slc12a4 | GGTGGCGCTTGACATGTCAT |
| SEQ ID NO: 2879 | mm15924_Slc12a4 | GTTACTCACGGAAACACGGG |
| SEQ ID NO: 2880 | mm15925_Slc12a4 | CCCAGAAGTCTATCCCAGTG |
| SEQ ID NO: 2881 | mm15926_Slc12a7 | AATGAAAGATGTAGTCACGA |
| SEQ ID NO: 2882 | mm15927_Slc12a7 | AACAACGTTACTGAGATACA |
| SEQ ID NO: 2883 | mm15928_Slc12a7 | TGGTCATGGAAAGGCCAACG |
| SEQ ID NO: 2884 | mm15929_Slc12a7 | AGCAGATGAACATCAGCGCG |
| SEQ ID NO: 2885 | mm15950_Slc34a1 | AGTTGAGCATCTTCACAAGG |
| SEQ ID NO: 2886 | mm15951_Slc34a1 | TGACCCACTACCTACCAAGC |
| SEQ ID NO: 2887 | mm15952_Slc34a1 | GTGTCACCCAGACACAACAG |
| SEQ ID NO: 2888 | mm15953_Slc34a1 | TGCCATCCTATCCAACCCAG |
| SEQ ID NO: 2889 | mm15962_Slc1a1 | CGACTCACCTAGTACCACGG |
| SEQ ID NO: 2890 | mm15963_Slc1a1 | TAGGATTACAGCAATGACGG |
| SEQ ID NO: 2891 | mm15964_Slc1a1 | ATCATGCTGGATACGATCAG |
| SEQ ID NO: 2892 | mm15965_Slc1a1 | TCACCTGATCAGGTCCAACA |
| SEQ ID NO: 2893 | mm15966_Slc1a2 | CATGTTGATAGCCTTCCCGG |
| SEQ ID NO: 2894 | mm15967_Slc1a2 | CCATAGCTCTCGTGCCTAGG |
| SEQ ID NO: 2895 | mm15968_Slc1a2 | TAATTGCCCATAGGTCTGAT |

TABLE 1-continued mmSurf sgRNA library sequences

| SEQ ID NO | id_gRNA Target | Sequence |
|---|---|---|
| SEQ ID NO: 2896 | mm15969_Slc1a2 | GTTCATGGTTTCATTCAACA |
| SEQ ID NO: 2897 | mm15970_Slc1a3 | GTATAAAATGAGCTACCGGG |
| SEQ ID NO: 2898 | mm15971_Slc1a3 | GACTCTGACCCGGATCCGGG |
| SEQ ID NO: 2899 | mm15972_Slc1a3 | GAGGCCGACAATGACTGTCA |
| SEQ ID NO: 2900 | mm15973_Slc1a3 | AGGCTTCTACCAGATTGGGA |
| SEQ ID NO: 2901 | mm15978_Slc1a5 | AATCCCTATCGATTCCTGTG |
| SEQ ID NO: 2902 | mm15979_Slc1a5 | TACAACAGAGTCGTTGATGG |
| SEQ ID NO: 2903 | mm15980_Slc1a5 | GCGGGAGATCAATTCAACCA |
| SEQ ID NO: 2904 | mm15981_Slc1a5 | GTGGTGTGCAGCCTGATCGG |
| SEQ ID NO: 2905 | mm15986_Slc20a2 | ATACTGTACACAAAGACTCG |
| SEQ ID NO: 2906 | mm15987_Slc20a2 | GCCTTACCATAGGAAGCCCG |
| SEQ ID NO: 2907 | mm15988_Slc20a2 | AAGTGGCGATATAAACCAGG |
| SEQ ID NO: 2908 | mm15989_Slc20a2 | ATGGTAGCAGCATAAAACAG |
| SEQ ID NO: 2909 | mm16002_Slc22a5 | TTTATGATCTGATCCGAACA |
| SEQ ID NO: 2910 | mm16003_Slc22a5 | GGGTCAGATCTCCAACTACG |
| SEQ ID NO: 2911 | mm16004_Slc22a5 | CACAAGGCAACGGTGCTCCG |
| SEQ ID NO: 2912 | mm16005_Slc22a5 | CACACCCACGAAAAACAAGG |
| SEQ ID NO: 2913 | mm16022_Slc2a1 | CCTGCTCATCAATCGTAACG |
| SEQ ID NO: 2914 | mm16023_Slc2a1 | TCAGCATGGAGTTCCGCCTG |
| SEQ ID NO: 2915 | mm16024_Slc2a1 | GTGTCACCTACAGCTCTACG |
| SEQ ID NO: 2916 | mm16025_Slc2a1 | CAAACATGGAACCACCGCTA |
| SEQ ID NO: 2917 | mm16030_Slc2a3 | TTAGAAGACCTACCAAGTGA |
| SEQ ID NO: 2918 | mm16031_Slc2a3 | GACCACGCCTGCTCCAATCG |
| SEQ ID NO: 2919 | mm16032_Slc2a3 | CTGGAATGATGGTTAAGCCA |
| SEQ ID NO: 2920 | mm16033_Slc2a3 | TGTGCCTATGTACATTGGAG |
| SEQ ID NO: 2921 | mm16034_Slc2a4 | GCAGCCTCTGATCATCGCAG |
| SEQ ID NO: 2922 | mm16035_Slc2a4 | AACAGAGCTACAATGCAACG |
| SEQ ID NO: 2923 | mm16036_Slc2a4 | AACCAGAATGCCAATGACGA |
| SEQ ID NO: 2924 | mm16037_Slc2a4 | CCAGGTCTAAAGCGCCTGAC |
| SEQ ID NO: 2925 | mm16046_Slc34a2 | TCATAGAGGAGCATCCCGAG |
| SEQ ID NO: 2926 | mm16047_Slc34a2 | CTCCATCACCAACACGATCG |
| SEQ ID NO: 2927 | mm16048_Slc34a2 | AGAGGTGCAGTTATCAGTCG |
| SEQ ID NO: 2928 | mm16049_Slc34a2 | CTCACCGATGAGTGGAGTCA |
| SEQ ID NO: 2929 | mm16054_Slc4a1 | CTCCATGGCGCATAACCGAG |
| SEQ ID NO: 2930 | mm16055_Slc4a1 | AATAACCTGGAGTATATCGT |
| SEQ ID NO: 2931 | mm16056_Slc4a1 | TCTACAACAGACTTGAACGG |
| SEQ ID NO: 2932 | mm16057_Slc4a1 | CTTACCCACTAGCACCAGTG |
| SEQ ID NO: 2933 | mm16062_Slc4a2 | GGAAGTCACTTAGGTAGTGG |

TABLE 1-continued mmSurf sgRNA library sequences

| SEQ ID NO | id_gRNA Target | Sequence |
|---|---|---|
| SEQ ID NO: 2934 | mm16063_Slc4a2 | GGGTACGGCGACACTTGGTG |
| SEQ ID NO: 2935 | mm16064_Slc4a2 | TAGCGGATGATGGATATGGT |
| SEQ ID NO: 2936 | mm16065_Slc4a2 | GAGCCCGCTGAGATGTTTCG |
| SEQ ID NO: 2937 | mm16074_Slc6a2 | CTTCACCACTAGTAGATCGG |
| SEQ ID NO: 2938 | mm16075_Slc6a2 | AGCAGTGGGATCCATGACAT |
| SEQ ID NO: 2939 | mm16076_Slc6a2 | AGCCGACATAGAGGGCAATG |
| SEQ ID NO: 2940 | mm16077_Slc6a2 | ATAAGGGAACCGCCACACGT |
| SEQ ID NO: 2941 | mm16086_Slc8a1 | CTGATTATGAATTCACGGAA |
| SEQ ID NO: 2942 | mm16087_Slc8a1 | AATCGCACTCTGTGTTTACG |
| SEQ ID NO: 2943 | mm16088_Slc8a1 | ACTCACGTGAGCGAGAGCAT |
| SEQ ID NO: 2944 | mm16089_Slc8a1 | CTGCAATAATAGAAACTCCA |
| SEQ ID NO: 2945 | mm16090_Slc9a1 | ACGGCCAACAGGTCGACCAG |
| SEQ ID NO: 2946 | mm16091_Slc9a1 | GGGGCGCATCACTACTCCTG |
| SEQ ID NO: 2947 | mm16092_Slc9a1 | CGCCCACAAACACCCCACCG |
| SEQ ID NO: 2948 | mm16093_Slc9a1 | GAAGGTCCAGTTCCACTGGT |
| SEQ ID NO: 2949 | mm16110_Slit1 | CAACCCCATCGAGACAACTG |
| SEQ ID NO: 2950 | mm16111_Slit1 | GTCGGCCCTTCAAAGCCGGA |
| SEQ ID NO: 2951 | mm16112_Slit1 | TGATACCGTTCAACTCCAGG |
| SEQ ID NO: 2952 | mm16113_Slit1 | TCCGCAAGCCATCTAGACCC |
| SEQ ID NO: 2953 | mm16114_Slit2 | TACATCGATAAAAATCAACG |
| SEQ ID NO: 2954 | mm16115_Slit2 | GTGAGAAATTACCTGAACAA |
| SEQ ID NO: 2955 | mm16116_Slit2 | TAAGATCACGGATATCGAGG |
| SEQ ID NO: 2956 | mm16117_Slit2 | GGATGGGAACCAGTTTACGC |
| SEQ ID NO: 2957 | mm16118_Slit3 | CAACCCTATTGAGACAAGCG |
| SEQ ID NO: 2958 | mm16119_Slit3 | GGAGATTCCCATCCAAGACG |
| SEQ ID NO: 2959 | mm16120_Slit3 | ACAGCGTCTTGAGGCTACTG |
| SEQ ID NO: 2960 | mm16121_Slit3 | CAGATTGGCTGCGACAACGG |
| SEQ ID NO: 2961 | mm16218_Siglec1 | ACTGAGTGTAACATGACGTG |
| SEQ ID NO: 2962 | mm16219_Siglec1 | GCGCTCCAGTCCATTGAGTG |
| SEQ ID NO: 2963 | mm16220_Siglec1 | TGCTATCACTGATCTCAAAG |
| SEQ ID NO: 2964 | mm16221_Siglec1 | CTCATACTACTGTAGGACGC |
| SEQ ID NO: 2965 | mm16322_Sorl1 | TCACGTCCTCTGACACAAGG |
| SEQ ID NO: 2966 | mm16323_Sorl1 | ACTGCTAGAGATGTACACAT |
| SEQ ID NO: 2967 | mm16324_Sorl1 | CTTCTCCATCCCATTCCGGG |
| SEQ ID NO: 2968 | mm16325_Sorl1 | GCACCCGGGAGGACTACGAA |
| SEQ ID NO: 2969 | mm16326_Sort1 | TTGTTATATAGACCCCACGG |
| SEQ ID NO: 2970 | mm16327_Sort1 | GCTGACCAACAATACGCACC |
| SEQ ID NO: 2971 | mm16328_Sort1 | TACCGCAAAGAACAAGAACG |

TABLE 1-continued mmSurf sgRNA library sequences

| SEQ ID NO | id_gRNA Target | Sequence |
|---|---|---|
| SEQ ID NO: 2972 | mm16329_Sort1 | TGGGCAGGTGATACTAACAG |
| SEQ ID NO: 2973 | mm16414_Spa17 | ACCCACTACCGAATTCCACA |
| SEQ ID NO: 2974 | mm16415_Spa17 | AAGACTATACCTTGAATGCG |
| SEQ ID NO: 2975 | mm16416_Spa17 | AAGGTTCTCAAAATACGCTG |
| SEQ ID NO: 2976 | mm16417_Spa17 | CTTTGATCCAGCAGAATGGG |
| SEQ ID NO: 2977 | mm16430_Spam1 | GTCCCAACTGAACGTTGTGT |
| SEQ ID NO: 2978 | mm16431_Spam1 | AACTCGGTAGCGGACATAGA |
| SEQ ID NO: 2979 | mm16432_Spam1 | GCTTGATAATCGCCCCTCTG |
| SEQ ID NO: 2980 | mm16433_Spam1 | TACCTCTGAATACCTTCTAG |
| SEQ ID NO: 2981 | mm16434_Sparc | AGAATTTGAGGACGGTGCAG |
| SEQ ID NO: 2982 | mm16435_Sparc | AGCCAGTCACGCATGCGCAG |
| SEQ ID NO: 2983 | mm16436_Sparc | ATGGTCCGATGTAGTCCAGG |
| SEQ ID NO: 2984 | mm16437_Sparc | ACCTTGTACGAGAGAGATGA |
| SEQ ID NO: 2985 | mm16502_Serpine2 | GTTGTACCATAAGCCATTCG |
| SEQ ID NO: 2986 | mm16503_Serpine2 | TGAAATACACTGCATTAACG |
| SEQ ID NO: 2987 | mm16504_Serpine2 | TACATTATATCGCATCACCG |
| SEQ ID NO: 2988 | mm16505_Serpine2 | GAGACAACAACGTTCTCATG |
| SEQ ID NO: 2989 | mm16546_Spn | ACAAGCTCTAACGAGACCAG |
| SEQ ID NO: 2990 | mm16547_Spn | GCAGCCAATCCTGTGACAGA |
| SEQ ID NO: 2991 | mm16548_Spn | GGGATCTTGGGTAGACGTCG |
| SEQ ID NO: 2992 | mm16549_Spn | CGAGCCCAGACAGTCTGCAG |
| SEQ ID NO: 2993 | mm16558_Sptb | AGAGGGCCTAGATACTGACT |
| SEQ ID NO: 2994 | mm16559_Sptb | CAGAACAACTCTCAGCCGCG |
| SEQ ID NO: 2995 | mm16560_Sptb | GAAGGTTGTGGAGTCAACCA |
| SEQ ID NO: 2996 | mm16561_Sptb | TCAACGAGTTGGCAAACTTG |
| SEQ ID NO: 2997 | mm16654_Scarb1 | GGGGCCGTGAAGCGATACGT |
| SEQ ID NO: 2998 | mm16655_Scarb1 | TGCGGTTCATAAAAGCACGC |
| SEQ ID NO: 2999 | mm16656_Scarb1 | GATGAACAACTCGAATTCTG |
| SEQ ID NO: 3000 | mm16657_Scarb1 | GAGGATTCGGGTGTCATGAA |
| SEQ ID NO: 3001 | mm16754_Stat4 | AATGTCTAAACTCCACTGAG |
| SEQ ID NO: 3002 | mm16755_Stat4 | GCATGCCAACGCACCCTCAG |
| SEQ ID NO: 3003 | mm16756_Stat4 | AAATCCAATGCATGTAGCTG |
| SEQ ID NO: 3004 | mm16757_Stat4 | TGGCCTCACCATTAACCTAG |
| SEQ ID NO: 3005 | mm16802_Stim1 | TGAGGATAAGCTTATCAGCG |
| SEQ ID NO: 3006 | mm16803_Stim1 | GAATACAGGAGCTAGCTCCG |
| SEQ ID NO: 3007 | mm16804_Stim1 | GAGCCGTCAAAAATATGCTG |
| SEQ ID NO: 3008 | mm16805_Stim1 | CAGCAGATCGAGATCCTCTG |
| SEQ ID NO: 3009 | mm16842_Wnt8a | GGGAGGCTGCAGCGACAACG |

TABLE 1-continued mmSurf sgRNA library sequences

| SEQ ID NO | id_gRNA Target | Sequence |
|---|---|---|
| SEQ ID NO: 3010 | mm16843_Wnt8a | CCGCGCGCTGAAAATTGAGA |
| SEQ ID NO: 3011 | mm16844_Wnt8a | TCTGACCTACACCGCCAGTG |
| SEQ ID NO: 3012 | mm16845_Wnt8a | AAAAGGACCTGCAAGTGTCA |
| SEQ ID NO: 3013 | mm16874_Stx4a | TGCTGGAATGGTGTCTGACG |
| SEQ ID NO: 3014 | mm16875_Stx4a | TCTCGTTTAGGCATGAAGCA |
| SEQ ID NO: 3015 | mm16876_Stx4a | ATTACAACTCAGTCAACACA |
| SEQ ID NO: 3016 | mm16877_Stx4a | CGAATACCGAGAGAAGAATG |
| SEQ ID NO: 3017 | mm16982_Sdc1 | GTCACATCTCATCCGCACGG |
| SEQ ID NO: 3018 | mm16983_Sdc1 | AGGAAAAGGAGGTCACCACC |
| SEQ ID NO: 3019 | mm16984_Sdc1 | CACACGTCCTTCCAAGTGGA |
| SEQ ID NO: 3020 | mm16985_Sdc1 | TGTCATCAAAGAGGTTGTCG |
| SEQ ID NO: 3021 | mm16986_Sdc3 | CACAACCGTTATCCAGCCCG |
| SEQ ID NO: 3022 | mm16987_Sdc3 | AGGAAGGGCTCGTGGCCTCG |
| SEQ ID NO: 3023 | mm16988_Sdc3 | AACTAGACGACCTCTACTCG |
| SEQ ID NO: 3024 | mm16989_Sdc3 | GGCGCAATGAGAACTTCGAG |
| SEQ ID NO: 3025 | mm16990_Sdc4 | GGACATGTCATCCCCCACGT |
| SEQ ID NO: 3026 | mm16991_Sdc4 | TTCTTAGATTCGAGAGACAG |
| SEQ ID NO: 3027 | mm16992_Sdc4 | TCAGGGATGTGGTTATCCAG |
| SEQ ID NO: 3028 | mm16993_Sdc4 | CAGCATCTTCGTCGTCGGGG |
| SEQ ID NO: 3029 | mm17010_Syp | GCACCCTCCTGCGTTAAAGG |
| SEQ ID NO: 3030 | mm17011_Syp | GTAGCTGCCGCACGTAGCAA |
| SEQ ID NO: 3031 | mm17012_Syp | CAAATTCGACTTCGATGTTG |
| SEQ ID NO: 3032 | mm17013_Syp | AAGTACCGAGAGAACAACAA |
| SEQ ID NO: 3033 | mm17046_Tacr1 | CATGGCTGCATTCAATACAG |
| SEQ ID NO: 3034 | mm17047_Tacr1 | GGTGGTCAAAATGATGATCG |
| SEQ ID NO: 3035 | mm17048_Tacr1 | GATTGGCTATGCATACACTG |
| SEQ ID NO: 3036 | mm17049_Tacr1 | CACCACGATGACCGTATAGG |
| SEQ ID NO: 3037 | mm17110_Slc6a6 | GGCCCCAGGCAGATTGCGT |
| SEQ ID NO: 3038 | mm17111_Slc6a6 | GGCCAGTACACATCAGAAGG |
| SEQ ID NO: 3039 | mm17112_Slc6a6 | AAACAGAATAGACCAAAAGG |
| SEQ ID NO: 3040 | mm17113_Slc6a6 | CATGGCAAACGGGAAAGTAG |
| SEQ ID NO: 3041 | mm17114_Cntn2 | GACCCCGTGAAAACCCACGA |
| SEQ ID NO: 3042 | mm17115_Cntn2 | CTCACCACCACACCCCCAGG |
| SEQ ID NO: 3043 | mm17116_Cntn2 | TGTGAATATCGAGGGCAACG |
| SEQ ID NO: 3044 | mm17117_Cntn2 | AAGGGCCGTGACACCGTCCA |
| SEQ ID NO: 3045 | mm17170_Tbxa2r | GACGTGCCATCGCGTCGCCA |
| SEQ ID NO: 3046 | mm17171_Tbxa2r | CTGACACTCGGGACACAGCG |
| SEQ ID NO: 3047 | mm17172_Tbxa2r | AGTGGCTCGCCAGTCCAACA |

TABLE 1-continued mmSurf sgRNA library sequences

| SEQ ID NO | id_gRNA Target | Sequence |
|---|---|---|
| SEQ ID NO: 3048 | mm17173_Tbxa2r | AGCGCTTCGTGGGCATCACA |
| SEQ ID NO: 3049 | mm17342_Tdgf1 | GGGTCCAAATTCAAACGCAC |
| SEQ ID NO: 3050 | mm17343_Tdgf1 | CAGTTGCGTCCATAGAAGGA |
| SEQ ID NO: 3051 | mm17344_Tdgf1 | CTGTTCTGTATCCCCACGGA |
| SEQ ID NO: 3052 | mm17345_Tdgf1 | AAGAACCTGCCGTACGCGAT |
| SEQ ID NO: 3053 | mm17394_Tek | TTAACTATGACCGTGGACAG |
| SEQ ID NO: 3054 | mm17395_Tek | AGTACAAGGACGGCTACAGT |
| SEQ ID NO: 3055 | mm17396_Tek | CTATACAGATCGTTTCTCAG |
| SEQ ID NO: 3056 | mm17397_Tek | CTGGTCCGTAGTAACCAGAT |
| SEQ ID NO: 3057 | mm17502_Tfpi | TGTGAACGATTCGTGTACGG |
| SEQ ID NO: 3058 | mm17503_Tfpi | TGTGAAGAATTTATATACGG |
| SEQ ID NO: 3059 | mm17504_Tfpi | ACCTTGTAGATTCTGAGCTG |
| SEQ ID NO: 3060 | mm17505_Tfpi | GATACCTCTTCATGTAACCT |
| SEQ ID NO: 3061 | mm17510_Tgfa | AACAGCACATCCCCCCTGAG |
| SEQ ID NO: 3062 | mm17511_Tgfa | GGGAATACTTACACACATGC |
| SEQ ID NO: 3063 | mm17512_Tgfa | ATGGAAGCAGTACTGAGTGT |
| SEQ ID NO: 3064 | mm17513_Tgfa | TTCCTGCACCAAAAACCGGC |
| SEQ ID NO: 3065 | mm17514_Tgfb1 | CCACTCAGGCGTATCAGTGG |
| SEQ ID NO: 3066 | mm17515_Tgfb1 | GGGATCAGCCCCAAACGTCG |
| SEQ ID NO: 3067 | mm17516_Tgfb1 | GCGGTCCACCATTAGCACGC |
| SEQ ID NO: 3068 | mm17517_Tgfb1 | TCTGCACGGGACAGCAATGG |
| SEQ ID NO: 3069 | mm17526_Tgfb2 | GTAATTATTAGACGGCACGA |
| SEQ ID NO: 3070 | mm17527_Tgfb2 | GCTCCGGATAGTCTTCCGGG |
| SEQ ID NO: 3071 | mm17528_Tgfb2 | CCAGCGCTACATCGATAGCA |
| SEQ ID NO: 3072 | mm17529_Tgfb2 | GCATAAACTGATCCATGTCG |
| SEQ ID NO: 3073 | mm17530_Tgfb3 | AAAGTGCCAGGACCTGATAG |
| SEQ ID NO: 3074 | mm17531_Tgfb3 | GGCATAGTACTCAGACTCCG |
| SEQ ID NO: 3075 | mm17532_Tgfb3 | GCCAAGCAGCGCTACATAGG |
| SEQ ID NO: 3076 | mm17533_Tgfb3 | AAGAGGGTGGAAGCCATTAG |
| SEQ ID NO: 3077 | mm17538_Tgfbr1 | AGAGCGTTCATGGTTCCGAG |
| SEQ ID NO: 3078 | mm17539_Tgfbr1 | ATGAAAGGGCGATCTAGTGA |
| SEQ ID NO: 3079 | mm17540_Tgfbr1 | ATTGTGTTACAAGAAAGCAT |
| SEQ ID NO: 3080 | mm17541_Tgfbr1 | GTGTCAGATTATCATGAGCA |
| SEQ ID NO: 3081 | mm17542_Tgfbr2 | CCTACGAGGAGTACTCCTCG |
| SEQ ID NO: 3082 | mm17543_Tgfbr2 | ACCTGCAGGAGTACCTCACG |
| SEQ ID NO: 3083 | mm17544_Tgfbr2 | GAAGCCGCATGAAGTCTGCG |
| SEQ ID NO: 3084 | mm17545_Tgfbr2 | CCTTGTAGACCTCGGCGAAG |
| SEQ ID NO: 3085 | mm17546_Tgfbr3 | GCTGTGGTACTAGACATAGG |

TABLE 1-continued mmSurf sgRNA library sequences

| SEQ ID NO | id_gRNA Target | Sequence |
|---|---|---|
| SEQ ID NO: 3086 | mm17547_Tgfbr3 | CATCTTCGGCTTGAGAACAA |
| SEQ ID NO: 3087 | mm17548_Tgfbr3 | ATTGTCACATTTGACTGACA |
| SEQ ID NO: 3088 | mm17549_Tgfbr3 | AACCTCCGCAGTACAGACCA |
| SEQ ID NO: 3089 | mm17582_Thbd | TACCTACAACACCCCGTTCG |
| SEQ ID NO: 3090 | mm17583_Thbd | GTGTGAGACAGGCTACCAGT |
| SEQ ID NO: 3091 | mm17584_Thbd | CTGTGAAGTAAAACTCACAG |
| SEQ ID NO: 3092 | mm17585_Thbd | TCGCAGTTAGATCCGAAACA |
| SEQ ID NO: 3093 | mm17586_Thbs1 | CCAGTGCAAAGACGTCGATG |
| SEQ ID NO: 3094 | mm17587_Thbs1 | GTCACAGAACAGGACGACCA |
| SEQ ID NO: 3095 | mm17588_Thbs1 | GAACTTGTCATCCGGCACAG |
| SEQ ID NO: 3096 | mm17589_Thbs1 | CTGTGATAAGATGGAGAGCG |
| SEQ ID NO: 3097 | mm17622_Thy1 | CCTTGGTGTTATTCTCATGG |
| SEQ ID NO: 3098 | mm17623_Thy1 | TAAGGACCTTGATATAGGGC |
| SEQ ID NO: 3099 | mm17624_Thy1 | CAGTCTTGCAGGTGTCCCGA |
| SEQ ID NO: 3100 | mm17625_Thy1 | CGTGTGCTCGGGTATCCCAA |
| SEQ ID NO: 3101 | mm17650_Trim28 | ATGAAGGAGCTGAATAAGCG |
| SEQ ID NO: 3102 | mm17651_Trim28 | CGCCGCAGCGAATAATTCGG |
| SEQ ID NO: 3103 | mm17652_Trim28 | GCACTCCACACAATAGCTAG |
| SEQ ID NO: 3104 | mm17653_Trim28 | AGGCGTTCAAGGCTCACACG |
| SEQ ID NO: 3105 | mm17670_Timp1 | GTAGGCGTACCGGATATCTG |
| SEQ ID NO: 3106 | mm17671_Timp1 | GCAGGGCTCAGAGTACGCCA |
| SEQ ID NO: 3107 | mm17672_Timp1 | CTTATAACGCTGGTATAAGG |
| SEQ ID NO: 3108 | mm17673_Timp1 | TGATGAGAAACTCTTCACTG |
| SEQ ID NO: 3109 | mm17674_Timp2 | AGACATCGAGTTTATCTACA |
| SEQ ID NO: 3110 | mm17675_Timp2 | CATACTGAATCCTCTTGATG |
| SEQ ID NO: 3111 | mm17676_Timp2 | GTGATGCTAAGCGTGTCCCA |
| SEQ ID NO: 3112 | mm17677_Timp2 | GCATTGCAAAACGCCTGTTG |
| SEQ ID NO: 3113 | mm17686_Tjp1 | TTCTGTTCGCTAAAGCACCG |
| SEQ ID NO: 3114 | mm17687_Tjp1 | AGAGCGAATGTCTAAACCTG |
| SEQ ID NO: 3115 | mm17688_Tjp1 | GTTCTACTGTCGTACGACAG |
| SEQ ID NO: 3116 | mm17689_Tjp1 | ATTAGATGTAACGCCAAATG |
| SEQ ID NO: 3117 | mm17690_Tjp2 | GCTTATGAACCCGACTACGG |
| SEQ ID NO: 3118 | mm17691_Tjp2 | TATGGGCCAAACAGAACCA |
| SEQ ID NO: 3119 | mm17692_Tjp2 | CCTCGGTCGTCATGACTGAG |
| SEQ ID NO: 3120 | mm17693_Tjp2 | CCACGCCGTTCAAGTCCACG |
| SEQ ID NO: 3121 | mm17730_Tlr1 | TAACGTGCCGAAGAGATTCG |
| SEQ ID NO: 3122 | mm17731_Tlr1 | TACTGTATATGTAACTTTGG |
| SEQ ID NO: 3123 | mm17732_Tlr1 | TGAACAATGTGGAAACAACG |

TABLE 1-continued mmSurf sgRNA library sequences

| SEQ ID NO | id_gRNA Target | Sequence |
|---|---|---|
| SEQ ID NO: 3124 | mm17733_Tlr1 | GCTTGAGGCTGACTGTTGGG |
| SEQ ID NO: 3125 | mm17734_Tlr4 | ATTCTCCCAAGATCAACCGA |
| SEQ ID NO: 3126 | mm17735_Tlr4 | TCTGACGAACCTAGTACATG |
| SEQ ID NO: 3127 | mm17736_Tlr4 | CAGAAACATTCGCCAAGCAA |
| SEQ ID NO: 3128 | mm17737_Tlr4 | TCAGTATCAAGTTTGAGAGG |
| SEQ ID NO: 3129 | mm17738_Tlr6 | GAGTTATCATATAAAAGGCG |
| SEQ ID NO: 3130 | mm17739_Tlr6 | GATAACTGAGAGAATCGACA |
| SEQ ID NO: 3131 | mm17740_Tlr6 | TTGCCAAATTCCTTACACAC |
| SEQ ID NO: 3132 | mm17741_Tlr6 | AACATCCAAAGTTTCCAGAG |
| SEQ ID NO: 3133 | mm17758_Tspan7 | TCAGCATCCATGGACTACCA |
| SEQ ID NO: 3134 | mm17759_Tspan7 | TGGAACCGGCACCACCATCG |
| SEQ ID NO: 3135 | mm17760_Tspan7 | ATCCGTGTAAGTCCTCAGGA |
| SEQ ID NO: 3136 | mm17761_Tspan7 | TCTCCTTTCGCAGATCACTG |
| SEQ ID NO: 3137 | mm17770_Tmpo | GCCCGACTTCTCGAGCGACG |
| SEQ ID NO: 3138 | mm17771_Tmpo | ATAGTGGAAAATATTTGCCG |
| SEQ ID NO: 3139 | mm17772_Tmpo | AATAAATAAACTCCGTCCAG |
| SEQ ID NO: 3140 | mm17773_Tmpo | CAAGAAAGTGAAGTCCGCTA |
| SEQ ID NO: 3141 | mm17786_Tnf | AAGAAATCTTACCTACGACG |
| SEQ ID NO: 3142 | mm17787_Tnf | GTAGACAAGGTACAACCCAT |
| SEQ ID NO: 3143 | mm17788_Tnf | TGGGCCATAGAACTGATGAG |
| SEQ ID NO: 3144 | mm17789_Tnf | CAGTAGACAGAAGAGCGTGG |
| SEQ ID NO: 3145 | mm17806_Tnfrsf10b | TAGAATGTACCTGCTAGACA |
| SEQ ID NO: 3146 | mm17807_Tnfrsf10b | AAATGACTCTAACCACAACA |
| SEQ ID NO: 3147 | mm17808_Tnfrsf10b | ACGGTGTGTCGATGCAAACC |
| SEQ ID NO: 3148 | mm17809_Tnfrsf10b | TGGTTGCTCTGTATAAAAAG |
| SEQ ID NO: 3149 | mm17810_Tnfrsf11a | ACCAGCACAACGGTCCCCTG |
| SEQ ID NO: 3150 | mm17811_Tnfrsf11a | ACACTGAGGAGACCACCCAA |
| SEQ ID NO: 3151 | mm17812_Tnfrsf11a | GTTTAAGCCAGTGTTTCACC |
| SEQ ID NO: 3152 | mm17813_Tnfrsf11a | AGACGCAAGGAGACCTCTCG |
| SEQ ID NO: 3153 | mm17818_Tnfrsf18 | GCCAAACACAATATCCCCTG |
| SEQ ID NO: 3154 | mm17819_Tnfrsf18 | GTCACACCTGAGTACCACTG |
| SEQ ID NO: 3155 | mm17820_Tnfrsf18 | GCAGTGACCGTCACGACCTG |
| SEQ ID NO: 3156 | mm17821_Tnfrsf18 | TTATTCTTGTCCAGGCAAGG |
| SEQ ID NO: 3157 | mm17822_Tnfrsf1a | AGTTGCAAGACATGTCGGAA |
| SEQ ID NO: 3158 | mm17823_Tnfrsf1a | AGACCTAGCAAGATAACCAG |
| SEQ ID NO: 3159 | mm17824_Tnfrsf1a | GATGGGGATACATCCATCAG |
| SEQ ID NO: 3160 | mm17825_Tnfrsf1a | GGATCCCGTGCCTGTCAAAG |
| SEQ ID NO: 3161 | mm17830_Cd40 | ATTCGCCTGAGTCACATGGG |

TABLE 1-continued mmSurf sgRNA library sequences

| SEQ ID NO | id_gRNA Target | Sequence |
|---|---|---|
| SEQ ID NO: 3162 | mm17831_Cd40 | GGGATGACAGACGGTATCAG |
| SEQ ID NO: 3163 | mm17832_Cd40 | AGTCAGACTAATGTCATCTG |
| SEQ ID NO: 3164 | mm17833_Cd40 | CTGCACCAGCAAGGATTGCG |
| SEQ ID NO: 3165 | mm17834_Cd27 | TCTCTCCAGACTACCACACC |
| SEQ ID NO: 3166 | mm17835_Cd27 | TGCTGCATACCTGTGCCATG |
| SEQ ID NO: 3167 | mm17836_Cd27 | AGACAAACACTACTGGACTG |
| SEQ ID NO: 3168 | mm17837_Cd27 | CTCAGGTACATTCTTTGTGA |
| SEQ ID NO: 3169 | mm17838_Tnfrsf8 | AGACCTCAGCCACTACCCAG |
| SEQ ID NO: 3170 | mm17839_Tnfrsf8 | GCAATTGGGACCAGATCCCG |
| SEQ ID NO: 3171 | mm17840_Tnfrsf8 | ATCTACCACAAGGCTTAGGG |
| SEQ ID NO: 3172 | mm17841_Tnfrsf8 | TACAGGCCTTCCAGTAACAC |
| SEQ ID NO: 3173 | mm17842_Tnfrsf9 | GTGCATACGTACTTCGTCCA |
| SEQ ID NO: 3174 | mm17843_Tnfrsf9 | TGTGCTTAAGACCGGGACCA |
| SEQ ID NO: 3175 | mm17844_Tnfrsf9 | CCAAGTACCTTCTCCAGCAT |
| SEQ ID NO: 3176 | mm17845_Tnfrsf9 | ACCAGGCTGACAGTTATCAC |
| SEQ ID NO: 3177 | mm17846_Tnfsf11 | GCCTCGATCGTGGTACCAAG |
| SEQ ID NO: 3178 | mm17847_Tnfsf11 | GACCCTCGTGTGGGACGCCG |
| SEQ ID NO: 3179 | mm17848_Tnfsf11 | GTTAAGCAACGGAAAACTAA |
| SEQ ID NO: 3180 | mm17849_Tnfsf11 | AGATTTGCAGGACTCGACTC |
| SEQ ID NO: 3181 | mm17862_Cd40lg | TATTTCAAAACAGGTCGAAG |
| SEQ ID NO: 3182 | mm17863_Cd40lg | AAGCTAAAGAGATGCAACAA |
| SEQ ID NO: 3183 | mm17864_Cd40lg | TTATACCATGAAAAGCAACT |
| SEQ ID NO: 3184 | mm17865_Cd40lg | TGAACTGTGAGGAGATGAGA |
| SEQ ID NO: 3185 | mm17870_Tnfsf8 | CACAACAAGGCACACCAGTG |
| SEQ ID NO: 3186 | mm17871_Tnfsf8 | CTGGTATATGAGTCCGTGGA |
| SEQ ID NO: 3187 | mm17872_Tnfsf8 | AATGATTTGAGCACTGCACG |
| SEQ ID NO: 3188 | mm17873_Tnfsf8 | GCTCTTACCTCCTTTAAGGG |
| SEQ ID NO: 3189 | mm17874_Tnfsf9 | GGGAGCTCATACCTATCTCA |
| SEQ ID NO: 3190 | mm17875_Tnfsf9 | AAAAATACGTAGTAGAGCCC |
| SEQ ID NO: 3191 | mm17876_Tnfsf9 | GGTTAATGTTCGGGATCGCG |
| SEQ ID NO: 3192 | mm17877_Tnfsf9 | AGTGTTGGGGCAGCCAATGT |
| SEQ ID NO: 3193 | mm17914_Tnr | GCACGTTGATGTTATACACA |
| SEQ ID NO: 3194 | mm17915_Tnr | ACGGAGTACTGGCTTAAGGG |
| SEQ ID NO: 3195 | mm17916_Tnr | TAAAGGACGTCACATCGCTG |
| SEQ ID NO: 3196 | mm17917_Tnr | CTGAGGAGGCTGTTACCATG |
| SEQ ID NO: 3197 | mm17954_Tpbg | GCCAGCCGAGAGATGCCCCG |
| SEQ ID NO: 3198 | mm17955_Tpbg | GAATCACATCGTGCCCCTG |
| SEQ ID NO: 3199 | mm17956_Tpbg | AAAAGGTTGCGCACGTAAGG |

TABLE 1-continued mmSurf sgRNA library sequences

| SEQ ID NO | id_gRNA Target | Sequence |
|---|---|---|
| SEQ ID NO: 3200 | mm17957_Tpbg | GCTGGGTTGGGTCTCCGCGT |
| SEQ ID NO: 3201 | mm17990_Tpo | GGTTTGGATCCGATAGTGAG |
| SEQ ID NO: 3202 | mm17991_Tpo | TCTAAATGAGTACCAACCGG |
| SEQ ID NO: 3203 | mm17992_Tpo | TGGCAGCGGTACACACCTTG |
| SEQ ID NO: 3204 | mm17993_Tpo | TGAGGGAAATTACCTGTATG |
| SEQ ID NO: 3205 | mm17998_Tpst2 | TGCCATAGCGGTACTCCACG |
| SEQ ID NO: 3206 | mm17999_Tpst2 | GCACTCCATGATCACGCGCA |
| SEQ ID NO: 3207 | mm18000_Tpst2 | CTGTGCGTACATCACCTCGA |
| SEQ ID NO: 3208 | mm18001_Tpst2 | GCCGCATGGCCAGCACACGA |
| SEQ ID NO: 3209 | mm18014_Hsp90b1 | AAGACCACTCAAATCGAACA |
| SEQ ID NO: 3210 | mm18015_Hsp90b1 | TCCACAGACAGAGACTGTTG |
| SEQ ID NO: 3211 | mm18016_Hsp90b1 | TATTCATCAAACAGACCTCG |
| SEQ ID NO: 3212 | mm18017_Hsp90b1 | AGAGGAAACACACTAGGTCG |
| SEQ ID NO: 3213 | mm18058_Trf | GGGGACCCTTAACAGCCCAA |
| SEQ ID NO: 3214 | mm18059_Trf | ACAGACCTACTACTACGCTG |
| SEQ ID NO: 3215 | mm18060_Trf | GTAGCCAAAGAATGGTTGAG |
| SEQ ID NO: 3216 | mm18061_Trf | AGAGAACCAAGTGTGACGAG |
| SEQ ID NO: 3217 | mm18062_Tfrc | CTACACGCTTACAATAGCCC |
| SEQ ID NO: 3218 | mm18063_Tfrc | GAATACATACACTCCTCGTG |
| SEQ ID NO: 3219 | mm18064_Tfrc | GGGCTCCTACTACAACATAA |
| SEQ ID NO: 3220 | mm18065_Tfrc | AACCCTCGGGAGACTCCACT |
| SEQ ID NO: 3221 | mm18070_Trhr | AGATACTGTCGGTTATGTTG |
| SEQ ID NO: 3222 | mm18071_Trhr | GGTGGTTACCATCTTACTTG |
| SEQ ID NO: 3223 | mm18072_Trhr | CACCTACAAAAACGCTGTTG |
| SEQ ID NO: 3224 | mm18073_Trhr | CTAAAGAAAACTCTAAGATG |
| SEQ ID NO: 3225 | mm18106_Trpc4 | AACTCCGTGTCTGATCTAGG |
| SEQ ID NO: 3226 | mm18107_Trpc4 | ATTAACTGCATCGACCCCCT |
| SEQ ID NO: 3227 | mm18108_Trpc4 | GGAGTGGATGATATTACCGT |
| SEQ ID NO: 3228 | mm18109_Trpc4 | GACATTATATGTGCCAAACA |
| SEQ ID NO: 3229 | mm18206_Tgoln1 | CAAACTGTGATCGGTCGCGG |
| SEQ ID NO: 3230 | mm18207_Tgoln1 | AAGACTACAAGGCCGACCGA |
| SEQ ID NO: 3231 | mm18208_Tgoln1 | CCGAGTTGAACGAAACTGCG |
| SEQ ID NO: 3232 | mm18209_Tgoln1 | GGAGTGGAGGACTGTTTGGA |
| SEQ ID NO: 3233 | mm18246_Tubb2a | CGGGCACCATGGACTCAGTG |
| SEQ ID NO: 3234 | mm18247_Tubb2a | GAGGTGATAAGCGATGAGCA |
| SEQ ID NO: 3235 | mm18248_Tubb2a | ACTCTGTCCTAGATGTGGTG |
| SEQ ID NO: 3236 | mm18249_Tubb2a | AACCTATTCCATTGACAATG |
| SEQ ID NO: 3237 | mm18258_Tubb5 | GAGGTGATAAGCGATGAACA |

TABLE 1-continued mmSurf sgRNA library sequences

| SEQ ID NO | id_gRNA Target | Sequence |
|---|---|---|
| SEQ ID NO: 3238 | mm18259_Tubb5 | GATCCACCAAGATAGCTCGA |
| SEQ ID NO: 3239 | mm18260_Tubb5 | TATCATGAATACCTTCAGTG |
| SEQ ID NO: 3240 | mm18261_Tubb5 | GGGTAAGTTCAGGCACAGTG |
| SEQ ID NO: 3241 | mm18278_Tnfrsf4 | GAGCCGCTGTGATCATACCA |
| SEQ ID NO: 3242 | mm18279_Tnfrsf4 | TCACACTTGGAGTTACAGCA |
| SEQ ID NO: 3243 | mm18280_Tnfrsf4 | TTCCAGATAAGGTACAACTG |
| SEQ ID NO: 3244 | mm18281_Tnfrsf4 | GTAGACCAGGCACCCAACCT |
| SEQ ID NO: 3245 | mm18282_Tnfsf4 | GAATGAGTATCAAACTATGG |
| SEQ ID NO: 3246 | mm18283_Tnfsf4 | ACTGGTGCATCTTACCGGAG |
| SEQ ID NO: 3247 | mm18284_Tnfsf4 | AGATGGGATTATGATCCTCC |
| SEQ ID NO: 3248 | mm18285_Tnfsf4 | CGGTTGTCATCAAGTGCGAT |
| SEQ ID NO: 3249 | mm18306_Tyro3 | GGAGTTTGACCATCCACACG |
| SEQ ID NO: 3250 | mm18307_Tyro3 | TAGGAGAGTTTGGATCAGTG |
| SEQ ID NO: 3251 | mm18308_Tyro3 | ACAGCTTATAAGGTCCTAGG |
| SEQ ID NO: 3252 | mm18309_Tyro3 | AACCCGTAACCATTTACTGG |
| SEQ ID NO: 3253 | mm18310_Tyrobp | CTGTACGGGACTTAATCCTA |
| SEQ ID NO: 3254 | mm18311_Tyrobp | AAGGAACAGAAGGCACCAGG |
| SEQ ID NO: 3255 | mm18312_Tyrobp | CAATCCCAGCCAGTACACCA |
| SEQ ID NO: 3256 | mm18313_Tyrobp | CTTGACCTCGGGAGACCAGG |
| SEQ ID NO: 3257 | mm18494_Unc5c | AGGCACTACGAAGAGTCGGA |
| SEQ ID NO: 3258 | mm18495_Unc5c | CTTACCATACACGATGACAG |
| SEQ ID NO: 3259 | mm18496_Unc5c | TCAGACCCTACTTACCCCTG |
| SEQ ID NO: 3260 | mm18497_Unc5c | ATGATGTGGCTCTCTACGTG |
| SEQ ID NO: 3261 | mm18638_Vamp1 | CCAACATGACCAGTAACAGG |
| SEQ ID NO: 3262 | mm18639_Vamp1 | GCTCTCAAATTGTGATGCTC |
| SEQ ID NO: 3263 | mm18640_Vamp1 | TCTGCAATCTCCTTAGGTGG |
| SEQ ID NO: 3264 | mm18641_Vamp1 | GGACATCATGCGTGTGAATG |
| SEQ ID NO: 3265 | mm18646_Vamp3 | TGACATCATGAGAGTCAATG |
| SEQ ID NO: 3266 | mm18647_Vamp3 | AGCACTTGTTTCAAACTGCG |
| SEQ ID NO: 3267 | mm18648_Vamp3 | GAGTCTTCGATTACTGCCAG |
| SEQ ID NO: 3268 | mm18649_Vamp3 | TGACCGCGCAGATGCACTGC |
| SEQ ID NO: 3269 | mm18650_Vamp8 | CCACCTCCGAAACAAGACAG |
| SEQ ID NO: 3270 | mm18651_Vamp8 | TTATGACCCAGAATGTGGAG |
| SEQ ID NO: 3271 | mm18652_Vamp8 | CTTCAAGACAACGTCCCAGA |
| SEQ ID NO: 3272 | mm18653_Vamp8 | GGAGCGGATCTTGGCCAGAG |
| SEQ ID NO: 3273 | mm18674_Vcam1 | GCTGGAACGAAGTATCCACG |
| SEQ ID NO: 3274 | mm18675_Vcam1 | AGACAGCCCACTAAACGCGA |
| SEQ ID NO: 3275 | mm18676_Vcam1 | CACAGAGCTCAACACAAGCG |

TABLE 1-continued mmSurf sgRNA library sequences

| SEQ ID NO | id_gRNA Target | Sequence |
|---|---|---|
| SEQ ID NO: 3276 | mm18677_Vcam1 | TCCCTCCACAAGGCTTCAAG |
| SEQ ID NO: 3277 | mm18682_Vdac1 | AAGAGGGAGCACATCAACCT |
| SEQ ID NO: 3278 | mm18683_Vdac1 | CGGCGAGAATGACGAATCAA |
| SEQ ID NO: 3279 | mm18684_Vdac1 | TGGAACACAGACAACACCCT |
| SEQ ID NO: 3280 | mm18685_Vdac1 | CTTCGCAGTTGGCTATAAGA |
| SEQ ID NO: 3281 | mm18694_Vegfa | AGATGTACTCTATCTCGTCG |
| SEQ ID NO: 3282 | mm18695_Vegfa | TGGTTTCGGAGGCCCGTCCG |
| SEQ ID NO: 3283 | mm18696_Vegfa | GCGCGGGCTTCGGTTCCTCG |
| SEQ ID NO: 3284 | mm18697_Vegfa | GCCGCAGGAGACAAACCGAT |
| SEQ ID NO: 3285 | mm18754_Vldlr | TTGATGAATGCCAAAACCCG |
| SEQ ID NO: 3286 | mm18755_Vldlr | TAGAATACAAACCCCGACAA |
| SEQ ID NO: 3287 | mm18756_Vldlr | AGTGCATTCACAAAAAATGG |
| SEQ ID NO: 3288 | mm18757_Vldlr | AGAGCAACTAAGGAACACGG |
| SEQ ID NO: 3289 | mm18762_Vnn1 | CATGCTCGTAAACAGCCGCG |
| SEQ ID NO: 3290 | mm18763_Vnn1 | CTATGCACCCGATTCTCCAA |
| SEQ ID NO: 3291 | mm18764_Vnn1 | TACCAGATTTGGCTCTACCC |
| SEQ ID NO: 3292 | mm18765_Vnn1 | AGGAAGGACGTCCATCCAGG |
| SEQ ID NO: 3293 | mm18766_Vpreb1 | AGGGAAGAAGATGCTAATGG |
| SEQ ID NO: 3294 | mm18767_Vpreb1 | CCGGGTCCAAAGATACGACC |
| SEQ ID NO: 3295 | mm18768_Vpreb1 | GCTGGCCTATCTCACAGGTA |
| SEQ ID NO: 3296 | mm18769_Vpreb1 | TCACACTCAGACAAGCACCA |
| SEQ ID NO: 3297 | mm18786_Trpv2 | TGCACCGATGAGTTCTACCG |
| SEQ ID NO: 3298 | mm18787_Trpv2 | CCGTGACCGACTCTTCAGTG |
| SEQ ID NO: 3299 | mm18788_Trpv2 | TGACAGCCTTCTCCAAATGG |
| SEQ ID NO: 3300 | mm18789_Trpv2 | TTTCCCGAAAGTTCACCGAG |
| SEQ ID NO: 3301 | mm18790_Vtn | GGACGTGTTCACTATGCCAG |
| SEQ ID NO: 3302 | mm18791_Vtn | CGAGGATTTAGGTCACCGGG |
| SEQ ID NO: 3303 | mm18792_Vtn | GCCTAAAGTGGAGCAACAGG |
| SEQ ID NO: 3304 | mm18793_Vtn | AGATGTTTCGGGGATAACCA |
| SEQ ID NO: 3305 | mm18794_Vwf | AAATTCCTAGCCATCCGTGG |
| SEQ ID NO: 3306 | mm18795_Vwf | GCAACTTACGACAGGCACTG |
| SEQ ID NO: 3307 | mm18796_Vwf | CATTGATGTACCATGGAATG |
| SEQ ID NO: 3308 | mm18797_Vwf | TGGTCTGAGAAAATGTCCGC |
| SEQ ID NO: 3309 | mm18854_Wisp2 | GCTGTCGAGTGTGTGCACGG |
| SEQ ID NO: 3310 | mm18855_Wisp2 | TTGTGCCGCTGTGATGACGG |
| SEQ ID NO: 3311 | mm18856_Wisp2 | GCTGTGAGGTGAATGGCCGC |
| SEQ ID NO: 3312 | mm18857_Wisp2 | CCTGGTCACACACCCACTCG |
| SEQ ID NO: 3313 | mm18862_Wnt1 | CCTGCACCTGCGACTACCGG |

TABLE 1-continued mmSurf sgRNA library sequences

| SEQ ID NO | id_gRNA Target | Sequence |
|---|---|---|
| SEQ ID NO: 3314 | mm18863_Wnt1 | TTCGGCAAGATCGTCAACCG |
| SEQ ID NO: 3315 | mm18864_Wnt1 | ATCCGTCAACAGGTTCGTGG |
| SEQ ID NO: 3316 | mm18865_Wnt1 | CCACGAACTCTCGGCCAAAG |
| SEQ ID NO: 3317 | mm18894_Wnt3a | ACCGTCACAACAATGAGGCT |
| SEQ ID NO: 3318 | mm18895_Wnt3a | GTGAAGTGAAGACCTGCTGG |
| SEQ ID NO: 3319 | mm18896_Wnt3a | GTGCTCAGAGAGGAGTACTG |
| SEQ ID NO: 3320 | mm18897_Wnt3a | CACTGCGAAAGCTACTCCAG |
| SEQ ID NO: 3321 | mm18898_Wnt4 | GTGATGGACTCAGTGCGCCG |
| SEQ ID NO: 3322 | mm18899_Wnt4 | GGTGGAGTGCAAGTGTCACG |
| SEQ ID NO: 3323 | mm18900_Wnt4 | TTACAGCCAATTGCTCGCGG |
| SEQ ID NO: 3324 | mm18901_Wnt4 | TTTGGGAAGGTGGTGACACA |
| SEQ ID NO: 3325 | mm18902_Wnt5a | AGGGAACGAATCCACGCTAA |
| SEQ ID NO: 3326 | mm18903_Wnt5a | ACAACAATGAAGCAGGCCGT |
| SEQ ID NO: 3327 | mm18904_Wnt5a | CTGGGCGAAGGAGAAAAACG |
| SEQ ID NO: 3328 | mm18905_Wnt5a | GCATGTGGTCCTGATACAAG |
| SEQ ID NO: 3329 | mm18906_Wnt5b | GGAGCACATGTCCTACATCG |
| SEQ ID NO: 3330 | mm18907_Wnt5b | GACATCAGCCATCTTATACA |
| SEQ ID NO: 3331 | mm18908_Wnt5b | GCGCCAATGATGAACATCTC |
| SEQ ID NO: 3332 | mm18909_Wnt5b | GGCGCTCACTGCATACGTGA |
| SEQ ID NO: 3333 | mm18910_Wnt6 | CCGCGCACGTCGATGGACTG |
| SEQ ID NO: 3334 | mm18911_Wnt6 | TGTGCAGTTGCACCAATGCA |
| SEQ ID NO: 3335 | mm18912_Wnt6 | GTAGTGGCAGAGCTTGCCCG |
| SEQ ID NO: 3336 | mm18913_Wnt6 | AAGCCCATGGCACTTACACT |
| SEQ ID NO: 3337 | mm18914_Wnt7a | GCCCGCAGCGATAATCGCAT |
| SEQ ID NO: 3338 | mm18915_Wnt7a | CATGAACTTACACAATAACG |
| SEQ ID NO: 3339 | mm18916_Wnt7a | GGCCAGTACCACCGGGACGA |
| SEQ ID NO: 3340 | mm18917_Wnt7a | TAGCCTAGCTCTCGGAACTG |
| SEQ ID NO: 3341 | mm18918_Wnt7b | CACGCTACCTAAGTTCCGCG |
| SEQ ID NO: 3342 | mm18919_Wnt7b | GAAGCAAGGCTACTACAACC |
| SEQ ID NO: 3343 | mm18920_Wnt7b | TCACAATGATGGCATCGGGT |
| SEQ ID NO: 3344 | mm18921_Wnt7b | CAGAGCATTGTCATCCGTGG |
| SEQ ID NO: 3345 | mm19006_Ybx1 | GTCTTACAGGAATGACACCA |
| SEQ ID NO: 3346 | mm19007_Ybx1 | TTGTTGAAGGAGAAAAGGTG |
| SEQ ID NO: 3347 | mm19008_Ybx1 | GCCGGCCCTATCGCAGGCGA |
| SEQ ID NO: 3348 | mm19009_Ybx1 | GAGAGTGGGAAAAGAACGA |
| SEQ ID NO: 3349 | mm19338_Slc30a1 | TGGGCCAGCGTCACGCATCG |
| SEQ ID NO: 3350 | mm19339_Slc30a1 | CCAGGAGGGAGACCAACACGC |
| SEQ ID NO: 3351 | mm19340_Slc30a1 | GGCATTCACGACCACGATCA |

TABLE 1-continued mmSurf sgRNA library sequences

| SEQ ID NO | id_gRNA Target | Sequence |
|---|---|---|
| SEQ ID NO: 3352 | mm19341_Slc30a1 | GGAGTCTGACAATCTGGAAG |
| SEQ ID NO: 3353 | mm19358_Zp3 | AGAGACTCTCCAGTTCACGG |
| SEQ ID NO: 3354 | mm19359_Zp3 | GGTGTCCGTGGATACCGACG |
| SEQ ID NO: 3355 | mm19360_Zp3 | CATCCTCAGGACTAACCGTG |
| SEQ ID NO: 3356 | mm19361_Zp3 | TCTCAGATAGACCATCCACA |
| SEQ ID NO: 3357 | mm19382_Adam23 | CGTGTGTTCTCGAATAAGAG |
| SEQ ID NO: 3358 | mm19383_Adam23 | TCTGCAGTTTCATTCCAGTG |
| SEQ ID NO: 3359 | mm19384_Adam23 | TTTGCTATCTTCTGACTACG |
| SEQ ID NO: 3360 | mm19385_Adam23 | GAAGTGTTCGCTCTCCAATG |
| SEQ ID NO: 3361 | mm19470_Cdh20 | AGAGATGAAGTATACCATTG |
| SEQ ID NO: 3362 | mm19471_Cdh20 | TTAGACAATCCCTCCCAAGT |
| SEQ ID NO: 3363 | mm19472_Cdh20 | TTGGATAACAGATGTACCTG |
| SEQ ID NO: 3364 | mm19473_Cdh20 | AACAACAGTGCACATCAGTG |
| SEQ ID NO: 3365 | mm19482_Clec5a | AGTGGTTCCGTAGCTCTCCG |
| SEQ ID NO: 3366 | mm19483_Clec5a | ACGAAAGTACCATGCCTACA |
| SEQ ID NO: 3367 | mm19484_Clec5a | AGTGTTGACAATTGCCAGTG |
| SEQ ID NO: 3368 | mm19485_Clec5a | TCCAGTCTGTCCCAGAAACT |
| SEQ ID NO: 3369 | mm19566_Ggt5 | GTGCGGAGGTCTTATACACA |
| SEQ ID NO: 3370 | mm19567_Ggt5 | AGATCTGCTCGGATATTGGA |
| SEQ ID NO: 3371 | mm19568_Ggt5 | TGCAGAGAAGTTGAACCCTG |
| SEQ ID NO: 3372 | mm19569_Ggt5 | GCTGGGCTAGATCTTCCCGG |
| SEQ ID NO: 3373 | mm19578_Grem1 | GGGAAAAAGAAAGGTTCCCA |
| SEQ ID NO: 3374 | mm19579_Grem1 | CCTGAAGCAGACCATCCACG |
| SEQ ID NO: 3375 | mm19580_Grem1 | TGCACTGGCCATAACAGAAG |
| SEQ ID NO: 3376 | mm19581_Grem1 | CTTGCGCTCTGTCACGTGCA |
| SEQ ID NO: 3377 | mm19594_Hcst | CATGTCACTCCTAATTGTAG |
| SEQ ID NO: 3378 | mm19595_Hcst | AGTGGCTGCAAGTCAGACAT |
| SEQ ID NO: 3379 | mm19596_Hcst | CAGAGACAGAGTCCCACATC |
| SEQ ID NO: 3380 | mm19597_Hcst | TGACCGCATCTGCAGCCACT |
| SEQ ID NO: 3381 | mm19598_Hs2st1 | GTAGGCTATATTGGTGAACG |
| SEQ ID NO: 3382 | mm19599_Hs2st1 | GTCCCGGGCGAAGCTAGGTG |
| SEQ ID NO: 3383 | mm19600_Hs2st1 | AATTTATATCAATGTCATCA |
| SEQ ID NO: 3384 | mm19601_Hs2st1 | TTGTGAAGAACATAACCACC |
| SEQ ID NO: 3385 | mm19650_Ly6h | CCGCTTAACGAAGTCGCAGG |
| SEQ ID NO: 3386 | mm19651_Ly6h | CTGGCACAAACGGTATCGGT |
| SEQ ID NO: 3387 | mm19652_Ly6h | TAGGGCCTGAAAGAGGCGCG |
| SEQ ID NO: 3388 | mm19653_Ly6h | GTCCTGGCACCACAGGCCAT |
| SEQ ID NO: 3389 | mm19714_Nt5e | TCATGAATTTGATAACGGTG |

TABLE 1-continued mmSurf sgRNA library sequences

| SEQ ID NO | id_gRNA Target | Sequence |
|---|---|---|
| SEQ ID NO: 3390 | mm19715_Nt5e | TGAATAAGATCATCGCCCTG |
| SEQ ID NO: 3391 | mm19716_Nt5e | TATGCCTTTGGCAAATACCT |
| SEQ ID NO: 3392 | mm19717_Nt5e | CCTGAAGCGGCACGTCTGAG |
| SEQ ID NO: 3393 | mm19758_Pebp1 | AAGGGTAATGACATTAGCAG |
| SEQ ID NO: 3394 | mm19759_Pebp1 | CGTACACCAGCCAGACATAG |
| SEQ ID NO: 3395 | mm19760_Pebp1 | GGAGTGGCACCACTTCCTGG |
| SEQ ID NO: 3396 | mm19761_Pebp1 | CCTGCGGGTCGACTACGCCG |
| SEQ ID NO: 3397 | mm19858_Ccl19 | TCTGGGGGTGCTAATGATG |
| SEQ ID NO: 3398 | mm19859_Ccl19 | TACAGGTTCACCACACTAAG |
| SEQ ID NO: 3399 | mm19860_Ccl19 | ATTAGCACCCCCAGAGTTG |
| SEQ ID NO: 3400 | mm19861_Ccl19 | CAAGCAACTCACACAACAGC |
| SEQ ID NO: 3401 | mm19866_Sgcb | CACACCCATTTGGCCCAATG |
| SEQ ID NO: 3402 | mm19867_Sgcb | AGGACCGGCTCCATAAGACT |
| SEQ ID NO: 3403 | mm19868_Sgcb | CCGTGCTCTTATAAAGCGGG |
| SEQ ID NO: 3404 | mm19869_Sgcb | TGACGGCCAGGATAAACAGG |
| SEQ ID NO: 3405 | mm19870_Sgcd | ATCCCCACTTTGTATATGTG |
| SEQ ID NO: 3406 | mm19871_Sgcd | GAGATTGAGAGTCTTAGGTG |
| SEQ ID NO: 3407 | mm19872_Sgcd | CATGACCTTGAGAATCCAGA |
| SEQ ID NO: 3408 | mm19873_Sgcd | CTTACCTTAGTTCCTTGAAG |
| SEQ ID NO: 3409 | mm19890_Sigirr | TTGGTACCAAGACACTTACG |
| SEQ ID NO: 3410 | mm19891_Sigirr | CCTCAGTTGGAGCGGCGTCG |
| SEQ ID NO: 3411 | mm19892_Sigirr | AAGCCACTTCAGCCTCCATG |
| SEQ ID NO: 3412 | mm19893_Sigirr | CGGAAGCTCTGGCTACACCA |
| SEQ ID NO: 3413 | mm19894_Slco2a1 | CCCACGGATGATCGGCATAG |
| SEQ ID NO: 3414 | mm19895_Slco2a1 | ACTCGGGGATGGTTTGCAG |
| SEQ ID NO: 3415 | mm19896_Slco2a1 | CTTCGTGGACTACGGCAGAG |
| SEQ ID NO: 3416 | mm19897_Slco2a1 | CTCTGCAAAGTCGTCCACAT |
| SEQ ID NO: 3417 | mm19926_Synj2bp | GGTGGATTATTTAGTCACGG |
| SEQ ID NO: 3418 | mm19927_Synj2bp | CTACGTCAGCCGTATCAAAG |
| SEQ ID NO: 3419 | mm19928_Synj2bp | CAGTATGTCTCCAACGACAG |
| SEQ ID NO: 3420 | mm19929_Synj2bp | CGAAGCCATTTCTCACCGAG |
| SEQ ID NO: 3421 | mm19954_Tlr2 | TCACTACGTCTGACTCCGAG |
| SEQ ID NO: 3422 | mm19955_Tlr2 | GGAGGTTCGCACACGCTCGG |
| SEQ ID NO: 3423 | mm19956_Tlr2 | GGAAAGGGGCCCGAACCAGG |
| SEQ ID NO: 3424 | mm19957_Tlr2 | CAGGGAACAACGAAGCATCT |
| SEQ ID NO: 3425 | mm20046_Angptl2 | TGTGACCAGAGACATGACCC |
| SEQ ID NO: 3426 | mm20047_Angptl2 | GTGGGTGGTTGGTAGACCCG |
| SEQ ID NO: 3427 | mm20048_Angptl2 | GCTGGCACACAACCAATCAG |

TABLE 1-continued mmSurf sgRNA library sequences

| SEQ ID NO | id_gRNA Target | Sequence |
|---|---|---|
| SEQ ID NO: 3428 | mm20049_Angptl2 | TTACCTCAACAGGTACAAGC |
| SEQ ID NO: 3429 | mm20054_Axl | GGATATCCGGATGTGATACG |
| SEQ ID NO: 3430 | mm20055_Axl | CCCAGCAGTACATACCACCA |
| SEQ ID NO: 3431 | mm20056_Axl | CAGACAACCTACGGAGCTAG |
| SEQ ID NO: 3432 | mm20057_Axl | TTGACCACCCCAACGTCATG |
| SEQ ID NO: 3433 | mm20058_Btd | CTTGCTGTTCATAGACGTCG |
| SEQ ID NO: 3434 | mm20059_Btd | GTACCAAAAGGACTTGAGAG |
| SEQ ID NO: 3435 | mm20060_Btd | ATACCAGTTTAACACAAATG |
| SEQ ID NO: 3436 | mm20061_Btd | CCGCGAGGCTGAGTACTACG |
| SEQ ID NO: 3437 | mm20066_Ceacam1 | ATAGTAATATGAATTTCACG |
| SEQ ID NO: 3438 | mm20067_Ceacam1 | AAGCAACAACTCCAATCCCG |
| SEQ ID NO: 3439 | mm20068_Ceacam1 | TTGTTGTCTTCAGCAACCTG |
| SEQ ID NO: 3440 | mm20069_Ceacam1 | AGCTCTTGGGAGGATGCATG |
| SEQ ID NO: 3441 | mm20074_Ceacam2 | TCGGCCTTTAGCTGGCACAA |
| SEQ ID NO: 3442 | mm20075_Ceacam2 | AGATCAAAACTATCGTCGTA |
| SEQ ID NO: 3443 | mm20076_Ceacam2 | ACAGGTAGGTTATATTATCA |
| SEQ ID NO: 3444 | mm20077_Ceacam2 | ACAGTCACTTGTGCAGTGGT |
| SEQ ID NO: 3445 | mm20094_Clcn6 | GAAAGGGCGAAGATACGAGG |
| SEQ ID NO: 3446 | mm20095_Clcn6 | CTACAAATGAGATCACCTAT |
| SEQ ID NO: 3447 | mm20096_Clcn6 | GCGTGACTTTGTGTCAGCGG |
| SEQ ID NO: 3448 | mm20097_Clcn6 | AGAATAAGGCCAGGGTGACG |
| SEQ ID NO: 3449 | mm20202_Map3k5 | ATGCGTAATGAAACTTCACG |
| SEQ ID NO: 3450 | mm20203_Map3k5 | ATAATCGATAAAGGACCACG |
| SEQ ID NO: 3451 | mm20204_Map3k5 | CTGAACGAAACGGTCCACGA |
| SEQ ID NO: 3452 | mm20205_Map3k5 | GGGCGGCCGGCGTACCACCG |
| SEQ ID NO: 3453 | mm20286_Plod2 | GTGTGATTACTACTTTAGTG |
| SEQ ID NO: 3454 | mm20287_Plod2 | ATGGAATGAACAGTATCGGA |
| SEQ ID NO: 3455 | mm20288_Plod2 | AAACGCTACCTGAATTCTGG |
| SEQ ID NO: 3456 | mm20289_Plod2 | TGCTCGCTCTGAAGATTACG |
| SEQ ID NO: 3457 | mm20290_Plod3 | AGAGAGAGATCCTGTCCGGG |
| SEQ ID NO: 3458 | mm20291_Plod3 | TCAGGCATATGTGATCCGCG |
| SEQ ID NO: 3459 | mm20292_Plod3 | CTGGCGGACAATCTGATGGA |
| SEQ ID NO: 3460 | mm20293_Plod3 | AGCTCCAGCTCAACTACCTG |
| SEQ ID NO: 3461 | mm20298_Psg16 | CTACGGACCGTAAATAGACG |
| SEQ ID NO: 3462 | mm20299_Psg16 | AGGGCTTTCCTGGTACAAAG |
| SEQ ID NO: 3463 | mm20300_Psg16 | TACAAACTCTGAGTAGACAT |
| SEQ ID NO: 3464 | mm20301_Psg16 | TCATCATCGATCCAATGCCA |
| SEQ ID NO: 3465 | mm20354_Rpl27a | GAGGCGCACACTTACCGATG |

TABLE 1-continued mmSurf sgRNA library sequences

| SEQ ID NO | id_gRNA Target | Sequence |
|---|---|---|
| SEQ ID NO: 3466 | mm20355_Rpl27a | CGAGCAGACACGGGTCAATG |
| SEQ ID NO: 3467 | mm20356_Rpl27a | CAAAGTAACCTGGGTGACTG |
| SEQ ID NO: 3468 | mm20357_Rpl27a | CCTGGATAAACTGTGGACAT |
| SEQ ID NO: 3469 | mm20358_Sema4g | ACAGTATGAGACACTACGTG |
| SEQ ID NO: 3470 | mm20359_Sema4g | GCCGCTGTAGAAATCGCACG |
| SEQ ID NO: 3471 | mm20360_Sema4g | AGAAAGAGCAGGTCATAGGT |
| SEQ ID NO: 3472 | mm20361_Sema4g | GGAGAAATGTCCTTATGACC |
| SEQ ID NO: 3473 | mm20426_Ror1 | AGCACGGGTGTAGACTACCG |
| SEQ ID NO: 3474 | mm20427_Ror1 | TCATCACGACACAAGTCACG |
| SEQ ID NO: 3475 | mm20428_Ror1 | ACTTCAAGTGAAATCGACAA |
| SEQ ID NO: 3476 | mm20429_Ror1 | ACAGCCGACATCGGAATGCG |
| SEQ ID NO: 3477 | mm20430_Ror2 | AGAGAATACATACTACACGG |
| SEQ ID NO: 3478 | mm20431_Ror2 | TGGTGGCGCAGATCGCTGCG |
| SEQ ID NO: 3479 | mm20432_Ror2 | GCTCTGGCGCCGATTACAGG |
| SEQ ID NO: 3480 | mm20433_Ror2 | CTGGTCTGACAGTTGCGTGG |
| SEQ ID NO: 3481 | mm20446_Slc7a11 | TCATTACACATACATTCTGG |
| SEQ ID NO: 3482 | mm20447_Slc7a11 | GAAGAGACACAAGTCTAATG |
| SEQ ID NO: 3483 | mm20448_Slc7a11 | GGGCTACGTACTGACAAACG |
| SEQ ID NO: 3484 | mm20449_Slc7a11 | ACAGGCAGACCAGAAAACCA |
| SEQ ID NO: 3485 | mm20478_B3galt1 | TCACCCTCAAAACCTTAATG |
| SEQ ID NO: 3486 | mm20479_B3galt1 | TTCACTGGTTACGTCATCAA |
| SEQ ID NO: 3487 | mm20480_B3galt1 | GGCATCAAATTCCTTGTGTG |
| SEQ ID NO: 3488 | mm20481_B3galt1 | GGGGATGAAAACAACTTCAA |
| SEQ ID NO: 3489 | mm20482_B3galt2 | ACCTGGCATCCAAATCATAC |
| SEQ ID NO: 3490 | mm20483_B3galt2 | AGAGAAAGCACACCCGTAAG |
| SEQ ID NO: 3491 | mm20484_B3galt2 | CCTGTGACATACACTTTCCG |
| SEQ ID NO: 3492 | mm20485_B3galt2 | TAACACCGAGCTATCACCAC |
| SEQ ID NO: 3493 | mm20486_B3galnt1 | CAAGCCATTAGAGTTACTTG |
| SEQ ID NO: 3494 | mm20487_B3galnt1 | GCTCGATCACATTGTAGTGG |
| SEQ ID NO: 3495 | mm20488_B3galnt1 | TCATGATATACTTGGCATTG |
| SEQ ID NO: 3496 | mm20489_B3galnt1 | GAGAACAGTTCGAGTGTTCG |
| SEQ ID NO: 3497 | mm20610_Racgap1 | GACACCGGTTAAGATTGGAG |
| SEQ ID NO: 3498 | mm20611_Racgap1 | TGGCAGTATTCAGCTGAGCG |
| SEQ ID NO: 3499 | mm20612_Racgap1 | GAAGTATCAAAGAACCAACC |
| SEQ ID NO: 3500 | mm20613_Racgap1 | TGGACGTGGAGATCAAGCGG |
| SEQ ID NO: 3501 | mm20674_Islr | TTCTGGAATAGACACCGCTG |
| SEQ ID NO: 3502 | mm20675_Islr | TGTGCCTATCGTGACCTAGA |
| SEQ ID NO: 3503 | mm20676_Islr | TCACACCCCGGGCGGCACGG |

TABLE 1-continued mmSurf sgRNA library sequences

| SEQ ID NO | id_gRNA Target | Sequence |
|---|---|---|
| SEQ ID NO: 3504 | mm20677_Islr | CTGGTAGCTTAGTTGCACTG |
| SEQ ID NO: 3505 | mm20698_Klrk1 | AAGGGTGAATCGAATTGCCA |
| SEQ ID NO: 3506 | mm20699_Klrk1 | ATATCCAGTTGTTAGGGCAT |
| SEQ ID NO: 3507 | mm20700_Klrk1 | GCACTAACTACCAGTCAACC |
| SEQ ID NO: 3508 | mm20701_Klrk1 | CGACCTCAAGCCAGCAAAGT |
| SEQ ID NO: 3509 | mm20710_Tspan32 | AGAGCCCATCTAGCAACTGG |
| SEQ ID NO: 3510 | mm20711_Tspan32 | GCAAAGCACAGGAAACCCTG |
| SEQ ID NO: 3511 | mm20712_Tspan32 | GGGGTTGTAGAATCTCCAGA |
| SEQ ID NO: 3512 | mm20713_Tspan32 | ACTGGAGCCATCATGTGTCA |
| SEQ ID NO: 3513 | mm20754_Fkbp9 | AAACCTATGACACGTACGTG |
| SEQ ID NO: 3514 | mm20755_Fkbp9 | TTGGGATGTGCGTAAACGAG |
| SEQ ID NO: 3515 | mm20756_Fkbp9 | CCGATACTTGGATAGTCCGA |
| SEQ ID NO: 3516 | mm20757_Fkbp9 | TCGTGCGCTACCACTACGTG |
| SEQ ID NO: 3517 | mm20822_Podxl | AAGCAAGTGTAGATGCCACT |
| SEQ ID NO: 3518 | mm20823_Podxl | GGGCACGTGTACTCACGCAA |
| SEQ ID NO: 3519 | mm20824_Podxl | AACCCCACGAGCAATCAAAG |
| SEQ ID NO: 3520 | mm20825_Podxl | GTGCTCGGTGAAGAATCCAC |
| SEQ ID NO: 3521 | mm20850_Slamf1 | ATCTGATGTTCATTCGTCAG |
| SEQ ID NO: 3522 | mm20851_Slamf1 | TAAAGTGCTAAACAAAACCC |
| SEQ ID NO: 3523 | mm20852_Slamf1 | GAGCTATCCAGATCACCTGG |
| SEQ ID NO: 3524 | mm20853_Slamf1 | AGGATGGTACTTGGTGAGCG |
| SEQ ID NO: 3525 | mm20882_Pla2g7 | GGAAATGGATCGTACCCCGT |
| SEQ ID NO: 3526 | mm20883_Pla2g7 | TTGGGATCCAAACAGTGTCG |
| SEQ ID NO: 3527 | mm20884_Pla2g7 | TAGTGGCCACTGTCGAACAC |
| SEQ ID NO: 3528 | mm20885_Pla2g7 | GCGATTCTTGACATTGAACA |
| SEQ ID NO: 3529 | mm20926_Tnfrsf12a | CCAAGCCGAATCCCAACACG |
| SEQ ID NO: 3530 | mm20927_Tnfrsf12a | CGCAGTCCATGCACTTGTCG |
| SEQ ID NO: 3531 | mm20928_Tnfrsf12a | GCTGCCGCTAGAGCATGGGG |
| SEQ ID NO: 3532 | mm20929_Tnfrsf12a | CTTGGTGTTGATGCGCGCCG |
| SEQ ID NO: 3533 | mm20982_Rpl3 | TTAGGTGCTTACCTGAGTGT |
| SEQ ID NO: 3534 | mm20983_Rpl3 | TGTGGAAACTCCCCCAATGG |
| SEQ ID NO: 3535 | mm20984_Rpl3 | CAGAGAAGGCAACACGGGCA |
| SEQ ID NO: 3536 | mm20985_Rpl3 | AAGCGCAGCAGCCGGCATCG |
| SEQ ID NO: 3537 | mm21014_Tjp3 | AAGATGGTCCAGTCTCGCGT |
| SEQ ID NO: 3538 | mm21015_Tjp3 | TGGCTCCTTTCAGATCAACG |
| SEQ ID NO: 3539 | mm21016_Tjp3 | ACTGACCGTTCCCGCCTCCG |
| SEQ ID NO: 3540 | mm21017_Tjp3 | CGTGGGCATCTTCGTATCCG |
| SEQ ID NO: 3541 | mm21062_Ptdss2 | ATCGTCGTAGACTTCAGACT |

TABLE 1-continued mmSurf sgRNA library sequences

| SEQ ID NO | id_gRNA Target | Sequence |
|---|---|---|
| SEQ ID NO: 3542 | mm21063_Ptdss2 | ATTGCCAGAGAGGGACTACG |
| SEQ ID NO: 3543 | mm21064_Ptdss2 | AACGGGCTGGGCATCTACTG |
| SEQ ID NO: 3544 | mm21065_Ptdss2 | TCATGCACATCCACCAGTCA |
| SEQ ID NO: 3545 | mm21070_Pign | CCAGCTCCCAAGTAACGAA |
| SEQ ID NO: 3546 | mm21071_Pign | GTGTTGTTAAGATAACCCAC |
| SEQ ID NO: 3547 | mm21072_Pign | TGCCACAAAACTGGATACGT |
| SEQ ID NO: 3548 | mm21073_Pign | AAGTCAATAGTGATTCAACC |
| SEQ ID NO: 3549 | mm21106_Abca7 | GTGTCGGCGCAAGAAAAGCG |
| SEQ ID NO: 3550 | mm21107_Abca7 | GAGAAACCATGCGTGCGATG |
| SEQ ID NO: 3551 | mm21108_Abca7 | CAGACACATTTCGGCCAGTG |
| SEQ ID NO: 3552 | mm21109_Abca7 | AATCCTAGGACAAATGATGG |
| SEQ ID NO: 3553 | mm21130_Abca3 | GAGGAGCCACGAAAAAGTAG |
| SEQ ID NO: 3554 | mm21131_Abca3 | AGCTGGCTACCACATGACGC |
| SEQ ID NO: 3555 | mm21132_Abca3 | ACACACGAAGAAATTACATG |
| SEQ ID NO: 3556 | mm21133_Abca3 | AAGGAGGCGGCTTTAATGAG |
| SEQ ID NO: 3557 | mm21150_Abcc5 | GGAGCTGATGAACTTAAATG |
| SEQ ID NO: 3558 | mm21151_Abcc5 | AAATCCGAGAGGAGGAACGT |
| SEQ ID NO: 3559 | mm21152_Abcc5 | CATTAAAGAAAAGTCCCTAG |
| SEQ ID NO: 3560 | mm21153_Abcc5 | AAAGACAAGAGGGCTACCAG |
| SEQ ID NO: 3561 | mm21170_Nagpa | AGCCACCGTTCTGAGCGATG |
| SEQ ID NO: 3562 | mm21171_Nagpa | GCGATGGAACCATAGTCACC |
| SEQ ID NO: 3563 | mm21172_Nagpa | AGCACCGAGAAAGTGCGTAG |
| SEQ ID NO: 3564 | mm21173_Nagpa | GTTCTTACCAGTGATCTGAA |
| SEQ ID NO: 3565 | mm21410_Slco1a4 | CCAACGCAAGACCCAACAGG |
| SEQ ID NO: 3566 | mm21411_Slco1a4 | GATAAGCCCAACTACAGACG |
| SEQ ID NO: 3567 | mm21412_Slco1a4 | AACCACCAATTAAATATCCG |
| SEQ ID NO: 3568 | mm21413_Slco1a4 | AAAATCAAGGAGGAAAACCG |
| SEQ ID NO: 3569 | mm21554_Cspg5 | CCTACCCGGTACGGCCCCAG |
| SEQ ID NO: 3570 | mm21555_Cspg5 | GTCGCGTGCCAATGACACGC |
| SEQ ID NO: 3571 | mm21556_Cspg5 | GTCCATGATAAGCCTAGTGT |
| SEQ ID NO: 3572 | mm21557_Cspg5 | GAAAATCACCCTGATACCGA |
| SEQ ID NO: 3573 | mm21562_Clic4 | TGTTCTCGTCGATTTCGTCG |
| SEQ ID NO: 3574 | mm21563_Clic4 | TCAAGACCAGAGGCTAATGA |
| SEQ ID NO: 3575 | mm21564_Clic4 | CTTCAACAGCGAAGTCAAGA |
| SEQ ID NO: 3576 | mm21565_Clic4 | CTTGACGAAGAGCTCGATGA |
| SEQ ID NO: 3577 | mm21626_Mfi2 | GCCGAGCCGACATCACTGAG |
| SEQ ID NO: 3578 | mm21627_Mfi2 | GAGAGATACTACGACTACAG |
| SEQ ID NO: 3579 | mm21628_Mfi2 | CTTGCCGCGAAGCTCGTCCA |

TABLE 1-continued mmSurf sgRNA library sequences

| SEQ ID NO | id_gRNA Target | Sequence |
|---|---|---|
| SEQ ID NO: 3580 | mm21629_Mfi2 | ACAGGCATTAACCGGACTGT |
| SEQ ID NO: 3581 | mm21650_Slc22a4 | CAGAGCAAAGTAACCCACTG |
| SEQ ID NO: 3582 | mm21651_Slc22a4 | GAGAACGCCTACGAAGAACA |
| SEQ ID NO: 3583 | mm21652_Slc22a4 | CGCAAAGATGAACAGCATCG |
| SEQ ID NO: 3584 | mm21653_Slc22a4 | AACCAGGCAACGGTGCTCGG |
| SEQ ID NO: 3585 | mm21694_Angptl3 | TGCTCTGCCGTTTATAACAG |
| SEQ ID NO: 3586 | mm21695_Angptl3 | TACACTACAAGTTAAAAACG |
| SEQ ID NO: 3587 | mm21696_Angptl3 | CATGGACATTAATTCAACAC |
| SEQ ID NO: 3588 | mm21697_Angptl3 | GAAGACAGCCCTTCAACACA |
| SEQ ID NO: 3589 | mm21698_Slamf6 | GAACGCCATTCATTAGCTGG |
| SEQ ID NO: 3590 | mm21699_Slamf6 | GATTACTTAGGTTGATAACG |
| SEQ ID NO: 3591 | mm21700_Slamf6 | TGGGACCTGCCAGATACACC |
| SEQ ID NO: 3592 | mm21701_Slamf6 | CACTGCGCAGATAACCACAA |
| SEQ ID NO: 3593 | mm21726_Tor2a | GCTTGTCCATCTCATCGAAG |
| SEQ ID NO: 3594 | mm21727_Tor2a | GGGGAGAAGTGATGGACGTG |
| SEQ ID NO: 3595 | mm21728_Tor2a | CAGGTCACATTCCAGACCTA |
| SEQ ID NO: 3596 | mm21729_Tor2a | CCGTGCAGGGAAAGGACCAA |
| SEQ ID NO: 3597 | mm21730_Tor1b | GGAACGGCCCCTCAACACGT |
| SEQ ID NO: 3598 | mm21731_Tor1b | CAGCTCCAGAAGTGGATCCG |
| SEQ ID NO: 3599 | mm21732_Tor1b | GTAGCCGGTGAGCGCCGACA |
| SEQ ID NO: 3600 | mm21733_Tor1b | CAATGCCTTGAGAATCACTT |
| SEQ ID NO: 3601 | mm21734_Tor3a | TTGAACCCTACCTGGAACCG |
| SEQ ID NO: 3602 | mm21735_Tor3a | CTTACCCAGAGGCGGCACGG |
| SEQ ID NO: 3603 | mm21736_Tor3a | TACTTAGAGATGCCCCAAGT |
| SEQ ID NO: 3604 | mm21737_Tor3a | ATGGACAACCTGTATCGGGA |
| SEQ ID NO: 3605 | mm21738_Slc46a2 | GATGGGCACCTATCGAACCC |
| SEQ ID NO: 3606 | mm21739_Slc46a2 | CATGACCCCGGACCAATAAG |
| SEQ ID NO: 3607 | mm21740_Slc46a2 | AGCCCAGGACTAAATCGATG |
| SEQ ID NO: 3608 | mm21741_Slc46a2 | GGAGTAGTCCTGCGTCGTAG |
| SEQ ID NO: 3609 | mm21890_Ero1l | CTGAAGGAGAAGGCCCACGA |
| SEQ ID NO: 3610 | mm21891_Ero1l | CTTGCTCACATTCTTCAATG |
| SEQ ID NO: 3611 | mm21892_Ero1l | CTTAACCCTGAGCGCTACAC |
| SEQ ID NO: 3612 | mm21893_Ero1l | AAAGGCCTTTGAATTGTCTG |
| SEQ ID NO: 3613 | mm21902_Mfap5 | GACAGACTGGCTACCCCTAG |
| SEQ ID NO: 3614 | mm21903_Mfap5 | GTCACCTGTATCGTCTGTAG |
| SEQ ID NO: 3615 | mm21904_Mfap5 | ACACCTTCCACAGATGACCT |
| SEQ ID NO: 3616 | mm21905_Mfap5 | CAAGACTGTACTCTGTCCAT |
| SEQ ID NO: 3617 | mm21910_Elane | CCGGCCACCAACAATCTCTG |

TABLE 1-continued mmSurf sgRNA library sequences

| SEQ ID NO | id_gRNA Target | Sequence |
|---|---|---|
| SEQ ID NO: 3618 | mm21911_Elane | CTCACAGGCCGTTCACACAG |
| SEQ ID NO: 3619 | mm21912_Elane | GAACGACATTGTGATTATCC |
| SEQ ID NO: 3620 | mm21913_Elane | ATGACCTCCACGCCTCTGCA |
| SEQ ID NO: 3621 | mm21918_Postn | GTACTTCGCGCCGAGTAACG |
| SEQ ID NO: 3622 | mm21919_Postn | CTGGCTATATGAGAATGGAA |
| SEQ ID NO: 3623 | mm21920_Postn | GGCCTTAGCGACCTCTACAA |
| SEQ ID NO: 3624 | mm21921_Postn | TTAACCAAGGACCTGAAACA |
| SEQ ID NO: 3625 | mm21922_Hist1h1c | GGCCGCCAAGAAGCCCGCCG |
| SEQ ID NO: 3626 | mm21923_Hist1h1c | GGGCATCCTGGTGCAAACCA |
| SEQ ID NO: 3627 | mm21924_Hist1h1c | GCAGGCGCCTTCTCCGCAGG |
| SEQ ID NO: 3628 | mm21925_Hist1h1c | TTCTGGCGAGGCCAAACCCC |
| SEQ ID NO: 3629 | mm21926_Hist1h1e | CTTGACGGGTGTCTTCTCGG |
| SEQ ID NO: 3630 | mm21927_Hist1h1e | GTGATGAGTTCGGACACCGG |
| SEQ ID NO: 3631 | mm21928_Hist1h1e | AGAAGCCCAAGAAGGCTGCG |
| SEQ ID NO: 3632 | mm21929_Hist1h1e | GGCTAAGCCCAAAGCAAAAA |
| SEQ ID NO: 3633 | mm21938_Icosl | GGACAATAGCCTAATAGACA |
| SEQ ID NO: 3634 | mm21939_Icosl | AGAGACTGAAGTCGGTGCAA |
| SEQ ID NO: 3635 | mm21940_Icosl | TGGCTGTATTCATAAATACC |
| SEQ ID NO: 3636 | mm21941_Icosl | TCCCTGGACTCCATGAAGCA |
| SEQ ID NO: 3637 | mm21978_Tfr2 | GAGGTCGCTCCAGTACAACG |
| SEQ ID NO: 3638 | mm21979_Tfr2 | AGTGCGTGTCAGTCCACACG |
| SEQ ID NO: 3639 | mm21980_Tfr2 | TGGTGTACGCCCACTACGGG |
| SEQ ID NO: 3640 | mm21981_Tfr2 | ACCCCCAGTGAAGATTAGCA |
| SEQ ID NO: 3641 | mm21982_Crim1 | TGGCCATCATCATAAGAACG |
| SEQ ID NO: 3642 | mm21983_Crim1 | GAGAGAACCGCACTTCACAG |
| SEQ ID NO: 3643 | mm21984_Crim1 | ACAGCTACGAAACGCAAGTG |
| SEQ ID NO: 3644 | mm21985_Crim1 | AGGTGGATCAATCGTGATGT |
| SEQ ID NO: 3645 | mm22030_Dkk3 | CGGAGTCCAAGTGACCGTCG |
| SEQ ID NO: 3646 | mm22031_Dkk3 | CTATCACAATGAGACCAGCA |
| SEQ ID NO: 3647 | mm22032_Dkk3 | GCTCAATGAGATGTTTCGAG |
| SEQ ID NO: 3648 | mm22033_Dkk3 | TAGATAACCAACAACCAGAG |
| SEQ ID NO: 3649 | mm22042_Ppap2c | CATGCAATACATGCCAAAGG |
| SEQ ID NO: 3650 | mm22043_Ppap2c | AGTTGGATCGCGAATAAAGA |
| SEQ ID NO: 3651 | mm22044_Ppap2c | CAGCCCTGCTAATGTCACGG |
| SEQ ID NO: 3652 | mm22045_Ppap2c | CATAGCCAGAACAGTTGACC |
| SEQ ID NO: 3653 | mm22046_Hs6st1 | GGCGCACGTTCTGCACTAGG |
| SEQ ID NO: 3654 | mm22047_Hs6st1 | ATGGCGACATGTACAGCGTG |
| SEQ ID NO: 3655 | mm22048_Hs6st1 | CTCATCCTTTACCAGTACGC |

TABLE 1-continued mmSurf sgRNA library sequences

| SEQ ID NO | id_gRNA Target | Sequence |
|---|---|---|
| SEQ ID NO: 3656 | mm22049_Hs6st1 | CCTATAACCTGGCTAACAAC |
| SEQ ID NO: 3657 | mm22050_Hs6st2 | GCGGTACGGATCCGGCACCG |
| SEQ ID NO: 3658 | mm22051_Hs6st2 | GGGTATAGTAAGGATAGATG |
| SEQ ID NO: 3659 | mm22052_Hs6st2 | CCGCCGGCATTCCAGAGTAG |
| SEQ ID NO: 3660 | mm22053_Hs6st2 | GCAGCCATGTGAGTGCCGCG |
| SEQ ID NO: 3661 | mm22154_Il17rb | GGAACTCGTCAAGACAAGTG |
| SEQ ID NO: 3662 | mm22155_Il17rb | TTCAACGGGACACGACATTG |
| SEQ ID NO: 3663 | mm22156_Il17rb | GCACAACTGTCCCTTCGCGT |
| SEQ ID NO: 3664 | mm22157_Il17rb | CTCCACAGGGAAGCCTACAT |
| SEQ ID NO: 3665 | mm22222_Il27ra | CAGTCACTGTAATTCGATAG |
| SEQ ID NO: 3666 | mm22223_Il27ra | TGCTCACTCCCACGTCACAG |
| SEQ ID NO: 3667 | mm22224_Il27ra | TCCCCGGGAACAGTTCACCA |
| SEQ ID NO: 3668 | mm22225_Il27ra | CCAGACGCCATTCTTAGGTG |
| SEQ ID NO: 3669 | mm22298_Ramp1 | AGCAGCCAGAGGCCGCACCG |
| SEQ ID NO: 3670 | mm22299_Ramp1 | GGATGAGAGTCCCATAGTCA |
| SEQ ID NO: 3671 | mm22300_Ramp1 | GAAGACGCTATGGTGTGACT |
| SEQ ID NO: 3672 | mm22301_Ramp1 | TTTCTGGCCCAATCCGGAAG |
| SEQ ID NO: 3673 | mm22302_Hnrnpu | AACGGCAGTCTCGACCTAGG |
| SEQ ID NO: 3674 | mm22303_Hnrnpu | AGTTATGGCAGAGAACATGT |
| SEQ ID NO: 3675 | mm22304_Hnrnpu | AGGAGCTGGAAAAACTACCT |
| SEQ ID NO: 3676 | mm22305_Hnrnpu | CGTCACCGCGAAGAGCGAGG |
| SEQ ID NO: 3677 | mm22370_Umodl1 | TGAACTGTCTGTAACAACGA |
| SEQ ID NO: 3678 | mm22371_Umodl1 | GTGCCACACAACATAGCCCG |
| SEQ ID NO: 3679 | mm22372_Umodl1 | GGTCCCGGGAGTTTGCATCG |
| SEQ ID NO: 3680 | mm22373_Umodl1 | CCCGAGGAGAGACCAATGTG |
| SEQ ID NO: 3681 | mm22414_Pvr | AGGTCAGGGTCAAGTTAGTG |
| SEQ ID NO: 3682 | mm22415_Pvr | AACTTAAGTGTAGAAGACGA |
| SEQ ID NO: 3683 | mm22416_Pvr | GAAGACAGCCACAAGAGCGT |
| SEQ ID NO: 3684 | mm22417_Pvr | GCTAAATGCATCTCTGCCAA |
| SEQ ID NO: 3685 | mm22418_Hgsnat | CCTGCAGGTTAACTCCACCT |
| SEQ ID NO: 3686 | mm22419_Hgsnat | ATGACTTCTATCCTGCAACG |
| SEQ ID NO: 3687 | mm22420_Hgsnat | GATGTGTGGACACATTTAGG |
| SEQ ID NO: 3688 | mm22421_Hgsnat | GTTGGGAGTGACATACTTCG |
| SEQ ID NO: 3689 | mm22498_Rcn3 | GCAGCGGCACATCCGTGACT |
| SEQ ID NO: 3690 | mm22499_Rcn3 | ATTTGACAAACTCAGCCCAG |
| SEQ ID NO: 3691 | mm22500_Rcn3 | ACCGGGCTCATAATGGCCAT |
| SEQ ID NO: 3692 | mm22501_Rcn3 | TTCCGGGTAGCCGACCAAGA |
| SEQ ID NO: 3693 | mm22542_Slc46a1 | AGAGCTAACATCTGCCACAG |

TABLE 1-continued mmSurf sgRNA library sequences

| SEQ ID NO | id_gRNA Target | Sequence |
|---|---|---|
| SEQ ID NO: 3694 | mm22543_Slc46a1 | GGGCAATGGATCGATGATGG |
| SEQ ID NO: 3695 | mm22544_Slc46a1 | TGGACCAGAAGAGTCCCACC |
| SEQ ID NO: 3696 | mm22545_Slc46a1 | GAACTGTGGGAACCAAAGCG |
| SEQ ID NO: 3697 | mm22578_Acaa2 | GCCCACGATGACACTATCGA |
| SEQ ID NO: 3698 | mm22579_Acaa2 | GCTGAGGTCGTCTTGTGTGG |
| SEQ ID NO: 3699 | mm22580_Acaa2 | CGAGGCTGGCTACTTCAATG |
| SEQ ID NO: 3700 | mm22581_Acaa2 | CGTCCGTGTTCAAGAAAGAC |
| SEQ ID NO: 3701 | mm22606_Tspan14 | GGGGTCGATTCCATGCAACC |
| SEQ ID NO: 3702 | mm22607_Tspan14 | CAGGTCGATGTCATCCCGAT |
| SEQ ID NO: 3703 | mm22608_Tspan14 | TAATTTCAGAATCAGTGCTG |
| SEQ ID NO: 3704 | mm22609_Tspan14 | TTGGAATAAAAGGCCAACA |
| SEQ ID NO: 3705 | mm22618_Adgre4 | ATGAGACTTGATACCTCATG |
| SEQ ID NO: 3706 | mm22619_Adgre4 | TAGTGGAGCCATTCGCTCAG |
| SEQ ID NO: 3707 | mm22620_Adgre4 | TAGACTTACCATAACAATCA |
| SEQ ID NO: 3708 | mm22621_Adgre4 | AGCTGGCAACAACACAATGA |
| SEQ ID NO: 3709 | mm22770_Lair1 | CAAGTCTTATGATCTCCCAA |
| SEQ ID NO: 3710 | mm22771_Lair1 | TAAACACGACTTGTATAACA |
| SEQ ID NO: 3711 | mm22772_Lair1 | GTCCGAACGTAGTAAGACGC |
| SEQ ID NO: 3712 | mm22773_Lair1 | ACAGCTATAATGTCCAGTAA |
| SEQ ID NO: 3713 | mm22826_Atp2a3 | CACGGAGCCAGGATCCACCG |
| SEQ ID NO: 3714 | mm22827_Atp2a3 | CCAGCGCAGAATCATTGCAG |
| SEQ ID NO: 3715 | mm22828_Atp2a3 | ACCTTGGGGTCAGCACGAGT |
| SEQ ID NO: 3716 | mm22829_Atp2a3 | CTGACCGCAAGGGTGTACAG |
| SEQ ID NO: 3717 | mm22850_Folh1 | GCAAATGCACCATACCAAAG |
| SEQ ID NO: 3718 | mm22851_Folh1 | TCTGGATAGGACTTCACCGC |
| SEQ ID NO: 3719 | mm22852_Folh1 | ATTAAAAGTGCCTTACAACG |
| SEQ ID NO: 3720 | mm22853_Folh1 | AGGACAGCAAGACATCGTAA |
| SEQ ID NO: 3721 | mm22854_Cntnap1 | GCTCCACTCTCACGTAAGGT |
| SEQ ID NO: 3722 | mm22855_Cntnap1 | TTCCTACAGATATTCATCGG |
| SEQ ID NO: 3723 | mm22856_Cntnap1 | AGAAGTATGAAGTCCCTGTG |
| SEQ ID NO: 3724 | mm22857_Cntnap1 | GAGGAACAGCATTTCTACTG |
| SEQ ID NO: 3725 | mm22866_Nptx2 | CTCTATCAGCACAATCTCGT |
| SEQ ID NO: 3726 | mm22867_Nptx2 | GCTGCCGAGCGACTTCCGAG |
| SEQ ID NO: 3727 | mm22868_Nptx2 | GTAGTTTGTACGGAGAGGAA |
| SEQ ID NO: 3728 | mm22869_Nptx2 | GCAACGCGGTGCACACGAAG |
| SEQ ID NO: 3729 | mm22962_Corin | GGATATGTTGATAGCAACTG |
| SEQ ID NO: 3730 | mm22963_Corin | CCTGGAACTTGGACCCGGAG |
| SEQ ID NO: 3731 | mm22964_Corin | CACTGCTGTTAGTCTCAGTG |

TABLE 1-continued mmSurf sgRNA library sequences

| SEQ ID NO | id_gRNA Target | Sequence |
|---|---|---|
| SEQ ID NO: 3732 | mm22965_Corin | ACAGTTTATTATGAGAACAC |
| SEQ ID NO: 3733 | mm22986_Cd164 | CAAGTCAGTGCGGTTCACCT |
| SEQ ID NO: 3734 | mm22987_Cd164 | TTGCGTCGTCGGGACCACTT |
| SEQ ID NO: 3735 | mm22988_Cd164 | GGTCGGCACCTCGGTCACGT |
| SEQ ID NO: 3736 | mm22989_Cd164 | TTGGCAATGTAACCAAAAGC |
| SEQ ID NO: 3737 | mm23038_Reck | CAATAGTAAAGGATGTTCCG |
| SEQ ID NO: 3738 | mm23039_Reck | AGTGCAATTTGGCCCCGTCG |
| SEQ ID NO: 3739 | mm23040_Reck | CTGACTTCATCGTCCGCCAG |
| SEQ ID NO: 3740 | mm23041_Reck | TTACTGAGGTACGTGTCCAG |
| SEQ ID NO: 3741 | mm23054_Vamp5 | CATGCTCAACAATTTCGACA |
| SEQ ID NO: 3742 | mm23055_Vamp5 | GGAGCGTCACGGCAAGCTGG |
| SEQ ID NO: 3743 | mm23056_Vamp5 | TTTAGCCCAGCAGAAGCGCT |
| SEQ ID NO: 3744 | mm23057_Vamp5 | ATCGGTCACACACCATGTCC |
| SEQ ID NO: 3745 | mm23062_Gria3 | TGTGACGAAAGATGTATGCA |
| SEQ ID NO: 3746 | mm23063_Gria3 | GTACAATGTCAGTAAAACCC |
| SEQ ID NO: 3747 | mm23064_Gria3 | TACCTCTATGACACAGAACG |
| SEQ ID NO: 3748 | mm23065_Gria3 | AGGAATCCAAGTGGTCTACG |
| SEQ ID NO: 3749 | mm23070_B3gnt2 | TGGGGCCGAGAAACCAACGT |
| SEQ ID NO: 3750 | mm23071_B3gnt2 | ACAGGGTGGCCAATCAGACA |
| SEQ ID NO: 3751 | mm23072_B3gnt2 | CAAACTTAAGCATGTCCGAA |
| SEQ ID NO: 3752 | mm23073_B3gnt2 | CTTTATCGCCAATAGTAAGA |
| SEQ ID NO: 3753 | mm23122_Rab11a | GAGTGATTTACGTCATCTCA |
| SEQ ID NO: 3754 | mm23123_Rab11a | AGATACTATCGTGGAGCAGT |
| SEQ ID NO: 3755 | mm23124_Rab11a | TGTTGCAAACTCTACTCCAA |
| SEQ ID NO: 3756 | mm23125_Rab11a | CCACGGCCTCACCTTTAAAG |
| SEQ ID NO: 3757 | mm23126_Cntn6 | TATCACTATAGGTTGGATGG |
| SEQ ID NO: 3758 | mm23127_Cntn6 | TGGTGGGTCATGAGACACT |
| SEQ ID NO: 3759 | mm23128_Cntn6 | GTGCGCAGCACTAAAGGCGT |
| SEQ ID NO: 3760 | mm23129_Cntn6 | AATCCCAAGTTCCAACAAG |
| SEQ ID NO: 3761 | mm23142_Slc5a3 | CCCCTGACCGGATGTAAATG |
| SEQ ID NO: 3762 | mm23143_Slc5a3 | CTGACCAAGTCATCGTACAG |
| SEQ ID NO: 3763 | mm23144_Slc5a3 | GAACACTGCATGCAAGTGTG |
| SEQ ID NO: 3764 | mm23145_Slc5a3 | CTGTGTAGATCACTGCAACA |
| SEQ ID NO: 3765 | mm23146_Celsr2 | GTACACCGTTCGGCTCAACG |
| SEQ ID NO: 3766 | mm23147_Celsr2 | CTGACGTACAGCTTCGAGCG |
| SEQ ID NO: 3767 | mm23148_Celsr2 | CGGGCATTGTGCGCACACTG |
| SEQ ID NO: 3768 | mm23149_Celsr2 | CGGCACAAACGGAGACACGG |
| SEQ ID NO: 3769 | mm23218_Lpar2 | TTTCTATAATAACAGCGGCA |

TABLE 1-continued mmSurf sgRNA library sequences

| SEQ ID NO | id_gRNA Target | Sequence |
|---|---|---|
| SEQ ID NO: 3770 | mm23219_Lpar2 | GTGGGCCAGTATGGAACATG |
| SEQ ID NO: 3771 | mm23220_Lpar2 | AGTGTGACCACACGGCCCCG |
| SEQ ID NO: 3772 | mm23221_Lpar2 | GTGTGGCCACTGACGCCGTG |
| SEQ ID NO: 3773 | mm23330_Icos | TGGTCTTGGTGAGTTCGCAG |
| SEQ ID NO: 3774 | mm23331_Icos | TATGCAAATATCCTCCACTA |
| SEQ ID NO: 3775 | mm23332_Icos | GCAGAAGTAATAGCTTCCCT |
| SEQ ID NO: 3776 | mm23333_Icos | AAATGAAAACATCCTATGAT |
| SEQ ID NO: 3777 | mm23414_Cd320 | TGGTCTCAGAACAGGCCTAG |
| SEQ ID NO: 3778 | mm23415_Cd320 | GCAACCACTGATGTTGTCAC |
| SEQ ID NO: 3779 | mm23416_Cd320 | CCATCACAGCGCCACGTGTG |
| SEQ ID NO: 3780 | mm23417_Cd320 | ACCTTCCAGTGTCTTACCAG |
| SEQ ID NO: 3781 | mm23430_Slc23a2 | CTGGCATCCCCGAATCCAAG |
| SEQ ID NO: 3782 | mm23431_Slc23a2 | GTGTTTCAGTGGCACGATCG |
| SEQ ID NO: 3783 | mm23432_Slc23a2 | ACAGGCGTAGTAGTCACCGA |
| SEQ ID NO: 3784 | mm23433_Slc23a2 | GCGTGCATAGTAGCCATAGT |
| SEQ ID NO: 3785 | mm23474_Gp9 | GGGGCAAGCCTGAGTATCTG |
| SEQ ID NO: 3786 | mm23475_Gp9 | GCATTAGGGCCTCGGGCATG |
| SEQ ID NO: 3787 | mm23476_Gp9 | TGGATGTGACACACAACCCC |
| SEQ ID NO: 3788 | mm23477_Gp9 | AGCCTGCGTTCAGTGCCACC |
| SEQ ID NO: 3789 | mm23482_Chst2 | GTGTCGCAAGTACCGCACGC |
| SEQ ID NO: 3790 | mm23483_Chst2 | AAATACCTTCATCCCGAGCG |
| SEQ ID NO: 3791 | mm23484_Chst2 | GGAAAACCGAAAGATCGCAG |
| SEQ ID NO: 3792 | mm23485_Chst2 | TCCATGCGAGAGTGAGCGCG |
| SEQ ID NO: 3793 | mm23502_Cacng6 | ACTTCAAATTCTTCACCACG |
| SEQ ID NO: 3794 | mm23503_Cacng6 | GGCTTGACTCCGGAGCGAGA |
| SEQ ID NO: 3795 | mm23504_Cacng6 | AGGTGTGCATCAAGCGACTG |
| SEQ ID NO: 3796 | mm23505_Cacng6 | GCTGTTCTTGGGCACGACGC |
| SEQ ID NO: 3797 | mm23522_Mtmr7 | GCTGCCAATAATTATCAGGG |
| SEQ ID NO: 3798 | mm23523_Mtmr7 | TCAGAGAGATGTACACGTCG |
| SEQ ID NO: 3799 | mm23524_Mtmr7 | GCCACGGCACACATCATCGT |
| SEQ ID NO: 3800 | mm23525_Mtmr7 | AAGTGACTTCATTTATGTCG |
| SEQ ID NO: 3801 | mm23546_Gabbr1 | ACGGCGTGCAGTATACATCG |
| SEQ ID NO: 3802 | mm23547_Gabbr1 | AAGAGAAACTTACCGAACGT |
| SEQ ID NO: 3803 | mm23548_Gabbr1 | GGATGTGTCCGAAAGAACGT |
| SEQ ID NO: 3804 | mm23549_Gabbr1 | GTTCAGCATGACAATCTCCG |
| SEQ ID NO: 3805 | mm23582_Ramp2 | GAATCAATCTCATCCCACTG |
| SEQ ID NO: 3806 | mm23583_Ramp2 | TTGGTGTGACCCGCGCCCAG |
| SEQ ID NO: 3807 | mm23584_Ramp2 | ACCAAGCCGAGATCCACCCG |

TABLE 1-continued mmSurf sgRNA library sequences

| SEQ ID NO | id_gRNA Target | Sequence |
|---|---|---|
| SEQ ID NO: 3808 | mm23585_Ramp2 | CTCCGGAAGAGATTGGTTCA |
| SEQ ID NO: 3809 | mm23586_Atp6ap1 | GAGGATTTCACAGCATACGG |
| SEQ ID NO: 3810 | mm23587_Atp6ap1 | GATATGACCCTCATGTGTGT |
| SEQ ID NO: 3811 | mm23588_Atp6ap1 | TAGCTAGATCCACATGCAAG |
| SEQ ID NO: 3812 | mm23589_Atp6ap1 | GTGTCATTGTAACTCACAGG |
| SEQ ID NO: 3813 | mm23622_Asah2 | TCGGGCCTCAATATTACACA |
| SEQ ID NO: 3814 | mm23623_Asah2 | GTATGATTTCCCAACGACTG |
| SEQ ID NO: 3815 | mm23624_Asah2 | TAGTGACAATATGGGCTATG |
| SEQ ID NO: 3816 | mm23625_Asah2 | GCTCACACAAATCTTAAACC |
| SEQ ID NO: 3817 | mm23682_Nup210 | GAAGTCCAACACACGGACGT |
| SEQ ID NO: 3818 | mm23683_Nup210 | GTGCTGCTGGTAATTCCGGG |
| SEQ ID NO: 3819 | mm23684_Nup210 | CTCAAGATAGAGCTCACGGG |
| SEQ ID NO: 3820 | mm23685_Nup210 | TGCTAAGAATGTTCGCCCTG |
| SEQ ID NO: 3821 | mm23686_Calcrl | TGTAACAATCATCCACCTCA |
| SEQ ID NO: 3822 | mm23687_Calcrl | ATCCGGATAGTAATAGAACA |
| SEQ ID NO: 3823 | mm23688_Calcrl | TTACCTGCACACACTCATCG |
| SEQ ID NO: 3824 | mm23689_Calcrl | CACTAGAAACAAGATCATGA |
| SEQ ID NO: 3825 | mm23734_Extl3 | GCCCAAGCCTCGCGTCACAG |
| SEQ ID NO: 3826 | mm23735_Extl3 | TCAGACATAGCATGGACAAG |
| SEQ ID NO: 3827 | mm23736_Extl3 | CCACACAGTGCCCACTCAGT |
| SEQ ID NO: 3828 | mm23737_Extl3 | ATTGCGGAGGTATTTAGGTG |
| SEQ ID NO: 3829 | mm23762_Pdgfc | AGAGCCAGATCGATGGCAGG |
| SEQ ID NO: 3830 | mm23763_Pdgfc | CTGGCATGATAATACTGTAG |
| SEQ ID NO: 3831 | mm23764_Pdgfc | ATACCCAAGAAATATGGTGC |
| SEQ ID NO: 3832 | mm23765_Pdgfc | CCCTGGCCGGCCAAAGAACG |
| SEQ ID NO: 3833 | mm23838_Plxnc1 | AATATCACCATGATCCTGCG |
| SEQ ID NO: 3834 | mm23839_Plxnc1 | CAGATTTACAGGGTACCGAG |
| SEQ ID NO: 3835 | mm23840_Plxnc1 | TATCCCTACAACTACACGAG |
| SEQ ID NO: 3836 | mm23841_Plxnc1 | GGTGTGGTGTACCGCGCGAG |
| SEQ ID NO: 3837 | mm23862_Cadm1 | ATATCGATCATCAAGTTACG |
| SEQ ID NO: 3838 | mm23863_Cadm1 | AGCCAGCGACGACCATCAGG |
| SEQ ID NO: 3839 | mm23864_Cadm1 | GCCGCGGCACTGATCCCCAC |
| SEQ ID NO: 3840 | mm23865_Cadm1 | ACTGACGAATGTCTCAATCT |
| SEQ ID NO: 3841 | mm23938_Slc1a4 | GTCTGCAACCGATTACACAG |
| SEQ ID NO: 3842 | mm23939_Slc1a4 | TAGAGCCACTCCTAACACCA |
| SEQ ID NO: 3843 | mm23940_Slc1a4 | GATGCCACCCAGACGCCCGA |
| SEQ ID NO: 3844 | mm23941_Slc1a4 | ACCCACCAACACTCCCGACA |
| SEQ ID NO: 3845 | mm23990_Panx1 | CCACTTCAAGTACCCAATCG |

TABLE 1-continued mmSurf sgRNA library sequences

| SEQ ID NO | id_gRNA Target | Sequence |
|---|---|---|
| SEQ ID NO: 3846 | mm23991_Panx1 | ACTCGTCCGAGAGTGAAGAG |
| SEQ ID NO: 3847 | mm23992_Panx1 | GCTTGCACTGGAAGCGATCG |
| SEQ ID NO: 3848 | mm23993_Panx1 | GATGGTCACATGTATTGCCG |
| SEQ ID NO: 3849 | mm24030_Slc2a8 | CCTGCGCCTCGGAGACAATG |
| SEQ ID NO: 3850 | mm24031_Slc2a8 | ACAGCAAAGCCAGTCACGAA |
| SEQ ID NO: 3851 | mm24032_Slc2a8 | GATTATGCCCACAGTGACCG |
| SEQ ID NO: 3852 | mm24033_Slc2a8 | TTGAGTGAGGAGAAAACGTG |
| SEQ ID NO: 3853 | mm24038_Tmem131 | ACAGATCACAACCGACTACG |
| SEQ ID NO: 3854 | mm24039_Tmem131 | GTATGGGCCTGCAATTACCC |
| SEQ ID NO: 3855 | mm24040_Tmem131 | CTGGATGTGAAACAGCGTGG |
| SEQ ID NO: 3856 | mm24041_Tmem131 | GTCGTAGAGATGTACTCGAG |
| SEQ ID NO: 3857 | mm24066_Rala | TCGACATCTTAGATACAGCG |
| SEQ ID NO: 3858 | mm24067_Rala | TCTGCAGTTCATGTACGACG |
| SEQ ID NO: 3859 | mm24068_Rala | CTTACACAAAGTCATCATGG |
| SEQ ID NO: 3860 | mm24069_Rala | CAACTACTTCCGAAGTGGGG |
| SEQ ID NO: 3861 | mm24078_Msln | TCCTAGGCACCTCACCGACG |
| SEQ ID NO: 3862 | mm24079_Msln | TGGATAGCCCCCCATCGAAG |
| SEQ ID NO: 3863 | mm24080_Msln | CATACACCCAAGGTTCCGAC |
| SEQ ID NO: 3864 | mm24081_Msln | CCAATGTGGATGTACTCCCA |
| SEQ ID NO: 3865 | mm24122_Astn2 | GGAGCCCTCGGAGATCGTTG |
| SEQ ID NO: 3866 | mm24123_Astn2 | GATGTCGCTTTCCCGCAGAG |
| SEQ ID NO: 3867 | mm24124_Astn2 | GAGGTGGTATCATAGGGCAA |
| SEQ ID NO: 3868 | mm24125_Astn2 | TCAGGTATGATGAGGCCATG |
| SEQ ID NO: 3869 | mm24142_Ramp3 | GCTTCATCACTGGAATCCAC |
| SEQ ID NO: 3870 | mm24143_Ramp3 | GAGATGGAGACCAACATCAT |
| SEQ ID NO: 3871 | mm24144_Ramp3 | CTTCTGCATCATGTCAGCGA |
| SEQ ID NO: 3872 | mm24145_Ramp3 | CTGGAAGTGGTGCAACCTGT |
| SEQ ID NO: 3873 | mm24182_Bace2 | ACACCTACTTTGACTCAGAG |
| SEQ ID NO: 3874 | mm24183_Bace2 | GTTTCAGTATAACGCAGACA |
| SEQ ID NO: 3875 | mm24184_Bace2 | AGGGCCAGACCATCGGCCCG |
| SEQ ID NO: 3876 | mm24185_Bace2 | TACCAACGGAGGTAGTCTTG |
| SEQ ID NO: 3877 | mm24190_Olfm1 | ACCTGGCCCGTACCTGACCA |
| SEQ ID NO: 3878 | mm24191_Olfm1 | ACTTGTACTCACGGACGAAG |
| SEQ ID NO: 3879 | mm24192_Olfm1 | CTGCAATACCAATTTGGCAT |
| SEQ ID NO: 3880 | mm24193_Olfm1 | GTATTGAGGCCCACCAGCGA |
| SEQ ID NO: 3881 | mm24330_Thsd1 | GATGCCGGTGACGGACCTAG |
| SEQ ID NO: 3882 | mm24331_Thsd1 | TCAGGGGCTTTGAGATACG |
| SEQ ID NO: 3883 | mm24332_Thsd1 | ACAACGTGGTGACCGTCACA |

TABLE 1-continued mmSurf sgRNA library sequences

| SEQ ID NO | id_gRNA Target | Sequence |
|---|---|---|
| SEQ ID NO: 3884 | mm24333_Thsd1 | AGAAGCCCCCAAACGCCCGG |
| SEQ ID NO: 3885 | mm24350_Cpxm1 | CTGACCTCAACACACAACTG |
| SEQ ID NO: 3886 | mm24351_Cpxm1 | ATAGCCATCAGGATTCATGG |
| SEQ ID NO: 3887 | mm24352_Cpxm1 | TCCTAATGACCTGTTCCCTG |
| SEQ ID NO: 3888 | mm24353_Cpxm1 | GGAAATGTCAGACCATCCTG |
| SEQ ID NO: 3889 | mm24778_Tspan3 | TCCTACAGCTATGATCACCA |
| SEQ ID NO: 3890 | mm24779_Tspan3 | AATTCATAACTATTCAGACT |
| SEQ ID NO: 3891 | mm24780_Tspan3 | TCTGCACATAGTCAATAGCA |
| SEQ ID NO: 3892 | mm24781_Tspan3 | TTACCGTGGCAAGTCCACAG |
| SEQ ID NO: 3893 | mm24838_Mbtps1 | GAACGAAAGACTTTCCGCTG |
| SEQ ID NO: 3894 | mm24839_Mbtps1 | ATGGCAAGGTAACCTGACCA |
| SEQ ID NO: 3895 | mm24840_Mbtps1 | TGTTTATAGGAATTACCAGG |
| SEQ ID NO: 3896 | mm24841_Mbtps1 | TGACTGAGTGTCCCTACATG |
| SEQ ID NO: 3897 | mm24854_Clptm1 | TGGCCAGACTCTCATTAATG |
| SEQ ID NO: 3898 | mm24855_Clptm1 | AGTGCGAGATTACTTCTACA |
| SEQ ID NO: 3899 | mm24856_Clptm1 | GGTTTCGGCTGGCGACACGT |
| SEQ ID NO: 3900 | mm24857_Clptm1 | GATGTAAAGGAGAACCACAA |
| SEQ ID NO: 3901 | mm24882_Ctsf | ACAATTACGGCCGTGCTGCG |
| SEQ ID NO: 3902 | mm24883_Ctsf | AAAGACAGTCAATCGCCACT |
| SEQ ID NO: 3903 | mm24884_Ctsf | ACCAGGGGATCATTGCAAGG |
| SEQ ID NO: 3904 | mm24885_Ctsf | CCTGAATCCCTCTTACAGA |
| SEQ ID NO: 3905 | mm24950_Tspan6 | TCTGAAAACAAATCCAACAA |
| SEQ ID NO: 3906 | mm24951_Tspan6 | AATGAGCACAAAAGGCACAT |
| SEQ ID NO: 3907 | mm24952_Tspan6 | CCCAAATGCCAACGGCAAGA |
| SEQ ID NO: 3908 | mm24953_Tspan6 | TTCACTTCTATAGTCTCCTG |
| SEQ ID NO: 3909 | mm24990_Slc22a21 | GGGACATATATCCAACTACG |
| SEQ ID NO: 3910 | mm24991_Slc22a21 | ACAACCCAGTAAAGCCATTG |
| SEQ ID NO: 3911 | mm24992_Slc22a21 | TTCGGACCAGATCATAAATG |
| SEQ ID NO: 3912 | mm24993_Slc22a21 | GAAGCTGAATCCGGTGTGCA |
| SEQ ID NO: 3913 | mm25018_Sept6 | CTTAAGCGAATGTCCTGTCG |
| SEQ ID NO: 3914 | mm25019_Sept6 | CCGCTATGCAGTTGAAAACG |
| SEQ ID NO: 3915 | mm25020_Sept6 | AACAACAGCAAACGGCAGGT |
| SEQ ID NO: 3916 | mm25021_Sept6 | TTCAAACTTGGTGTTAAACA |
| SEQ ID NO: 3917 | mm25090_Raet1d | AGATGAAGTGAAGTGCTTCG |
| SEQ ID NO: 3918 | mm25091_Raet1d | GAACTCACCATCTAGCCCGT |
| SEQ ID NO: 3919 | mm25092_Raet1d | TCTACACAGAGATTATGAGC |
| SEQ ID NO: 3920 | mm25093_Raet1d | CAGCAAATGCCACTGAAGTG |
| SEQ ID NO: 3921 | mm25154_Slc15a1 | TTGTCCAATCGTGTAGACGA |

TABLE 1-continued mmSurf sgRNA library sequences

| SEQ ID NO | id_gRNA Target | Sequence |
|---|---|---|
| SEQ ID NO: 3922 | mm25155_Slc15a1 | GAAGTAAGGCATATCCCAAG |
| SEQ ID NO: 3923 | mm25156_Slc15a1 | CCACCAAACGCAGACACACA |
| SEQ ID NO: 3924 | mm25157_Slc15a1 | CTGGGACGACAATCTCTCCA |
| SEQ ID NO: 3925 | mm25174_Crtap | CACGCGCTCGACCAGTACAG |
| SEQ ID NO: 3926 | mm25175_Crtap | CTTGGAAACCAAGTCGTACG |
| SEQ ID NO: 3927 | mm25176_Crtap | CGAAGAGGCGTAGTTCGGCG |
| SEQ ID NO: 3928 | mm25177_Crtap | GAGAACGTCCATTTCCGACA |
| SEQ ID NO: 3929 | mm25286_Igdcc4 | CTGTACGCTTCGGCCCCTGG |
| SEQ ID NO: 3930 | mm25287_Igdcc4 | CACGCGTGATTTCGCCACTG |
| SEQ ID NO: 3931 | mm25288_Igdcc4 | ACAAGATAGAGTACGGTTTG |
| SEQ ID NO: 3932 | mm25289_Igdcc4 | ACTCTGTCCAGACACTACCG |
| SEQ ID NO: 3933 | mm25306_Tex101 | GCTCTTACTGGCCAAAACGA |
| SEQ ID NO: 3934 | mm25307_Tex101 | TTCTTCTAATCGCCTCACGT |
| SEQ ID NO: 3935 | mm25308_Tex101 | TGAGTTGTGCCATTGGCACA |
| SEQ ID NO: 3936 | mm25309_Tex101 | CCGCCACTGCCCGACATGTG |
| SEQ ID NO: 3937 | mm25310_Sez61 | GGTCCGACGTGAACTCAATG |
| SEQ ID NO: 3938 | mm25311_Sez61 | AGAGTGTCAACCTCTCCGAG |
| SEQ ID NO: 3939 | mm25312_Sez61 | AGATGAGCCTCGTATACCTG |
| SEQ ID NO: 3940 | mm25313_Sez61 | AGCAACTCAACTCGGCCCGG |
| SEQ ID NO: 3941 | mm25322_Tacstd2 | GGGCTCCTCATAGTGTACCG |
| SEQ ID NO: 3942 | mm25323_Tacstd2 | CGTCACACTCCGGGTCGTAG |
| SEQ ID NO: 3943 | mm25324_Tacstd2 | GTTTACGCACCAGCACACCG |
| SEQ ID NO: 3944 | mm25325_Tacstd2 | CTGACCTAGACTCCGAGCTG |
| SEQ ID NO: 3945 | mm25330_Clec1b | CTTCAGGCGTAACCTAACAT |
| SEQ ID NO: 3946 | mm25331_Clec1b | GCCACGAAGTGGAGATACCA |
| SEQ ID NO: 3947 | mm25332_Clec1b | ACAGCAAAAGTATCTACTGG |
| SEQ ID NO: 3948 | mm25333_Clec1b | CATCACACGCCACCAAGAAG |
| SEQ ID NO: 3949 | mm25354_Tmem9b | GTGGAGCCCATGCCTGTACG |
| SEQ ID NO: 3950 | mm25355_Tmem9b | TTCTTATTATAAATGTGCCC |
| SEQ ID NO: 3951 | mm25356_Tmem9b | GAGAAGCTCTGTCACAATCA |
| SEQ ID NO: 3952 | mm25357_Tmem9b | CACGACATGAAGGCAATCAC |
| SEQ ID NO: 3953 | mm25362_Scube2 | TGTGACAACACACTCAACGG |
| SEQ ID NO: 3954 | mm25363_Scube2 | ATCTGCAAGGAGGCCCCAAG |
| SEQ ID NO: 3955 | mm25364_Scube2 | TCAGCATGCAACCTATACCG |
| SEQ ID NO: 3956 | mm25365_Scube2 | ACAGACGAGAAGTCTTGCCA |
| SEQ ID NO: 3957 | mm25394_Cacna2d2 | GTAATAGCGAGTGACTCCCG |
| SEQ ID NO: 3958 | mm25395_Cacna2d2 | AGTGATTCGGAACTACACCT |
| SEQ ID NO: 3959 | mm25396_Cacna2d2 | AGCAGTTAGTGGAACGTGTG |

TABLE 1-continued mmSurf sgRNA library sequences

| SEQ ID NO | id_gRNA Target | Sequence |
|---|---|---|
| SEQ ID NO: 3960 | mm25397_Cacna2d2 | GTGTTCAAGGAAGCTGTGCA |
| SEQ ID NO: 3961 | mm25490_Htr3b | TATCAAGAGGCTCACAACGT |
| SEQ ID NO: 3962 | mm25491_Htr3b | GCAGAATGCTATTAAAGGTG |
| SEQ ID NO: 3963 | mm25492_Htr3b | TTACCACATCCAATACAGCA |
| SEQ ID NO: 3964 | mm25493_Htr3b | CTTACAACAGTACCACAAGG |
| SEQ ID NO: 3965 | mm25494_Pdxp | CTCGTCGTAGCCTACGAGCA |
| SEQ ID NO: 3966 | mm25495_Pdxp | CGGGTGCCAAGGGTCGCGAT |
| SEQ ID NO: 3967 | mm25496_Pdxp | TGTTCGTGAGCAACAACAGC |
| SEQ ID NO: 3968 | mm25497_Pdxp | TCGACTGCGACGGAGTGCTG |
| SEQ ID NO: 3969 | mm25502_Slc12a5 | CCAAGGGGTGATTGTCGAG |
| SEQ ID NO: 3970 | mm25503_Slc12a5 | AGCCATGGCGAGACAGCGTG |
| SEQ ID NO: 3971 | mm25504_Slc12a5 | TGGATTACAGAGCCTCACAG |
| SEQ ID NO: 3972 | mm25505_Slc12a5 | GCAGGATCTCGATCGTGCCA |
| SEQ ID NO: 3973 | mm25562_Xpo4 | AAGTAGTGGCAATCCCACTG |
| SEQ ID NO: 3974 | mm25563_Xpo4 | GTGTGCTAGATAATCAACCT |
| SEQ ID NO: 3975 | mm25564_Xpo4 | GCTGAACAGTGTCATTCGCG |
| SEQ ID NO: 3976 | mm25565_Xpo4 | GGAAGCGGTTGTCCGAGAGT |
| SEQ ID NO: 3977 | mm25630_Bcam | CGAGAGTCTACCTCGTATGG |
| SEQ ID NO: 3978 | mm25631_Bcam | ACCATGTGATCCGAGGCACG |
| SEQ ID NO: 3979 | mm25632_Bcam | GGAGGATTACGATGCCGACG |
| SEQ ID NO: 3980 | mm25633_Bcam | GTCCATCGCACAGTAGGAGT |
| SEQ ID NO: 3981 | mm25718_B4galt3 | GAAACTCCGCCAAAGTACTG |
| SEQ ID NO: 3982 | mm25719_B4galt3 | GGGCTAAAGGATACTGACAC |
| SEQ ID NO: 3983 | mm25720_B4galt3 | TGGAAATGGAACGTTTAACA |
| SEQ ID NO: 3984 | mm25721_B4galt3 | GAATAGTCGAATGTTGGGCC |
| SEQ ID NO: 3985 | mm25730_Mogs | TCTAGGTCATTCTTCCCACG |
| SEQ ID NO: 3986 | mm25731_Mogs | TCGGCAGCATATCCACGATG |
| SEQ ID NO: 3987 | mm25732_Mogs | TGCCGAAATAGACGTGTGGG |
| SEQ ID NO: 3988 | mm25733_Mogs | GAGGTCCTACTACCAGAGAT |
| SEQ ID NO: 3989 | mm25742_Tmem27 | GCTTTGCAACATAACCCAGA |
| SEQ ID NO: 3990 | mm25743_Tmem27 | TCCTGCAGCTGAAGTACAGT |
| SEQ ID NO: 3991 | mm25744_Tmem27 | CCGAATACAATAATCCAGAC |
| SEQ ID NO: 3992 | mm25745_Tmem27 | TTCAAGGCTACGTACCTGGA |
| SEQ ID NO: 3993 | mm25818_Slc15a2 | AGGAGGTATCAAACCCTGTG |
| SEQ ID NO: 3994 | mm25819_Slc15a2 | ACATTCCAAAGCGACAACAT |
| SEQ ID NO: 3995 | mm25820_Slc15a2 | TATCGGCTGATCTCCAAGTG |
| SEQ ID NO: 3996 | mm25821_Slc15a2 | CTGATGGACTCCACCAAGAG |
| SEQ ID NO: 3997 | mm25902_Cd200r1 | ACATGGATAATAAAGCTCAG |

TABLE 1-continued mmSurf sgRNA library sequences

| SEQ ID NO | id_gRNA Target | Sequence |
|---|---|---|
| SEQ ID NO: 3998 | mm25903_Cd200r1 | AGTTCATCTCCTCTGACACA |
| SEQ ID NO: 3999 | mm25904_Cd200r1 | GGTTACTTCAGGGGGCACTG |
| SEQ ID NO: 4000 | mm25905_Cd200r1 | TGTCAGGAGCACATGCCACT |
| SEQ ID NO: 4001 | mm25922_Rpl35a | AACAAAACCAGAGTGATCTG |
| SEQ ID NO: 4002 | mm25923_Rpl35a | TTGTCTTAGGCTGTGGTGCA |
| SEQ ID NO: 4003 | mm25924_Rpl35a | GATGAAACGGAGTTCTACTT |
| SEQ ID NO: 4004 | mm25925_Rpl35a | ACCAGCAATACAGTGACTCC |
| SEQ ID NO: 4005 | mm25926_Cdon | GAACAGATAAAGATTCATCG |
| SEQ ID NO: 4006 | mm25927_Cdon | ATCACAGGTAAAATGTACGG |
| SEQ ID NO: 4007 | mm25928_Cdon | CTATTTCGTGAAGTACCGAA |
| SEQ ID NO: 4008 | mm25929_Cdon | GGCTGGTTATCAATCCATGG |
| SEQ ID NO: 4009 | mm25962_Angptl4 | CCTGTGGTAACGCTTGTCAG |
| SEQ ID NO: 4010 | mm25963_Angptl4 | TCGTCCCAGGATGCAAAGCG |
| SEQ ID NO: 4011 | mm25964_Angptl4 | TCCATTGTCTAGGTGCGTGG |
| SEQ ID NO: 4012 | mm25965_Angptl4 | GCTTCGGAGATCCCCAAGGT |
| SEQ ID NO: 4013 | mm25998_Crlf2 | GGAAGTCATAGCAGCGTACG |
| SEQ ID NO: 4014 | mm25999_Crlf2 | CCCACACCACTCACGCCAGG |
| SEQ ID NO: 4015 | mm26000_Crlf2 | GCGCCGGACAGGAAATATCG |
| SEQ ID NO: 4016 | mm26001_Crlf2 | AGCGGTGACAAGGCTTTCCG |
| SEQ ID NO: 4017 | mm26006_Tnfrsf13b | GTACTACGACCATCTCCTGG |
| SEQ ID NO: 4018 | mm26007_Tnfrsf13b | GAAGTCAGGTCAGACAACTC |
| SEQ ID NO: 4019 | mm26008_Tnfrsf13b | GTGGCTCTCCTCTACGCCTG |
| SEQ ID NO: 4020 | mm26009_Tnfrsf13b | ATCAGTACTGGGACTCCTCA |
| SEQ ID NO: 4021 | mm26030_Klrc3 | TTTGTGCTGAAGATAGACTG |
| SEQ ID NO: 4022 | mm26031_Klrc3 | ACTGAAACGGAGCTGCGCCT |
| SEQ ID NO: 4023 | mm26032_Klrc3 | CAATTGTTATTACATTGGCA |
| SEQ ID NO: 4024 | mm26033_Klrc3 | AATCAATAAGGTAAACCAGA |
| SEQ ID NO: 4025 | mm26090_Pdcd1lg2 | CCCCGCAGATGACCAGGCAA |
| SEQ ID NO: 4026 | mm26091_Pdcd1lg2 | GATAGACACTAGGATCCTGG |
| SEQ ID NO: 4027 | mm26092_Pdcd1lg2 | CCAGTTCAGTGCATTCTCTG |
| SEQ ID NO: 4028 | mm26093_Pdcd1lg2 | CTAGGGGATAACCTCTAGCC |
| SEQ ID NO: 4029 | mm26098_Slc43a3 | TGACCGCTTCAAGACTACTG |
| SEQ ID NO: 4030 | mm26099_Slc43a3 | GATTCATCTTGCACGTGGTG |
| SEQ ID NO: 4031 | mm26100_Slc43a3 | TGCTCCAGAGCAATGTAACA |
| SEQ ID NO: 4032 | mm26101_Slc43a3 | TACCCATAGCTGTAGTTGGG |
| SEQ ID NO: 4033 | mm26162_Pyrl1 | TCCACTCGTTTCTCGTAGGG |
| SEQ ID NO: 4034 | mm26163_Pyrl1 | CAGGAAATTCGGAACCCCAA |
| SEQ ID NO: 4035 | mm26164_Pyrl1 | TCTGGGCCTCTACACCCTTG |

TABLE 1-continued mmSurf sgRNA library sequences

| SEQ ID NO | id_gRNA Target | Sequence |
|---|---|---|
| SEQ ID NO: 4036 | mm26165_Pyrl1 | CCGGGTGCCCTCAATCCAGT |
| SEQ ID NO: 4037 | mm26166_Nkain4 | ATACCGGCCACGCTACATCG |
| SEQ ID NO: 4038 | mm26167_Nkain4 | TGGGCCAGGCTGTCTTCACG |
| SEQ ID NO: 4039 | mm26168_Nkain4 | ACGATGCCCAGAGAGATTGA |
| SEQ ID NO: 4040 | mm26169_Nkain4 | TGGGTGCCCACTGGTAACCC |
| SEQ ID NO: 4041 | mm26206_Chst11 | AGCCAACGAAGCCCACGTGT |
| SEQ ID NO: 4042 | mm26207_Chst11 | GCAGACACCAGCCTCTCGAA |
| SEQ ID NO: 4043 | mm26208_Chst11 | AGCAGATGTCCACACCGAAG |
| SEQ ID NO: 4044 | mm26209_Chst11 | ACCTCCTTCCACAAGCGCTA |
| SEQ ID NO: 4045 | mm26262_Slco1c1 | GAAGACATAAACCCACATGG |
| SEQ ID NO: 4046 | mm26263_Slco1c1 | CCATATAACAATCACCCCAA |
| SEQ ID NO: 4047 | mm26264_Slco1c1 | AGCTAACAAACGTTATGACC |
| SEQ ID NO: 4048 | mm26265_Slco1c1 | GGGATGTGAAAATTCTAGTG |
| SEQ ID NO: 4049 | mm26318_Sumf1 | GCAGCCGCACGAGCCCGCAA |
| SEQ ID NO: 4050 | mm26319_Sumf1 | CTCGACTGGCTATTTGACAG |
| SEQ ID NO: 4051 | mm26320_Sumf1 | AGTGAAAACGCATATCCACC |
| SEQ ID NO: 4052 | mm26321_Sumf1 | AGCTAATTGGAGACACCCAG |
| SEQ ID NO: 4053 | mm26338_Pvrl3 | TTTCCCACAAGATTTGCTCG |
| SEQ ID NO: 4054 | mm26339_Pvrl3 | AAAGCCGTTACATTCCCACT |
| SEQ ID NO: 4055 | mm26340_Pvrl3 | CTTAGCTGGATCAATTATTG |
| SEQ ID NO: 4056 | mm26341_Pvrl3 | GCCAGTCGCACAGATTGACT |
| SEQ ID NO: 4057 | mm26386_Moxd1 | ACTACGATAATCCCGCACGG |
| SEQ ID NO: 4058 | mm26387_Moxd1 | GGTACGCACGAACGGCTACG |
| SEQ ID NO: 4059 | mm26388_Moxd1 | TCTTCCACACAATTCCCCCA |
| SEQ ID NO: 4060 | mm26389_Moxd1 | GAAACTGTGATTCTCGCCTG |
| SEQ ID NO: 4061 | mm26422_Usp14 | TATCAGATGGAATTGCCATG |
| SEQ ID NO: 4062 | mm26423_Usp14 | TCAGCACAGTATATTACTGC |
| SEQ ID NO: 4063 | mm26424_Usp14 | GAATACTGATGAACCTCCAA |
| SEQ ID NO: 4064 | mm26425_Usp14 | TTGAAATAGGATGATGACTG |
| SEQ ID NO: 4065 | mm26446_Chst12 | ATTGTATATTGGGACAACGT |
| SEQ ID NO: 4066 | mm26447_Chst12 | GATCATCACTCGCTTCCAGT |
| SEQ ID NO: 4067 | mm26448_Chst12 | AGAACGTGAGAGGCTACGAC |
| SEQ ID NO: 4068 | mm26449_Chst12 | GACGGGAGAACTTTCCGTAG |
| SEQ ID NO: 4069 | mm26514_Mettl9 | CTGTACGTGAACATGACTAG |
| SEQ ID NO: 4070 | mm26515_Mettl9 | ACAGCATTGAGAAATCTGGC |
| SEQ ID NO: 4071 | mm26516_Mettl9 | GAGTGCTTGGTATAAATGAA |
| SEQ ID NO: 4072 | mm26517_Mettl9 | ATCTGGTGAGAACACAAACA |
| SEQ ID NO: 4073 | mm26538_Tpm3 | CTGGATCCTGCGGTTCAAGG |

TABLE 1-continued mmSurf sgRNA library sequences

| SEQ ID NO | id_gRNA Target | Sequence |
|---|---|---|
| SEQ ID NO: 4074 | mm26539_Tpm3 | AGGAGACTTGGAACGCACGG |
| SEQ ID NO: 4075 | mm26540_Tpm3 | ACATTGCAGAAGAGGCCGAT |
| SEQ ID NO: 4076 | mm26541_Tpm3 | TGGGCTCTGGCTCCAGCTAG |
| SEQ ID NO: 4077 | mm26574_Ncstn | CCAGCAGAACCATGTAAGGG |
| SEQ ID NO: 4078 | mm26575_Ncstn | GTGCTATCAAGATCACAACC |
| SEQ ID NO: 4079 | mm26576_Ncstn | AGGGACAGAACTCACCCGTG |
| SEQ ID NO: 4080 | mm26577_Ncstn | GGTGACTCACCGATTGTGGA |
| SEQ ID NO: 4081 | mm26586_Gpa33 | TCTTACCGTGGAAACTACAC |
| SEQ ID NO: 4082 | mm26587_Gpa33 | CACCTATGTTTCAGACCGAG |
| SEQ ID NO: 4083 | mm26588_Gpa33 | CAGTGACACGGAGCACTCGT |
| SEQ ID NO: 4084 | mm26589_Gpa33 | GTAGTAACCCGCTGTCTCCG |
| SEQ ID NO: 4085 | mm26606_Chst7 | GAAACCCGGATCGATCCCCC |
| SEQ ID NO: 4086 | mm26607_Chst7 | TGACCTTGTTGGTCCGCCAG |
| SEQ ID NO: 4087 | mm26608_Chst7 | CGTACAAGTAGAAAACGTCC |
| SEQ ID NO: 4088 | mm26609_Chst7 | CGAGTGCCGCAAGTACCCGG |
| SEQ ID NO: 4089 | mm26662_Il21r | GCACGTGTACCATATATGTG |
| SEQ ID NO: 4090 | mm26663_Il21r | AGGACGCTATGATATCTCCT |
| SEQ ID NO: 4091 | mm26664_Il21r | GCCACCTCACCACAGCATAG |
| SEQ ID NO: 4092 | mm26665_Il21r | GGGCTGGAAGAAACTCTCAG |
| SEQ ID NO: 4093 | mm26698_Cd274 | TGCTGCATAATCAGCTACGG |
| SEQ ID NO: 4094 | mm26699_Cd274 | TCCAAAGGACTTGTACGTGG |
| SEQ ID NO: 4095 | mm26700_Cd274 | CTCAGCACAGCAACTTCAGG |
| SEQ ID NO: 4096 | mm26701_Cd274 | GCTTGCGTTAGTGGTGTACT |
| SEQ ID NO: 4097 | mm26754_Trpv4 | TCAGCACATCATCCGACGTG |
| SEQ ID NO: 4098 | mm26755_Trpv4 | GGTGTACAACAGCAAGATCG |
| SEQ ID NO: 4099 | mm26756_Trpv4 | CTCACAAGAAAGCTGACATG |
| SEQ ID NO: 4100 | mm26757_Trpv4 | CTACCCTTACCGGACCACAG |
| SEQ ID NO: 4101 | mm26778_Slc29a1 | GCTGATGCAGAAACGAGTTG |
| SEQ ID NO: 4102 | mm26779_Slc29a1 | GCATGATTGATCAGTGTCCG |
| SEQ ID NO: 4103 | mm26780_Slc29a1 | TACACAGCCCCCATCATGAG |
| SEQ ID NO: 4104 | mm26781_Slc29a1 | GGCCAAAATGACAACTGCAC |
| SEQ ID NO: 4105 | mm26814_Sv2a | GCGGTAATAGCCGTCCGCAG |
| SEQ ID NO: 4106 | mm26815_Sv2a | TGTGGACACTCACCCGACCC |
| SEQ ID NO: 4107 | mm26816_Sv2a | TGAGAAAGACATGTGCCTGT |
| SEQ ID NO: 4108 | mm26817_Sv2a | AGCCCCGATGGCAAACACAG |
| SEQ ID NO: 4109 | mm26830_Clstn2 | GAGCTGCAGACTAATTACAT |
| SEQ ID NO: 4110 | mm26831_Clstn2 | ATAGCCATGCAACTTACTGT |
| SEQ ID NO: 4111 | mm26832_Clstn2 | TGGATCGAGACATCGTATCA |

TABLE 1-continued mmSurf sgRNA library sequences

| SEQ ID NO | id_gRNA Target | Sequence |
|---|---|---|
| SEQ ID NO: 4112 | mm26833_Clstn2 | AGGGTGCCAAGATCCCTGAT |
| SEQ ID NO: 4113 | mm26854_Ctsz | TTGCTACCATCCCATTCGCG |
| SEQ ID NO: 4114 | mm26855_Ctsz | GGGCATACTCCCACACCGGA |
| SEQ ID NO: 4115 | mm26856_Ctsz | TGAGACCTGCAACAACTACC |
| SEQ ID NO: 4116 | mm26857_Ctsz | CAGACCGAATCAACATCAAG |
| SEQ ID NO: 4117 | mm26870_Sv2b | TTCTTATCACGAGAGAAACG |
| SEQ ID NO: 4118 | mm26871_Sv2b | ATACAAACATGAGAGCTAAG |
| SEQ ID NO: 4119 | mm26872_Sv2b | ATAGGGCTGATAGTCTACCT |
| SEQ ID NO: 4120 | mm26873_Sv2b | TTGCAGTTACTACGGCCTGA |
| SEQ ID NO: 4121 | mm26922_Gprc5b | TCGCACAGGGACACGTACTG |
| SEQ ID NO: 4122 | mm26923_Gprc5b | TGTGTGGCAAGTTCAAACGG |
| SEQ ID NO: 4123 | mm26924_Gprc5b | TCCATCCGACGCTTCCTCTG |
| SEQ ID NO: 4124 | mm26925_Gprc5b | AGCGCCATCACAAAATCCAT |
| SEQ ID NO: 4125 | mm26934_Fndc4 | TGCAGCGACAGAATGGCCCG |
| SEQ ID NO: 4126 | mm26935_Fndc4 | GTCACATTCACAGGAGAGGG |
| SEQ ID NO: 4127 | mm26936_Fndc4 | CTTCTTAGGTGATATTACAG |
| SEQ ID NO: 4128 | mm26937_Fndc4 | GTGTCCTGGGACGTTCCAGA |
| SEQ ID NO: 4129 | mm26990_Dip2a | AGGCGTGTAGGTCTCAACGG |
| SEQ ID NO: 4130 | mm26991_Dip2a | TGTGATCCGAGTTGACACTG |
| SEQ ID NO: 4131 | mm26992_Dip2a | ACATCAACACGTTACATGGG |
| SEQ ID NO: 4132 | mm26993_Dip2a | CATATCTCGGGACTTTACCA |
| SEQ ID NO: 4133 | mm27070_Scube1 | TGAGAATGACTACTACAACG |
| SEQ ID NO: 4134 | mm27071_Scube1 | GAGTGCTTGATGAATAACGG |
| SEQ ID NO: 4135 | mm27072_Scube1 | ACCAGAAGGACTGCACACGT |
| SEQ ID NO: 4136 | mm27073_Scube1 | CTCTACGGGACAACCCACTG |
| SEQ ID NO: 4137 | mm27078_Svep1 | ATTTCCTGTCGGGAATCACG |
| SEQ ID NO: 4138 | mm27079_Svep1 | AGAAAGCATAGTGCCCCTCG |
| SEQ ID NO: 4139 | mm27080_Svep1 | AACATCCAGGAAGTGATCGT |
| SEQ ID NO: 4140 | mm27081_Svep1 | CAAGGGATTCTATATCAAGG |
| SEQ ID NO: 4141 | mm27134_Rtn4r | ACACTGCACCTAGACCGATG |
| SEQ ID NO: 4142 | mm27135_Rtn4r | GCCGAAATCTCACTATCCTG |
| SEQ ID NO: 4143 | mm27136_Rtn4r | TGTGTGCTACAATGAGCCCA |
| SEQ ID NO: 4144 | mm27137_Rtn4r | CAGAGGTCCTAATGCCCCTG |
| SEQ ID NO: 4145 | mm27222_Clstn1 | TCCAAGTGTGACTCTCTACG |
| SEQ ID NO: 4146 | mm27223_Clstn1 | CCCAGACGTGCCGTTCACTG |
| SEQ ID NO: 4147 | mm27224_Clstn1 | AGTCACCGAGAACGATAACA |
| SEQ ID NO: 4148 | mm27225_Clstn1 | CAACGAGGCGGCTTGCATCG |
| SEQ ID NO: 4149 | mm27246_Cubn | GTGTATCTGGAACATTCGCG |

TABLE 1-continued mmSurf sgRNA library sequences

| SEQ ID NO | id_gRNA Target | Sequence |
|---|---|---|
| SEQ ID NO: 4150 | mm27247_Cubn | AGTTATCAACTTCACCCACG |
| SEQ ID NO: 4151 | mm27248_Cubn | ACAGCTCCGAATGCTACTGG |
| SEQ ID NO: 4152 | mm27249_Cubn | CCACCTGTGTGAACACTATG |
| SEQ ID NO: 4153 | mm27250_Lima1 | GGCAAGCAAGAGCGACAATG |
| SEQ ID NO: 4154 | mm27251_Lima1 | ATGGAGGTTTCTGAGAGGCG |
| SEQ ID NO: 4155 | mm27252_Lima1 | CTGGACCCAAAGCCGAAATG |
| SEQ ID NO: 4156 | mm27253_Lima1 | TACAACTGAGAATAGTCTAG |
| SEQ ID NO: 4157 | mm27274_Sostdc1 | TCCACCAAATACATTTCGGA |
| SEQ ID NO: 4158 | mm27275_Sostdc1 | ATGTGAATAAAGGATTTCTG |
| SEQ ID NO: 4159 | mm27276_Sostdc1 | ACAGCACCCTGAATCAAGCC |
| SEQ ID NO: 4160 | mm27277_Sostdc1 | CTTCCCAACTGGATCGGAGG |
| SEQ ID NO: 4161 | mm27470_Tspan13 | AGCTCCAATTAGCCCCACCA |
| SEQ ID NO: 4162 | mm27471_Tspan13 | GGCTACTCACGGTATACAGC |
| SEQ ID NO: 4163 | mm27472_Tspan13 | CAATGACCACACCCACCACT |
| SEQ ID NO: 4164 | mm27473_Tspan13 | ACTGGACAATAAATACAAGT |
| SEQ ID NO: 4165 | mm27558_Ifitm3 | CTGACAGAAGCCGATCCGTG |
| SEQ ID NO: 4166 | mm27559_Ifitm3 | TTGATTCTTTCGTAGTTTGG |
| SEQ ID NO: 4167 | mm27560_Ifitm3 | AATCAAGGAAGAATATGAGG |
| SEQ ID NO: 4168 | mm27561_Ifitm3 | TCTAGGGATCGGAAGATGGT |
| SEQ ID NO: 4169 | mm27566_Eef1e1 | CCAGTTCTACAGACAAACAA |
| SEQ ID NO: 4170 | mm27567_Eef1e1 | GGCCTGCTTGACTAGATGGG |
| SEQ ID NO: 4171 | mm27568_Eef1e1 | TGAGCACTGTACTTATTCCC |
| SEQ ID NO: 4172 | mm27569_Eef1e1 | TGCAGGACATAACATCACCC |
| SEQ ID NO: 4173 | mm27758_Cd302 | GAGGACCTAGTTGATACCTG |
| SEQ ID NO: 4174 | mm27759_Cd302 | AAATATGACATTCGACAAGT |
| SEQ ID NO: 4175 | mm27760_Cd302 | ACAGTGCACTGACCACGGTA |
| SEQ ID NO: 4176 | mm27761_Cd302 | ACTTTGCAAAAGCGATGGAA |
| SEQ ID NO: 4177 | mm27846_Tmem9 | GGCAGTAGGCTTCCACATCG |
| SEQ ID NO: 4178 | mm27847_Tmem9 | GCTCTGCGAGTGTAGGTACG |
| SEQ ID NO: 4179 | mm27848_Tmem9 | CAACCAGAATGTGTCTCAGA |
| SEQ ID NO: 4180 | mm27849_Tmem9 | CCGCTGATGTTTCTGTAAGG |
| SEQ ID NO: 4181 | mm27886_Ssr2 | ACAATGCCGAAGTCTTCTGG |
| SEQ ID NO: 4182 | mm27887_Ssr2 | AGCCAGCTTTGAGAGGACGC |
| SEQ ID NO: 4183 | mm27888_Ssr2 | CAGTATAACATCTACAACGT |
| SEQ ID NO: 4184 | mm27889_Ssr2 | CTGGGCCAGGTAAGTAATCG |
| SEQ ID NO: 4185 | mm28082_Aqp11 | CCCCCGAAATGGGTGCCGTG |
| SEQ ID NO: 4186 | mm28083_Aqp11 | GGCACAGCTAGCAACCCGTG |
| SEQ ID NO: 4187 | mm28084_Aqp11 | GATGATCGCTTTGGACATGT |

TABLE 1-continued mmSurf sgRNA library sequences

| SEQ ID NO | id_gRNA Target | Sequence |
|---|---|---|
| SEQ ID NO: 4188 | mm28085_Aqp11 | CTGTTGCCGGGCGATCACGC |
| SEQ ID NO: 4189 | mm28462_Rps23 | CATGCCACTTCTGGTCCCGT |
| SEQ ID NO: 4190 | mm28463_Rps23 | GCATGAGAGGCACCCCCAAA |
| SEQ ID NO: 4191 | mm28464_Rps23 | TTGATATTGCAGAGGGGTTG |
| SEQ ID NO: 4192 | mm28465_Rps23 | AAGTCACCTCAATGAAGTTC |
| SEQ ID NO: 4193 | mm28494_Rpl35 | CGGGTCGCCAAAGTGACAGG |
| SEQ ID NO: 4194 | mm28495_Rpl35 | ATTAAGGCTCGGGACCTGCG |
| SEQ ID NO: 4195 | mm28496_Rpl35 | GAAACAACTGGACGATCTGA |
| SEQ ID NO: 4196 | mm28497_Rpl35 | CTCAAGGCCCACTTACATCT |
| SEQ ID NO: 4197 | mm28634_Sppl2a | TTGATTCATAGGATGCCATG |
| SEQ ID NO: 4198 | mm28635_Sppl2a | TGTAATTGCTGTGTTCACTG |
| SEQ ID NO: 4199 | mm28636_Sppl2a | TGGCATAAGGAACAAGGCAG |
| SEQ ID NO: 4200 | mm28637_Sppl2a | GTGGGCTGTATTTCGAAATG |
| SEQ ID NO: 4201 | mm28914_Sorcs3 | TCACACCAAGGGTTCGCGAG |
| SEQ ID NO: 4202 | mm28915_Sorcs3 | CCAGTCCAGACACCGACCTG |
| SEQ ID NO: 4203 | mm28916_Sorcs3 | CTTCAGTCCGTATCTCCCCG |
| SEQ ID NO: 4204 | mm28917_Sorcs3 | ACGTGGGATCTACTTTACCC |
| SEQ ID NO: 4205 | mm28946_Dcbld1 | TGACATCTAAGAATTATCCA |
| SEQ ID NO: 4206 | mm28947_Dcbld1 | TTAATAACCTGTTTGGAACG |
| SEQ ID NO: 4207 | mm28948_Dcbld1 | AGGAATGAATATTACAACTG |
| SEQ ID NO: 4208 | mm28949_Dcbld1 | GCAAAGCTGCCATCCACGCA |
| SEQ ID NO: 4209 | mm28970_Aspn | GAACAACGGGATAGAACCAG |
| SEQ ID NO: 4210 | mm28971_Aspn | GCTCCAGCAAAGTTGGTGGT |
| SEQ ID NO: 4211 | mm28972_Aspn | ATACAAAAGGACACGTTCAA |
| SEQ ID NO: 4212 | mm28973_Aspn | GAACAACTCGAGAGTAACAT |
| SEQ ID NO: 4213 | mm29178_Cntnap2 | ATTTATACGAAGTAGCACAC |
| SEQ ID NO: 4214 | mm29179_Cntnap2 | ATGGAAAGCATCAACTACAA |
| SEQ ID NO: 4215 | mm29180_Cntnap2 | GGCACTAATCTGGTCCATGG |
| SEQ ID NO: 4216 | mm29181_Cntnap2 | CAGATGTGTGGCCATAGATG |
| SEQ ID NO: 4217 | mm29190_Tspan1 | TGGTGTACACCACATTGGTG |
| SEQ ID NO: 4218 | mm29191_Tspan1 | CAGGAAAGATGTCCCATCGA |
| SEQ ID NO: 4219 | mm29192_Tspan1 | GCCATGCAGTTTGTCAACGT |
| SEQ ID NO: 4220 | mm29193_Tspan1 | GAACAAGTGTGTGCTCATGA |
| SEQ ID NO: 4221 | mm29330_Clec14a | AAGAACAGCTAACCCTCGAG |
| SEQ ID NO: 4222 | mm29331_Clec14a | CCTGACTGTCTAGATCACTT |
| SEQ ID NO: 4223 | mm29332_Clec14a | TTGGAAACTCAAATTAGAGG |
| SEQ ID NO: 4224 | mm29333_Clec14a | AGAGGACAGCCCACTACCGT |
| SEQ ID NO: 4225 | mm29386_Pcyox1 | CCTACCGATCCTGTTCGGCG |

TABLE 1-continued mmSurf sgRNA library sequences

| SEQ ID NO | id_gRNA Target | Sequence |
|---|---|---|
| SEQ ID NO: 4226 | mm29387_Pcyox1 | GGTGCAAGGTCATGACTACG |
| SEQ ID NO: 4227 | mm29388_Pcyox1 | CATCTCGTTGAGAAACGTCT |
| SEQ ID NO: 4228 | mm29389_Pcyox1 | GTAATAAAATTGTTTGCTCG |
| SEQ ID NO: 4229 | mm29410_Lman2 | GCAAATGTAGAAATGTCGTG |
| SEQ ID NO: 4230 | mm29411_Lman2 | ATCTCGGTGATGGTGAACAA |
| SEQ ID NO: 4231 | mm29412_Lman2 | CCCGGGAATAGCGTACAGCT |
| SEQ ID NO: 4232 | mm29413_Lman2 | ACTTCAAAGTCCATGGCACA |
| SEQ ID NO: 4233 | mm29562_Tmem206 | GAGGTGGAATAACCTCATAG |
| SEQ ID NO: 4234 | mm29563_Tmem206 | TCCGGGAGTTCATGCAAAGG |
| SEQ ID NO: 4235 | mm29564_Tmem206 | CATGTCCGTGTCTTACAAGG |
| SEQ ID NO: 4236 | mm29565_Tmem206 | TCGCCTGAACCAGAGCAATG |
| SEQ ID NO: 4237 | mm29606_Edem3 | GTGGATAAGAGCTGTCCGAG |
| SEQ ID NO: 4238 | mm29607_Edem3 | GTCCGCCCAAAAGACCCCTA |
| SEQ ID NO: 4239 | mm29608_Edem3 | ACTGGAGACTGGGTACGCAA |
| SEQ ID NO: 4240 | mm29609_Edem3 | AAGGCATGAGCTCATCAGCT |
| SEQ ID NO: 4241 | mm29722_Rbm7 | ATGCTGGGATATGACACAC |
| SEQ ID NO: 4242 | mm29723_Rbm7 | AATCCCAACTGATCCGCATG |
| SEQ ID NO: 4243 | mm29724_Rbm7 | CTTCTCCAGAAGATTATCAG |
| SEQ ID NO: 4244 | mm29725_Rbm7 | GTACCTGTTAGGAGATGTGG |
| SEQ ID NO: 4245 | mm29990_Fgf22 | CACTCACCGACCCATAGAGG |
| SEQ ID NO: 4246 | mm29991_Fgf22 | GAGATCCGTTCTGTCCGTGT |
| SEQ ID NO: 4247 | mm29992_Fgf22 | TCCCCTGCACCCGACCACCA |
| SEQ ID NO: 4248 | mm29993_Fgf22 | GTGATCAAAGCTGTGTACTC |
| SEQ ID NO: 4249 | mm30018_Mastl | AACATACAGAATTAGAACTG |
| SEQ ID NO: 4250 | mm30019_Mastl | TGACTCCACACTGGATACGA |
| SEQ ID NO: 4251 | mm30020_Mastl | GCATTCGGGAAAGTGTACCT |
| SEQ ID NO: 4252 | mm30021_Mastl | GAGAACATGACCATTGACAA |
| SEQ ID NO: 4253 | mm30030_Tspan31 | TGCGCTGTGCGCTCTCAACG |
| SEQ ID NO: 4254 | mm30031_Tspan31 | CCAGTCCTGCCACCGCGATG |
| SEQ ID NO: 4255 | mm30032_Tspan31 | GGCTATTAACAGAAACACAC |
| SEQ ID NO: 4256 | mm30033_Tspan31 | GAATGCTAGACACCACACCG |
| SEQ ID NO: 4257 | mm30058_Nop56 | CAGCCTGTCAGCCTTAATTG |
| SEQ ID NO: 4258 | mm30059_Nop56 | TAAATTTAATGTGAACCGAG |
| SEQ ID NO: 4259 | mm30060_Nop56 | GAGGAATGTGTGCTTAACCT |
| SEQ ID NO: 4260 | mm30061_Nop56 | GGGTACAACTGCCAGACTGG |
| SEQ ID NO: 4261 | mm30146_Lpar6 | TTCAGTCGACCCACTCTCAG |
| SEQ ID NO: 4262 | mm30147_Lpar6 | TACAACGTACATGATTAACC |
| SEQ ID NO: 4263 | mm30148_Lpar6 | CAAGTTACGTTCAAAATGAG |

TABLE 1-continued mmSurf sgRNA library sequences

| SEQ ID NO | id_gRNA Target | Sequence |
|---|---|---|
| SEQ ID NO: 4264 | mm30149_Lpar6 | AGATCGTTTGCATTGCTGTG |
| SEQ ID NO: 4265 | mm30182_Rplp2 | AAGAAAATACTAGACAGCGT |
| SEQ ID NO: 4266 | mm30183_Rplp2 | TTCAGCTCACTGATGACCTG |
| SEQ ID NO: 4267 | mm30184_Rplp2 | TAGGAGAGGAGTTGCCCCCG |
| SEQ ID NO: 4268 | mm30185_Rplp2 | GCTGAATGGAAAGAACATTG |
| SEQ ID NO: 4269 | mm30218_Eif2s2 | GAAATACTAGAAAAAGACGA |
| SEQ ID NO: 4270 | mm30219_Eif2s2 | CCTACTCGGACGACCTGTGG |
| SEQ ID NO: 4271 | mm30220_Eif2s2 | AAGAGACTACACATATGAGG |
| SEQ ID NO: 4272 | mm30221_Eif2s2 | GATGACCTTGACATTATGCT |
| SEQ ID NO: 4273 | mm30454_Cltc | AAGCAACACAAGCCAGATGG |
| SEQ ID NO: 4274 | mm30455_Cltc | GATGTTCACCCACTATGACC |
| SEQ ID NO: 4275 | mm30456_Cltc | GCTGTGCGGAACAACTTAGC |
| SEQ ID NO: 4276 | mm30457_Cltc | ATAACCACAGGAAGTCGACT |
| SEQ ID NO: 4277 | mm30586_Jam2 | TGAAATCTATCATCTCAGCA |
| SEQ ID NO: 4278 | mm30587_Jam2 | TCTTTAAACCAGATGTACTC |
| SEQ ID NO: 4279 | mm30588_Jam2 | GTCACAGTAATAGAGTTCCA |
| SEQ ID NO: 4280 | mm30589_Jam2 | CTTCCAGTCATAACAGAAGT |
| SEQ ID NO: 4281 | mm30646_Erp29 | GGCAGCGGCCTACACACGAA |
| SEQ ID NO: 4282 | mm30647_Erp29 | GAACCCTGTGCTGTACAATG |
| SEQ ID NO: 4283 | mm30648_Erp29 | GCTGAGTGAGAAGTACAAGC |
| SEQ ID NO: 4284 | mm30649_Erp29 | TCCCAAAAGCAAGTTCGTCT |
| SEQ ID NO: 4285 | mm30682_Armcx2 | TCATTATCTCAATATCGACG |
| SEQ ID NO: 4286 | mm30683_Armcx2 | AGAGATTGGACTGCCATGGG |
| SEQ ID NO: 4287 | mm30684_Armcx2 | TGTGGCAGCCCAATCTACTG |
| SEQ ID NO: 4288 | mm30685_Armcx2 | GGAAACAAGAACCGGAGTGG |
| SEQ ID NO: 4289 | mm30770_Plxdc2 | CCGGTTCCAGTTCGCCCACG |
| SEQ ID NO: 4290 | mm30771_Plxdc2 | ACTCTCAAGCATACAACCAC |
| SEQ ID NO: 4291 | mm30772_Plxdc2 | GCAGTTGAAACCAATCTGCG |
| SEQ ID NO: 4292 | mm30773_Plxdc2 | ACAACCCGACTTTCACTGGA |
| SEQ ID NO: 4293 | mm30794_Ergic2 | GCCAAATGTGCATGCCCTCG |
| SEQ ID NO: 4294 | mm30795_Ergic2 | TCTATGTCAATAAAGTAGCA |
| SEQ ID NO: 4295 | mm30796_Ergic2 | ACTGGATTTAGCAGAGACCA |
| SEQ ID NO: 4296 | mm30797_Ergic2 | TTCTGTCACAGAGAACTGAT |
| SEQ ID NO: 4297 | mm30862_Ero1lb | TGTGCAAACTACCTTCTGGA |
| SEQ ID NO: 4298 | mm30863_Ero1lb | CAGACTTGAGAGGAAGCTCA |
| SEQ ID NO: 4299 | mm30864_Ero1lb | CAAAGAAGCGTTCATTGACT |
| SEQ ID NO: 4300 | mm30865_Ero1lb | ACTCACCTTATTTGAACGCC |
| SEQ ID NO: 4301 | mm30942_Tmed9 | AGCGCGCTGTATTTCCACAT |

TABLE 1-continued mmSurf sgRNA library sequences

| SEQ ID NO | id_gRNA Target | Sequence |
|---|---|---|
| SEQ ID NO: 4302 | mm30943_Tmed9 | GCTGTATGACAAACAGCGGG |
| SEQ ID NO: 4303 | mm30944_Tmed9 | TGGGCTTGGCATGTTCGTAG |
| SEQ ID NO: 4304 | mm30945_Tmed9 | CGCCCCGCACCGATGACCA |
| SEQ ID NO: 4305 | mm30994_Zswim3 | TCCTGTAAGATCGCTCGGTG |
| SEQ ID NO: 4306 | mm30995_Zswim3 | TGGTACATACATGTGAGGAA |
| SEQ ID NO: 4307 | mm30996_Zswim3 | CTATGTAATCCACAAAGTGA |
| SEQ ID NO: 4308 | mm30997_Zswim3 | CAAGGAGCGAGAGAGTCGAG |
| SEQ ID NO: 4309 | mm31010_Slc39a8 | TCAGCTGCTGTAAGATCGCG |
| SEQ ID NO: 4310 | mm31011_Slc39a8 | AGGGGGTTAAAATCAATCCC |
| SEQ ID NO: 4311 | mm31012_Slc39a8 | CGTTAGGCTCAGTGACAGCG |
| SEQ ID NO: 4312 | mm31013_Slc39a8 | CGGCGCCAACCGGAGCCTGT |
| SEQ ID NO: 4313 | mm31098_Tctn3 | ACCCTATAGAATAGTACTGG |
| SEQ ID NO: 4314 | mm31099_Tctn3 | GCAGCTCACCTTACACTACC |
| SEQ ID NO: 4315 | mm31100_Tctn3 | GTCTACGAGATAGAGACCAA |
| SEQ ID NO: 4316 | mm31101_Tctn3 | CTAAGAGTGGCTTCCCAGTG |
| SEQ ID NO: 4317 | mm31278_Sdhb | TGCGCCATGAACATCAACGG |
| SEQ ID NO: 4318 | mm31279_Sdhb | ACAGTATCTGCAGTCCATCG |
| SEQ ID NO: 4319 | mm31280_Sdhb | ACCTCGAATGCAGACGTACG |
| SEQ ID NO: 4320 | mm31281_Sdhb | TAGAAGTTACTCAAATCCTG |
| SEQ ID NO: 4321 | mm31330_Kirrel3 | ACCTCGTTTCATCCACACGA |
| SEQ ID NO: 4322 | mm31331_Kirrel3 | GGAGCTGTATAGGACCACGG |
| SEQ ID NO: 4323 | mm31332_Kirrel3 | GACATCAGGGCGCTACACAG |
| SEQ ID NO: 4324 | mm31333_Kirrel3 | ACCGCTTGTCAACTTGTCCG |
| SEQ ID NO: 4325 | mm31478_Slc38a2 | CCACCAAAGCAGCTTCCACG |
| SEQ ID NO: 4326 | mm31479_Slc38a2 | CTCAAGACTGCCAACGAAGG |
| SEQ ID NO: 4327 | mm31480_Slc38a2 | GCAGTGACAATGGAAGAATG |
| SEQ ID NO: 4328 | mm31481_Slc38a2 | GAGTTGAAGATGAAATAGCG |
| SEQ ID NO: 4329 | mm31518_Rtp4 | CCACGACACACGCAATTGTG |
| SEQ ID NO: 4330 | mm31519_Rtp4 | CCTGCGATTTCAAAGTGTCC |
| SEQ ID NO: 4331 | mm31520_Rtp4 | TGCAGAGATACTATGGACAC |
| SEQ ID NO: 4332 | mm31521_Rtp4 | ATCCAAATGCAGGCTCCACT |
| SEQ ID NO: 4333 | mm31622_Rer1 | GAAAAATCTGTACACCACCG |
| SEQ ID NO: 4334 | mm31623_Rer1 | CAGTGTCACAACCCACCGGA |
| SEQ ID NO: 4335 | mm31624_Rer1 | AGGTCACAATGTACCAACCC |
| SEQ ID NO: 4336 | mm31625_Rer1 | ACGCAATGAAAAGGTTTAGG |
| SEQ ID NO: 4337 | mm31814_Rpl4 | GCAAAATGAGAAACCGACGG |
| SEQ ID NO: 4338 | mm31815_Rpl4 | AGAAAACAGATGTGTCGTGG |
| SEQ ID NO: 4339 | mm31816_Rpl4 | GCTGTATGGCACTTGGCGGA |

TABLE 1-continued mmSurf sgRNA library sequences

| SEQ ID NO | id_gRNA Target | Sequence |
|---|---|---|
| SEQ ID NO: 4340 | mm31817_Rp14 | GTTAGGTCATCGTATTGAGG |
| SEQ ID NO: 4341 | mm31834_Ccdc80 | TGGCCATCAGGACCCAAATG |
| SEQ ID NO: 4342 | mm31835_Ccdc80 | GGGTGAGCTAATCTCAACAC |
| SEQ ID NO: 4343 | mm31836_Ccdc80 | TACGGAGGATCACCAATGAA |
| SEQ ID NO: 4344 | mm31837_Ccdc80 | GCTATACCCTCTACCTCGGA |
| SEQ ID NO: 4345 | mm31882_Ppap2b | CATTGCAGTAAAACCCTCGA |
| SEQ ID NO: 4346 | mm31883_Ppap2b | GCAGCTCTCTATAAGCAAGT |
| SEQ ID NO: 4347 | mm31884_Ppap2b | GTCCCTGAGAGTAAGAACGG |
| SEQ ID NO: 4348 | mm31885_Ppap2b | CAGTCAGATCAATTGCTCCG |
| SEQ ID NO: 4349 | mm31938_Myl12b | GCTAAACGGCACTGACCCCG |
| SEQ ID NO: 4350 | mm31939_Myl12b | GCGTCCAGGTAGGCATCAGT |
| SEQ ID NO: 4351 | mm31940_Myl12b | GTTTAGCTTCTCCCCAAACA |
| SEQ ID NO: 4352 | mm31941_Myl12b | CCAGATCCAGGAGTTCAAAG |
| SEQ ID NO: 4353 | mm31978_Tubb6 | AGCTAAGAAGTACGTACCCA |
| SEQ ID NO: 4354 | mm31979_Tubb6 | GACCAGGCCGGAGGCTACGT |
| SEQ ID NO: 4355 | mm31980_Tubb6 | GCCAGGGAAACGCAGTGATG |
| SEQ ID NO: 4356 | mm31981_Tubb6 | CTGGGCCAAGGGTCACTACA |
| SEQ ID NO: 4357 | mm32058_Tmx3 | GACTTGGCATATAATTACCG |
| SEQ ID NO: 4358 | mm32059_Tmx3 | TGTTCGACCATGTACGGAAG |
| SEQ ID NO: 4359 | mm32060_Tmx3 | AAGATGGCGATCTGTCCTCA |
| SEQ ID NO: 4360 | mm32061_Tmx3 | GTGTGGCCATTGTAAAAAGT |
| SEQ ID NO: 4361 | mm32110_Trap1 | TTGTAGTGCAAAGTGAAGCG |
| SEQ ID NO: 4362 | mm32111_Trap1 | CAGAGAGCCCAGGTTACCAG |
| SEQ ID NO: 4363 | mm32112_Trap1 | AGGACAGTTATACAGCACAC |
| SEQ ID NO: 4364 | mm32113_Trap1 | TTGGCACAATTGCCAGATCG |
| SEQ ID NO: 4365 | mm32418_Spire1 | AGGAAACACCTACGAACGTG |
| SEQ ID NO: 4366 | mm32419_Spire1 | CTACGTACTGGATTTAAAGG |
| SEQ ID NO: 4367 | mm32420_Spire1 | GTGCCTCCGACTCAGTTGGG |
| SEQ ID NO: 4368 | mm32421_Spire1 | GATGAGGGATTTGCGAAATG |
| SEQ ID NO: 4369 | mm32666_Stt3b | AGGGTACATATCTCGGTCAG |
| SEQ ID NO: 4370 | mm32667_Stt3b | CGACAGCATGCAGACGACCG |
| SEQ ID NO: 4371 | mm32668_Stt3b | GTCATCTATCTGACATACAC |
| SEQ ID NO: 4372 | mm32669_Stt3b | TACAGCAAGAGAGTCTACAT |
| SEQ ID NO: 4373 | mm32830_Lmbrd1 | TTACAAACAGCAACGCAACG |
| SEQ ID NO: 4374 | mm32831_Lmbrd1 | AAGGCACGTCTATCCCTCGC |
| SEQ ID NO: 4375 | mm32832_Lmbrd1 | CATCATCTGTTTCAGGCGTA |
| SEQ ID NO: 4376 | mm32833_Lmbrd1 | AACGGTATTCTCAATCTGTA |
| SEQ ID NO: 4377 | mm32850_Rpl34 | TTCTACAGGTTCGTGCTGTG |

TABLE 1-continued mmSurf sgRNA library sequences

| SEQ ID NO | id_gRNA Target | Sequence |
|---|---|---|
| SEQ ID NO: 4378 | mm32851_Rpl34 | AAAGCACCTAAATCTGCATG |
| SEQ ID NO: 4379 | mm32852_Rpl34 | AGCGTTTGACATACCGCCGT |
| SEQ ID NO: 4380 | mm32853_Rpl34 | CTTCCTAGGTCTCGAACCCC |
| SEQ ID NO: 4381 | mm32866_Gpihbp1 | GCAGGTATCAGTACACCACA |
| SEQ ID NO: 4382 | mm32867_Gpihbp1 | CACTGTGCAATATTCCACCC |
| SEQ ID NO: 4383 | mm32868_Gpihbp1 | CTGTCAAGTGCTTCACAGCG |
| SEQ ID NO: 4384 | mm32869_Gpihbp1 | CCTGCTTCCAGGGATCATGT |
| SEQ ID NO: 4385 | mm32886_Ly6g6c | GTGACATCGAGTATCAGCTG |
| SEQ ID NO: 4386 | mm32887_Ly6g6c | TCGTTGAAGACCTCCCGACA |
| SEQ ID NO: 4387 | mm32888_Ly6g6c | CCTGCCTCTAGGGAAGATGT |
| SEQ ID NO: 4388 | mm32889_Ly6g6c | CGTTTGTTGTCAGGCATTTG |
| SEQ ID NO: 4389 | mm32914_Mpzl1 | GGATGCGGTCCTTACCGACA |
| SEQ ID NO: 4390 | mm32915_Mpzl1 | TGGACACATTAGGCTCCACG |
| SEQ ID NO: 4391 | mm32916_Mpzl1 | CACAACTGGATGGTTGACCA |
| SEQ ID NO: 4392 | mm32917_Mpzl1 | GTGACTCGGTCTTTAAATGG |
| SEQ ID NO: 4393 | mm33002_Evc2 | CCTTTCCCTCAATGACCAAG |
| SEQ ID NO: 4394 | mm33003_Evc2 | GATATTTCAAGAGAAGCCCG |
| SEQ ID NO: 4395 | mm33004_Evc2 | ACCAGAGATTAATAACCAGG |
| SEQ ID NO: 4396 | mm33005_Evc2 | CCTTACTCTGGACCAAGCCG |
| SEQ ID NO: 4397 | mm33174_Tm2d3 | AACTACAATACTTACGACAC |
| SEQ ID NO: 4398 | mm33175_Tm2d3 | GGACAGGAAAAGCAGCACGC |
| SEQ ID NO: 4399 | mm33176_Tm2d3 | GCGCTGCCGAGGGCAAGCCA |
| SEQ ID NO: 4400 | mm33177_Tm2d3 | GACACTTCGTCATGTAAGGA |
| SEQ ID NO: 4401 | mm33186_Abhd14a | ACAGGTGCAGAATACTGTGT |
| SEQ ID NO: 4402 | mm33187_Abhd14a | AAAGATTCGAGAGTTGCCTC |
| SEQ ID NO: 4403 | mm33188_Abhd14a | AGCATTTAATTCCCACACAT |
| SEQ ID NO: 4404 | mm33189_Abhd14a | CAGACTTCGCGACTCTGGAG |
| SEQ ID NO: 4405 | mm33246_Slc44a2 | ATCAACAACCTTGTACACGG |
| SEQ ID NO: 4406 | mm33247_Slc44a2 | GAACATTACAGATCTAGTGG |
| SEQ ID NO: 4407 | mm33248_Slc44a2 | GGTGAAACGCATTACCTGAG |
| SEQ ID NO: 4408 | mm33249_Slc44a2 | TCAAGTGCAGGTACACTCGG |
| SEQ ID NO: 4409 | mm33426_Srpx2 | ATGGTGGTTATGAACGCCAG |
| SEQ ID NO: 4410 | mm33427_Srpx2 | TTCAATGTGTAACACCATCG |
| SEQ ID NO: 4411 | mm33428_Srpx2 | TAGAACAGCTATAGTCACAA |
| SEQ ID NO: 4412 | mm33429_Srpx2 | CAGAATCTTTCACTAAGGGT |
| SEQ ID NO: 4413 | mm33522_Lrrn4cl | GGCAACGGTCATAGTCGCAA |
| SEQ ID NO: 4414 | mm33523_Lrrn4cl | CAAAGGACATAAGCAACCCC |
| SEQ ID NO: 4415 | mm33524_Lrrn4cl | CCAGGGTCAAGATCTGAGGT |

TABLE 1-continued mmSurf sgRNA library sequences

| SEQ ID NO | id_gRNA Target | Sequence |
|---|---|---|
| SEQ ID NO: 4416 | mm33525_Lrrn4cl | TCTGCTTTGGGAAAGCAACG |
| SEQ ID NO: 4417 | mm33590_Disp1 | GAGGGACCACGATAGGACAG |
| SEQ ID NO: 4418 | mm33591_Disp1 | ACTCGAAGTTAAAGACGACT |
| SEQ ID NO: 4419 | mm33592_Disp1 | GACGTAATTCACCAATATGG |
| SEQ ID NO: 4420 | mm33593_Disp1 | GGCGTAGTCAGCCGTCTTTG |
| SEQ ID NO: 4421 | mm34030_Cd209b | CCAAAACCCCAAATACCGAG |
| SEQ ID NO: 4422 | mm34031_Cd209b | TGGGACTGGACATTCCTCCT |
| SEQ ID NO: 4423 | mm34032_Cd209b | GCTTAGAATCATCCTTTACC |
| SEQ ID NO: 4424 | mm34033_Cd209b | AGGGAAGAATGAGTCCATGC |
| SEQ ID NO: 4425 | mm34050_Tmem110 | GAGGGCGCACTGTCCTACCC |
| SEQ ID NO: 4426 | mm34051_Tmem110 | GGCATGCTGCTCATTTATGT |
| SEQ ID NO: 4427 | mm34052_Tmem110 | CATGATCTTTGAAAAGTCCG |
| SEQ ID NO: 4428 | mm34053_Tmem110 | GAGAACCAAAGCATGAAAGA |
| SEQ ID NO: 4429 | mm34122_Carkd | TAGGCCAGGTCCCACGACAA |
| SEQ ID NO: 4430 | mm34123_Carkd | CTGACGTCGAAGAAGCACAA |
| SEQ ID NO: 4431 | mm34124_Carkd | CATTCTCACCCCCAACCACG |
| SEQ ID NO: 4432 | mm34125_Carkd | CCATACAGCACATGCGACAA |
| SEQ ID NO: 4433 | mm34526_Esam | ACCTACTGCTCAGTACCAGT |
| SEQ ID NO: 4434 | mm34527_Esam | TCTGCACATTGACAGAACAG |
| SEQ ID NO: 4435 | mm34528_Esam | GGAGTCATGACAAATAAACC |
| SEQ ID NO: 4436 | mm34529_Esam | GTCGTGGTCCCACCCCCGGG |
| SEQ ID NO: 4437 | mm34554_Dnase1l1 | GAAGCACCATGATATCACAT |
| SEQ ID NO: 4438 | mm34555_Dnase1l1 | TGAGCAGGGGAGCCATAACA |
| SEQ ID NO: 4439 | mm34556_Dnase1l1 | TCCTAAACAGCTCATTGCTG |
| SEQ ID NO: 4440 | mm34557_Dnase1l1 | AGAGTGAAATGGGCCACAAA |
| SEQ ID NO: 4441 | mm34558_Antxr1 | ACATGCACGAAGGATTCGAG |
| SEQ ID NO: 4442 | mm34559_Antxr1 | TGAACCATCCACCATCTGCG |
| SEQ ID NO: 4443 | mm34560_Antxr1 | TGAAGGACATCCTTAGCTGT |
| SEQ ID NO: 4444 | mm34561_Antxr1 | CTGCTCATCCCATAGTCAGA |
| SEQ ID NO: 4445 | mm34598_Bst2 | CGCCGTCACAGCGAACAGCG |
| SEQ ID NO: 4446 | mm34599_Bst2 | CCGTGCCCATGGATGAGATG |
| SEQ ID NO: 4447 | mm34600_Bst2 | AAACTCCTGCAACCTGACCG |
| SEQ ID NO: 4448 | mm34601_Bst2 | CTGGCGCTGCAACAGGTGCG |
| SEQ ID NO: 4449 | mm34634_Hilpda | ACATGATGCCCAGCACATAG |
| SEQ ID NO: 4450 | mm34635_Hilpda | GTTAGAGTGATGGAGTCTCT |
| SEQ ID NO: 4451 | mm34636_Hilpda | GGGAGCTCCTGGATCACGAG |
| SEQ ID NO: 4452 | mm34637_Hilpda | CTCCATCACTCTAACAAAGA |
| SEQ ID NO: 4453 | mm34658_Tnfsf13 | TCAACCAAAGAGCAACCGAA |

TABLE 1-continued mmSurf sgRNA library sequences

| SEQ ID NO | id_gRNA Target | Sequence |
| --- | --- | --- |
| SEQ ID NO: 4454 | mm34659_Tnfsf13 | GGCAACCAGTACTTAGGCGT |
| SEQ ID NO: 4455 | mm34660_Tnfsf13 | ATGGGGCGAAATCTCGGAGA |
| SEQ ID NO: 4456 | mm34661_Tnfsf13 | GCTGCAAAGCCTAAGGCGGG |
| SEQ ID NO: 4457 | mm34662_Hfe2 | GGCTCACCGGACACGCCGCG |
| SEQ ID NO: 4458 | mm34663_Hfe2 | GTTGGCTCCCGACGAAACCG |
| SEQ ID NO: 4459 | mm34664_Hfe2 | CTATGCCATGCACCGCAGAG |
| SEQ ID NO: 4460 | mm34665_Hfe2 | ACAAACTCGAGCCCCCAGGT |
| SEQ ID NO: 4461 | mm34758_Cd164l2 | CGTTTGGCCTACTACCCAAG |
| SEQ ID NO: 4462 | mm34759_Cd164l2 | ATTACCAGCTAGAACCAGCT |
| SEQ ID NO: 4463 | mm34760_Cd164l2 | TCTCCCACCAGGACACTGTG |
| SEQ ID NO: 4464 | mm34761_Cd164l2 | GGGACACTGTGAACACTGTG |
| SEQ ID NO: 4465 | mm34802_Txndc15 | ACCACCATGGGATCTCCGCG |
| SEQ ID NO: 4466 | mm34803_Txndc15 | CCAAGTGTTGGAAACGCCCG |
| SEQ ID NO: 4467 | mm34804_Txndc15 | TTGGGTTTAGGAAATCCATG |
| SEQ ID NO: 4468 | mm34805_Txndc15 | TGTGTATCTGCATGAAGAGG |
| SEQ ID NO: 4469 | mm34810_Pxdn | CAGAAGTATAGGACGCACGA |
| SEQ ID NO: 4470 | mm34811_Pxdn | TGATGGTCAAGAATCCTTCG |
| SEQ ID NO: 4471 | mm34812_Pxdn | CCACTGTGTATGGATCCCGT |
| SEQ ID NO: 4472 | mm34813_Pxdn | GAATCAGAGAGATCCAACCC |
| SEQ ID NO: 4473 | mm35242_Tmem30a | GACAGACCAATTGCGCCATG |
| SEQ ID NO: 4474 | mm35243_Tmem30a | CAACAACATCCGTGAGATCG |
| SEQ ID NO: 4475 | mm35244_Tmem30a | TACTTACAAGCAAAGCACTA |
| SEQ ID NO: 4476 | mm35245_Tmem30a | CAAGCACAAGATGTCACATT |
| SEQ ID NO: 4477 | mm35266_Ace2 | TGTAGAACGTACCTTCGCAG |
| SEQ ID NO: 4478 | mm35267_Ace2 | ACTTGTACAGATATTACACA |
| SEQ ID NO: 4479 | mm35268_Ace2 | AATGGATTTCAGATGCTTGG |
| SEQ ID NO: 4480 | mm35269_Ace2 | GATGTGTCCCATCTCGTGAT |
| SEQ ID NO: 4481 | mm35418_Slc44a4 | TGGGCACGAGGAATTCAACG |
| SEQ ID NO: 4482 | mm35419_Slc44a4 | GATGTCGAAGTATAGAACGT |
| SEQ ID NO: 4483 | mm35420_Slc44a4 | TCTCCATCCCCAGATAGTGG |
| SEQ ID NO: 4484 | mm35421_Slc44a4 | AGTTGGTAGTGAAGCCCAGT |
| SEQ ID NO: 4485 | mm35618_Copb1 | TCTTGTCCTAGGATTTACCG |
| SEQ ID NO: 4486 | mm35619_Copb1 | TAGTAAGAGTTACACACCAC |
| SEQ ID NO: 4487 | mm35620_Copb1 | GATCATTATGATTCTGAATG |
| SEQ ID NO: 4488 | mm35621_Copb1 | CTCCGTAACCAATTTCTGAA |
| SEQ ID NO: 4489 | mm35738_Megf10 | GCGATGTCCATAAAAACCGG |
| SEQ ID NO: 4490 | mm35739_Megf10 | CCGGACAGCCTACCGCCACG |
| SEQ ID NO: 4491 | mm35740_Megf10 | TTTATCCCGTAGCGTCCCAG |

TABLE 1-continued mmSurf sgRNA library sequences

| SEQ ID NO | id_gRNA Target | Sequence |
|---|---|---|
| SEQ ID NO: 4492 | mm35741_Megf10 | TCTTTCCAAAGCGACCCTCA |
| SEQ ID NO: 4493 | mm35754_Tspan15 | CTGAACGACAACATCCGGAG |
| SEQ ID NO: 4494 | mm35755_Tspan15 | ATCACTCACCCAGAACACGG |
| SEQ ID NO: 4495 | mm35756_Tspan15 | GTCAGTGGGATCTACGCAG |
| SEQ ID NO: 4496 | mm35757_Tspan15 | CTGGTCATGGAGCTTATTGG |
| SEQ ID NO: 4497 | mm35842_Atp6ap2 | TTAGCATATTAAGATCGCCA |
| SEQ ID NO: 4498 | mm35843_Atp6ap2 | TGAACTTGGGAAGCGTTATG |
| SEQ ID NO: 4499 | mm35844_Atp6ap2 | CCGGTGGAATAGGTTACCCA |
| SEQ ID NO: 4500 | mm35845_Atp6ap2 | TGGACAGTGCAGCTACGTCT |
| SEQ ID NO: 4501 | mm35866_Stambp | GATTACGGGCACCACGATG |
| SEQ ID NO: 4502 | mm35867_Stambp | TTACAGTCTGGAGTCTGCGT |
| SEQ ID NO: 4503 | mm35868_Stambp | TGAGCAGTATAAAGAGCGAA |
| SEQ ID NO: 4504 | mm35869_Stambp | GAGCGTCGCTTTCCCTAAAG |
| SEQ ID NO: 4505 | mm35870_Lrfn2 | TGGAACCTGTGATGTCCGAA |
| SEQ ID NO: 4506 | mm35871_Lrfn2 | GCGACCCTTGAGACTTCCGG |
| SEQ ID NO: 4507 | mm35872_Lrfn2 | GTCCTCCGGTCAATGTCAGG |
| SEQ ID NO: 4508 | mm35873_Lrfn2 | CAACCGGCTACCTAGCCTTG |
| SEQ ID NO: 4509 | mm35894_Tmtc4 | ATGGACAGCAAACAGCAACG |
| SEQ ID NO: 4510 | mm35895_Tmtc4 | ATTAACTACTACCTGTCCGG |
| SEQ ID NO: 4511 | mm35896_Tmtc4 | CCAGTCAGACACGCCCCTTG |
| SEQ ID NO: 4512 | mm35897_Tmtc4 | CAAGGTACCTTAGCATTGAG |
| SEQ ID NO: 4513 | mm35934_Cpm | GTTGTCCCGAAGCTTAACCC |
| SEQ ID NO: 4514 | mm35935_Cpm | GGACGGCTTCGAATCCATCG |
| SEQ ID NO: 4515 | mm35936_Cpm | GTAGCCGTTGATAATCCCGT |
| SEQ ID NO: 4516 | mm35937_Cpm | AAATACGTGGCGAATATGCA |
| SEQ ID NO: 4517 | mm36062_Adgra2 | AACATCACCACCATTCAGTG |
| SEQ ID NO: 4518 | mm36063_Adgra2 | TGTGGCAAGCAACATCATGT |
| SEQ ID NO: 4519 | mm36064_Adgra2 | GTCATGTTCAGACGAAACGT |
| SEQ ID NO: 4520 | mm36065_Adgra2 | AATGAGCTGGAGCTTATAGA |
| SEQ ID NO: 4521 | mm36110_Tspan2 | CACACACTGTGACTCACGCA |
| SEQ ID NO: 4522 | mm36111_Tspan2 | TGTACAGAGCATGTATGAGG |
| SEQ ID NO: 4523 | mm36112_Tspan2 | TCGATTTGGAGGTACCATGA |
| SEQ ID NO: 4524 | mm36113_Tspan2 | TACCTTAAAGACAGGGCAAG |
| SEQ ID NO: 4525 | mm36226_P2ry12 | ATATCAGTATATCGTTCCTG |
| SEQ ID NO: 4526 | mm36227_P2ry12 | TGGCACACCAAGGTTCTCAG |
| SEQ ID NO: 4527 | mm36228_P2ry12 | CTTGTAGTCTCTGACGCACA |
| SEQ ID NO: 4528 | mm36229_P2ry12 | TCATTACCAAAGAACTCTAT |
| SEQ ID NO: 4529 | mm36346_Mmrn1 | AGTGTCCAGTATCACTGTCG |

TABLE 1-continued mmSurf sgRNA library sequences

| SEQ ID NO | id_gRNA Target | Sequence |
|---|---|---|
| SEQ ID NO: 4530 | mm36347_Mmrn1 | GAATGATTTGACATATGACA |
| SEQ ID NO: 4531 | mm36348_Mmrn1 | AGTCACACCGCTGTTGACCA |
| SEQ ID NO: 4532 | mm36349_Mmrn1 | TGCAAGAAAATCAGCCCACG |
| SEQ ID NO: 4533 | mm36522_Gpr39 | GTAAACGTACCCACTCACAA |
| SEQ ID NO: 4534 | mm36523_Gpr39 | TTACAGGACAGAGCATAGCT |
| SEQ ID NO: 4535 | mm36524_Gpr39 | CGTCACCATCAGGGTTACGC |
| SEQ ID NO: 4536 | mm36525_Gpr39 | AGACCTCCCAACGGTTGGAG |
| SEQ ID NO: 4537 | mm36546_Scara5 | TAGGTCCATGTCACAAACGG |
| SEQ ID NO: 4538 | mm36547_Scara5 | CTGGTAGAGTTCCAGCTGTG |
| SEQ ID NO: 4539 | mm36548_Scara5 | CAGCGCCTTCAAGTCATCTG |
| SEQ ID NO: 4540 | mm36549_Scara5 | GGGAACACTCCATCGCCTTG |
| SEQ ID NO: 4541 | mm36598_Clec12b | AAGTCAAATTACCAGAAGCG |
| SEQ ID NO: 4542 | mm36599_Clec12b | GCTGTCAATCTTCACCAGAG |
| SEQ ID NO: 4543 | mm36600_Clec12b | GGCAGCGCCTCGCCAAAGTG |
| SEQ ID NO: 4544 | mm36601_Clec12b | AGGACTCTGCAAGAGTGAGG |
| SEQ ID NO: 4545 | mm36682_Mfap31 | CATGGGCGTGTACTATATGG |
| SEQ ID NO: 4546 | mm36683_Mfap31 | GGTGACTGCTCATCATACAC |
| SEQ ID NO: 4547 | mm36684_Mfap31 | GAACTGCAGGACGATCATGG |
| SEQ ID NO: 4548 | mm36685_Mfap31 | GAAGCATCCGAGTCAGCGGT |
| SEQ ID NO: 4549 | mm36702_Treml1 | ACCTGGTGGAAGAACCAACA |
| SEQ ID NO: 4550 | mm36703_Treml1 | TCACGCCGTCTGAACTCGTG |
| SEQ ID NO: 4551 | mm36704_Treml1 | CCCACTAGTGACCTCAGCGG |
| SEQ ID NO: 4552 | mm36705_Treml1 | CTCAGCTGACAGTCATCCCG |
| SEQ ID NO: 4553 | mm36722_Ano9 | TCCCGGAAGTACCATGAACA |
| SEQ ID NO: 4554 | mm36723_Ano9 | AGCCACTCAGAAAGACGATG |
| SEQ ID NO: 4555 | mm36724_Ano9 | TGAAGAATATATGGGCTCGG |
| SEQ ID NO: 4556 | mm36725_Ano9 | CCAGGCGCGTGGATTTCCCA |
| SEQ ID NO: 4557 | mm36838_Ptk7 | GAGCGTACAACTGTGTACCA |
| SEQ ID NO: 4558 | mm36839_Ptk7 | TGTTGTTGTAGCAAGGAACG |
| SEQ ID NO: 4559 | mm36840_Ptk7 | CTTGCGCATCAATAGTGTGG |
| SEQ ID NO: 4560 | mm36841_Ptk7 | TGTCTGTCACCCATTCAGGG |
| SEQ ID NO: 4561 | mm36914_Clmp | TGTCTACAATAACTTGACCG |
| SEQ ID NO: 4562 | mm36915_Clmp | CCTACAGATTACAACAACCC |
| SEQ ID NO: 4563 | mm36916_Clmp | CCAGTGCACAGCAGGCAACG |
| SEQ ID NO: 4564 | mm36917_Clmp | TGTGCAGAGCATTGGCATGG |
| SEQ ID NO: 4565 | mm37026_Atp5h | TACAGCATACTGACCTGGCG |
| SEQ ID NO: 4566 | mm37027_Atp5h | CCTGAAGATTCCTGTGCCTG |
| SEQ ID NO: 4567 | mm37028_Atp5h | CACAGCCCTGGTGGACCAGG |

TABLE 1-continued mmSurf sgRNA library sequences

| SEQ ID NO | id_gRNA Target | Sequence |
|---|---|---|
| SEQ ID NO: 4568 | mm37029_Atp5h | GGCTTACTACAGGGCCAATG |
| SEQ ID NO: 4569 | mm37150_Susd2 | GGCCGGCGCTTCATATAACG |
| SEQ ID NO: 4570 | mm37151_Susd2 | CTGCCCGGAAGTCGTCACCC |
| SEQ ID NO: 4571 | mm37152_Susd2 | AGTGCCGTAGTATTGCCAAT |
| SEQ ID NO: 4572 | mm37153_Susd2 | AAGTGAAGAAGCCGGTATTG |
| SEQ ID NO: 4573 | mm37286_Anxa9 | TGTGGACTATGATACCATTG |
| SEQ ID NO: 4574 | mm37287_Anxa9 | GAAACTCAAGAACGTCCTGA |
| SEQ ID NO: 4575 | mm37288_Anxa9 | TGGCAATCTGGAGAAAATCG |
| SEQ ID NO: 4576 | mm37289_Anxa9 | TGAGACCAATGGTATCCTGC |
| SEQ ID NO: 4577 | mm37498_Apmap | GAAACTCTGAGGATCTATGG |
| SEQ ID NO: 4578 | mm37499_Apmap | GAGAAATAGAGACCATCGCT |
| SEQ ID NO: 4579 | mm37500_Apmap | GAATCCATAGTAAATATTGG |
| SEQ ID NO: 4580 | mm37501_Apmap | AGTTGTAACATACGTTTCTG |
| SEQ ID NO: 4581 | mm37546_Tmem106b | TTCAGCGTCGTAGCTGACAT |
| SEQ ID NO: 4582 | mm37547_Tmem106b | AAAACACAGCCAATCCAGAC |
| SEQ ID NO: 4583 | mm37548_Tmem106b | AGTGAAGTGCACAACGAAGA |
| SEQ ID NO: 4584 | mm37549_Tmem106b | TTCAAAAACCGTGATTGGAA |
| SEQ ID NO: 4585 | mm37594_Antxr2 | GTCACGTCGATCAGTCACGA |
| SEQ ID NO: 4586 | mm37595_Antxr2 | CAGTACGAAGTACAAATCGA |
| SEQ ID NO: 4587 | mm37596_Antxr2 | TTGACGGACGGTAAGCTGGA |
| SEQ ID NO: 4588 | mm37597_Antxr2 | CAAAATTGGCAAAGGACTGG |
| SEQ ID NO: 4589 | mm37622_Itfg1 | CAACCGCAGATACTGCTAGG |
| SEQ ID NO: 4590 | mm37623_Itfg1 | GAGTGCGTTGGTAACAAGTG |
| SEQ ID NO: 4591 | mm37624_Itfg1 | AAAACCTAAAAATCTGGTGG |
| SEQ ID NO: 4592 | mm37625_Itfg1 | CCTCAACTCCGACAAACAGA |
| SEQ ID NO: 4593 | mm37626_Tmem123 | GAGGCAGTAGGCGTCACATG |
| SEQ ID NO: 4594 | mm37627_Tmem123 | CAGGACCCGACCGACGCTCA |
| SEQ ID NO: 4595 | mm37628_Tmem123 | CAATAAACTACTGTGGGCTG |
| SEQ ID NO: 4596 | mm37629_Tmem123 | TACCAACCAGACCATGAGTG |
| SEQ ID NO: 4597 | mm37802_Synpr | AAGTACCGCGAAAACAACCG |
| SEQ ID NO: 4598 | mm37803_Synpr | GGTGACAAAGAATTCTGCTG |
| SEQ ID NO: 4599 | mm37804_Synpr | GCAGCCTTCCAACAAGTGCA |
| SEQ ID NO: 4600 | mm37805_Synpr | CTCACAGGTGGGCACTTCAA |
| SEQ ID NO: 4601 | mm37810_Zfyve19 | AGTGCCACACAATCCTGACC |
| SEQ ID NO: 4602 | mm37811_Zfyve19 | CTGGACTTCATCCTTCAGTG |
| SEQ ID NO: 4603 | mm37812_Zfyve19 | AGTTACCTGAGGCTCTTGGT |
| SEQ ID NO: 4604 | mm37813_Zfyve19 | CCACACACTCACCGGTCTCA |
| SEQ ID NO: 4605 | mm37814_Btbd17 | CTTGGCGTAATGCAACGGCG |

TABLE 1-continued mmSurf sgRNA library sequences

| SEQ ID NO | id_gRNA Target | Sequence |
| --- | --- | --- |
| SEQ ID NO: 4606 | mm37815_Btbd17 | GCAGCTCAGAGAGCCGATGT |
| SEQ ID NO: 4607 | mm37816_Btbd17 | CCCCGGTGCTAACAGCGTAG |
| SEQ ID NO: 4608 | mm37817_Btbd17 | CGAGTAGCATCCTTGCAGCG |
| SEQ ID NO: 4609 | mm37846_Slc39a4 | GGTCCTGAATACGGATAGTG |
| SEQ ID NO: 4610 | mm37847_Slc39a4 | CAGTTGGGGAAGATCTACAC |
| SEQ ID NO: 4611 | mm37848_Slc39a4 | CATGCAGCGTGATATTGGGA |
| SEQ ID NO: 4612 | mm37849_Slc39a4 | TGGAGAGGGTCACACCCATG |
| SEQ ID NO: 4613 | mm37870_Sulf2 | GACGGTGAGATATACCACGT |
| SEQ ID NO: 4614 | mm37871_Sulf2 | ACAAATGTAAAGGCCCCATG |
| SEQ ID NO: 4615 | mm37872_Sulf2 | ACATGGCTCAGACTACTCCA |
| SEQ ID NO: 4616 | mm37873_Sulf2 | GCACATTGGTGTAGTCACGA |
| SEQ ID NO: 4617 | mm37886_Tnfrsf13c | CAGACTCACTAGACCCACCA |
| SEQ ID NO: 4618 | mm37887_Tnfrsf13c | GACACGCAGTTTCTCACCAG |
| SEQ ID NO: 4619 | mm37888_Tnfrsf13c | CTCCGCGCTGAGACCCGACG |
| SEQ ID NO: 4620 | mm37889_Tnfrsf13c | GCACTCGGTCTGATTGCACT |
| SEQ ID NO: 4621 | mm37890_Kdelc1 | ACCCGGGCTAAAAGCACACG |
| SEQ ID NO: 4622 | mm37891_Kdelc1 | AGATAGAGGTTAAACACCAT |
| SEQ ID NO: 4623 | mm37892_Kdelc1 | TGTCGGTGCAAGCTAACACA |
| SEQ ID NO: 4624 | mm37893_Kdelc1 | GATGAGCAGTTCACGAGAGT |
| SEQ ID NO: 4625 | mm37914_Igsf5 | AACAGTCCTAAAGGACTCAG |
| SEQ ID NO: 4626 | mm37915_Igsf5 | GTGGACTCTTAACCAAATGG |
| SEQ ID NO: 4627 | mm37916_Igsf5 | AGTGCTGTTGTAACTGGCAT |
| SEQ ID NO: 4628 | mm37917_Igsf5 | TCTTGTAGACAGTATTGGAG |
| SEQ ID NO: 4629 | mm38114_Dhx36 | AGGGTCGCGAGATCGGCCTG |
| SEQ ID NO: 4630 | mm38115_Dhx36 | CAGCGTATATAAAGGAACTG |
| SEQ ID NO: 4631 | mm38116_Dhx36 | TGTCCAATGATACATATACC |
| SEQ ID NO: 4632 | mm38117_Dhx36 | GCCTACCGTCAACCAGACAC |
| SEQ ID NO: 4633 | mm38134_Mfsd8 | AGCAATGTATGATCGGACAA |
| SEQ ID NO: 4634 | mm38135_Mfsd8 | TGGACCGAGAATAAAGCCCA |
| SEQ ID NO: 4635 | mm38136_Mfsd8 | GGATATGTACGCCTGGACCC |
| SEQ ID NO: 4636 | mm38137_Mfsd8 | GAGCATCGTGTGGATGACTT |
| SEQ ID NO: 4637 | mm38346_Plxdc1 | ATTGTCAAAGTAAGCAACCG |
| SEQ ID NO: 4638 | mm38347_Plxdc1 | ACTCTGCATGGACTGCCAAG |
| SEQ ID NO: 4639 | mm38348_Plxdc1 | GGTTAGATTCGAGGACACGC |
| SEQ ID NO: 4640 | mm38349_Plxdc1 | TGTGGATCTTCACATGACTC |
| SEQ ID NO: 4641 | mm38410_Psca | GATAACTGTCACGAGTCCAA |
| SEQ ID NO: 4642 | mm38411_Psca | GCGATGTAAAGCAACTGTGC |
| SEQ ID NO: 4643 | mm38412_Psca | CTCGTGACAGTTATCAGTAA |

TABLE 1-continued mmSurf sgRNA library sequences

| SEQ ID NO | id_gRNA Target | Sequence |
|---|---|---|
| SEQ ID NO: 4644 | mm38413_Psca | ACCTACTTAGCCCTGCATCC |
| SEQ ID NO: 4645 | mm38446_Slc43a1 | GGATATCCCTGGTACCTCAG |
| SEQ ID NO: 4646 | mm38447_Slc43a1 | CTGACCCACAATGGTTACAT |
| SEQ ID NO: 4647 | mm38448_Slc43a1 | CTTAACGTTTACCTCACTCA |
| SEQ ID NO: 4648 | mm38449_Slc43a1 | CGGTCCATGAGAATTCCCAG |
| SEQ ID NO: 4649 | mm38526_Tmem87b | GCAGATACTCACATTCAATG |
| SEQ ID NO: 4650 | mm38527_Tmem87b | CAATGATTACCCTGATCTGG |
| SEQ ID NO: 4651 | mm38528_Tmem87b | GATGCAGAGATGTACCCATG |
| SEQ ID NO: 4652 | mm38529_Tmem87b | TGCATCACTGTTCCTAAGCG |
| SEQ ID NO: 4653 | mm38566_Rps6kb1 | ACTTCGGGTACTTGGTAAAG |
| SEQ ID NO: 4654 | mm38567_Rps6kb1 | TATTCATGGAAGACACAGCG |
| SEQ ID NO: 4655 | mm38568_Rps6kb1 | CTCTTAGCCTCCATTCACTG |
| SEQ ID NO: 4656 | mm38569_Rps6kb1 | AATGATAGTGAGGAATGCTA |
| SEQ ID NO: 4657 | mm38626_Naalad2 | AGAGAACATCGTAATGAACC |
| SEQ ID NO: 4658 | mm38627_Naalad2 | GAGGGATTGACCCTACCACT |
| SEQ ID NO: 4659 | mm38628_Naalad2 | TGTCAACTACGTCGTACTG |
| SEQ ID NO: 4660 | mm38629_Naalad2 | CAAAAATGCCATGCTAGCTG |
| SEQ ID NO: 4661 | mm38774_Calhm2 | TCCATACAGGTAGTTCCGGG |
| SEQ ID NO: 4662 | mm38775_Calhm2 | CAACCTATCGAGCTTCCGAG |
| SEQ ID NO: 4663 | mm38776_Calhm2 | CCCCCCAGCCCATGCTACGG |
| SEQ ID NO: 4664 | mm38777_Calhm2 | TAGTCGCCGAGTGCCAGTAC |
| SEQ ID NO: 4665 | mm38814_B3gat3 | GGACTCGCGGTGTCTCAGTG |
| SEQ ID NO: 4666 | mm38815_B3gat3 | TCTACACTGGCTGCTAGTGG |
| SEQ ID NO: 4667 | mm38816_B3gat3 | AATGACATAGATAGTAGGCA |
| SEQ ID NO: 4668 | mm38817_B3gat3 | ACGGAGATCAGCTTGCAACT |
| SEQ ID NO: 4669 | mm38902_Scn2b | CTGACACGTCGTACTTACTG |
| SEQ ID NO: 4670 | mm38903_Scn2b | AGTTAAGAGAGAACTGCTTG |
| SEQ ID NO: 4671 | mm38904_Scn2b | GGAGTGTAACAATTGCACAG |
| SEQ ID NO: 4672 | mm38905_Scn2b | TTGAGGACACTAAGAGTGGT |
| SEQ ID NO: 4673 | mm38982_Hepacam | CACTGACGACACCTTCACCG |
| SEQ ID NO: 4674 | mm38983_Hepacam | GCACCAAGCCTAGCTACACG |
| SEQ ID NO: 4675 | mm38984_Hepacam | GGTGCAGTCTATAGGCACAG |
| SEQ ID NO: 4676 | mm38985_Hepacam | CTCACTGAGCTCCAGCACAG |
| SEQ ID NO: 4677 | mm39026_Slc17a7 | TGGCGATGATGTAGCGACGA |
| SEQ ID NO: 4678 | mm39027_Slc17a7 | GGAGGAGCGCAAATACATTG |
| SEQ ID NO: 4679 | mm39028_Slc17a7 | GACACAGCCATAGTGAACGC |
| SEQ ID NO: 4680 | mm39029_Slc17a7 | TCCATCCTGAATACTGCACA |
| SEQ ID NO: 4681 | mm39122_Slc22a23 | GCCCGATTTCTGGTGCCGCG |

TABLE 1-continued mmSurf sgRNA library sequences

| SEQ ID NO | id_gRNA Target | Sequence |
|---|---|---|
| SEQ ID NO: 4682 | mm39123_Slc22a23 | TCGAGAAAGAGCTTTCACGG |
| SEQ ID NO: 4683 | mm39124_Slc22a23 | AAATTGCGACTGCCACGCGT |
| SEQ ID NO: 4684 | mm39125_Slc22a23 | AAAACGGTTCATAATTACCA |
| SEQ ID NO: 4685 | mm39230_Sppl2b | GCCAGTGATGGACTACAACA |
| SEQ ID NO: 4686 | mm39231_Sppl2b | TCCAATGATCACGTAGACTG |
| SEQ ID NO: 4687 | mm39232_Sppl2b | CTTCACCAACCAAATCGCAC |
| SEQ ID NO: 4688 | mm39233_Sppl2b | CATCACCCCCTTCCTGACCA |
| SEQ ID NO: 4689 | mm39358_Nptxr | AGACCGCATCGAGCGCATCG |
| SEQ ID NO: 4690 | mm39359_Nptxr | GGATGGTGTCCCGGTCTGCG |
| SEQ ID NO: 4691 | mm39360_Nptxr | CAGAGGAAGCGACTGAGCAG |
| SEQ ID NO: 4692 | mm39361_Nptxr | TCGGCCATGGTGTCGCGGCG |
| SEQ ID NO: 4693 | mm39398_Dcbld2 | GCTGCAGATAGACCTTAACA |
| SEQ ID NO: 4694 | mm39399_Dcbld2 | TGGATTCCAGCCATACACAA |
| SEQ ID NO: 4695 | mm39400_Dcbld2 | AGGTTATTGCCGTTCCGAGG |
| SEQ ID NO: 4696 | mm39401_Dcbld2 | GTCACAGTGCTGTTCATGAG |
| SEQ ID NO: 4697 | mm39610_Defb30 | AGAGCACGAGGGTCAACTGT |
| SEQ ID NO: 4698 | mm39611_Defb30 | AGAGCAAGACAAAGAGCACG |
| SEQ ID NO: 4699 | mm39612_Defb30 | AACGGATTTACGACACATGC |
| SEQ ID NO: 4700 | mm39613_Defb30 | TTGCTCTCCTATGTTCCACC |
| SEQ ID NO: 4701 | mm39674_Gucy2g | AAGAACCAGGAACGTCACCG |
| SEQ ID NO: 4702 | mm39675_Gucy2g | AACATGTCGTATGTCGCCAG |
| SEQ ID NO: 4703 | mm39676_Gucy2g | GGGTGGCACAAGTGTCACGC |
| SEQ ID NO: 4704 | mm39677_Gucy2g | AGCAAGTCTCCCAAGAACTG |
| SEQ ID NO: 4705 | mm39722_Psd | GAAGCAGGTAGGCCATTCAG |
| SEQ ID NO: 4706 | mm39723_Psd | GCCAGAATCAGGTTCAAGAG |
| SEQ ID NO: 4707 | mm39724_Psd | ATTACACTGGAAATATCGCT |
| SEQ ID NO: 4708 | mm39725_Psd | CCTTCCTGAAGCCATCGAGT |
| SEQ ID NO: 4709 | mm39914_Psd2 | GAGGGCTCGAGATAGCCCCG |
| SEQ ID NO: 4710 | mm39915_Psd2 | GGCGAACCAGATGTACGTGA |
| SEQ ID NO: 4711 | mm39916_Psd2 | CCAGGCCATTGGTCAAAGAG |
| SEQ ID NO: 4712 | mm39917_Psd2 | AACTTGGACCAGCTGAACGA |
| SEQ ID NO: 4713 | mm39982_Nfam1 | CAGGCAAACACATCAGCCAC |
| SEQ ID NO: 4714 | mm39983_Nfam1 | GAGGAAACATATCAGAGCGA |
| SEQ ID NO: 4715 | mm39984_Nfam1 | TTCATACGGATATCCATGGC |
| SEQ ID NO: 4716 | mm39985_Nfam1 | CCCCAATGTTCAGTCAAAGA |
| SEQ ID NO: 4717 | mm40078_Slc35a5 | ATTGAACTATAATCAGAACG |
| SEQ ID NO: 4718 | mm40079_Slc35a5 | AAGAGACAATTGTACATCGA |
| SEQ ID NO: 4719 | mm40080_Slc35a5 | GATTCTGTTCTTGTCTATCG |

TABLE 1-continued mmSurf sgRNA library sequences

| SEQ ID NO | id_gRNA Target | Sequence |
|---|---|---|
| SEQ ID NO: 4720 | mm40081_Slc35a5 | CTCTGAGCACACGTTCACAG |
| SEQ ID NO: 4721 | mm40182_Tm9sf1 | TATTTGCCAATGTTTCGGTG |
| SEQ ID NO: 4722 | mm40183_Tm9sf1 | CCATGTAGCCCACAAAACCA |
| SEQ ID NO: 4723 | mm40184_Tm9sf1 | GGACAACCAATGGATTTCCA |
| SEQ ID NO: 4724 | mm40185_Tm9sf1 | GTTCAACGTGCACCGTCACG |
| SEQ ID NO: 4725 | mm40194_Robo4 | GACTATCTGAGCTAGCCCAG |
| SEQ ID NO: 4726 | mm40195_Robo4 | CAGAGGGCCGATGTAACAGG |
| SEQ ID NO: 4727 | mm40196_Robo4 | GAGCAGAGAAGAATGACTCG |
| SEQ ID NO: 4728 | mm40197_Robo4 | TTCACCCACTACGGTCCAGT |
| SEQ ID NO: 4729 | mm40822_Hyal5 | TACATGCCAATAGACAATGT |
| SEQ ID NO: 4730 | mm40823_Hyal5 | TGTGAAACAAGACTCAGTTG |
| SEQ ID NO: 4731 | mm40824_Hyal5 | CTTCGGCCAAATCACTTATG |
| SEQ ID NO: 4732 | mm40825_Hyal5 | TTTGACTTTAGACACTCGAA |
| SEQ ID NO: 4733 | mm41010_Cd200r3 | GTGATGTGCAGGGACCCTAG |
| SEQ ID NO: 4734 | mm41011_Cd200r3 | AAAGGAAATGAATCATCCGG |
| SEQ ID NO: 4735 | mm41012_Cd200r3 | GTCGGATAGAAACAACAGAT |
| SEQ ID NO: 4736 | mm41013_Cd200r3 | CTGTAGGGTAGTCTGCAGGA |
| SEQ ID NO: 4737 | mm41022_Scpep1 | AAACTCCATACTTACCCACG |
| SEQ ID NO: 4738 | mm41023_Scpep1 | GGATTATGTGACTGTCCGAA |
| SEQ ID NO: 4739 | mm41024_Scpep1 | CACAACAGATGCCTACGCAA |
| SEQ ID NO: 4740 | mm41025_Scpep1 | CAAGCCTCGAAATACTACCT |
| SEQ ID NO: 4741 | mm41170_Mxra8 | TCACTGACACGCGATCACGC |
| SEQ ID NO: 4742 | mm41171_Mxra8 | TGTGCGCCTCGAGGTTACAG |
| SEQ ID NO: 4743 | mm41172_Mxra8 | GACTGACCGCCATTTAGAGG |
| SEQ ID NO: 4744 | mm41173_Mxra8 | CTTGTGGATATGTATTCGGC |
| SEQ ID NO: 4745 | mm41174_Mdga1 | CTTCAACGTACGACCCCGGG |
| SEQ ID NO: 4746 | mm41175_Mdga1 | CAGACAGTGAGCGATGTCCG |
| SEQ ID NO: 4747 | mm41176_Mdga1 | GTGTCCGTGCGCAATGTGTG |
| SEQ ID NO: 4748 | mm41177_Mdga1 | GCTTTCTTTGATCATGTCGG |
| SEQ ID NO: 4749 | mm41450_Sv2c | ATCCCGAATTTGGTATGCAT |
| SEQ ID NO: 4750 | mm41451_Sv2c | GAAGTCACCTTACCGTAGTG |
| SEQ ID NO: 4751 | mm41452_Sv2c | TGGCGAAACCTACAGTGGGG |
| SEQ ID NO: 4752 | mm41453_Sv2c | GACACCAACATGAGAGCCCG |
| SEQ ID NO: 4753 | mm41566_Slamf7 | ACATGTCAGATTGATTACGC |
| SEQ ID NO: 4754 | mm41567_Slamf7 | CCTGAGTGAAGTTAGATCCG |
| SEQ ID NO: 4755 | mm41568_Slamf7 | GAATGTCACAGATCCATCAA |
| SEQ ID NO: 4756 | mm41569_Slamf7 | AGACCAGGCCTTAACATGCA |
| SEQ ID NO: 4757 | mm41594_Defb29 | AGAGAGACTCGAGTTACCTG |

TABLE 1-continued mmSurf sgRNA library sequences

| SEQ ID NO | id_gRNA Target | Sequence |
|---|---|---|
| SEQ ID NO: 4758 | mm41595_Defb29 | GTCATACTTCATGACTGTGG |
| SEQ ID NO: 4759 | mm41596_Defb29 | TAAAGCTCACACGCAATCCA |
| SEQ ID NO: 4760 | mm41597_Defb29 | ATTGCGTGTGAGCTTTACCA |
| SEQ ID NO: 4761 | mm41926_Gns | CCAAAGTGTTGTTAACGACG |
| SEQ ID NO: 4762 | mm41927_Gns | TGCTGGGAAGTATTTAAACG |
| SEQ ID NO: 4763 | mm41928_Gns | TCAGACAACGGCTACCACAC |
| SEQ ID NO: 4764 | mm41929_Gns | CAGAGGAACCTACCGTCCCG |
| SEQ ID NO: 4765 | mm42162_Dcstamp | AAGCGTTCCTACCTTCACGG |
| SEQ ID NO: 4766 | mm42163_Dcstamp | GCTCATATGAATGACACTAG |
| SEQ ID NO: 4767 | mm42164_Dcstamp | AAGGCCGTAAATCCACTGGA |
| SEQ ID NO: 4768 | mm42165_Dcstamp | CCCACATGTAGAGATAGGTC |
| SEQ ID NO: 4769 | mm42166_Rab11fip1 | CAAGGAGAAGTACGCCACGT |
| SEQ ID NO: 4770 | mm42167_Rab11fip1 | CGGGAACTCACCATCCGAGG |
| SEQ ID NO: 4771 | mm42168_Rab11fip1 | GAGCAACGCGCGGTGCAGGA |
| SEQ ID NO: 4772 | mm42169_Rab11fip1 | CGTTGATACAGACGGTAGAG |
| SEQ ID NO: 4773 | mm42366_Cant1 | GGAGTGGGATAAAGACCACG |
| SEQ ID NO: 4774 | mm42367_Cant1 | CAGCACCCACAAAGGACGTG |
| SEQ ID NO: 4775 | mm42368_Cant1 | CCATCAGAAAGGATCACCCA |
| SEQ ID NO: 4776 | mm42369_Cant1 | GGAGTGGACCACCACGACAG |
| SEQ ID NO: 4777 | mm42542_Slc38a3 | AGCTGTCGCATCAGTGCTAG |
| SEQ ID NO: 4778 | mm42543_Slc38a3 | CATGACATACATGACAGCAA |
| SEQ ID NO: 4779 | mm42544_Slc38a3 | GATGTATAGGTAGCTGGACA |
| SEQ ID NO: 4780 | mm42545_Slc38a3 | ACCTGCTCCTCAAGTCTTCG |
| SEQ ID NO: 4781 | mm42578_Mfap4 | CTTCTGCGACATGACAACTG |
| SEQ ID NO: 4782 | mm42579_Mfap4 | TGTGATGATATCTACGCCCA |
| SEQ ID NO: 4783 | mm42580_Mfap4 | GAAGTCAATGTACTTGGCAT |
| SEQ ID NO: 4784 | mm42581_Mfap4 | CCTCGAAGCCAGCCACGTAG |
| SEQ ID NO: 4785 | mm42590_Erp44 | TGTAATCTACAAACCACCCG |
| SEQ ID NO: 4786 | mm42591_Erp44 | AATGTTATTTCTCGGACAAG |
| SEQ ID NO: 4787 | mm42592_Erp44 | GTGCTGATCACAATCAACTC |
| SEQ ID NO: 4788 | mm42593_Erp44 | CATCTAGACTCTGAATCTCG |
| SEQ ID NO: 4789 | mm42740_Prss23 | TGAGTCCCTACACCGTTCCG |
| SEQ ID NO: 4790 | mm42741_Prss23 | AAGGGCAATGCCAATGACAT |
| SEQ ID NO: 4791 | mm42742_Prss23 | GTGACACTGAGGTCCACATG |
| SEQ ID NO: 4792 | mm42743_Prss23 | CTGCCCACTGCATACACGAT |
| SEQ ID NO: 4793 | mm42792_Glt8d1 | AACAATGTAAAACATCACAT |
| SEQ ID NO: 4794 | mm42793_Glt8d1 | TAAAGCAGGATCCTGACCAG |
| SEQ ID NO: 4795 | mm42794_Glt8d1 | TCCCCGGATGATGACTTTAG |

TABLE 1-continued mmSurf sgRNA library sequences

| SEQ ID NO | id_gRNA Target | Sequence |
|---|---|---|
| SEQ ID NO: 4796 | mm42795_Glt8d1 | GCACTGGCGACAAAGTCTAT |
| SEQ ID NO: 4797 | mm42796_Ly6k | TGTCGAAACAGTGCACCCGA |
| SEQ ID NO: 4798 | mm42797_Ly6k | GATGGTGGATTAGTGCTAGG |
| SEQ ID NO: 4799 | mm42798_Ly6k | TGTTCTGCGCCTCACACACA |
| SEQ ID NO: 4800 | mm42799_Ly6k | TTATAAAATAGGAAGGGCAT |
| SEQ ID NO: 4801 | mm42832_Plet1 | CACTGACTGAATCGTTCACG |
| SEQ ID NO: 4802 | mm42833_Plet1 | GATGTTATCAAGGACCACGC |
| SEQ ID NO: 4803 | mm42834_Plet1 | CTTGACATCCCAAAGCCAGT |
| SEQ ID NO: 4804 | mm42835_Plet1 | TCATCCGTGAAAATGGAACA |
| SEQ ID NO: 4805 | mm42900_Mfsd2a | TCAGGGACGGAAAGTTCACA |
| SEQ ID NO: 4806 | mm42901_Mfsd2a | GCAGCCGGTCAACTGGTACG |
| SEQ ID NO: 4807 | mm42902_Mfsd2a | GAGGGACTTACTGTATGCCG |
| SEQ ID NO: 4808 | mm42903_Mfsd2a | TCTCTACTTACCAGGGCATG |
| SEQ ID NO: 4809 | mm43032_Arpc2 | AGTTGTTAAAGAGAGTGTAT |
| SEQ ID NO: 4810 | mm43033_Arpc2 | TCTTAGATTCCACATACCTG |
| SEQ ID NO: 4811 | mm43034_Arpc2 | GAAGTATTTCTCAAACACAG |
| SEQ ID NO: 4812 | mm43035_Arpc2 | CATCGGAAAGGTGTTCATGC |
| SEQ ID NO: 4813 | mm43072_Alpi | AAACTAAGGTATTACCCATG |
| SEQ ID NO: 4814 | mm43073_Alpi | AAGGCCAACTACAAGACCAT |
| SEQ ID NO: 4815 | mm43074_Alpi | AGCCGGCACCTACGCACACA |
| SEQ ID NO: 4816 | mm43075_Alpi | ACAGTAACCAGTCTGGAACC |
| SEQ ID NO: 4817 | mm43148_Calcoco2 | GATGAAGATGGTTTAGTCCG |
| SEQ ID NO: 4818 | mm43149_Calcoco2 | AGCGCTCCACATCCTTGGGA |
| SEQ ID NO: 4819 | mm43150_Calcoco2 | CCAATCCAGTCCTTGCGTCG |
| SEQ ID NO: 4820 | mm43151_Calcoco2 | GAGAAGTTCTATGCTCCTAG |
| SEQ ID NO: 4821 | mm43308_Hnrnpm | ATTGGCATGGGATTAGGACC |
| SEQ ID NO: 4822 | mm43309_Hnrnpm | AGGTGATGGCTACGACTGGT |
| SEQ ID NO: 4823 | mm43310_Hnrnpm | GCCCATGCGCTCAATACTGG |
| SEQ ID NO: 4824 | mm43311_Hnrnpm | CTAAGTAATGCACTGAAGAG |
| SEQ ID NO: 4825 | mm43436_Hyal4 | TGATATTGAATATTCAGCCA |
| SEQ ID NO: 4826 | mm43437_Hyal4 | TTCGGGTGCGTGAATCACTG |
| SEQ ID NO: 4827 | mm43438_Hyal4 | GATATAAATAATAACCCCAA |
| SEQ ID NO: 4828 | mm43439_Hyal4 | TGCTGTTCCAGAGCCAAGAG |
| SEQ ID NO: 4829 | mm43656_Myh10 | TCTGCATCATCCACTACGCG |
| SEQ ID NO: 4830 | mm43657_Myh10 | AGATAAGTCCTGAATAGTAG |
| SEQ ID NO: 4831 | mm43658_Myh10 | GAATGTGATGGAGTTCACTC |
| SEQ ID NO: 4832 | mm43659_Myh10 | TGTAACTGGCTATATTGTTG |
| SEQ ID NO: 4833 | mm43748_Defb12 | GAAGAATCTCCCCTCAAACA |

TABLE 1-continued mmSurf sgRNA library sequences

| SEQ ID NO | id_gRNA Target | Sequence |
|---|---|---|
| SEQ ID NO: 4834 | mm43749_Defb12 | TTTACCTCCTGGAAATGACT |
| SEQ ID NO: 4835 | mm43750_Defb12 | GGAATACTCAAGTCCTGCCC |
| SEQ ID NO: 4836 | mm43751_Defb12 | ATTGTAGTTGAACTGCCATC |
| SEQ ID NO: 4837 | mm43756_Bsph2 | TGGCGGTACTGTACAGCACA |
| SEQ ID NO: 4838 | mm43757_Bsph2 | AACACCAATCATAGTCACTG |
| SEQ ID NO: 4839 | mm43758_Bsph2 | GATGAGCCATCTTGTGCACT |
| SEQ ID NO: 4840 | mm43759_Bsph2 | GGAGGGAGATACAACTGTAG |
| SEQ ID NO: 4841 | mm43812_Ulbp1 | GAAGTTTATAGAAATGTGCA |
| SEQ ID NO: 4842 | mm43813_Ulbp1 | TTCCGTGTTGACACAAGCAC |
| SEQ ID NO: 4843 | mm43814_Ulbp1 | CACGCATAGAATAATCATCA |
| SEQ ID NO: 4844 | mm43815_Ulbp1 | GTGCAGGAGACTAACACAAC |
| SEQ ID NO: 4845 | mm43984_Lpar4 | CTGATGGTACGCGATCGGAA |
| SEQ ID NO: 4846 | mm43985_Lpar4 | GCAGTTGCATTTCCCAACCT |
| SEQ ID NO: 4847 | mm43986_Lpar4 | GCGGAAGCAGAAGACAAACA |
| SEQ ID NO: 4848 | mm43987_Lpar4 | GAAGCCTTCAAAGCAAGTGG |
| SEQ ID NO: 4849 | mm44128_Ttyh3 | GGAAATGCAAGATGTTGTCG |
| SEQ ID NO: 4850 | mm44129_Ttyh3 | GAGCACTCAGTACTGAGTGG |
| SEQ ID NO: 4851 | mm44130_Ttyh3 | GAACCCCGGAGTATCGCTGG |
| SEQ ID NO: 4852 | mm44131_Ttyh3 | ACGCCATGCCAACCGCACAG |
| SEQ ID NO: 4853 | mm44244_Adgra3 | GCTGCGAGTGTATACCGCAG |
| SEQ ID NO: 4854 | mm44245_Adgra3 | GAGCGGGTGACCAACAACCG |
| SEQ ID NO: 4855 | mm44246_Adgra3 | TCTCCATAGGAGCCCCATTG |
| SEQ ID NO: 4856 | mm44247_Adgra3 | GCTGAATGCATTCCCGCGGG |
| SEQ ID NO: 4857 | mm44464_P2ry10 | TGATCTTGGGTACAAACAGA |
| SEQ ID NO: 4858 | mm44465_P2ry10 | TGGAAGCGTAGGTACGATGT |
| SEQ ID NO: 4859 | mm44466_P2ry10 | TTTCCAGGTACAACATGCAA |
| SEQ ID NO: 4860 | mm44467_P2ry10 | GTAAGGACAGGATATGAGCA |
| SEQ ID NO: 4861 | mm44532_Igsf3 | CGAGTACGGGACCTACGCCG |
| SEQ ID NO: 4862 | mm44533_Igsf3 | AGTACAGATCGTTAGCACGG |
| SEQ ID NO: 4863 | mm44534_Igsf3 | CCAGCAGCGAATATGCCCAG |
| SEQ ID NO: 4864 | mm44535_Igsf3 | AGTGCCAAGATGAACCTAGT |
| SEQ ID NO: 4865 | mm44576_Pigt | GATCCGAATCCCAACGCGTG |
| SEQ ID NO: 4866 | mm44577_Pigt | AAACAAGTCATAGACGGCAT |
| SEQ ID NO: 4867 | mm44578_Pigt | GGTAACTGGTGTGGAACAAG |
| SEQ ID NO: 4868 | mm44579_Pigt | TGAGAGTCCGGGAGAACATG |
| SEQ ID NO: 4869 | mm44620_Tnfrsf23 | GTCACCCAGGAACATTCACA |
| SEQ ID NO: 4870 | mm44621_Tnfrsf23 | ATTAGACTGGTATTCACCAT |
| SEQ ID NO: 4871 | mm44622_Tnfrsf23 | GATTGCAGACCAGAATATGG |

TABLE 1-continued mmSurf sgRNA library sequences

| SEQ ID NO | id_gRNA Target | Sequence |
|---|---|---|
| SEQ ID NO: 4872 | mm44623_Tnfrsf23 | TGTTGCAAGACCTGTCCCTC |
| SEQ ID NO: 4873 | mm44624_Tnfrsf22 | AGCAAAGTATACAAGCATCC |
| SEQ ID NO: 4874 | mm44625_Tnfrsf22 | TTTAGACCAGTATTCACCAG |
| SEQ ID NO: 4875 | mm44626_Tnfrsf22 | TGAGTATGGGGATTTCGCA |
| SEQ ID NO: 4876 | mm44627_Tnfrsf22 | GATTGCAGATCAGGAAATGG |
| SEQ ID NO: 4877 | mm44736_Pofut2 | ACTGCTCATACTCTATAACG |
| SEQ ID NO: 4878 | mm44737_Pofut2 | CGTCCTACAAGGTTACGCCG |
| SEQ ID NO: 4879 | mm44738_Pofut2 | TTTGGGCTACGAAGAAACA |
| SEQ ID NO: 4880 | mm44739_Pofut2 | CTCCGGGCCATCTTATCAG |
| SEQ ID NO: 4881 | mm44812_Lrfn1 | ACACACACAAATCATAGGCG |
| SEQ ID NO: 4882 | mm44813_Lrfn1 | CCGGGATGGACCAGAAATAG |
| SEQ ID NO: 4883 | mm44814_Lrfn1 | TGTTGCCGAGGATCAAGTGG |
| SEQ ID NO: 4884 | mm44815_Lrfn1 | CTACATAAATTGCCCCCCGA |
| SEQ ID NO: 4885 | mm44828_Klrb1b | ATCAGTACAAAAAATCTGCG |
| SEQ ID NO: 4886 | mm44829_Klrb1b | CAATCACGACCAGCACAAGA |
| SEQ ID NO: 4887 | mm44830_Klrb1b | AGAGCCAACCGATGCCAGCG |
| SEQ ID NO: 4888 | mm44831_Klrb1b | ATGCAGATTTAAACCTAGCC |
| SEQ ID NO: 4889 | mm44852_Hist1h1a | CCTGGTGAATAAAGGCACAC |
| SEQ ID NO: 4890 | mm44853_Hist1h1a | TCCGACACCGAAGGTCCCGC |
| SEQ ID NO: 4891 | mm44854_Hist1h1a | AGCCAGCGACTTCTTGAGCG |
| SEQ ID NO: 4892 | mm44855_Hist1h1a | GAAACCTAAGAAGACTGCTG |
| SEQ ID NO: 4893 | mm45080_Sil1 | CCTACAGACTGGAGTAAACG |
| SEQ ID NO: 4894 | mm45081_Sil1 | TGTTCCACCCAACTCAAGAG |
| SEQ ID NO: 4895 | mm45082_Sil1 | AGCAGCATACTCCTTCACCA |
| SEQ ID NO: 4896 | mm45083_Sil1 | CAAGGAAAAACAATACCTGA |
| SEQ ID NO: 4897 | mm45116_Sorcs2 | GGGAATAGCGAACCCCACGC |
| SEQ ID NO: 4898 | mm45117_Sorcs2 | GTACCGTGCCTGACACATAG |
| SEQ ID NO: 4899 | mm45118_Sorcs2 | GTAGGTTGTCCCAAAATCTG |
| SEQ ID NO: 4900 | mm45119_Sorcs2 | CAACCCATCCACGAACACTG |
| SEQ ID NO: 4901 | mm45140_Cacng7 | GCCGCAGAACCAGACCACCG |
| SEQ ID NO: 4902 | mm45141_Cacng7 | ACTTTCACTATCGCTACGGG |
| SEQ ID NO: 4903 | mm45142_Cacng7 | TCGGCCACATCCGACCTCAG |
| SEQ ID NO: 4904 | mm45143_Cacng7 | CATCTCCAGCATCAACGACG |
| SEQ ID NO: 4905 | mm45144_Cacng8 | GATGACGGACCACCCCATCG |
| SEQ ID NO: 4906 | mm45145_Cacng8 | GTGTACATATCGGCCAACGC |
| SEQ ID NO: 4907 | mm45146_Cacng8 | AGCCGCGAAGGCGCCGATGG |
| SEQ ID NO: 4908 | mm45147_Cacng8 | GGACTACGACCACGACAGCG |
| SEQ ID NO: 4909 | mm45152_Tmem108 | GAAGAGAAGTAGCCCCCGAG |

TABLE 1-continued mmSurf sgRNA library sequences

| SEQ ID NO | id_gRNA Target | Sequence |
|---|---|---|
| SEQ ID NO: 4910 | mm45153_Tmem108 | ACTCTCACACCCGTACCGGG |
| SEQ ID NO: 4911 | mm45154_Tmem108 | GGCTTTATCAGATCCAACCA |
| SEQ ID NO: 4912 | mm45155_Tmem108 | AGGGTCTGTAGAGATTCCCT |
| SEQ ID NO: 4913 | mm45172_Siglece | GACCAGCTTAGGTTCGCAGG |
| SEQ ID NO: 4914 | mm45173_Siglece | CATGTGGGACAAGATGACTC |
| SEQ ID NO: 4915 | mm45174_Siglece | TGTACCAGAATCCATGAACT |
| SEQ ID NO: 4916 | mm45175_Siglece | CCTCACATGACACGTTGAGA |
| SEQ ID NO: 4917 | mm45212_Ctns | AGGCATCATTACTGTCGACG |
| SEQ ID NO: 4918 | mm45213_Ctns | TGGAGGGCCATGACACACGC |
| SEQ ID NO: 4919 | mm45214_Ctns | TAACAGGTTATAGTGCCTCG |
| SEQ ID NO: 4920 | mm45215_Ctns | CCCAAGGGTGATGTCGACGT |
| SEQ ID NO: 4921 | mm45224_Trem2 | TATGACGCCTTGAAGCACTG |
| SEQ ID NO: 4922 | mm45225_Trem2 | CGAAACTCGATGACTCCTCG |
| SEQ ID NO: 4923 | mm45226_Trem2 | TACCAGTGTCAGAGTCTCCG |
| SEQ ID NO: 4924 | mm45227_Trem2 | ACTCTGAAGAACCTCCAAGC |
| SEQ ID NO: 4925 | mm45240_Chrdl1 | TGTTTGGTGGAGGATCGTAG |
| SEQ ID NO: 4926 | mm45241_Chrdl1 | CAGGGGATGCAGAATTATCG |
| SEQ ID NO: 4927 | mm45242_Chrdl1 | TCAAGACAAGAAGTATAGAG |
| SEQ ID NO: 4928 | mm45243_Chrdl1 | AGCAAGTCATGCGAATACAA |
| SEQ ID NO: 4929 | mm45328_Elovl4 | TTCATGGGATCATACAACGC |
| SEQ ID NO: 4930 | mm45329_Elovl4 | ACACCGTGGAGTTCTATCGC |
| SEQ ID NO: 4931 | mm45330_Elovl4 | TGCAGTGGTGGTACACGTGA |
| SEQ ID NO: 4932 | mm45331_Elovl4 | CGATACAAAATACCACCACA |
| SEQ ID NO: 4933 | mm45372_Slc12a9 | TAGATGCCGATCAACACGAG |
| SEQ ID NO: 4934 | mm45373_Slc12a9 | GCCATGCCGGTGTGGCACGG |
| SEQ ID NO: 4935 | mm45374_Slc12a9 | GCTCTTCTCACCGCACGAGG |
| SEQ ID NO: 4936 | mm45375_Slc12a9 | AAACACGACTATGCTAAACA |
| SEQ ID NO: 4937 | mm45424_Tmem2 | ACCATTGGCTTCGACACACT |
| SEQ ID NO: 4938 | mm45425_Tmem2 | TTGTCGCTTTGGATCTATAG |
| SEQ ID NO: 4939 | mm45426_Tmem2 | GGAAGCTGGAGACCGAATTG |
| SEQ ID NO: 4940 | mm45427_Tmem2 | GATTTGCAGATAACGGAAAG |
| SEQ ID NO: 4941 | mm45452_Jam3 | TTCAGCCATCTATCGCTGTG |
| SEQ ID NO: 4942 | mm45453_Jam3 | TTGCGGTACCAGCTGTAGTG |
| SEQ ID NO: 4943 | mm45454_Jam3 | TTTCAAATTCATGTACCACT |
| SEQ ID NO: 4944 | mm45455_Jam3 | GAATGGAAGAAAATCCAAGA |
| SEQ ID NO: 4945 | mm45456_Enpp5 | AATAGGTCGGGAAACTATCG |
| SEQ ID NO: 4946 | mm45457_Enpp5 | TGGGAAGAACCCGATGACAC |
| SEQ ID NO: 4947 | mm45458_Enpp5 | TCATCGTCACGAGCGACCAT |

TABLE 1-continued mmSurf sgRNA library sequences

| SEQ ID NO | id_gRNA Target | Sequence |
|---|---|---|
| SEQ ID NO: 4948 | mm45459_Enpp5 | CGTTAGATTAGGATGGGCAC |
| SEQ ID NO: 4949 | mm45480_Mcam | CCTGCCGAAAAGCACCATAG |
| SEQ ID NO: 4950 | mm45481_Mcam | ACTATTCAAGCCAATGTCGT |
| SEQ ID NO: 4951 | mm45482_Mcam | AGGAACATTCGCTCATCATG |
| SEQ ID NO: 4952 | mm45483_Mcam | CCACATGAAGGAATCTAAGG |
| SEQ ID NO: 4953 | mm45496_Plvap | CGGACGTGCTGAGTGCGTGG |
| SEQ ID NO: 4954 | mm45497_Plvap | GCTGTCGGCGCGGATCTCCG |
| SEQ ID NO: 4955 | mm45498_Plvap | CGGAGTACGCGTCCCTCCGT |
| SEQ ID NO: 4956 | mm45499_Plvap | CCTGTGGCAAAGCACGCGAA |
| SEQ ID NO: 4957 | mm45528_Cd96 | AGTGGGTAGATGTTTCGTTG |
| SEQ ID NO: 4958 | mm45529_Cd96 | CCAGTCCAAATCCAAGACGA |
| SEQ ID NO: 4959 | mm45530_Cd96 | CCACAGTAGAGGCCATATTG |
| SEQ ID NO: 4960 | mm45531_Cd96 | TACAGTCTACAACCTCATTG |
| SEQ ID NO: 4961 | mm45576_Cd163 | ACCTGTCCTTCGGAACACGT |
| SEQ ID NO: 4962 | mm45577_Cd163 | GTACAAGTTCTGTCTAGCGG |
| SEQ ID NO: 4963 | mm45578_Cd163 | CTCTGGGACTGCAAACACCG |
| SEQ ID NO: 4964 | mm45579_Cd163 | AAACTGGGGCAACAAATACG |
| SEQ ID NO: 4965 | mm45592_Clec2i | GGGCAAATGTCCAGTTACGT |
| SEQ ID NO: 4966 | mm45593_Clec2i | TGCACACCTCCAGTTCCAAG |
| SEQ ID NO: 4967 | mm45594_Clec2i | GCTTGCTCAAAAAACTGGAC |
| SEQ ID NO: 4968 | mm45595_Clec2i | AGCTCGGTTTGACAACGAGG |
| SEQ ID NO: 4969 | mm45608_Glce | AGGACATAAACACACCGTCA |
| SEQ ID NO: 4970 | mm45609_Glce | CTTGAGTAGTGGATTCAGAG |
| SEQ ID NO: 4971 | mm45610_Glce | GGGGGCTTCAATAGCAACGG |
| SEQ ID NO: 4972 | mm45611_Glce | TCTCTACCCAAGTGAATGGA |
| SEQ ID NO: 4973 | mm45616_Entpd7 | TCTGAATTATGGACTCGTGG |
| SEQ ID NO: 4974 | mm45617_Entpd7 | AGATAGCCAACTGTTGCCTG |
| SEQ ID NO: 4975 | mm45618_Entpd7 | CCTGTCCCGTGGTAACGAAG |
| SEQ ID NO: 4976 | mm45619_Entpd7 | GTGGTTAAGAAAATAAAGCC |
| SEQ ID NO: 4977 | mm45648_Clec2d | AAGCTTAGCACAAGACTCAG |
| SEQ ID NO: 4978 | mm45649_Clec2d | GGGCGAATGTCCAGTTACTT |
| SEQ ID NO: 4979 | mm45650_Clec2d | ACTAGCTCGGTTTGACAACC |
| SEQ ID NO: 4980 | mm45651_Clec2d | TTACCCACTTCTACCTCCTG |
| SEQ ID NO: 4981 | mm45652_Gpnmb | AGAGAGCACAACCAATTACG |
| SEQ ID NO: 4982 | mm45653_Gpnmb | TCCATGGATTTGTAACCAGT |
| SEQ ID NO: 4983 | mm45654_Gpnmb | GGCATACATTCCCATCTCGA |
| SEQ ID NO: 4984 | mm45655_Gpnmb | AGGAAATGGCAGAGTCGTTG |
| SEQ ID NO: 4985 | mm45856_Igsf9 | CAATGCAGAAGTACCCCCCG |

TABLE 1-continued mmSurf sgRNA library sequences

| SEQ ID NO | id_gRNA Target | Sequence |
|---|---|---|
| SEQ ID NO: 4986 | mm45857_Igsf9 | ACTGACGTAGCTATCAGCGA |
| SEQ ID NO: 4987 | mm45858_Igsf9 | ACGTAATCGGGGTCAATTCG |
| SEQ ID NO: 4988 | mm45859_Igsf9 | GGGCTGGTCTATAAAAGCCG |
| SEQ ID NO: 4989 | mm45960_Fzd10 | GGGTCACGAGAACCAGCGCG |
| SEQ ID NO: 4990 | mm45961_Fzd10 | GGAAGATGATAGGACGTTCG |
| SEQ ID NO: 4991 | mm45962_Fzd10 | GGTACTTTACTACTTCGGCA |
| SEQ ID NO: 4992 | mm45963_Fzd10 | GAGCACCCACTAAAGGACGG |
| SEQ ID NO: 4993 | mm45984_Tm2d1 | GGCGACCGTCACGAGCCACA |
| SEQ ID NO: 4994 | mm45985_Tm2d1 | GAGGATATTGTCCCACCCTG |
| SEQ ID NO: 4995 | mm45986_Tm2d1 | TGTACAAACTACACAGCTCA |
| SEQ ID NO: 4996 | mm45987_Tm2d1 | ATAACTTGTAAGGATTTGAG |
| SEQ ID NO: 4997 | mm46060_Csmd1 | GTACTTACCAATGCACAAAG |
| SEQ ID NO: 4998 | mm46061_Csmd1 | GTCACACACTCAATGGACGA |
| SEQ ID NO: 4999 | mm46062_Csmd1 | CGAACTGAAACCCAATTCTG |
| SEQ ID NO: 5000 | mm46063_Csmd1 | GTGGTACTCTCCTATGAGTG |
| SEQ ID NO: 5001 | mm46076_Mcoln1 | GACATAGGCATACCGGCCCA |
| SEQ ID NO: 5002 | mm46077_Mcoln1 | TTTGACAATAAAGCGCACAG |
| SEQ ID NO: 5003 | mm46078_Mcoln1 | ATACCTTTGACATTGATCCA |
| SEQ ID NO: 5004 | mm46079_Mcoln1 | TGGCCCGGAACTTGTCACAT |
| SEQ ID NO: 5005 | mm46128_Spock2 | AGACGCAGTAGACTGCTCCG |
| SEQ ID NO: 5006 | mm46129_Spock2 | TCTGCTTGGAGTTCTCACGA |
| SEQ ID NO: 5007 | mm46130_Spock2 | ACAGCGGCAAGATTAAGCAC |
| SEQ ID NO: 5008 | mm46131_Spock2 | AGAGCTGTAGGTATGGCCGT |
| SEQ ID NO: 5009 | mm46136_Lrp1b | AAGACGTTCTGAGATCCGAG |
| SEQ ID NO: 5010 | mm46137_Lrp1b | GTGGGAGTAGTAGACTACCA |
| SEQ ID NO: 5011 | mm46138_Lrp1b | ACACAGCGACGATTGTAGCA |
| SEQ ID NO: 5012 | mm46139_Lrp1b | TATGATCCACGAAAACAACA |
| SEQ ID NO: 5013 | mm46144_Cnnm2 | ACCGTCGTGGTAAATCCAGG |
| SEQ ID NO: 5014 | mm46145_Cnnm2 | CGGCGATTGAGAATGATGTG |
| SEQ ID NO: 5015 | mm46146_Cnnm2 | TGCTAACCGGATAAGAAGCG |
| SEQ ID NO: 5016 | mm46147_Cnnm2 | CTGCTTCATGATAACCGGCG |
| SEQ ID NO: 5017 | mm46148_Cnnm4 | AGAGCGTGATCCTAGGCATG |
| SEQ ID NO: 5018 | mm46149_Cnnm4 | CCATGATGCCAGACCCGATG |
| SEQ ID NO: 5019 | mm46150_Cnnm4 | GAAAACAAAATGTACCGGG |
| SEQ ID NO: 5020 | mm46151_Cnnm4 | GCATCCCCGACGTGTTCCCG |
| SEQ ID NO: 5021 | mm46176_Slc4a10 | AGAGAACATCTGGCACGTAG |
| SEQ ID NO: 5022 | mm46177_Slc4a10 | CACGATGCCTGTGACGACGA |
| SEQ ID NO: 5023 | mm46178_Slc4a10 | TGAGATTTGCTGGCGTGAAG |

TABLE 1-continued mmSurf sgRNA library sequences

| SEQ ID NO | id_gRNA Target | Sequence |
|---|---|---|
| SEQ ID NO: 5024 | mm46179_Slc4a10 | TTCCTGATACCAAGTCATTG |
| SEQ ID NO: 5025 | mm46204_Slc24a3 | AATCCCAATTAAGCACACAG |
| SEQ ID NO: 5026 | mm46205_Slc24a3 | GGCCCCAGAGCTGTTCACGT |
| SEQ ID NO: 5027 | mm46206_Slc24a3 | CAGCAACTGCGATGCCACTG |
| SEQ ID NO: 5028 | mm46207_Slc24a3 | TCCAATGAAGACCGACGACA |
| SEQ ID NO: 5029 | mm46244_Cadm3 | CTGGTTATAAGTCATCATTG |
| SEQ ID NO: 5030 | mm46245_Cadm3 | CTGAATCCGATTATCTCGAA |
| SEQ ID NO: 5031 | mm46246_Cadm3 | AGCTGTTGTTACATTGTGAG |
| SEQ ID NO: 5032 | mm46247_Cadm3 | GACATCTGATGAAACAGTTG |
| SEQ ID NO: 5033 | mm46252_Loxl2 | ACAGAGCCTAAATATACAGG |
| SEQ ID NO: 5034 | mm46253_Loxl2 | TACTGGCAAAGAGTCGACCC |
| SEQ ID NO: 5035 | mm46254_Lox12 | GGAACCTTGAGGGTCCATCG |
| SEQ ID NO: 5036 | mm46255_Lox12 | GGGGATGTTGCATCGCACCC |
| SEQ ID NO: 5037 | mm46260_Prg4 | GCCTGAACCTACAACCCCCA |
| SEQ ID NO: 5038 | mm46261_Prg4 | TCAGAATTAGGTGCAAGACT |
| SEQ ID NO: 5039 | mm46262_Prg4 | GCCTGAACCCACAACTCCCA |
| SEQ ID NO: 5040 | mm46263_Prg4 | TCGAGTCCTTCGCTCGAGGG |
| SEQ ID NO: 5041 | mm46268_Tmem62 | GCCAAAACAAAGGAACACTT |
| SEQ ID NO: 5042 | mm46269_Tmem62 | TCAGCCCACCAAGCGTATGG |
| SEQ ID NO: 5043 | mm46270_Tmem62 | GAATGGAAGAGCCTTTCTAG |
| SEQ ID NO: 5044 | mm46271_Tmem62 | GAAGCCAACAACATCTTCTG |
| SEQ ID NO: 5045 | mm46396_Tmem132a | AGCCGCACCGGAATACGCTG |
| SEQ ID NO: 5046 | mm46397_Tmem132a | GGTCTAACTTAGCAGTCCAG |
| SEQ ID NO: 5047 | mm46398_Tmem132a | TATGCGAGGATCTTGCACAT |
| SEQ ID NO: 5048 | mm46399_Tmem132a | ACCACTCTGGAACAAATCCG |
| SEQ ID NO: 5049 | mm46436_Slamf9 | GCAGTGGATCCTCGATACCG |
| SEQ ID NO: 5050 | mm46437_Slamf9 | GATGGTAAGACTTCGTGATG |
| SEQ ID NO: 5051 | mm46438_Slamf9 | AGCACTAACACATCCCATGA |
| SEQ ID NO: 5052 | mm46439_Slamf9 | TTAGAGTTCACAGTGATGTG |
| SEQ ID NO: 5053 | mm46572_Nat10 | GTCAATCCGATACGCCCCTG |
| SEQ ID NO: 5054 | mm46573_Nat10 | TCACCGCTTTATTAAACTCG |
| SEQ ID NO: 5055 | mm46574_Nat10 | TGGTGGGAAGATTTAACGAG |
| SEQ ID NO: 5056 | mm46575_Nat10 | TGTTCACCCAGATTATCAAG |
| SEQ ID NO: 5057 | mm46632_Tm9sf4 | GAGTTCATGTACCCTACCCG |
| SEQ ID NO: 5058 | mm46633_Tm9sf4 | TCCGGATGATAATCATGCTG |
| SEQ ID NO: 5059 | mm46634_Tm9sf4 | ACCGAACTCTAAAAGGCCAT |
| SEQ ID NO: 5060 | mm46635_Tm9sf4 | TGGCTTCACGGATGTCAACA |
| SEQ ID NO: 5061 | mm46696_Fgg | TTAGTGTACTGTGAAATCGA |

TABLE 1-continued mmSurf sgRNA library sequences

| SEQ ID NO | id_gRNA Target | Sequence |
|---|---|---|
| SEQ ID NO: 5062 | mm46697_Fgg | TAACCCACGAGACAAGCATT |
| SEQ ID NO: 5063 | mm46698_Fgg | TGTCAGGAAATTGCCAACAA |
| SEQ ID NO: 5064 | mm46699_Fgg | ATTTCCCAGCCAAAACTCTG |
| SEQ ID NO: 5065 | mm46744_Kcnc4 | GTGACGGAGATTCATCGGGT |
| SEQ ID NO: 5066 | mm46745_Kcnc4 | CTATTATGCCGAGCGAATTG |
| SEQ ID NO: 5067 | mm46746_Kcnc4 | AGCATCGCGGTGCTGCCGGT |
| SEQ ID NO: 5068 | mm46747_Kcnc4 | GTACAAAGCGTACCACACGC |
| SEQ ID NO: 5069 | mm46808_Pcsk9 | GCTGCCAGGAACCTACATTG |
| SEQ ID NO: 5070 | mm46809_Pcsk9 | TGGAGCGAATTATCCCAGCA |
| SEQ ID NO: 5071 | mm46810_Pcsk9 | AGGACCAGCCAGTTACCTTG |
| SEQ ID NO: 5072 | mm46811_Pcsk9 | CATGCTTCATGTCACAGAGT |
| SEQ ID NO: 5073 | mm46868_Smpdl3b | CAACCGCATCTATAACCAGG |
| SEQ ID NO: 5074 | mm46869_Smpdl3b | GCCACCGGAACTGCTCGCCG |
| SEQ ID NO: 5075 | mm46870_Smpdl3b | TTATTGGCCACGTGCCCCCG |
| SEQ ID NO: 5076 | mm46871_Smpdl3b | AGCACCATCGGGTCATAGCA |
| SEQ ID NO: 5077 | mm46880_Slc44a1 | CTGGAAGCAATACCGAACAG |
| SEQ ID NO: 5078 | mm46881_Slc44a1 | GTACATGTGGTGGTACCACG |
| SEQ ID NO: 5079 | mm46882_Slc44a1 | GTGGCACGGGTGTATTATGG |
| SEQ ID NO: 5080 | mm46883_Slc44a1 | CACCATCGCCTTGTTCCACG |
| SEQ ID NO: 5081 | mm46916_Slc15a4 | GCGTGGAGGGCCGTTCACAG |
| SEQ ID NO: 5082 | mm46917_Slc15a4 | GACACGACGCTGACCCGTTG |
| SEQ ID NO: 5083 | mm46918_Slc15a4 | TATCACCACCACCCATCACA |
| SEQ ID NO: 5084 | mm46919_Slc15a4 | CCAATTGAAAATCTCCGAG |
| SEQ ID NO: 5085 | mm46920_Lrrc8c | AGTGGACCCCGGACAAACTG |
| SEQ ID NO: 5086 | mm46921_Lrrc8c | TGGTTGACAAATCTGCTGCG |
| SEQ ID NO: 5087 | mm46922_Lrrc8c | CTCCTGCCGGACATACTCGA |
| SEQ ID NO: 5088 | mm46923_Lrrc8c | AGACATTGGGAACGGAAGAG |
| SEQ ID NO: 5089 | mm47008_Emilin1 | ATGATACTTCGGGAACAGTG |
| SEQ ID NO: 5090 | mm47009_Emilin1 | TGCCCATTGTTACCTCCACG |
| SEQ ID NO: 5091 | mm47010_Emilin1 | ACAGTGCTAAGTGGACGCAG |
| SEQ ID NO: 5092 | mm47011_Emilin1 | GAGGGCCGGTTACAGCTAGT |
| SEQ ID NO: 5093 | mm47068_Hepacam2 | GTGGACAGTGTATGACGGCA |
| SEQ ID NO: 5094 | mm47069_Hepacam2 | TGAGGGCAATTACATCGTGA |
| SEQ ID NO: 5095 | mm47070_Hepacam2 | AGGCTCCGTTAATAAGTCTG |
| SEQ ID NO: 5096 | mm47071_Hepacam2 | AGTTACTTACAATATATGGT |
| SEQ ID NO: 5097 | mm47208_Ano1 | GGAGCGTCGAGTACTTCTCG |
| SEQ ID NO: 5098 | mm47209_Ano1 | GAAGAGAACAACGTGCACCA |
| SEQ ID NO: 5099 | mm47210_Ano1 | GATGAGGCTCAACTACCGAT |

TABLE 1-continued mmSurf sgRNA library sequences

| SEQ ID NO | id_gRNA Target | Sequence |
|---|---|---|
| SEQ ID NO: 5100 | mm47211_Ano1 | TGACAAACGCTTCAGACGGG |
| SEQ ID NO: 5101 | mm47412_Cd276 | CGCGTCCGAGTAACCGACGA |
| SEQ ID NO: 5102 | mm47413_Cd276 | ATCACGTGCTCTAGCTACCA |
| SEQ ID NO: 5103 | mm47414_Cd276 | ATCGAACAAGCCCCGCTCGT |
| SEQ ID NO: 5104 | mm47415_Cd276 | AGCTGTGCCAGACTGAAGCC |
| SEQ ID NO: 5105 | mm47432_Slc6a8 | GGAAGCGCCACACGTTACCG |
| SEQ ID NO: 5106 | mm47433_Slc6a8 | GCATCAGTGTGACAGCCCGT |
| SEQ ID NO: 5107 | mm47434_Slc6a8 | GCACAACGAGGACCACGTAG |
| SEQ ID NO: 5108 | mm47435_Slc6a8 | ACTCGATGACAGGGGACCGG |
| SEQ ID NO: 5109 | mm47456_Slc6a15 | TTCCCGGTACCAGTAATAGG |
| SEQ ID NO: 5110 | mm47457_Slc6a15 | GAAACATATAAGGACCACGT |
| SEQ ID NO: 5111 | mm47458_Slc6a15 | TTGTTCCAAACATGCTGCCG |
| SEQ ID NO: 5112 | mm47459_Slc6a15 | ACATAAGCCCTAAATTGGGT |
| SEQ ID NO: 5113 | mm47520_Ncln | GTAATGAGCCACGATGACAA |
| SEQ ID NO: 5114 | mm47521_Ncln | GGGGGCAAGTTCAACTACCA |
| SEQ ID NO: 5115 | mm47522_Ncln | GGAGCCGCATAAGCACGCAG |
| SEQ ID NO: 5116 | mm47523_Ncln | GTACACGGTGAACTCGTGCG |
| SEQ ID NO: 5117 | mm47536_Mgat4b | CCACGCCCATACCTCCGGTG |
| SEQ ID NO: 5118 | mm47537_Mgat4b | TCTGCGAGACCGTTTGCACG |
| SEQ ID NO: 5119 | mm47538_Mgat4b | TCATGAGGAAGCAGTAATCG |
| SEQ ID NO: 5120 | mm47539_Mgat4b | GAAGGAAGACTCAGTCATCG |
| SEQ ID NO: 5121 | mm47568_Tmed4 | GCTTCTCAGTCTCGCCGATG |
| SEQ ID NO: 5122 | mm47569_Tmed4 | TATCCTTAGCAGCGATCTCG |
| SEQ ID NO: 5123 | mm47570_Tmed4 | CAACTATCGAACTCAGATGT |
| SEQ ID NO: 5124 | mm47571_Tmed4 | AGAATGGCTCTCTTCGCTGG |
| SEQ ID NO: 5125 | mm47640_Rpn1 | TCTCCCGCTACGATTACCAG |
| SEQ ID NO: 5126 | mm47641_Rpn1 | CGAGGACGTGAAGCGCACGG |
| SEQ ID NO: 5127 | mm47642_Rpn1 | TCACTTGCTCATCAAACACG |
| SEQ ID NO: 5128 | mm47643_Rpn1 | GTGAGATACCTCGATGACCC |
| SEQ ID NO: 5129 | mm47720_Acly | GAGAGAGATTGACCCCGACG |
| SEQ ID NO: 5130 | mm47721_Acly | AGAGCGATTCGAGATTACCA |
| SEQ ID NO: 5131 | mm47722_Acly | TTGTCACCTGTACACGACGG |
| SEQ ID NO: 5132 | mm47723_Acly | GGACGAAAAGCTGAATACCG |
| SEQ ID NO: 5133 | mm47896_Pld4 | GATGGGCGACACATCTACGT |
| SEQ ID NO: 5134 | mm47897_Pld4 | AGTGAGGGACCAGTAGTACG |
| SEQ ID NO: 5135 | mm47898_Pld4 | CAGTCATCGGATGTTCCCTG |
| SEQ ID NO: 5136 | mm47899_Pld4 | GCTATGTGGATCATGAGATG |
| SEQ ID NO: 5137 | mm48012_Epdr1 | GATCCCAGGATTCCACCAAG |

TABLE 1-continued mmSurf sgRNA library sequences

| SEQ ID NO | id_gRNA Target | Sequence |
|---|---|---|
| SEQ ID NO: 5138 | mm48013_Epdr1 | AAGATCAGTACTCCATCGGA |
| SEQ ID NO: 5139 | mm48014_Epdr1 | GCTGATCCCTGCAAGAGGT |
| SEQ ID NO: 5140 | mm48015_Epdr1 | GCGCTGGTTGAGACCATCGT |
| SEQ ID NO: 5141 | mm48016_Golm1 | GAATGTCAACAAGCTACACC |
| SEQ ID NO: 5142 | mm48017_Golm1 | GATTGCTAGCTCGAGAAGCG |
| SEQ ID NO: 5143 | mm48018_Golm1 | GTGTGACGAGCGGATAGAGG |
| SEQ ID NO: 5144 | mm48019_Golm1 | ACAGATGCCACAAGAGAAAG |
| SEQ ID NO: 5145 | mm48132_Ano6 | GGTGATAAACGAGATCACTC |
| SEQ ID NO: 5146 | mm48133_Ano6 | CAGATTCAACTATGAGTCGG |
| SEQ ID NO: 5147 | mm48134_Ano6 | TGAAGAAGGAATCTCTATCG |
| SEQ ID NO: 5148 | mm48135_Ano6 | CAAATTCGTGGGCTATCCCG |
| SEQ ID NO: 5149 | mm48136_Slc38a1 | ATACTTTGGTGTGCACGCGT |
| SEQ ID NO: 5150 | mm48137_Slc38a1 | TGCATGGTGTATGAGAAGCT |
| SEQ ID NO: 5151 | mm48138_Slc38a1 | TCACCATCACCACCAACACT |
| SEQ ID NO: 5152 | mm48139_Slc38a1 | AGATTGGCAGGACGGACGGG |
| SEQ ID NO: 5153 | mm48184_Lmf2 | AGAAGGCAGTAAGTCGTAGG |
| SEQ ID NO: 5154 | mm48185_Lmf2 | CAGAATGGGAGGTCTTCATG |
| SEQ ID NO: 5155 | mm48186_Lmf2 | GCAGGCACTGAGTCTCATAG |
| SEQ ID NO: 5156 | mm48187_Lmf2 | CTGGGGCTGGATACTGCCCA |
| SEQ ID NO: 5157 | mm48240_Slc45a4 | AGGTCGCTCATGCTTCGGGA |
| SEQ ID NO: 5158 | mm48241_Slc45a4 | CGTAGCCAATGGCCCCACCA |
| SEQ ID NO: 5159 | mm48242_Slc45a4 | GCATGACCCATAGGCGTGTG |
| SEQ ID NO: 5160 | mm48243_Slc45a4 | GGAAAAGTGCAACACCAATG |
| SEQ ID NO: 5161 | mm48252_Txndc11 | TGTTGCAGGACCATATCCCG |
| SEQ ID NO: 5162 | mm48253_Txndc11 | TTTGGACCAATCGAATACAA |
| SEQ ID NO: 5163 | mm48254_Txndc11 | GGAATACAATAACTGTCATG |
| SEQ ID NO: 5164 | mm48255_Txndc11 | CTAAGGATACCAGTCTCGCA |
| SEQ ID NO: 5165 | mm48332_Itfg3 | AAAGGAAAAATGCCACTGTG |
| SEQ ID NO: 5166 | mm48333_Itfg3 | CTGTCCATCCAGCAACACGC |
| SEQ ID NO: 5167 | mm48334_Itfg3 | GCAGCATCCAACATACCACA |
| SEQ ID NO: 5168 | mm48335_Itfg3 | TGGCATGGCACACTTTACAA |
| SEQ ID NO: 5169 | mm48444_Slc39a6 | CGTGGTCCGAGTGATGCTCG |
| SEQ ID NO: 5170 | mm48445_Slc39a6 | AGGAATCATTCTCTCCGTAG |
| SEQ ID NO: 5171 | mm48446_Slc39a6 | CAGCCACGGAACTTACGTGT |
| SEQ ID NO: 5172 | mm48447_Slc39a6 | GACAGCGTTGTATACCGCCG |
| SEQ ID NO: 5173 | mm48552_Tm9sf3 | GGAAGTCTGTATGCTAGACA |
| SEQ ID NO: 5174 | mm48553_Tm9sf3 | GATGTTAATCTAACTAGTGA |
| SEQ ID NO: 5175 | mm48554_Tm9sf3 | ACGAGCACGAACACACGGTG |

TABLE 1-continued mmSurf sgRNA library sequences

| SEQ ID NO | id_gRNA Target | Sequence |
|---|---|---|
| SEQ ID NO: 5176 | mm48555_Tm9sf3 | ATAGATGACTTACCAATATG |
| SEQ ID NO: 5177 | mm48580_Unc5a | CTGCGTGGCCAAGAACATCG |
| SEQ ID NO: 5178 | mm48581_Unc5a | TCTCGTAGATCTTTCCTCGG |
| SEQ ID NO: 5179 | mm48582_Unc5a | AACCCGGCACCTCTCAACGG |
| SEQ ID NO: 5180 | mm48583_Unc5a | AGCAGGATTGCCAACCATGG |
| SEQ ID NO: 5181 | mm48584_Unc5b | GCAGGGGCGAATTAGTCATG |
| SEQ ID NO: 5182 | mm48585_Unc5b | CACACCATAGACGATGACTG |
| SEQ ID NO: 5183 | mm48586_Unc5b | GGAGGAACTCTTCGGGCTCG |
| SEQ ID NO: 5184 | mm48587_Unc5b | CCTGTATCTACATATCAACA |
| SEQ ID NO: 5185 | mm48600_Eprs | GACAGTCAGATTCCCCCCAG |
| SEQ ID NO: 5186 | mm48601_Eprs | ATGGTCACATTTATAAACTG |
| SEQ ID NO: 5187 | mm48602_Eprs | CAATAAAGTCGCTGCCCAAG |
| SEQ ID NO: 5188 | mm48603_Eprs | CCACGAACTGTAGGAAACCG |
| SEQ ID NO: 5189 | mm48604_Ssr1 | GTCCTGAGGATAACGGAACG |
| SEQ ID NO: 5190 | mm48605_Ssr1 | ACACTGTAGTGCCACCCCAG |
| SEQ ID NO: 5191 | mm48606_Ssr1 | CCAAGGGTCGTCCTCCCAT |
| SEQ ID NO: 5192 | mm48607_Ssr1 | GCCGCCTCGGAGCAGCACGG |
| SEQ ID NO: 5193 | mm48608_Lgr4 | CTGATTCGTGAAATTCACAG |
| SEQ ID NO: 5194 | mm48609_Lgr4 | ACAGCACTACCAAGCTTGAA |
| SEQ ID NO: 5195 | mm48610_Lgr4 | CCATATTACCTCAGTCCCGG |
| SEQ ID NO: 5196 | mm48611_Lgr4 | AAGCCCTGTGAATATTTACT |
| SEQ ID NO: 5197 | mm48612_Ece2 | TCGGTGGTTGGAACATAACG |
| SEQ ID NO: 5198 | mm48613_Ece2 | TTTAGGTAGTAATCTCGAGA |
| SEQ ID NO: 5199 | mm48614_Ece2 | TACTGGAGAGTAATCCACAC |
| SEQ ID NO: 5200 | mm48615_Ece2 | CCACCTTCTTGGTACCGTAG |
| SEQ ID NO: 5201 | mm48640_Col16a1 | TGATGCAAATGGGTACCCAC |
| SEQ ID NO: 5202 | mm48641_Col16a1 | GGAGGAACCTCAGAACAGCA |
| SEQ ID NO: 5203 | mm48642_Col16a1 | GTATCGCCAAAACTACCCTG |
| SEQ ID NO: 5204 | mm48643_Col16a1 | CATCGAGAAACACCTCCTCA |
| SEQ ID NO: 5205 | mm48656_Mylk | GAAGCCAAAGACCATATCCG |
| SEQ ID NO: 5206 | mm48657_Mylk | GGTATACCAAAGCCTGACGT |
| SEQ ID NO: 5207 | mm48658_Mylk | CTGCACGTTCTTTAGAACCA |
| SEQ ID NO: 5208 | mm48659_Mylk | TGTCATCCACACTGTCCGCG |
| SEQ ID NO: 5209 | mm48680_Snrpd2 | CCCCATCAGGCACTGCAACA |
| SEQ ID NO: 5210 | mm48681_Snrpd2 | GACTGCGTGAGCACTGAGAG |
| SEQ ID NO: 5211 | mm48682_Snrpd2 | CAAGAGTGAGATGACCCCAG |
| SEQ ID NO: 5212 | mm48683_Snrpd2 | TGTGAAGGAGATGTGGACTG |
| SEQ ID NO: 5213 | mm48692_Slc12a6 | AATCCCCAGGATGTTACGGA |

TABLE 1-continued mmSurf sgRNA library sequences

| SEQ ID NO | id_gRNA Target | Sequence |
|---|---|---|
| SEQ ID NO: 5214 | mm48693_Slc12a6 | AACTATACAAATCTGACACA |
| SEQ ID NO: 5215 | mm48694_Slc12a6 | AATGGGGGATGGTATCCGT |
| SEQ ID NO: 5216 | mm48695_Slc12a6 | CAAGATCGACACAATTACAC |
| SEQ ID NO: 5217 | mm48784_Mgat5 | GGTACTGGAGCCATAAACAG |
| SEQ ID NO: 5218 | mm48785_Mgat5 | GTCGCTTGAGAAAATTAATG |
| SEQ ID NO: 5219 | mm48786_Mgat5 | CCTTAATGTACCTCTTGCTG |
| SEQ ID NO: 5220 | mm48787_Mgat5 | TTTGCTCTCCAAGGTAAACG |
| SEQ ID NO: 5221 | mm48792_Celsr3 | GAGTTCCACTATCGACCGAG |
| SEQ ID NO: 5222 | mm48793_Celsr3 | GTGCTGATAAGACCCGAACG |
| SEQ ID NO: 5223 | mm48794_Celsr3 | GTACCACCTTCGGCTCAATG |
| SEQ ID NO: 5224 | mm48795_Celsr3 | AAAGTAAAACAGCTCCACGT |
| SEQ ID NO: 5225 | mm48896_Grm3 | CTCACGGATCACGCTGTCGT |
| SEQ ID NO: 5226 | mm48897_Grm3 | GGTATTCATAGGGCTCACAT |
| SEQ ID NO: 5227 | mm48898_Grm3 | CAGAGGTATCCAACGCCTGG |
| SEQ ID NO: 5228 | mm48899_Grm3 | TGACTCCTGCAATGAGTAGT |
| SEQ ID NO: 5229 | mm48900_Grm5 | TAGTCATGCATTATATCCGG |
| SEQ ID NO: 5230 | mm48901_Grm5 | GTACCTGTCAAGTCGTCAGT |
| SEQ ID NO: 5231 | mm48902_Grm5 | GACCGATGCCAATTCTCTGA |
| SEQ ID NO: 5232 | mm48903_Grm5 | AAATGGATGATGATGAAGTG |
| SEQ ID NO: 5233 | mm48908_Grm7 | TCCGTTGGTGCAACGCACGT |
| SEQ ID NO: 5234 | mm48909_Grm7 | TGATACTGGTATCCATCACA |
| SEQ ID NO: 5235 | mm48910_Grm7 | CCAACCTAAGAGAGCGACTG |
| SEQ ID NO: 5236 | mm48911_Grm7 | GCCCTGCGGCGACATCAAGA |
| SEQ ID NO: 5237 | mm48912_Ltbp4 | ATTGACGAGTGTCGTGAACG |
| SEQ ID NO: 5238 | mm48913_Ltbp4 | GGCTGATTGAAGGTCACTCG |
| SEQ ID NO: 5239 | mm48914_Ltbp4 | TCATGATTGTCACCCGTGCG |
| SEQ ID NO: 5240 | mm48915_Ltbp4 | AGGCCGCTGCGACAACACCG |
| SEQ ID NO: 5241 | mm48940_Slco1a5 | CTGGTAGGAAACATCATACG |
| SEQ ID NO: 5242 | mm48941_Slco1a5 | AGACAGAAGGTACTCAAACA |
| SEQ ID NO: 5243 | mm48942_Slco1a5 | AGAATACTTACCGGCCCATG |
| SEQ ID NO: 5244 | mm48943_Slco1a5 | AATGAACGGACATACCTATG |
| SEQ ID NO: 5245 | mm48976_Slco4a1 | CATCCATCTCTACCTCATAG |
| SEQ ID NO: 5246 | mm48977_Slco4a1 | GCGCTACGTTGTTATGAGAG |
| SEQ ID NO: 5247 | mm48978_Slco4a1 | TGACCACTGACAGCCCACTG |
| SEQ ID NO: 5248 | mm48979_Slco4a1 | AGGTGCAGTATGTGTCCTCG |
| SEQ ID NO: 5249 | mm48980_Slco3a1 | TAAGTTACTTCGGAGCACGT |
| SEQ ID NO: 5250 | mm48981_Slco3a1 | GTGCCTACCTATGTAGAGCG |
| SEQ ID NO: 5251 | mm48982_Slco3a1 | TGGGAACCCAAACATCAGGA |

TABLE 1-continued mmSurf sgRNA library sequences

| SEQ ID NO | id_gRNA Target | Sequence |
|---|---|---|
| SEQ ID NO: 5252 | mm48983_Slco3a1 | GAGGCTGGCGAGATCCGATG |
| SEQ ID NO: 5253 | mm48984_U2af1 | TGCAGGTGCTGTGAGCGACG |
| SEQ ID NO: 5254 | mm48985_U2af1 | GGTGGGAACGTGTATGTCA |
| SEQ ID NO: 5255 | mm48986_U2af1 | ACACAAACCTGGCTAAAGGT |
| SEQ ID NO: 5256 | mm48987_U2af1 | AAAATCGGAGCATGTCGTCA |
| SEQ ID NO: 5257 | mm49108_Pttg1ip | CGTGTATGGACTACCCAGTG |
| SEQ ID NO: 5258 | mm49109_Pttg1ip | AAATTGAGTTCCGCTCGCTG |
| SEQ ID NO: 5259 | mm49110_Pttg1ip | CCGAGGAGCATCACCCAGTG |
| SEQ ID NO: 5260 | mm49111_Pttg1ip | GCGCAGGAACCTCCGAGAGT |
| SEQ ID NO: 5261 | mm49424_Tspan9 | ACAACACAGAGAACAACGTG |
| SEQ ID NO: 5262 | mm49425_Tspan9 | GAAGCCCGTCACCATGACGA |
| SEQ ID NO: 5263 | mm49426_Tspan9 | CCCACAGATGCGGTGTTGTG |
| SEQ ID NO: 5264 | mm49427_Tspan9 | CTTCTTCGTCTACATGGACA |
| SEQ ID NO: 5265 | mm49480_Cdcp1 | AGGACTGCCTATAGCAGTAG |
| SEQ ID NO: 5266 | mm49481_Cdcp1 | AGTTCGCAACCCCTCGACTG |
| SEQ ID NO: 5267 | mm49482_Cdcp1 | ATCATCGAGTCAGTATTTGA |
| SEQ ID NO: 5268 | mm49483_Cdcp1 | ACCGAGTTGATTATCAGACC |
| SEQ ID NO: 5269 | mm49484_Pkn2 | CATCGTTGTATCGGATCCAG |
| SEQ ID NO: 5270 | mm49485_Pkn2 | TTTGAAGCTAGATAATACTG |
| SEQ ID NO: 5271 | mm49486_Pkn2 | TGTGCCAGAATGATTTACTG |
| SEQ ID NO: 5272 | mm49487_Pkn2 | ATAGAATTTGCAGTAGCCGA |
| SEQ ID NO: 5273 | mm49528_Upk1a | GACCGGATCATGATTGAGGT |
| SEQ ID NO: 5274 | mm49529_Upk1a | CGCCCATCAGTGGGTACACG |
| SEQ ID NO: 5275 | mm49530_Upk1a | CCACACTGTCTCCGCAAACA |
| SEQ ID NO: 5276 | mm49531_Upk1a | CCCCACTCACATAGTCGCGG |
| SEQ ID NO: 5277 | mm49560_Ank2 | TCAGAATCATTATCCCACCT |
| SEQ ID NO: 5278 | mm49561_Ank2 | TGCTCAGTACTCCACCCTCG |
| SEQ ID NO: 5279 | mm49562_Ank2 | ACCGCAACCTGGCTTCAATG |
| SEQ ID NO: 5280 | mm49563_Ank2 | CAGTGCCATGATTGACGACA |
| SEQ ID NO: 5281 | mm49576_Itga1 | ATTCGGATTCTCGAACGGTG |
| SEQ ID NO: 5282 | mm49577_Itga1 | ACTTTAGTCACCAATCCGAA |
| SEQ ID NO: 5283 | mm49578_Itga1 | GCAAACAAAATAGGCCGCAG |
| SEQ ID NO: 5284 | mm49579_Itga1 | TGGCCGGTGTGATTGTACCG |
| SEQ ID NO: 5285 | mm49672_Gusb | GTATCTTGGGTCCATCGCCG |
| SEQ ID NO: 5286 | mm49673_Gusb | TGTTCGAATCCCGATAGGAA |
| SEQ ID NO: 5287 | mm49674_Gusb | GGAGCGCGCACCTCCCGTAG |
| SEQ ID NO: 5288 | mm49675_Gusb | GGTGTCAGTCTTGTAGACGA |
| SEQ ID NO: 5289 | mm49696_Bmp3 | TCCAACGTAGAAATACAGTG |

TABLE 1-continued mmSurf sgRNA library sequences

| SEQ ID NO | id_gRNA Target | Sequence |
|---|---|---|
| SEQ ID NO: 5290 | mm49697_Bmp3 | GAGCACACGAGCTACCCAAG |
| SEQ ID NO: 5291 | mm49698_Bmp3 | TCGGGCTACCACCTGTCGCG |
| SEQ ID NO: 5292 | mm49699_Bmp3 | ACCGTGTTACCACCGCGCAG |
| SEQ ID NO: 5293 | mm49732_Fgb | GAAGACGCGAAGAAGTACTG |
| SEQ ID NO: 5294 | mm49733_Fgb | GGAGCACACGAAGATTAAGG |
| SEQ ID NO: 5295 | mm49734_Fgb | TGTTGCAATGTACATCCCGT |
| SEQ ID NO: 5296 | mm49735_Fgb | TACTCTGTACGGCTTGATGG |
| SEQ ID NO: 5297 | mm49864_Ly6a | CCATACTTTCAATATTAGGA |
| SEQ ID NO: 5298 | mm49865_Ly6a | GAGTAACACAGACTCCATCA |
| SEQ ID NO: 5299 | mm49866_Ly6a | GGTAGGGGCAGGTAATTGAT |
| SEQ ID NO: 5300 | mm49867_Ly6a | TTCTTGCAGATTCTCAAACA |
| SEQ ID NO: 5301 | mm49892_H2-Q6 | AGACCTGAAAACCTGGACGG |
| SEQ ID NO: 5302 | mm49893_H2-Q6 | CGGGCCAGGACACAGCAGTG |
| SEQ ID NO: 5303 | mm49894_H2-Q6 | GGATGTATGGCTGTGACGTG |
| SEQ ID NO: 5304 | mm49895_H2-Q6 | ACAGAAAGCCAAGGGCCATG |
| SEQ ID NO: 5305 | mm49960_Adgrv1 | GGACACGTTGAGGATCGACA |
| SEQ ID NO: 5306 | mm49961_Adgrv1 | ACATCCGAATACTTCCGCTG |
| SEQ ID NO: 5307 | mm49962_Adgrv1 | TATGGTGTAATACGAACTCG |
| SEQ ID NO: 5308 | mm49963_Adgrv1 | TGATCTGCCGGAGTTATCCG |
| SEQ ID NO: 5309 | mm50016_Kcnq3 | GTTCGCCTTTCTAATCCTCG |
| SEQ ID NO: 5310 | mm50017_Kcnq3 | GGATGTTGCTGTCGATACAA |
| SEQ ID NO: 5311 | mm50018_Kcnq3 | TGCGCATGCTTCGAATGGAT |
| SEQ ID NO: 5312 | mm50019_Kcnq3 | CAATCGAAGGAACTTACTGC |
| SEQ ID NO: 5313 | mm50056_Hspa13 | GAGGACAAGACTTCAATCAG |
| SEQ ID NO: 5314 | mm50057_Hspa13 | GTGTTGGTCATAGACTTGGG |
| SEQ ID NO: 5315 | mm50058_Hspa13 | AAATACACCAACCGAACAGT |
| SEQ ID NO: 5316 | mm50059_Hspa13 | GACAATTCATCAGTCTGCCC |
| SEQ ID NO: 5317 | mm50072_D1Pas1 | CACAAGGACGAACTCGAGAG |
| SEQ ID NO: 5318 | mm50073_D1Pas1 | AAGGCGTTCTACGACAAAGA |
| SEQ ID NO: 5319 | mm50074_D1Pas1 | ACATCACACAGAAAGTCGTG |
| SEQ ID NO: 5320 | mm50075_D1Pas1 | CGGAGTGACTACGAGAGTGT |
| SEQ ID NO: 5321 | mm50252_Kiss1r | GTCAACGCCTCGGATGACCC |
| SEQ ID NO: 5322 | mm50253_Kiss1r | CGGCGGTGAAGTGCACGCAG |
| SEQ ID NO: 5323 | mm50254_Kiss1r | ACAGTTACCAACTTCTACAT |
| SEQ ID NO: 5324 | mm50255_Kiss1r | GTGCGGGCGTACAGCCGCA |
| SEQ ID NO: 5325 | mm50280_Slc5a5 | CTGCACCTTGTACACGACCG |
| SEQ ID NO: 5326 | mm50281_Slc5a5 | GCTGGCCGCTAGCTTCATGT |
| SEQ ID NO: 5327 | mm50282_Slc5a5 | GTCCACCAGTATCAACGCTA |

TABLE 1-continued mmSurf sgRNA library sequences

| SEQ ID NO | id_gRNA Target | Sequence |
|---|---|---|
| SEQ ID NO: 5328 | mm50283_Slc5a5 | GTACATGCCATTGCTCGTGT |
| SEQ ID NO: 5329 | mm50296_Clic1 | CACAGACACCAACAAGATCG |
| SEQ ID NO: 5330 | mm50297_Clic1 | CACCTTCAACGTTACCACTG |
| SEQ ID NO: 5331 | mm50298_Clic1 | TCTTGCACAGACCTAGAGAA |
| SEQ ID NO: 5332 | mm50299_Clic1 | GAGCACCATGAACAGTCTCT |
| SEQ ID NO: 5333 | mm50344_Ly6g5c | CTTCGGTCTCCAGCAGACAT |
| SEQ ID NO: 5334 | mm50345_Ly6g5c | TCTAGGTGATACCAAGCTCG |
| SEQ ID NO: 5335 | mm50346_Ly6g5c | GACATTAAAACCGCTGCCTA |
| SEQ ID NO: 5336 | mm50347_Ly6g5c | TGTTAAGAGGACAGCACACA |
| SEQ ID NO: 5337 | mm50348_Ly6g6d | AAGCAGACAGTGATCACTTG |
| SEQ ID NO: 5338 | mm50349_Ly6g6d | CGCAGTCATAGCACCGCGTG |
| SEQ ID NO: 5339 | mm50350_Ly6g6d | CAAGTGGCCATAGAGTCAGT |
| SEQ ID NO: 5340 | mm50351_Ly6g6d | GTGATGGCTCAAGGTCGCGG |
| SEQ ID NO: 5341 | mm50428_Dscaml1 | GAAGTTCGCTCAGTACGGCG |
| SEQ ID NO: 5342 | mm50429_Dscaml1 | AAGGTCAATGCGTGGCAACG |
| SEQ ID NO: 5343 | mm50430_Dscaml1 | GCGGATTGGCATGTCCCCCG |
| SEQ ID NO: 5344 | mm50431_Dscaml1 | CAGGACGTGGCGTATCAGCA |
| SEQ ID NO: 5345 | mm50456_Egfrl1 | GATGGCCGCACAATCCACAG |
| SEQ ID NO: 5346 | mm50457_Egfrl1 | CGTGACCACACATCACCCGT |
| SEQ ID NO: 5347 | mm50458_Egfrl1 | AGCCCATGGTATTTGCACCT |
| SEQ ID NO: 5348 | mm50459_Egfrl1 | CACGTGCCGTGTATCTAACA |
| SEQ ID NO: 5349 | mm50588_Ttyh2 | GAAACAGCGAGACCAACGAT |
| SEQ ID NO: 5350 | mm50589_Ttyh2 | CCTGGTAAGTTTCGTCGCCG |
| SEQ ID NO: 5351 | mm50590_Ttyh2 | ACAGGGAGCCAGATCAACTC |
| SEQ ID NO: 5352 | mm50591_Ttyh2 | TCACCTGTAGTATTCCACAT |
| SEQ ID NO: 5353 | mm50592_Steap4 | TGTGTACTGTGCAATACGAG |
| SEQ ID NO: 5354 | mm50593_Steap4 | GATAATCAACTAGTTCCGTG |
| SEQ ID NO: 5355 | mm50594_Steap4 | AATACCAGGGAGGTACACCA |
| SEQ ID NO: 5356 | mm50595_Steap4 | GTTAAATGCTTTGACCACGT |
| SEQ ID NO: 5357 | mm50632_B3galt6 | GCGCGCCAGGTACAACAGAG |
| SEQ ID NO: 5358 | mm50633_B3galt6 | CCTGGTGGACCTACGCGCAC |
| SEQ ID NO: 5359 | mm50634_B3galt6 | GTTCTCGTAGGCGTCGCGCA |
| SEQ ID NO: 5360 | mm50635_B3galt6 | TGGCGGACCCGAGGACGTGT |
| SEQ ID NO: 5361 | mm50644_Boc | GGGAAGCCGCCGTTCCCTCG |
| SEQ ID NO: 5362 | mm50645_Boc | GTAGGCTGTACCGACGACGT |
| SEQ ID NO: 5363 | mm50646_Boc | CCGATGTATGGCCAGCAATG |
| SEQ ID NO: 5364 | mm50647_Boc | CTACGTAGTGAAGCATCGTA |
| SEQ ID NO: 5365 | mm50668_Cspg4 | CCACGGTTGAAAGTACGCGT |

TABLE 1-continued mmSurf sgRNA library sequences

| SEQ ID NO | id_gRNA Target | Sequence |
|---|---|---|
| SEQ ID NO: 5366 | mm50669_Cspg4 | GGAATCAGCCGACCCCTAAG |
| SEQ ID NO: 5367 | mm50670_Cspg4 | AAGGCCCGCTTTGTTCACGA |
| SEQ ID NO: 5368 | mm50671_Cspg4 | GTCAGTAGAAACGAACGCGG |
| SEQ ID NO: 5369 | mm50684_Strc | GCTTTACCAAAGGACGACTG |
| SEQ ID NO: 5370 | mm50685_Strc | TGTTATTAGAGGGTACACGC |
| SEQ ID NO: 5371 | mm50686_Strc | AGGGCCGGAGAAGTGTACTG |
| SEQ ID NO: 5372 | mm50687_Strc | CATGTCGATAAAGAGTTGGG |
| SEQ ID NO: 5373 | mm50708_Igf2bp1 | AGAGGCTTACGAGAACGACG |
| SEQ ID NO: 5374 | mm50709_Igf2bp1 | ATAGCGCCTACATACTGCGT |
| SEQ ID NO: 5375 | mm50710_Igf2bp1 | TCATCGCCCAGTGCTCGTCG |
| SEQ ID NO: 5376 | mm50711_Igf2bp1 | CGTCGGGCGACTCATTGGCA |
| SEQ ID NO: 5377 | mm50760_Igsf8 | TCACGCCTCACAGTGCACGA |
| SEQ ID NO: 5378 | mm50761_Igsf8 | GCAGTTCTAAGGGTTCGCCT |
| SEQ ID NO: 5379 | mm50762_Igsf8 | CCATTCCGGAGGCGCCAGTG |
| SEQ ID NO: 5380 | mm50763_Igsf8 | TCCACAGATACGCAGTACCT |
| SEQ ID NO: 5381 | mm50764_Plxnb2 | GCAGTACTACGAGTGTCGGG |
| SEQ ID NO: 5382 | mm50765_Plxnb2 | TGACGTCAAGAAGATAACTG |
| SEQ ID NO: 5383 | mm50766_Plxnb2 | ACCGTCCATCCGTATCAGCA |
| SEQ ID NO: 5384 | mm50767_Plxnb2 | TTCTCACGGACTTTATCTAG |
| SEQ ID NO: 5385 | mm50768_Plxnb3 | GGACGAGTGATTCGAGTCAG |
| SEQ ID NO: 5386 | mm50769_Plxnb3 | GGGCACCACTAGGCCTACTG |
| SEQ ID NO: 5387 | mm50770_Plxnb3 | GTGCCCATCTATGTAACCAG |
| SEQ ID NO: 5388 | mm50771_Plxnb3 | GGGGTGGTACAGACCACATG |
| SEQ ID NO: 5389 | mm50792_Emid1 | GACAGTCCGGGTCACCACGT |
| SEQ ID NO: 5390 | mm50793_Emid1 | CGTGGACGGACAGCGGCATG |
| SEQ ID NO: 5391 | mm50794_Emid1 | CAGTGACGGCCCGAGAATGG |
| SEQ ID NO: 5392 | mm50795_Emid1 | GAGTGCTACAGAACTGCCCG |
| SEQ ID NO: 5393 | mm50836_Colec12 | GACTAGTGTGTTATTCAAGG |
| SEQ ID NO: 5394 | mm50837_Colec12 | GGAGAAGTTGCAAGCAAATG |
| SEQ ID NO: 5395 | mm50838_Colec12 | AGACCTTCAGGACTTACACA |
| SEQ ID NO: 5396 | mm50839_Colec12 | CAACAACCTGAACCTAACCC |
| SEQ ID NO: 5397 | mm50892_Tlr3 | CTTAGATGAAATCCCAGTCG |
| SEQ ID NO: 5398 | mm50893_Tlr3 | GTTGTAGGAAAGATCGAGCT |
| SEQ ID NO: 5399 | mm50894_Tlr3 | GAATGGTCAAGTTACGAAGA |
| SEQ ID NO: 5400 | mm50895_Tlr3 | ATCTACAAAGTTGGGAACGG |
| SEQ ID NO: 5401 | mm50936_Cntnap4 | GGAGGACCAAATAACTCCTG |
| SEQ ID NO: 5402 | mm50937_Cntnap4 | TTGTGTCCAACAAATACCAG |
| SEQ ID NO: 5403 | mm50938_Cntnap4 | AAGATTGTGATTACGGACAC |

TABLE 1-continued mmSurf sgRNA library sequences

| SEQ ID NO | id_gRNA Target | Sequence |
|---|---|---|
| SEQ ID NO: 5404 | mm50939_Cntnap4 | ACTCACCTTGCTGATTAACG |
| SEQ ID NO: 5405 | mm50956_Kirrel | TGGGTAAACTACAATCCGGG |
| SEQ ID NO: 5406 | mm50957_Kirrel | GAGCCCACGACCCGGTACCG |
| SEQ ID NO: 5407 | mm50958_Kirrel | CACCATTAATAATGTCATGG |
| SEQ ID NO: 5408 | mm50959_Kirrel | CATCGTGCCTCGGATCGGAG |
| SEQ ID NO: 5409 | mm51084_Tlr8 | AGTTCAAGAAATTGCCTCGG |
| SEQ ID NO: 5410 | mm51085_Tlr8 | CTCCAAGAGTTACTTATCAG |
| SEQ ID NO: 5411 | mm51086_Tlr8 | TACTGAAATAGTGTGCATTG |
| SEQ ID NO: 5412 | mm51087_Tlr8 | AACTTGGCAACCATCAACTT |
| SEQ ID NO: 5413 | mm51180_Cd209e | TGAAGAACGTCCAATCCCAA |
| SEQ ID NO: 5414 | mm51181_Cd209e | CCAAGAAAATAGCTACACC |
| SEQ ID NO: 5415 | mm51182_Cd209e | AGTCATCATCAAAAGTCATG |
| SEQ ID NO: 5416 | mm51183_Cd209e | GCTGCAACACCAGGGGAATG |
| SEQ ID NO: 5417 | mm51184_Cd209a | CAAGTTGAGCCCCCACATTG |
| SEQ ID NO: 5418 | mm51185_Cd209a | GTGCCAAGGGGACTTGACTG |
| SEQ ID NO: 5419 | mm51186_Cd209a | ACCTACGCCAGCCTTCAACT |
| SEQ ID NO: 5420 | mm51187_Cd209a | GGAAGTGCGTCCAGTCCCAG |
| SEQ ID NO: 5421 | mm51276_Il17rc | CTGTGGAACGATGACAACAT |
| SEQ ID NO: 5422 | mm51277_Il17rc | AGCAATACTTACCCCAGAGG |
| SEQ ID NO: 5423 | mm51278_Il17rc | GGAGCCACAAGATTTCCAGT |
| SEQ ID NO: 5424 | mm51279_Il17rc | ATCTAGCTGCCATACCCCTG |
| SEQ ID NO: 5425 | mm51284_Fut10 | CCAGCATCATCCGATGACCA |
| SEQ ID NO: 5426 | mm51285_Fut10 | CGACTGAACATATACCAATG |
| SEQ ID NO: 5427 | mm51286_Fut10 | GTGGGGATCCGTAATACAC |
| SEQ ID NO: 5428 | mm51287_Fut10 | ACTGCGTAGTCAGTGGCAAG |
| SEQ ID NO: 5429 | mm51616_Havcr1 | GGAATCACAACGACATGTTG |
| SEQ ID NO: 5430 | mm51617_Havcr1 | TGGTCTGTATTGTTGTCGAG |
| SEQ ID NO: 5431 | mm51618_Havcr1 | TCCCCATGAGACAACAGCTG |
| SEQ ID NO: 5432 | mm51619_Havcr1 | GCAGTCGGTACAACTTAAAG |
| SEQ ID NO: 5433 | mm51620_Timd2 | GATATACGGTCACACATCAG |
| SEQ ID NO: 5434 | mm51621_Timd2 | GGAATCGTTCCTATGTGTTG |
| SEQ ID NO: 5435 | mm51622_Timd2 | TGTTGGAAGTTAAACCAGGT |
| SEQ ID NO: 5436 | mm51623_Timd2 | CTGATCTGGATAAAATGTAG |
| SEQ ID NO: 5437 | mm51624_Havcr2 | GTTACACTCTATCTACACCT |
| SEQ ID NO: 5438 | mm51625_Havcr2 | TTCTCCAAGAACCCTAACCA |
| SEQ ID NO: 5439 | mm51626_Havcr2 | CTAAAGGGCGATCTCAACAA |
| SEQ ID NO: 5440 | mm51627_Havcr2 | ATCAGTTCTGAGCAACTCGT |
| SEQ ID NO: 5441 | mm51632_Trpm8 | CAAAAGCAAGATCCCTTGTG |

TABLE 1-continued mmSurf sgRNA library sequences

| SEQ ID NO | id_gRNA Target | Sequence |
|---|---|---|
| SEQ ID NO: 5442 | mm51633_Trpm8 | CTCACCTTTGTACAGCGCAT |
| SEQ ID NO: 5443 | mm51634_Trpm8 | CCTGATGAAGTACATAGGCG |
| SEQ ID NO: 5444 | mm51635_Trpm8 | GTCCACACCTAAATGATACG |
| SEQ ID NO: 5445 | mm51644_Il17rd | TGGCCAGAATCACATGAACG |
| SEQ ID NO: 5446 | mm51645_Il17rd | CTTCCCGCCGGGATTCAAGT |
| SEQ ID NO: 5447 | mm51646_Il17rd | ACTCGCCTTGCGCCTCGCCG |
| SEQ ID NO: 5448 | mm51647_Il17rd | CCTCCAAAACGTTTCTCCAG |
| SEQ ID NO: 5449 | mm51648_Gpr3711 | CCTACCAGAATGCCCGCATG |
| SEQ ID NO: 5450 | mm51649_Gpr3711 | GGGCATAGACCGATTCCATG |
| SEQ ID NO: 5451 | mm51650_Gpr3711 | TCTCGGTCACCGGATACAGG |
| SEQ ID NO: 5452 | mm51651_Gpr3711 | TCGACCCCGAAGAGGCACCA |
| SEQ ID NO: 5453 | mm51744_Nlgn1 | CAAACACAGTGATTCGCAAG |
| SEQ ID NO: 5454 | mm51745_Nlgn1 | GCGTTCCGGATGTCAGACCA |
| SEQ ID NO: 5455 | mm51746_Nlgn1 | AAGGCTATGTGGTATCGGGC |
| SEQ ID NO: 5456 | mm51747_Nlgn1 | GTGAGCCAAAGTTCGAGTGA |
| SEQ ID NO: 5457 | mm51772_Stab1 | GTGTGCAAAAACGACGAGGT |
| SEQ ID NO: 5458 | mm51773_Stab1 | GCTTGTGTTTCGCTACCACG |
| SEQ ID NO: 5459 | mm51774_Stab1 | GCGACATCACGTGATCCTTG |
| SEQ ID NO: 5460 | mm51775_Stab1 | CATCCGTAGACTGAGCCTCG |
| SEQ ID NO: 5461 | mm51776_Stab2 | AATGCATCCAAGCTAGCACG |
| SEQ ID NO: 5462 | mm51777_Stab2 | GCAGATTCTGGCAAACAACG |
| SEQ ID NO: 5463 | mm51778_Stab2 | TCCTGCCGCACATTTGCACG |
| SEQ ID NO: 5464 | mm51779_Stab2 | AGGTAGGAACAACTTGCGTG |
| SEQ ID NO: 5465 | mm51804_Lrrc4 | GGCTAAGTTGAGTTCCACGA |
| SEQ ID NO: 5466 | mm51805_Lrrc4 | AAGGTGGTGTGCACCCGCCG |
| SEQ ID NO: 5467 | mm51806_Lrrc4 | CCCCCAAGTCCAGACGCATG |
| SEQ ID NO: 5468 | mm51807_Lrrc4 | CCAGAGTGTTGAGACTGGCG |
| SEQ ID NO: 5469 | mm51820_Prom2 | CGTGCGACGATTCCTCTCCG |
| SEQ ID NO: 5470 | mm51821_Prom2 | AACACACACATAGTCAGACG |
| SEQ ID NO: 5471 | mm51822_Prom2 | AACAATATGAGACATACAGG |
| SEQ ID NO: 5472 | mm51823_Prom2 | GCCACGAGGAGAATTGCAAG |
| SEQ ID NO: 5473 | mm51928_Trpv1 | TAAGCTGAATAACACCGTTG |
| SEQ ID NO: 5474 | mm51929_Trpv1 | AAGCCACATACTCCTTGCGA |
| SEQ ID NO: 5475 | mm51930_Trpv1 | CCTGCGATCATAGAGCCTTG |
| SEQ ID NO: 5476 | mm51931_Trpv1 | GCTCCACGAGAAGCATGTCG |
| SEQ ID NO: 5477 | mm52152_Ggt7 | GGTCATGCAAATCTACTTCG |
| SEQ ID NO: 5478 | mm52153_Ggt7 | CGCAGGCGGTGTCATAACCG |
| SEQ ID NO: 5479 | mm52154_Ggt7 | GCGACGGCCTGATCTCGCTG |

TABLE 1-continued mmSurf sgRNA library sequences

| SEQ ID NO | id_gRNA Target | Sequence |
|---|---|---|
| SEQ ID NO: 5480 | mm52155_Ggt7 | TGTTGGTACATGATATCCGG |
| SEQ ID NO: 5481 | mm52200_Elfn2 | GAACGAGATTTCCTACATCG |
| SEQ ID NO: 5482 | mm52201_Elfn2 | GCACCAAGTCACCTTCACCT |
| SEQ ID NO: 5483 | mm52202_Elfn2 | GATAGTCATGATGTAGTGCG |
| SEQ ID NO: 5484 | mm52203_Elfn2 | CCTATTCCACGGATGCGCAG |
| SEQ ID NO: 5485 | mm52228_Thsd4 | TGATAACACGGGCTGCCAGG |
| SEQ ID NO: 5486 | mm52229_Thsd4 | ACTATGAGTACGTGATCATG |
| SEQ ID NO: 5487 | mm52230_Thsd4 | ATGAACCAGCTGGGACATCG |
| SEQ ID NO: 5488 | mm52231_Thsd4 | TTCTGACGTGAATACCTCAG |
| SEQ ID NO: 5489 | mm52380_Btla | CAGTGCAACTTACTATTACG |
| SEQ ID NO: 5490 | mm52381_Btla | TTCATAGACCTAATGTGACT |
| SEQ ID NO: 5491 | mm52382_Btla | TCACATGGATGGTTACTGAA |
| SEQ ID NO: 5492 | mm52383_Btla | TTTGATACTTACTTATTAGT |
| SEQ ID NO: 5493 | mm52408_Ghsr | GCTCGACACCCATACCATCA |
| SEQ ID NO: 5494 | mm52409_Ghsr | CAACCTCTACCTATCCAGCA |
| SEQ ID NO: 5495 | mm52410_Ghsr | CGGCACTCGTTGGTGTCCCG |
| SEQ ID NO: 5496 | mm52411_Ghsr | CACCACGAAGAGCGCCACGC |
| SEQ ID NO: 5497 | mm52424_Tmem132c | TTGGGTGAGGACGCGCACTG |
| SEQ ID NO: 5498 | mm52425_Tmem132c | AGGAAGCTATAATCAGCACA |
| SEQ ID NO: 5499 | mm52426_Tmem132c | GGAAGAGAATAGCACCCTGA |
| SEQ ID NO: 5500 | mm52427_Tmem132c | TAGCTGACGTTTAATACCGG |
| SEQ ID NO: 5501 | mm52436_Tor1aip1 | GAAAACTCTTAGAACACCAG |
| SEQ ID NO: 5502 | mm52437_Tor1aip1 | AGAGTCAAAACGAGAAGCTG |
| SEQ ID NO: 5503 | mm52438_Tor1aip1 | AGCGATTCTCTTGAGTCAAG |
| SEQ ID NO: 5504 | mm52439_Tor1aip1 | ACCAAAATAGTCCCACTGCA |
| SEQ ID NO: 5505 | mm52576_Tmem63a | AGATGCGTATCCCACGTGTG |
| SEQ ID NO: 5506 | mm52577_Tmem63a | AAGGTACCTGGTGAGACCGA |
| SEQ ID NO: 5507 | mm52578_Tmem63a | CCAGGGCCTTCGGTGCAAAG |
| SEQ ID NO: 5508 | mm52579_Tmem63a | CACCCAGCAAGTCTCCCGAG |
| SEQ ID NO: 5509 | mm52712_Enox2 | ACACTTACCAGACAGATAGA |
| SEQ ID NO: 5510 | mm52713_Enox2 | TCTGAATAGTGGACCACTGG |
| SEQ ID NO: 5511 | mm52714_Enox2 | TTTGCTACCGGCATATCTGG |
| SEQ ID NO: 5512 | mm52715_Enox2 | TGGGACAGAGCAGATCATTG |
| SEQ ID NO: 5513 | mm52728_Igsf1 | TTCCTGGCCCCGGATTGGAA |
| SEQ ID NO: 5514 | mm52729_Igsf1 | GGAACAATTGAAAGTCACTC |
| SEQ ID NO: 5515 | mm52730_Igsf1 | ACTTGGAATGTCTTGTAAGG |
| SEQ ID NO: 5516 | mm52731_Igsf1 | TAGATTACCAAGTCCCAACT |
| SEQ ID NO: 5517 | mm52744_Wfdc6a | CCAGAGAGTTACCTTGCCTG |

TABLE 1-continued mmSurf sgRNA library sequences

| SEQ ID NO | id_gRNA Target | Sequence |
|---|---|---|
| SEQ ID NO: 5518 | mm52745_Wfdc6a | AAGAGTCAGAGTGAAGTGTG |
| SEQ ID NO: 5519 | mm52746_Wfdc6a | AAGAAAGAAATGAGTGTACA |
| SEQ ID NO: 5520 | mm52747_Wfdc6a | AGGTGTTGCCTGTTCAGCTG |
| SEQ ID NO: 5521 | mm52760_Itih5 | GCATGCTCTACTACGTCAGG |
| SEQ ID NO: 5522 | mm52761_Itih5 | AAATAACCATTCAGAACCTG |
| SEQ ID NO: 5523 | mm52762_Itih5 | GCAGAAGCTCTTCATAACTG |
| SEQ ID NO: 5524 | mm52763_Itih5 | AGGTGGGTTTCCCATCGGTG |
| SEQ ID NO: 5525 | mm52820_Enpp3 | GGTTTGTATCCGGAGTCACA |
| SEQ ID NO: 5526 | mm52821_Enpp3 | ACATAGATGGTATAAAAACT |
| SEQ ID NO: 5527 | mm52822_Enpp3 | GTGCAATTTATTCCGTTGTG |
| SEQ ID NO: 5528 | mm52823_Enpp3 | ATATTACGAGTCCTGATTCG |
| SEQ ID NO: 5529 | mm52892_Slc38a5 | AGCTACAGGCAGGAACGCGA |
| SEQ ID NO: 5530 | mm52893_Slc38a5 | ACCTGCCGGGAAAGTAGTCG |
| SEQ ID NO: 5531 | mm52894_Slc38a5 | GGAAGGTGCCAATAACAAGG |
| SEQ ID NO: 5532 | mm52895_Slc38a5 | ACCTCAGCAACGCTATCATG |
| SEQ ID NO: 5533 | mm52928_Iglon5 | ACAGACGGTTTCACCTCAGA |
| SEQ ID NO: 5534 | mm52929_Iglon5 | GCTGCTCATCAACACACCCG |
| SEQ ID NO: 5535 | mm52930_Iglon5 | TGTGAACATCTCCTCACCCG |
| SEQ ID NO: 5536 | mm52931_Iglon5 | CACACTGTATAGTTGTCCGC |
| SEQ ID NO: 5537 | mm52980_Gprc6a | CTACTCTGAAACATCCATCG |
| SEQ ID NO: 5538 | mm52981_Gprc6a | TCCCGATTGTCGGATCAGGT |
| SEQ ID NO: 5539 | mm52982_Gprc6a | ACCAGTATTTAAATCCCCGT |
| SEQ ID NO: 5540 | mm52983_Gprc6a | ATGCAACAATGAAACCCACT |
| SEQ ID NO: 5541 | mm53084_Unc5d | ACCATGGCAAGAATCACTCG |
| SEQ ID NO: 5542 | mm53085_Unc5d | GTGAGTCTACTCATACCACA |
| SEQ ID NO: 5543 | mm53086_Unc5d | CTGTATGGCAGCCAACATCG |
| SEQ ID NO: 5544 | mm53087_Unc5d | ACCTGGGAACGTCCAAGAGT |
| SEQ ID NO: 5545 | mm53172_Lrrc25 | CTGCATGGTTCACCCGAGCA |
| SEQ ID NO: 5546 | mm53173_Lrrc25 | CCTGCAGGCCATTCTTAGAC |
| SEQ ID NO: 5547 | mm53174_Lrrc25 | CTGGTTGTGGGTGACAATCA |
| SEQ ID NO: 5548 | mm53175_Lrrc25 | GGCACCTGCCTCAATTTCAG |
| SEQ ID NO: 5549 | mm53188_Cln5 | GACAAAATTCGAACAGTCGT |
| SEQ ID NO: 5550 | mm53189_Cln5 | CCAGCGTTGCCCAGACGTCG |
| SEQ ID NO: 5551 | mm53190_Cln5 | GCCCCTTGGTTACACCAGAA |
| SEQ ID NO: 5552 | mm53191_Cln5 | ATATTTAAATTCCCAAATCG |
| SEQ ID NO: 5553 | mm53196_Nrg1 | AGTCGTGGAGTGATGAGCTG |
| SEQ ID NO: 5554 | mm53197_Nrg1 | GGTGGTCGGCATCATGTGTG |
| SEQ ID NO: 5555 | mm53198_Nrg1 | GCAAGGTGACCATGTCGCTG |

TABLE 1-continued mmSurf sgRNA library sequences

| SEQ ID NO | id_gRNA Target | Sequence |
| --- | --- | --- |
| SEQ ID NO: 5556 | mm53199_Nrg1 | CAGCCATCTCATAAAGTGTG |
| SEQ ID NO: 5557 | mm53248_Tmem87a | GTTGACTTACAATCATCAGT |
| SEQ ID NO: 5558 | mm53249_Tmem87a | AGGAGTCCTCAGAGTTACAG |
| SEQ ID NO: 5559 | mm53250_Tmem87a | TTTCAGAATATCCGATACAA |
| SEQ ID NO: 5560 | mm53251_Tmem87a | AGATGAAATAGAGTCATACT |
| SEQ ID NO: 5561 | mm53268_Mrgprf | GATGTGTCCTGGTATGAGCG |
| SEQ ID NO: 5562 | mm53269_Mrgprf | GCTGAAGAGGTACATCCCAT |
| SEQ ID NO: 5563 | mm53270_Mrgprf | TCTTCGAATGTAGTCGGGGA |
| SEQ ID NO: 5564 | mm53271_Mrgprf | GAATGATAGCATCCAGAGCA |
| SEQ ID NO: 5565 | mm53280_Ptchd1 | AACCCAAGTAGGCCTAACCA |
| SEQ ID NO: 5566 | mm53281_Ptchd1 | TCTGACGGCTAGATTCAGTG |
| SEQ ID NO: 5567 | mm53282_Ptchd1 | TATAATGGGCACCAACTCGG |
| SEQ ID NO: 5568 | mm53283_Ptchd1 | TTGAAATGTTATCCTCGTGG |
| SEQ ID NO: 5569 | mm53584_Dse | GTCAAAGTATAAGCATGACC |
| SEQ ID NO: 5570 | mm53585_Dse | CAGCACACAGAACATTGCCA |
| SEQ ID NO: 5571 | mm53586_Dse | AGTTTCATACATATAGCCCG |
| SEQ ID NO: 5572 | mm53587_Dse | TAATGAACGGCACACCATTG |
| SEQ ID NO: 5573 | mm53624_Wbscr17 | TGACCGAAGTATCACAGACA |
| SEQ ID NO: 5574 | mm53625_Wbscr17 | GGGCCACCCTTGAACATGGA |
| SEQ ID NO: 5575 | mm53626_Wbscr17 | ATCTGGAATAGACCGGTCCA |
| SEQ ID NO: 5576 | mm53627_Wbscr17 | GCTACGAGAACTCCGCCCAC |
| SEQ ID NO: 5577 | mm53664_Slc39a14 | GAGCGAGCGATCTCAGATCG |
| SEQ ID NO: 5578 | mm53665_Slc39a14 | GTAGAGGGTTCCAATCGCCA |
| SEQ ID NO: 5579 | mm53666_Slc39a14 | TAAAATGGTTATGCCCGTGA |
| SEQ ID NO: 5580 | mm53667_Slc39a14 | GTGACCGAGAAGCTACAGAA |
| SEQ ID NO: 5581 | mm53708_Tapbpl | GCCGCCACTCCACGCCAGTG |
| SEQ ID NO: 5582 | mm53709_Tapbpl | AAGGCATCACAGATTTCCAG |
| SEQ ID NO: 5583 | mm53710_Tapbpl | GGAGCCTGAGGAGCTACTCA |
| SEQ ID NO: 5584 | mm53711_Tapbpl | GAAATACTTGGAGATCTCGC |
| SEQ ID NO: 5585 | mm53848_Slc44a3 | AGGATGGCACACGTCCACAG |
| SEQ ID NO: 5586 | mm53849_Slc44a3 | GTTCATCATGGGTTATTCGG |
| SEQ ID NO: 5587 | mm53850_Slc44a3 | GAACCGGAAGGCGAACAACA |
| SEQ ID NO: 5588 | mm53851_Slc44a3 | CCACCACATATACCGAATGC |
| SEQ ID NO: 5589 | mm53884_Casd1 | CATGCACATTCGAGTTCTGG |
| SEQ ID NO: 5590 | mm53885_Casd1 | TGTGAATACCTTCTCTCGAG |
| SEQ ID NO: 5591 | mm53886_Casd1 | TGTGGTGTTATGTATCGTAA |
| SEQ ID NO: 5592 | mm53887_Casd1 | GAAGATAGACGCCTACAATG |
| SEQ ID NO: 5593 | mm53932_Slc18a2 | CGAGCCATACGTACCTACGA |

TABLE 1-continued mmSurf sgRNA library sequences

| SEQ ID NO | id_gRNA Target | Sequence |
|---|---|---|
| SEQ ID NO: 5594 | mm53933_Slc18a2 | CCATCTGCTTTGCAAACATG |
| SEQ ID NO: 5595 | mm53934_Slc18a2 | GTACATACCTAAGACCCCCA |
| SEQ ID NO: 5596 | mm53935_Slc18a2 | ATGCAGAATCCAGCAAACAT |
| SEQ ID NO: 5597 | mm53948_Nipal4 | ATTCCTTTGCCCGTAACGTG |
| SEQ ID NO: 5598 | mm53949_Nipal4 | GCTACCTGAAGGACCCAATG |
| SEQ ID NO: 5599 | mm53950_Nipal4 | TGCCTCTCACGATCTGACAG |
| SEQ ID NO: 5600 | mm53951_Nipal4 | GGATGACACTGGTGCCGATG |
| SEQ ID NO: 5601 | mm53988_Disp2 | CAAGTGTACCGGAAGCAACG |
| SEQ ID NO: 5602 | mm53989_Disp2 | GCTTCCACTAAACACAGCGT |
| SEQ ID NO: 5603 | mm53990_Disp2 | CTACAGTACAGAGTACGGCC |
| SEQ ID NO: 5604 | mm53991_Disp2 | CGAAACTTAATGACACCACA |
| SEQ ID NO: 5605 | mm54068_Tmprss4 | CCACGGCCAAGAATCCACAG |
| SEQ ID NO: 5606 | mm54069_Tmprss4 | AGGGCAGGCTCAAACATACT |
| SEQ ID NO: 5607 | mm54070_Tmprss4 | CTGTGACTTGAGCAACAGGG |
| SEQ ID NO: 5608 | mm54071_Tmprss4 | GCTGCTGTGAGGATCCAGTG |
| SEQ ID NO: 5609 | mm54112_Sidt2 | ATAGTTGTAACCCTCGTAAG |
| SEQ ID NO: 5610 | mm54113_Sidt2 | TCTTGGACCATAGATATCAG |
| SEQ ID NO: 5611 | mm54114_Sidt2 | CAAAAACGTCATTCGAACCA |
| SEQ ID NO: 5612 | mm54115_Sidt2 | TGTTGTCCAGATCATAGACA |
| SEQ ID NO: 5613 | mm54188_Lman2l | TCTTGACATAGCGAATCACG |
| SEQ ID NO: 5614 | mm54189_Lman2l | TCTTACCACCCGGTTCCACA |
| SEQ ID NO: 5615 | mm54190_Lman2l | TCGCTGTCGAAGCCCTACCA |
| SEQ ID NO: 5616 | mm54191_Lman2l | CTTGGCAATCTGGTACACAA |
| SEQ ID NO: 5617 | mm54360_Rab11fip3 | GGACGGCTTCGTCCGCATCG |
| SEQ ID NO: 5618 | mm54361_Rab11fip3 | CGCACCGTGCCTCTTGACGG |
| SEQ ID NO: 5619 | mm54362_Rab11fip3 | GGAGCAGCAGCAATGCACCA |
| SEQ ID NO: 5620 | mm54363_Rab11fip3 | ATTCTGTCACTTGCTCAAGG |
| SEQ ID NO: 5621 | mm54400_Rnpep | TGATAACGTCGGCTAACGAG |
| SEQ ID NO: 5622 | mm54401_Rnpep | AGCAGTAACCTTTCTCGTAG |
| SEQ ID NO: 5623 | mm54402_Rnpep | TGTGATGAGTGCAGACACCT |
| SEQ ID NO: 5624 | mm54403_Rnpep | TGGCACCTTACCAAACAGGA |
| SEQ ID NO: 5625 | mm54464_Adgrg6 | AATGCTGTTGATATTAGCCG |
| SEQ ID NO: 5626 | mm54465_Adgrg6 | CTTGTGTGGAATAATTCTTG |
| SEQ ID NO: 5627 | mm54466_Adgrg6 | CATCACTAGAGGATGGACTG |
| SEQ ID NO: 5628 | mm54467_Adgrg6 | CACATGCATCTCATTCACGC |
| SEQ ID NO: 5629 | mm54504_Fam26f | GGGACACTGGAACACCACTG |
| SEQ ID NO: 5630 | mm54505_Fam26f | CGCTCCCGCTGACAGCACAT |
| SEQ ID NO: 5631 | mm54506_Fam26f | GGTGAGGGGCGCGAATGCCG |

TABLE 1-continued mmSurf sgRNA library sequences

| SEQ ID NO | id_gRNA Target | Sequence |
|---|---|---|
| SEQ ID NO: 5632 | mm54507_Fam26f | GGAGCGCGCGATTCAGTTCG |
| SEQ ID NO: 5633 | mm54544_Lrrtm3 | GGGGGTTAACGTGATCGATG |
| SEQ ID NO: 5634 | mm54545_Lrrtm3 | CAACCGGCAGATATACTCGA |
| SEQ ID NO: 5635 | mm54546_Lrrtm3 | CACTGAGAACCATCCCGGTG |
| SEQ ID NO: 5636 | mm54547_Lrrtm3 | TCTCGTCGATATTGCTGATG |
| SEQ ID NO: 5637 | mm54624_Ckap4 | TCTGTCGGACGGGATCCACG |
| SEQ ID NO: 5638 | mm54625_Ckap4 | AGAGGACATCCGGAGACTGG |
| SEQ ID NO: 5639 | mm54626_Ckap4 | CCGCACCTCTGTGTAGACGT |
| SEQ ID NO: 5640 | mm54627_Ckap4 | CCGCAGAACCAGGCGCACCG |
| SEQ ID NO: 5641 | mm54672_Tspan8 | TGAGGCAAAAGACTTCCAGA |
| SEQ ID NO: 5642 | mm54673_Tspan8 | GTATGTGGTACACTGATCTT |
| SEQ ID NO: 5643 | mm54674_Tspan8 | ACGTACCTCAGGTTTGAAAG |
| SEQ ID NO: 5644 | mm54675_Tspan8 | AGATATTCACAGCAATGAAG |
| SEQ ID NO: 5645 | mm54684_Tmem5 | TGCATAAATTAACCACTGGG |
| SEQ ID NO: 5646 | mm54685_Tmem5 | GCGCCCGAAGAAGACGTGGT |
| SEQ ID NO: 5647 | mm54686_Tmem5 | ATGTCTGCACCATTAATCCA |
| SEQ ID NO: 5648 | mm54687_Tmem5 | TCTTTACAGTGACTTACCAA |
| SEQ ID NO: 5649 | mm54900_Nlgn2 | ACCAGCCGCTCAAGTACACG |
| SEQ ID NO: 5650 | mm54901_Nlgn2 | GCTCACAAAAAACGTGACG |
| SEQ ID NO: 5651 | mm54902_Nlgn2 | GAAAGTGTAAAAGTAGACGG |
| SEQ ID NO: 5652 | mm54903_Nlgn2 | CCGAGATCCTCATGCAACAG |
| SEQ ID NO: 5653 | mm55124_Fam171a2 | CCCGAGACTTAGCATCCTCG |
| SEQ ID NO: 5654 | mm55125_Fam171a2 | GTGGCCCAGATAATGGTCGA |
| SEQ ID NO: 5655 | mm55126_Fam171a2 | GGTACCCAGGCGGTAACTGA |
| SEQ ID NO: 5656 | mm55127_Fam171a2 | CTGTGGGTACGAAATGGCAC |
| SEQ ID NO: 5657 | mm55140_Abca9 | TGGGCGCTTACAAAGCGATG |
| SEQ ID NO: 5658 | mm55141_Abca9 | GCTGCCCATCGCAATGTAAG |
| SEQ ID NO: 5659 | mm55142_Abca9 | TAGGTAAGTACGGACATCAA |
| SEQ ID NO: 5660 | mm55143_Abca9 | CTGGGTTGGATCCACTCTCG |
| SEQ ID NO: 5661 | mm55208_Rhbdf2 | ACAGATATCCTCTTGCGGCG |
| SEQ ID NO: 5662 | mm55209_Rhbdf2 | GTGAACGAACGTCAGCCAGT |
| SEQ ID NO: 5663 | mm55210_Rhbdf2 | TAAAGTGGCAGAATGATACT |
| SEQ ID NO: 5664 | mm55211_Rhbdf2 | ACCAGAAAAGAATACAGCGG |
| SEQ ID NO: 5665 | mm55216_Tmc6 | GGAGTCATGTCGCTCCAGAG |
| SEQ ID NO: 5666 | mm55217_Tmc6 | TTTCCAAGGTCGCAGCCGTG |
| SEQ ID NO: 5667 | mm55218_Tmc6 | GACCAGAAAACGTAGGCACG |
| SEQ ID NO: 5668 | mm55219_Tmc6 | TACCGGGTTGGCAGTACCAA |
| SEQ ID NO: 5669 | mm55316_Mgat2 | GAAGTTCAACTGGTACACCA |

TABLE 1-continued mmSurf sgRNA library sequences

| SEQ ID NO | id_gRNA Target | Sequence |
|---|---|---|
| SEQ ID NO: 5670 | mm55317_Mgat2 | TGTAATGGCCGAAGGAGTCA |
| SEQ ID NO: 5671 | mm55318_Mgat2 | AAAAGTCTGGGGCTAAGTAG |
| SEQ ID NO: 5672 | mm55319_Mgat2 | CTGGACGCGGAGCCCGTACG |
| SEQ ID NO: 5673 | mm55380_Tmem63c | CCTGACCTCACTGATCTACG |
| SEQ ID NO: 5674 | mm55381_Tmem63c | GATTACAAGTACATCCATTG |
| SEQ ID NO: 5675 | mm55382_Tmem63c | GAATGACCACCATAAACACC |
| SEQ ID NO: 5676 | mm55383_Tmem63c | TCTCCCAACTCCAGTTCACG |
| SEQ ID NO: 5677 | mm55384_Pomt2 | TGGACAGATCCAGTACGGTG |
| SEQ ID NO: 5678 | mm55385_Pomt2 | GTAGTCCTTATGCAAATAGG |
| SEQ ID NO: 5679 | mm55386_Pomt2 | CCTGCACAGTCACTATCATG |
| SEQ ID NO: 5680 | mm55387_Pomt2 | TCTTTATCATCGTGCAAGTG |
| SEQ ID NO: 5681 | mm55568_Clptm1l | CCTACGACAAGATCTCATTG |
| SEQ ID NO: 5682 | mm55569_Clptm1l | TGAGTGTTTACACCACCACA |
| SEQ ID NO: 5683 | mm55570_Clptm1l | CTGGCGTTGCTTCAGCACTG |
| SEQ ID NO: 5684 | mm55571_Clptm1l | CAAACCCCCAGGATTCAGCT |
| SEQ ID NO: 5685 | mm55592_Serinc5 | CCAGAGAGATTAGCACGCAT |
| SEQ ID NO: 5686 | mm55593_Serinc5 | GCACCGTCCGTAATAAGCTG |
| SEQ ID NO: 5687 | mm55594_Serinc5 | TGCCGGGCCTACATTCACAA |
| SEQ ID NO: 5688 | mm55595_Serinc5 | ACACCGCAGAATACCCTACC |
| SEQ ID NO: 5689 | mm55640_Il31ra | GAAGGTGCGATTGTTGTGGA |
| SEQ ID NO: 5690 | mm55641_Il31ra | ACGAACTGGACCATCGAGCA |
| SEQ ID NO: 5691 | mm55642_Il31ra | AACCGCGTGAAAAGACTCGT |
| SEQ ID NO: 5692 | mm55643_Il31ra | TGCCAGTTCACCACCAACAG |
| SEQ ID NO: 5693 | mm55672_Slc4a7 | TCAGGAACATAAGGTCCATG |
| SEQ ID NO: 5694 | mm55673_Slc4a7 | TCTGCAAAGGATCGAACCAG |
| SEQ ID NO: 5695 | mm55674_Slc4a7 | ACAGTATAGGAAAAGAATCG |
| SEQ ID NO: 5696 | mm55675_Slc4a7 | GCAGATCCATTAGGAAACAC |
| SEQ ID NO: 5697 | mm56140_Rtp2 | GAGCAGTGTTACGATGAGGA |
| SEQ ID NO: 5698 | mm56141_Rtp2 | GCTATCAGTGCGGCACGTCG |
| SEQ ID NO: 5699 | mm56142_Rtp2 | ATGCTGGAGGAGAATATCGA |
| SEQ ID NO: 5700 | mm56143_Rtp2 | TGGAGCAACATGCCTCAGGC |
| SEQ ID NO: 5701 | mm56152_Atp13a3 | ATAGTGCAGGACTGACACAG |
| SEQ ID NO: 5702 | mm56153_Atp13a3 | TTCAGCGAGTGGAAAATACC |
| SEQ ID NO: 5703 | mm56154_Atp13a3 | TTAATAAGTACTGCATCACA |
| SEQ ID NO: 5704 | mm56155_Atp13a3 | TAACCGGATCATGCCTACTG |
| SEQ ID NO: 5705 | mm56212_Cldnd1 | TGACTCGAATAAAATCGCCT |
| SEQ ID NO: 5706 | mm56213_Cldnd1 | TGCCGCTATTGTGGTTGCCG |
| SEQ ID NO: 5707 | mm56214_Cldnd1 | ATCTACATGGCGGCCTCCAT |

TABLE 1-continued mmSurf sgRNA library sequences

| SEQ ID NO | id_gRNA Target | Sequence |
|---|---|---|
| SEQ ID NO: 5708 | mm56215_Cldnd1 | ACTGGTATGCGCCACCGGAA |
| SEQ ID NO: 5709 | mm56384_Adgrf5 | GTACGCTGTGACTTTCCACG |
| SEQ ID NO: 5710 | mm56385_Adgrf5 | AAGAGCATGGTGATAAAACG |
| SEQ ID NO: 5711 | mm56386_Adgrf5 | TCCCTCGAATTGGAAAACTG |
| SEQ ID NO: 5712 | mm56387_Adgrf5 | CTCACCGTTCCACTCTCGGG |
| SEQ ID NO: 5713 | mm56388_Enpp4 | TGTTATAGACTTGACCCCTG |
| SEQ ID NO: 5714 | mm56389_Enpp4 | AAGGATACCAGAAGTAACCG |
| SEQ ID NO: 5715 | mm56390_Enpp4 | TGATCATTACAAGCGATCAT |
| SEQ ID NO: 5716 | mm56391_Enpp4 | GACTGGGTAACGTTACCACA |
| SEQ ID NO: 5717 | mm56400_Tmem63b | ATGATCAACCCCAAACCGTG |
| SEQ ID NO: 5718 | mm56401_Tmem63b | CAGTAGCGTAGGGAAGAACT |
| SEQ ID NO: 5719 | mm56402_Tmem63b | GCTCTGTCGACTTTGACCAA |
| SEQ ID NO: 5720 | mm56403_Tmem63b | AAAGTGAACGAGAAACCTCT |
| SEQ ID NO: 5721 | mm56672_Mppe1 | ATTGGCTGGACAAATTACGA |
| SEQ ID NO: 5722 | mm56673_Mppe1 | AAGTGGAGCTCCGATCAGGT |
| SEQ ID NO: 5723 | mm56674_Mppe1 | CATGGTCAACAGCGTTGCAA |
| SEQ ID NO: 5724 | mm56675_Mppe1 | TAAACTGAATTGCTCCCAAG |
| SEQ ID NO: 5725 | mm56704_Cd226 | ATTGACGCATAACTTAACCC |
| SEQ ID NO: 5726 | mm56705_Cd226 | ACTTCCTAAACTCAACAGTG |
| SEQ ID NO: 5727 | mm56706_Cd226 | GCTAAGATGTCTACCTGATG |
| SEQ ID NO: 5728 | mm56707_Cd226 | TGCAGACAGGTAGCTATCCG |
| SEQ ID NO: 5729 | mm56732_Lrfn4 | CAAAGGAGCGAGCCCCAATG |
| SEQ ID NO: 5730 | mm56733_Lrfn4 | GCTGTTTGTGCCACCCAACG |
| SEQ ID NO: 5731 | mm56734_Lrfn4 | TGTGTGTGCCGGGCAATCAG |
| SEQ ID NO: 5732 | mm56735_Lrfn4 | CTCATCGATGCACTACCCCC |
| SEQ ID NO: 5733 | mm56836_Ermp1 | GCATCTCCGTAGATATACAG |
| SEQ ID NO: 5734 | mm56837_Ermp1 | ATTGCGTACCCTTCTCGTGT |
| SEQ ID NO: 5735 | mm56838_Ermp1 | GATGTTGAGTAATAAAACCA |
| SEQ ID NO: 5736 | mm56839_Ermp1 | TGGTGCTGAGCCGGACCTCG |
| SEQ ID NO: 5737 | mm57020_Lamc1 | ATGTAGCGATGGGTACTATG |
| SEQ ID NO: 5738 | mm57021_Lamc1 | TTGACCTCTATCAAGATCCG |
| SEQ ID NO: 5739 | mm57022_Lamc1 | ACGTACTCAAAGGCTAACCG |
| SEQ ID NO: 5740 | mm57023_Lamc1 | CAGTCGCGGCCAGACACATG |
| SEQ ID NO: 5741 | mm57200_Slc39a10 | CGTGCGTATGCTGATGACTG |
| SEQ ID NO: 5742 | mm57201_Slc39a10 | TGAACAATATGAGCATAACC |
| SEQ ID NO: 5743 | mm57202_Slc39a10 | AGTCGTTGAGATTAATCACG |
| SEQ ID NO: 5744 | mm57203_Slc39a10 | CGATCTGATACAGCAATGCA |
| SEQ ID NO: 5745 | mm57256_Aamp | TGGATGTGGAAGGTCCCGAA |

TABLE 1-continued mmSurf sgRNA library sequences

| SEQ ID NO | id_gRNA Target | Sequence |
|---|---|---|
| SEQ ID NO: 5746 | mm57257_Aamp | ATCACCGAGCCTCCACACGA |
| SEQ ID NO: 5747 | mm57258_Aamp | AAGACCACTCATGTCCCCTG |
| SEQ ID NO: 5748 | mm57259_Aamp | GGAGGGCCCGGATGATAGTG |
| SEQ ID NO: 5749 | mm57268_Dner | AACACTCTAAGTCATTTGAG |
| SEQ ID NO: 5750 | mm57269_Dner | CATTCCCACAGGCAACATCA |
| SEQ ID NO: 5751 | mm57270_Dner | GAACAATGGCACTTGCTACG |
| SEQ ID NO: 5752 | mm57271_Dner | CACACTTCGACCATCTATGA |
| SEQ ID NO: 5753 | mm57304_Slco4c1 | TTATAGTTCGGATCTGACTG |
| SEQ ID NO: 5754 | mm57305_Slco4c1 | ACAAAGATACGTGCTTAACA |
| SEQ ID NO: 5755 | mm57306_Slco4c1 | TTTCCCCTTAGAATTTGATG |
| SEQ ID NO: 5756 | mm57307_Slco4c1 | AGAGAGGACACAAACCTCGC |
| SEQ ID NO: 5757 | mm57400_Qsox2 | TGGTGCAGTTCCACTCGTCG |
| SEQ ID NO: 5758 | mm57401_Qsox2 | GAGGAGAAAAACGATCGTAG |
| SEQ ID NO: 5759 | mm57402_Qsox2 | AGAAGTGGATGTCATATGTG |
| SEQ ID NO: 5760 | mm57403_Qsox2 | GGGATGTCAAGGAAGTCGAT |
| SEQ ID NO: 5761 | mm57612_Lrp4 | ATAGTGCCAACAAGTTTACG |
| SEQ ID NO: 5762 | mm57613_Lrp4 | TGACATCTGTCCAATACACG |
| SEQ ID NO: 5763 | mm57614_Lrp4 | GACAACAGTGACGAGCAATG |
| SEQ ID NO: 5764 | mm57615_Lrp4 | TGGTATAATACAATGGCCCG |
| SEQ ID NO: 5765 | mm58020_Pbxip1 | TGTTGATACCCTGATTCTCG |
| SEQ ID NO: 5766 | mm58021_Pbxip1 | GAGCCTCGGACCAGACACAC |
| SEQ ID NO: 5767 | mm58022_Pbxip1 | CGTGGTACCCGTAGATGTGG |
| SEQ ID NO: 5768 | mm58023_Pbxip1 | TATGCTGCTCCAATAAGCTG |
| SEQ ID NO: 5769 | mm58060_Adamtsl4 | TGAGATTTCCCGAAACCAGG |
| SEQ ID NO: 5770 | mm58061_Adamtsl4 | GGGGAATCCGCACCTGACGT |
| SEQ ID NO: 5771 | mm58062_Adamtsl4 | CATACTGATAAAAAACACCT |
| SEQ ID NO: 5772 | mm58063_Adamtsl4 | GAACTGAACTGCCGCCCCCG |
| SEQ ID NO: 5773 | mm58136_Amigo1 | GCTTGCAGTCGCACTCCAAG |
| SEQ ID NO: 5774 | mm58137_Amigo1 | CGGGACAACTAACCACAGAT |
| SEQ ID NO: 5775 | mm58138_Amigo1 | AGTACCTAAGGTTGGGTACG |
| SEQ ID NO: 5776 | mm58139_Amigo1 | GCAAGGCATGACCAAAGTGT |
| SEQ ID NO: 5777 | mm58248_Npr2 | CAGCGGGGTACACACAACCG |
| SEQ ID NO: 5778 | mm58249_Npr2 | ATGGCAGGACAATCGAACCC |
| SEQ ID NO: 5779 | mm58250_Npr2 | ACAGGACGAAATCAGTCTCG |
| SEQ ID NO: 5780 | mm58251_Npr2 | CAACTCGGATCGCTATCACA |
| SEQ ID NO: 5781 | mm58268_Tmeff1 | GCACCAGAAAGACATAACCG |
| SEQ ID NO: 5782 | mm58269_Tmeff1 | ATTGTTATAGGAACTCCCGT |
| SEQ ID NO: 5783 | mm58270_Tmeff1 | CCCTGTCTGTGGGTCAAACG |

TABLE 1-continued mmSurf sgRNA library sequences

| SEQ ID NO | id_gRNA Target | Sequence |
|---|---|---|
| SEQ ID NO: 5784 | mm58271_Tmeff1 | CGCCGTCTGCGGCTACACGT |
| SEQ ID NO: 5785 | mm58312_Megf9 | GGACGGACACACTCCCACCA |
| SEQ ID NO: 5786 | mm58313_Megf9 | TGGGAATTGCCAATGCAAAG |
| SEQ ID NO: 5787 | mm58314_Megf9 | CACCACAGTCCGCAAAACCG |
| SEQ ID NO: 5788 | mm58315_Megf9 | CTGTGTAACCATCTTTACAT |
| SEQ ID NO: 5789 | mm58364_Fam151a | ATCAATGCTGACATCCTGAG |
| SEQ ID NO: 5790 | mm58365_Fam151a | GTACTGGCCTCATCTCAGAA |
| SEQ ID NO: 5791 | mm58366_Fam151a | CTTGTAAATAGGCGATGTCA |
| SEQ ID NO: 5792 | mm58367_Fam151a | GGAGATCTTCTACTGACACG |
| SEQ ID NO: 5793 | mm58368_Yipf1 | CAACGACTCTGACGAGACCG |
| SEQ ID NO: 5794 | mm58369_Yipf1 | GGGGTCCTCAATGTTTATCG |
| SEQ ID NO: 5795 | mm58370_Yipf1 | TGCTATGGCAAAGACCAACG |
| SEQ ID NO: 5796 | mm58371_Yipf1 | GACACACACGATCTCCAGAA |
| SEQ ID NO: 5797 | mm58476_Epha10 | GCGATGGTGTCAATCTTGCG |
| SEQ ID NO: 5798 | mm58477_Epha10 | GCTTCACGCAGGGTGACCTG |
| SEQ ID NO: 5799 | mm58478_Epha10 | GACTGCACTGCCAAGCACTG |
| SEQ ID NO: 5800 | mm58479_Epha10 | CAGACAGGCTGGATCAGCCG |
| SEQ ID NO: 5801 | mm58592_Ece1 | GCACGCACGGTAGTACACTT |
| SEQ ID NO: 5802 | mm58593_Ece1 | AGTGACACGGAAAACAACCT |
| SEQ ID NO: 5803 | mm58594_Ece1 | CAATGAGTCTGAGCCAATCG |
| SEQ ID NO: 5804 | mm58595_Ece1 | CTTCTCTGTTTATGTCAGCG |
| SEQ ID NO: 5805 | mm58608_Igsf21 | GTATCTACGACCGAGCCACG |
| SEQ ID NO: 5806 | mm58609_Igsf21 | TCACGGTGGACTGATACACA |
| SEQ ID NO: 5807 | mm58610_Igsf21 | TCGGCGCTGTGTACCCAACG |
| SEQ ID NO: 5808 | mm58611_Igsf21 | AACCTCCAAGCACTTACCAT |
| SEQ ID NO: 5809 | mm58660_Ajap1 | TTCAACGATTTCGACTTCCG |
| SEQ ID NO: 5810 | mm58661_Ajap1 | TGCGAAGTGGACCCCCAACG |
| SEQ ID NO: 5811 | mm58662_Ajap1 | GCCACCCTCGGACCCAAAGG |
| SEQ ID NO: 5812 | mm58663_Ajap1 | GCAAACACGGAAGACAACGG |
| SEQ ID NO: 5813 | mm58676_Tnfrsf14 | TGGGCGGTATATGTCTGTGG |
| SEQ ID NO: 5814 | mm58677_Tnfrsf14 | TATGTGCTGACTGCCTAACA |
| SEQ ID NO: 5815 | mm58678_Tnfrsf14 | CCTGGATCACAGACTCCGCA |
| SEQ ID NO: 5816 | mm58679_Tnfrsf14 | GCCCATGTGCAACCCAGGT |
| SEQ ID NO: 5817 | mm58832_Tmprss11d | TACGGAGCTGTACCCGTCGT |
| SEQ ID NO: 5818 | mm58833_Tmprss11d | CTAATAATGTCCACCACTG |
| SEQ ID NO: 5819 | mm58834_Tmprss11d | CCTAAACGTTGAATACACTG |
| SEQ ID NO: 5820 | mm58835_Tmprss11d | TCGTTGTCATAATAACGGTA |
| SEQ ID NO: 5821 | mm58864_Fras1 | TGGTGGGTGTGCTTACAACG |

TABLE 1-continued mmSurf sgRNA library sequences

| SEQ ID NO | id_gRNA Target | Sequence |
|---|---|---|
| SEQ ID NO: 5822 | mm58865_Fras1 | CCCCACTTGGCAATAAACCG |
| SEQ ID NO: 5823 | mm58866_Fras1 | ACTGGGGCTGAATAACACTT |
| SEQ ID NO: 5824 | mm58867_Fras1 | CTGAAGAGTACGCCATACAG |
| SEQ ID NO: 5825 | mm58924_P2rx2 | GGAATACGTAAAGCCCCCGG |
| SEQ ID NO: 5826 | mm58925_P2rx2 | CTGTGTACCCTATTACCATG |
| SEQ ID NO: 5827 | mm58926_P2rx2 | TTTGATGAGAGTTCGAGTGG |
| SEQ ID NO: 5828 | mm58927_P2rx2 | ATCTCCACCCTAGAGCATGA |
| SEQ ID NO: 5829 | mm59160_Tmem150a | GCCAAGTCTCTACACTACAT |
| SEQ ID NO: 5830 | mm59161_Tmem150a | GCACACGTGGCGGTTCATCA |
| SEQ ID NO: 5831 | mm59162_Tmem150a | GAAAATTGCCGACCACCACG |
| SEQ ID NO: 5832 | mm59163_Tmem150a | TAGGCCATAGCCATGTCCAG |
| SEQ ID NO: 5833 | mm59244_Slc6a1 | CACCAACATGACCAGCGCCG |
| SEQ ID NO: 5834 | mm59245_Slc6a1 | GCAGAAATACACGAGCACCC |
| SEQ ID NO: 5835 | mm59246_Slc6a1 | TACCTCTGTGGGAAAAACGG |
| SEQ ID NO: 5836 | mm59247_Slc6a1 | TCCATGTGTCCCGGTCAGGG |
| SEQ ID NO: 5837 | mm59264_A2m | CCCTTGACTCACGATGAAGG |
| SEQ ID NO: 5838 | mm59265_A2m | CCGGAAGACCGATATTTGGG |
| SEQ ID NO: 5839 | mm59266_A2m | GGGCACGTCCCTAACTGTCA |
| SEQ ID NO: 5840 | mm59267_A2m | AAGGCTTGGAAATCGATCAC |
| SEQ ID NO: 5841 | mm59276_Clstn3 | CAGACGCTCCACAAAGACCG |
| SEQ ID NO: 5842 | mm59277_Clstn3 | CAGTTACCTGCATAGCGCAG |
| SEQ ID NO: 5843 | mm59278_Clstn3 | ACCGAGACAACTATTCAGAG |
| SEQ ID NO: 5844 | mm59279_Clstn3 | AGTAGTGGTGGATCAGCAAG |
| SEQ ID NO: 5845 | mm59292_Klrb1f | AATAAACATTTGTTCCAGTG |
| SEQ ID NO: 5846 | mm59293_Klrb1f | GAAGATGCTTGCTTATACCC |
| SEQ ID NO: 5847 | mm59294_Klrb1f | CTAAGACACTGAGTCCAATC |
| SEQ ID NO: 5848 | mm59295_Klrb1f | AGAGCCAAATGATGCCAGTG |
| SEQ ID NO: 5849 | mm59300_Clec12a | AACTCAATCAGTATGGAACA |
| SEQ ID NO: 5850 | mm59301_Clec12a | GAGATTGTGCTTCAGCTGTA |
| SEQ ID NO: 5851 | mm59302_Clec12a | CAGAAGTCTGACAAATGTGG |
| SEQ ID NO: 5852 | mm59303_Clec12a | GAGCTGTATAGCAAAGAACC |
| SEQ ID NO: 5853 | mm59304_Clec9a | CATTGGTGAACCTTACACAG |
| SEQ ID NO: 5854 | mm59305_Clec9a | ATTACCTGAACATTTGCTAG |
| SEQ ID NO: 5855 | mm59306_Clec9a | CAAGCCCATACAGACCACAC |
| SEQ ID NO: 5856 | mm59307_Clec9a | GTTACTATGTCTTTGAACGC |
| SEQ ID NO: 5857 | mm59372_Tspan33 | GCCAGGCTAATGAAGCACGC |
| SEQ ID NO: 5858 | mm59373_Tspan33 | GAATATGTACTTCAACTGCT |
| SEQ ID NO: 5859 | mm59374_Tspan33 | AAGGCAGATGTTCTCCCGAA |

TABLE 1-continued mmSurf sgRNA library sequences

| SEQ ID NO | id_gRNA Target | Sequence |
|---|---|---|
| SEQ ID NO: 5860 | mm59375_Tspan33 | CGTGCATTATCGAGATGACC |
| SEQ ID NO: 5861 | mm59608_Lrfn3 | CCTAGGCAACGTCAACACGT |
| SEQ ID NO: 5862 | mm59609_Lrfn3 | CCTAAGCGTGTTGTGCCCAG |
| SEQ ID NO: 5863 | mm59610_Lrfn3 | GGTGATACCCAACGCACTCG |
| SEQ ID NO: 5864 | mm59611_Lrfn3 | GCACCAGCTGTGACCCCCCG |
| SEQ ID NO: 5865 | mm59712_Siglech | GATGCACAAAAGGGTGACAA |
| SEQ ID NO: 5866 | mm59713_Siglech | CAAAACATGGAATTTCTGTG |
| SEQ ID NO: 5867 | mm59714_Siglech | GTTCCCCGTTCACAAGCCCA |
| SEQ ID NO: 5868 | mm59715_Siglech | ACTGAGGAGAGTGTGGTCGT |
| SEQ ID NO: 5869 | mm59760_Picalm | CCTCAGGGAGCGAGTACATG |
| SEQ ID NO: 5870 | mm59761_Picalm | TGGCCTATCTCTGACCAAAG |
| SEQ ID NO: 5871 | mm59762_Picalm | AGTTCATTACTATTAACCTA |
| SEQ ID NO: 5872 | mm59763_Picalm | GCCACGACCCACGAGATCAT |
| SEQ ID NO: 5873 | mm59788_Gdpd5 | AGTCGCTCCAGTAGCCCATG |
| SEQ ID NO: 5874 | mm59789_Gdpd5 | CCCCGTGATCACCCCTACCG |
| SEQ ID NO: 5875 | mm59790_Gdpd5 | CTCGCACGATGACACCACGC |
| SEQ ID NO: 5876 | mm59791_Gdpd5 | GAACCTGCACTGGATACACA |
| SEQ ID NO: 5877 | mm59824_Spon1 | TCACTGAAAGCACCCCTCGG |
| SEQ ID NO: 5878 | mm59825_Spon1 | GTCCGAGAAGACTCATCCGA |
| SEQ ID NO: 5879 | mm59826_Spon1 | GAACGTGGGCCTATCTGCAG |
| SEQ ID NO: 5880 | mm59827_Spon1 | AGGTGGGTCCATCACACAAG |
| SEQ ID NO: 5881 | mm59836_Acsm2 | AAACTAATACCCATACAGTG |
| SEQ ID NO: 5882 | mm59837_Acsm2 | CAACATCCGGTAAATGATGG |
| SEQ ID NO: 5883 | mm59838_Acsm2 | GTGTCTGAAAACAGTCGAGA |
| SEQ ID NO: 5884 | mm59839_Acsm2 | CTGTGGTGGATGAATGGCAG |
| SEQ ID NO: 5885 | mm59880_Slc5a11 | CGATGCCAGAATATCTAAGG |
| SEQ ID NO: 5886 | mm59881_Slc5a11 | GCGATGTCTGAACAGCCAGA |
| SEQ ID NO: 5887 | mm59882_Slc5a11 | ATGTGGAAGGCATCTTCTCG |
| SEQ ID NO: 5888 | mm59883_Slc5a11 | CCTGCACAATGGGGATCCAG |
| SEQ ID NO: 5889 | mm59908_Sez6l2 | TATGCTAACACTGTTCGACG |
| SEQ ID NO: 5890 | mm59909_Sez6l2 | GGATACAATGCGACCCAGTG |
| SEQ ID NO: 5891 | mm59910_Sez6l2 | GTCAGAGTCGTAAATCACAG |
| SEQ ID NO: 5892 | mm59911_Sez6l2 | CCACACATTCGATAGCATTG |
| SEQ ID NO: 5893 | mm60040_Gpm6a | GAGGATGTGTGAATCTACTG |
| SEQ ID NO: 5894 | mm60041_Gpm6a | CCGGAACACCACTCTAGTGG |
| SEQ ID NO: 5895 | mm60042_Gpm6a | TGTACATGTATTTCAATGTG |
| SEQ ID NO: 5896 | mm60043_Gpm6a | TGCTTGGATCTGCGTCAGTT |
| SEQ ID NO: 5897 | mm60060_Psd3 | TCTAGACAGATTCAAGAGAT |

TABLE 1-continued mmSurf sgRNA library sequences

| SEQ ID NO | id_gRNA Target | Sequence |
| --- | --- | --- |
| SEQ ID NO: 5898 | mm60061_Psd3 | TAGATGCTGGTTCTGAAATG |
| SEQ ID NO: 5899 | mm60062_Psd3 | TCTCATCAGTACCTTCTGAG |
| SEQ ID NO: 5900 | mm60063_Psd3 | GTTGAGCAGCATCATAGCAC |
| SEQ ID NO: 5901 | mm60292_Spire2 | GTACGAGCAGCCCATCAACG |
| SEQ ID NO: 5902 | mm60293_Spire2 | CTGCATCAGCATCTCGAAGG |
| SEQ ID NO: 5903 | mm60294_Spire2 | GGGACGGTTCGGTTGGCGCG |
| SEQ ID NO: 5904 | mm60295_Spire2 | GGTCGTGTTCCGAAAAGAG |
| SEQ ID NO: 5905 | mm60380_Adamts15 | TAATGACATACTCCGCACCT |
| SEQ ID NO: 5906 | mm60381_Adamts15 | AATGGTCAAGTTTCACGGCG |
| SEQ ID NO: 5907 | mm60382_Adamts15 | CAACGGTGGAAAATACTGCG |
| SEQ ID NO: 5908 | mm60383_Adamts15 | ATGAGCTTACACTTGTCACG |
| SEQ ID NO: 5909 | mm60528_Prtg | GTGTTGCAGATCTACGACGT |
| SEQ ID NO: 5910 | mm60529_Prtg | CGGCTCTCTATACATCAGTG |
| SEQ ID NO: 5911 | mm60530_Prtg | AAATAACGAGGAATATCAGG |
| SEQ ID NO: 5912 | mm60531_Prtg | GCTTGACATCTGATATAATG |
| SEQ ID NO: 5913 | mm60544_Cd109 | ACTGTGACGGAATCACTCAC |
| SEQ ID NO: 5914 | mm60545_Cd109 | AGTCTAATGTGATCCAACAG |
| SEQ ID NO: 5915 | mm60546_Cd109 | TTTGGCTAGACGCCTACATG |
| SEQ ID NO: 5916 | mm60547_Cd109 | CTCAATGAGTATCACAACCT |
| SEQ ID NO: 5917 | mm60604_Plxnb1 | TAAGACCGTAACGACCACCC |
| SEQ ID NO: 5918 | mm60605_Plxnb1 | GCTTCCCGGGCCACACAACG |
| SEQ ID NO: 5919 | mm60606_Plxnb1 | CTTGCTGATACCGGTCCATG |
| SEQ ID NO: 5920 | mm60607_Plxnb1 | GGACGTGAGATATGGGTCCG |
| SEQ ID NO: 5921 | mm60612_Soap | CTGTTGGATGTACGCCACGG |
| SEQ ID NO: 5922 | mm60613_Soap | ATGATGTAGGTGGTCACGAG |
| SEQ ID NO: 5923 | mm60614_Soap | CCTTAGGTCCGGACTCCCAG |
| SEQ ID NO: 5924 | mm60615_Soap | GCGTAGCCGTAGTCATCGCA |
| SEQ ID NO: 5925 | mm60640_Rtp3 | GTACCTCCCTTACCTAGCAA |
| SEQ ID NO: 5926 | mm60641_Rtp3 | TAGGGAACACCAGTCTCGAA |
| SEQ ID NO: 5927 | mm60642_Rtp3 | TTGAGGTACAGCTAATCTTG |
| SEQ ID NO: 5928 | mm60643_Rtp3 | ATGAGGGTCCATTTGTGCCA |
| SEQ ID NO: 5929 | mm60744_Slc9a7 | TACTTACGAGGATAGTACAA |
| SEQ ID NO: 5930 | mm60745_Slc9a7 | CATGAAGGAAACGCACCCGG |
| SEQ ID NO: 5931 | mm60746_Slc9a7 | CAGAAATCTTATGTATGGAG |
| SEQ ID NO: 5932 | mm60747_Slc9a7 | CCCTGGCAAGATCAACAACG |
| SEQ ID NO: 5933 | mm60848_Adgrg2 | GGCTTGCTGGAAGACGATAA |
| SEQ ID NO: 5934 | mm60849_Adgrg2 | GGATGTTCGAGATAGGTCCT |
| SEQ ID NO: 5935 | mm60850_Adgrg2 | GTCTTGGGCTGCAAAAGTCG |

TABLE 1-continued mmSurf sgRNA library sequences

| SEQ ID NO | id_gRNA Target | Sequence |
|---|---|---|
| SEQ ID NO: 5936 | mm60851_Adgrg2 | CAGTTCTGTAGGGACAGATG |
| SEQ ID NO: 5937 | mm60872_Lrp11 | CGGTACGGCGGTCTACCGGG |
| SEQ ID NO: 5938 | mm60873_Lrp11 | CAGTTGAACAGGTAGCAGCG |
| SEQ ID NO: 5939 | mm60874_Lrp11 | TTACACCCTCAGTCGCGCCG |
| SEQ ID NO: 5940 | mm60875_Lrp11 | CTGAAGCAGCCTATCCACTC |
| SEQ ID NO: 5941 | mm60928_Lingo3 | CAGGTGACCCAGCGACTCCG |
| SEQ ID NO: 5942 | mm60929_Lingo3 | GTGTGATGGACAACGACGTG |
| SEQ ID NO: 5943 | mm60930_Lingo3 | GATTGCCCACGTGGAACCTG |
| SEQ ID NO: 5944 | mm60931_Lingo3 | CCCATCAGCATGGTGCCACG |
| SEQ ID NO: 5945 | mm61016_Col23a1 | CCTGGAGCGCCTGTTACGGG |
| SEQ ID NO: 5946 | mm61017_Col23a1 | TGGTAATCGACTATGACGGC |
| SEQ ID NO: 5947 | mm61018_Col23a1 | GGGACTTCCAGGCCCCAAAG |
| SEQ ID NO: 5948 | mm61019_Col23a1 | GCCATCCATCATCCCCCTG |
| SEQ ID NO: 5949 | mm61048_Rtn4rl1 | CCTTCGCAGCCATTCCCACA |
| SEQ ID NO: 5950 | mm61049_Rtn4rl1 | GGGTAGCACACACAGTCTCG |
| SEQ ID NO: 5951 | mm61050_Rtn4rl1 | GCCCTCTACCTCTATAAGTG |
| SEQ ID NO: 5952 | mm61051_Rtn4rl1 | GCATGAGAACCAGCTACAGT |
| SEQ ID NO: 5953 | mm61120_Sdk2 | CCGCTGGAGCGAGATCCCGG |
| SEQ ID NO: 5954 | mm61121_Sdk2 | TGCGCACACACGAGGACGGT |
| SEQ ID NO: 5955 | mm61122_Sdk2 | GGGGCCTCTGGTGATATTAG |
| SEQ ID NO: 5956 | mm61123_Sdk2 | ATGGACCAATTACGAGATCG |
| SEQ ID NO: 5957 | mm61188_Tmem30b | GCTCGTAGTAGAGGTACACG |
| SEQ ID NO: 5958 | mm61189_Tmem30b | CGAGCGGCACCTCGACGAAG |
| SEQ ID NO: 5959 | mm61190_Tmem30b | GAGCTGGAGTACGACTACAC |
| SEQ ID NO: 5960 | mm61191_Tmem30b | CGATAGGCAGACCGTCGGAG |
| SEQ ID NO: 5961 | mm61196_Kcnh5 | ACTCGTATTGTAGCGATATG |
| SEQ ID NO: 5962 | mm61197_Kcnh5 | ATAGAGGATGACTCAACGAA |
| SEQ ID NO: 5963 | mm61198_Kcnh5 | ATACATTTGCTGGAAAATTG |
| SEQ ID NO: 5964 | mm61199_Kcnh5 | ATTGGCACACGCATGAGCAA |
| SEQ ID NO: 5965 | mm61232_Slc24a4 | TCTCATCCACCATAACCACG |
| SEQ ID NO: 5966 | mm61233_Slc24a4 | ACCCACGGAGATGTCGGTGT |
| SEQ ID NO: 5967 | mm61234_Slc24a4 | TCTGTGCAGTTCTTAGCCAG |
| SEQ ID NO: 5968 | mm61235_Slc24a4 | AAACGGGAGACATGAGAACA |
| SEQ ID NO: 5969 | mm61252_Adam6a | TCTCATGACTGTGTATACCG |
| SEQ ID NO: 5970 | mm61253_Adam6a | TAGGCCTAAAACATGATGAG |
| SEQ ID NO: 5971 | mm61254_Adam6a | TCTGTATATAGTGCTTCTGG |
| SEQ ID NO: 5972 | mm61255_Adam6a | ATGCTGTTAATCCAGCTGAG |
| SEQ ID NO: 5973 | mm61268_Btn2a2 | GGCAACCATGAAGCTTATGG |

TABLE 1-continued mmSurf sgRNA library sequences

| SEQ ID NO | id_gRNA Target | Sequence |
|---|---|---|
| SEQ ID NO: 5974 | mm61269_Btn2a2 | GAGCAGATGGTGGCATACCG |
| SEQ ID NO: 5975 | mm61270_Btn2a2 | TGGTCCTATGACAGTAAACT |
| SEQ ID NO: 5976 | mm61271_Btn2a2 | CAGGTACAACTTCATCATAG |
| SEQ ID NO: 5977 | mm61336_Pde4d | TCACATCTGCAGACTCAAGT |
| SEQ ID NO: 5978 | mm61337_Pde4d | CTGCTATTCGGAAAACGTGG |
| SEQ ID NO: 5979 | mm61338_Pde4d | ATGGATGGTTGGTTGCACAT |
| SEQ ID NO: 5980 | mm61339_Pde4d | GGTCATAGTCGCTGTCAGAT |
| SEQ ID NO: 5981 | mm61440_Slitrk6 | TTTGTATCTTGAGTACAATG |
| SEQ ID NO: 5982 | mm61441_Slitrk6 | CCAATTGGAGGACAATAAGT |
| SEQ ID NO: 5983 | mm61442_Slitrk6 | CTTAAGTGGAAAGGTCGTGA |
| SEQ ID NO: 5984 | mm61443_Slitrk6 | ATGTATTCTTGCTTGATAGG |
| SEQ ID NO: 5985 | mm61480_Rspo2 | AGAACAACTTCTGTTGACAT |
| SEQ ID NO: 5986 | mm61481_Rspo2 | GGTGTCCATAATACCCTGAT |
| SEQ ID NO: 5987 | mm61482_Rspo2 | CATTCCATAGTCTCATCTAA |
| SEQ ID NO: 5988 | mm61483_Rspo2 | GTTGGTCATTGGAGCGAATG |
| SEQ ID NO: 5989 | mm61552_Slc2a13 | CATGGCCCCGACACCACGC |
| SEQ ID NO: 5990 | mm61553_Slc2a13 | CCTCGGTGGCTGATTCAGAA |
| SEQ ID NO: 5991 | mm61554_Slc2a13 | CACATCCCACAACTAACGCT |
| SEQ ID NO: 5992 | mm61555_Slc2a13 | AAGGATAATCAGTGCTACTG |
| SEQ ID NO: 5993 | mm61608_Rtp1 | TGGAAGAGGATGACTACATG |
| SEQ ID NO: 5994 | mm61609_Rtp1 | GCTACGAGTGCGGTACAGCA |
| SEQ ID NO: 5995 | mm61610_Rtp1 | ATGTGTAAGAGTGTGACCAC |
| SEQ ID NO: 5996 | mm61611_Rtp1 | CTACACTTTATAGAGAACGT |
| SEQ ID NO: 5997 | mm61640_Cd200r4 | TAAATGCAGTATTAATCACA |
| SEQ ID NO: 5998 | mm61641_Cd200r4 | TGAACTTCAGATCAGTGCAG |
| SEQ ID NO: 5999 | mm61642_Cd200r4 | AGTTCATCTTCTCTGACACA |
| SEQ ID NO: 6000 | mm61643_Cd200r4 | CTGAGGTAACCTACTTTCCA |
| SEQ ID NO: 6001 | mm61652_Cadm2 | GACGAAAATCCACTAATCTG |
| SEQ ID NO: 6002 | mm61653_Cadm2 | CCGCCACTCCATCATCGCTA |
| SEQ ID NO: 6003 | mm61654_Cadm2 | TCCACTAACTCAGAATGTCA |
| SEQ ID NO: 6004 | mm61655_Cadm2 | ATGATAACACCTCCCTCCAG |
| SEQ ID NO: 6005 | mm61680_Lnpep | ATATTGGAATATGCCAAAGG |
| SEQ ID NO: 6006 | mm61681_Lnpep | TCCTGTTAGAAGAGGTTCCG |
| SEQ ID NO: 6007 | mm61682_Lnpep | TGTGAAAATGAGCACATACC |
| SEQ ID NO: 6008 | mm61683_Lnpep | TGCAGTGGTGGAATGACCTG |
| SEQ ID NO: 6009 | mm61696_Mmp25 | AGAAACGCACCCTGACATGG |
| SEQ ID NO: 6010 | mm61697_Mmp25 | ATCAGGCCTTACATTCCAGG |
| SEQ ID NO: 6011 | mm61698_Mmp25 | CGTTCAGCTTGGACGGACCG |

TABLE 1-continued mmSurf sgRNA library sequences

| SEQ ID NO | id_gRNA Target | Sequence |
|---|---|---|
| SEQ ID NO: 6012 | mm61699_Mmp25 | CTGAGACTGGACAAATGGGT |
| SEQ ID NO: 6013 | mm61920_Sulf1 | CAGTTGACGACTCTGTCGAG |
| SEQ ID NO: 6014 | mm61921_Sulf1 | AGAAATACGTACATCGACCC |
| SEQ ID NO: 6015 | mm61922_Sulf1 | GCACGCAACCTCTACTCTCG |
| SEQ ID NO: 6016 | mm61923_Sulf1 | CTGGCGTGATACATTCCTAG |
| SEQ ID NO: 6017 | mm61956_Tor1aip2 | AGTGCCCTAGTTCTAAACTA |
| SEQ ID NO: 6018 | mm61957_Tor1aip2 | TAATACGGTCTAAGAACACT |
| SEQ ID NO: 6019 | mm61958_Tor1aip2 | TTCTATTAGCAGGATTGTCA |
| SEQ ID NO: 6020 | mm61959_Tor1aip2 | ATTCACACTGCCCTGATTGT |
| SEQ ID NO: 6021 | mm61968_Tnfsf18 | GTGTGAATACGACATCTGAT |
| SEQ ID NO: 6022 | mm61969_Tnfsf18 | ATATATCTGTACTACGAAGG |
| SEQ ID NO: 6023 | mm61970_Tnfsf18 | CTACGGCCAAGTGATTCCTG |
| SEQ ID NO: 6024 | mm61971_Tnfsf18 | CTCACCAAACTTAACCATGC |
| SEQ ID NO: 6025 | mm62004_Pgap1 | ATAGACAACAATATGCGACA |
| SEQ ID NO: 6026 | mm62005_Pgap1 | ATATGTAACTTACCACACGA |
| SEQ ID NO: 6027 | mm62006_Pgap1 | AGAATTTGCTCCTACAAGTG |
| SEQ ID NO: 6028 | mm62007_Pgap1 | GTCGTCAGACTGTCAGTATG |
| SEQ ID NO: 6029 | mm62068_Itga8 | CAGCCGGATATCGTAGAAGG |
| SEQ ID NO: 6030 | mm62069_Itga8 | TTTGCAGGCAAGGATCAACG |
| SEQ ID NO: 6031 | mm62070_Itga8 | ATATACTTACTGTTTCGACA |
| SEQ ID NO: 6032 | mm62071_Itga8 | AATTCTCGCTCCATAAAGAG |
| SEQ ID NO: 6033 | mm62076_Gpr158 | GGCACAAAAACTAGCCGAGG |
| SEQ ID NO: 6034 | mm62077_Gpr158 | TTGTTCACTGAGAAGACACG |
| SEQ ID NO: 6035 | mm62078_Gpr158 | CTGCTGTCATGTAATCCCAG |
| SEQ ID NO: 6036 | mm62079_Gpr158 | GATGCGACTCTCCTCGCGGG |
| SEQ ID NO: 6037 | mm62092_Lrrc8a | TCGACACCAGTACAACTACG |
| SEQ ID NO: 6038 | mm62093_Lrrc8a | CTCGTTCGAGTCGATCCGAG |
| SEQ ID NO: 6039 | mm62094_Lrrc8a | ACGGATTGAGCAGGGCATCG |
| SEQ ID NO: 6040 | mm62095_Lrrc8a | GATGTTGTGCACATAGTAGA |
| SEQ ID NO: 6041 | mm62112_Crb2 | GACTGCCCGAGACCTTACCG |
| SEQ ID NO: 6042 | mm62113_Crb2 | AAGGCCCATAGGTCCCCGGT |
| SEQ ID NO: 6043 | mm62114_Crb2 | TCTGACCCGACCTTGTACGG |
| SEQ ID NO: 6044 | mm62115_Crb2 | ACTCTCGAGACATGGCACTG |
| SEQ ID NO: 6045 | mm62168_Tspan18 | GAGCTTACCAAGCACTACCA |
| SEQ ID NO: 6046 | mm62169_Tspan18 | CGTCAGCAGCCGAAACACGG |
| SEQ ID NO: 6047 | mm62170_Tspan18 | GATCATGACTGAATTCCAGG |
| SEQ ID NO: 6048 | mm62171_Tspan18 | TGGCTGCTGAGAGCTCTACC |
| SEQ ID NO: 6049 | mm62280_Frem2 | AATTTCCTACTGGAATAGCG |

TABLE 1-continued mmSurf sgRNA library sequences

| SEQ ID NO | id_gRNA Target | Sequence |
|---|---|---|
| SEQ ID NO: 6050 | mm62281_Frem2 | TTGGAGTGCACGGATCGAAG |
| SEQ ID NO: 6051 | mm62282_Frem2 | GGTCGAGCTGCATTCGCGAG |
| SEQ ID NO: 6052 | mm62283_Frem2 | TGGGAGAACCCAGAATAACA |
| SEQ ID NO: 6053 | mm62288_Igsf10 | ATAGAGACTTAACACATCGA |
| SEQ ID NO: 6054 | mm62289_Igsf10 | TCAGGACGTGAAATATCCCG |
| SEQ ID NO: 6055 | mm62290_Igsf10 | ACAGGTTCGGCACATCCCAG |
| SEQ ID NO: 6056 | mm62291_Igsf10 | GTTGTGATCCAGGTGCAACC |
| SEQ ID NO: 6057 | mm62292_Ppm1l | GTCCCGGCTAGACTTAACGA |
| SEQ ID NO: 6058 | mm62293_Ppm1l | TCCCCGAGAGTCACCAACGT |
| SEQ ID NO: 6059 | mm62294_Ppm1l | CTTCGAAGCGATCTTCCATG |
| SEQ ID NO: 6060 | mm62295_Ppm1l | GCAGATCTTGTCAATTGACC |
| SEQ ID NO: 6061 | mm62308_Vtcn1 | AAAGCCAATGATGAGTGCGA |
| SEQ ID NO: 6062 | mm62309_Vtcn1 | GGTGCGGATGTAACATGTGT |
| SEQ ID NO: 6063 | mm62310_Vtcn1 | AACCTTGAGTATAAGACCGG |
| SEQ ID NO: 6064 | mm62311_Vtcn1 | TCAACGGCATCGTCATCCAG |
| SEQ ID NO: 6065 | mm62324_Pde5a | AACCCTCTGATCCTTTAACG |
| SEQ ID NO: 6066 | mm62325_Pde5a | TCAACTTCTGCATTGAACCG |
| SEQ ID NO: 6067 | mm62326_Pde5a | TCATCACTATCAAATCTTGG |
| SEQ ID NO: 6068 | mm62327_Pde5a | TGGCAAGGTCAAGTAACACC |
| SEQ ID NO: 6069 | mm62356_Impad1 | ATTCCTGTGTAGCATCAAGT |
| SEQ ID NO: 6070 | mm62357_Impad1 | TCCTTCACGAGAAGTCCAAG |
| SEQ ID NO: 6071 | mm62358_Impad1 | CTCCCACTAGATAAATACTG |
| SEQ ID NO: 6072 | mm62359_Impad1 | GCTTGGGCAATGGTAGATGG |
| SEQ ID NO: 6073 | mm62392_Tmem8b | GAATCCATAGGTGAGCGCGT |
| SEQ ID NO: 6074 | mm62393_Tmem8b | CAGCACGTATCGGCTCCGAA |
| SEQ ID NO: 6075 | mm62394_Tmem8b | ATTCGGATGCCTGACTCATG |
| SEQ ID NO: 6076 | mm62395_Tmem8b | GCCCAGCTGTATTTGCCCTG |
| SEQ ID NO: 6077 | mm62400_Gabbr2 | CCTGCGACTCTACGACACCG |
| SEQ ID NO: 6078 | mm62401_Gabbr2 | CATGGAAGGCTACATCGGAG |
| SEQ ID NO: 6079 | mm62402_Gabbr2 | GCTGACAGGATGCTATACAG |
| SEQ ID NO: 6080 | mm62403_Gabbr2 | CTTATCCGCAAGAACAGGCG |
| SEQ ID NO: 6081 | mm62696_Elfn1 | CTACATTGAAGTGCGCACGG |
| SEQ ID NO: 6082 | mm62697_Elfn1 | GTTTCCGAAGCGGCTCAGGG |
| SEQ ID NO: 6083 | mm62698_Elfn1 | CACCAACTACACATACTGCG |
| SEQ ID NO: 6084 | mm62699_Elfn1 | CCTACAGGCCAACCTCATCG |
| SEQ ID NO: 6085 | mm62700_Slc29a4 | GCTGTTGCACCGATACGTCG |
| SEQ ID NO: 6086 | mm62701_Slc29a4 | ACTGCCCAAGAGGTACACGC |
| SEQ ID NO: 6087 | mm62702_Slc29a4 | GTGGTGAAGATAGTCGACAT |

TABLE 1-continued mmSurf sgRNA library sequences

| SEQ ID NO | id_gRNA Target | Sequence |
|---|---|---|
| SEQ ID NO: 6088 | mm62703_Slc29a4 | TGTGCTCCTAAACAACGTTG |
| SEQ ID NO: 6089 | mm62704_Tmem130 | TCTAACCTCGACCATCCACG |
| SEQ ID NO: 6090 | mm62705_Tmem130 | TCAGCATCGTTGGATCTGCG |
| SEQ ID NO: 6091 | mm62706_Tmem130 | GTTGATAACTGACAACCCTG |
| SEQ ID NO: 6092 | mm62707_Tmem130 | GCTGACGGTCCTGCTACCGT |
| SEQ ID NO: 6093 | mm62788_Slc6a11 | CTCCCAGAACTCCATGACCG |
| SEQ ID NO: 6094 | mm62789_Slc6a11 | AGGCATTGGCTATGCAACAC |
| SEQ ID NO: 6095 | mm62790_Slc6a11 | GTTGTTGTAACTCCCCAGAG |
| SEQ ID NO: 6096 | mm62791_Slc6a11 | GGGTACTAAGTCGACTGGAA |
| SEQ ID NO: 6097 | mm62808_Klre1 | AGCCATCAGGAGAAGGCACA |
| SEQ ID NO: 6098 | mm62809_Klre1 | CAGACCCAGTTCTCTGGACA |
| SEQ ID NO: 6099 | mm62810_Klre1 | AATTGTCATCCATTGAGCAG |
| SEQ ID NO: 6100 | mm62811_Klre1 | CTCACACTTTGTGGTAAAAG |
| SEQ ID NO: 6101 | mm62820_Plxna4 | GAAGGAACATTATCTCTCGG |
| SEQ ID NO: 6102 | mm62821_Plxna4 | GCCACACTCGAAATCCGGGT |
| SEQ ID NO: 6103 | mm62822_Plxna4 | ACATGATGTAGAGTTGCTCG |
| SEQ ID NO: 6104 | mm62823_Plxna4 | CATTGGCTGTGAGCGCAATG |
| SEQ ID NO: 6105 | mm62844_Gp6 | CGATATAAATCCACATCTGG |
| SEQ ID NO: 6106 | mm62845_Gp6 | TGATGATGGGGAAATTGGCC |
| SEQ ID NO: 6107 | mm62846_Gp6 | CCAGTAACCACAAGCACTAG |
| SEQ ID NO: 6108 | mm62847_Gp6 | TTAGCTCAAGCTGGTCACTT |
| SEQ ID NO: 6109 | mm62872_Fkrp | GCTGGACTTGACCTTCGCCG |
| SEQ ID NO: 6110 | mm62873_Fkrp | CCAATGGCAGAAGTCCGGCG |
| SEQ ID NO: 6111 | mm62874_Fkrp | CCATCCAAAGCGTCGCAGCG |
| SEQ ID NO: 6112 | mm62875_Fkrp | CACAAACTCGGTGGCTACGT |
| SEQ ID NO: 6113 | mm62880_Mill2 | AGGAAGCGAGGTATCTCTGG |
| SEQ ID NO: 6114 | mm62881_Mill2 | TGTCAGAGCCCATTCTCTGG |
| SEQ ID NO: 6115 | mm62882_Mill2 | CCCTTAATCCAGCATCCCAA |
| SEQ ID NO: 6116 | mm62883_Mill2 | CTGCTCCTTAGAGACTCACG |
| SEQ ID NO: 6117 | mm62980_Rgma | ACCATCGTGGTGCGACAGGT |
| SEQ ID NO: 6118 | mm62981_Rgma | ACAGAACTCCGGCACGTCGT |
| SEQ ID NO: 6119 | mm62982_Rgma | GAGGGTCGGCCACAATCCCA |
| SEQ ID NO: 6120 | mm62983_Rgma | AGGTAATTATTGTCGATGAG |
| SEQ ID NO: 6121 | mm63056_5830411N06Rik | TCAGGTGTCAAAACATACCG |
| SEQ ID NO: 6122 | mm63057_5830411N06Rik | CCTTCAATCTTACACCCAGG |
| SEQ ID NO: 6123 | mm63058_5830411N06Rik | GCCATAAGACCATTCCTGTG |
| SEQ ID NO: 6124 | mm63059_5830411N06Rik | GTGGTACCACACTACAAATG |
| SEQ ID NO: 6125 | mm63060_Tnfrsf26 | ACTCTGAAAACTGTTTGGAG |

TABLE 1-continued mmSurf sgRNA library sequences

| SEQ ID NO | id_gRNA Target | Sequence |
| --- | --- | --- |
| SEQ ID NO: 6126 | mm63061_Tnfrsf26 | GAACTCACCAATCTTACACA |
| SEQ ID NO: 6127 | mm63062_Tnfrsf26 | AGTAGGTGCCCTGCTTACAC |
| SEQ ID NO: 6128 | mm63063_Tnfrsf26 | TCTCCTGGCATGGATTCCGG |
| SEQ ID NO: 6129 | mm63164_Pkd1l3 | GCGACTTCTTCATCGTGCCG |
| SEQ ID NO: 6130 | mm63165_Pkd1l3 | AAGTGGAGCGTCATTAGGAG |
| SEQ ID NO: 6131 | mm63166_Pkd1l3 | GCTGACGAGCAGCTCCGACA |
| SEQ ID NO: 6132 | mm63167_Pkd1l3 | GTTGTTGTTAGACGTCCAAG |
| SEQ ID NO: 6133 | mm63188_Sipa1l2 | TTCAGAACGGTTATCCACGG |
| SEQ ID NO: 6134 | mm63189_Sipa1l2 | CATCAGTGATATCGATACGG |
| SEQ ID NO: 6135 | mm63190_Sipa1l2 | AGTTATCATCCAGCCCCACG |
| SEQ ID NO: 6136 | mm63191_Sipa1l2 | GTCGCAGTTCAACTACAGGG |
| SEQ ID NO: 6137 | mm63220_Olfm2 | GAGAGCCATTGTATACCACA |
| SEQ ID NO: 6138 | mm63221_Olfm2 | GGACTTGCAACAGCGCGTGA |
| SEQ ID NO: 6139 | mm63222_Olfm2 | CAGTAACCCTATTACCATCC |
| SEQ ID NO: 6140 | mm63223_Olfm2 | GCAGCTTTATACGTCAGCCC |
| SEQ ID NO: 6141 | mm63308_Col6a6 | TGCGTCATGAGATTCCCCGT |
| SEQ ID NO: 6142 | mm63309_Col6a6 | ATGGGCAGCAGGATCAACGC |
| SEQ ID NO: 6143 | mm63310_Col6a6 | TGAGGCTCAGGACATAGTAA |
| SEQ ID NO: 6144 | mm63311_Col6a6 | ATGGGTGGGAATACCAACAC |
| SEQ ID NO: 6145 | mm63388_Slitrk4 | AAGCAAGAACTATGCCCCAT |
| SEQ ID NO: 6146 | mm63389_Slitrk4 | AGATGATAGAAATTAGACCA |
| SEQ ID NO: 6147 | mm63390_Slitrk4 | CTTTAATGCTACCAAGTCGC |
| SEQ ID NO: 6148 | mm63391_Slitrk4 | TTAATCAAGTATATTGAACG |
| SEQ ID NO: 6149 | mm63392_Slitrk2 | CTGACTCACTTAGACCTGAG |
| SEQ ID NO: 6150 | mm63393_Slitrk2 | CAAACTGGAGGTATTGCGAG |
| SEQ ID NO: 6151 | mm63394_Slitrk2 | GAGGTTAATCAAAGCATCAA |
| SEQ ID NO: 6152 | mm63395_Slitrk2 | CTGATAGATGCGATACTGGG |
| SEQ ID NO: 6153 | mm63404_Dkc1 | TTTACTGCAGCAATAAGTGG |
| SEQ ID NO: 6154 | mm63405_Dkc1 | TCTCTACCCGAAGTATTCGT |
| SEQ ID NO: 6155 | mm63406_Dkc1 | TACGCATAGTGTCCGAATGT |
| SEQ ID NO: 6156 | mm63407_Dkc1 | ATGATGTACTCGATGCTCAG |
| SEQ ID NO: 6157 | mm63428_Eda2r | CTACCGAAAGACACGCATTG |
| SEQ ID NO: 6158 | mm63429_Eda2r | CCCTGGACAGGAGCTCTCGA |
| SEQ ID NO: 6159 | mm63430_Eda2r | ACAAGTGTGGCTTCCCTAGG |
| SEQ ID NO: 6160 | mm63431_Eda2r | ACACACTGAACCTCGGAAGA |
| SEQ ID NO: 6161 | mm63556_Atg9a | AGATAAACTTGATAAGCCGG |
| SEQ ID NO: 6162 | mm63557_Atg9a | CTCGGCTTGCTGGTACACTG |
| SEQ ID NO: 6163 | mm63558_Atg9a | CTTCATCCCAGACCAGCACA |

TABLE 1-continued mmSurf sgRNA library sequences

| SEQ ID NO | id_gRNA Target | Sequence |
|---|---|---|
| SEQ ID NO: 6164 | mm63559_Atg9a | AGGCCGAGTACAAACGTGGA |
| SEQ ID NO: 6165 | mm63620_Defb15 | AGAAATGCAGCAGGGTTAAT |
| SEQ ID NO: 6166 | mm63621_Defb15 | GTTCTCTTCTTTCTGGACCC |
| SEQ ID NO: 6167 | mm63622_Defb15 | CACAGCACTTCAGATTCTTC |
| SEQ ID NO: 6168 | mm63623_Defb15 | GAGAAATGCAGCAGGGTTAA |
| SEQ ID NO: 6169 | mm63624_Defb13 | CTTCTCATTCAACTTTACCC |
| SEQ ID NO: 6170 | mm63625_Defb13 | TAAAGCACTCAGCTTCACAT |
| SEQ ID NO: 6171 | mm63626_Defb13 | CCTGGGGCACATTGTACAGA |
| SEQ ID NO: 6172 | mm63627_Defb13 | TTCCTCTGTAAAAAGATGAA |
| SEQ ID NO: 6173 | mm63628_Defb35 | CAAAAAACAAAAAACGTCTG |
| SEQ ID NO: 6174 | mm63629_Defb35 | GCAGCTCTTTCCTGGCACAG |
| SEQ ID NO: 6175 | mm63630_Defb35 | TTGCTGTGTGCGAGACATGC |
| SEQ ID NO: 6176 | mm63631_Defb35 | GAGACATGCAGGCTCGGCCG |
| SEQ ID NO: 6177 | mm63652_Kcne2 | TGAGCACGGTGAAGTCGAAG |
| SEQ ID NO: 6178 | mm63653_Kcne2 | CGGCATGTTCTCGTTCATCG |
| SEQ ID NO: 6179 | mm63654_Kcne2 | ACATGCCGATCATCACCATG |
| SEQ ID NO: 6180 | mm63655_Kcne2 | TTATTACTTATATGGACAGC |
| SEQ ID NO: 6181 | mm63656_Vasn | TGGGGCAGTCGATAGTACGG |
| SEQ ID NO: 6182 | mm63657_Vasn | AGACCTTATAGTAGGTACTG |
| SEQ ID NO: 6183 | mm63658_Vasn | TATTGCCCAGATACGGCCCG |
| SEQ ID NO: 6184 | mm63659_Vasn | ACATGGTTCTCACGCACCCA |
| SEQ ID NO: 6185 | mm63668_Otoa | TGCTACTTCAGGCATCGCGG |
| SEQ ID NO: 6186 | mm63669_Otoa | GAAGGCATTTCATGGCGGTG |
| SEQ ID NO: 6187 | mm63670_Otoa | GAGCTGAAGTCTGGTCATAG |
| SEQ ID NO: 6188 | mm63671_Otoa | GCTGTTCCAGCTTTGACGTG |
| SEQ ID NO: 6189 | mm63692_Fcgr4 | ACTTGATAGAATTGTCCTCG |
| SEQ ID NO: 6190 | mm63693_Fcgr4 | TATGGACCTCTAGTTGCACT |
| SEQ ID NO: 6191 | mm63694_Fcgr4 | GCAAAACAGACCTGTACGGA |
| SEQ ID NO: 6192 | mm63695_Fcgr4 | GGTGAACCTAGACCCCAAGT |
| SEQ ID NO: 6193 | mm63732_Defb19 | TGGGTAACAGAGGATTCTGT |
| SEQ ID NO: 6194 | mm63733_Defb19 | GCAACGGAACTGGTCGTGTC |
| SEQ ID NO: 6195 | mm63734_Defb19 | TTACCCATGCATTGAAGGAT |
| SEQ ID NO: 6196 | mm63735_Defb19 | CAGTTCCGTTGCCACAAGTA |
| SEQ ID NO: 6197 | mm63740_Emilin2 | CTCCCCGACTTACACCAGGG |
| SEQ ID NO: 6198 | mm63741_Emilin2 | TGAATCACTCCGAATGTACG |
| SEQ ID NO: 6199 | mm63742_Emilin2 | CGGAGTGATAGAGCTGATCG |
| SEQ ID NO: 6200 | mm63743_Emilin2 | GCTGGATCTCCAGTCCACCG |
| SEQ ID NO: 6201 | mm63876_Cables2 | GGGTATATACCTCTGCACCG |

TABLE 1-continued mmSurf sgRNA library sequences

| SEQ ID NO | id_gRNA Target | Sequence |
|---|---|---|
| SEQ ID NO: 6202 | mm63877_Cables2 | TCTGCCTACAGGAAGCGACG |
| SEQ ID NO: 6203 | mm63878_Cables2 | GTATAACCAGAGCATTAGTA |
| SEQ ID NO: 6204 | mm63879_Cables2 | AAGCAGAGGCACCCATCCGG |
| SEQ ID NO: 6205 | mm63884_Tpcn1 | AGAAACACGAGGTAACTCCA |
| SEQ ID NO: 6206 | mm63885_Tpcn1 | CCTCGATGAACTGCACCACG |
| SEQ ID NO: 6207 | mm63886_Tpcn1 | CAAGCCCCGGATGAGTGCAA |
| SEQ ID NO: 6208 | mm63887_Tpcn1 | CTGGGAGATGAATTATCAAG |
| SEQ ID NO: 6209 | mm63896_Nod2 | CCGACCCATCGTAAGTACTG |
| SEQ ID NO: 6210 | mm63897_Nod2 | AGATGCCGACACCATACTGG |
| SEQ ID NO: 6211 | mm63898_Nod2 | GCAGAGTCTGGACTGACGTG |
| SEQ ID NO: 6212 | mm63899_Nod2 | GTTGTAGAGTCTCCTCACAA |
| SEQ ID NO: 6213 | mm67724_Cadm4 | GTGGATCGCAAGGACGACGG |
| SEQ ID NO: 6214 | mm67725_Cadm4 | GAGCGTGGCGATCTGATGGT |
| SEQ ID NO: 6215 | mm67726_Cadm4 | TCGTCATTCAGAACCCAGCC |
| SEQ ID NO: 6216 | mm67727_Cadm4 | ACAGACCGAGAATGTGACTG |
| SEQ ID NO: 6217 | mm67784_Ly6g5b | GCTGTCCACAGCCCCGTACG |
| SEQ ID NO: 6218 | mm67785_Ly6g5b | CAGAAATGCAGCCTAGCGAA |
| SEQ ID NO: 6219 | mm67786_Ly6g5b | TAGATGGTGATCACCATACA |
| SEQ ID NO: 6220 | mm67787_Ly6g5b | AGCACCAGAGCACCCTGCGT |
| SEQ ID NO: 6221 | mm67788_Defb36 | CTCGTGTCCCAGCTCACTCC |
| SEQ ID NO: 6222 | mm67789_Defb36 | GAGTGAGCTGGGACACGAGC |
| SEQ ID NO: 6223 | mm67790_Defb36 | CAGAAATGCTGGAATCTCCA |
| SEQ ID NO: 6224 | mm67791_Defb36 | CCGCCACCGATGCTCCAGGA |
| SEQ ID NO: 6225 | mm67816_Mill1 | GGGTGACAACCAAAGACTGG |
| SEQ ID NO: 6226 | mm67817_Mill1 | GACCTTCAGGAACTATCCAG |
| SEQ ID NO: 6227 | mm67818_Mill1 | CTCATCATCGAAGTATCTCA |
| SEQ ID NO: 6228 | mm67819_Mill1 | GAAGACTCTCACATGGACAG |
| SEQ ID NO: 6229 | mm67820_Rps15a | CTCACCGTGCTTCATCATCA |
| SEQ ID NO: 6230 | mm67821_Rps15a | CCTCACAGGAAGGTTGAACA |
| SEQ ID NO: 6231 | mm67822_Rps15a | CTTTAGAACATGGCCTGATG |
| SEQ ID NO: 6232 | mm67823_Rps15a | ATCAACAACGCTGAGAAGAG |
| SEQ ID NO: 6233 | mm67896_Rab11fip4 | CCACGCGTAGAAAGCCGTCG |
| SEQ ID NO: 6234 | mm67897_Rab11fip4 | CGCCTCTCTTATCAGCAACG |
| SEQ ID NO: 6235 | mm67898_Rab11fip4 | GGCATGTCGCATCTTCCTTG |
| SEQ ID NO: 6236 | mm67899_Rab11fip4 | GAACGACAGCCTGACGAGCG |
| SEQ ID NO: 6237 | mm67932_Mgat5b | GGAGCCAGCGTACAACCACG |
| SEQ ID NO: 6238 | mm67933_Mgat5b | TCTCATAGTACACGGTACCG |
| SEQ ID NO: 6239 | mm67934_Mgat5b | GGCAGCCTTGGTCCACTGTG |

TABLE 1-continued mmSurf sgRNA library sequences

| SEQ ID NO | id_gRNA Target | Sequence |
|---|---|---|
| SEQ ID NO: 6240 | mm67935_Mgat5b | TGGCCTGGATCCTTTCAATG |
| SEQ ID NO: 6241 | mm67960_Serpina5 | AAGGCTAAAGAGTCCTCGGT |
| SEQ ID NO: 6242 | mm67961_Serpina5 | ATTTACCACTATCATGACAT |
| SEQ ID NO: 6243 | mm67962_Serpina5 | GACCCCAAAAGGACCACAC |
| SEQ ID NO: 6244 | mm67963_Serpina5 | AACTCATAGACACGCTCAAG |
| SEQ ID NO: 6245 | mm67988_Slc38a9 | GAGACTTGACCATTGCCCAA |
| SEQ ID NO: 6246 | mm67989_Slc38a9 | TACTCACATAGTAACTAAGC |
| SEQ ID NO: 6247 | mm67990_Slc38a9 | TTCACATTGACAATGTTGGT |
| SEQ ID NO: 6248 | mm67991_Slc38a9 | TGTTCGCTTAGGATTCCATC |
| SEQ ID NO: 6249 | mm68028_Egflam | CGGTCACACAACGTCCCGGT |
| SEQ ID NO: 6250 | mm68029_Egflam | GTGTCAATGACTACGCCTGG |
| SEQ ID NO: 6251 | mm68030_Egflam | AGAGCAACAGGGACAAACCG |
| SEQ ID NO: 6252 | mm68031_Egflam | CACAGAGTAGGACTGAATTG |
| SEQ ID NO: 6253 | mm68100_Scube3 | CGAGTGCCGCTTAAACAACG |
| SEQ ID NO: 6254 | mm68101_Scube3 | CTGCAAGTCCGGCTACACGG |
| SEQ ID NO: 6255 | mm68102_Scube3 | TTGACGTGGCAGCCGCACCG |
| SEQ ID NO: 6256 | mm68103_Scube3 | GAATGTAGCATCAATAAGGG |
| SEQ ID NO: 6257 | mm68124_Ltbp1 | GGGTACCGGATGTCACGGAG |
| SEQ ID NO: 6258 | mm68125_Ltbp1 | CCACACTGGTCGCATCAAGG |
| SEQ ID NO: 6259 | mm68126_Ltbp1 | GGGCAGTGCAGAAATACCGA |
| SEQ ID NO: 6260 | mm68127_Ltbp1 | ATGAATAGTTGAAACCCCTG |
| SEQ ID NO: 6261 | mm68176_Dpp10 | TACAGTGCTCCAGTAAACCG |
| SEQ ID NO: 6262 | mm68177_Dpp10 | GAGAACATACTTTAAATCTG |
| SEQ ID NO: 6263 | mm68178_Dpp10 | AGAAACAAGACTGTCACTAG |
| SEQ ID NO: 6264 | mm68179_Dpp10 | TGGTAGATTCACAGAGTGTG |
| SEQ ID NO: 6265 | mm68184_Nfasc | CGAGCGGTACCGAACCAGTG |
| SEQ ID NO: 6266 | mm68185_Nfasc | GGAAAACCTAGACCCCGTCG |
| SEQ ID NO: 6267 | mm68186_Nfasc | TGCCACTCCGAAGATCGTCA |
| SEQ ID NO: 6268 | mm68187_Nfasc | TGATCCTTTATAACCGGACA |
| SEQ ID NO: 6269 | mm68236_Acvr1c | GACTAAGAGACACAACGTGG |
| SEQ ID NO: 6270 | mm68237_Acvr1c | TGAGAGATCTTGGTTCCGTG |
| SEQ ID NO: 6271 | mm68238_Acvr1c | CCTGAGCATTTAGTTCCGGG |
| SEQ ID NO: 6272 | mm68239_Acvr1c | CGTAGGAAAGGTCGGTTTG |
| SEQ ID NO: 6273 | mm68240_Rtn4rl2 | TGCAGAGCATAGGACAGCTG |
| SEQ ID NO: 6274 | mm68241_Rtn4rl2 | GAACTCGAGCGCCGGCAGGT |
| SEQ ID NO: 6275 | mm68242_Rtn4rl2 | CACCCAGGATGACTTGTTCG |
| SEQ ID NO: 6276 | mm68243_Rtn4rl2 | CTCACGGAGCACGTGTTCCG |
| SEQ ID NO: 6277 | mm68244_Muc15 | TCATTTCATTACCATTTGCG |

TABLE 1-continued mmSurf sgRNA library sequences

| SEQ ID NO | id_gRNA Target | Sequence |
|---|---|---|
| SEQ ID NO: 6278 | mm68245_Muc15 | GGGAGGAACAGAATATGTGG |
| SEQ ID NO: 6279 | mm68246_Muc15 | GAATGTTCGGAGACCTGTAA |
| SEQ ID NO: 6280 | mm68247_Muc15 | AAGGTTGTAGATAAATTCAA |
| SEQ ID NO: 6281 | mm68260_Slc28a2 | TCTTGAGCAAAGATACACAC |
| SEQ ID NO: 6282 | mm68261_Slc28a2 | TGGACAAGGCAAGTGCACAA |
| SEQ ID NO: 6283 | mm68262_Slc28a2 | AGAGAGTCCTACGAACACCC |
| SEQ ID NO: 6284 | mm68263_Slc28a2 | TGGTTCCTGCAAATTACCAT |
| SEQ ID NO: 6285 | mm68264_Slc4a11 | ATCCAAAAGCAATGGTCGGT |
| SEQ ID NO: 6286 | mm68265_Slc4a11 | AGCGGTTTAGCATAGTTCGG |
| SEQ ID NO: 6287 | mm68266_Slc4a11 | CTGCTGTCAGATACCATCCA |
| SEQ ID NO: 6288 | mm68267_Slc4a11 | GGCTGGCGTTGAGTGCAGTG |
| SEQ ID NO: 6289 | mm68300_Lrig2 | TTGCGCCATATGGTGGACAT |
| SEQ ID NO: 6290 | mm68301_Lrig2 | ACTGGAGAGATTGAATTTAG |
| SEQ ID NO: 6291 | mm68302_Lrig2 | ACAGATACTCAAGGGACTCA |
| SEQ ID NO: 6292 | mm68303_Lrig2 | AGCACATTCTAATCTTGCCA |
| SEQ ID NO: 6293 | mm68464_Megf8 | GATGTGTCCCTAGTCTACCG |
| SEQ ID NO: 6294 | mm68465_Megf8 | GAATTGCAACGCCCACACCG |
| SEQ ID NO: 6295 | mm68466_Megf8 | CACACCCTTACTGCCCGTCG |
| SEQ ID NO: 6296 | mm68467_Megf8 | TGTTCTAGGAAACTACATGG |
| SEQ ID NO: 6297 | mm68472_Chsy1 | GGTGTAAGGTGATCGCTCGG |
| SEQ ID NO: 6298 | mm68473_Chsy1 | GCGTGTGAACCCCATGTACG |
| SEQ ID NO: 6299 | mm68474_Chsy1 | AAGAGAAAGTTCCTGTCGCG |
| SEQ ID NO: 6300 | mm68475_Chsy1 | CAAGTACGAGTGGTTTATGA |
| SEQ ID NO: 6301 | mm68572_Fat3 | GTGACAATCAGACCTGACCG |
| SEQ ID NO: 6302 | mm68573_Fat3 | CAAAGTAACCGAGATTGTAG |
| SEQ ID NO: 6303 | mm68574_Fat3 | ACGAGACAATCATAATGGAG |
| SEQ ID NO: 6304 | mm68575_Fat3 | ACTTCTGGTGTATCAGATTG |
| SEQ ID NO: 6305 | mm68584_Amica1 | TATGACTCCAACATGCGTAG |
| SEQ ID NO: 6306 | mm68585_Amica1 | TACACTTGCAGCATCTACGT |
| SEQ ID NO: 6307 | mm68586_Amica1 | CCAACCTTAGCGTGCCTACG |
| SEQ ID NO: 6308 | mm68587_Amica1 | GTGGGTGAATCAGTCTTGAT |
| SEQ ID NO: 6309 | mm68600_Myo9a | TTTATCAAGAGCATAATGAA |
| SEQ ID NO: 6310 | mm68601_Myo9a | ACTATATAAAGACTTAGCCA |
| SEQ ID NO: 6311 | mm68602_Myo9a | CATGCTTAAAGCGATTCCGT |
| SEQ ID NO: 6312 | mm68603_Myo9a | CCGAAGCTGTCTTAGTACCA |
| SEQ ID NO: 6313 | mm68608_Ephb1 | GTGTTGTAGCCTGTCCTGCG |
| SEQ ID NO: 6314 | mm68609_Ephb1 | GATAGATGTCTCATTCACGA |
| SEQ ID NO: 6315 | mm68610_Ephb1 | CAGCACGTATCGATGGGCTA |

TABLE 1-continued mmSurf sgRNA library sequences

| SEQ ID NO | id_gRNA Target | Sequence |
| --- | --- | --- |
| SEQ ID NO: 6316 | mm68611_Ephb1 | TCATCCAATAAGGCTCCCCA |
| SEQ ID NO: 6317 | mm68700_Cd200r2 | ACAGACACTATGGTGTACAC |
| SEQ ID NO: 6318 | mm68701_Cd200r2 | TGAAGTAACCTACTTTCTCG |
| SEQ ID NO: 6319 | mm68702_Cd200r2 | TCCTGACCTTCAGATCAGTG |
| SEQ ID NO: 6320 | mm68703_Cd200r2 | TGTGAGATAACAACACCTGA |
| SEQ ID NO: 6321 | mm68776_Lppr1 | AAGTGATAGAAAAAGCTCGG |
| SEQ ID NO: 6322 | mm68777_Lppr1 | GTATTTCATAAAGTCAACAA |
| SEQ ID NO: 6323 | mm68778_Lppr1 | ACTTAATGAAGCCTTACCCG |
| SEQ ID NO: 6324 | mm68779_Lppr1 | TGATGATCCTTCGGAGTAAG |
| SEQ ID NO: 6325 | mm68796_Lrrc4b | CACAGGCACATCCATGACGT |
| SEQ ID NO: 6326 | mm68797_Lrrc4b | CACGGCCGACACGTTAAGCG |
| SEQ ID NO: 6327 | mm68798_Lrrc4b | CCTGGTGCGAAAGATCGAGG |
| SEQ ID NO: 6328 | mm68799_Lrrc4b | GAGGCTGGAGTACATATCTG |
| SEQ ID NO: 6329 | mm68856_Pigs | ACCATAATGCCACCCCAGCG |
| SEQ ID NO: 6330 | mm68857_Pigs | GGGCGACCTGGACTATGCGA |
| SEQ ID NO: 6331 | mm68858_Pigs | GATCTCTCGCTCATGCACAA |
| SEQ ID NO: 6332 | mm68859_Pigs | CTACCTAAGCTGGACTTGAG |
| SEQ ID NO: 6333 | mm69064_Tlr13 | AATATTCGGACTCTCAACCA |
| SEQ ID NO: 6334 | mm69065_Tlr13 | AGTAATTGGGAGCTTAGACA |
| SEQ ID NO: 6335 | mm69066_Tlr13 | AACTTTGTGAGGTTAATCAG |
| SEQ ID NO: 6336 | mm69067_Tlr13 | TCAATTTGGAAGATCGACGA |
| SEQ ID NO: 6337 | mm69068_Pcdh19 | GCTCGCTATTGACCGACAGG |
| SEQ ID NO: 6338 | mm69069_Pcdh19 | GAGCCGAGTTGGACACCACG |
| SEQ ID NO: 6339 | mm69070_Pcdh19 | TTGGCCTGGAAATAAAGACG |
| SEQ ID NO: 6340 | mm69071_Pcdh19 | GTTCTCATTAAAGGTACGAG |
| SEQ ID NO: 6341 | mm69332_Rpl17 | TTACCTTAAAGTGAACACGA |
| SEQ ID NO: 6342 | mm69333_Rpl17 | GAGAATCTACGTCTAAACCC |
| SEQ ID NO: 6343 | mm69334_Rpl17 | TGGAGTTGGTAGGTGCGCCC |
| SEQ ID NO: 6344 | mm69335_Rpl17 | AGCAATGTGTGCCATTCCGG |
| SEQ ID NO: 6345 | mm69424_Dpep2 | CAAGCACCCAATGACCCTTG |
| SEQ ID NO: 6346 | mm69425_Dpep2 | AGAAACTTCGAAGCACAGCG |
| SEQ ID NO: 6347 | mm69426_Dpep2 | TTACGTACCATGCCAGACGC |
| SEQ ID NO: 6348 | mm69427_Dpep2 | AGGAGTTCCCGCTTATAGAT |
| SEQ ID NO: 6349 | mm69456_Itga11 | CAACGTGACCAGATACGCTG |
| SEQ ID NO: 6350 | mm69457_Itga11 | CCAAAGTAGGAGCCTATCTG |
| SEQ ID NO: 6351 | mm69458_Itga11 | TTAAGGTAGGACTCTCGGTG |
| SEQ ID NO: 6352 | mm69459_Itga11 | TGGCGTTGATTTGAACTACA |
| SEQ ID NO: 6353 | mm69472_Nrcam | GGACGTATACTTGTGTCGCA |

TABLE 1-continued mmSurf sgRNA library sequences

| SEQ ID NO | id_gRNA Target | Sequence |
|---|---|---|
| SEQ ID NO: 6354 | mm69473_Nrcam | GCCGGAGGTAATCCAATCGG |
| SEQ ID NO: 6355 | mm69474_Nrcam | CATTAGTTTACCGTAAATGG |
| SEQ ID NO: 6356 | mm69475_Nrcam | GCTGATGTGAGAATCCGAGG |
| SEQ ID NO: 6357 | mm69516_Defb20 | GCAACGTAGAAGGCTACTGT |
| SEQ ID NO: 6358 | mm69517_Defb20 | TAGGAAGAAATGCAGATTAG |
| SEQ ID NO: 6359 | mm69518_Defb20 | TTAGTGGAGATATCTGAGAT |
| SEQ ID NO: 6360 | mm69519_Defb20 | GTGCCACAAACAGCAAAACA |
| SEQ ID NO: 6361 | mm69588_Podxl2 | GCTATAGTTCTGAACCCCCG |
| SEQ ID NO: 6362 | mm69589_Podxl2 | CTTACCTGAGTAGAGTCCCA |
| SEQ ID NO: 6363 | mm69590_Podxl2 | TCCTGCAGAGGCATATGCCA |
| SEQ ID NO: 6364 | mm69591_Podxl2 | TGGGACTGAGGTCCCCAGTG |
| SEQ ID NO: 6365 | mm69636_Smo | GAACTCCAATCGCTACCCTG |
| SEQ ID NO: 6366 | mm69637_Smo | TCAGAACCCGCTGTTCACCG |
| SEQ ID NO: 6367 | mm69638_Smo | CAAGTGTGAGAATGACCGAG |
| SEQ ID NO: 6368 | mm69639_Smo | GTAGATGGAGACTCCGTGAG |
| SEQ ID NO: 6369 | mm69676_Rc3h2 | GTTTCTCAGCTAATCCCACG |
| SEQ ID NO: 6370 | mm69677_Rc3h2 | AGAATTCATTCGATCTCGAG |
| SEQ ID NO: 6371 | mm69678_Rc3h2 | AGTGGCAAAAAATGCGTAG |
| SEQ ID NO: 6372 | mm69679_Rc3h2 | GCCGAGATTTACGACAACAA |
| SEQ ID NO: 6373 | mm69784_Casc4 | TCAAGCGGCTAGAATACGAG |
| SEQ ID NO: 6374 | mm69785_Casc4 | CTGAAGCAGAACGTGGCGGG |
| SEQ ID NO: 6375 | mm69786_Casc4 | AGGCCTGGGAAGAGATGCG |
| SEQ ID NO: 6376 | mm69787_Casc4 | ATGGGGAAGATGATTGCTTG |
| SEQ ID NO: 6377 | mm69796_Sidt1 | TTTCGATCGCGTCTACAGCG |
| SEQ ID NO: 6378 | mm69797_Sidt1 | TTGTGCTTGTCCATCATGTG |
| SEQ ID NO: 6379 | mm69798_Sidt1 | CCCGCGGCTACAGATACCAA |
| SEQ ID NO: 6380 | mm69799_Sidt1 | GAACGGAGACAACTGAACAC |
| SEQ ID NO: 6381 | mm69808_Nceh1 | TAGATGACGCTGCGTCGCAG |
| SEQ ID NO: 6382 | mm69809_Nceh1 | TACCTAACCATGACATGACG |
| SEQ ID NO: 6383 | mm69810_Nceh1 | ATTCTTCAGGCTGGCAACGT |
| SEQ ID NO: 6384 | mm69811_Nceh1 | TCACTCAATAGAAACGATGA |
| SEQ ID NO: 6385 | mm70116_Lmbrd2 | GCTCCATTCCAGTATGACCG |
| SEQ ID NO: 6386 | mm70117_Lmbrd2 | TCAAGTACAACCACCCACTG |
| SEQ ID NO: 6387 | mm70118_Lmbrd2 | TACCATTCTAAATGCAAACG |
| SEQ ID NO: 6388 | mm70119_Lmbrd2 | GATAGACAAAACCACAGCAA |
| SEQ ID NO: 6389 | mm70120_Cachd1 | CCTACCGTTCATGAGGGCGT |
| SEQ ID NO: 6390 | mm70121_Cachd1 | TCCAACCGGATGATTGATG |
| SEQ ID NO: 6391 | mm70122_Cachd1 | TGGGTGTTGCTATGTAACGG |

TABLE 1-continued mmSurf sgRNA library sequences

| SEQ ID NO | id_gRNA Target | Sequence |
|---|---|---|
| SEQ ID NO: 6392 | mm70123_Cachd1 | TGGGTATCGACTTCACACTG |
| SEQ ID NO: 6393 | mm70132_Tmem104 | TGGAAATGACTCTTGCGGCG |
| SEQ ID NO: 6394 | mm70133_Tmem104 | TGGTATTCGTAGGCTTCATG |
| SEQ ID NO: 6395 | mm70134_Tmem104 | TCAGCCAAGACAACTACGAG |
| SEQ ID NO: 6396 | mm70135_Tmem104 | ACCCCCAAGAAGTTGGCTAG |
| SEQ ID NO: 6397 | mm70164_Islr2 | AAGATTACGGTACTAAGGCG |
| SEQ ID NO: 6398 | mm70165_Islr2 | GCAGCGCGCTCAAGTTACGA |
| SEQ ID NO: 6399 | mm70166_Islr2 | ATGGTTAGACACATAGCGAG |
| SEQ ID NO: 6400 | mm70167_Islr2 | CACCCGTAAGGACGTTGAGT |
| SEQ ID NO: 6401 | mm70276_Tmem117 | AGCTGGGACAAACTGAACCG |
| SEQ ID NO: 6402 | mm70277_Tmem117 | ACATCGTCATCCACGACCCA |
| SEQ ID NO: 6403 | mm70278_Tmem117 | TCTGGAAGAAAGGCAACGTG |
| SEQ ID NO: 6404 | mm70279_Tmem117 | ATATACTGTCCATATTCATG |
| SEQ ID NO: 6405 | mm70292_Slc26a9 | TTGTGGGGAGATCCGACAA |
| SEQ ID NO: 6406 | mm70293_Slc26a9 | GGGTCTGGAAGATCACAACC |
| SEQ ID NO: 6407 | mm70294_Slc26a9 | AGAGAGCGCAGCAAATGACG |
| SEQ ID NO: 6408 | mm70295_Slc26a9 | TTCTAGACTCACAAAGACGA |
| SEQ ID NO: 6409 | mm70324_Mdga2 | TTACTACAAGGATCTGACAA |
| SEQ ID NO: 6410 | mm70325_Mdga2 | AAAGTTATGATGGGACCCTG |
| SEQ ID NO: 6411 | mm70326_Mdga2 | GCATTCTTGGAAATCCGTCA |
| SEQ ID NO: 6412 | mm70327_Mdga2 | TTAGTATGTGTTACAACTGG |
| SEQ ID NO: 6413 | mm70336_Pkn1 | GCTCAAGCTGGACAACACAG |
| SEQ ID NO: 6414 | mm70337_Pkn1 | CAGTAAGTCTAGGCGTCGAG |
| SEQ ID NO: 6415 | mm70338_Pkn1 | ATGATCCAGACCTATAGCAA |
| SEQ ID NO: 6416 | mm70339_Pkn1 | AAAGTCGCCCCTGACACTTG |
| SEQ ID NO: 6417 | mm70372_Negr1 | AGATGAACCTGCATTGTCCG |
| SEQ ID NO: 6418 | mm70373_Negr1 | AATGTGGAAATGGAAACTCG |
| SEQ ID NO: 6419 | mm70374_Negr1 | TTATGGAATTACAAGGGACC |
| SEQ ID NO: 6420 | mm70375_Negr1 | CAGAGCCTGTCATTTCCTGG |
| SEQ ID NO: 6421 | mm70396_Cdh10 | ATAAAAACGTGGATCCACAT |
| SEQ ID NO: 6422 | mm70397_Cdh10 | AAGCCACTGATGCTGACACG |
| SEQ ID NO: 6423 | mm70398_Cdh10 | TGATTATCAATATGTAGGCA |
| SEQ ID NO: 6424 | mm70399_Cdh10 | TGAGATAATTCACGATCAAG |
| SEQ ID NO: 6425 | mm70404_Itgb8 | CCAGATAATAAAGATCCACG |
| SEQ ID NO: 6426 | mm70405_Itgb8 | ACATGAATGTATCCATGGGG |
| SEQ ID NO: 6427 | mm70406_Itgb8 | ATTTCAGAACACAATAGATG |
| SEQ ID NO: 6428 | mm70407_Itgb8 | ATGAAAACATGTGATATCAT |
| SEQ ID NO: 6429 | mm70428_Lrrn4 | GAGTGGTGACTCCCGCGGCG |

TABLE 1-continued mmSurf sgRNA library sequences

| SEQ ID NO | id_gRNA Target | Sequence |
|---|---|---|
| SEQ ID NO: 6430 | mm70429_Lrrn4 | CAAAAACTGAATGATCGAAG |
| SEQ ID NO: 6431 | mm70430_Lrrn4 | ATTAGGCTCAAGGATATGTG |
| SEQ ID NO: 6432 | mm70431_Lrrn4 | CGCCCAGGAGGCATTCGCGG |
| SEQ ID NO: 6433 | mm70512_Tmem26 | CTCACCCTCAAGTTCAAGCG |
| SEQ ID NO: 6434 | mm70513_Tmem26 | TAATATTAATCATTGGACGG |
| SEQ ID NO: 6435 | mm70514_Tmem26 | CCAGACCGGTTCACATACCA |
| SEQ ID NO: 6436 | mm70515_Tmem26 | GTGCATTTCAAGAAGCCACA |
| SEQ ID NO: 6437 | mm70732_Mslnl | GGCAAGCAGCCACCACACTG |
| SEQ ID NO: 6438 | mm70733_Mslnl | GCTTACTGTCATGCAGACTG |
| SEQ ID NO: 6439 | mm70734_Mslnl | TCCACTGGCCTATTTCAGCG |
| SEQ ID NO: 6440 | mm70735_Mslnl | GCAGGGAGATCCTGTGTCCG |
| SEQ ID NO: 6441 | mm70760_Treml2 | GAACCGCCGGAACTTAGTTG |
| SEQ ID NO: 6442 | mm70761_Treml2 | CAAGGTAGTCCGTATCACCA |
| SEQ ID NO: 6443 | mm70762_Treml2 | CGTGACAAATCCATCCATGG |
| SEQ ID NO: 6444 | mm70763_Treml2 | TACAGTTTCATCGATACCAG |
| SEQ ID NO: 6445 | mm70792_Pkd2l1 | TCAGTACAATAACATGAACG |
| SEQ ID NO: 6446 | mm70793_Pkd2l1 | CGTGCGCAATGACTCCTGTG |
| SEQ ID NO: 6447 | mm70794_Pkd2l1 | CACACAGACAGATGTCCACG |
| SEQ ID NO: 6448 | mm70795_Pkd2l1 | GATCCGCTATGTGAATAACT |
| SEQ ID NO: 6449 | mm70836_Tnn | AATTGATGGACCAACCAATG |
| SEQ ID NO: 6450 | mm70837_Tnn | GGGTGTCTGCCAGTGCCACG |
| SEQ ID NO: 6451 | mm70838_Tnn | GGCTGACATCGACAGGTATG |
| SEQ ID NO: 6452 | mm70839_Tnn | CAGCACACCTATGACATCAC |
| SEQ ID NO: 6453 | mm70916_Fat4 | GACATCGTGGACGATCGAGG |
| SEQ ID NO: 6454 | mm70917_Fat4 | CAGTTATCTCATCACTACCG |
| SEQ ID NO: 6455 | mm70918_Fat4 | GGGATGTCGAAAGAGTACAC |
| SEQ ID NO: 6456 | mm70919_Fat4 | ATTAGATCCTATGTCCGCGT |
| SEQ ID NO: 6457 | mm70960_Tmem67 | TCACAAATGTTGGTTCGCAG |
| SEQ ID NO: 6458 | mm70961_Tmem67 | ATTGATTGGGAACGGCCGAA |
| SEQ ID NO: 6459 | mm70962_Tmem67 | TTGCTACCCAGATTTCACTG |
| SEQ ID NO: 6460 | mm70963_Tmem67 | GCTGCTTCCTATGATATACG |
| SEQ ID NO: 6461 | mm71032_Slc5a6 | CTTACTTAATCCCAGAGATG |
| SEQ ID NO: 6462 | mm71033_Slc5a6 | CAAACATGACCAGACCAATG |
| SEQ ID NO: 6463 | mm71034_Slc5a6 | GCAGTTCACCAACGGTATGG |
| SEQ ID NO: 6464 | mm71035_Slc5a6 | ATCCTATAGGTGATATACAT |
| SEQ ID NO: 6465 | mm71088_Sdk1 | TGTGAAATCATATCCGAGGG |
| SEQ ID NO: 6466 | mm71089_Sdk1 | AATGAGGCAAGTGAACATCG |
| SEQ ID NO: 6467 | mm71090_Sdk1 | TGTGCGAGGCGACACTCCGG |

TABLE 1-continued mmSurf sgRNA library sequences

| SEQ ID NO | id_gRNA Target | Sequence |
|---|---|---|
| SEQ ID NO: 6468 | mm71091_Sdk1 | GAAGGTGTGAGGACTACCGC |
| SEQ ID NO: 6469 | mm71096_Pon2 | AGGTGAAATATTGATCCCGT |
| SEQ ID NO: 6470 | mm71097_Pon2 | GACATACTTGAACCTACACT |
| SEQ ID NO: 6471 | mm71098_Pon2 | GCGGTTCCTAGCGCTCAGGT |
| SEQ ID NO: 6472 | mm71099_Pon2 | ATCTCAAAGACGAGAGACCG |
| SEQ ID NO: 6473 | mm71100_Thsd7a | CTGTAGGGGATGTGACATCG |
| SEQ ID NO: 6474 | mm71101_Thsd7a | CATCTGTGTGCGAGTCAACG |
| SEQ ID NO: 6475 | mm71102_Thsd7a | TGTGCGTTATATTTGTCACA |
| SEQ ID NO: 6476 | mm71103_Thsd7a | CGCGAAAAGCCTTATAACGG |
| SEQ ID NO: 6477 | mm71176_Bsph1 | ATTTCACTTCTATACAAGAA |
| SEQ ID NO: 6478 | mm71177_Bsph1 | ATTTCAATCTGAAACACAAG |
| SEQ ID NO: 6479 | mm71178_Bsph1 | GATTATTATGCACCAACTAT |
| SEQ ID NO: 6480 | mm71179_Bsph1 | CACAGTATTTCCAGTAACCT |
| SEQ ID NO: 6481 | mm71320_Slc9a9 | CACTTACCCTATGACCACAC |
| SEQ ID NO: 6482 | mm71321_Slc9a9 | TGTTGACTAGTAGAGTTGAT |
| SEQ ID NO: 6483 | mm71322_Slc9a9 | GAGTGTACTGAATGATGCGG |
| SEQ ID NO: 6484 | mm71323_Slc9a9 | ATCCGATGACAGATTGTTGT |
| SEQ ID NO: 6485 | mm71352_Il1rapl1 | TTGAAAATGGAAACGGACGT |
| SEQ ID NO: 6486 | mm71353_Il1rapl1 | AATTTCATGCCGAGACATAG |
| SEQ ID NO: 6487 | mm71354_Il1rapl1 | CCAGTGGAATCAAGAGACTG |
| SEQ ID NO: 6488 | mm71355_Il1rapl1 | CAACATTACTACAGGACAGT |
| SEQ ID NO: 6489 | mm71544_Cd59b | TATTATGAGCCGATTAGACG |
| SEQ ID NO: 6490 | mm71545_Cd59b | ATGCTACAACTGTTTAGACC |
| SEQ ID NO: 6491 | mm71546_Cd59b | GGCAAGTGTATCAACAGTGT |
| SEQ ID NO: 6492 | mm71547_Cd59b | TTGATACACTTGCCTTCCTG |
| SEQ ID NO: 6493 | mm71592_Ust | CAAGTGTGGCAGTCGTACCG |
| SEQ ID NO: 6494 | mm71593_Ust | GAATAAATAGGGCTGTTCGG |
| SEQ ID NO: 6495 | mm71594_Ust | TAGACAGAAATCTACTGACG |
| SEQ ID NO: 6496 | mm71595_Ust | ACAGGCCTTACCTTACTAGG |
| SEQ ID NO: 6497 | mm71692_Gjd3 | TCGACCGTGTGCGGACAAGG |
| SEQ ID NO: 6498 | mm71693_Gjd3 | GAACACCGCACCTCCCACCG |
| SEQ ID NO: 6499 | mm71694_Gjd3 | GAGTAGATGACGAACAGCAC |
| SEQ ID NO: 6500 | mm71695_Gjd3 | GTGTGTAACACGTTGCAGCC |
| SEQ ID NO: 6501 | mm71816_Defb34 | AGAAATGCAGCAGGATTAAT |
| SEQ ID NO: 6502 | mm71817_Defb34 | AAGAACTTGTTGCTCTCTGC |
| SEQ ID NO: 6503 | mm71818_Defb34 | TCTTTGCTGTTCTCTTCTTT |
| SEQ ID NO: 6504 | mm71819_Defb34 | AAAAAAAATGCATTCT |
| SEQ ID NO: 6505 | mm71888_Lrrc24 | TCCCACCGGGAATCCCTCCG |

TABLE 1-continued mmSurf sgRNA library sequences

| SEQ ID NO | id_gRNA Target | Sequence |
|---|---|---|
| SEQ ID NO: 6506 | mm71889_Lrrc24 | AGTCTACTAGAAGTATCTGG |
| SEQ ID NO: 6507 | mm71890_Lrrc24 | GCTTGAGGCTTACCATCGCG |
| SEQ ID NO: 6508 | mm71891_Lrrc24 | GAGGTCCAGTAGGGCTAAGG |
| SEQ ID NO: 6509 | mm71892_Raet1e | GAGCACTTCACGTCACACCA |
| SEQ ID NO: 6510 | mm71893_Raet1e | TCCTGGCACAAATCGTTCAG |
| SEQ ID NO: 6511 | mm71894_Raet1e | GAACTCACCATCCAGCCCGT |
| SEQ ID NO: 6512 | mm71895_Raet1e | TCTACACAGAGAATATGAGC |
| SEQ ID NO: 6513 | mm71948_Tmem102 | CTGCCTGGGGTGGAAAACGA |
| SEQ ID NO: 6514 | mm71949_Tmem102 | AAGCCAAGTCCCAAAGCCGT |
| SEQ ID NO: 6515 | mm71950_Tmem102 | GCTCTTCGACTTGATCCCGG |
| SEQ ID NO: 6516 | mm71951_Tmem102 | GTGCCATCCAGAGAAAACAC |
| SEQ ID NO: 6517 | mm72092_Tmem106c | CAGCCAACTCACGTTCTCTG |
| SEQ ID NO: 6518 | mm72093_Tmem106c | TGATGCCGTTATCGTCCACG |
| SEQ ID NO: 6519 | mm72094_Tmem106c | CACATAGGGGAACTGAGCGA |
| SEQ ID NO: 6520 | mm72095_Tmem106c | GAACTCCAACTTCTATCCTG |
| SEQ ID NO: 6521 | mm72404_Gpr176 | TGTAGATCAGAACATACACC |
| SEQ ID NO: 6522 | mm72405_Gpr176 | GGTGCTCAAATTCCTACACA |
| SEQ ID NO: 6523 | mm72406_Gpr176 | CCGGTGGTGCAACTGCACCA |
| SEQ ID NO: 6524 | mm72407_Gpr176 | AGTCTGGTAGACAACCAGGG |
| SEQ ID NO: 6525 | mm72448_Dpy19l4 | CATCATGAAAGTGTACGTCG |
| SEQ ID NO: 6526 | mm72449_Dpy19l4 | AAGGCGCCGTCATTCGAGAG |
| SEQ ID NO: 6527 | mm72450_Dpy19l4 | AAGATTCAAGGTCACCGGCA |
| SEQ ID NO: 6528 | mm72451_Dpy19l4 | GTTACAAGTTGGCTTATGAG |
| SEQ ID NO: 6529 | mm72628_Clec4b2 | GGCATCCCAGAATAAGAGTG |
| SEQ ID NO: 6530 | mm72629_Clec4b2 | TGAGATTGGAATGGTATGTG |
| SEQ ID NO: 6531 | mm72630_Clec4b2 | CTGCTTTAGTGAAGGAACTA |
| SEQ ID NO: 6532 | mm72631_Clec4b2 | CTGGTCCCTGAGACTCTGGA |
| SEQ ID NO: 6533 | mm73048_Fndc5 | GCTCTTCAAGACCCCACGCG |
| SEQ ID NO: 6534 | mm73049_Fndc5 | GATGCTCCGGTTCATTCAGG |
| SEQ ID NO: 6535 | mm73050_Fndc5 | CAGGACATCCCAGCTGACCA |
| SEQ ID NO: 6536 | mm73051_Fndc5 | GCCGGACGGTCACGTTCACA |
| SEQ ID NO: 6537 | mm73304_Tas2r118 | TTGGAAGGTATCAGTCGTCT |
| SEQ ID NO: 6538 | mm73305_Tas2r118 | TGTTAAATATCACATCCAGA |
| SEQ ID NO: 6539 | mm73306_Tas2r118 | CTTTCAAAGACTGTCACCGG |
| SEQ ID NO: 6540 | mm73307_Tas2r118 | AATTGTGCAAAGTTGCACAA |
| SEQ ID NO: 6541 | mm73472_Defb21 | GGTAATATTTGCATGATCCA |
| SEQ ID NO: 6542 | mm73473_Defb21 | TCTACCTCCCAAGAGCCATG |
| SEQ ID NO: 6543 | mm73474_Defb21 | TGGGGTAGAAGAGCAAGGAC |

TABLE 1-continued mmSurf sgRNA library sequences

| SEQ ID NO | id_gRNA Target | Sequence |
|---|---|---|
| SEQ ID NO: 6544 | mm73475_Defb21 | CTTCTACCCCAAGTGACACC |
| SEQ ID NO: 6545 | mm73820_Itprip | ATAAACAAGTGGCACCGTAG |
| SEQ ID NO: 6546 | mm73821_Itprip | ACTGTATCCGGAGCACCACG |
| SEQ ID NO: 6547 | mm73822_Itprip | TCAAAATCAAGTTCCGCTCG |
| SEQ ID NO: 6548 | mm73823_Itprip | GTTGCGACAGAACCATCAGG |
| SEQ ID NO: 6549 | mm73860_Gnptab | TGTTTGCAATGGACGCGTGG |
| SEQ ID NO: 6550 | mm73861_Gnptab | TCTGCCCATGCCAATCGACG |
| SEQ ID NO: 6551 | mm73862_Gnptab | AGGAGTGAAATATTTACCCG |
| SEQ ID NO: 6552 | mm73863_Gnptab | CATGCTGGACCGTTTAAGGG |
| SEQ ID NO: 6553 | mm73900_Dnaic2 | ACAGCCAACCAAGTTCATGG |
| SEQ ID NO: 6554 | mm73901_Dnaic2 | GGCGTTAATCATGTCGAGGG |
| SEQ ID NO: 6555 | mm73902_Dnaic2 | CAACGCCATCGACATCTACG |
| SEQ ID NO: 6556 | mm73903_Dnaic2 | GAACTACGACTCCTACATCT |
| SEQ ID NO: 6557 | mm74076_Defb45 | TAGGTTACCTGGAATGACCT |
| SEQ ID NO: 6558 | mm74077_Defb45 | AGACTTCCAGCATCTTTCAG |
| SEQ ID NO: 6559 | mm74078_Defb45 | GAAGACTGCGGTGTTAACTA |
| SEQ ID NO: 6560 | mm74079_Defb45 | GAAAGATGCTGGAAGTCTTT |
| SEQ ID NO: 6561 | mm74188_Lrrc8b | CAGTGGCGGAACAGTCAGTG |
| SEQ ID NO: 6562 | mm74189_Lrrc8b | CGTGTACCATTCGTCCCTGG |
| SEQ ID NO: 6563 | mm74190_Lrrc8b | CAAGCTCGTGAAAAACTCGC |
| SEQ ID NO: 6564 | mm74191_Lrrc8b | AGGTCGTTCTGGATCCGGAG |
| SEQ ID NO: 6565 | mm74625_Defb22 | GCAACGAGCAAATGTCCCAT |
| SEQ ID NO: 6566 | mm74626_Defb22 | ATAATCTTGTCACAGCAGGT |
| SEQ ID NO: 6567 | mm74627_Defb22 | TTCAAAATTAGTGGTCACTG |
| SEQ ID NO: 6568 | mm74628_Defb22 | AAAAAGTGTGCAAACACATT |
| SEQ ID NO: 6569 | mm74793_Iqgap2 | CACAAGTTAACACTGCGTTG |
| SEQ ID NO: 6570 | mm74794_Iqgap2 | GGTCACATCAGATTACATCC |
| SEQ ID NO: 6571 | mm74795_Iqgap2 | AAACAACAGATGTCTACGAT |
| SEQ ID NO: 6572 | mm74796_Iqgap2 | AGAAACAGAACACATCGGTG |
| SEQ ID NO: 6573 | mm74857_Gal3st3 | TAGACGCCGCAGCAGCACGA |
| SEQ ID NO: 6574 | mm74858_Gal3st3 | ATTGTCGCCTCCAAGGTCGT |
| SEQ ID NO: 6575 | mm74859_Gal3st3 | GCTGAAAAGCGACTCGAACA |
| SEQ ID NO: 6576 | mm74860_Gal3st3 | CCACAGGAAAATTCTGCTGT |
| SEQ ID NO: 6577 | mm74909_Defb28 | AGAGCTTATTGTGTCCCGAG |
| SEQ ID NO: 6578 | mm74910_Defb28 | TTTCCCCAAGCCATAAAAGC |
| SEQ ID NO: 6579 | mm74911_Defb28 | GAAATGCAGGCGCATATGCA |
| SEQ ID NO: 6580 | mm74912_Defb28 | CCACAAGGACAGCTAAGGTC |
| SEQ ID NO: 6581 | mm75020_Pilrb2 | AATTCAGCAAGATCAAACGG |

TABLE 1-continued mmSurf sgRNA library sequences

| SEQ ID NO | id_gRNA Target | Sequence |
|---|---|---|
| SEQ ID NO: 6582 | mm75021_Pilrb2 | CTTCCCCTGGAAGTTAGCCA |
| SEQ ID NO: 6583 | mm75022_Pilrb2 | CTCATGTATGAAAGGCATGG |
| SEQ ID NO: 6584 | mm75023_Pilrb2 | CCTTAAAGTTCAGGATTCTG |
| SEQ ID NO: 6585 | mm75028_Cyp2w1 | CTGGTCAATGAGACTCAGCA |
| SEQ ID NO: 6586 | mm75029_Cyp2w1 | AGCTTCTACATAACTCTGCG |
| SEQ ID NO: 6587 | mm75030_Cyp2w1 | CCCAGATGGATTGTGAACAT |
| SEQ ID NO: 6588 | mm75031_Cyp2w1 | TGTGCAACAGCCATCCATGG |
| SEQ ID NO: 6589 | mm76081_Defb23 | ATGTCCTCATCCGGTATGTG |
| SEQ ID NO: 6590 | mm76082_Defb23 | ACCGTGAAAAGATGCTTAGT |
| SEQ ID NO: 6591 | mm76083_Defb23 | AACGAAAAGAATTCCACAG |
| SEQ ID NO: 6592 | mm76084_Defb23 | CTGAGACTGAAGCATGAGAC |
| SEQ ID NO: 6593 | mm76137_Cd101 | GAGATGGGTGTGTTGCACGG |
| SEQ ID NO: 6594 | mm76138_Cd101 | AGACCACCGGAAATCCTGCG |
| SEQ ID NO: 6595 | mm76139_Cd101 | TGCCGAGCAGCGTACTGTGT |
| SEQ ID NO: 6596 | mm76140_Cd101 | GGTGTATCGGTGTACAGTGG |
| SEQ ID NO: 6597 | mm76373_Defb26 | CAGAGTCCGATGTCAAGAAG |
| SEQ ID NO: 6598 | mm76374_Defb26 | TTGCTAACTCAGGGGAACAA |
| SEQ ID NO: 6599 | mm76375_Defb26 | CGGGTCGCTGATGAATTCAC |
| SEQ ID NO: 6600 | mm76376_Defb26 | ACTCTTGTTACAGTGTGTAT |
| SEQ ID NO: 6601 | mm76377_Defb43 | CAGAGGAACTATGGATAACA |
| SEQ ID NO: 6602 | mm76378_Defb43 | TTGAACAGTCCTGATTCTCA |
| SEQ ID NO: 6603 | mm76379_Defb43 | TTGTTATCCATAGTTCCTCT |
| SEQ ID NO: 6604 | mm76380_Defb43 | CAAGGTGAGGACCCCCAGGA |
| SEQ ID NO: 6605 | mm76381_Defb25 | AAAGTGGATTCTGCTCATTG |
| SEQ ID NO: 6606 | mm76382_Defb25 | TACCTGGTGGTACATGACTC |
| SEQ ID NO: 6607 | mm76383_Defb25 | CACACACAAGGGTTACCTGG |
| SEQ ID NO: 6608 | mm76384_Defb25 | ATCCGGACACAGGTGCATGA |
| SEQ ID NO: 6609 | mm76401_Tctn1 | CCCACAGCCCACTAAATACG |
| SEQ ID NO: 6610 | mm76402_Tctn1 | GTACCCACCGTCCGTGACCG |
| SEQ ID NO: 6611 | mm76403_Tctn1 | ATGAGTTTAAAGTCACGGTG |
| SEQ ID NO: 6612 | mm76404_Tctn1 | GAGACCGATACATTACAGAC |
| SEQ ID NO: 6613 | mm77059_Fcrl6 | GCTGTAAAGTTGGATTCTTG |
| SEQ ID NO: 6614 | mm77060_Fcrl6 | GAATGAGTAAAGATTGGAA |
| SEQ ID NO: 6615 | mm77061_Fcrl6 | AGAAATCCTAGGGAAACCCC |
| SEQ ID NO: 6616 | mm77062_Fcrl6 | ACAACCATGTCATTCAAGAC |
| SEQ ID NO: 6617 | mm77174_Btnl1 | CAGCTCGCATGCACATCCGA |
| SEQ ID NO: 6618 | mm77175_Btnl1 | GTGCAGATGCCGGAATACAG |
| SEQ ID NO: 6619 | mm77176_Btnl1 | AGAAAACCAAGACACTTCTG |

TABLE 1-continued mmSurf sgRNA library sequences

| SEQ ID NO | id_gRNA Target | Sequence |
|---|---|---|
| SEQ ID NO: 6620 | mm77177_Btnl1 | AGGGGCAGAGCCTAAACCTG |
| SEQ ID NO: 6621 | mm77704_Ccl21b | GCTTCCGGGGTAAGAACCTG |
| SEQ ID NO: 6622 | mm77705_Ccl21b | GAGCCAGGACCAGGCTAAGG |
| SEQ ID NO: 6623 | mm77706_Ccl21b | ATTCCCTACAGTATTGTCCG |
| SEQ ID NO: 6624 | mm77707_Ccl21b | CTCTGCATCCCCTGGACCCA |
| SEQ ID NO: 6625 | mm77945_Tigit | CCTATCATACGTATCCTGGT |
| SEQ ID NO: 6626 | mm77946_Tigit | CAGGCACGATAGATACAAAG |
| SEQ ID NO: 6627 | mm77947_Tigit | TCTCTGACAATGAATGACAC |
| SEQ ID NO: 6628 | mm77948_Tigit | CCATTTATAGTGTTGACCTG |
| SEQ ID NO: 6629 | NTC | AAAAAGTCCGCGATTACGTC |
| SEQ ID NO: 6630 | NTC | AAAACGGCTCGATCGGTGAT |
| SEQ ID NO: 6631 | NTC | AAAACGTAATTATACCGAGC |
| SEQ ID NO: 6632 | NTC | AAAATTGCACCTTCCCGGCC |
| SEQ ID NO: 6633 | NTC | AAACCCCGCGCGGAGCGTC |
| SEQ ID NO: 6634 | NTC | AAACCTAGCGTAGATTCGGC |
| SEQ ID NO: 6635 | NTC | AAACGAGGCTGTTCGTACAC |
| SEQ ID NO: 6636 | NTC | AAACTCATACGTAGCGAATC |
| SEQ ID NO: 6637 | NTC | AAACTCCGTGTCAACCGAT |
| SEQ ID NO: 6638 | NTC | AAAGACGTGCATTCAGCGAG |
| SEQ ID NO: 6639 | NTC | AACATGTTAAGTCGCGTTAT |
| SEQ ID NO: 6640 | NTC | AACCAGCATTTGACCGCGCT |
| SEQ ID NO: 6641 | NTC | AACCCCGGCTGTCATCGCCG |
| SEQ ID NO: 6642 | NTC | AACCCGCCGGAACAATCAGC |
| SEQ ID NO: 6643 | NTC | AACCGGCTGCGCGTTTGCAA |
| SEQ ID NO: 6644 | NTC | AACCGTACTGCGAGGAGCAT |
| SEQ ID NO: 6645 | NTC | AACCTCGTCTCATGTACGAA |
| SEQ ID NO: 6646 | NTC | AACGCCCCGGATTTCGTTGA |
| SEQ ID NO: 6647 | NTC | AACGGCTGCGCCCGCGGCAA |
| SEQ ID NO: 6648 | NTC | AACGGGCGCAATACCCTTTT |
| SEQ ID NO: 6649 | NTC | AACGGTAGCGTACCCGTGAA |
| SEQ ID NO: 6650 | NTC | AACGGTCAAATCCGTGAGGG |
| SEQ ID NO: 6651 | NTC | AACGTCACCAACCTCGATCC |
| SEQ ID NO: 6652 | NTC | AACGTTATAGCTTCGTCTCT |
| SEQ ID NO: 6653 | NTC | AACTAACTCACTACGCACGA |
| SEQ ID NO: 6654 | NTC | AACTCCTCATCGTACGCTAA |
| SEQ ID NO: 6655 | NTC | AACTCGCGTGGGAAGTCCGG |
| SEQ ID NO: 6656 | NTC | AACTTATACGTAATCTGATC |
| SEQ ID NO: 6657 | NTC | AAGACTCCTACGTATCGAGC |

TABLE 1-continued mmSurf sgRNA library sequences

| SEQ ID NO | id_gRNA Target | Sequence |
|---|---|---|
| SEQ ID NO: 6658 | NTC | AAGCACAAGAACGGTCCGCC |
| SEQ ID NO: 6659 | NTC | AAGCAGCGACTACTCGACGC |
| SEQ ID NO: 6660 | NTC | AAGCCTAACGGAGCTCGCGG |
| SEQ ID NO: 6661 | NTC | AAGCCTACTTCACCGGTCGG |
| SEQ ID NO: 6662 | NTC | AAGCGAGCCGCAGACCGTTT |
| SEQ ID NO: 6663 | NTC | AAGCGTACCCCACTCGTTAA |
| SEQ ID NO: 6664 | NTC | AAGCGTGAGATTCACCGCCG |
| SEQ ID NO: 6665 | NTC | AAGGCCTTAACACGTCGACC |
| SEQ ID NO: 6666 | NTC | AAGGCGTAAACGAGTACACG |
| SEQ ID NO: 6667 | NTC | AAGGGTAAGTACAGTATCGT |
| SEQ ID NO: 6668 | NTC | AAGTCCCCTTCGGGAACTCC |
| SEQ ID NO: 6669 | NTC | AAGTCTATGCGGGCTCGTA |
| SEQ ID NO: 6670 | NTC | AATAAGCCTACCCGGCGAGA |
| SEQ ID NO: 6671 | NTC | AATACCGTACCGACTCAGTG |
| SEQ ID NO: 6672 | NTC | AATAGGAACTCCGCACCCGA |
| SEQ ID NO: 6673 | NTC | AATCAACCGTGATAGTCTCG |
| SEQ ID NO: 6674 | NTC | AATCACCGACAACGTAAGAC |
| SEQ ID NO: 6675 | NTC | AATGAAGCACCGATTGCGGA |
| SEQ ID NO: 6676 | NTC | AATGAGCGTCTCTCGATCGC |
| SEQ ID NO: 6677 | NTC | AATGAGCTTCGAGTTCGTCT |
| SEQ ID NO: 6678 | NTC | AATGCTGCGTACGATAACCG |
| SEQ ID NO: 6679 | NTC | AATTCTGAGATTCCGCGGCT |
| SEQ ID NO: 6680 | NTC | AATTGTCTGATCGCGCCATA |
| SEQ ID NO: 6681 | NTC | AATTTTTTCGGAATCTAGCG |
| SEQ ID NO: 6682 | NTC | ACAACAATTACTGGCCGCGA |
| SEQ ID NO: 6683 | NTC | ACAACACGCCGACACGTCTA |
| SEQ ID NO: 6684 | NTC | ACAATTCGGTTTATGCGCGT |
| SEQ ID NO: 6685 | NTC | ACACAAACTGGTCGTAGATG |
| SEQ ID NO: 6686 | NTC | ACACCCGTGTATGCACCGGG |
| SEQ ID NO: 6687 | NTC | ACACGACCGACCGGTGGAAT |
| SEQ ID NO: 6688 | NTC | ACACGTCTTCGGCTATACGC |
| SEQ ID NO: 6689 | NTC | ACAGACCGAATAACCGACGA |
| SEQ ID NO: 6690 | NTC | ACAGAGTCGTGTGCCGAACG |
| SEQ ID NO: 6691 | NTC | ACAGCAGGGGCCGCGAATAA |
| SEQ ID NO: 6692 | NTC | ACAGCGGCCTAATACTTCGC |
| SEQ ID NO: 6693 | NTC | ACCAACGCTACGATCCCGGA |
| SEQ ID NO: 6694 | NTC | ACCAATAACGGGTACAAGTC |
| SEQ ID NO: 6695 | NTC | ACCACCGTGCCGGGGACGCG |

TABLE 1-continued mmSurf sgRNA library sequences

| SEQ ID NO | id_gRNA Target | Sequence |
|---|---|---|
| SEQ ID NO: 6696 | NTC | ACCAGGACTGCCGCGTGAGG |
| SEQ ID NO: 6697 | NTC | ACCAGGCGCGGACCGCACAT |
| SEQ ID NO: 6698 | NTC | ACCATACGGGGTCTTGTCGA |
| SEQ ID NO: 6699 | NTC | ACCATAGTTTCAACCTGCGG |
| SEQ ID NO: 6700 | NTC | ACCATCCGATATTACGAGCA |
| SEQ ID NO: 6701 | NTC | ACCATGATGTCACCGCCGCA |
| SEQ ID NO: 6702 | NTC | ACCCACGTATGTACTCGGGA |
| SEQ ID NO: 6703 | NTC | ACCCAGATTCGCATTCGGAT |
| SEQ ID NO: 6704 | NTC | ACCCATCCCCGCGTCCGAGA |
| SEQ ID NO: 6705 | NTC | ACCCATCGGGTGCGATATGG |
| SEQ ID NO: 6706 | NTC | ACCCGCATATGCCGCCTAAG |
| SEQ ID NO: 6707 | NTC | ACCCTAGCCTCATCGCGACC |
| SEQ ID NO: 6708 | NTC | ACCGCACGTTCTCGCAGAGA |
| SEQ ID NO: 6709 | NTC | ACCGCGCATCATTGACGGTG |
| SEQ ID NO: 6710 | NTC | ACCGGACTGCGATATGCCGT |
| SEQ ID NO: 6711 | NTC | ACCGGATGTGGGCGCCTCTC |
| SEQ ID NO: 6712 | NTC | ACCGGTCGAAGTCTGGGATT |
| SEQ ID NO: 6713 | NTC | ACCGGTTCAGCCGCCGGAAC |
| SEQ ID NO: 6714 | NTC | ACCGTACAAGACTCGCTCCA |
| SEQ ID NO: 6715 | NTC | ACCGTCTCTATTATACGGCA |
| SEQ ID NO: 6716 | NTC | ACCGTCTGATGTTCCCGGCT |
| SEQ ID NO: 6717 | NTC | ACCGTTGTTTCCGTCGAAAC |
| SEQ ID NO: 6718 | NTC | ACCTCGTGCAAATCGGTGGC |
| SEQ ID NO: 6719 | NTC | ACCTTGTGTTCGACGGTAGG |
| SEQ ID NO: 6720 | NTC | ACGACGAGAGATACTTAGGC |
| SEQ ID NO: 6721 | NTC | ACGACGTCCGCTGTGTGTAT |
| SEQ ID NO: 6722 | NTC | ACGAGGAGAAGTCGAGTATT |
| SEQ ID NO: 6723 | NTC | ACGCAAGCGGAACGCGTCTA |
| SEQ ID NO: 6724 | NTC | ACGCACCCATACAGGCGCTT |
| SEQ ID NO: 6725 | NTC | ACGCGAAGTGTCGCAGAGTG |
| SEQ ID NO: 6726 | NTC | ACGCTATAGTGTACGTCTAA |
| SEQ ID NO: 6727 | NTC | ACGCTCTTGGCAGATAATCG |
| SEQ ID NO: 6728 | NTC | ACGCTGTTCGTAACCGCGGG |
| SEQ ID NO: 6729 | NTC | ACGGAACCCGATCGGAACGG |
| SEQ ID NO: 6730 | NTC | ACGGATTGCTGACGCTATCA |
| SEQ ID NO: 6731 | NTC | ACGGGTCAACTTCTTGCCGC |
| SEQ ID NO: 6732 | NTC | ACGGTCCCAACGAGCGCCGG |
| SEQ ID NO: 6733 | NTC | ACGGTCCCTCTCGGGTCAAT |

TABLE 1-continued mmSurf sgRNA library sequences

| SEQ ID NO | id_gRNA Target | Sequence |
|---|---|---|
| SEQ ID NO: 6734 | NTC | ACGGTCGAGCACGGTTATGA |
| SEQ ID NO: 6735 | NTC | ACGTCGATGCTTATCCGTCT |
| SEQ ID NO: 6736 | NTC | ACGTCGGTCTAGAGTTAAGT |
| SEQ ID NO: 6737 | NTC | ACGTGTAAGGCGAACGCCTT |
| SEQ ID NO: 6738 | NTC | ACGTGTTCTCGTACTTAGCT |
| SEQ ID NO: 6739 | NTC | ACGTTGCAGCTCGCGTTTCG |
| SEQ ID NO: 6740 | NTC | ACTAAGGAGTCCCGGTCCGA |
| SEQ ID NO: 6741 | NTC | ACTAGCTCCATAACGTGTAC |
| SEQ ID NO: 6742 | NTC | ACTCACCTCGCACGATCGTA |
| SEQ ID NO: 6743 | NTC | ACTCGACCTAACGTCGATGT |
| SEQ ID NO: 6744 | NTC | ACTCGCGAAACCGTACATGA |
| SEQ ID NO: 6745 | NTC | ACTGCGCGTATAGGACGCAA |
| SEQ ID NO: 6746 | NTC | ACTGTCCCATTGTACGACGG |
| SEQ ID NO: 6747 | NTC | ACTTCCCGCGGTTCCGTTGA |
| SEQ ID NO: 6748 | NTC | ACTTGTATACGACGGCTAGA |
| SEQ ID NO: 6749 | NTC | ACTTTACATCATGTCGTCGT |
| SEQ ID NO: 6750 | NTC | AGAAAGGCACGTGCGACGTC |
| SEQ ID NO: 6751 | NTC | AGAAATCCAGTCCCGCCTAA |
| SEQ ID NO: 6752 | NTC | AGACCTCGTTAGCCGTAGCT |
| SEQ ID NO: 6753 | NTC | AGACGTTGATTTACCGGCCA |
| SEQ ID NO: 6754 | NTC | AGACTCGTGTGCCACGAGGA |
| SEQ ID NO: 6755 | NTC | AGAGGCGGAGCAATACTCGC |
| SEQ ID NO: 6756 | NTC | AGATAGCGCAATCCCGCATG |
| SEQ ID NO: 6757 | NTC | AGATTCTCGCGTAACCAGAG |
| SEQ ID NO: 6758 | NTC | AGCACGCGCACAAGAGCCGC |
| SEQ ID NO: 6759 | NTC | AGCACTAGGATCGCGGCCTT |
| SEQ ID NO: 6760 | NTC | AGCAGTTCGGGTAACGCCCA |
| SEQ ID NO: 6761 | NTC | AGCATGGAGTCAACGTCCGC |
| SEQ ID NO: 6762 | NTC | AGCCGCGCCGCAAAGCTTTT |
| SEQ ID NO: 6763 | NTC | AGCCGGGCTTTCCGTCAAGC |
| SEQ ID NO: 6764 | NTC | AGCCTAGTCGCGCTAATATT |
| SEQ ID NO: 6765 | NTC | AGCGAGTGTCCGTGACGTTC |
| SEQ ID NO: 6766 | NTC | AGCGATGTTCACGCACAGCG |
| SEQ ID NO: 6767 | NTC | AGCGCCATAGGACGCCAAAC |
| SEQ ID NO: 6768 | NTC | AGCGCGTAAGGCGTAGTTAC |
| SEQ ID NO: 6769 | NTC | AGCGTATCTTATGTACCGCT |
| SEQ ID NO: 6770 | NTC | AGCGTCCACGCGTCTATGGA |
| SEQ ID NO: 6771 | NTC | AGCGTGTCGAGAACGGCTTG |

TABLE 1-continued mmSurf sgRNA library sequences

| SEQ ID NO | id_gRNA Target | Sequence |
|---|---|---|
| SEQ ID NO: 6772 | NTC | AGCGTTCGCAGCTGGTCAAC |
| SEQ ID NO: 6773 | NTC | AGCTATCCCACGTTCGCGG |
| SEQ ID NO: 6774 | NTC | AGCTTAGATCGTGCGTCGTA |
| SEQ ID NO: 6775 | NTC | AGGACTATCCGCGGGATTAG |
| SEQ ID NO: 6776 | NTC | AGGCAGCCCGCGTTAGAGAT |
| SEQ ID NO: 6777 | NTC | AGGCCCCGAGACGCGCCACA |
| SEQ ID NO: 6778 | NTC | AGGGCAATCGCGTGCCCAAC |
| SEQ ID NO: 6779 | NTC | AGGGTTAGGCTGACCCGCGA |
| SEQ ID NO: 6780 | NTC | AGGTCCGCTGGCGCAATGGG |
| SEQ ID NO: 6781 | NTC | AGGTCGTGGACCCGCATGTA |
| SEQ ID NO: 6782 | NTC | AGGTGCGTGTCAACCGGTAG |
| SEQ ID NO: 6783 | NTC | AGTACACTACATCGACTTCG |
| SEQ ID NO: 6784 | NTC | AGTACAGCCGACGAGTGCGA |
| SEQ ID NO: 6785 | NTC | AGTAGACGCTATGTTCGCGC |
| SEQ ID NO: 6786 | NTC | AGTAGAGTCGCGAACGCTAC |
| SEQ ID NO: 6787 | NTC | AGTCACTAGGCGCTCTCGCG |
| SEQ ID NO: 6788 | NTC | AGTCAGCTCCGGGGTATACG |
| SEQ ID NO: 6789 | NTC | AGTCATCCTCTATGCGCGTA |
| SEQ ID NO: 6790 | NTC | AGTCCCACGTTTGCCGTCAA |
| SEQ ID NO: 6791 | NTC | AGTCCGGTCGAAATCTGTAT |
| SEQ ID NO: 6792 | NTC | AGTGCCGGGGTGTATACCG |
| SEQ ID NO: 6793 | NTC | AGTGTCACGGCAAAGTCGAG |
| SEQ ID NO: 6794 | NTC | AGTTAAGCGCGTATCTACGT |
| SEQ ID NO: 6795 | NTC | AGTTAAGCTCCAATCGTCTG |
| SEQ ID NO: 6796 | NTC | AGTTTACGTGGTCCGATGTC |
| SEQ ID NO: 6797 | NTC | ATAAAGTCCCAGGTGCGCGC |
| SEQ ID NO: 6798 | NTC | ATAACTTACTCGTTACGACT |
| SEQ ID NO: 6799 | NTC | ATAACTTATGCGCTTCGGGG |
| SEQ ID NO: 6800 | NTC | ATAATGCGCGCGAATACTTA |
| SEQ ID NO: 6801 | NTC | ATACCTCCGCTAGACCGTCT |
| SEQ ID NO: 6802 | NTC | ATACGCATAGATCGGTAAGC |
| SEQ ID NO: 6803 | NTC | ATACGCGTGATGACCTTATG |
| SEQ ID NO: 6804 | NTC | ATAGATGTCTACGCGCCGTT |
| SEQ ID NO: 6805 | NTC | ATAGCCCGGTTTGCCCGTCT |
| SEQ ID NO: 6806 | NTC | ATAGGCGCACGGGCTACTCC |
| SEQ ID NO: 6807 | NTC | ATATCGAATGATGTCCGCAT |
| SEQ ID NO: 6808 | NTC | ATATGAGCCCGACCTCTCGA |
| SEQ ID NO: 6809 | NTC | ATATGCTCGACCCATCGTCC |

TABLE 1-continued mmSurf sgRNA library sequences

| SEQ ID NO | id_gRNA Target | Sequence |
|---|---|---|
| SEQ ID NO: 6810 | NTC | ATATTGTCCCATACGATCGG |
| SEQ ID NO: 6811 | NTC | ATCACACGTTAAACGGGGCG |
| SEQ ID NO: 6812 | NTC | ATCATGCCTTCGCATTAACC |
| SEQ ID NO: 6813 | NTC | ATCCACGCTCCGCGGTACTT |
| SEQ ID NO: 6814 | NTC | ATCCCCCCGACTTAGGGATT |
| SEQ ID NO: 6815 | NTC | ATCCGAGATCTGCGAATTAT |
| SEQ ID NO: 6816 | NTC | ATCCGGGCATAGCGTTTAAA |
| SEQ ID NO: 6817 | NTC | ATCCGTACCAAACACGCTAC |
| SEQ ID NO: 6818 | NTC | ATCGAGCACCGAGTTGTGAT |
| SEQ ID NO: 6819 | NTC | ATCGATATTGATAAACGCGA |
| SEQ ID NO: 6820 | NTC | ATCGCAGGTCTACGCAGAGT |
| SEQ ID NO: 6821 | NTC | ATCGCCTAGCCCAAGCGACG |
| SEQ ID NO: 6822 | NTC | ATCGCGGCGCGTTAAGGCAG |
| SEQ ID NO: 6823 | NTC | ATCGCTAATTTACGAAGGCG |
| SEQ ID NO: 6824 | NTC | ATCGTAAATTACACGTACAG |
| SEQ ID NO: 6825 | NTC | ATCTTAACCAGCGCATCCCG |
| SEQ ID NO: 6826 | NTC | ATGACACTTACGGTACTCGT |
| SEQ ID NO: 6827 | NTC | ATHACCTCTTCGTTCGAGAG |
| SEQ ID NO: 6828 | NTC | ATGATGTGATCCTTCGCCGA |
| SEQ ID NO: 6829 | NTC | ATGCCAATGCCGTTGTTAGC |
| SEQ ID NO: 6830 | NTC | ATGGACCCTTCAGTGCGGTA |
| SEQ ID NO: 6831 | NTC | ATGGGAAAGCCCACGACAAT |
| SEQ ID NO: 6832 | NTC | ATGGTGGCTGTACTCGTAAC |
| SEQ ID NO: 6833 | NTC | ATGTGTATGAAGCCCGTCAT |
| SEQ ID NO: 6834 | NTC | ATGTGTCATAGCGGCGTAGG |
| SEQ ID NO: 6835 | NTC | ATGTTACGTACGTGATCTCC |
| SEQ ID NO: 6836 | NTC | ATGTTGCAGCGCTGTACGCC |
| SEQ ID NO: 6837 | NTC | ATGTTGCAGTTCGGCTCGAT |
| SEQ ID NO: 6838 | NTC | ATTAGGTGACTGGAACACGT |
| SEQ ID NO: 6839 | NTC | ATTATAGCAGCCCCCCGAAT |
| SEQ ID NO: 6840 | NTC | ATTATTCCTCCGGATGACGA |
| SEQ ID NO: 6841 | NTC | ATTCAGTGTACCGGTCAAAT |
| SEQ ID NO: 6842 | NTC | ATTCCGTTTGCAGCGAGACC |
| SEQ ID NO: 6843 | NTC | ATTCGGACCGTTATCTCACC |
| SEQ ID NO: 6844 | NTC | ATTCGTGCATCGCGGGGTTT |
| SEQ ID NO: 6845 | NTC | ATTGTTCGACCGTCTACGGG |
| SEQ ID NO: 6846 | NTC | ATTTGAATGCTCCCGTCGAC |
| SEQ ID NO: 6847 | NTC | ATTTGCCCGTCCATACGCGG |

TABLE 1-continued mmSurf sgRNA library sequences

| SEQ ID NO | id_gRNA Target | Sequence |
|---|---|---|
| SEQ ID NO: 6848 | NTC | CAAACGAGGCCACGTACGTG |
| SEQ ID NO: 6849 | NTC | CAAAGTAACTATCTCGTCGA |
| SEQ ID NO: 6850 | NTC | CAACACGTGCGAGCGAACTG |
| SEQ ID NO: 6851 | NTC | CAACCGTGCGATGCGCGCTA |
| SEQ ID NO: 6852 | NTC | CAACCTGCCTAGCGACCCGC |
| SEQ ID NO: 6853 | NTC | CAACGATCAGGCGTGTTATC |
| SEQ ID NO: 6854 | NTC | CAACGGTCACGCTAGAATAA |
| SEQ ID NO: 6855 | NTC | CAAGAGTTAACCTCGACCGG |
| SEQ ID NO: 6856 | NTC | CAAGGATCGTGCCGTGATTT |
| SEQ ID NO: 6857 | NTC | CAAGGGTGGTCATTGCGAC |
| SEQ ID NO: 6858 | NTC | CAATACACCGTTAACCCTCT |
| SEQ ID NO: 6859 | NTC | CAATATCTAAGCGCTAACGA |
| SEQ ID NO: 6860 | NTC | CAATATGCACGTAGCCTCGT |
| SEQ ID NO: 6861 | NTC | CAATATTCGACCTACGCTCC |
| SEQ ID NO: 6862 | NTC | CAATGGCGTCTGCCGTTCAG |
| SEQ ID NO: 6863 | NTC | CACAACGCCTACCAGCGGAC |
| SEQ ID NO: 6864 | NTC | CACAATACGCGGCAGAGGTC |
| SEQ ID NO: 6865 | NTC | CACACGCCGCGGGCCGTGAG |
| SEQ ID NO: 6866 | NTC | CACCCCGTAGCAACGATAAA |
| SEQ ID NO: 6867 | NTC | CACCCGACTCGGCCGTAAAG |
| SEQ ID NO: 6868 | NTC | CACCGCTGCCCTAGTACCGG |
| SEQ ID NO: 6869 | NTC | CACCTATTCCCCTCCGCAAC |
| SEQ ID NO: 6870 | NTC | CACCTCGCGTCATATCACTA |
| SEQ ID NO: 6871 | NTC | CACCTTTCGAGGTAACACCG |
| SEQ ID NO: 6872 | NTC | CACGAATAACTACAGGTTGC |
| SEQ ID NO: 6873 | NTC | CACGCAGGAGCGGCGACACT |
| SEQ ID NO: 6874 | NTC | CACGCCTTCGTCAACCCTAT |
| SEQ ID NO: 6875 | NTC | CACGGCAGGCATCTCGTCTA |
| SEQ ID NO: 6876 | NTC | CACGGGCAGCGATCTAGTTG |
| SEQ ID NO: 6877 | NTC | CACGTAAGACGCTCCACTTA |
| SEQ ID NO: 6878 | NTC | CACGTATACTTAGGTCAGCG |
| SEQ ID NO: 6879 | NTC | CACTCAGCGGTTGGACGCCC |
| SEQ ID NO: 6880 | NTC | CAGAAACTCTTACCGAGCGC |
| SEQ ID NO: 6881 | NTC | CAGCACCACGCGTCGTGCGG |
| SEQ ID NO: 6882 | NTC | CAGCCACCGCACCGGCGTAA |
| SEQ ID NO: 6883 | NTC | CAGCGACTCTGATCGGCGTA |
| SEQ ID NO: 6884 | NTC | CAGCTCACCCTGCGTACGGT |
| SEQ ID NO: 6885 | NTC | CAGCTGACCGTTAATCGATA |

TABLE 1-continued mmSurf sgRNA library sequences

| SEQ ID NO | id_gRNA Target | Sequence |
|---|---|---|
| SEQ ID NO: 6886 | NTC | CAGGGACGTAGCCGCCGTTA |
| SEQ ID NO: 6887 | NTC | CAGGTTTCCCCTAGTCGAAT |
| SEQ ID NO: 6888 | NTC | CAGTGCCGGTAGCGGCACGG |
| SEQ ID NO: 6889 | NTC | CATACCCGCGCCGTGACTCC |
| SEQ ID NO: 6890 | NTC | CATACCCGGTGTTTCCTAGC |
| SEQ ID NO: 6891 | NTC | CATACTGTTATCGACCCGCA |
| SEQ ID NO: 6892 | NTC | CATAGATCCGCGATTGTACG |
| SEQ ID NO: 6893 | NTC | CATAGCAACGCCCAAACTCG |
| SEQ ID NO: 6894 | NTC | CATATACTCTTGCGCTAGAC |
| SEQ ID NO: 6895 | NTC | CATATGCCTATAACCGGCGG |
| SEQ ID NO: 6896 | NTC | CATATGCTCGACGGTATAAA |
| SEQ ID NO: 6897 | NTC | CATCAGCCCATTATGACTCG |
| SEQ ID NO: 6898 | NTC | CATCCCCGACTACGACTAC |
| SEQ ID NO: 6899 | NTC | CATCGAGGGTAAACGCCATT |
| SEQ ID NO: 6900 | NTC | CATCGCCGACGATCCTCTGG |
| SEQ ID NO: 6901 | NTC | CATCGGCTATGTCGGGGACA |
| SEQ ID NO: 6902 | NTC | CATCGGTAGTCACTACGCCC |
| SEQ ID NO: 6903 | NTC | CATCGTAACACACGTACGAG |
| SEQ ID NO: 6904 | NTC | CATCTATGAGACGTGCGTAC |
| SEQ ID NO: 6905 | NTC | CATGCCCGTCTGCGCCGCAT |
| SEQ ID NO: 6906 | NTC | CATGGGACCCCCCCTCACGT |
| SEQ ID NO: 6907 | NTC | CATTACGTGTCGAGCTCCGG |
| SEQ ID NO: 6908 | NTC | CATTCGGTCCGTTCATCTCG |
| SEQ ID NO: 6909 | NTC | CATTCTCTGACGAATGCGCC |
| SEQ ID NO: 6910 | NTC | CATTGTAGACTCGTACGGAT |
| SEQ ID NO: 6911 | NTC | CATTTCCGGGGTCCGATGCA |
| SEQ ID NO: 6912 | NTC | CCAACATCGGGGCGCATAAT |
| SEQ ID NO: 6913 | NTC | CCAACCCGGCATCGTCCGCT |
| SEQ ID NO: 6914 | NTC | CCAACCTAAGGCAATACGGT |
| SEQ ID NO: 6915 | NTC | CCAAGGCGCACGCTACGTGG |
| SEQ ID NO: 6916 | NTC | CCAGCGGACGGCGAACTCCA |
| SEQ ID NO: 6917 | NTC | CCAGCTAACGTTTTAGTACG |
| SEQ ID NO: 6918 | NTC | CCATCGGTTCGACTTACCGC |
| SEQ ID NO: 6919 | NTC | CCATTAGTACGAACATTGCG |
| SEQ ID NO: 6920 | NTC | CCCACTTAATAACGCCGCTT |
| SEQ ID NO: 6921 | NTC | CCCATCATTCGCGCTGACGT |
| SEQ ID NO: 6922 | NTC | CCCATTCAACACCGTTTGTA |
| SEQ ID NO: 6923 | NTC | CCCCTATAGGCGCGCTAAGG |

TABLE 1-continued mmSurf sgRNA library sequences

| SEQ ID NO | id_gRNA Target | Sequence |
|---|---|---|
| SEQ ID NO: 6924 | NTC | CCCCTTCGATATCCGATGAC |
| SEQ ID NO: 6925 | NTC | CCCGCCTGGCGATTCACGGG |
| SEQ ID NO: 6926 | NTC | CCCGGCAGACTAACTAGCGC |
| SEQ ID NO: 6927 | NTC | CCCGGGTACACCAATAGCCA |
| SEQ ID NO: 6928 | NTC | CCCGGTCGGGGATACTAACT |
| SEQ ID NO: 6929 | NTC | CCCGTAGGGGTCGTGGTTTT |
| SEQ ID NO: 6930 | NTC | CCCTAAACCATAGTTTCGCC |
| SEQ ID NO: 6931 | NTC | CCCTAGCTCGGTTAGAGAAT |
| SEQ ID NO: 6932 | NTC | CCCTATATGCGAGATCCATA |
| SEQ ID NO: 6933 | NTC | CCCTCGGTTGAGCAGCGCGA |
| SEQ ID NO: 6934 | NTC | CCCTGATGTGCTATACGCGC |
| SEQ ID NO: 6935 | NTC | CCCTTAAAGTGACGGACGAA |
| SEQ ID NO: 6936 | NTC | CCGACCGTGTGAGAGTACGT |
| SEQ ID NO: 6937 | NTC | CCGACTGCCGAGCTAGGCGT |
| SEQ ID NO: 6938 | NTC | CCGAGAGGTACTCCAATTCG |
| SEQ ID NO: 6939 | NTC | CCGAGATGGCTCGGATAGAC |
| SEQ ID NO: 6940 | NTC | CCGAGCACCCTATTTATCTA |
| SEQ ID NO: 6941 | NTC | CCGAGCCGAATTGGGCGTGT |
| SEQ ID NO: 6942 | NTC | CCGATACCATTGTCACCAAT |
| SEQ ID NO: 6943 | NTC | CCGCACCGCAGTCATGGTAA |
| SEQ ID NO: 6944 | NTC | CCGCCCCTGCGAACTGCGTT |
| SEQ ID NO: 6945 | NTC | CCGCCCGGGTGTGAGTTGAG |
| SEQ ID NO: 6946 | NTC | CCGCGCATTAACGATCAGTA |
| SEQ ID NO: 6947 | NTC | CCGCGCCGTTAGGGAACGAG |
| SEQ ID NO: 6948 | NTC | CCGCGTGACGCAATCCCTTG |
| SEQ ID NO: 6949 | NTC | CCGCTTGGGCGCTATTAATT |
| SEQ ID NO: 6950 | NTC | CCGGACTTGTTATACTTGAT |
| SEQ ID NO: 6951 | NTC | CCGGAGCGCGTTGCAGTTCT |
| SEQ ID NO: 6952 | NTC | CCGGATCGGCTACGCTACGG |
| SEQ ID NO: 6953 | NTC | CCGGCGCTGCGGTCGGCTTG |
| SEQ ID NO: 6954 | NTC | CCGGCTTGAATACCGTGCGG |
| SEQ ID NO: 6955 | NTC | CCGGGCGCCGTATCCCCTAC |
| SEQ ID NO: 6956 | NTC | CCGGTTTATAAATTACGTGG |
| SEQ ID NO: 6957 | NTC | CCGTATACGTATCTATGCCG |
| SEQ ID NO: 6958 | NTC | CCGTCGAGCAATCCCGCCAA |
| SEQ ID NO: 6959 | NTC | CCGTGATTTCGGTAGCGTAC |
| SEQ ID NO: 6960 | NTC | CCGTTCAATTATGCTGGCGT |
| SEQ ID NO: 6961 | NTC | CCGTTCTGACGACGCTAAAG |

TABLE 1-continued mmSurf sgRNA library sequences

| SEQ ID NO | id_gRNA Target | Sequence |
|---|---|---|
| SEQ ID NO: 6962 | NTC | CCGTTTCGCCTATTGGTGCG |
| SEQ ID NO: 6963 | NTC | CCTAACTCGAAGTCTCGTCA |
| SEQ ID NO: 6964 | NTC | CCTACTAACGACGAGTCAAA |
| SEQ ID NO: 6965 | NTC | CCTATTAGTCCGGTTTAGTC |
| SEQ ID NO: 6966 | NTC | CCTCAAATAGCGAACGTCAA |
| SEQ ID NO: 6967 | NTC | CCTCCAGTAGCGTCATTAAC |
| SEQ ID NO: 6968 | NTC | CCTCCTTCAGTTCGATCTGG |
| SEQ ID NO: 6969 | NTC | CCTGCTATTCTCGCATGCGA |
| SEQ ID NO: 6970 | NTC | CCTTACGGCGGAGAACGAGT |
| SEQ ID NO: 6971 | NTC | CCTTAGACCGGGTGTACCTC |
| SEQ ID NO: 6972 | NTC | CCTTCGGATTCGTAGGCTGG |
| SEQ ID NO: 6973 | NTC | CCTTGTGGCGTGCCAAACGA |
| SEQ ID NO: 6974 | NTC | CCTTTGATGGGCGCGTACTC |
| SEQ ID NO: 6975 | NTC | CGAAACCATACCTCCTTCGA |
| SEQ ID NO: 6976 | NTC | CGAAAGGCCCGACTGCGTGG |
| SEQ ID NO: 6977 | NTC | CGAACTTCTACCGTTGTGCG |
| SEQ ID NO: 6978 | NTC | CGAAGTACACGGTTCTCTCG |
| SEQ ID NO: 6979 | NTC | CGAATCGGGAAGGCGCGTGT |
| SEQ ID NO: 6980 | NTC | CGAATGCACAGGCTCGCGGT |
| SEQ ID NO: 6981 | NTC | CGAATGCGCCGGAGAATATT |
| SEQ ID NO: 6982 | NTC | CGACACGATGGTCATACTAC |
| SEQ ID NO: 6983 | NTC | CGACACTTGGGCTGACGCGC |
| SEQ ID NO: 6984 | NTC | CGACGACCCATTTCGGTTAT |
| SEQ ID NO: 6985 | NTC | CGACGACCTTGGATTGGCAG |
| SEQ ID NO: 6986 | NTC | CGACGGTTGTGCTGAGGCTT |
| SEQ ID NO: 6987 | NTC | CGACTATTGCCGTCCATCTC |
| SEQ ID NO: 6988 | NTC | CGACTCCGGGAATATCCGTT |
| SEQ ID NO: 6989 | NTC | CGACTCGCTTAACCGTGCAG |
| SEQ ID NO: 6990 | NTC | CGAGACGAATCCATCATGCG |
| SEQ ID NO: 6991 | NTC | CGAGAGAATCGTCCGTCATA |
| SEQ ID NO: 6992 | NTC | CGAGCCTCGTCTTTCATGGG |
| SEQ ID NO: 6993 | NTC | CGAGCTCGGCAAATTTGATT |
| SEQ ID NO: 6994 | NTC | CGAGGATGTACATACGTAAA |
| SEQ ID NO: 6995 | NTC | CGAGGCTTAACGCCAGATTC |
| SEQ ID NO: 6996 | NTC | CGAGTAATTATTTGCGGTCG |
| SEQ ID NO: 6997 | NTC | CGAGTATCAGCATGTCGACG |
| SEQ ID NO: 6998 | NTC | CGATACGCTATAGAATAGTC |
| SEQ ID NO: 6999 | NTC | CGATGTCGAAAGTCGGTCAA |

TABLE 1-continued mmSurf sgRNA library sequences

| SEQ ID NO | id_gRNA Target | Sequence |
|---|---|---|
| SEQ ID NO: 7000 | NTC | CGATTGACGTTGGGCTCTCA |
| SEQ ID NO: 7001 | NTC | CGCACTTCTAGTAGCTGTCG |
| SEQ ID NO: 7002 | NTC | CGCAGAGTTCAAATCCGCGC |
| SEQ ID NO: 7003 | NTC | CGCATAGTGTACCGTTGCGC |
| SEQ ID NO: 7004 | NTC | CGCCAATGGTGGCCGACTCG |
| SEQ ID NO: 7005 | NTC | CGCCAGTATACCACATTCGT |
| SEQ ID NO: 7006 | NTC | CGCCCCTAGTTGTCCCGCCC |
| SEQ ID NO: 7007 | NTC | CGCCGGATGACTGGTGGATA |
| SEQ ID NO: 7008 | NTC | CGCCTAGTATCTTCGGGGAT |
| SEQ ID NO: 7009 | NTC | CGCGACGTACGGCTGGAGCA |
| SEQ ID NO: 7010 | NTC | CGCGCCGAGGGCCTCGTTAC |
| SEQ ID NO: 7011 | NTC | CGCGCCTACCCTTTTACCGC |
| SEQ ID NO: 7012 | NTC | CGCGCGACTGCAGCTAATCT |
| SEQ ID NO: 7013 | NTC | CGCGCGGATATTTAAACTTC |
| SEQ ID NO: 7014 | NTC | CGCGCGGATCTTCCGTACAA |
| SEQ ID NO: 7015 | NTC | CGCGTATATGTCACACGGCA |
| SEQ ID NO: 7016 | NTC | CGCTACAGTAATCGCAACGA |
| SEQ ID NO: 7017 | NTC | CGCTCCGTATCCTCTCATAA |
| SEQ ID NO: 7018 | NTC | CGCTCGGTAAGGTCGATTGG |
| SEQ ID NO: 7019 | NTC | CGCTCGGTGACGTATACACG |
| SEQ ID NO: 7020 | NTC | CGCTTCATTGCCCGAACGCT |
| SEQ ID NO: 7021 | NTC | CGCTTCGTCTCTCGCAAACA |
| SEQ ID NO: 7022 | NTC | CGGAATACGCCAAAACCTAT |
| SEQ ID NO: 7023 | NTC | CGGACTTACCGCAGATTATA |
| SEQ ID NO: 7024 | NTC | CGGATCCGGTACGGTCAGTT |
| SEQ ID NO: 7025 | NTC | CGGATCCTCCCGTACTATCC |
| SEQ ID NO: 7026 | NTC | CGGCAAGCGCATTCCTATGG |
| SEQ ID NO: 7027 | NTC | CGGCAATGTGTGGCGACCGC |
| SEQ ID NO: 7028 | NTC | CGGCCGTAGTGACGAATGGA |
| SEQ ID NO: 7029 | NTC | CGGCGATAACAGCGACATCG |
| SEQ ID NO: 7030 | NTC | CGGGCAATATGATCGTAGGC |
| SEQ ID NO: 7031 | NTC | CGGGCACTAACCCGATACAC |
| SEQ ID NO: 7032 | NTC | CGGGCGGTAAGAGCTCTACG |
| SEQ ID NO: 7033 | NTC | CGGGCGTCACCTGCTAGTAA |
| SEQ ID NO: 7034 | NTC | CGGGGCGTACATGTGTGGCC |
| SEQ ID NO: 7035 | NTC | CGGGTTATAGATAGTCGTCG |
| SEQ ID NO: 7036 | NTC | CGGTAAGATGGTTATACCGT |
| SEQ ID NO: 7037 | NTC | CGGTAAGGTCGGTCTCCATC |

TABLE 1-continued mmSurf sgRNA library sequences

| SEQ ID NO | id_gRNA Target | Sequence |
|---|---|---|
| SEQ ID NO: 7038 | NTC | CGGTACCACGCCCCACCTCG |
| SEQ ID NO: 7039 | NTC | CGGTCAGTCGTCTTCCCGGA |
| SEQ ID NO: 7040 | NTC | CGGTCGATTGTGGAGTAATG |
| SEQ ID NO: 7041 | NTC | CGGTCGTGACAGACCTGGTG |
| SEQ ID NO: 7042 | NTC | CGGTGAGGATCCCTCTTGCG |
| SEQ ID NO: 7043 | NTC | CGTAAACCATAACGTTGGTC |
| SEQ ID NO: 7044 | NTC | CGTAACCGGAGATAATATTA |
| SEQ ID NO: 7045 | NTC | CGTACCGACAGTAGTCCAAG |
| SEQ ID NO: 7046 | NTC | CGTACGGGCGCGCCGTCCAT |
| SEQ ID NO: 7047 | NTC | CGTAGATGCCTGCTCGAGCA |
| SEQ ID NO: 7048 | NTC | CGTCAATGTGTCCGGACGGT |
| SEQ ID NO: 7049 | NTC | CGTCACCGCTAGTAATGATG |
| SEQ ID NO: 7050 | NTC | CGTCATGGCAAGATCGATAA |
| SEQ ID NO: 7051 | NTC | CGTCCTCGCAGCGTAGACTG |
| SEQ ID NO: 7052 | NTC | CGTCGAAGATACGCAGGCTG |
| SEQ ID NO: 7053 | NTC | CGTCGATCCCTCTATACTGG |
| SEQ ID NO: 7054 | NTC | CGTCGCATGTTGTTGCTCAT |
| SEQ ID NO: 7055 | NTC | CGTGAATCGACCCTCAATAA |
| SEQ ID NO: 7056 | NTC | CGTGATTCCTAAGCCCCCGC |
| SEQ ID NO: 7057 | NTC | CGTGCGTTCGTAATAAAAGG |
| SEQ ID NO: 7058 | NTC | CGTGTAGTCGGGTCGCATGT |
| SEQ ID NO: 7059 | NTC | CGTGTGTTTACAGCCCTTAC |
| SEQ ID NO: 7060 | NTC | CGTGTTTGGCGGCCAACTTT |
| SEQ ID NO: 7061 | NTC | CGTGTTTTACCTCGCTTCGA |
| SEQ ID NO: 7062 | NTC | CGTTAATAAACGCGGTTTCA |
| SEQ ID NO: 7063 | NTC | CGTTAATCCACCGTATGGGC |
| SEQ ID NO: 7064 | NTC | CGTTACGTTTCTTGCCAGGA |
| SEQ ID NO: 7065 | NTC | CGTTAGACCGAATCTCCGGG |
| SEQ ID NO: 7066 | NTC | CGTTATATCTACACTTTGCG |
| SEQ ID NO: 7067 | NTC | CGTTATTGTACACCACGCTC |
| SEQ ID NO: 7068 | NTC | CGTTGCGAATCCACCCTATT |
| SEQ ID NO: 7069 | NTC | CGTTGTTTGGAGCCCGTCCA |
| SEQ ID NO: 7070 | NTC | CTAACAGCGCCGTTATCTAC |
| SEQ ID NO: 7071 | NTC | CTAACGTGGTAGCACTACAA |
| SEQ ID NO: 7072 | NTC | CTAAGTCGACTGTTTCGACC |
| SEQ ID NO: 7073 | NTC | CTAATACACCCGGACGGTAC |
| SEQ ID NO: 7074 | NTC | CTAATACACTCCTTCTCCGC |
| SEQ ID NO: 7075 | NTC | CTAATTCCAATATCCGTCTG |

TABLE 1-continued mmSurf sgRNA library sequences

| SEQ ID NO | id_gRNA Target | Sequence |
|---|---|---|
| SEQ ID NO: 7076 | NTC | CTACCCCGCTGTGCAACGT |
| SEQ ID NO: 7077 | NTC | CTACCCGTCTATTACGATCT |
| SEQ ID NO: 7078 | NTC | CTACCGGTCACGTTGTGACC |
| SEQ ID NO: 7079 | NTC | CTACGAGATTCGGCTAAGCT |
| SEQ ID NO: 7080 | NTC | CTACGAGGGCCGCGAGCGGT |
| SEQ ID NO: 7081 | NTC | CTACGGATAGGCGCGGGTGA |
| SEQ ID NO: 7082 | NTC | CTACTTGTGACGACCTCGCG |
| SEQ ID NO: 7083 | NTC | CTATCGGCCCGCAGTGATGG |
| SEQ ID NO: 7084 | NTC | CTATTGGGAGCGGCCTCTCG |
| SEQ ID NO: 7085 | NTC | CTCAAACCTCCGTTACCCCG |
| SEQ ID NO: 7086 | NTC | CTCATGTACGCCTTCGCTAC |
| SEQ ID NO: 7087 | NTC | CTCCCATCCCCGTAGCGGCC |
| SEQ ID NO: 7088 | NTC | CTCCGACGACTACGCAAGGA |
| SEQ ID NO: 7089 | NTC | CTCCGGACGTGCATCCGAGA |
| SEQ ID NO: 7090 | NTC | CTCCTCGAGGCTGGCTACGT |
| SEQ ID NO: 7091 | NTC | CTCGACCCAGTAGTAGACGG |
| SEQ ID NO: 7092 | NTC | CTCGATGCCACGGAAGGCGG |
| SEQ ID NO: 7093 | NTC | CTCGGACGGCATACGACAAT |
| SEQ ID NO: 7094 | NTC | CTCGGAGATTCGTTAGAAGA |
| SEQ ID NO: 7095 | NTC | CTCGGATGGTGTGTTGAACC |
| SEQ ID NO: 7096 | NTC | CTCGGCTTTACGATCGATCA |
| SEQ ID NO: 7097 | NTC | CTCGGGCTATTCAGCGATAG |
| SEQ ID NO: 7098 | NTC | CTCGTATAGTATTGCGTGGT |
| SEQ ID NO: 7099 | NTC | CTCGTATCTTTTCCCACGGC |
| SEQ ID NO: 7100 | NTC | CTCGTCGGCTTTCGTGCTGC |
| SEQ ID NO: 7101 | NTC | CTCGTGAAACAAGATCCGAC |
| SEQ ID NO: 7102 | NTC | CTCGTGAACCTGTTCGCGCA |
| SEQ ID NO: 7103 | NTC | CTCGTGTCACTCCTCGGTTC |
| SEQ ID NO: 7104 | NTC | CTCTAATAAACCGCACAAGC |
| SEQ ID NO: 7105 | NTC | CTCTCTGCGAGTCGATGATT |
| SEQ ID NO: 7106 | NTC | CTGATCGGTGCATATCTCGG |
| SEQ ID NO: 7107 | NTC | CTGCACGGCACGACATCCAA |
| SEQ ID NO: 7108 | NTC | CTGCGTGTAACGTGTTGGGA |
| SEQ ID NO: 7109 | NTC | CTGCTTGAACGCCTAGACGG |
| SEQ ID NO: 7110 | NTC | CTGGGGCCGCTGAACCGCCG |
| SEQ ID NO: 7111 | NTC | CTGTCTTCAACGTCTGGCCG |
| SEQ ID NO: 7112 | NTC | CTTAAGTTCGCGACGGAATG |
| SEQ ID NO: 7113 | NTC | CTTATCCATAATAGGCGGCG |

TABLE 1-continued mmSurf sgRNA library sequences

| SEQ ID NO | id_gRNA Target | Sequence |
| --- | --- | --- |
| SEQ ID NO: 7114 | NTC | CTTATCGATTTGGGTTCAAC |
| SEQ ID NO: 7115 | NTC | CTTCACGCCTTGGACCGATA |
| SEQ ID NO: 7116 | NTC | CTTGAAAAAGGGGCGACTAT |
| SEQ ID NO: 7117 | NTC | CTTGACACCTCGTCCGCATC |
| SEQ ID NO: 7118 | NTC | CTTTAGTCACGATATACGTC |
| SEQ ID NO: 7119 | NTC | CTTTATACCGCGCGTCGGCA |
| SEQ ID NO: 7120 | NTC | CTTTATTCCGTTGCATGTCG |
| SEQ ID NO: 7121 | NTC | CTTTGGCGTCGAGAAGCGCA |
| SEQ ID NO: 7122 | NTC | GAACCACGAGCGAGCGTATA |
| SEQ ID NO: 7123 | NTC | GAACCAGTATCTAACCCGAC |
| SEQ ID NO: 7124 | NTC | GAACCCGGGAAACACGTCCG |
| SEQ ID NO: 7125 | NTC | GAACCGGCGTGCGTTAGCGG |
| SEQ ID NO: 7126 | NTC | GAACCTTCGCGCAACTTAAC |
| SEQ ID NO: 7127 | NTC | GAACGTAACGGCATGCATCA |
| SEQ ID NO: 7128 | NTC | GAACTCGTTAGGCCGTGAAG |
| SEQ ID NO: 7129 | NTC | GAATTGAGCCGCAACTCGGC |
| SEQ ID NO: 7130 | NTC | GACAATCGACACGCCGCTTC |
| SEQ ID NO: 7131 | NTC | GACAGCCGGTTGACCGGGTC |
| SEQ ID NO: 7132 | NTC | GACAGTTGACGCGACGGAGA |
| SEQ ID NO: 7133 | NTC | GACAGTTGGATAACCGTGTC |
| SEQ ID NO: 7134 | NTC | GACCAACCTTACGGTAACTC |
| SEQ ID NO: 7135 | NTC | GACCACTATGTACTTATCGC |
| SEQ ID NO: 7136 | NTC | GACCATACGCCTCGTATGCC |
| SEQ ID NO: 7137 | NTC | GACCGACGGTATACCCTACT |
| SEQ ID NO: 7138 | NTC | GACCGGCCAACGGTAGCGGC |
| SEQ ID NO: 7139 | NTC | GACCGGTGTGTTTACGCGTG |
| SEQ ID NO: 7140 | NTC | GACCGTCGGGATCCTTAATT |
| SEQ ID NO: 7141 | NTC | GACCTCGCAATTGAGCGCTC |
| SEQ ID NO: 7142 | NTC | GACGAAAGGTCCTACGAAGT |
| SEQ ID NO: 7143 | NTC | GACGGTCCCCCCTATGAAAT |
| SEQ ID NO: 7144 | NTC | GACGTATTGGATTCGCAACC |
| SEQ ID NO: 7145 | NTC | GACGTCTAATTTCTGGCCGT |
| SEQ ID NO: 7146 | NTC | GACTAGCACGAACTGCGGTT |
| SEQ ID NO: 7147 | NTC | GACTCCGGGTACTAAATGTC |
| SEQ ID NO: 7148 | NTC | GACTTCGACGAGAAAACGTT |
| SEQ ID NO: 7149 | NTC | GAGACCCATTATGATCCTAG |
| SEQ ID NO: 7150 | NTC | GAGATTAAATTAACGCCGGC |
| SEQ ID NO: 7151 | NTC | GAGATTCGATACTGCGGTCA |

TABLE 1-continued mmSurf sgRNA library sequences

| SEQ ID NO | id_gRNA Target | Sequence |
|---|---|---|
| SEQ ID NO: 7152 | NTC | GAGCCCCAACGCGCGAAGCA |
| SEQ ID NO: 7153 | NTC | GAGCGCCAAGCGTGCGTTGA |
| SEQ ID NO: 7154 | NTC | GAGCGCGGGCCAGCGAACGT |
| SEQ ID NO: 7155 | NTC | GAGCGTCCCGTGATTTAAAG |
| SEQ ID NO: 7156 | NTC | GAGCTAATCTGTAGACGTCG |
| SEQ ID NO: 7157 | NTC | GAGGACCTAGGTTCCCGGAT |
| SEQ ID NO: 7158 | NTC | GAGGCGGGCTCTTCTATCGT |
| SEQ ID NO: 7159 | NTC | GAGGCGTACTTCGGCTCTAA |
| SEQ ID NO: 7160 | NTC | GAGTCGAGTTAATAACGCTC |
| SEQ ID NO: 7161 | NTC | GATAAGACTCCGCGAGCTTC |
| SEQ ID NO: 7162 | NTC | GATACGTGAGGTTGCCGGTG |
| SEQ ID NO: 7163 | NTC | GATAGAACAACAGCGGTGCA |
| SEQ ID NO: 7164 | NTC | GATATTTACCGGCGATAAGA |
| SEQ ID NO: 7165 | NTC | GATCACTCCCGAAAGTAGTG |
| SEQ ID NO: 7166 | NTC | GATCCCCTACGCTTCAACCT |
| SEQ ID NO: 7167 | NTC | GATCGAGTGACACCCACCCG |
| SEQ ID NO: 7168 | NTC | GATCTTACCACTCGTCGTAG |
| SEQ ID NO: 7169 | NTC | GATGCGGACCCACGTTAAGC |
| SEQ ID NO: 7170 | NTC | GATGCGGGTGGAAAACGTTA |
| SEQ ID NO: 7171 | NTC | GATGGCCAGTAACGGCGTCA |
| SEQ ID NO: 7172 | NTC | GATTACGGGGTTCCGTAACT |
| SEQ ID NO: 7173 | NTC | GATTCATTATCGGCATACGG |
| SEQ ID NO: 7174 | NTC | GATTCCGTATAGTAATCGAG |
| SEQ ID NO: 7175 | NTC | GATTGAGAAGCCGCGGTATC |
| SEQ ID NO: 7176 | NTC | GATTGGACGGTCGCAGGATA |
| SEQ ID NO: 7177 | NTC | GATTTCTCGTATCGGATAAC |
| SEQ ID NO: 7178 | NTC | GCAAAAAGCGGACACGCGAC |
| SEQ ID NO: 7179 | NTC | GCAAATAGGTCGGAGCGTGT |
| SEQ ID NO: 7180 | NTC | GCAACCCACGGACGGCACCG |
| SEQ ID NO: 7181 | NTC | GCAACGGACAGTCATCGAAC |
| SEQ ID NO: 7182 | NTC | GCAATAGTCGCACGGGTGAT |
| SEQ ID NO: 7183 | NTC | GCAATTCTGCAACGCACGTC |
| SEQ ID NO: 7184 | NTC | GCACCTCTAGCGCGCTCGGC |
| SEQ ID NO: 7185 | NTC | GCACGAACCCGTTCGTATGG |
| SEQ ID NO: 7186 | NTC | GCAGAGCGTAATCGGCATCG |
| SEQ ID NO: 7187 | NTC | GCAGGGTTATTCCGCTTCTA |
| SEQ ID NO: 7188 | NTC | GCAGGTAGGCTCGATACTTG |
| SEQ ID NO: 7189 | NTC | GCATAACGGCCGAGCACCAC |

TABLE 1-continued mmSurf sgRNA library sequences

| SEQ ID NO | id_gRNA Target | Sequence |
|---|---|---|
| SEQ ID NO: 7190 | NTC | GCATGCGCTCGCGTGGACTG |
| SEQ ID NO: 7191 | NTC | GCATTAAGACGCCCACATAT |
| SEQ ID NO: 7192 | NTC | GCATTCCCGCTTACGTAATT |
| SEQ ID NO: 7193 | NTC | GCATTCTTGAGCTCCGCGCC |
| SEQ ID NO: 7194 | NTC | GCATTGGTGCTCGCGCGTTC |
| SEQ ID NO: 7195 | NTC | GCCACGACCTGCGAATAATT |
| SEQ ID NO: 7196 | NTC | GCCACTCCGCTCGTTCTAGA |
| SEQ ID NO: 7197 | NTC | GCCAGCCTCGGTATAACTCG |
| SEQ ID NO: 7198 | NTC | GCCATAGCCAATCGCTAGTT |
| SEQ ID NO: 7199 | NTC | GCCCATGACGCGTGTTAGTA |
| SEQ ID NO: 7200 | NTC | GCCCGACCTCCACGTAAATC |
| SEQ ID NO: 7201 | NTC | GCCCGAGCGGATTCACCGCG |
| SEQ ID NO: 7202 | NTC | GCCCGATAGAATTACCCATT |
| SEQ ID NO: 7203 | NTC | GCCCGTTGTGAGCGGCATGC |
| SEQ ID NO: 7204 | NTC | GCCCTCGAGCTCACGATGAG |
| SEQ ID NO: 7205 | NTC | GCCGAATCGCGTTATTCCAA |
| SEQ ID NO: 7206 | NTC | GCCGACCAACGATGACCACG |
| SEQ ID NO: 7207 | NTC | GCCGAGAGGCGTAAGCGCGA |
| SEQ ID NO: 7208 | NTC | GCCGCAACGTTAGATGTATA |
| SEQ ID NO: 7209 | NTC | GCCGCGCCATAATATGCCAT |
| SEQ ID NO: 7210 | NTC | GCCGCTCTTGATAACGACGC |
| SEQ ID NO: 7211 | NTC | GCCGTAAGCGGGCCGGTTGA |
| SEQ ID NO: 7212 | NTC | GCCGTTGGAAAACTCCGGCC |
| SEQ ID NO: 7213 | NTC | GCCTATGTGAATCGCGAATT |
| SEQ ID NO: 7214 | NTC | GCCTTCCTCGCAGACCCGAC |
| SEQ ID NO: 7215 | NTC | GCCTTTTCCGCCCGTTCAAG |
| SEQ ID NO: 7216 | NTC | GCGACAAGCGTTGAGTTCGC |
| SEQ ID NO: 7217 | NTC | GCGACGTGTATCGATCACTC |
| SEQ ID NO: 7218 | NTC | GCGAGCGCTATCCCGGTGGA |
| SEQ ID NO: 7219 | NTC | GCGAGGTATTCGGCTCCGCG |
| SEQ ID NO: 7220 | NTC | GCGAGTTATTTCGCTATAGG |
| SEQ ID NO: 7221 | NTC | GCGATCGCCGGTATAGCTTT |
| SEQ ID NO: 7222 | NTC | GCGATTATCAGTAGTCCACG |
| SEQ ID NO: 7223 | NTC | GCGCCTAGGGTTCCGACTCA |
| SEQ ID NO: 7224 | NTC | GCGCGAGGGCACCGACAAGT |
| SEQ ID NO: 7225 | NTC | GCGCGAGTGCCAAACGAGTG |
| SEQ ID NO: 7226 | NTC | GCGCGCGTGGATCACCCGCA |
| SEQ ID NO: 7227 | NTC | GCGCGTACATATAAATAGGT |

TABLE 1-continued mmSurf sgRNA library sequences

| SEQ ID NO | id_gRNA Target | Sequence |
|---|---|---|
| SEQ ID NO: 7228 | NTC | GCGCTACTCCCACCGATGTT |
| SEQ ID NO: 7229 | NTC | GCGCTCGAACAAACATGGTC |
| SEQ ID NO: 7230 | NTC | GCGCTCGTTCGAGACGATCT |
| SEQ ID NO: 7231 | NTC | GCGGATCTGACGGTTACTTA |
| SEQ ID NO: 7232 | NTC | GCGGCCCGTGACCGTTCAAT |
| SEQ ID NO: 7233 | NTC | GCGGGACCCCCGGTATAGTC |
| SEQ ID NO: 7234 | NTC | GCGGTTACCGCGAAAACCAT |
| SEQ ID NO: 7235 | NTC | GCGTACCTATCGATAAACCA |
| SEQ ID NO: 7236 | NTC | GCGTATCTACCCTACCGCCG |
| SEQ ID NO: 7237 | NTC | GCGTGACGCGATCAAACGGT |
| SEQ ID NO: 7238 | NTC | GCGTGACGTCCCACCCTGAG |
| SEQ ID NO: 7239 | NTC | GCGTGAGATTCGTTGCTCGA |
| SEQ ID NO: 7240 | NTC | GCGTGCCATGGGAGGCCGTT |
| SEQ ID NO: 7241 | NTC | GCGTGGAGTTCGTCGCTCTT |
| SEQ ID NO: 7242 | NTC | GCGTGGTACTCACATCGCGA |
| SEQ ID NO: 7243 | NTC | GCTAAAAACAACCGGCGCGG |
| SEQ ID NO: 7244 | NTC | GCTAAACGTATTTTACGGGC |
| SEQ ID NO: 7245 | NTC | GCTAAGATTCATCCGAACAC |
| SEQ ID NO: 7246 | NTC | GCTAATCGGTACTACTCCGG |
| SEQ ID NO: 7247 | NTC | GCTACAGATTTGCGTTCGAG |
| SEQ ID NO: 7248 | NTC | GCTAGCGTTCAGCCCGATGT |
| SEQ ID NO: 7249 | NTC | GCTAGTTCTCCCGGGCGAAA |
| SEQ ID NO: 7250 | NTC | GCTATTCCGCTCGTCAATTT |
| SEQ ID NO: 7251 | NTC | GCTCATACTGATGAACGTCC |
| SEQ ID NO: 7252 | NTC | GCTCCAGGTGCGAGATAGGC |
| SEQ ID NO: 7253 | NTC | GCTCGAAAGTACGCTTCCTT |
| SEQ ID NO: 7254 | NTC | GCTCGCTGATGTGTAATCCG |
| SEQ ID NO: 7255 | NTC | GCTCGGACCTTTTAGACGTC |
| SEQ ID NO: 7256 | NTC | GCTGATTAGACCCGGCGTAA |
| SEQ ID NO: 7257 | NTC | GCTTACCTACTCCGCCCCGC |
| SEQ ID NO: 7258 | NTC | GCTTATCGTCATGCGGGTGA |
| SEQ ID NO: 7259 | NTC | GCTTATCGTTCCGCTACGAT |
| SEQ ID NO: 7260 | NTC | GCTTCATTATTAACCGGCGT |
| SEQ ID NO: 7261 | NTC | GCTTCGACCACGGGTACTGC |
| SEQ ID NO: 7262 | NTC | GCTTCGGAGGCTACGTAGTA |
| SEQ ID NO: 7263 | NTC | GCTTCTACTCGCAACGTATT |
| SEQ ID NO: 7264 | NTC | GCTTGAGGCAACGCGACTGA |
| SEQ ID NO: 7265 | NTC | GCTTGTAATCTAAAGACGCG |

TABLE 1-continued mmSurf sgRNA library sequences

| SEQ ID NO | id_gRNA Target | Sequence |
|---|---|---|
| SEQ ID NO: 7266 | NTC | GCTTTCACGGAGGTTCGACG |
| SEQ ID NO: 7267 | NTC | GGAAACGTTACATTCGACGC |
| SEQ ID NO: 7268 | NTC | GGAAACTCTTGCTCGACACG |
| SEQ ID NO: 7269 | NTC | GGACACTCGCCGACCCCACT |
| SEQ ID NO: 7270 | NTC | GGACCAATGTTACCGTAGGT |
| SEQ ID NO: 7271 | NTC | GGACGGATGGGACGACTAGT |
| SEQ ID NO: 7272 | NTC | GGACGTAGATTAGGGCGTAA |
| SEQ ID NO: 7273 | NTC | GGACTGAAACCGATAGTATC |
| SEQ ID NO: 7274 | NTC | GGAGTCTCACGCAATTAGCG |
| SEQ ID NO: 7275 | NTC | GGAGTTCAAGCGTAACTTCG |
| SEQ ID NO: 7276 | NTC | GGATACATCGGCGCGCTAGT |
| SEQ ID NO: 7277 | NTC | GGATAGCCCGGTTGGTGCGT |
| SEQ ID NO: 7278 | NTC | GGATATTCGCGCGGTCTTCA |
| SEQ ID NO: 7279 | NTC | GGATCGATCCGAGGAACGTG |
| SEQ ID NO: 7280 | NTC | GGATTCGTGCGGGAGATACG |
| SEQ ID NO: 7281 | NTC | GGATTGACGAGACGATATCG |
| SEQ ID NO: 7282 | NTC | GGCAACGCACGCTGGGTTGT |
| SEQ ID NO: 7283 | NTC | GGCACCGCGTTTATTGCACT |
| SEQ ID NO: 7284 | NTC | GGCACCGTTCGGAAACCGAC |
| SEQ ID NO: 7285 | NTC | GGCAGCCTAATCAGTCGAGG |
| SEQ ID NO: 7286 | NTC | GGCCAGTGTGGCCGTTACGC |
| SEQ ID NO: 7287 | NTC | GGCCCAACGAAACTAGCGTG |
| SEQ ID NO: 7288 | NTC | GGCCCGAAGGGTCACAAGCG |
| SEQ ID NO: 7289 | NTC | GGCGCTACTGTAATGACGGT |
| SEQ ID NO: 7290 | NTC | GGCGGGTTAGGCCCCGTTTT |
| SEQ ID NO: 7291 | NTC | GGCGTCGTAACAAGAACTTG |
| SEQ ID NO: 7292 | NTC | GGCTTATAGACGAGACTCGA |
| SEQ ID NO: 7293 | NTC | GGCTTTACGTAAGGAGCGTA |
| SEQ ID NO: 7294 | NTC | GGGACGCTCATCGAGTGACG |
| SEQ ID NO: 7295 | NTC | GGGCAACGTCATCTGGCGAC |
| SEQ ID NO: 7296 | NTC | GGGCCGGCACTCTGTCGGAC |
| SEQ ID NO: 7297 | NTC | GGGCGCGTCATAGACACACG |
| SEQ ID NO: 7298 | NTC | GGGCGGGACGTAATATTATG |
| SEQ ID NO: 7299 | NTC | GGGCTAGTGCGTTGTTACGA |
| SEQ ID NO: 7300 | NTC | GGGGATGGCCTTACGTCGCG |
| SEQ ID NO: 7301 | NTC | GGGGGGTCTAATACCGATTG |
| SEQ ID NO: 7302 | NTC | GGGGTAGGCCTAATTACGGA |
| SEQ ID NO: 7303 | NTC | GGGGTTGGATACGCGATTTA |

TABLE 1-continued mmSurf sgRNA library sequences

| SEQ ID NO | id_gRNA Target | Sequence |
|---|---|---|
| SEQ ID NO: 7304 | NTC | GGGTAGCACCCCGCCGACAC |
| SEQ ID NO: 7305 | NTC | GGGTCGCACCCCAATAGCTG |
| SEQ ID NO: 7306 | NTC | GGGTGCACACGCCGGCCTAT |
| SEQ ID NO: 7307 | NTC | GGTAAAAAGCGTAACGAGTA |
| SEQ ID NO: 7308 | NTC | GGTAACATAGGCGGCGATCT |
| SEQ ID NO: 7309 | NTC | GGTCAAAGCGATGTTAGCCG |
| SEQ ID NO: 7310 | NTC | GGTCGCTCGATTTCATTTAA |
| SEQ ID NO: 7311 | NTC | GGTCTAGATAATCTTACCGA |
| SEQ ID NO: 7312 | NTC | GGTCTCGTAATGTCCTATAT |
| SEQ ID NO: 7313 | NTC | GGTCTGTCCGTTGCGACCAC |
| SEQ ID NO: 7314 | NTC | GGTGCAGTCCGTTTAGTCGG |
| SEQ ID NO: 7315 | NTC | GGTGTGGACCGCTTTTACGC |
| SEQ ID NO: 7316 | NTC | GGTTAAAAATTAAGCGGTCC |
| SEQ ID NO: 7317 | NTC | GTACATGCGGCAAGTCGACT |
| SEQ ID NO: 7318 | NTC | GTACCACTTATCGACCTTGC |
| SEQ ID NO: 7319 | NTC | GTACCATGATAACCGTACTA |
| SEQ ID NO: 7320 | NTC | GTACGCAGGGTGTAGCGACC |
| SEQ ID NO: 7321 | NTC | GTACTGACGTTACGTTCATA |
| SEQ ID NO: 7322 | NTC | GTAGACATATTGCGTAATCG |
| SEQ ID NO: 7323 | NTC | GTAGCTGACCGCTTAACTAA |
| SEQ ID NO: 7324 | NTC | GTAGCTTCATGTCCGGTCGG |
| SEQ ID NO: 7325 | NTC | GTAGGCCGCTGATCGAATAA |
| SEQ ID NO: 7326 | NTC | GTAGTGCGTGTGATGTCGGG |
| SEQ ID NO: 7327 | NTC | GTATCCTCCTTACGGCCCGT |
| SEQ ID NO: 7328 | NTC | GTATCCTCGCAATCGTTAGG |
| SEQ ID NO: 7329 | NTC | GTCAAGCCGAACGCTGCCGG |
| SEQ ID NO: 7330 | NTC | GTCACAAAAAACGAGCGTTA |
| SEQ ID NO: 7331 | NTC | GTCCTAGATCCTATCGGGAG |
| SEQ ID NO: 7332 | NTC | GTCGATTAGATGATGCCCGG |
| SEQ ID NO: 7333 | NTC | GTCGCGTATCCTGACGACAC |
| SEQ ID NO: 7334 | NTC | GTCGCTCGAACTCACGTAGC |
| SEQ ID NO: 7335 | NTC | GTCGGCCGCTTAACCCTTTC |
| SEQ ID NO: 7336 | NTC | GTCGGCTCATCGGAAAATAT |
| SEQ ID NO: 7337 | NTC | GTCGTGGGGCACGATGCGTA |
| SEQ ID NO: 7338 | NTC | GTCGTTAACGACCCGGATTC |
| SEQ ID NO: 7339 | NTC | GTCTAACATCGGCGCACGTG |
| SEQ ID NO: 7340 | NTC | GTGATGGCCACGTCCGAACC |
| SEQ ID NO: 7341 | NTC | GTGCAACGACTGACCCGCGG |

TABLE 1-continued mmSurf sgRNA library sequences

| SEQ ID NO | id_gRNA Target | Sequence |
|---|---|---|
| SEQ ID NO: 7342 | NTC | GTGCCAGCGTCGATTGACGC |
| SEQ ID NO: 7343 | NTC | GTGCCTGATAGTGTGAAGCG |
| SEQ ID NO: 7344 | NTC | GTGCGAATTAACCGTTAGGA |
| SEQ ID NO: 7345 | NTC | GTGCGCGCGTATAGAAAAAA |
| SEQ ID NO: 7346 | NTC | GTGGGCTGACCGTTCTCGAC |
| SEQ ID NO: 7347 | NTC | GTGGTTACGTTAACGACTAC |
| SEQ ID NO: 7348 | NTC | GTGTATGACGAGAAGCGAAG |
| SEQ ID NO: 7349 | NTC | GTGTCTTTCGGTCTTACGAG |
| SEQ ID NO: 7350 | NTC | GTGTGCCTCGACAGCGTAAG |
| SEQ ID NO: 7351 | NTC | GTGTGGTATATCCCCGTTTT |
| SEQ ID NO: 7352 | NTC | GTGTTGTCCGAGAACCCGAC |
| SEQ ID NO: 7353 | NTC | GTTAAGTAGATCGGTGACAT |
| SEQ ID NO: 7354 | NTC | GTTAATATTGTGGCCCGCAC |
| SEQ ID NO: 7355 | NTC | GTTACCCCTTTGGCCGGAAG |
| SEQ ID NO: 7356 | NTC | GTTACCGTGACGATAAGAAT |
| SEQ ID NO: 7357 | NTC | GTTACTTACCTGACCGGCAA |
| SEQ ID NO: 7358 | NTC | GTTATACCACCTACTATGAC |
| SEQ ID NO: 7359 | NTC | GTTATTGCGCCTTGGCCGTA |
| SEQ ID NO: 7360 | NTC | GTTATTTGTCTGTCGAAACG |
| SEQ ID NO: 7361 | NTC | GTTCCGGATATATACGGTTA |
| SEQ ID NO: 7362 | NTC | GTTCGCGGGGCTTCTATCA |
| SEQ ID NO: 7363 | NTC | GTTCGGTTGCAGCTTACACG |
| SEQ ID NO: 7364 | NTC | GTTCTTCAAAGACGGGCGGC |
| SEQ ID NO: 7365 | NTC | GTTGCGGCGACCTAGATATC |
| SEQ ID NO: 7366 | NTC | GTTGCGTCCATTCCGTCGCC |
| SEQ ID NO: 7367 | NTC | GTTGCGTGTGTCCGTACAAA |
| SEQ ID NO: 7368 | NTC | GTTTCAGCGCGAGTTGCGCG |
| SEQ ID NO: 7369 | NTC | GTTTCAGGAACGACGGCGAG |
| SEQ ID NO: 7370 | NTC | GTTTCCCGGGACTGTCGCGT |
| SEQ ID NO: 7371 | NTC | GTTTGCGAGTCAAAGTACGC |
| SEQ ID NO: 7372 | NTC | TAAAAACGCTGGCGGCCTAG |
| SEQ ID NO: 7373 | NTC | TAAAACCGATCACGATACGA |
| SEQ ID NO: 7374 | NTC | TAAAAGTGGTGCGTCGTCGT |
| SEQ ID NO: 7375 | NTC | TAAACGATTCACCGATAACA |
| SEQ ID NO: 7376 | NTC | TAACACGCACTCACGTCCGG |
| SEQ ID NO: 7377 | NTC | TAACAGCTTCCGCGTAATAT |
| SEQ ID NO: 7378 | NTC | TAACCCTTGATCAACCGATA |
| SEQ ID NO: 7379 | NTC | TAACGTTATGTCAAACGCTC |

TABLE 1-continued mmSurf sgRNA library sequences

| SEQ ID NO | id_gRNA Target | Sequence |
|---|---|---|
| SEQ ID NO: 7380 | NTC | TAACTCTAATGCGTTCCAAG |
| SEQ ID NO: 7381 | NTC | TAAGACTGGGTGTCCCGCGT |
| SEQ ID NO: 7382 | NTC | TAAGCGGCGTCATGTCGCCC |
| SEQ ID NO: 7383 | NTC | TAAGTGACACTTCGTATCGT |
| SEQ ID NO: 7384 | NTC | TAATAAACTATGTCCCGCCG |
| SEQ ID NO: 7385 | NTC | TAATGAGTAACGCTCATCGG |
| SEQ ID NO: 7386 | NTC | TAATGCGAATGCGACCTCTC |
| SEQ ID NO: 7387 | NTC | TAATGGAAGATGCGCGATAC |
| SEQ ID NO: 7388 | NTC | TAATGGCACTTACCGGGTCT |
| SEQ ID NO: 7389 | NTC | TAATTCGCAACTCGGATCAT |
| SEQ ID NO: 7390 | NTC | TAATTCTTTAGTACGTGCAA |
| SEQ ID NO: 7391 | NTC | TACACGCCCTAAGCTAGTAA |
| SEQ ID NO: 7392 | NTC | TACAGTTATACGTCGCGGTG |
| SEQ ID NO: 7393 | NTC | TACATCGAACAACCAACCGA |
| SEQ ID NO: 7394 | NTC | TACATGCGGTTGACACGTTC |
| SEQ ID NO: 7395 | NTC | TACCCCTCTGCGATGCCGGT |
| SEQ ID NO: 7396 | NTC | TACCCCTTGAGGGGCGCATA |
| SEQ ID NO: 7397 | NTC | TACGACATCGCATGGTAACG |
| SEQ ID NO: 7398 | NTC | TACGACGAGGACGCATCGAG |
| SEQ ID NO: 7399 | NTC | TACGCTCACTTCTGCGAAGG |
| SEQ ID NO: 7400 | NTC | TACGGACGTCGAATTGAGCA |
| SEQ ID NO: 7401 | NTC | TACGTCTGCGCAAATAGAAT |
| SEQ ID NO: 7402 | NTC | TACTGCGTACCGCAGTAAGC |
| SEQ ID NO: 7403 | NTC | TACTTACCGACCGACAAACG |
| SEQ ID NO: 7404 | NTC | TACTTAGGTCCGCGTAAAGC |
| SEQ ID NO: 7405 | NTC | TAGACGTCCACCGACTCTGA |
| SEQ ID NO: 7406 | NTC | TAGAGCAGATCCCCTCAACG |
| SEQ ID NO: 7407 | NTC | TAGATGGTGCTTCTGTCGCG |
| SEQ ID NO: 7408 | NTC | TAGCCCGTCGAGTACTCCCC |
| SEQ ID NO: 7409 | NTC | TAGCCGAGTTCACGCCAGTA |
| SEQ ID NO: 7410 | NTC | TAGCTGTTTACGCCGACCTG |
| SEQ ID NO: 7411 | NTC | TAGGCCGCTCAGGCCGCACT |
| SEQ ID NO: 7412 | NTC | TAGGCGGACGGTTACATATA |
| SEQ ID NO: 7413 | NTC | TAGGGGTGCGCATTAGACTA |
| SEQ ID NO: 7414 | NTC | TAGGTGGCGCCCAATCGGAC |
| SEQ ID NO: 7415 | NTC | TAGTAAAAAATTCGCCCTCC |
| SEQ ID NO: 7416 | NTC | TAGTAGGCCGGAGCGCATCC |
| SEQ ID NO: 7417 | NTC | TAGTAGGTTGATCGCGTCGC |

TABLE 1-continued mmSurf sgRNA library sequences

| SEQ ID NO | id_gRNA Target | Sequence |
|---|---|---|
| SEQ ID NO: 7418 | NTC | TAGTCAGTCGGCCTCCGTGC |
| SEQ ID NO: 7419 | NTC | TAGTCCTAGTTAGATTCGCG |
| SEQ ID NO: 7420 | NTC | TAGTGCGAACAGTCACGGCG |
| SEQ ID NO: 7421 | NTC | TAGTGTTGTGAGCGTCGTAC |
| SEQ ID NO: 7422 | NTC | TAGTTAACCGTAAAGTGGGC |
| SEQ ID NO: 7423 | NTC | TAGTTATCTGCAACGCATAG |
| SEQ ID NO: 7424 | NTC | TATACTCGCCTGTCACAGCG |
| SEQ ID NO: 7425 | NTC | TATCCCGATCCGGAAACTAG |
| SEQ ID NO: 7426 | NTC | TATCGAACTGCACACGCAAC |
| SEQ ID NO: 7427 | NTC | TATCTAATCGCGGAGTCGTA |
| SEQ ID NO: 7428 | NTC | TATCTCTGGATGCCGTCGGT |
| SEQ ID NO: 7429 | NTC | TATGAAACATCTCGGCGACG |
| SEQ ID NO: 7430 | NTC | TATGAACCTCCGGATCGGTG |
| SEQ ID NO: 7431 | NTC | TATGAACTAGGCGTAAACGG |
| SEQ ID NO: 7432 | NTC | TATGACACACAATCTGCGAC |
| SEQ ID NO: 7433 | NTC | TATGACTGCACGACTCGCTA |
| SEQ ID NO: 7434 | NTC | TATGATCGTATGGCCCTTCC |
| SEQ ID NO: 7435 | NTC | TATGCCATATGCCCGTTTTT |
| SEQ ID NO: 7436 | NTC | TCAAACGCCCGGGCGCCCCA |
| SEQ ID NO: 7437 | NTC | TCAACTATGAACCGCCGTGC |
| SEQ ID NO: 7438 | NTC | TCAACTTAACCTCGAGTCCG |
| SEQ ID NO: 7439 | NTC | TCAATAGTTCTGCGCGAATT |
| SEQ ID NO: 7440 | NTC | TCAATCTGCGGTGACTCGTT |
| SEQ ID NO: 7441 | NTC | TCAATTAGTGGCCGCCAAGC |
| SEQ ID NO: 7442 | NTC | TCACAACCCCCGACTATCGC |
| SEQ ID NO: 7443 | NTC | TCACACGGGATCTCGCCGGT |
| SEQ ID NO: 7444 | NTC | TCACATGACACTCGTTACGA |
| SEQ ID NO: 7445 | NTC | TCACCCGCGTATACGACCTG |
| SEQ ID NO: 7446 | NTC | TCACGCACGACTAAGGGAAT |
| SEQ ID NO: 7447 | NTC | TCACTCAAAGTGCGTAGTCG |
| SEQ ID NO: 7448 | NTC | TCACTTCGGGCATTACGAGC |
| SEQ ID NO: 7449 | NTC | TCACTTTAAGCACCCCGCGC |
| SEQ ID NO: 7450 | NTC | TCAGCAGAATTGGGCCCGTA |
| SEQ ID NO: 7451 | NTC | TCAGCTACGATCGGACCCAA |
| SEQ ID NO: 7452 | NTC | TCAGTCAGTCGGCCCCCTGC |
| SEQ ID NO: 7453 | NTC | TCATATTAGACAATCTCCGC |
| SEQ ID NO: 7454 | NTC | TCATCTACGGTATCGAAAGG |
| SEQ ID NO: 7455 | NTC | TCATGCGCCTCGTAATACCT |

TABLE 1-continued mmSurf sgRNA library sequences

| SEQ ID NO | id_gRNA Target | Sequence |
|---|---|---|
| SEQ ID NO: 7456 | NTC | TCATGTTGCGTCGTCCGTTA |
| SEQ ID NO: 7457 | NTC | TCCCCCGTACGTGTATGTCG |
| SEQ ID NO: 7458 | NTC | TCCCCTTCGTCGGCGCCAGG |
| SEQ ID NO: 7459 | NTC | TCCCGGGAGGTACGGTGTAC |
| SEQ ID NO: 7460 | NTC | TCCGAACAGGCGCGTTTCTC |
| SEQ ID NO: 7461 | NTC | TCCGCGGCAACGTTTGGGTC |
| SEQ ID NO: 7462 | NTC | TCCGTACATCGACCTATTAC |
| SEQ ID NO: 7463 | NTC | TCCGTAGGACGTATATATTC |
| SEQ ID NO: 7464 | NTC | TCCTACACCACCCCGGCCGT |
| SEQ ID NO: 7465 | NTC | TCCTAGGCCTGATTTACCCG |
| SEQ ID NO: 7466 | NTC | TCCTATAATTGAGCGAACGG |
| SEQ ID NO: 7467 | NTC | TCCTCCGATCGACCAGGGTA |
| SEQ ID NO: 7468 | NTC | TCCTGCGCGATGACCGTCGG |
| SEQ ID NO: 7469 | NTC | TCCTGCGTTCCACTCGTACT |
| SEQ ID NO: 7470 | NTC | TCGAGTCTTGACTCAACGCT |
| SEQ ID NO: 7471 | NTC | TCGATCGTCGGCGGAGCGGA |
| SEQ ID NO: 7472 | NTC | TCGCAAAATGCGGATTCCGT |
| SEQ ID NO: 7473 | NTC | TCGCACTCTAGGCCGTTATT |
| SEQ ID NO: 7474 | NTC | TCGCGAATTGCTGCCGAACT |
| SEQ ID NO: 7475 | NTC | TCGCTAAGCCGGGTAATACT |
| SEQ ID NO: 7476 | NTC | TCGCTCATTAGGAGCGCTAT |
| SEQ ID NO: 7477 | NTC | TCGCTCCGCTAGTAGTGGGT |
| SEQ ID NO: 7478 | NTC | TCGCTGAGCAACGAAGCAAC |
| SEQ ID NO: 7479 | NTC | TCGCTTCTGATTGATCCACG |
| SEQ ID NO: 7480 | NTC | TCGGAATTCCGCAGGCCGAG |
| SEQ ID NO: 7481 | NTC | TCGGACTATAGCGTGAACGT |
| SEQ ID NO: 7482 | NTC | TCGGATCGGTACATAAAGTT |
| SEQ ID NO: 7483 | NTC | TCGGATTTTAATCCTTACGC |
| SEQ ID NO: 7484 | NTC | TCGGCGCAGCCTAATGTATA |
| SEQ ID NO: 7485 | NTC | TCGTAAAGTCGCAGCGACGT |
| SEQ ID NO: 7486 | NTC | TCGTAAGTTCGCTATATGCC |
| SEQ ID NO: 7487 | NTC | TCGTACCGCACGTGTAAGCC |
| SEQ ID NO: 7488 | NTC | TCGTGCCGGAATAACCACTA |
| SEQ ID NO: 7489 | NTC | TCGTGCCTAGCTCGGTTGAG |
| SEQ ID NO: 7490 | NTC | TCGTGTCTAGCTATCGAGTG |
| SEQ ID NO: 7491 | NTC | TCGTTACATACCCCGCGGAA |
| SEQ ID NO: 7492 | NTC | TCGTTGTGTCGACATCCGCA |
| SEQ ID NO: 7493 | NTC | TCTACACGCGCGTTCAACCG |

TABLE 1-continued mmSurf sgRNA library sequences

| SEQ ID NO | id_gRNA Target | Sequence |
|---|---|---|
| SEQ ID NO: 7494 | NTC | TCTAGGATACTCTTAACGGG |
| SEQ ID NO: 7495 | NTC | TCTATATCTAGTCTCGGCGC |
| SEQ ID NO: 7496 | NTC | TCTCAGTTCGTAGCGAACGA |
| SEQ ID NO: 7497 | NTC | TCTCCGGGCCGTGTTAGACC |
| SEQ ID NO: 7498 | NTC | TCTCCGTCCGAAACGGCGAC |
| SEQ ID NO: 7499 | NTC | TCTCGAATAAATTTTCTCGC |
| SEQ ID NO: 7500 | NTC | TCTCTTCGCGCCCGCTTTGC |
| SEQ ID NO: 7501 | NTC | TCTGCACCGCGACTTAGCTT |
| SEQ ID NO: 7502 | NTC | TCTGGACGCGAGATGACGGG |
| SEQ ID NO: 7503 | NTC | TCTTCTAGTGCGAGTTCCGC |
| SEQ ID NO: 7504 | NTC | TCTTCTCGAGCGTGCGGGCC |
| SEQ ID NO: 7505 | NTC | TCTTGACTCCGACTTCGGGC |
| SEQ ID NO: 7506 | NTC | TGACAACCGCGGTACCTCTA |
| SEQ ID NO: 7507 | NTC | TGACCCGTCTCTTCGCGCAC |
| SEQ ID NO: 7508 | NTC | TGACCCTCTTAATCTCCGGT |
| SEQ ID NO: 7509 | NTC | TGACGCGCCTCGGACCAACC |
| SEQ ID NO: 7510 | NTC | TGACGCTAAGGCCCGCTAAC |
| SEQ ID NO: 7511 | NTC | TGACTTGACACGTTCGATAT |
| SEQ ID NO: 7512 | NTC | TGAGACCAATGCCGCGGAAT |
| SEQ ID NO: 7513 | NTC | TGAGAGCAAGGCGCATACGC |
| SEQ ID NO: 7514 | NTC | TGAGCCGGTGCGCTCTCGGT |
| SEQ ID NO: 7515 | NTC | TGAGCCTTTGTGGACCGCGG |
| SEQ ID NO: 7516 | NTC | TGAGCGCTTTCCCGATCCGG |
| SEQ ID NO: 7517 | NTC | TGAGGGCTCAATACTTCCGC |
| SEQ ID NO: 7518 | NTC | TGAGGTTACCGCCGGCTTTT |
| SEQ ID NO: 7519 | NTC | TGATAAACGATGCGAACTCG |
| SEQ ID NO: 7520 | NTC | TGATCAACGTCGGTGGACGG |
| SEQ ID NO: 7521 | NTC | TGATCCCCGTCCCGAAGTTA |
| SEQ ID NO: 7522 | NTC | TGATGCCGGTACCCGTAACT |
| SEQ ID NO: 7523 | NTC | TGATGGACGCGATACGTTTA |
| SEQ ID NO: 7524 | NTC | TGATTGGGGTCGTTCGCCA |
| SEQ ID NO: 7525 | NTC | TGCAACGATGGTTACGGTAC |
| SEQ ID NO: 7526 | NTC | TGCACCGGTACGGGCGACTC |
| SEQ ID NO: 7527 | NTC | TGCAGATCGCGAAGCGACTA |
| SEQ ID NO: 7528 | NTC | TGCAGTAGTCGCGGATAGGC |
| SEQ ID NO: 7529 | NTC | TGCCCTGCGTCCGCTACGTC |
| SEQ ID NO: 7530 | NTC | TGCCGACGCGACGCAGCGTA |
| SEQ ID NO: 7531 | NTC | TGCCTACTGTCGTTCCCGCG |

TABLE 1-continued mmSurf sgRNA library sequences

| SEQ ID NO | id_gRNA Target | Sequence |
|---|---|---|
| SEQ ID NO: 7532 | NTC | TGCCTTCAGTCGACCGTTAC |
| SEQ ID NO: 7533 | NTC | TGCGCGTCCTGTTATGACCG |
| SEQ ID NO: 7534 | NTC | TGCGGCAATGTTAACCCTTA |
| SEQ ID NO: 7535 | NTC | TGCGTAAAACTTGCGCTCGA |
| SEQ ID NO: 7536 | NTC | TGCGTCTCAGCTTCGGCTAT |
| SEQ ID NO: 7537 | NTC | TGCTGGCCGATACGTGCTTG |
| SEQ ID NO: 7538 | NTC | TGCTTAGGGCCCTTCGGCGG |
| SEQ ID NO: 7539 | NTC | TGCTTTACCGCGTTGGGTAA |
| SEQ ID NO: 7540 | NTC | TGGATCCGCTTCGCACGGCG |
| SEQ ID NO: 7541 | NTC | TGGCACGGAGTTGCATACGC |
| SEQ ID NO: 7542 | NTC | TGGCCCACAAGGTGCGATAT |
| SEQ ID NO: 7543 | NTC | TGGCGCTCCTGCGCACACGA |
| SEQ ID NO: 7544 | NTC | TGGCTTAATGGACAGCGCGA |
| SEQ ID NO: 7545 | NTC | TGGGCCATAGTGGCGCGTGA |
| SEQ ID NO: 7546 | NTC | TGGGCGGTTCAAAGCGAATT |
| SEQ ID NO: 7547 | NTC | TGGGTCCTAAACGCGGTTCA |
| SEQ ID NO: 7548 | NTC | TGGGTTCCGGCCCCATGTAC |
| SEQ ID NO: 7549 | NTC | TGGTACCACTCGCCGAATCT |
| SEQ ID NO: 7550 | NTC | TGGTTCACCACTCGAGATCG |
| SEQ ID NO: 7551 | NTC | TGGTTCGACCAACATGGTTC |
| SEQ ID NO: 7552 | NTC | TGGTTGGCATGTCGCCAGCG |
| SEQ ID NO: 7553 | NTC | TGTAACGATCTGGGCGGTCT |
| SEQ ID NO: 7554 | NTC | TGTACTCGCATAGCGGGGGC |
| SEQ ID NO: 7555 | NTC | TGTATAGTCATCGCCGTAAT |
| SEQ ID NO: 7556 | NTC | TGTATCCACCGTGACCCGGT |
| SEQ ID NO: 7557 | NTC | TGTCCCGACGATGTGTAAAT |
| SEQ ID NO: 7558 | NTC | TGTCCTACCGAATGAACCGT |
| SEQ ID NO: 7559 | NTC | TGTCGCCGATGGTCAGTCGC |
| SEQ ID NO: 7560 | NTC | TGTCGGACCCATTGTCGAAC |
| SEQ ID NO: 7561 | NTC | TGTCTATGTTTGGCCACGCA |
| SEQ ID NO: 7562 | NTC | TGTCTGCCGCATACGCTATA |
| SEQ ID NO: 7563 | NTC | TGTGCCACGCCGCTGCAACG |
| SEQ ID NO: 7564 | NTC | TGTGCCTACGCCATTCGGCT |
| SEQ ID NO: 7565 | NTC | TGTGTAATTACGTTTCGCGG |
| SEQ ID NO: 7566 | NTC | TGTTAATGCCAACGGGACAT |
| SEQ ID NO: 7567 | NTC | TGTTCGCCCTCTCACGATTG |
| SEQ ID NO: 7568 | NTC | TGTTTATGCGGAACTTCCGC |
| SEQ ID NO: 7569 | NTC | TTAACGTCTGTGCGCACTAC |

TABLE 1-continued mmSurf sgRNA library sequences

| SEQ ID NO | id_gRNA Target | Sequence |
|---|---|---|
| SEQ ID NO: 7570 | NTC | TTAACTGGGGGACCGGACG |
| SEQ ID NO: 7571 | NTC | TTACAGTTCATACCGTCGCC |
| SEQ ID NO: 7572 | NTC | TTACCGTGGTACGTCAGGTT |
| SEQ ID NO: 7573 | NTC | TTACGCAAAGCTGCGATGAG |
| SEQ ID NO: 7574 | NTC | TTACTGATCAGTCGGACGCA |
| SEQ ID NO: 7575 | NTC | TTACTTGGTGCAACAACCGG |
| SEQ ID NO: 7576 | NTC | TTAGCCTTGCCCCGTCATAC |
| SEQ ID NO: 7577 | NTC | TTAGGACGTGCTTCCGAGGG |
| SEQ ID NO: 7578 | NTC | TTAGTTCGACCACTCCTGAT |
| SEQ ID NO: 7579 | NTC | TTATACCGTCACGAGTGCCC |
| SEQ ID NO: 7580 | NTC | TTATCGCACAACCCCGAAAG |
| SEQ ID NO: 7581 | NTC | TTATCGTACTAGTACGTACA |
| SEQ ID NO: 7582 | NTC | TTATGACCTCGATGCGACAT |
| SEQ ID NO: 7583 | NTC | TTATGTGCCTCTCGGCGCAT |
| SEQ ID NO: 7584 | NTC | TTATTGGTTTCAACGGTTGT |
| SEQ ID NO: 7585 | NTC | TTATTTACGCGCTGAACTTG |
| SEQ ID NO: 7586 | NTC | TTCAACGACGGAAGACGCGC |
| SEQ ID NO: 7587 | NTC | TTCAAGTGTTATGGACGCGC |
| SEQ ID NO: 7588 | NTC | TTCAATTGTTCGCCCGAACA |
| SEQ ID NO: 7589 | NTC | TTCATCCTTCGTAGCGCAGC |
| SEQ ID NO: 7590 | NTC | TTCATCGCAGATCGATTTCG |
| SEQ ID NO: 7591 | NTC | TTCCAGTATACCGAATTCGC |
| SEQ ID NO: 7592 | NTC | TTCCCCGCCCGTGCGGTCAT |
| SEQ ID NO: 7593 | NTC | TTCGAAGTCTAACCCGCGGG |
| SEQ ID NO: 7594 | NTC | TTCGACGTGCGGCGTATTGG |
| SEQ ID NO: 7595 | NTC | TTCGACTGCGCACGCCATGA |
| SEQ ID NO: 7596 | NTC | TTCGAGACGGATACGTCTGC |
| SEQ ID NO: 7597 | NTC | TTCGAGATTTTAATAGCGCA |
| SEQ ID NO: 7598 | NTC | TTCGATATAGGGGACGGCGG |
| SEQ ID NO: 7599 | NTC | TTCGCCGGCGACGAAGTGCA |
| SEQ ID NO: 7600 | NTC | TTCGCGAGTAAGGTAGGCAT |
| SEQ ID NO: 7601 | NTC | TTCGGCTCAATGGCGCGAGC |
| SEQ ID NO: 7602 | NTC | TTCGGCTGGTGTGCGTTCAC |
| SEQ ID NO: 7603 | NTC | TTCGTGGCCGAAGGCGCCGC |
| SEQ ID NO: 7604 | NTC | TTCTCCATACCGTAACTCCG |
| SEQ ID NO: 7605 | NTC | TTCTGATTAGATACGTACGA |
| SEQ ID NO: 7606 | NTC | TTGAACACGACACCCGTGCC |
| SEQ ID NO: 7607 | NTC | TTGAAGTAGGGTCGGATTGA |

TABLE 1-continued mmSurf sgRNA library sequences

| SEQ ID NO | id_gRNA Target | Sequence |
|---|---|---|
| SEQ ID NO: 7608 | NTC | TTGAATCCGAGGCGCCGATG |
| SEQ ID NO: 7609 | NTC | TTGAGCGGACCCCCCTACAA |
| SEQ ID NO: 7610 | NTC | TTGATAAACCGCGGCCGAAA |
| SEQ ID NO: 7611 | NTC | TTGCACCCCAGTTCGTTGC |
| SEQ ID NO: 7612 | NTC | TTGCAGCAACGGCGACGGCT |
| SEQ ID NO: 7613 | NTC | TTGCGTGTGCGTTGTTAACG |
| SEQ ID NO: 7614 | NTC | TTGGACGTACACTTTCGTTC |
| SEQ ID NO: 7615 | NTC | TTGGCGGCTCGCTCCTGCGT |
| SEQ ID NO: 7616 | NTC | TTGTCAACTTCGGCCAACGC |
| SEQ ID NO: 7617 | NTC | TTGTCGCTAACTCAGAATAG |
| SEQ ID NO: 7618 | NTC | TTGTTTCAGCCTTGAGCGCG |
| SEQ ID NO: 7619 | NTC | TTTACGTATGCTGTGCGCGA |
| SEQ ID NO: 7620 | NTC | TTTAGTCAGACGAGCCGGAT |
| SEQ ID NO: 7621 | NTC | TTTCAGTTGTCGCGCGACTC |
| SEQ ID NO: 7622 | NTC | TTTCTAATTACCCGATACGT |
| SEQ ID NO: 7623 | NTC | TTTCTAGGGCCGCCGCCCGC |
| SEQ ID NO: 7624 | NTC | TTTGACATTTTCGTCTCGCG |
| SEQ ID NO: 7625 | NTC | TTTTAGTAGGTCAACGCTGT |
| SEQ ID NO: 7626 | NTC | TTTTCGTCGACTAAGTCAAG |
| SEQ ID NO: 7627 | NTC | TTTTGGCGACGCATCGCTGG |
| SEQ ID NO: 7628 | NTC | TTTTTAGACCTAATTCGCGC |

TABLE 2

PCR Primers

SEQ ID NO: 7629
BC_F1 AATGATACGGCGACCACCGAGATCTACACTCTTTCCCTACACGAC
GCTCTTCCGATCTTAAGTAGAGTCTTGTGGAAAGGACGAAACACCG

SEQ ID NO: 7630
BC_F2 AATGATACGGCGACCACCGAGATCTACACTCTTTCCCTACACGAC
GCTCTTCCGATCTATACACGATCTCTTGTGGAAAGGACGAAACACCG

SEQ ID NO: 7631
BC_F3 AATGATACGGCGACCACCGAGATCTACACTCTTTCCCTACACGAC
GCTCTTCCGATCTGATCGCGCGGTTCTTGTGGAAAGGACGAAACACCG

SEQ ID NO: 7632
BC_F4 AATGATACGGCGACCACCGAGATCTACACTCTTTCCCTACACGAC
GCTCTTCCGATCTCGATCATGATCGTCTTGTGGAAAGGACGAAACACCG

SEQ ID NO: 7633
BC_F5 AATGATACGGCGACCACCGAGATCTACACTCTTTCCCTACACGAC
GCTCTTCCGATCTTCGATCGTTACCATCTTGTGGAAAGGACGAAACACCG

SEQ ID NO: 7634
BC_F6 AATGATACGGCGACCACCGAGATCTACACTCTTTCCCTACACGAC
GCTCTTCCGATCTATCGATTCCTTGGTTCTTGTGGAAAGGACGAAACACCG

TABLE 2-continued

PCR Primers

SEQ ID NO: 7635
BC_F7 AATGATACGGCGACCACCGAGATCTACACTCTTTCCCTACACGAC
GCTCTTCCGATCTGATCGATAACGCATTTCTTGTGGAAAGGACGAAACACCG

SEQ ID NO: 7636
BC_F8 AATGATACGGCGACCACCGAGATCTACACTCTTTCCCTACACGAC
GCTCTTCCGATCTCGATCGATACAGGTATTCTTGTGGAAAGGACGAAACACCG

SEQ ID NO: 7637
BC_F9 AATGATACGGCGACCACCGAGATCTACACTCTTTCCCTACACGAC
GCTCTTCCGATCTACGATCGATAGGTAAGGTCTTGTGGAAAGGACGAAACACCG

SEQ ID NO: 7638
BC_F10 AATGATACGGCGACCACCGAGATCTACACTCTTTCCCTACACGA
CGCTCTTCCGATCTTAACAATGGTCTTGTGGAAAGGACGAAACACCG

SEQ ID NO: 7639
BC_F11 AATGATACGGCGACCACCGAGATCTACACTCTTTCCCTACACGA
CGCTCTTCCGATCTATACTGTATCTCTTGTGGAAAGGACGAAACACCG

TABLE 2-continued

PCR Primers

SEQ ID NO: 7640
BC_F12 AATGATACGGCGACCACCGAGATCTACACTCTTTCCCTACACGA
CGCTCTTCCGATCTGATAGGTCGCATCTTGTGGAAAGGACGAAACACCG

SEQ ID NO: 7641
BC-R1 CAAGCAGAAGACGGCATACGAGATGTAACGCGGTGACTGGAGTTC
AGACGTGTGCTCTTCCGATCTgactcggtgccactttttcaagttg SEQ ID NO: 7642
BC-R2 CAAGCAGAAGACGGCATACGAGATGAAGGTCTGTGACTGGAGTTC
AGACGTGTGCTCTTCCGATCTgactcggtgccactttttcaagttg SEQ ID NO: 7643
BC-R3 CAAGCAGAAGACGGCATACGAGATTTGGAACAGTGACTGGAGTTC
AGACGTGTGCTCTTCCGATCTgactcggtgccactttttcaagttg SEQ ID NO: 7644
BC-R4 CAAGCAGAAGACGGCATACGAGATCCTTAGACGTGACTGGAGTTC
AGACGTGTGCTCTTCCGATCTgactcggtgccactttttcaagttg

TABLE 3

CDR sequences of anti-human MGAT5 antibody clones

| Seq ID No | Well # | Antibody Chain | Sequence |
|---|---|---|---|
| 7645 | A01 | H1 | GFNFSSSSIHWV |
| 7646 | A01 | H2 | LEWVASISSYYSSTYYADS |
| 7647 | A01 | H3 | YYCARTVRGSKKPYFSGWAMDYWGQ |
| 7648 | A01 | L3 | YYCQQWYHYSYPITFG |
| 7649 | A02 | H1 | GFNLYYYSMHWV |
| 7650 | A02 | H2 | LEWVASISSSYGYTYYADS |
| 7651 | A02 | H3 | YYCARTVRGSKKPYFSGWAMDYWGQ |
| 7652 | A02 | L3 | YYCQQSYAYSPFTFGQ |
| 7653 | A03 | H1 | GFNFSSSSIHWV |
| 7654 | A03 | H2 | LEWVASISSSYGYTYYADS |
| 7655 | A03 | H3 | YYCARTVRGSKKPYFSGWAMDYWGQ |
| 7656 | A03 | L3 | YYCQQWYHYSYPITFG |
| 7657 | A04 | H1 | GFNFSSSSIHWV |
| 7658 | A04 | H2 | LEWVASISSYYSSTYYADS |
| 7659 | A04 | H3 | YYCARTVRGSKKPYFSGWAMDYWGQ |
| 7660 | A04 | L3 | YYCQQWYHYSYPITFG |
| 7661 | A05 | H1 | GFNFSSSSIHWV |
| 7662 | A05 | H2 | LEWVASISSYYSSTYYADS |
| 7663 | A05 | H3 | YYCARTVRGSKKPYFSGWAMDYWGQ |
| 7664 | A05 | L3 | YYCQQWYHYSYPITFG |
| 7665 | A06 | H1 | GFNFSSSSIHWV |
| 7666 | A06 | H2 | LEWVASISSYYSSTYYADS |
| 7667 | A06 | H3 | YYCARTVRGSKKPYFSGWAMDYWGQ |
| 7668 | A06 | L3 | YYCQQWYHYSYPITFG |

TABLE 3-continued

CDR sequences of anti-human MGAT5 antibody clones

| Seq ID No | Well # | Antibody Chain | Sequence |
|---|---|---|---|
| 7669 | A07 | H1 | GFNFSSSSIHWV |
| 7670 | A07 | H2 | LEWVASISSSYGYTYYADS |
| 7671 | A07 | H3 | YYCARTVRGSKKPYFSGWAMDYWGQ |
| 7672 | A07 | L3 | YYCQQWAYYSYPITFG |
| 7673 | A08 | H1 | GFNFSSSSIHWV |
| 7674 | A08 | H2 | LEWVASISSYYSSTYYADS |
| 7675 | A08 | H3 | YYCARTVRGSKKPYFSGWAMDYWGQ |
| 7676 | A08 | L3 | YYCQQWYHYSYPITFG |
| 7677 | A09 | H1 | GFNFSSSSIHWV |
| 7678 | A09 | H2 | LEWVASISSYYSSTYYADS |
| 7679 | A09 | H3 | YYCARTVRGSKKPYFSGWAMDYWGQ |
| 7680 | A09 | L3 | YYCQQWYHYSYPITFG |
| 7681 | A10 | H1 | GFNLYYYSMHWV |
| 7682 | A10 | H2 | LEWVASISSSYGYTYYADS |
| 7683 | A10 | H3 | YYCARTVRGSKKPYFSGWAMDYWGQ |
| 7684 | A10 | L3 | YYCQQSYAYSPFTFGQ |
| 7685 | B01 | H1 | GFNFSSSSIHWV |
| 7686 | B01 | H2 | LEWVASISSYYSSTYYADS |
| 7687 | B01 | H3 | YYCARTVRGSKKPYFSGWAMDYWGQ |
| 7688 | B01 | L3 | YYCQQWYHYSYPITFG |
| 7689 | B02 | H1 | GFNFSSSSIHWV |
| 7690 | B02 | H2 | LEWVASISSYYGSTYYADS |
| 7691 | B02 | H3 | YYCARTVRGSKKPYFSGWAMDYWGQ |
| 7692 | B02 | L3 | YYCQQWYHYSYPITFG |
| 7693 | B05 | H1 | GFNFSSSSIHWV |
| 7694 | B05 | H2 | LEWVASISSSYGYTYYADS |
| 7695 | B05 | H3 | YYCARTVRGSKKPYFSGWAMDYWGQ |
| 7696 | B06 | H1 | GFNFSSSSIHWV |
| 7697 | B06 | H2 | LEWVASISSYYSSTYYADS |
| 7698 | B06 | H3 | YYCARTVRGSKKPYFSGWAMDYWGQ |
| 7699 | B07 | H1 | GFNFSSSSIHWV |
| 7700 | B07 | H2 | LEWVASISSYYSSTYYADS |
| 7701 | B07 | H3 | YYCARTVRGSKKPYFSGWAMDYWGQ |
| 7702 | B08 | L3 | YYCQQWYHYSYPITFG |
| 7703 | B09 | H1 | GFNFSSSSIHWV |
| 7704 | B09 | H2 | LEWVASISSYYSSTYYADS |
| 7705 | B09 | H3 | YYCARTVRGSKKPYFSGWAMDYWGQ |

TABLE 3-continued

CDR sequences of anti-human MGAT5 antibody clones

| Seq ID No | Well # | Antibody Chain | Sequence |
|---|---|---|---|
| 7706 | B09 | L3 | YYCQQWYHYSYPITFG |
| 7707 | B10 | H1 | GFNFSSSSIHWV |
| 7708 | B10 | H2 | LEWVASISSYYSSTYYADS |
| 7709 | B10 | H3 | YYCARTVRGSKKPYFSGWAMDYWGQ |
| 7710 | B10 | L3 | YYCQQWYHYSYPITFG |
| 7711 | B11 | H1 | GFNFSSSSIHWV |
| 7712 | B11 | H2 | LEWVASISSYYSSTYYADS |
| 7713 | B11 | H3 | YYCARTVRGSKKPYFSGWAMDYWGQ |
| 7714 | B11 | L3 | YYCQQWYHYSYPITFG |
| 7715 | B12 | H1 | GFNFSSSSIHWV |
| 7716 | B12 | H2 | LEWVASISSYYSSTYYADS |
| 7717 | B12 | H3 | YYCARTVRGSKKPYFSGWAMDYWGQ |
| 7718 | B12 | L3 | YYCQQWYHYSYPITFG |
| 7719 | C01 | H1 | GFNFSSSSIHWV |
| 7720 | C01 | H2 | LEWVASISSSYGYTYYADS |
| 7721 | C01 | H3 | YYCARTVRGSKKPYFSGWAMDYWGQ |
| 7722 | C02 | H1 | GFNFSSSSIHWV |
| 7723 | C02 | H2 | LEWVASISSSYGYTYYADS |
| 7724 | C02 | H3 | YYCARTVRGSKKPYFSGWAMDYWGQ |
| 7725 | C03 | H1 | GFNFSSSSIHWV |
| 7726 | C03 | H2 | LEWVASISSYYSSTYYADS |
| 7727 | C03 | H3 | YYCARTVRGSKKPYFSGWAMDYWGQ |
| 7728 | C03 | L3 | YYCQQWYHYSYPITFG |
| 7729 | C04 | H1 | GFNFSSSSIHWV |
| 7730 | C04 | H2 | LEWVASISSYYSSTYYADS |
| 7731 | C04 | H3 | YYCARTVRGSKKPYFSGWAMDYWGQ |

TABLE 4

CDR sequences of anti-human PDIA3 antibody clones

| Seq ID No | Well # | Antibody CDR | Round | Sequence |
|---|---|---|---|---|
| 7732 | A01 | H1 | R3r | GFNLYSYYMHWV |
| 7733 | A01 | H2 | R3r | LEWVAYIYPYYSYTYYADS |
| 7734 | A01 | H3 | R3r | YYCARYPDSFHSSDYPSYSYYAMDYWGQG |
| 7735 | A01 | L3 | R3r | YYCQQSGAGGYPFTFGQG |
| 7736 | A02 | H1 | R3r | GFNFSSSSIHWV |
| 7737 | A02 | H2 | R3r | LEWVASISSSYGYTYYADS |
| 7738 | A02 | H3 | R3r | YYCARTVRGSKKPYFSGWAMDYWGQG |
| 7739 | A02 | L3 | R3r | YYCQQSSYSLITFGQG |
| 7740 | A03 | H1 | R3r | GFNLYYYYIHWV |
| 7741 | A03 | H2 | R3r | LEWVASIYSYYSYTYYADS |
| 7742 | A03 | H3 | R3r | YYCARSSDASSYGGGGYAIDYWGQG |
| 7743 | A03 | L3 | R3r | YYCQQGFYSSPITFGQG |
| 7744 | A04 | H1 | R3r | GFNFSSSSIHWV |
| 7745 | A04 | H2 | R3r | LEWVASISSSYGYTYYADS |
| 7746 | A04 | H3 | R3r | YYCARTVRGSKKPYFSGWAMDYWGQG |
| 7747 | A04 | L3 | R3r | YYCQQHSHYGSPITFGQG |
| 7748 | A05 | H1 | R3r | GFNLSSSYIHWV |
| 7749 | A05 | H2 | R3r | LEWVASISSSYGYTYYADS |
| 7750 | A05 | H3 | R3r | YYCARSYDDYYGGALDYWGQG |
| 7751 | A05 | L3 | R3r | YYCQQHYHPITFGQG |
| 7752 | A06 | H1 | R3r | GFNLSSSYIHWV |
| 7753 | A06 | H2 | R3r | LEWVAYIYPSYGYTYYADS |
| 7754 | A06 | H3 | R3r | YYCARGFASSGIDYWGQG |
| 7755 | A06 | L3 | R3r | YYCQQASSYYYPFTFGQG |
| 7756 | A07 | H1 | R4 | GFTSLLLLCTG |
| 7757 | A07 | H2 | R4 | LEWVASISSYYGYTSYADS |
| 7758 | A07 | H3 | R4 | YYCARHAHHGSGWDAYYYDYSAMDYWGQG |
| 7759 | A07 | L3 | R4 | YYCQQSYSYYDALITFGQG |
| 7760 | A08 | H1 | R4 | GFNFSSSSIHWV |
| 7761 | A08 | H2 | R4 | LEWVASISSSYGYTYYADS |
| 7762 | A08 | H3 | R4 | YYCARTVRGSKKPYFSGWAMDYWGQG |
| 7763 | A08 | L3 | R4 | YYCQQYYPSSLFTFGQG |
| 7764 | A09 | H1 | R4 | GFNLYYSYMHWV |
| 7765 | A09 | H2 | R4 | LEWVTSIYPSYGYTYYADS |
| 7766 | A09 | H3 | R4 | YYCARGYPFSDSFYWAGYALDYWGQG |
| 7767 | A09 | L3 | R4 | YYCQQYFHYYLITFGQG |
| 7768 | A10 | H1 | R4 | GFNLSSSYYIHWV |
| 7769 | A10 | H2 | R4 | LEWVASISSYSGSTYYADS |
| 7770 | A10 | H3 | R4 | YYCARAGSYWSYAFDYWGQG |
| 7771 | A10 | L3 | R4 | YYCQQSYGPITFGQG |
| 7772 | A11 | H1 | R4 | GFNFSSSSIHWV |

TABLE 4-continued

CDR sequences of anti-human PDIA3 antibody clones

| Seq ID No | Well # | Antibody CDR | Round | Sequence |
|---|---|---|---|---|
| 7773 | A11 | H2 | R4 | LEWVASISSSYGYTYYADS |
| 7774 | A11 | H3 | R4 | YYCARTVRGSKKPYFSGWAMDYWGQG |
| 7775 | A11 | L3 | R4 | YYCQQSSYSLITFGQG |
| 7776 | A12 | H1 | R4 | GFNLSSSYIHWV |
| 7777 | A12 | H2 | R4 | LEWVASIYSYYGSTYYADS |
| 7778 | A12 | H3 | R4 | YYCARPSFSYYAMDYWGQG |
| 7779 | A12 | L3 | R4 | YYCQQGFFFAPITFGQG |
| 7780 | B01 | H1 | R4r | GFNLYSYSMHWV |
| 7781 | B01 | H2 | R4r | LEWVAYIYSYSGYTYYADS |
| 7782 | B01 | H3 | R4r | YYCARASYYGLDYWGQG |
| 7783 | B01 | L3 | R4r | YYCQQSAYGYGHPITFGQG |
| 7784 | B02 | H1 | R4r | GFNLYYYSMHWV |
| 7785 | B02 | H2 | R4r | LEWVAYIYSSYSSYTYYADS |
| 7786 | B02 | H3 | R4r | YYCARWSYPGGDGGMDYWGQG |
| 7787 | B02 | L3 | R4r | YYCQQSSDAYSLITLDR |
| 7788 | B03 | H1 | R4r | GFNFSSSSIHWV |
| 7789 | B03 | H2 | R4r | LEWVASISSSYGYTYYADS |
| 7790 | B03 | H3 | R4r | YYCARTVRGSKKPYFSGWAMDYWGQG |
| 7791 | B03 | L3 | R4r | YYCQQGAYYGAPITFGQG |
| 7792 | B04 | H1 | R4r | ASTSFFLMHG |
| 7793 | B04 | H2 | R4r | LEWVAYIYSSSSSTSYADS |
| 7794 | B04 | H3 | R4r | YYCARSSSASGYPGFSYFSYDGMDYWGQG |
| 7795 | B04 | L3 | R4r | YYCQQSSYSLITFGQG |
| 7796 | B05 | H1 | R4r | GFNFSSSSIHWV |
| 7797 | B05 | H2 | R4r | LEWVASISSSYGYTYYADS |
| 7798 | B05 | H3 | R4r | YYCARTVRGSKKPYFSGWAMDYWGQG |
| 7799 | B05 | L3 | R4r | YYCQQSSYSLITFGQG |
| 7800 | B06 | H1 | R4r | GFNIYYSYMHWV |
| 7801 | B06 | H2 | R4r | LEWVASIYPYSSYTSYADS |
| 7802 | B06 | H3 | R4r | YYCARFSWFGWYSYAGMDYWGQG |
| 7803 | B06 | L3 | R4r | YYCQQSSYSLITFGQG |
| 7804 | B07 | H1 | R5 | GFNLSSSSMHWV |
| 7805 | B07 | H2 | R5 | LEWVAYIYSYSGYTSYADS |
| 7806 | B07 | H3 | R5 | YYCARTVRGSNKPYFSGWAMDYWGQG |
| 7807 | B07 | L3 | R5 | YYCQQAPAALITFGQG |
| 7808 | B08 | H1 | R5 | GFNLYYSYMHWV |
| 7809 | B08 | H2 | R5 | LEWVAYIYPYYGSTSYADS |
| 7810 | B08 | H3 | R5 | YYCARYSYPYWYYFGSGLDYWGQG |
| 7811 | B08 | L3 | R5 | YYCQQWYLITFGQG |
| 7812 | B09 | H1 | R5 | GFNLYYYMHWV |
| 7813 | B09 | H2 | R5 | LEWVAYISPSYGYTYYADS |
| 7814 | B09 | H3 | R5 | YYCARSSSGYSYGAFYYPSAIDYWGQG |
| 7815 | B09 | L3 | R5 | YYCQQGYDLITFGQG |
| 7816 | B11 | H1 | R5 | GFNIYYSYMHWV |
| 7817 | B11 | H2 | R5 | LEWVASIYSYYSSTSYADS |
| 7818 | B11 | H3 | R5 | YYCARSALDYWGQG |
| 7819 | B11 | L3 | R5 | YYCQQYYYLITFGQG |
| 7820 | B12 | H1 | R3r | GFNFSSSSIHWV |
| 7821 | B12 | H2 | R3r | LEWVASISSSYGYTYYADS |
| 7822 | B12 | H3 | R3r | YYCARHYAGYPGYYGYGIDYWGQG |
| 7823 | B12 | L3 | R3r | YYCQQSSYSLITFGQG |

For the above MGAT5 and PDIA3 antibodies, the sequences comprising L1 and L2 are constant across all clones:

Amino acid sequence SEQ ID NO. 7,824:
IQMTQSPSSLSASVGDRVTITCRASQSVSSAVAWYQQKPGKAPKLLIYSA
SSLYSGVPSRFSGSRSGTDFTLTISSLQPEDFAT Nucleic acid sequence SEQ ID NO. 69,837
ATCCAGATGACCCAGTCCCCGAGCTCCCTGTCCGCCTCTGTGGGCGATAG
GGTCACCATCACCTGCCGTGCCAGTCAGTCCGTGTCCAGCGCTGTAGCCT
GGTATCAACAGAAACCAGGAAAAGCTCCGAAGCTTCTGATTTACTCGGCA
TCCAGCCTCTACTCTGGAGTCCCTTCTCGCTTCTCTGGTAGCCGTTCCGG
GACGGATTTCACTCTGACCATCAGCAGTCTGCAGCCGGAAGACTTCGCAA
CT Based on these antibody clone sequences, mouse IgG1 expression vectors were constructed for the top 3 clones for both human MGAT5 and PDIA3 and termed anti-MGAT5 and anti-PDIA3 monoclonal antibodies (a-MGAT5 and a-PDIA3 mAbs). Each antibody consists of a heavy chain and a light chain. (Table 5).

TABLE 5

Sequence ID NOs for a-MGAT5 and a-PDIA3 mAbs in mIgG1 heavy and light chains. Full sequences are below.

| SEQ ID No | Sequence file | Identity |
|---|---|---|
| 7825 | pLYM10H_pFUSEss-CHIg-mG1 | a-MGAT5 clone 10 heavy chain |
| 7826 | pLYM10L_pFUSE2ss-CLIg-mk | a-MGAT5 clone 10 light chain |
| 7827 | pLYM3H_pFUSEss-CHIg-mG1 | a-MGAT5 clone 3 heavy chain |
| 7828 | pLYM3L_pFUSE2ss-CLIg-mk | a-MGAT5 clone 3 light chain |
| 7829 | pLYM9H_pFUSEss-CHIg-mG1 | a-MGAT5 clone 9 heavy chain |
| 7830 | pLYM9L_pFUSE2ss-CLIg-mk | a-MGAT5 clone 9 light chain |

TABLE 5-continued

Sequence ID NOs for a-MGAT5 and a-PDIA3 mAbs in mIgG1 heavy and light chains. Full sequences are below.

| SEQ ID No | Sequence file | Identity |
|---|---|---|
| 7831 | pLYP17H_pFUSEss-CHIg-mG1 | a-PDIA3 clone 17 heavy chain |
| 7832 | pLYP17L_pFUSE2ss-CLIg-mk | a-PDIA3 clone 17 light chain |
| 7833 | pLYP21H_pFUSEss-CHIg-mG1 | a-PDIA3 clone 21 heavy chain |
| 7834 | pLYP21L_pFUSE2ss-CLIg-mk | a-PDIA3 clone 21 light chain |
| 7835 | pLYP22H_pFUSEss-CHIg-mG1 | a-PDIA3 clone 22 heavy chain |
| 7836 | pLYP22L_pFUSE2ss-CLIg-mk | a-PDIA3 clone 22 light chain |

```
SEQ ID No 7,825:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCACCGGCGAAGGAGGGCCACCATGTACAGGATGCAACTCCTGTCTTGCATTGC

ACTAAGTCTTGCACTTGTCACGAATTCGGAGGTTCAGCTGGTGGAGTCTGGCGGT

GGCCTGGTGCAGCCAGGGGGCTCACTCCGTTTGTCCTGTGCAGCTTCTGGCTTCA

ACCTCTATTATTATTCTATGCACTGGGTGCGTCAGGCCCCGGGTAAGGGCCTGGA

ATGGGTTGCATCTATTTCTTCTTCTTATGGCTATACTTATTATGCCGATAGCGTCA

AGGGCCGTTTCACTATAAGCGCAGACACATCCAAAAACACAGCCTACCTACAAA

TGAACAGCTTAAGAGCTGAGGACACTGCCGTCTATTATTGTGCTCGCACTGTTCG

TGGATCCAAAAAACCGTACTTCTCTGGTTGGGCTATGGACTACTGGGGTCAAGGA

ACCCTGGTCACCGTCTCCTCGAGTGCTAGCAGCGCTAAAACGACACCCCCATCTG

TCTATCCACTGGCCCCTGGATCTGCTGCCCAAACTAACTCCATGGTGACCCTGGG

ATGCCTGGTCAAGGGCTATTTCCCTGAGCCAGTGACAGTGACCTGGAACTCTGGA

TCCCTGTCCAGCGGTGTGCACACCTTCCCAGCTGTCCTGCAGTCTGACCTCTACA

CTCTGAGCAGCTCAGTGACTGTCCCCTCCAGCACCTGGCCCAGCGAGACCGTCAC

CTGCAACGTTGCCCACCCGGCCAGCAGCACCAAGGTGGACAAGAAAATTGTGCC

CAGGGATTGTGGTTGTAAGCCTTGCATATGTACAGTCCCAGAAGTATCATCTGTC

TTCATCTTCCCCCCAAAGCCCAAGGATGTGCTCACCATTACTCTGACTCCTAAGG

TCACGTGTGTTGTGGTAGACATCAGCAAGGATGATCCCGAGGTCCAGTTCAGCTG

GTTTGTAGATGATGTGGAGGTGCACACAGCTCAGACGCAACCCCGGGAGGAGCA

GTTCAACAGCACTTTCCGCTCAGTCAGTGAACTTCCCATCATGCACCAGGACTGG

CTCAATGGCAAGGAGTTCAAATGCAGGGTCAACAGTGCAGCTTTCCCTGCCCCCA

TCGAGAAAACCATCTCCAAAACCAAAGGCAGACCGAAGGCTCCGCAGGTGTACA
```

-continued

```
CCATTCCACCTCCCAAGGAGCAGATGGCCAAGGATAAAGTCAGTCTGACCTGCA
TGATAACAGACTTCTTCCCTGAAGACATTACTGTGGAGTGGCAGTGGAATGGGCA
GCCAGCGGAGAACTACAAGAACACTCAGCCCATCATGGACACAGATGGCTCTTA
CTTCGTCTACAGCAAGCTCAATGTGCAGAAGAGCAACTGGGAGGCAGGAAATAC
TTTCACCTGCTCTGTGTTACATGAGGGCCTGCACAACCACCATACTGAGAAGAGC
CTCTCCCACTCTCCTGGTAAATGATCCCAGTGTCCCTAGCTGGCCAGACATGATA
AGATACATTGATGAGTTTGGACAAACCACAACTAGAATGCAGTGAAAAAAATGC
TTTATTTGTGAAATTTGTGATGCTATTGCTTTATTTGTAACCATTATAAGCTGCAA
TAAACAAGTTAACAACAACAATTGCATTCATTTTATGTTTCAGGTTCAGGGGGAG
GTGTGGGAGGTTTTTTAAAGCAAGTAAAACCTCTACAAATGTGGTATGGAATTAA
TTCTAAAATACAGCATAGCAAAACTTTAACCTCCAAATCAAGCCTCTACTTGAAT
CCTTTTCTGAGGGATGAATAAGGCATAGGCATCAGGGGCTGTTGCCAATGTGCAT
TAGCTGTTTGCAGCCTCACCTTCTTTCATGGAGTTTAAGATATAGTGTATTTTCCC
AAGGTTTGAACTAGCTCTTCATTTCTTTATGTTTTAAATGCACTGACCTCCCACAT
TCCCTTTTTAGTAAAATATTCAGAAATAATTTAAATACATCATTGCAATGAAAAT
AAATGTTTTTATTAGGCAGAATCCAGATGCTCAAGGCCCTTCATAATATCCCCC
AGTTTAGTAGTTGGACTTAGGGAACAAAGGAACCTTTAATAGAAATTGGACAGC
AAGAAAGCGAGCTTCTAGCTTATCCTCAGTCCTGCTCCTCTGCCACAAAGTGCAC
GCAGTTGCCGGCCGGGTCGCGCAGGGCGAACTCCCGCCCCCACGGCTGCTCGCC
GATCTCGGTCATGGCCGGCCCGGAGGCGTCCCGGAAGTTCGTGGACACGACCTC
CGACCACTCGGCGTACAGCTCGTCCAGGCCGCGCACCCACACCCAGGCCAGGGT
GTTGTCCGGCACCACCTGGTCCTGGACCGCGCTGATGAACAGGGTCACGTCGTCC
CGGACCACACCGGCGAAGTCGTCCTCCACGAAGTCCCGGGAGAACCCGAGCCGG
TCGGTCCAGAACTCGACCGCTCCGGCGACGTCGCGCGCGGTGAGCACCGGAACG
GCACTGGTCAACTTGGCCATGATGGCTCCTCctgtcaggagaggaaagagaaga
aggttagtacaattgCTATAGTGAGTTGTATTATACTATGCAGATATACTATG
CCAATGATTAATTGTCAAACTAGGGCTGCAgggttcatagtgccacttttcct
gcactgccccatctcctgcccacccttcccaggcatagacagtcagtgactt
acCAAACTCACAGGAGGGAGAAGGCAGAAGCTTGAGACAGACCCGCGGGAC
CGCCGAACTGCGAGGGGACGTGGCTAGGGCGGCTTCTTTTATGGTGCGCCGGCC
CTCGGAGGCAGGGCGCTCGGGGAGGCCTAGCGGCCAATCTGCGGTGGCAGGAGG
CGGGGCCGAAGGCCGTGCCTGACCAATCCGGAGCACATAGGAGTCTCAGCCCCC
CGCCCCAAAGCAAGGGGAAGTCACGCGCCTGTAGCGCCAGCGTGTTGTGAAATG
GGGGCTTGGGGGGGTTGGGGCCCTGACTAGTCAAAACAAACTCCCATTGACGTC
AATGGGGTGGAGACTTGGAAATCCCCGTGAGTCAAACCGCTATCCACGCCCATT
GATGTACTGCCAAAACCGCATCATCATGGTAATAGCGATGACTAATACGTAGAT
GTACTGCCAAGTAGGAAAGTCCCATAAGGTCATGTACTGGGCATAATGCCAGGC
GGGCCATTTACCGTCATTGACGTCAATAGGGGGCGTACTTGGCATATGATACACT
TGATGTACTGCCAAGTGGGCAGTTTACCGTAAATACTCCACCCATTGACGTCAAT
GGAAAGTCCCTATTGGCGTTACTATGGGAACATACGTCATTATTGACGTCAATGG
GCGGGGGTCGTTGGGCGGTCAGCCAGGCGGGCCATTTACCGTAAGTTATGTAAC
```

```
GCCTGCAGGTTAATTAAGAACATGTGAGCAAAAGGCCAGCAAAAGGCCAGGAAC

CGTAAAAAGGCCGCGTTGCTGGCGTTTTTCCATAGGCTCCGCCCCCCTGACGAGC

ATCACAAAAATCGACGCTCAAGTCAGAGGTGGCGAAACCCGACAGGACTATAAA

GATACCAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGCTTTCTC

ATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTAT

CGTCTTGAGTCCAACCCGGTAAGACACGACTTATCGCCACTGGCAGCAGCCACTG

GTAACAGGATTAGCAGAGCGAGGTATGTAGGCGGTGCTACAGAGTTCTTGAAGT

GGTGGCCTAACTACGGCTACACTAGAAGAACAGTATTTGGTATCTGCGCTCTGCT

GAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCAGTGGA

ACGAAAACTCACGTTAAGGGATTTTGGTCATGGCTAGTTAATTAACATTTAAATC

AGCGGCCGCAATAAAATATCTTTATTTTCATTACATCTGTGTGTTGGTTTTTTGTG

TGAATCGTAACTAACATACGCTCTCCATCAAAACAAAACGAAACAAAACAAACT

AGCAAAATAGGCTGTCCCCAGTGCAAGTGCAGGTGCCAGAACATTTCTCTATCGA

A

SEQ ID No 7,826:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCAACATGTACAGGATGCAACTCCTGTCTTGCATTGCACTAAGTCTTGCACTTG

TCACGAATTCAGATATCCAGATGACCCAGTCCCCGAGCTCCCTGTCCGCCTCTGT

GGGCGATAGGGTCACCATCACCTGCCGTGCCAGTCAGTCCGTGTCCAGCGCTGTA

GCCTGGTATCAACAGAAACCAGGAAAAGCTCCGAAGCTTCTGATTTACTCGGCAT

CCAGCCTCTACTCTGGAGTCCCTTCTCGCTTCTCTGGTAGCCGTTCCGGGACGGAT

TTCACTCTGACCATCAGCAGTCTGCAGCCGGAAGACTTCGCAACTTATTACTGTC

AGCAATCTTACGCTTACTCTCCGTTCACGTTCGGACAGGGTACCAAGGTGGAGAT

CAAACGACTCGAGATCAAACGGGCAGATGCTGCACCAACTGTATCCATCTTCCC

ACCATCCAGTGAGCAGTTAACATCTGGAGGTGCCTCAGTCGTGTGCTTCTTGAAC

AACTTCTACCCCAAAGACATCAATGTCAAGTGGAAGATTGATGGCAGTGAACGA

CAAAATGGCGTCCTGAACAGTTGGACTGATCAGGACAGCAAAGACAGCACCTAC

AGCATGAGCAGCACCCTCACGTTGACCAAGGACGAGTATGAACGACATAACAGC
```

```
TATACCTGTGAGGCCACTCACAAGACATCAACTTCACCCATTGTCAAGAGCTTCA

ACAGGAATGAGTGTTAGAGACAAAGGTCCTGAGAGCTAGCTGGCCAGACATGAT

AAGATACATTGATGAGTTTGGACAAACCACAACTAGAATGCAGTGAAAAAAATG

CTTTATTTGTGAAATTTGTGATGCTATTGCTTTATTTGTAACCATTATAAGCTGCA

ATAAACAAGTTAACAACAACAATTGCATTCATTTTATGTTTCAGGTTCAGGGGGA

GGTGTGGGAGGTTTTTTAAAGCAAGTAAAACCTCTACAAATGTGGTATGGAATTA

ATTCTAAAATACAGCATAGCAAAACTTTAACCTCCAAATCAAGCCTCTACTTGAA

TCCTTTTCTGAGGGATGAATAAGGCATAGGCATCAGGGGCTGTTGCCAATGTGCA

TTAGCTGTTTGCAGCCTCACCTTCTTTCATGGAGTTTAAGATATAGTGTATTTTCC

CAAGGTTTGAACTAGCTCTTCATTTCTTTATGTTTTAAATGCACTGACCTCCCACA

TTCCCTTTTAGTAAAATATTCAGAAATAATTTAAATACATCATTGCAATGAAAA

TAAATGTTTTTTATTAGGCAGAATCCAGATGCTCAAGGCCCTTCATAATATCCCC

CAGTTTAGTAGTTGGACTTAGGGAACAAAGGAACCTTTAATAGAAATTGGACAG

CAAGAAAGCGAGCTTCTAGCTTTAGTTCCTGGTGTACTTGAGGGGGATGAGTTCC

TCAATGGTGGTTTTGACCAGCTTGCCATTCATCTCAATGAGCACAAAGCAGTCAG

GAGCATAGTCAGAGATGAGCTCTCTGCACATGCCACAGGGGCTGACCACCCTGA

TGGATCTGTCCACCTCATCAGAGTAGGGGTGCCTGACAGCCACAATGGTGTCAAA

GTCCTTCTGCCCGTTGCTCACAGCAGACCCAATGGCAATGGCTTCAGCACAGACA

GTGACCCTGCCAATGTAGGCCTCAATGTGGACAGCAGAGATGATCTCCCCAGTCT

TGGTCCTGATGGCCGCCCCGACATGGTGCTTGTTGTCCTCATAGAGCATGGTGAT

CTTCTCAGTGGCGACCTCCACCAGCTCCAGATCCTGCTGAGAGATGTTGAAGGTC

TTCATGATGGCTCCTCctgtcaggagaggaaagagaagaaggttagtacaatt gCTATAGTGAGTTGTATTATACTATGCTTATGATTAATTGTCAAACTAGGGCT GCAgggttcatagtgccacttttcctgcactgccccatctectgcccaccatt tcccaggcatagacagtcagtgacttacCAAACTCACAGGAGGGAGAAGGCAG

AAGCTTGAGACAGACCCGCGGGACCGCCGAACTGCGAGGGGACGTGGCTA

GGGCGGCTTCTTTTATGGTGCGCCGGCCCTCGGAGGCAGGGCGCTCGGGGAGGC

CTAGCGGCCAATCTGCGGTGGCAGGAGGCGGGGCCGAAGGCCGTGCCTGACCAA

TCCGGAGCACATAGGAGTCTCAGCCCCCCGCCCCAAAGCAAGGGGAAGTCACGC

GCCTGTAGCGCCAGCGTGTTGTGAAATGGGGGCTTGGGGGGGTTGGGGCCCTGA

CTAGTCAAAACAAACTCCCATTGACGTCAATGGGGTGGAGACTTGGAAATCCCC

GTGAGTCAAACCGCTATCCACGCCCATTGATGTACTGCCAAAACCGCATCATCAT

GGTAATAGCGATGACTAATACGTAGATGTACTGCCAAGTAGGAAAGTCCCATAA

GGTCATGTACTGGGCATAATGCCAGGCGGGCCATTTACCGTCATTGACGTCAATA

GGGGGCGTACTTGGCATATGATACACTTGATGTACTGCCAAGTGGGCAGTTTACC

GTAAATACTCCACCCATTGACGTCAATGGAAAGTCCCTATTGGCGTTACTATGGG

AACATACGTCATTATTGACGTCAATGGGCGGGGTCGTTGGGCGGTCAGCCAGG

CGGGCCATTTACCGTAAGTTATGTAACGCCTGCAGGTTAATTAAGAACATGTGAG

CAAAAGGCCAGCAAAAGGCCAGGAACCGTAAAAAGGCCGCGTTGCTGGCGTTTT

TCCATAGGCTCCGCCCCCCTGACGAGCATCACAAAAATCGACGCTCAAGTCAGA
```

-continued

GGTGGCGAAACCCGACAGGACTATAAAGATACCAGGCGTTTCCCCCTGGAAGCT

CCCTCGTGCGCTCTCCTGTTCCGACCCTGCCGCTTACCGGATACCTGTCCGCCTTT

CTCCCTTCGGGAAGCGTGGCGCTTTCTCATAGCTCACGCTGTAGGTATCTCAGTTC

GGTGTAGGTCGTTCGCTCCAAGCTGGGCTGTGTGCACGAACCCCCCGTTCAGCCC

GACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTATG

TAGGCGGTGCTACAGAGTTCTTGAAGTGGTGGCCTAACTACGGCTACACTAGAA

GAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTT

TGCAAGCAGCAGATTACGCGCAGAAAAAAAGGATCTCAAGAAGATCCTTTGATC

TTTTCTACGGGGTCTGACGCTCAGTGGAACGAAAACTCACGTTAAGGGATTTTGG

TCATGGCTAGTTAATTAACATTTAAATCAGCGGCCGCAATAAAATATCTTTATTTT

CATTACATCTGTGTGTTGGTTTTTTGTGTGAATCGTAACTAACATACGCTCTCCAT

CAAAACAAAACGAAACAAAACAAACTAGCAAAATAGGCTGTCCCCAGTGCAAGT

GCAGGTGCCAGAACATTTCTCTATCGAA

SEQ ID NO 7,827:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCAACATGTACAGGATGCAACTCCTGTCTTGCATTGCACTAAGTCTTGCACTTG

TCACGAATTCAGATATCCAGATGACCCAGTCCCCGAGCTCCCTGTCCGCCTCTGT

GGGCGATAGGGTCACCATCACCTGCCGTGCCAGTCAGTCCGTGTCCAGCGCTGTA

GCCTGGTATCAACAGAAACCAGGAAAAGCTCCGAAGCTTCTGATTTACTCGGCAT

CCAGCCTCTACTCTGGAGTCCCTTCTCGCTTCTCTGGTAGCCGTTCCGGGACGGAT

TTCACTCTGACCATCAGCAGTCTGCAGCCGGAAGACTTCGCAACTTATTACTGTC

AGCAATCTTACGCTTACTCTCCGTTCACGTTCGGACAGGGTACCAAGGTGGAGAT

CAAACGACTCGAGATCAAACGGGCAGATGCTGCACCAACTGTATCCATCTTCCC

ACCATCCAGTGAGCAGTTAACATCTGGAGGTGCCTCAGTCGTGTGCTTCTTGAAC

AACTTCTACCCCAAAGACATCAATGTCAAGTGGAAGATTGATGGCAGTGAACGA

CAAAATGGCGTCCTGAACAGTTGGACTGATCAGGACAGCAAAGACAGCACCTAC

AGCATGAGCAGCACCCTCACGTTGACCAAGGACGAGTATGAACGACATAACAGC

TATACCTGTGAGGCCACTCACAAGACATCAACTTCACCCATTGTCAAGAGCTTCA

ACAGGAATGAGTGTTAGAGACAAAGGTCCTGAGAGCTAGCTGGCCAGACATGAT

AAGATACATTGATGAGTTTGGACAAACCACAACTAGAATGCAGTGAAAAAAATG

-continued
CTTTATTTGTGAAATTTGTGATGCTATTGCTTTATTTGTAACCATTATAAGCTGCA
ATAAACAAGTTAACAACAACAATTGCATTCATTTTATGTTTCAGGTTCAGGGGGA
GGTGTGGGAGGTTTTTTAAAGCAAGTAAAACCTCTACAAATGTGGTATGGAATTA
ATTCTAAAATACAGCATAGCAAAACTTTAACCTCCAAATCAAGCCTCTACTTGAA
TCCTTTTCTGAGGGATGAATAAGGCATAGGCATCAGGGGCTGTTGCCAATGTGCA
TTAGCTGTTTGCAGCCTCACCTTCTTTCATGGAGTTTAAGATATAGTGTATTTTCC
CAAGGTTTGAACTAGCTCTTCATTTCTTTATGTTTTAAATGCACTGACCTCCCACA
TTCCCTTTTTAGTAAAATATTCAGAAATAATTTAAATACATCATTGCAATGAAAA
TAAATGTTTTTTATTAGGCAGAATCCAGATGCTCAAGGCCCTTCATAATATCCCC
CAGTTTAGTAGTTGGACTTAGGGAACAAAGGAACCTTTAATAGAAATTGGACAG
CAAGAAAGCGAGCTTCTAGCTTTAGTTCCTGGTGTACTTGAGGGGGATGAGTTCC
TCAATGGTGGTTTTGACCAGCTTGCCATTCATCTCAATGAGCACAAAGCAGTCAG
GAGCATAGTCAGAGATGAGCTCTCTGCACATGCCACAGGGGCTGACCACCCTGA
TGGATCTGTCCACCTCATCAGAGTAGGGGTGCCTGACAGCCACAATGGTGTCAAA
GTCCTTCTGCCCGTTGCTCACAGCAGACCCAATGGCAATGGCTTCAGCACAGACA
GTGACCCTGCCAATGTAGGCCTCAATGTGGACAGCAGAGATGATCTCCCCAGTCT
TGGTCCTGATGGCCGCCCCGACATGGTGCTTGTTGTCCTCATAGAGCATGGTGAT
CTTCTCAGTGGCGACCTCCACCAGCTCCAGATCCTGCTGAGAGATGTTGAAGGTC
TTCATGATGGCTCCTCctgtcaggagaggaaagagaagaaggttagtacaattg
CTATAGTGAGTTGTATTATACTATGCTTATGATTAATTGTCAAACTAGGGCTGC
Agggttcatagtgccacttttcctgcactgccccatctectgcccaccattccc
aggcatagacagtcagtgacttacCAAACTCACAGGAGGGAGAAGG
CAGAAGCTTGAGACAGACCCGCGGGACCGCCGAACTGCGAGGGGACGTGGCTA
GGGCGGCTTCTTTTATGGTGCGCCGGCCCTCGGAGGCAGGGCGCTCGGGGAGGC
CTAGCGGCCAATCTGCGGTGGCAGGAGGCGGGGCCGAAGGCCGTGCCTGACCAA
TCCGGAGCACATAGGAGTCTCAGCCCCCCGCCCCAAAGCAAGGGGAAGTCACGC
GCCTGTAGCGCCAGCGTGTTGTGAAATGGGGGCTTGGGGGGGTTGGGGCCCTGA
CTAGTCAAAACAAACTCCCATTGACGTCAATGGGGTGGAGACTTGGAAATCCCC
GTGAGTCAAACCGCTATCCACGCCCATTGATGTACTGCCAAAACCGCATCATCAT
GGTAATAGCGATGACTAATACGTAGATGTACTGCCAAGTAGGAAAGTCCCATAA
GGTCATGTACTGGGCATAATGCCAGGCGGGCCATTTACCGTCATTGACGTCAATA
GGGGGCGTACTTGGCATATGATACACTTGATGTACTGCCAAGTGGGCAGTTTACC
GTAAATACTCCACCCATTGACGTCAATGGAAAGTCCCTATTGGCGTTACTATGGG
AACATACGTCATTATTGACGTCAATGGGCGGGGTCGTTGGGCGGTCAGCCAGG
CGGGCCATTTACCGTAAGTTATGTAACGCCTGCAGGTTAATTAAGAACATGTGAG
CAAAAGGCCAGCAAAAGGCCAGGAACCGTAAAAAGGCCGCGTTGCTGGCGTTTT
TCCATAGGCTCCGCCCCCCTGACGAGCATCACAAAAATCGACGCTCAAGTCAGA
GGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTT
CTCCCTTCGGGAAGCGTGGCGCTTTCTCATAGCTCACGCTGTAGGTATCTCAGTTC
GGTGTAGGTCGTTCGCTCCAAGCTGGGCTGTGTGCACGAACCCCCCGTTCAGCCC -continued

```
GACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTATG

TAGGCGGTGCTACAGAGTTCTTGAAGTGGTGGCCTAACTACGGCTACACTAGAA

GAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTT

TGCAAGCAGCAGATTACGCGCAGAAAAAAAGGATCTCAAGAAGATCCTTTGATC

TTTTCTACGGGGTCTGACGCTCAGTGGAACGAAAACTCACGTTAAGGGATTTTGG

TCATGGCTAGTTAATTAACATTTAAATCAGCGGCCGCAATAAAATATCTTTATTTT

CATTACATCTGTGTGTTGGTTTTTTGTGTGAATCGTAACTAACATACGCTCTCCAT

CAAAACAAAACGAAACAAAACAAACTAGCAAAATAGGCTGTCCCCAGTGCAAGT

GCAGGTGCCAGAACATTTCTCTATCGAA

SEQ ID NO 7,828:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCAACATGTACAGGATGCAACTCCTGTCTTGCATTGCACTAAGTCTTGCACTTG

TCACGAATTCAGATATCCAGATGACCCAGTCCCCGAGCTCCCTGTCCGCCTCTGT

GGGCGATAGGGTCACCATCACCTGCCGTGCCAGTCAGTCCGTGTCCAGCGCTGTA

GCCTGGTATCAACAGAAACCAGGAAAAGCTCCGAAGCTTCTGATTTACTCGGCAT

CCAGCCTCTACTCTGGAGTCCCTTCTCGCTTCTCTGGTAGCCGTTCCGGGACGGAT

TTCACTCTGACCATCAGCAGTCTGCAGCCGGAAGACTTCGCAACTTATTACTGTC

AGCAATGGTACCATTACTCTTACCCGATCACGTTCGGACAGGGTACCAAGGTGGA

GATCAAACGACTCGAGATCAAACGGGCAGATGCTGCACCAACTGTATCCATCTTC

CCACCATCCAGTGAGCAGTTAACATCTGGAGGTGCCTCAGTCGTGTGCTTCTTGA

ACAACTTCTACCCCAAAGACATCAATGTCAAGTGGAAGATTGATGGCAGTGAAC

GACAAAATGGCGTCCTGAACAGTTGGACTGATCAGGACAGCAAAGACAGCACCT

ACAGCATGAGCAGCACCCTCACGTTGACCAAGGACGAGTATGAACGACATAACA

GCTATACCTGTGAGGCCACTCACAAGACATCAACTTCACCCATTGTCAAGAGCTT

CAACAGGAATGAGTGTTAGAGACAAAGGTCCTGAGAGCTAGCTGGCCAGACATG

ATAAGATACATTGATGAGTTTGGACAAACCACAACTAGAATGCAGTGAAAAAAA

TGCTTTATTTGTGAAATTTGTGATGCTATTGCTTTATTTGTAACCATTATAAGCTG

CAATAAACAAGTTAACAACAACAATTGCATTCATTTTATGTTTCAGGTTCAGGGG

GAGGTGTGGGAGGTTTTTTAAAGCAAGTAAAACCTCTACAAATGTGGTATGGAA

TTAATTCTAAAATACAGCATAGCAAAACTTTAACCTCCAAATCAAGCCTCTACTT
```

-continued

```
GAATCCTTTTCTGAGGGATGAATAAGGCATAGGCATCAGGGGCTGTTGCCAATGT

GCATTAGCTGTTTGCAGCCTCACCTTCTTTCATGGAGTTTAAGATATAGTGTATTT

TCCCAAGGTTTGAACTAGCTCTTCATTTCTTTATGTTTTAAATGCACTGACCTCCC

ACATTCCCTTTTTAGTAAAATATTCAGAAATAATTTAAATACATCATTGCAATGA

AAATAAATGTTTTTTATTAGGCAGAATCCAGATGCTCAAGGCCCTTCATAATATC

CCCCAGTTTAGTAGTTGGACTTAGGGAACAAAGGAACCTTTAATAGAAATTGGA

CAGCAAGAAAGCGAGCTTCTAGCTTTAGTTCCTGGTGTACTTGAGGGGATGAGT

TCCTCAATGGTGGTTTTGACCAGCTTGCCATTCATCTCAATGAGCACAAAGCAGT

CAGGAGCATAGTCAGAGATGAGCTCTCTGCACATGCCACAGGGGCTGACCACCC

TGATGGATCTGTCCACCTCATCAGAGTAGGGGTGCCTGACAGCCACAATGGTGTC

AAAGTCCTTCTGCCCGTTGCTCACAGCAGACCCAATGGCAATGGCTTCAGCACAG

ACAGTGACCCTGCCAATGTAGGCCTCAATGTGGACAGCAGAGATGATCTCCCCA

GTCTTGGTCCTGATGGCCGCCCCGACATGGTGCTTGTTGTCCTCATAGAGCATGG

TGATCTTCTCAGTGGCGACCTCCACCAGCTCCAGATCCTGCTGAGAGATGTTGAA

GGTCTTCATGATGGCTCCTCctgtcaggagaggaaagagaagaaggttagtaca attgCTATAGTGAGTTGTATTATACTATGCTTATGATTAATTGTCAAACTAGGG CTGCAgggttcatagtgccacttttcctgcactgccccatctcctgcccaccct ttcccaggcatagacagtcagtgacttacCAAACTCACAGGAGGGAGA

AGGCAGAAGCTTGAGACAGACCCGCGGGACCGCCGAACTGCGAGGGGACGTGG

CTAGGGCGGCTTCTTTTATGGTGCGCCGGCCCTCGGAGGCAGGGCGCTCGGGGA

GGCCTAGCGGCCAATCTGCGGTGGCAGGAGGCGGGGCCGAAGGCCGTGCCTGAC

CAATCCGGAGCACATAGGAGTCTCAGCCCCCCGCCCCAAAGCAAGGGGAAGTCA

CGCGCCTGTAGCGCCAGCGTGTTGTGAAATGGGGGCTTGGGGGGGTTGGGGCCC

TGACTAGTCAAAACAAACTCCCATTGACGTCAATGGGGTGGAGACTTGGAAATC

CCCGTGAGTCAAACCGCTATCCACGCCCATTGATGTACTGCCAAAACCGCATCAT

CATGGTAATAGCGATGACTAATACGTAGATGTACTGCCAAGTAGGAAAGTCCCA

TAAGGTCATGTACTGGGCATAATGCCAGGCGGGCCATTTACCGTCATTGACGTCA

ATAGGGGGCGTACTTGGCATATGATACACTTGATGTACTGCCAAGTGGGCAGTTT

ACCGTAAATACTCCACCCATTGACGTCAATGGAAAGTCCCTATTGGCGTTACTAT

GGGAACATACGTCATTATTGACGTCAATGGGCGGGGTCGTTGGGCGGTCAGCC

AGGCGGGCCATTTACCGTAAGTTATGTAACGCCTGCAGGTTAATTAAGAACATGT

GAGCAAAAGGCCAGCAAAAGGCCAGGAACCGTAAAAAGGCCGCGTTGCTGGCG

TTTTTCCATAGGCTCCGCCCCCCTGACGAGCATCACAAAAATCGACGCTCAAGTC

AGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCC

TTTCTCCCTTCGGGAAGCGTGGCGCTTTCTCATAGCTCACGCTGTAGGTATCTCAG

TTCGGTGTAGGTCGTTCGCTCCAAGCTGGGCTGTGTGCACGAACCCCCCGTTCAG

CCCGACCGCTGCGCCTTATCCGGTAACTATCGTCTTGAGTCCAACCCGGTAAGAC

ACGACTTATCGCCACTGGCAGCAGCCACTGGTAACAGGATTAGCAGAGCGAGGT

ATGTAGGCGGTGCTACAGAGTTCTTGAAGTGGTGGCCTAACTACGGCTACACTAG
```

-continued

AAGAACAGTATTTGGTATCTGCGCTCTGCTGAAGCCAGTTACCTTCGGAAAAAGA

GTTGGTAGCTCTTGATCCGGCAAACAAACCACCGCTGGTAGCGGTGGTTTTTTTG

TTTGCAAGCAGCAGATTACGCGCAGAAAAAAAGGATCTCAAGAAGATCCTTTGA

TCTTTTCTACGGGGTCTGACGCTCAGTGGAACGAAAACTCACGTTAAGGGATTTT

GGTCATGGCTAGTTAATTAACATTTAAATCAGCGGCCGCAATAAAATATCTTTAT

TTTCATTACATCTGTGTGTTGGTTTTTTGTGTGAATCGTAACTAACATACGCTCTC

CATCAAAACAAAACGAAACAAAACAAACTAGCAAAATAGGCTGTCCCCAGTGCA

AGTGCAGGTGCCAGAACATTTCTCTATCGAA

SEQ ID NO 7,829:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCACCGGCGAAGGAGGGCCACCATGTACAGGATGCAACTCCTGTCTTGCATTGC

ACTAAGTCTTGCACTTGTCACGAATTCGGAGGTTCAGCTGGTGGAGTCTGGCGGT

GGCCTGGTGCAGCCAGGGGGCTCACTCCGTTTGTCCTGTGCAGCTTCTGGCTTCA

ACTTTTCTTCTTCTTCTATACACTGGGTGCGTCAGGCCCCGGGTAAGGGCCTGGA

ATGGGTTGCATCTATTTCTTCTTATTATAGCTCTACTTATTATGCCGATAGCGTCA

AGGGCCGTTTCACTATAAGCGCAGACACATCCAAAAACACAGCCTACCTACAAA

TGAACAGCTTAAGAGCTGAGGACACTGCCGTCTATTATTGTGCTCGCACTGTTCG

TGGATCCAAAAAACCGTACTTCTCTGGTTGGGCTATGGACTACTGGGGTCAAGGA

ACCCTGGTCACCGTCTCCTCGAGTGCTAGCAGCGCTAAAACGACACCCCCATCTG

TCTATCCACTGGCCCCTGGATCTGCTGCCCAAACTAACTCCATGGTGACCCTGGG

ATGCCTGGTCAAGGGCTATTTCCCTGAGCCAGTGACAGTGACCTGGAACTCTGGA

TCCCTGTCCAGCGGTGTGCACACCTTCCCAGCTGTCCTGCAGTCTGACCTCTACA

CTCTGAGCAGCTCAGTGACTGTCCCCTCCAGCACCTGGCCCAGCGAGACCGTCAC

CTGCAACGTTGCCCACCCGGCCAGCAGCACCAAGGTGGACAAGAAAATTGTGCC

CAGGGATTGTGGTTGTAAGCCTTGCATATGTACAGTCCCAGAAGTATCATCTGTC

TTCATCTTCCCCCCAAAGCCCAAGGATGTGCTCACCATTACTCTGACTCCTAAGG

TCACGTGTGTTGTGGTAGACATCAGCAAGGATGATCCCGAGGTCCAGTTCAGCTG

GTTTGTAGATGATGTGGAGGTGCACACAGCTCAGACGCAACCCCGGGAGGAGCA

GTTCAACAGCACTTTCCGCTCAGTCAGTGAACTTCCCATCATGCACCAGGACTGG

CTCAATGGCAAGGAGTTCAAATGCAGGGTCAACAGTGCAGCTTTCCCTGCCCCCA

TCGAGAAAACCATCTCCAAAACCAAAGGCAGACCGAAGGCTCCGCAGGTGTACA

CCATTCCACCTCCCAAGGAGCAGATGGCCAAGGATAAAGTCAGTCTGACCTGCA

-continued

```
TGATAACAGACTTCTTCCCTGAAGACATTACTGTGGAGTGGCAGTGGAATGGGCA

GCCAGCGGAGAACTACAAGAACACTCAGCCCATCATGGACACAGATGGCTCTTA

CTTCGTCTACAGCAAGCTCAATGTGCAGAAGAGCAACTGGGAGGCAGGAAATAC

TTTCACCTGCTCTGTGTTACATGAGGGCCTGCACAACCACCATACTGAGAAGAGC

CTCTCCCACTCTCCTGGTAAATGATCCCAGTGTCCCTAGCTGGCCAGACATGATA

AGATACATTGATGAGTTTGGACAAACCACAACTAGAATGCAGTGAAAAAAATGC

TTTATTTGTGAAATTTGTGATGCTATTGCTTTATTTGTAACCATTATAAGCTGCAA

TAAACAAGTTAACAACAACAATTGCATTCATTTTATGTTTCAGGTTCAGGGGGAG

GTGTGGAGGTTTTTTAAAGCAAGTAAAACCTCTACAAATGTGGTATGGAATTAA

TTCTAAAATACAGCATAGCAAAACTTTAACCTCCAAATCAAGCCTCTACTTGAAT

CCTTTTCTGAGGGATGAATAAGGCATAGGCATCAGGGGCTGTTGCCAATGTGCAT

TAGCTGTTTGCAGCCTCACCTTCTTTCATGGAGTTTAAGATATAGTGTATTTTCCC

AAGGTTTGAACTAGCTCTTCATTTCTTTATGTTTTAAATGCACTGACCTCCCACAT

TCCCTTTTTAGTAAAATATTCAGAAATAATTTAAATACATCATTGCAATGAAAAT

AAATGTTTTTATTAGGCAGAATCCAGATGCTCAAGGCCCTTCATAATATCCCCC

AGTTTAGTAGTTGGACTTAGGGAACAAAGGAACCTTTAATAGAAATTGGACAGC

AAGAAAGCGAGCTTCTAGCTTATCCTCAGTCCTGCTCCTCTGCCACAAAGTGCAC

GCAGTTGCCGGCCGGGTCGCGCAGGGCGAACTCCCGCCCCCACGGCTGCTCGCC

GATCTCGGTCATGGCCGGCCCGGAGGCGTCCCGGAAGTTCGTGGACACGACCTC

CGACCACTCGGCGTACAGCTCGTCCAGGCCGCGCACCCACACCCAGGCCAGGGT

GTTGTCCGGCACCACCTGGTCCTGGACCGCGCTGATGAACAGGGTCACGTCGTCC

CGGACCACACCGGCGAAGTCGTCCTCCACGAAGTCCCGGGAGAACCCGAGCCGG

TCGGTCCAGAACTCGACCGCTCCGGCGACGTCGCGCGCGGTGAGCACCGGAACG

GCACTGGTCAACTTGGCCATGATGGCTCCTCctgtcaggagaggaaagagaaga aggttagtacaattgCTATAGTGAGTTGTATTATACTATGCAGATATACTATGC CAATGATTAATTGTCAAACTAGGGCTGCAgggttcatagtgccacttttcctgc actgccccatctcctgcccacccttttcccaggcatagacagtcagtgacttacC

AAACTCACAGGAGGGAGAAGGCAGAAGCTTGAGACAGACCCGCGGGA

CCGCCGAACTGCGAGGGGACGTGGCTAGGGCGGCTTCTTTTATGGTGCGCCGGCC

CTCGGAGGCAGGGCGCTCGGGGAGGCCTAGCGGCCAATCTGCGGTGGCAGGAGG

CGGGGCCGAAGGCCGTGCCTGACCAATCCGGAGCACATAGGAGTCTCAGCCCCC

CGCCCCAAAGCAAGGGGAAGTCACGCGCCTGTAGCGCCAGCGTGTTGTGAAATG

GGGGCTTGGGGGGGTTGGGGCCCTGACTAGTCAAAACAAACTCCCATTGACGTC

AATGGGGTGGAGACTTGGAAATCCCCGTGAGTCAAACCGCTATCCACGCCCATT

GATGTACTGCCAAAACCGCATCATCATGGTAATAGCGATGACTAATACGTAGAT

GTACTGCCAAGTAGGAAAGTCCCATAAGGTCATGTACTGGGCATAATGCCAGGC

GGGCCATTTACCGTCATTGACGTCAATAGGGGGCGTACTTGGCATATGATACACT

TGATGTACTGCCAAGTGGGCAGTTTACCGTAAATACTCCACCCATTGACGTCAAT

GGAAAGTCCCTATTGGCGTTACTATGGGAACATACGTCATTATTGACGTCAATGG

GCGGGGGTCGTTGGGCGGTCAGCCAGGCGGGCCATTTACCGTAAGTTATGTAAC

GCCTGCAGGTTAATTAAGAACATGTGAGCAAAAGGCCAGCAAAAGGCCAGGAAC
```

```
CGTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTC
ATAGCTCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGT
GGTGGCCTAACTACGGCTACACTAGAAGAACAGTATTTGGTATCTGCGCTCTGCT
GAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCAGTGGA
ACGAAAACTCACGTTAAGGGATTTTGGTCATGGCTAGTTAATTAACATTTAAATC
AGCGGCCGCAATAAAATATCTTTATTTTCATTACATCTGTGTGTTGGTTTTTTGTG
TGAATCGTAACTAACATACGCTCTCCATCAAAACAAAACGAAACAAAACAAACT
AGCAAAATAGGCTGTCCCCAGTGCAAGTGCAGGTGCCAGAACATTTCTCTATCGA
A

SEQ ID NO 7,830:
GGATCTGCGATCGCTCCGGTGCCCGTCAGTGGGCAGAGCGCACATCGCCCACAG
TCCCCGAGAAGTTGGGGGGAGGGGTCGGCAATTGAACGGGTGCCTAGAGAAGGT
GGCGCGGGGTAAACTGGGAAAGTGATGTCGTGTACTGGCTCCGCCTTTTTCCCGA
GGGTGGGGGAGAACCGTATATAAGTGCAGTAGTCGCCGTGAACGTTCTTTTTCGC
AACGGGTTTGCCGCCAGAACACAGCTGAAGCTTCGAGGGGCTCGCATCTCTCCTT
CACGCGCCCGCCGCCCTACCTGAGGCCGCCATCCACGCCGGTTGAGTCGCGTTCT
GCCGCCTCCCGCCTGTGGTGCCTCCTGAACTGCGTCCGCCGTCTAGGTAAGTTTA
AAGCTCAGGTCGAGACCGGGCCTTTGTCCGGCGCTCCCTTGGAGCCTACCTAGAC
TCAGCCGGCTCTCCACGCTTTGCCTGACCCTGCTTGCTCAACTCTACGTCTTTGTT
TCGTTTTCTGTTCTGCGCCGTTACAGATCCAAGCTGTGACCGGCGCCTACCTGAG
ATCAACATGTACAGGATGCAACTCCTGTCTTGCATTGCACTAAGTCTTGCACTTG
TCACGAATTCAGATATCCAGATGACCCAGTCCCCGAGCTCCCTGTCCGCCTCTGT
GGGCGATAGGGTCACCATCACCTGCCGTGCCAGTCAGTCCGTGTCCAGCGCTGTA
GCCTGGTATCAACAGAAACCAGGAAAAGCTCCGAAGCTTCTGATTTACTCGGCAT
CCAGCCTCTACTCTGGAGTCCCTTCTCGCTTCTCTGGTAGCCGTTCCGGGACGGAT
TTCACTCTGACCATCAGCAGTCTGCAGCCGGAAGACTTCGCAACTTATTACTGTC
AGCAATGGTACCATTACTCTTACCCGATCACGTTCGGACAGGGTACCAAGGTGGA
GATCAAACGACTCGAGATCAAACGGGCAGATGCTGCACCAACTGTATCCATCTTC
CCACCATCCAGTGAGCAGTTAACATCTGGAGGTGCCTCAGTCGTGTGCTTCTTGA
ACAACTTCTACCCCAAAGACATCAATGTCAAGTGGAAGATTGATGGCAGTGAAC
GACAAAATGGCGTCCTGAACAGTTGGACTGATCAGGACAGCAAAGACAGCACCT
ACAGCATGAGCAGCACCCTCACGTTGACCAAGGACAGAGTATGAACGCACATAACA
GCTATACCTGTGAGGCCACTCACAAGACATCAACTTCACCCATTGTCAAGAGCTT
```

```
CAACAGGAATGAGTGTTAGAGACAAAGGTCCTGAGAGCTAGCTGGCCAGACATG

ATAAGATACATTGATGAGTTTGGACAAACCACAACTAGAATGCAGTGAAAAAA

TGCTTTATTTGTGAAATTTGTGATGCTATTGCTTTATTTGTAACCATTATAAGCTG

CAATAAACAAGTTAACAACAACAATTGCATTCATTTTATGTTTCAGGTTCAGGGG

GAGGTGTGGGAGGTTTTTTAAAGCAAGTAAAACCTCTACAAATGTGGTATGGAA

TTAATTCTAAAATACAGCATAGCAAAACTTTAACCTCCAAATCAAGCCTCTACTT

GAATCCTTTTCTGAGGGATGAATAAGGCATAGGCATCAGGGGCTGTTGCCAATGT

GCATTAGCTGTTTGCAGCCTCACCTTCTTTCATGGAGTTTAAGATATAGTGTATTT

TCCCAAGGTTTGAACTAGCTCTTCATTTCTTTATGTTTTAAATGCACTGACCTCCC

ACATTCCCTTTTTAGTAAAATATTCAGAAATAATTTAAATACATCATTGCAATGA

AAATAAATGTTTTTTATTAGGCAGAATCCAGATGCTCAAGGCCCTTCATAATATC

CCCCAGTTTAGTAGTTGGACTTAGGGAACAAAGGAACCTTTAATAGAAATTGGA

CAGCAAGAAAGCGAGCTTCTAGCTTTAGTTCCTGGTGTACTTGAGGGGATGAGT

TCCTCAATGGTGGTTTTGACCAGCTTGCCATTCATCTCAATGAGCACAAAGCAGT

CAGGAGCATAGTCAGAGATGAGCTCTCTGCACATGCCACAGGGGCTGACCACCC

TGATGGATCTGTCCACCTCATCAGAGTAGGGGTGCCTGACAGCCACAATGGTGTC

AAAGTCCTTCTGCCCGTTGCTCACAGCAGACCCAATGGCAATGGCTTCAGCACAG

ACAGTGACCCTGCCAATGTAGGCCTCAATGTGGACAGCAGAGATGATCTCCCCA

GTCTTGGTCCTGATGGCCGCCCCGACATGGTGCTTGTTGTCCTCATAGAGCATGG

TGATCTTCTCAGTGGCGACCTCCACCAGCTCCAGATCCTGCTGAGAGATGTTGAA

GGTCTTCATGATGGCTCCTCctgtcaggagaggaaagagaagaaggttagtaca attgCTATAGTGAGTTGTATTATACTATGCTTATGATTAATTGTCAAACTAGGG CTGCAggggttcatagtgccacttttcctgcactgccccatctcctgccaccct ttcccaggcatagacagtcagtgacttacCAAACTCACAGGAGGGAGAAGGCAG

AAGCTTGAGACAGACCCGCGGGACCGCCGAACTGCGAGGGGACGTGG

CTAGGGCGGCTTCTTTTATGGTGCGCCGGCCCTCGGAGGCAGGGCGCTCGGGGA

GGCCTAGCGGCCAATCTGCGGTGGCAGGAGGCGGGGCCGAAGGCCGTGCCTGAC

CAATCCGGAGCACATAGGAGTCTCAGCCCCCCGCCCCAAAGCAAGGGGAAGTCA

CGCGCCTGTAGCGCCAGCGTGTTGTGAAATGGGGGCTTGGGGGGTTGGGGCCC

TGACTAGTCAAAACAAACTCCCATTGACGTCAATGGGGTGGAGACTTGGAAATC

CCCGTGAGTCAAACCGCTATCCACGCCCATTGATGTACTGCCAAAACCGCATCAT

CATGGTAATAGCGATGACTAATACGTAGATGTACTGCCAAGTAGGAAAGTCCCA

TAAGGTCATGTACTGGGCATAATGCCAGGCGGGCCATTTACCGTCATTGACGTCA

ATAGGGGGCGTACTTGGCATATGATACACTTGATGTACTGCCAAGTGGGCAGTTT

ACCGTAAATACTCCACCCATTGACGTCAATGGAAAGTCCCTATTGGCGTTACTAT

GGGAACATACGTCATTATTGACGTCAATGGGCGGGGTCGTTGGGCGGTCAGCC

AGGCGGGCCATTTACCGTAAGTTATGTAACGCCTGCAGGTTAATTAAGAACATGT

GAGCAAAAGGCCAGCAAAAGGCCAGGAACCGTAAAAAGGCCGCGTTGCTGGCG

TTTTTCCATAGGCTCCGCCCCCCTGACGAGCATCACAAAAATCGACGCTCAAGTC

AGAGGTGGCGAAACCCGACAGGACTATAAAGATACCAGGCGTTTCCCCCTGGAA
```

-continued
GCTCCCTCGTGCGCTCTCCTGTTCCGACCCTGCCGCTTACCGGATACCTGTCCGCC

TTTCTCCCTTCGGGAAGCGTGGCGCTTTCTCATAGCTCACGCTGTAGGTATCTCAG

TTCGGTGTAGGTCGTTCGCTCCAAGCTGGGCTGTGTGCACGAACCCCCCGTTCAG

CCCGACCGCTGCGCCTTATCCGGTAACTATCGTCTTGAGTCCAACCCGGTAAGAC

ACGACTTATCGCCACTGGCAGCAGCCACTGGTAACAGGATTAGCAGAGCGAGGT

ATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGA

GTTGGTAGCTCTTGATCCGGCAAACAAACCACCGCTGGTAGCGGTGGTTTTTTTG

TTTGCAAGCAGCAGATTACGCGCAGAAAAAAAGGATCTCAAGAAGATCCTTTGA

TCTTTTCTACGGGGTCTGACGCTCAGTGGAACGAAAACTCACGTTAAGGGATTTT

GGTCATGGCTAGTTAATTAACATTTAAATCAGCGGCCGCAATAAAATATCTTTAT

TTTCATTACATCTGTGTGTTGGTTTTTTGTGTGAATCGTAACTAACATACGCTCTC

CATCAAAACAAAACGAAACAAAACAAACTAGCAAAATAGGCTGTCCCCAGTGCA

AGTGCAGGTGCCAGAACATTTCTCTATCGAA

SEQ ID NO 7,831:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCACCGGCGAAGGAGGGCCACCATGTACAGGATGCAACTCCTGTCTTGCATTGC

ACTAAGTCTTGCACTTGTCACGAATTCGGAGGTTCAGCTGGTGGAGTCTGGCGGT

GGCCTGGTGCAGCCAGGGGCTCACTCCGTTTGTCCTGTGCAGCTTCTGGCTTCA

ACTTTTCTTCTTCTTCTATACACTGGGTGCGTCAGGCCCCGGGTAAGGGCCTGGA

ATGGGTTGCATCTATTTCTTCTTCTTATGGCTATACTTATTATGCCGATAGCGTCA

AGGGCCGTTTCACTATAAGCGCAGACACATCCAAAAACACAGCCTACCTACAAA

TGAACAGCTTAAGAGCTGAGGACACTGCCGTCTATTATTGTGCTCGCACTGTTCG

TGGATCCAAAAAACCGTACTTCTCTGGTTGGGCTATGGACTACTGGGGTCAAGGA

ACCCTGGTCACCGTCTCCTCGAGTGCTAGCAGCGCTAAAACGACACCCCCATCTG

TCTATCCACTGGCCCCTGGATCTGCTGCCCAAACTAACTCCATGGTGACCCTGGG

ATGCCTGGTCAAGGGCTATTTCCCTGAGCCAGTGACAGTGACCTGGAACTCTGGA

TCCCTGTCCAGCGGTGTGCACACCTTCCCAGCTGTCCTGCAGTCTGACCTCTACA

CTCTGAGCAGCTCAGTGACTGTCCCCTCCAGCACCTGGCCCAGCGAGACCGTCAC

CTGCAACGTTGCCCACCCGGCCAGCAGCACCAAGGTGGACAAGAAAATTGTGCC

CAGGGATTGTGGTTGTAAGCCTTGCATATGTACAGTCCCAGAAGTATCATCTGTC

TTCATCTTCCCCCCAAAGCCCAAGGATGTGCTCACCATTACTCTGACTCCTAAGG

-continued

```
TCACGTGTGTTGTGGTAGACATCAGCAAGGATGATCCCGAGGTCCAGTTCAGCTG

GTTTGTAGATGATGTGGAGGTGCACACAGCTCAGACGCAACCCCGGGAGGAGCA

GTTCAACAGCACTTTCCGCTCAGTCAGTGAACTTCCCATCATGCACCAGGACTGG

CTCAATGGCAAGGAGTTCAAATGCAGGGTCAACAGTGCAGCTTTCCCTGCCCCCA

TCGAGAAAACCATCTCCAAAACCAAAGGCAGACCGAAGGCTCCGCAGGTGTACA

CCATTCCACCTCCCAAGGAGCAGATGGCCAAGGATAAAGTCAGTCTGACCTGCA

TGATAACAGACTTCTTCCCTGAAGACATTACTGTGGAGTGGCAGTGGAATGGGCA

GCCAGCGGAGAACTACAAGAACACTCAGCCCATCATGGACACAGATGGCTCTTA

CTTCGTCTACAGCAAGCTCAATGTGCAGAAGAGCAACTGGGAGGCAGGAAATAC

TTTCACCTGCTCTGTGTTACATGAGGGCCTGCACAACCACCATACTGAAGAGC

CTCTCCCACTCTCCTGGTAAATGATCCCAGTGTCCCTAGCTGGCCAGACATGATA

AGATACATTGATGAGTTTGGACAAACCACAACTAGAATGCAGTGAAAAAAATGC

TTTATTTGTGAAATTTGTGATGCTATTGCTTTATTTGTAACCATTATAAGCTGCAA

TAAACAAGTTAACAACAACAATTGCATTCATTTTATGTTTCAGGTTCAGGGGGAG

GTGTGGGAGGTTTTTTAAAGCAAGTAAAACCTCTACAAATGTGGTATGGAATTAA

TTCTAAAATACAGCATAGCAAAACTTTAACCTCCAAATCAAGCCTCTACTTGAAT

CCTTTTCTGAGGGATGAATAAGGCATAGGCATCAGGGGCTGTTGCCAATGTGCAT

TAGCTGTTTGCAGCCTCACCTTCTTTCATGGAGTTTAAGATATAGTGTATTTTCCC

AAGGTTTGAACTAGCTCTTCATTTCTTTATGTTTTAAATGCACTGACCTCCCACAT

TCCCTTTTTAGTAAAATATTCAGAAATAATTTAAATACATCATTGCAATGAAAAT

AAATGTTTTTATTAGGCAGAATCCAGATGCTCAAGGCCCTTCATAATATCCCCC

AGTTTAGTAGTTGGACTTAGGGAACAAAGGAACCTTTAATAGAAATTGGACAGC

AAGAAAGCGAGCTTCTAGCTTATCCTCAGTCCTGCTCCTCTGCCACAAAGTGCAC

GCAGTTGCCGGCCGGGTCGCGCAGGGCGAACTCCCGCCCCCACGGCTGCTCGCC

GATCTCGGTCATGGCCGGCCCGGAGGCGTCCCGGAAGTTCGTGGACACGACCTC

CGACCACTCGGCGTACAGCTCGTCCAGGCCGCGCACCCACACCCAGGCCAGGGT

GTTGTCCGGCACCACCTGGTCCTGGACCGCGCTGATGAACAGGGTCACGTCGTCC

CGGACCACACCGGCGAAGTCGTCCTCCACGAAGTCCCGGGAGAACCCGAGCCGG

TCGGTCCAGAACTCGACCGCTCCGGCGACGTCGCGCGCGGTGAGCACCGGAACG

GCACTGGTCAACTTGGCCATGATGGCTCCTCctgtcaggagaggaaagagaag aaggttagtacaattgCTATAGTGAGTTGTATTATACTATGCAGATATACTAT GCCAATGATTAATTGTCAAACTAGGGCTGCAgggttcatagtgccacttttcc tgcactgccccatctcctgcccacccttcccaggcatagacagtcagtgact tacCAAACTCACAGGAGGGAGAAGGCAGAAGCTTGAGACAGACCCGCGGGACC

GCCGAACTGCGAGGGGACGTGGCTAGGGCGGCTTCTTTTATGGTGCGCCGGCC

CTCGGAGGCAGGGCGCTCGGGGAGGCCTAGCGGCCAATCTGCGGTGGCAGGAGG

CGGGGCCGAAGGCCGTGCCTGACCAATCCGGAGCACATAGGAGTCTCAGCCCCC

CGCCCCAAAGCAAGGGGAAGTCACGCGCCTGTAGCGCCAGCGTGTTGTGAAATG

GGGGCTTGGGGGGTTGGGGCCCTGACTAGTCAAAACAAACTCCCATTGACGTC

AATGGGGTGGAGACTTGGAAATCCCCGTGAGTCAAACCGCTATCCACGCCCATT

GATGTACTGCCAAAACCGCATCATCATGGTAATAGCGATGACTAATACGTAGAT
```

-continued

```
GTACTGCCAAGTAGGAAAGTCCCATAAGGTCATGTACTGGGCATAATGCCAGGC

GGGCCATTTACCGTCATTGACGTCAATAGGGGGCGTACTTGGCATATGATACACT

TGATGTACTGCCAAGTGGGCAGTTTACCGTAAATACTCCACCCATTGACGTCAAT

GGAAAGTCCCTATTGGCGTTACTATGGGAACATACGTCATTATTGACGTCAATGG

GCGGGGTCGTTGGGCGGTCAGCCAGGCGGGCCATTTACCGTAAGTTATGTAAC

GCCTGCAGGTTAATTAAGAACATGTGAGCAAAAGGCCAGCAAAAGGCCAGGAAC

CGTAAAAAGGCCGCGTTGCTGGCGTTTTCCATAGGCTCCGCCCCCCTGACGAGC

ATCACAAAAATCGACGCTCAAGTCAGAGGTGGCGAAACCCGACAGGACTATAAA

GATACCAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGCTTTCTC

ATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTAT

CGTCTTGAGTCCAACCCGGTAAGACACGACTTATCGCCACTGGCAGCAGCCACTG

GTAACAGGATTAGCAGAGCGAGGTATGTAGGCGGTGCTACAGAGTTCTTGAAGT

GGTGGCCTAACTACGGCTACACTAGAAGAACAGTATTTGGTATCTGCGCTCTGCT

GAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCAGTGGA

ACGAAAACTCACGTTAAGGGATTTTGGTCATGGCTAGTTAATTAACATTTAAATC

AGCGGCCGCAATAAAATATCTTTATTTTCATTACATCTGTGTGTTGGTTTTTTGTG

TGAATCGTAACTAACATACGCTCTCCATCAAAACAAAACGAAACAAAACAAACT

AGCAAAATAGGCTGTCCCCAGTGCAAGTGCAGGTGCCAGAACATTTCTCTATCGA

A

SEQ ID NO 7,832:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCAACATGTACAGGATGCAACTCCTGTCTTGCATTGCACTAAGTCTTGCACTTG

TCACGAATTCAGATATCCAGATGACCCAGTCCCCGAGCTCCCTGTCCGCCTCTGT

GGGCGATAGGGTCACCATCACCTGCCGTGCCAGTCAGTCCGTGTCCAGCGCTGTA

GCCTGGTATCAACAGAAACCAGGAAAAGCTCCGAAGCTTCTGATTTACTCGGCAT

CCAGCCTCTACTCTGGAGTCCCTTCTCGCTTCTCTGGTAGCCGTTCCGGGACGGAT

TTCACTCTGACCATCAGCAGTCTGCAGCCGGAAGACTTCGCAACTTATTACTGTC

AGCAATCTTCTTATTCTCTGATCACGTTCGGACAGGGTACCAAGGTGGAGATCAA
```

-continued

```
ACGACTCGAGATCAAACGGGCAGATGCTGCACCAACTGTATCCATCTTCCCACCA

TCCAGTGAGCAGTTAACATCTGGAGGTGCCTCAGTCGTGTGCTTCTTGAACAACT

TCTACCCCAAAGACATCAATGTCAAGTGGAAGATTGATGGCAGTGAACGACAAA

ATGGCGTCCTGAACAGTTGGACTGATCAGGACAGCAAAGACAGCACCTACAGCA

TGAGCAGCACCCTCACGTTGACCAAGGACGAGTATGAACGACATAACAGCTATA

CCTGTGAGGCCACTCACAAGACATCAACTTCACCCATTGTCAAGAGCTTCAACAG

GAATGAGTGTTAGAGACAAAGGTCCTGAGAGCTAGCTGGCCAGACATGATAAGA

TACATTGATGAGTTTGGACAAACCACAACTAGAATGCAGTGAAAAAAATGCTTT

ATTTGTGAAATTTGTGATGCTATTGCTTTATTTGTAACCATTATAAGCTGCAATAA

ACAAGTTAACAACAACAATTGCATTCATTTTATGTTTCAGGTTCAGGGGAGGTG

TGGGAGGTTTTTTAAAGCAAGTAAAACCTCTACAAATGTGGTATGGAATTAATTC

TAAAATACAGCATAGCAAAACTTTAACCTCCAAATCAAGCCTCTACTTGAATCCT

TTTCTGAGGGATGAATAAGGCATAGGCATCAGGGGCTGTTGCCAATGTGCATTAG

CTGTTTGCAGCCTCACCTTCTTTCATGGAGTTTAAGATATAGTGTATTTTCCCAAG

GTTTGAACTAGCTCTTCATTTCTTTATGTTTTAAATGCACTGACCTCCCACATTCC

CTTTTTAGTAAAATATTCAGAAATAATTTAAATACATCATTGCAATGAAAATAAA

TGTTTTTTATTAGGCAGAATCCAGATGCTCAAGGCCCTTCATAATATCCCCCAGTT

TAGTAGTTGGACTTAGGGAACAAAGGAACCTTTAATAGAAATTGGACAGCAAGA

AAGCGAGCTTCTAGCTTTAGTTCCTGGTGTACTTGAGGGGATGAGTTCCTCAAT

GGTGGTTTTGACCAGCTTGCCATTCATCTCAATGAGCACAAAGCAGTCAGGAGCA

TAGTCAGAGATGAGCTCTCTGCACATGCCACAGGGGCTGACCACCCTGATGGATC

TGTCCACCTCATCAGAGTAGGGGTGCCTGACAGCCACAATGGTGTCAAAGTCCTT

CTGCCCGTTGCTCACAGCAGACCCAATGGCAATGGCTTCAGCACAGACAGTGAC

CCTGCCAATGTAGGCCTCAATGTGGACAGCAGAGATGATCTCCCCAGTCTTGGTC

CTGATGGCCGCCCCGACATGGTGCTTGTTGTCCTCATAGAGCATGGTGATCTTCT

CAGTGGCGACCTCCACCAGCTCCAGATCCTGCTGAGAGATGTTGAAGGTCTTCAT

GATGGCTCCTCctgtcaggagaggaaagagaagaaggttagtacaattgCTATA

GTGAGTTGTATTATACTATGCTTATGATTAATTGTCAAACTAGGGCTGCAgggt tcatagtgccacttttcctgcactgccccatctcctgccaccattcccaggca tagacagtcagtgacttacCAAACTCACAGGAGGGAGAAGGCAGAAGCTTGAG

ACAGACCCGCGGGACCGCCGAACTGCGAGGGGACGTGGCTAGGGCGGC

TTCTTTTATGGTGCGCCGGCCCTCGGAGGCAGGGCGCTCGGGGAGGCCTAGCG

GCCAATCTGCGGTGGCAGGAGGCGGGGCCGAAGGCCGTGCCTGACCAATCCGGA

GCACATAGGAGTCTCAGCCCCCCGCCCCAAAGCAAGGGGAAGTCACGCGCCTGT

AGCGCCAGCGTGTTGTGAAATGGGGGCTTGGGGGGGTTGGGGCCCTGACTAGTC

AAAACAAACTCCCATTGACGTCAATGGGGTGGAGACTTGGAAATCCCCGTGAGT

CAAACCGCTATCCACGCCCATTGATGTACTGCCAAAACCGCATCATCATGGTAAT

AGCGATGACTAATACGTAGATGTACTGCCAAGTAGGAAAGTCCCATAAGGTCAT

GTACTGGGCATAATGCCAGGCGGGCCATTTACCGTCATTGACGTCAATAGGGGG

CGTACTTGGCATATGATACACTTGATGTACTGCCAAGTGGGCAGTTTACCGTAAA
```

-continued

TACTCCACCCATTGACGTCAATGGAAAGTCCCTATTGGCGTTACTATGGGAACAT

ACGTCATTATTGACGTCAATGGGCGGGGGTCGTTGGGCGGTCAGCCAGGCGGGC

CATTTACCGTAAGTTATGTAACGCCTGCAGGTTAATTAAGAACATGTGAGCAAAA

GGCCAGCAAAAGGCCAGGAACCGTAAAAAGGCCGCGTTGCTGGCGTTTTTCCAT

AGGCTCCGCCCCCCTGACGAGCATCACAAAAATCGACGCTCAAGTCAGAGGTGG

CGAAACCCGACAGGACTATAAAGATACCAGGCGTTTCCCCCTGGAAGCTCCCTC

GTGCGCTCTCCTGTTCCGACCCTGCCGCTTACCGGATACCTGTCCGCCTTTCTCCC

TTCGGGAAGCGTGGCGCTTTCTCATAGCTCACGCTGTAGGTATCTCAGTTCGGTG

TAGGTCGTTCGCTCCAAGCTGGGCTGTGTGCACGAACCCCCCGTTCAGCCCGACC

GCTGCGCCTTATCCGGTAACTATCGTCTTGAGTCCAACCCGGTAAGACACGACTT

ATCGCCACTGGCAGCAGCCACTGGTAACAGGATTAGCAGAGCGAGGTATGTAGG

CGGTGCTACAGAGTTCTTGAAGTGGTGGCCTAACTACGGCTACACTAGAAGAAC

AGTATTTGGTATCTGCGCTCTGCTGAAGCCAGTTACCTTCGGAAAAAGAGTTGGT

AGCTCTTGATCCGGCAAACAAACCACCGCTGGTAGCGGTGGTTTTTTTGTTTGCA

AGCAGCAGATTACGCGCAGAAAAAAAGGATCTCAAGAAGATCCTTTGATCTTTT

CTACGGGGTCTGACGCTCAGTGGAACGAAAACTCACGTTAAGGGATTTTGGTCAT

GGCTAGTTAATTAACATTTAAATCAGCGGCCGCAATAAAATATCTTTATTTTCATT

ACATCTGTGTGTTGGTTTTTTGTGTGAATCGTAACTAACATACGCTCTCCATCAAA

ACAAAACGAAACAAACAAACTAGCAAAATAGGCTGTCCCCAGTGCAAGTGCAG

GTGCCAGAACATTTCTCTATCGAA

SEQ ID NO 7,833:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCACCGGCGAAGGAGGGCCACCATGTACAGGATGCAACTCCTGTCTTGCATTGC

ACTAAGTCTTGCACTTGTCACGAATTCGGAGGTTCAGCTGGTGGAGTCTGGCGGT

GGCCTGGTGCAGCCAGGGGGCTCACTCCGTTTGTCCTGTGCAGCTTCTGGCTTCA

ACCTCTATTATTATTATATGCACTGGGTGCGTCAGGCCCCGGGTAAGGGCCTGGA

ATGGGTTGCATATATTTCTCCTTCTTATGGCTATACTTATTATGCCGATAGCGTCA

AGGGCCGTTTCACTATAAGCGCAGACACATCCAAAAACACAGCCTACCTACAAA

TGAACAGCTTAAGAGCTGAGGACACTGCCGTCTATTATTGTGCTCGCTCTTCTTCT

GGTTACTCTTACGGTGCTTTCTACTACCCGTCTGCTATTGACTACTGGGGTCAAGG

AACCCTGGTCACCGTCTCCTCGAGTGCTAGCAGCGCTAAAACGACACCCCCATCT

GTCTATCCACTGGCCCCTGGATCTGCTGCCCAAACTAACTCCATGGTGACCCTGG

```
GATGCCTGGTCAAGGGCTATTTCCCTGAGCCAGTGACAGTGACCTGGAACTCTGG

ATCCCTGTCCAGCGGTGTGCACACCTTCCCAGCTGTCCTGCAGTCTGACCTCTAC

ACTCTGAGCAGCTCAGTGACTGTCCCCTCCAGCACCTGGCCCAGCGAGACCGTCA

CCTGCAACGTTGCCCACCCGGCCAGCAGCACCAAGGTGGACAAGAAAATTGTGC

CCAGGGATTGTGGTTGTAAGCCTTGCATATGTACAGTCCCAGAAGTATCATCTGT

CTTCATCTTCCCCCCAAAGCCCAAGGATGTGCTCACCATTACTCTGACTCCTAAG

GTCACGTGTGTTGTGGTAGACATCAGCAAGGATGATCCCGAGGTCCAGTTCAGCT

GGTTTGTAGATGATGTGGAGGTGCACACAGCTCAGACGCAACCCCGGGAGGAGC

AGTTCAACAGCACTTTCCGCTCAGTCAGTGAACTTCCCATCATGCACCAGGACTG

GCTCAATGGCAAGGAGTTCAAATGCAGGGTCAACAGTGCAGCTTTCCCTGCCCCC

ATCGAGAAACCATCTCCAAAACCAAAGGCAGACCGAAGGCTCCGCAGGTGTAC

ACCATTCCACCTCCCAAGGAGCAGATGGCCAAGGATAAAGTCAGTCTGACCTGC

ATGATAACAGACTTCTTCCCTGAAGACATTACTGTGGAGTGGCAGTGGAATGGGC

AGCCAGCGGAGAACTACAAGAACACTCAGCCCATCATGGACACAGATGGCTCTT

ACTTCGTCTACAGCAAGCTCAATGTGCAGAAGAGCAACTGGGAGGCAGGAAATA

CTTTCACCTGCTCTGTGTTACATGAGGGCCTGCACAACCACCATACTGAGAAGAG

CCTCTCCCACTCTCCTGGTAAATGATCCCAGTGTCCCTAGCTGGCCAGACATGAT

AAGATACATTGATGAGTTTGGACAAACCACAACTAGAATGCAGTGAAAAAAATG

CTTTATTTGTGAAATTTGTGATGCTATTGCTTTATTTGTAACCATTATAAGCTGCA

ATAAACAAGTTAACAACAACAATTGCATTCATTTTATGTTTCAGGTTCAGGGGGA

GGTGTGGGAGGTTTTTTAAAGCAAGTAAAACCTCTACAAATGTGGTATGGAATTA

ATTCTAAAATACAGCATAGCAAAACTTTAACCTCCAAATCAAGCCTCTACTTGAA

TCCTTTTCTGAGGGATGAATAAGGCATAGGCATCAGGGGCTGTTGCCAATGTGCA

TTAGCTGTTTGCAGCCTCACCTTCTTTCATGGAGTTTAAGATATAGTGTATTTTCC

CAAGGTTTGAACTAGCTCTTCATTTCTTTATGTTTTAAATGCACTGACCTCCCACA

TTCCCTTTTTAGTAAAATATTCAGAAATAATTTAAATACATCATTGCAATGAAAA

TAAATGTTTTTTATTAGGCAGAATCCAGATGCTCAAGGCCCTTCATAATATCCCC

CAGTTTAGTAGTTGGACTTAGGGAACAAAGGAACCTTTAATAGAAATTGGACAG

CAAGAAAGCGAGCTTCTAGCTTATCCTCAGTCCTGCTCCTCTGCCACAAAGTGCA

CGCAGTTGCCGGCCGGGTCGCGCAGGGCGAACTCCCGCCCCCACGGCTGCTCGC

CGATCTCGGTCATGGCCGGCCCGGAGGCGTCCCGGAAGTTCGTGGACACGACCT

CCGACCACTCGGCGTACAGCTCGTCCAGGCCGCGCACCCACACCCAGGCCAGGG

TGTTGTCCGGCACCACCTGGTCCTGGACCGCGCTGATGAACAGGGTCACGTCGTC

CCGGACCACACCGGCGAAGTCGTCCTCCACGAAGTCCCGGGAGAACCCGAGCCG

GTCGGTCCAGAACTCGACCGCTCCGGCGACGTCGCGCGCGGTGAGCACCGGAAC

GGCACTGGTCAACTTGGCCATGATGGCTCCTCctgtcaggagaggaaagagaag aaggttagtacaattgCTATAGTGAGTTGTATTATACTATGCAGATATACTATG CCAATGATTAATTGTCAAACTAGGGCTGCAgggttcatagtgccacttttcct gcactgccccatctcctgcccacccttttcccaggcatagacagtcagtg acttacCAAACTCACAGGAGGGAGAAGGCAGAAGCTTGAGACAGACCCGCGGGA

CCGCCGAACTGCGAGGGGACGTGGCTAGGGCGGCTTCTTTTATGGTGCGCCGGCC
```

```
CTCGGAGGCAGGGCGCTCGGGGAGGCCTAGCGGCCAATCTGCGGTGGCAGGAGG

CGGGGCCGAAGGCCGTGCCTGACCAATCCGGAGCACATAGGAGTCTCAGCCCCC

CGCCCCAAAGCAAGGGGAAGTCACGCGCCTGTAGCGCCAGCGTGTTGTGAAATG

GGGGCTTGGGGGGGTTGGGGCCCTGACTAGTCAAAACAAACTCCCATTGACGTC

AATGGGGTGGAGACTTGGAAATCCCCGTGAGTCAAACCGCTATCCACGCCCATT

GATGTACTGCCAAAACCGCATCATCATGGTAATAGCGATGACTAATACGTAGAT

GTACTGCCAAGTAGGAAAGTCCCATAAGGTCATGTACTGGGCATAATGCCAGGC

GGGCCATTTACCGTCATTGACGTCAATAGGGGGCGTACTTGGCATATGATACACT

TGATGTACTGCCAAGTGGGCAGTTTACCGTAAATACTCCACCCATTGACGTCAAT

GGAAAGTCCCTATTGGCGTTACTATGGGAACATACGTCATTATTGACGTCAATGG

GCGGGGGTCGTTGGGCGGTCAGCCAGGCGGGCCATTTACCGTAAGTTATGTAAC

GCCTGCAGGTTAATTAAGAACATGTGAGCAAAAGGCCAGCAAAAGGCCAGGAAC

CGTAAAAAGGCCGCGTTGCTGGCGTTTTTCCATAGGCTCCGCCCCCCTGACGAGC

ATCACAAAAATCGACGCTCAAGTCAGAGGTGGCGAAACCCGACAGGACTATAAA

GATACCAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGCTTTCTC

ATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTAT

CGTCTTGAGTCCAACCCGGTAAGACACGACTTATCGCCACTGGCAGCAGCCACTG

GTAACAGGATTAGCAGAGCGAGGTATGTAGGCGGTGCTACAGAGTTCTTGAAGT

GGTGGCCTAACTACGGCTACACTAGAAGAACAGTATTTGGTATCTGCGCTCTGCT

GAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCAGTGGA

ACGAAAACTCACGTTAAGGGATTTTGGTCATGGCTAGTTAATTAACATTTAAATC

AGCGGCCGCAATAAAATATCTTTATTTTCATTACATCTGTGTGTTGGTTTTTTGTG

TGAATCGTAACTAACATACGCTCTCCATCAAAACAAAACGAAACAAAACAAACT

AGCAAAATAGGCTGTCCCCAGTGCAAGTGCAGGTGCCAGAACATTTCTCTATCGA

A

SEQ ID NO 7,834:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCAACATGTACAGGATGCAACTCCTGTCTTGCATTGCACTAAGTCTTGCACTTG
```

-continued

```
TCACGAATTCAGATATCCAGATGACCCAGTCCCCGAGCTCCCTGTCCGCCTCTGT

GGGCGATAGGGTCACCATCACCTGCCGTGCCAGTCAGTCCGTGTCCAGCGCTGTA

GCCTGGTATCAACAGAAACCAGGAAAAGCTCCGAAGCTTCTGATTTACTCGGCAT

CCAGCCTCTACTCTGGAGTCCCTTCTCGCTTCTCTGGTAGCCGTTCCGGGACGGAT

TTCACTCTGACCATCAGCAGTCTGCAGCCGGAAGACTTCGCAACTTATTACTGTC

AGCAAGGTTACGACCTGATCACGTTCGGACAGGGTACCAAGGTGGAGATCAAAC

GACTCGAGATCAAACGGGCAGATGCTGCACCAACTGTATCCATCTTCCCACCATC

CAGTGAGCAGTTAACATCTGGAGGTGCCTCAGTCGTGTGCTTCTTGAACAACTTC

TACCCCAAAGACATCAATGTCAAGTGGAAGATTGATGGCAGTGAACGACAAAAT

GGCGTCCTGAACAGTTGGACTGATCAGGACAGCAAAGACAGCACCTACAGCATG

AGCAGCACCCTCACGTTGACCAAGGACGAGTATGAACGACATAACAGCTATACC

TGTGAGGCCACTCACAAGACATCAACTTCACCCATTGTCAAGAGCTTCAACAGGA

ATGAGTGTTAGAGACAAAGGTCCTGAGAGCTAGCTGGCCAGACATGATAAGATA

CATTGATGAGTTTGGACAAACCACAACTAGAATGCAGTGAAAAAAATGCTTTATT

TGTGAAATTTGTGATGCTATTGCTTTATTTGTAACCATTATAAGCTGCAATAAACA

AGTTAACAACAACAATTGCATTCATTTTATGTTTCAGGTTCAGGGGAGGTGTGG

GAGGTTTTTTAAAGCAAGTAAAACCTCTACAAATGTGGTATGGAATTAATTCTAA

AATACAGCATAGCAAAACTTTAACCTCCAAATCAAGCCTCTACTTGAATCCTTTT

CTGAGGGATGAATAAGGCATAGGCATCAGGGGCTGTTGCCAATGTGCATTAGCT

GTTTGCAGCCTCACCTTCTTTCATGGAGTTTAAGATATAGTGTATTTTCCCAAGGT

TTGAACTAGCTCTTCATTTCTTTATGTTTTAAATGCACTGACCTCCCACATTCCCTT

TTTAGTAAAATATTCAGAAATAATTTAAATACATCATTGCAATGAAAATAAATGT

TTTTTATTAGGCAGAATCCAGATGCTCAAGGCCCTTCATAATATCCCCCAGTTTA

GTAGTTGGACTTAGGGAACAAAGGAACCTTTAATAGAAATTGGACAGCAAGAAA

GCGAGCTTCTAGCTTTAGTTCCTGGTGTACTTGAGGGGGATGAGTTCCTCAATGG

TGGTTTTGACCAGCTTGCCATTCATCTCAATGAGCACAAAGCAGTCAGGAGCATA

GTCAGAGATGAGCTCTCTGCACATGCCACAGGGGCTGACCACCCTGATGGATCTG

TCCACCTCATCAGAGTAGGGGTGCCTGACAGCCACAATGGTGTCAAAGTCCTTCT

GCCCGTTGCTCACAGCAGACCCAATGGCAATGGCTTCAGCACAGACAGTGACCC

TGCCAATGTAGGCCTCAATGTGGACAGCAGAGATGATCTCCCCAGTCTTGGTCCT

GATGGCCGCCCCGACATGGTGCTTGTTGTCCTCATAGAGCATGGTGATCTTCTCA

GTGGCGACCTCCACCAGCTCCAGATCCTGCTGAGAGATGTTGAAGGTCTTCATGA

TGGCTCCTCctgtcaggagaggaaagagaagaaggttagtacaattgCTATAGT

GAGTTGTATTATACTATGCTTATGATTAATTGTCAAACTAGGGCTGCAgggtt catagtgccacttttcctgcactgccccatctcctgccaccctttccca ggcatagacagtcagtgacttacCAAACTCACAGGAGGGAGAAGGCAGAAGC

TTGAGACAGACCCGCGGGACCGCCGAACTGCGAGGGGACGTGGCTAGGGCGGCT

TCTTTTATGGTGCGCCGGCCCTCGGAGGCAGGGCGCTCGGGGAGGCCTAGCGGC

CAATCTGCGGTGGCAGGAGGCGGGGCCGAAGGCCGTGCCTGACCAATCCGGAGC

ACATAGGAGTCTCAGCCCCCCGCCCCAAAGCAAGGGGAAGTCACGCGCCTGTAG
```

-continued
CGCCAGCGTGTTGTGAAATGGGGGCTTGGGGGGGTTGGGGCCCTGACTAGTCAA

AACAAACTCCCATTGACGTCAATGGGGTGGAGACTTGGAAATCCCCGTGAGTCA

AACCGCTATCCACGCCCATTGATGTACTGCCAAAACCGCATCATCATGGTAATAG

CGATGACTAATACGTAGATGTACTGCCAAGTAGGAAAGTCCCATAAGGTCATGT

ACTGGGCATAATGCCAGGCGGGCCATTTACCGTCATTGACGTCAATAGGGGCG

TACTTGGCATATGATACACTTGATGTACTGCCAAGTGGGCAGTTTACCGTAAATA

CTCCACCCATTGACGTCAATGGAAAGTCCCTATTGGCGTTACTATGGGAACATAC

GTCATTATTGACGTCAATGGGCGGGGGTCGTTGGGCGGTCAGCCAGGCGGGCCA

TTTACCGTAAGTTATGTAACGCCTGCAGGTTAATTAAGAACATGTGAGCAAAAGG

CCAGCAAAAGGCCAGGAACCGTAAAAAGGCCGCGTTGCTGGCGTTTTTCCATAG

GCTCCGCCCCCTGACGAGCATCACAAAAATCGACGCTCAAGTCAGAGGTGGCG

AAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCTT

CGGGAAGCGTGGCGCTTTCTCATAGCTCACGCTGTAGGTATCTCAGTTCGGTGTA

GGTCGTTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGACTTAT

CGCCACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGAACAG

TATTTGGTATCTGCGCTCTGCTGAAGCCAGTTACCTTCGGAAAAAGAGTTGGTAG

CTCTTGATCCGGCAAACAAACCACCGCTGGTAGCGGTGGTTTTTTTGTTTGCAAG

CAGCAGATTACGCGCAGAAAAAAAGGATCTCAAGAAGATCCTTTGATCTTTTCTA

CGGGGTCTGACGCTCAGTGGAACGAAAACTCACGTTAAGGGATTTTGGTCATGG

CTAGTTAATTAACATTTAAATCAGCGGCCGCAATAAAATATCTTTATTTTCATTAC

ATCTGTGTGTTGGTTTTTTGTGTGAATCGTAACTAACATACGCTCTCCATCAAAAC

AAAACGAAACAAAACAAACTAGCAAAATAGGCTGTCCCCAGTGCAAGTGCAGGT

GCCAGAACATTTCTCTATCGAA

SEQ ID NO 7,835:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCACCGGCGAAGGAGGGCCACCATGTACAGGATGCAACTCCTGTCTTGCATTGC

ACTAAGTCTTGCACTTGTCACGAATTCGGAGGTTCAGCTGGTGGAGTCTGGCGGT

GGCCTGGTGCAGCCAGGGGGCTCACTCCGTTTGTCCTGTGCAGCTTCTGGCTTCA

ACCTCTATTATTATTCTATCCACTGGGTGCGTCAGGCCCCGGGTAAGGGCCTGGA

-continued
```
ATGGGTTGCATCTATTTCTTCTTATTATAGCTCTACTTCTTATGCCGATAGCGTCA

AGGGCCGTTTCACTATAAGCGCAGACACATCCAAAAACACAGCCTACCTACAAA

TGAACAGCTTAAGAGCTGAGGACACTGCCGTCTATTATTGTGCTCGCTTCTACTC

TGGTTACGCTGGTATGGACTACTGGGGTCAAGGAACCCTGGTCACCGTCTCCTCG

AGTGCTAGCAGCGCTAAAACGACACCCCCATCTGTCTATCCACTGGCCCCTGGAT

CTGCTGCCCAAACTAACTCCATGGTGACCCTGGGATGCCTGGTCAAGGGCTATTT

CCCTGAGCCAGTGACAGTGACCTGGAACTCTGGATCCCTGTCCAGCGGTGTGCAC

ACCTTCCCAGCTGTCCTGCAGTCTGACCTCTACACTCTGAGCAGCTCAGTGACTG

TCCCCTCCAGCACCTGGCCCAGCGAGACCGTCACCTGCAACGTTGCCCACCCGGC

CAGCAGCACCAAGGTGGACAAGAAAATTGTGCCCAGGGATTGTGGTTGTAAGCC

TTGCATATGTACAGTCCCAGAAGTATCATCTGTCTTCATCTTCCCCCCAAAGCCCA

AGGATGTGCTCACCATTACTCTGACTCCTAAGGTCACGTGTGTTGTGGTAGACAT

CAGCAAGGATGATCCCGAGGTCCAGTTCAGCTGGTTTGTAGATGATGTGGAGGT

GCACACAGCTCAGACGCAACCCCGGGAGGAGCAGTTCAACAGCACTTTCCGCTC

AGTCAGTGAACTTCCCATCATGCACCAGGACTGGCTCAATGGCAAGGAGTTCAA

ATGCAGGGTCAACAGTGCAGCTTTCCCTGCCCCCATCGAGAAAACCATCTCCAAA

ACCAAAGGCAGACCGAAGGCTCCGCAGGTGTACACCATTCCACCTCCCAAGGAG

CAGATGGCCAAGGATAAAGTCAGTCTGACCTGCATGATAACAGACTTCTTCCCTG

AAGACATTACTGTGGAGTGGCAGTGGAATGGGCAGCAGCGGAGAACTACAAGA

ACACTCAGCCCATCATGGACACAGATGGCTCTTACTTCGTCTACAGCAAGCTCAA

TGTGCAGAAGAGCAACTGGGAGGCAGGAAATACTTTCACCTGCTCTGTGTTACAT

GAGGGCCTGCACAACCACCATACTGAGAAGAGCCTCTCCCACTCTCCTGGTAAAT

GATCCCAGTGTCCCTAGCTGGCCAGACATGATAAGATACATTGATGAGTTTGGAC

AAACCACAACTAGAATGCAGTGAAAAAAATGCTTTATTTGTGAAATTTGTGATGC

TATTGCTTTATTTGTAACCATTATAAGCTGCAATAAACAAGTTAACAACAACAAT

TGCATTCATTTTATGTTTCAGGTTCAGGGGGAGGTGTGGGAGGTTTTTTAAAGCA

AGTAAAACCTCTACAAATGTGGTATGGAATTAATTCTAAAATACAGCATAGCAA

AACTTTAACCTCCAAATCAAGCCTCTACTTGAATCCTTTTCTGAGGGATGAATAA

GGCATAGGCATCAGGGGCTGTTGCCAATGTGCATTAGCTGTTTGCAGCCTCACCT

TCTTTCATGGAGTTTAAGATATAGTGTATTTTCCCAAGGTTTGAACTAGCTCTTCA

TTTCTTTATGTTTTAAATGCACTGACCTCCCACATTCCCTTTTTAGTAAAATATTC

AGAAATAATTTAAATACATCATTGCAATGAAAATAAATGTTTTTTATTAGGCAGA

ATCCAGATGCTCAAGGCCCTTCATAATATCCCCCAGTTTAGTAGTTGGACTTAGG

GAACAAAGGAACCTTTAATAGAAATTGGACAGCAAGAAAGCGAGCTTCTAGCTT

ATCCTCAGTCCTGCTCCTCTGCCACAAAGTGCACGCAGTTGCCGGCCGGGTCGCG

CAGGGCGAACTCCCGCCCCCACGGCTGCTCGCCGATCTCGGTCATGGCCGGCCCG

GAGGCGTCCCGGAAGTTCGTGGACACGACCTCCGACCACTCGGCGTACAGCTCG

TCCAGGCCGCGCACCCACACCCAGGCCAGGGTGTTGTCCGGCACCACCTGGTCCT

GGACCGCGCTGATGAACAGGGTCACGTCGTCCCGGACCACACCGGCGAAGTCGT

CCTCCACGAAGTCCCGGGAGAACCCGAGCCGGTCGGTCCAGAACTCGACCGCTC

CGGCGACGTCGCGCGCGGTGAGCACCGGAACGGCACTGGTCAACTTGGCCATGA
```

-continued

TGGCTCCTCctgtcaggagaggaaagagaagaaggttagtacaattgCTATAG

TGAGTTGTATTATACTATGCAGATATACTATGCCAATGATTAATTGTCAAACT

AGGGCTGCAgggttcatagtgccacttttcctgcactgccccatctcctgccc accctttcccaggcatagacagtcagtgacttacCAAACTCACAGGAGGGA

GAAGGCAGAAGCTTGAGACAGACCCGCGGGACCGCCGAACTGCGAGGGGACGT

GGCTAGGGCGGCTTCTTTTATGGTGCGCCGGCCCTCGGAGGCAGGGCGCTCGGG

GAGGCCTAGCGGCCAATCTGCGGTGGCAGGAGGCGGGGCCGAAGGCCGTGCCTG

ACCAATCCGGAGCACATAGGAGTCTCAGCCCCCCGCCCCAAAGCAAGGGGAAGT

CACGCGCCTGTAGCGCCAGCGTGTTGTGAAATGGGGCTTGGGGGGGTTGGGGC

CCTGACTAGTCAAAACAAACTCCCATTGACGTCAATGGGGTGGAGACTTGGAAA

TCCCCGTGAGTCAAACCGCTATCCACGCCCATTGATGTACTGCCAAAACCGCATC

ATCATGGTAATAGCGATGACTAATACGTAGATGTACTGCCAAGTAGGAAAGTCC

CATAAGGTCATGTACTGGGCATAATGCCAGGCGGGCCATTTACCGTCATTGACGT

CAATAGGGGCGTACTTGGCATATGATACACTTGATGTACTGCCAAGTGGGCAGT

TTACCGTAAATACTCCACCCATTGACGTCAATGGAAAGTCCCTATTGGCGTTACT

ATGGGAACATACGTCATTATTGACGTCAATGGGCGGGGTCGTTGGGCGGTCAG

CCAGGCGGGCCATTTACCGTAAGTTATGTAACGCCTGCAGGTTAATTAAGAACAT

GTGAGCAAAAGGCCAGCAAAAGGCCAGGAACCGTAAAAAGGCCGCGTTGCTGG

CGTTTTTCCATAGGCTCCGCCCCCCTGACGAGCATCACAAAAATCGACGCTCAAG

TCAGAGGTGGCGAAACCCGACAGGACTATAAAGATACCAGGCGTTTCCCCCTGG

AAGCTCCCTCGTGCGCTCTCCTGTTCCGACCCTGCCGCTTACCGGATACCTGTCCG

CCTTTCTCCCTTCGGGAAGCGTGGCGCTTTCTCATAGCTCACGCTGTAGGTATCTC

AGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAG

ACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACT

AGAAGAACAGTATTTGGTATCTGCGCTCTGCTGAAGCCAGTTACCTTCGGAAAAA

GAGTTGGTAGCTCTTGATCCGGCAAACAAACCACCGCTGGTAGCGGTGGTTTTTT

TGTTTGCAAGCAGCAGATTACGCGCAGAAAAAAAGGATCTCAAGAAGATCCTTT

GATCTTTTCTACGGGGTCTGACGCTCAGTGGAACGAAAACTCACGTTAAGGGATT

TTGGTCATGGCTAGTTAATTAACATTTAAATCAGCGGCCGCAATAAAATATCTTT

ATTTTCATTACATCTGTGTGTTGGTTTTTTGTGTGAATCGTAACTAACATACGCTC

TCCATCAAAACAAAACGAAACAAAACAAACTAGCAAAATAGGCTGTCCCCAGTG

CAAGTGCAGGTGCCAGAACATTTCTCTATCGAA

SEQ ID NO 7,836:
GGATCTGCGATCGCTCCGGTGCCCGTCAGTGGGCAGAGCGCACATCGCCCACAG

TCCCCGAGAAGTTGGGGGGAGGGGTCGGCAATTGAACGGGTGCCTAGAGAAGGT

GGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGC

AACGGGTTTGCCGCCAGAACACAGCTGAAGCTTCGAGGGGCTCGCATCTCTCCTT

CACGCGCCCGCCGCCCTACCTGAGGCCGCCATCCACGCCGGTTGAGTCGCGTTCT

-continued

```
GCCGCCTCCCGCCTGTGGTGCCTCCTGAACTGCGTCCGCCGTCTAGGTAAGTTTA

AAGCTCAGGTCGAGACCGGGCCTTTGTCCGGCGCTCCCTTGGAGCCTACCTAGAC

TCAGCCGGCTCTCCACGCTTTGCCTGACCCTGCTTGCTCAACTCTACGTCTTTGTT

TCGTTTTCTGTTCTGCGCCGTTACAGATCCAAGCTGTGACCGGCGCCTACCTGAG

ATCAACATGTACAGGATGCAACTCCTGTCTTGCATTGCACTAAGTCTTGCACTTG

TCACGAATTCAGATATCCAGATGACCCAGTCCCCGAGCTCCCTGTCCGCCTCTGT

GGGCGATAGGGTCACCATCACCTGCCGTGCCAGTCAGTCCGTGTCCAGCGCTGTA

GCCTGGTATCAACAGAAACCAGGAAAAGCTCCGAAGCTTCTGATTTACTCGGCAT

CCAGCCTCTACTCTGGAGTCCCTTCTCGCTTCTCTGGTAGCCGTTCCGGGACGGAT

TTCACTCTGACCATCAGCAGTCTGCAGCCGGAAGACTTCGCAACTTATTACTGTC

AGCAATCTGGTTACCTGATCACGTTCGGACAGGGTACCAAGGTGGAGATCAAAC

GACTCGAGATCAAACGGGCAGATGCTGCACCAACTGTATCCATCTTCCCACCATC

CAGTGAGCAGTTAACATCTGGAGGTGCCTCAGTCGTGTGCTTCTTGAACAACTTC

TACCCCAAAGACATCAATGTCAAGTGGAAGATTGATGGCAGTGAACGACAAAAT

GGCGTCCTGAACAGTTGGACTGATCAGGACAGCAAAGACAGCACCTACAGCATG

AGCAGCACCCTCACGTTGACCAAGGACGAGTATGAACGACATAACAGCTATACC

TGTGAGGCCACTCACAAGACATCAACTTCACCCATTGTCAAGAGCTTCAACAGGA

ATGAGTGTTAGAGACAAAGGTCCTGAGAGCTAGCTGGCCAGACATGATAAGATA

CATTGATGAGTTTGGACAAACCACAACTAGAATGCAGTGAAAAAAATGCTTTATT

TGTGAAATTTGTGATGCTATTGCTTTATTTGTAACCATTATAAGCTGCAATAAACA

AGTTAACAACAACAATTGCATTCATTTTATGTTTCAGGTTCAGGGGGAGGTGTGG

GAGGTTTTTTAAAGCAAGTAAAACCTCTACAAATGTGGTATGGAATTAATTCTAA

AATACAGCATAGCAAAACTTTAACCTCCAAATCAAGCCTCTACTTGAATCCTTTT

CTGAGGGATGAATAAGGCATAGGCATCAGGGGCTGTTGCCAATGTGCATTAGCT

GTTTGCAGCCTCACCTTCTTTCATGGAGTTTAAGATATAGTGTATTTTCCCAAGGT

TTGAACTAGCTCTTCATTTCTTTATGTTTTAAATGCACTGACCTCCCACATTCCCTT

TTTAGTAAAATATTCAGAAATAATTTAAATACATCATTGCAATGAAAATAAATGT

TTTTTATTAGGCAGAATCCAGATGCTCAAGGCCCTTCATAATATCCCCCAGTTTA

GTAGTTGGACTTAGGGAACAAAGGAACCTTTAATAGAAATTGGACAGCAAGAAA

GCGAGCTTCTAGCTTTAGTTCCTGGTGTACTTGAGGGGGATGAGTTCCTCAATGG

TGGTTTTGACCAGCTTGCCATTCATCTCAATGAGCACAAAGCAGTCAGGAGCATA

GTCAGAGATGAGCTCTCTGCACATGCCACAGGGGCTGACCACCCTGATGGATCTG

TCCACCTCATCAGAGTAGGGGTGCCTGACAGCCACAATGGTGTCAAAGTCCTTCT

GCCCGTTGCTCACAGCAGACCCAATGGCAATGGCTTCAGCACAGACAGTGACCC

TGCCAATGTAGGCCTCAATGTGGACAGCAGAGATGATCTCCCCAGTCTTGGTCCT

GATGGCCGCCCCGACATGGTGCTTGTTGTCCTCATAGAGCATGGTGATCTTCTCA

GTGGCGACCTCCACCAGCTCCAGATCCTGCTGAGAGATGTTGAAGGTCTTCATGA

TGGCTCCTCctgtcaggagaggaaagagaagaaggttagtacaattgCTATAGT

GAGTTGTATTATACTATGCTTATGATTAATTGTCAAACTAGGGCTGCAgggttc atagtgccacttttcctgcactgccccatctcctgcccaccctttcccaggcat
```

-continued
```
agacagtcagtgacttacCAAACTCACAGGAGGGAGAAGGCAGAAGC

TTGAGACAGACCCGCGGGACCGCCGAACTGCGAGGGGACGTGGCTAGGGCGGCT

TCTTTTATGGTGCGCCGGCCCTCGGAGGCAGGGCGCTCGGGGAGGCCTAGCGGC

CAATCTGCGGTGGCAGGAGGCGGGGCCGAAGGCCGTGCCTGACCAATCCGGAGC

ACATAGGAGTCTCAGCCCCCCGCCCCAAAGCAAGGGGAAGTCACGCGCCTGTAG

CGCCAGCGTGTTGTGAAATGGGGGCTTGGGGGGGTTGGGGCCCTGACTAGTCAA

AACAAACTCCCATTGACGTCAATGGGGTGGAGACTTGGAAATCCCCGTGAGTCA

AACCGCTATCCACGCCCATTGATGTACTGCCAAAACCGCATCATCATGGTAATAG

CGATGACTAATACGTAGATGTACTGCCAAGTAGGAAAGTCCCATAAGGTCATGT

ACTGGGCATAATGCCAGGCGGGCCATTTACCGTCATTGACGTCAATAGGGGCG

TACTTGGCATATGATACACTTGATGTACTGCCAAGTGGGCAGTTTACCGTAAATA

CTCCACCCATTGACGTCAATGGAAAGTCCCTATTGGCGTTACTATGGGAACATAC

GTCATTATTGACGTCAATGGGCGGGGTCGTTGGGCGGTCAGCCAGGCGGGCCA

TTTACCGTAAGTTATGTAACGCCTGCAGGTTAATTAAGAACATGTGAGCAAAAGG

CCAGCAAAAGGCCAGGAACCGTAAAAAGGCCGCGTTGCTGGCGTTTTTCCATAG

GCTCCGCCCCCTGACGAGCATCACAAAAATCGACGCTCAAGTCAGAGGTGGCG

AAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCTT

CGGGAAGCGTGGCGCTTTCTCATAGCTCACGCTGTAGGTATCTCAGTTCGGTGTA

GGTCGTTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGACTTAT

CGCCACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGAACAG

TATTTGGTATCTGCGCTCTGCTGAAGCCAGTTACCTTCGGAAAAAGAGTTGGTAG

CTCTTGATCCGGCAAACAAACCACCGCTGGTAGCGGTGGTTTTTTTGTTTGCAAG

CAGCAGATTACGCGCAGAAAAAAAGGATCTCAAGAAGATCCTTTGATCTTTTCTA

CGGGGTCTGACGCTCAGTGGAACGAAAACTCACGTTAAGGGATTTTGGTCATGG

CTAGTTAATTAACATTTAAATCAGCGGCCGCAATAAAATATCTTTATTTTCATTAC

ATCTGTGTGTTGGTTTTTTGTGTGAATCGTAACTAACATACGCTCTCCATCAAAAC

AAAACGAAACAAAACAAACTAGCAAAATAGGCTGTCCCCAGTGCAAGTGCAGGT

GCCAGAACATTTCTCTATCGAA
```

TABLE 6

A non-limiting list of cancers that the T cell based therapy of the disclosed methods and compositions can target.

| | | | | |
|---|---|---|---|---|
| Acute Lymphoblastic Leukemia (ALL) | Acute Myeloid Leukemia (AML) | Adrenocortical Carcinoma | AIDS-Related Cancers | Kaposi Sarcoma |
| AIDS-Related Lymphoma | Primary CNS Lymphoma | Anal Cancer | Appendix Cancer (Gastrointestinal Carcinoid Tumors) | Astrocytomas |

TABLE 6-continued

A non-limiting list of cancers that the T cell based therapy of the disclosed methods and compositions can target.

| | | | | |
|---|---|---|---|---|
| Atypical Teratoid/Rhabdoid Tumor | Brain Cancer | Basal Cell Carcinoma of the Skin | Bile Duct Cancer | Bladder Cancer |
| Bone Cancer (includes Ewing Sarcoma and Osteosarcoma and Malignant Fibrous Histiocytoma) | Brain Tumors | Breast Cancer | Bronchial Tumors | Burkitt Lymphoma |
| Non-Hodgkin Lymphoma | Carcinoid Tumors | Carcinoma of Unknown Primary | Cardiac (Heart) Tumors | Embryonal Tumors |
| Germ Cell Tumor | Primary CNS Lymphoma | Cervical Cancer | Cholangio-carcinoma | Chordoma |
| Chronic Lymphocytic Leukemia (CLL) | Chronic Myelogenous Leukemia (CML) | Chronic Myeloproliferative Neoplasms | Colorectal Cancer | Cranio-pharyngioma |
| Cutaneous T-Cell Lymphoma (Mycosis Fungoides and Sézary Syndrome) | Ductal Carcinoma In Situ (DCIS) | Endometrial Cancer | Ependymoma | Esophageal Cancer |
| Esthesioneuro-blastoma | Ewing Sarcoma | Extracranial Germ Cell Tumor | Eye Cancer | Intraocular Melanoma |
| Fallopian Tube Cancer | Fibrous Histiocytoma of Bone | Osteosarcoma | Gallbladder Cancer | Gastric Cancer |
| Stomach Cancer | Gastrointestinal Carcinoid Tumor | Gastrointestinal Stromal Tumors (GIST) | Central Nervous System Germ Cell Tumors | Extracranial Germ Cell Tumors |
| Extragonadal Germ Cell Tumors | Ovarian Germ Cell Tumors | Testicular Cancer | Gestational Trophoblastic Disease | Hairy Cell Leukemia |
| Head and Neck Cancer | Heart Tumors | Hepatocellular (Liver) Cancer | Histiocytosis (Langerhans Cell) | Hodgkin Lymphoma |
| Hypopharyngeal Cancer | Intraocular Melanoma | Islet Cell Tumors | Pancreatic Neuroendocrine Tumors | Kidney Cancer |
| Renal Cell Cancer | Langerhans Cell Histiocytosis | Laryngeal Cancer | Leukemia | Lip and Oral Cavity Cancer |
| Liver Cancer | Lung Cancer (Non-Small Cell and Small Cell) | Lymphoma | Male Breast Cancer | Malignant Fibrous Histiocytoma of Bone and Osteosarcoma |
| Melanoma | Intraocular (Eye) Melanoma | Merkel Cell Carcinoma (Skin Cancer) | Malignant Mesothelioma | Metastatic Cancer |
| Metastatic Squamous Neck Cancer with Occult Primary | Midline Tract Carcinoma With NUT Gene Changes | Mouth Cancer | Multiple Endocrine Neoplasia Syndromes | Multiple Myeloma/Plasma Cell Neoplasms |
| Mycosis Fungoides (Lymphoma) | Myelodysplastic Syndromes | Myelodysplastic/Myeloproliferative Neoplasms | Nasal Cavity and Paranasal Sinus Cancer | Nasopharyngeal Cancer |
| Neuroblastoma | Non-Small Cell Lung Cancer | Oral Cancer | and Oropharyngeal Cancer | Ovarian Cancer |
| Pancreatic Cancer | Papillomatosis | Paraganglioma | Paranasal Sinus and Nasal Cavity Cancer | Parathyroid Cancer |
| Penile Cancer | Pharyngeal Cancer | Pheochromocytoma | Pituitary Tumor | Plasma Cell Neoplasm/Multiple Myeloma |
| Pleuropulmonary Blastoma | Primary Central Nervous System (CNS) Lymphoma | Primary Peritoneal Cancer | Prostate Cancer | Rectal Cancer |
| Recurrent Cancer | Retinoblastoma | Rhabdomyosarcoma | Salivary Gland Cancer | Sarcoma |
| Vascular Tumors | Uterine Sarcoma | Sézary Syndrome (Lymphoma) | Small Cell Lung Cancer | Small Intestine Cancer |
| Soft Tissue Sarcoma | Squamous Cell Carcinoma | Stomach (Gastric) Cancer | Throat Cancer | Thymoma |
| Thymic Carcinoma | Thyroid Cancer | Transitional Cell Cancer of the Renal Pelvis and Ureter | Carcinoma of Unknown Primary | Ureter and Renal Pelvis |
| Transitional Cell Cancer | Urethral Cancer | Uterine Cancer | Vaginal Cancer | Vulvar Cancer |
| Wilms Tumor | | | | |

TABLE 7

Splinkerette PCR primers

| SEQ ID NO: | Primer Name: | Sequence: |
|---|---|---|
| 69,824 | Splinkerette adaptor-F | CGAAGAGTAACCGTTGCTAGGAGAGACCGTGGCTGAATGAGACTGGTGTCGACACTAGTGG |
| 69,825 | Splinkerette adaptor-R | GATCCCACTAGTGTCGACACCAGTCTCTAATTTTTTTTTCAAAAAAA |
| 69,826 | Splink 1 | CGAAGAGTAACCGTTGCTAGGAGAGACC |
| 69,827 | SB-Right1 | ACTGACCTAAGACAGGGAATTTTTACTAGG |
| 69,828 | Splink 2 | GTGGCTGAATGAGACTGGTGTCGAC |
| 69,829 | SB-Right 2 | AGTGAGTTTAAATGTATTTGGCTAAGGTGTATG |

TABLE 8

Primers used for HDR arm amplification and detection

| SEQ ID NO. | Primer Name | Sequence |
|---|---|---|
| 69,830 | TRAC-left-F | GACCACTCCAGATTtCAAGATGTACAG |
| 69,831 | TRAC-left-R | GGTCAGGGTTCTGGATATCTGTGG |
| 69,832 | TARC-right-F | GAGAGACTCTAAATCCAGTGACAAGTC |
| 69,833 | TARC-right-R | GTGGGTTAATGAGTGACTGCGT |
| 69,834 | HDRwt-F2 | GAGAGAGCAATCTCCTGGTAATGTGAT |
| 69,835 | HDRwt-R3 | AGGCAGACAGACTTGTCACTGG |
| 69,836 | EGFRvIII-R1 | TCTGGATGTCGGGGATCAGCAG |

Lenti-EGFRvIII expression vector
(SEQ ID NO: 69,748)
GTGCCACCTGCAGCCTGAATATGGGCCAAACAGGATATCTGTGGTAAGCAGTTCC
TGCCCCGGCTCAGGGCCAAGAACAGATGGAACAGCTGAATATGGGCCAAACAGG
ATATCTGTGGTAAGCAGTTCCTGCCCCGGCTCAGGGCCAAGAACAGATGGTCCCC
AGATGCGGTCCAGCCCTCAGCAGTTTCTAGAGAACCATCAGATGTTTCCAGGGTG
CCCCAAGGACCTGAAATGACCCTGTGCCTTATTTGAACTAACCAATCAGTTCGCT
TCTCGCTTCTGTTCGCGCGCTTCTGCTCCCCGAGCTCAATAAAAGAGCCCACAAC
CCCTCACTCGGGGCGCCAGTCCTCCGATTGACTGAGTCGCCCGGGTACCCGTGTA
TCCAATAAACCCTCTTGCAGTTGCATCCGACTTGTGGTCTCGCTGTTCCTTGGGAG
GGTCTCCTCTGAGTGATTGACTACCCGTCAGCGGGGGTCTTTCATTTGGGGGCTC
GTCCGGGATCGGGAGACCCCTGCCCAGGGACCACCGACCCACCACCGGGAGGCA
AGCTGGCCAGCAACTTATCTGTGTCTGTCCGATTGTCTAGTGTCTATGACTGATTT
TATGCGCCTGCGTCGGTACTAGTTAGCTAACTAGCTCTGTATCTGGCGGACCCGT
GGTGGAACTGACGAGTTCTGAACACCCGGCCGCAACCCTGGGAGACGTCCCAGG
GACTTTGGGGCCGTTTTTGTGGCCCGACCTGAGGAAGGGAGTCGATGTGGAATC
CGACCCCGTCAGGATATGTGGTTCTGGTAGGAGACGAGAACCTAAAACAGTTCC
CGCCTCCGTCTGAATTTTTGCTTTCGGTTTGGAACCGAAGCCGCGTCTTGTCTG
CTGCAGCGCTGCAGCATCGTTCTGTGTTGTCTCTGTCTGACTGTGTTTCTGTATTT
GTCTGAAAATTAGGGCCAGACTGTTACCACTCCCTTAAGTTTGACCTTAGGTCAC
TGGAAAGATGTCGAGCGGATCGCTCACAACCAGTCGGTAGATGTCAAGAAGAGA
CGTTGGGTTACCTTCTGCTCTGCAGAATGGCCAACCTTTAACGTCGGATGGCCGC -continued

```
GAGACGGCACCTTTAACCGAGACCTCATCACCCAGGTTAAGATCAAGGTCTTTTC

ACCTGGCCCGCATGGACACCCAGACCAGGTCCCCTACATCGTGACCTGGGAAGC

CTTGGCTTTTGACCCCCCTCCCTGGGTCAAGCCCTTTGTACACCCTAAGCCTCCGC

CTCCTCTTCCTCCATCCGCCCCGTCTCTCCCCCTTGAACCTCCTCGTTCGACCCCG

CCTCGATCCTCCCTTTATCCAGCCCTCACTCCTTCTCTAGGCGCCGGCCGGATCCC

AGTGTGGTGGTACATCATGCGACCCTCCGGGACGGCCGGGGCAGCGCTCCTGGC

GCTGCTGGCTGCGCTCTGCCCGGCGAGTCGGGCTCTGGAGGAAAAGAAAGGTAA

TTATGTGGTGACAGATCACGGCTCGTGCGTCCGAGCCTGTGGGGCCGACAGCTAT

GAGATGGAGGAAGACGGCGTCCGCAAGTGTAAGAAGTGCGAAGGGCCTTGCCGC

AAAGTGTGTAACGGAATAGGTATTGGTGAATTTAAAGACTCACTCTCCATAAATG

CTACGAATATTAAACACTTCAAAAACTGCACCTCCATCAGTGGCGATCTCCACAT

CCTGCCGGTGGCATTTAGGGGTGACTCCTTCACACATACTCCTCCTCTGGATCCA

CAGGAACTGGATATTCTGAAAACCGTAAAGGAAATCACAGGGTTTTTGCTGATTC

AGGCTTGGCCTGAAAACAGGACGGACCTCCATGCCTTTGAGAACCTAGAAATCA

TACGCGGCAGGACCAAGCAACATGGTCAGTTTTCTCTTGCAGTCGTCAGCCTGAA

CATAACATCCTTGGGATTACGCTCCCTCAAGGAGATAAGTGATGGAGATGTGATA

ATTTCAGGAAACAAAAATTTGTGCTATGCAAATACAATAAACTGGAAAAAACTG

TTTGGGACCTCCGGTCAGAAAACCAAAATTATAAGCAACAGAGGTGAAAACAGC

TGCAAGGCCACAGGCCAGGTCTGCCATGCCTTGTGCTCCCCCGAGGGCTGCTGGG

GCCCGGAGCCCAGGGACTGCGTCTCTTGCCGGAATGTCAGCCGAGGCAGGGAAT

GCGTGGACAAGTGCAACCTTCTGGAGGGTGAGCCAAGGGAGTTTGTGGAGAACT

CTGAGTGCATACAGTGCCACCCAGAGTGCCTGCCTCAGGCCATGAACATCACCTG

CACAGGACGGGACCAGACAACTGTATCCAGTGTGCCCACTACATTGACGGCCC

CCACTGCGTCAAGACCTGCCCGGCAGGAGTCATGGGAGAAAACAACACCCTGGT

CTGGAAGTACGCAGACGCCGGCCATGTGTGCCACCTGTGCCATCCAAACTGCAC

CTACGGATGCACTGGGCCAGGTCTTGAAGGCTGTCCAACGAATGGGCCTAAGAT

CCCGTCCATCGCCACTGGGATGGTGGGGCCCTCCTCTTGCTGCTGGTGGTGGCC

CTGGGGATCGGCCTCTTCATGCGAAGGCGCCACATCGTTCGGAAGCGCACGCTG

CGGAGGCTGCTGCAGGAGAGGGAGCTTGTGGAGCCTCTTACACCCAGTGGAGAA

GCTCCCAACCAAGCTCTCTTGAGGATCTTGAAGGAAACTGAATTCAAAAAGATC

AAAGTGCTGGGCTCCGGTGCGTTCGGCACGGTGTATAAGGGACTCTGGATCCCA

GAAGGTGAGAAAGTTAAAATTCCCGTCGCTATCAAGGAATTAAGAGAAGCAACA

TCTCCGAAAGCCAACAAGGAAATCCTCGATGAAGCCTACGTGATGGCCAGCGTG

GACAACCCCCACGTGTGCCGCCTGCTGGGCATCTGCCTCACCTCCACCGTGCAAC

TCATCACGCAGCTCATGCCCTTCGGCTGCCTCCTGGACTATGTCCGGGAACACAA

AGACAATATTGGCTCCCAGTACCTGCTCAACTGGTGTGTGCAGATCGCAAAGGGC

ATGAACTACTTGGAGGACCGTCGCTTGGTGCACCGCGACCTGGCAGCCAGGAAC

GTACTGGTGAAAACACCGCAGCATGTCAAGATCACAGATTTTGGGCTGGCCAAA

CTGCTGGGTGCGGAAGAGAAAGAATACCATGCAGAAGGAGGCAAAGTGCCTATC

AAGTGGATGGCATTGGAATCAATTTTACACAGAATCTATACCCACCAGAGTGATG
```

-continued

```
TCTGGAGCTACGGGGTGACCGTTTGGGAGTTGATGACCTTTGGATCCAAGCCATA
TGACGGAATCCCTGCCAGCGAGATCTCCTCCATCCTGGAGAAAGGAGAACGCCT
CCCTCAGCCACCCATATGTACCATCGATGTCTACATGATCATGGTCAAGTGCTGG
ATGATAGACGCAGATAGTCGCCCAAAGTTCCGTGAGTTGATCATCGAATTCTCCA
AAATGGCCCGAGACCCCCAGCGCTACCTTGTCATTCAGGGGGATGAAAGAATGC
ATTTGCCAAGTCCTACAGACTCCAACTTCTACCGTGCCCTGATGGATGAAGAAGA
CATGGACGACGTGGTGGATGCCGACGAGTACCTCATCCCACAGCAGGGCTTCTTC
AGCAGCCCCTCCACGTCACGGACTCCCCTCCTGAGCTCTCTGAGTGCAACCAGCA
ACAATTCCACCGTGGCTTGCATTGATAGAAATGGGCTGCAAAGCTGTCCCATCAA
GGAAGACAGCTTCTTGCAGCGATACAGCTCAGACCCCACAGGCGCCTTGACTGA
GGACAGCATAGACGACACCTTCCTCCCAGTGCCTGAATACATAAACCAGTCCGTT
CCCAAAAGGCCCGCTGGCTCTGTGCAGAATCCTGTCTATCACAATCAGCCTCTGA
ACCCCGCGCCCAGCAGAGACCCACACTACCAGGACCCCCACAGCACTGCAGTGG
GCAACCCCGAGTATCTCAACACTGTCCAGCCCACCTGTGTCAACAGCACATTCGA
CAGCCCTGCCCACTGGGCCCAGAAAGGCAGCCACCAAATTAGCCTGGACAACCC
TGACTACCAGCAGGACTTCTTTCCCAAGGAAGCCAAGCCAAATGGCATCTTTAAG
GGCTCCACAGCTGAAAATGCAGAATACCTAAGGGTCGCGCCACAAAGCAGTGAA
TTTATTGGAGCATGAGATGTAGGAATTCGCCAGCACAGTGGTCGACCCTGTGGAA
TGTGTGTCAGTTAGGGTGTGGAAAGTCCCCAGGCTCCCCAGCAGGCAGAAGTAT
GCAAAGCATGCATCTCAATTAGTCAGCAACCAGGTGTGGAAAGTCCCCAGGCTC
CCCAGCAGGCAGAAGTATGCAAAGCATGCATCTCAATTAGTCAGCAACCATAGT
CCCGCCCCTAACTCCGCCCATCCCGCCCCTAACTCCGCCCAGTTCCGCCCATTCTC
CGCCCCATGGCTGACTAATTTTTTTATTTATGCAGAGGCCGAGGCCGCCTCGGC
CTCTGAGCTATTCCAGAAGTAGTGAGGAGGCTTTTTTGGAGGCCTAGGCTTTTGC
AAAAAGCTTACCATGACCGAGTACAAGCCCACGGTGCGCCTCGCCACCCGCGAC
GACGTCCCCAGGGCCGTACGCACCCTCGCCGCCGCGTTCGCCGACTACCCCGCCA
CGCGCCACACCGTCGATCCGGACCGCCACATCGAGCGGGTCACCGAGCTGCAAG
AACTCTTCCTCACGCGCGTCGGGCTCGACATCGGCAAGGTGTGGGTCGCGGACG
ACGGCGCCGCGGTGGCGGTCTGGACCACGCCGGAGAGCGTCGAAGCGGGGGCG
GTGTTCGCCGAGATCGGCCCGCGCATGGCCGAGTTGAGCGGTTCCCGGCTGGCC
GCGCAGCAACAGATGGAAGGCCTCCTGGCGCCGCACCGGCCCAAGGAGCCCGCG
TGGTTCCTGGCCACCGTCGGCGTCTCGCCCGACCACCAGGGCAAGGGTCTGGGC
AGCGCCGTCGTGCTCCCCGGAGTGGAGGCGGCCGAGCGCGCCGGGGTGCCCGCC
TTCCTGGAGACCTCCGCGCCCCGCAACCTCCCCTTCTACGAGCGGCTCGGCTTCA
CCGTCACCGCCGACGTCGAGGTGCCCGAAGGACCGCGCACCTGGTGCATGACCC
GCAAGCCCGGTGCCTGACGCCCGCCCCACGACCCGCAGCGCCCGACCGAAAGGA
GCGCACGACCCCATGCATCGATAAAATAAAAGATTTTATTTAGTCTCCAGAAAAA
GGGGGGAATGAAAGACCCCACCTGTAGGTTTGGCAAGCTAGCTTAAGTAACGCC
ATTTTGCAAGGCATGGAAAAATACATAACTGAGAATAGAGAAGTTCAGATCAAG
GTCAGGAACAGATGGAACAGCTGAATATGGGCCAAACAGGATATCTGTGGTAAG
CAGTTCCTGCCCCGGCTCAGGGCCAAGAACAGATGGAACAGCTGAATATGGGCC
```

-continued

```
AAACAGGATATCTGTGGTAAGCAGTTCCTGCCCCGGCTCAGGGCCAAGAACAGA

TGGTCCCCAGATGCGGTCCAGCCCTCAGCAGTTTCTAGAGAACCATCAGATGTTT

CCAGGGTGCCCCAAGGACCTGAAATGACCCTGTGCCTTATTTGAACTAACCAATC

AGTTCGCTTCTCGCTTCTGTTCGCGCGCTTCTGCTCCCCGAGCTCAATAAAAGAGC

CCACAACCCCTCACTCGGGGCGCCAGTCCTCCGATTGACTGAGTCGCCCGGGTAC

CCGTGTATCCAATAAACCCTCTTGCAGTTGCATCCGACTTGTGGTCTCGCTGTTCC

TTGGGAGGGTCTCCTCTGAGTGATTGACTACCCGTCAGCGGGGGTCTTTCACATG

CAGCATGTATCAAAATTAATTTGGTTTTTTTTCTTAAGTATTTACATTAAATGGCC

ATAGTTGCATTAATGAATCGGCCAACGCGCGGGGAGAGGCGGTTTGCGTATTGG

GCGCTCTTCCGCTTCCTCGCTCACTGACTCGCTGCGCTCGGTCGTTCGGCTGCGGC

GAGCGGTATCAGCTCACTCAAAGGCGGTAATACGGTTATCCACAGAATCAGGGG

ATAACGCAGGAAAGAACATGTGAGCAAAAGGCCAGCAAAAGGCCAGGAACCGT

AAAAAGGCCGCGTTGCTGGCGTTTTTCCATAGGCTCCGCCCCCCTGACGAGCATC

ACAAAAATCGACGCTCAAGTCAGAGGTGGCGAAACCCGACAGGACTATAAAGAT

ACCAGGCGTTTCCCCCTGGAAGCTCCCTCGTGCGCTCTCCTGTTCCGACCCTGCC

GCTTACCGGATACCTGTCCGCCTTTCTCCCTTCGGGAAGCGTGGCGCTTTCTCATA

GCTCACGCTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAACTATCGT

CTTGAGTCCAACCCGGTAAGACACGACTTATCGCCACTGGCAGCAGCCACTGGT

AACAGGATTAGCAGAGCGAGGTATGTAGGCGGTGCTACAGAGTTCTTGAAGTGG

TGGCCTAACTACGGCTACACTAGAAGAACAGTATTTGGTATCTGCGCTCTGCTGA

AGCCAGTTACCTTCGGAAAAAGAGTTGGTAGCTCTTGATCCGGCAAACAAACCA

CCGCTGGTAGCGGTGGTTTTTTGTTTGCAAGCAGCAGATTACGCGCAGAAAAAA

AGGATCTCAAGAAGATCCTTTGATCTTTTCTACGGGGTCTGACGCTCAGTGGAAC

GAAAACTCACGTTAAGGGATTTTGGTCATGAGATTATCAAAAAGGATCTTCACCT

AGATCCTTTTGCGGCCGCAAATCAATCTAAAGTATATATGAGTAAACTTGGTCTG

ACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGC

TTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTC

CTGCAACTTTATCCGCCTCCATCCAGTCTATTAATTGTTGCCGGGAAGCTAGAGT

AAGTAGTTCGCCAGTTAATAGTTTGCGCAACGTTGTTGCCATTGCTACAGGCATC

GTGGTGTCACGCTCGTCGTTTGGTATGGCTTCATTCAGCTCCGGTTCCCAACGATC

AAGGCGAGTTACATGATCCCCCATGTTGTGCAAAAAAGCGGTTAGCTCCTTCGGT

CCTCCGATCGTTGTCAGAAGTAAGTTGGCCGCAGTGTTATCACTCATGGTTATGG

CAGCACTGCATAATTCTCTTACTGTCATGCCATCCGTAAGATGCTTTTCTGTGACT

GGTGAGTACTCAACCAAGTCATTCTGAGAATAGTGTATGCGGCGACCGAGTTGCT

CTTGCCCGGCGTCAATACGGGATAATACCGCGCCACATAGCAGAACTTTAAAAG

TGCTCATCATTGGAAAACGTTCTTCGGGGCGAAAACTCTCAAGGATCTTACCGCT

GTTGAGATCCAGTTCGATGTAACCCACTCGTGCACCCAACTGATCTTCAGCATCT
```

```
-continued
TTTACTTTCACCAGCGTTTCTGGGTGAGCAAAAACAGGAAGGCAAAATGCCGCA

AAAAAGGGAATAAGGGCGACACGGAAATGTTGAATACTCATACTCTTCCTTTTTC

AATATTATTGAAGCATTTATCAGGGTTATTGTCTCATGAGCGGATACATATTTGA

ATGTATTTAGAAAAATAAACAAATAGGGGTTCCGCGCACATTTCCCCGAAAA

EGFRvIII CAR (pLY60_TRAC-LHA-pAAV-EFS-h139-41BBz-RHA)
                                             (SEQ ID NO: 69,749)
CCTGCAGGCAGCTGCGCGCTCGCTCGCTCACTGAGGCCGCCCGGGCAAAGCCCG

GGCGTCGGGCGACCTTTGGTCGCCCGGCCTCAGTGAGCGAGCGAGCGCGCAGAG

AGGGAGTGGCCAACTCCATCACTAGGGGTTCCTGCGGCCGCACGCGTGACCACT

CCAGATTTCAAGATGTACAGTTTGCTTTGCTGGGCCTTTTTCCCATGCCTGCCTTT

ACTCTGCCAGAGTTATATTGCTGGGGTTTTGAAGAAGATCCTATTAAATAAAAGA

ATAAGCAGTATTATTAAGTAGCCCTGCATTTCAGGTTTCCTTGAGTGGCAGGCCA

GGCCTGGCCGTGAACGTTCACTGAAATCATGGCCTCTTGGCCAAGATTGATAGCT

TGTGCCTGTCCCTGAGTCCCAGTCCGTCACGAGCAGCTGGTTTCTAATATGCTATT

TCCCGTATAAAGCATGAGACCGTGACTTGCCAGCCCCACAGAGCCCCGCCCTTGT

CCATCACTGGCATCTGGACTCCAGCCTGGGTTGGGGCAAAGAGGGAAATGAGAT

CATGTCCTAACCCTGATCCTCTTGTCCCACAGATATCCAGAACCCTGACCCCTAG

GTCTTGAAAGGAGTGGGAATTGGCTCCGGTGCCCGTCAGTGGGCAGAGCGCACA

TCGCCCACAGTCCCCGAGAAGTTGGGGGGAGGGGTCGGCAATTGATCCGGTGCC

TAGAGAAGGTGGCGCGGGGTAAACTGGGAAAGTGATGTCGTGTACTGGCTCCGC

CTTTTTCCCGAGGGTGGGGGAGAACCGTATATAAGTGCAGTAGTCGCCGTGAAC

GTTCTTTTTCGCAACGGGTTTGCCGCCAGAACACAGGACCGGTTCTAGACGTACG

GCCACCATGGTTCTGCTGGTCACCAGCCTACTACTGTGCGAACTGCCCCACCCCG

CCTTTCTGCTGATCCCCGACATCCAGATGACCCAGAGCCCTAGCAGCCTGAGCGC

CAGCGTGGGCGACAGAGTGACCATCACCTGTCGAGCCAGCCAGGGCATCAGAAA

CAACCTGGCCTGGTATCAGCAGAAGCCAGGCAAGGCCCCAAAGAGACTGATCTA

CGCTGCCAGCAATCTGCAGAGCGGCGTGCCAAGCAGATTCACCGGAAGCGGCTC

CGGCACCGAGTTCACCCTGATCGTGTCCAGCCTGCAGCCCGAGGACTTCGCCAC

CTACTACTGCCTGCAGCACCACAGCTACCCTCTGACCAGCGGCGGAGGCACCAA

GGTGGAGATCAAGCGAACCGGAAGCACCAGCGGAAGCGGCAAGCCTGGCAGCG

GAGAAGGAAGCGAGGTCCAGGTGCTGGAATCTGGCGGCGGACTGGTGCAGCCTG

GCGGCAGCCTGAGACTGAGCTGTGCCGCCAGCGGCTTCACCTTCAGCAGCTACG

CCATGTCTTGGGTCCGGCAGGCTCCTGGAAAGGGCCTGGAATGGGTGTCCGCCAT

CAGCGGCTCTGGCGGCTCCACCAACTACGCCGACAGCGTGAAGGGCCGGTTCAC

CATCAGCCGGGACAACAGCAAGAACACCCTGTATCTGCAGATGAACAGCCTGAG

AGCCGAGGACACCGCCGTGTATTATTGTGCCGGCAGCAGCGGGTGGAGCGAGTA

CTGGGGACAGGGCACACTGGTCACAGTGTCTAGCGCGGCCGCACTCGAGACCAC

GACACCAGCGCCACGACCACCAACACCGGCGCCAACCATCGCGTCGCAGCCACT

GTCCCTGCGCCCAGAAGCATGCCGACCAGCAGCAGGAGGAGCAGTGCACACGAG

GGGGCTGGACTTCGCCTGTGATATCTACATCTGGGCGCCCTTGGCCGGGACTTGT

GGGGTCCTTCTCCTGTCACTGGTTATCACCCTTTACTGCAAACGGGGCAGAAAGA

AACTCCTGTATATATTCAAACAACCATTTATGAGACCAGTACAAACTACTCAAGA
```

-continued

```
GGAAGATGGCTGTAGCTGCCGATTTCCAGAAGAAGAAGAAGGAGGATGTGAACT

GAGAGTGAAGTTCAGCAGGAGCGCAGACGCCCCCGCGTACCAGCAGGGCCAGA

ACCAGCTCTATAACGAGCTCAATCTAGGACGAAGAGAGGAGTACGATGTTTTGG

ACAAGAGACGTGGCCGGGACCCTGAGATGGGGGAAAGCCGAGAAGGAAGAAC

CCTCAGGAAGGCCTGTACAATGAACTGCAGAAAGATAAGATGGCGGAGGCCTAC

AGTGAGATTGGGATGAAAGGCGAGCGCCGGAGGGGCAAGGGGCACGATGGCCT

TTACCAGGGTCTCAGTACAGCCACCAAGGACACCTACGACGCCCTTCACATGCA

GGCCCTGCCCCCTCGCTAAGCTAGCAATAAAAGATCTTTATTTTCATTAGATCTGT

GTGTTGGTTTTTTGTGTGGTACCGAGAGACTCTAAATCCAGTGACAAGTCTGTCT

GCCTATTCACCGATTTTGATTCTCAAACAAATGTGTCACAAAGTAAGGATTCTGA

TGTGTATATCACAGACAAAACTGTGCTAGACATGAGGTCTATGGACTTCAAGAGC

AACAGTGCTGTGGCCTGGAGCAACAAATCTGACTTTGCATGTGCAAACGCCTTCA

ACAACAGCATTATTCCAGAAAACACCTTCTTCCCCAGCCCAGGTAAGGGCAGCTT

TGGTGCCTTCGCAGGCTGTTTCCTTGCTTCAGGAATGGCCAGGTTCTGCCCAGAG

CTCTGGTCAATGATGTCTAAAACTCCTCTGATTGGTGGTCTCGGCCTTATCCATTG

CCACCAAAACCCTCTTTTTACTAAGAAACAGTGAGCCTTGTTCTGGCAGTCCAGA

GAATGACACGGAAAAAAAGCAGATGAAGAGAAGGTGGCAGGAGAGGGCACGTG

GCCCAGCCTCAGTCTCTCCAACTGAGTTCCTGCCTGCCTGCCTTTGCTCAGACTGT

TTGCCCCTTACTGCTCTTCTAGGCCTCATTCTAAGCCCCTTCTCCAAGTTGCCTCT

CCTTATTTCTCCCTGTCTGCCAAAAAATCTTTCCCAGCTCACTAAGTCAGTCTCAC

GCAGTCACTCATTAACCCACCGGACCGAGCGGCCGCAGGAACCCCTAGTGATGG

AGTTGGCCACTCCCTCTCTGCGCGCTCGCTCGCTCACTGAGGCCGGGCGACCAAA

GGTCGCCCGACGCCCGGGCTTTGCCCGGGCGGCCTCAGTGAGCGAGCGAGCGCG

CAGCTGCCTGCAGGGGCGCCTGATGCGGTATTTTCTCCTTACGCATCTGTGCGGT

ATTTCACACCGCATACGTCAAAGCAACCATAGTACGCGCCCTGTAGCGGCGCATT

AAGCGCGGCGGGTGTGGTGGTTACGCGCAGCGTGACCGCTACACTTGCCAGCGC

CCTAGCGCCCGCTCCTTTCGCTTTCTTCCCTTCCTTTCTCGCCACGTTCGCCGGCTT

TCCCCGTCAAGCTCTAAATCGGGGCTCCCTTTAGGGTTCCGATTTAGTGCTTTAC

GGCACCTCGACCCCAAAAAACTTGATTTGGGTGATGGTTCACGTAGTGGGCCATC

GCCCTGATAGACGGTTTTTCGCCCTTTGACGTTGGAGTCCACGTTCTTTAATAGTG

GACTCTTGTTCCAAACTGGAACAACACTCAACCCTATCTCGGGCTATTCTTTTGAT

TTATAAGGGATTTTGCCGATTTCGGCCTATTGGTTAAAAAATGAGCTGATTTAAC

AAAAATTTAACGCGAATTTTAACAAAATATTAACGTTTACAATTTTATGGTGCAC

TCTCAGTACAATCTGCTCTGATGCCGCATAGTTAAGCCAGCCCCGACACCCGCCA

ACACCCGCTGACGCGCCCTGACGGGCTTGTCTGCTCCCGGCATCCGCTTACAGAC

AAGCTGTGACCGTCTCCGGGAGCTGCATGTGTCAGAGGTTTTCACCGTCATCACC

GAAACGCGCGAGACGAAAGGGCCTCGTGATACGCCTATTTTTATAGGTTAATGTC

ATGATAATAATGGTTTCTTAGACGTCAGGTGGCACTTTTCGGGGAAATGTGCGCG

GAACCCCTATTTGTTTATTTTTCTAAATACATTCAAATATGTATCCGCTCATGAGA

CAATAACCCTGATAAATGCTTCAATAATATTGAAAAAGGAAGAGTATGAGTATT
```

```
-continued
CAACATTTCCGTGTCGCCCTTATTCCCTTTTTGCGGCATTTTGCCTTCCTGTTTTT

GCTCACCCAGAAACGCTGGTGAAAGTAAAAGATGCTGAAGATCAGTTGGGTGCA

CGAGTGGGTTACATCGAACTGGATCTCAACAGCGGTAAGATCCTTGAGAGTTTTC

GCCCCGAAGAACGTTTTCCAATGATGAGCACTTTTAAAGTTCTGCTATGTGGCGC

GGTATTATCCCGTATTGACGCCGGGCAAGAGCAACTCGGTCGCCGCATACACTAT

TCTCAGAATGACTTGGTTGAGTACTCACCAGTCACAGAAAAGCATCTTACGGATG

GCATGACAGTAAGAGAATTATGCAGTGCTGCCATAACCATGAGTGATAACACTG

CGGCCAACTTACTTCTGACAACGATCGGAGGACCGAAGGAGCTAACCGCTTTTTT

GCACAACATGGGGGATCATGTAACTCGCCTTGATCGTTGGGAACCGGAGCTGAA

TGAAGCCATACCAAACGACGAGCGTGACACCACGATGCCTGTAGCAATGGCAAC

AACGTTGCGCAAACTATTAACTGGCGAACTACTTACTCTAGCTTCCCGGCAACAA

TTAATAGACTGGATGGAGGCGGATAAAGTTGCAGGACCACTTCTGCGCTCGGCC

CTTCCGGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTAGTTAT

CTACACGACGGGGAGTCAGGCAACTATGGATGAACGAAATAGACAGATCGCTGA

GATAGGTGCCTCACTGATTAAGCATTGGTAACTGTCAGACCAAGTTTACTCATAT

ATACTTTAGATTGATTTAAAACTTCATTTTTAATTTAAAAGGATCTAGGTGAAGA

TCCTTTTTGATAATCTCATGACCAAAATCCCTTAACGTGAGTTTTCGTTCCACTGA

GCGTCAGACCCCGTAGAAAAGATCAAAGGATCTTCTTGAGATCCTTTTTTTCTGC

GCGTAATCTGCTGCTTGCAAACAAAAAAACCACCGCTACCAGCGGTGGTTTGTTT

GCCGGATCAAGAGCTACCAACTCTTTTTCCGAAGGTAACTGGCTTCAGCAGAGCG

CAGATACCAAATACTGTCCTTCTAGTGTAGCCGTAGTTAGGCCACCACTTCAAGA

ACTCTGTAGCACCGCCTACATACCTCGCTCTGCTAATCCTGTTACCAGTGGCTGCT

GCCAGTGGCGATAAGTCGTGTCTTACCGGGTTGGACTCAAGACGATAGTTACCGG

ATAAGGCGCAGCGGTCGGGCTGAACGGGGGGTTCGTGCACACAGCCCAGCTTGG

AGCGAACGACCTACACCGAACTGAGATACCTACAGCGTGAGCTATGAGAAAGCG

CCACGCTTCCCGAAGGGAGAAAGGCGGACAGGTATCCGGTAAGCGGCAGGGTCG

GAACAGGAGAGCGCACGAGGGAGCTTCCAGGGGGAAACGCCTGGTATCTTTATA

GTCCTGTCGGGTTTCGCCACCTCTGACTTGAGCGTCGATTTTTGTGATGCTCGTCA

GGGGGGCGGAGCCTATGGAAAAACGCCAGCAACGCGGCCTTTTTACGGTTCCTG

GCCTTTTGCTGGCCTTTTGCTCACATGT
```

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

SEQUENCE LISTING

The patent contains a lengthy sequence listing. A copy of the sequence listing is available in electronic form from the USPTO web site (https://seqdata.uspto.gov/?pageRequest=docDetail&DocID=US12297428B2). An electronic copy of the sequence listing will also be available from the USPTO upon request and payment of the fee set forth in 37 CFR 1.19(b)(3).

What is claimed is:
1. An adeno-associated virus (AAV) vector comprising the nucleic acid sequence set forth in SEQ ID NO: 69,821.

* * * * *